US009187524B2

(12) United States Patent
Romesberg et al.

(10) Patent No.: US 9,187,524 B2
(45) Date of Patent: Nov. 17, 2015

(54) BROAD SPECTRUM ANTIBIOTIC ARYLOMYCIN ANALOGS

(75) Inventors: Floyd E. Romesberg, La Jolla, CA (US); Peter A. Smith, La Jolla, CA (US); Tucker C. Roberts, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/821,195

(22) PCT Filed: Aug. 31, 2011

(86) PCT No.: PCT/US2011/049967
§ 371 (c)(1),
(2), (4) Date: May 28, 2013

(87) PCT Pub. No.: WO2012/036907
PCT Pub. Date: Mar. 22, 2012

(65) Prior Publication Data
US 2013/0281360 A1    Oct. 24, 2013

Related U.S. Application Data

(60) Provisional application No. 61/382,988, filed on Sep. 15, 2010.

(51) Int. Cl.
| | | |
|---|---|---|
| *C07K 7/06* | (2006.01) |
| *C07K 9/00* | (2006.01) |
| *A61K 38/08* | (2006.01) |
| *A61K 38/14* | (2006.01) |
| *A61K 45/06* | (2006.01) |
| *A61K 38/00* | (2006.01) |

(52) U.S. Cl.
CPC . *C07K 7/06* (2013.01); *A61K 38/08* (2013.01); *A61K 38/14* (2013.01); *A61K 45/06* (2013.01); *C07K 9/001* (2013.01); *A61K 38/00* (2013.01)

(58) Field of Classification Search
None
See application file for complete search history.

(56) References Cited

U.S. PATENT DOCUMENTS

| 6,048,694 | A | 4/2000 | Bramucci et al. |
| 6,951,840 | B2 | 10/2005 | Belvo et al. |
| 2003/0130172 | A1 | 7/2003 | Belvo et al. |
| 2008/0275018 | A1 | 11/2008 | Endermann et al. |
| 2015/0045286 | A1 | 2/2015 | Romesberg et al. |

FOREIGN PATENT DOCUMENTS

| CN | 104284664 A | 1/2015 |
| JP | 2013539751 A | 10/2013 |
| KR | 10-2014-0140580 A | 12/2014 |
| WO | WO-2012/166665 A2 | 12/2002 |
| WO | WO-2011/112441 A1 | 9/2011 |
| WO | WO-2012/036907 A2 | 3/2012 |
| WO | WO-2013138187 A1 | 9/2013 |

OTHER PUBLICATIONS

Holtzel et al. Arylomycins A and B, New Biaryl-bridged Lipopeptide Antibiotics Produced by Streptomyces sp. Tu 6075. II. Structure Elucidation. The Journal of Antibiotics. Jun. 2002, vol. 55, No. 6, pp. 571-577.*
"Chinese Application Serial No. 201180055018.6, Office Action mailed Jan. 15, 2014", (w/English Translation), 13 pgs.
"European Application Serial No. 11825668.4, Supplementary European Search Report mailed Jan. 28, 2014", 13 pgs.
Butler, Mark S., "Natural products—The future scaffolds for novel antibiotics?", *Biochemical Pharmacology*, 71, (2006), 919-929.
Hellmark, B., "Antibiotic susceptibility among Staphylococcus epidermidis isolated from prosthetic joint infections with special focus on rifampicin and variability of the rpoB gene", *Clin. Microbiol. Infect.* 15(3), (2009), 238-244.
Li, Tong, et al., "Computational alanine scanning and free energy decompostion for E. coli type I signal peptidase with lipopeptide inhibitor complex", *J. Mol. Graph. Modelling*. 26(5), (2008), 813-823.
Luo, Chuanyun, et al., "Crystallographic Analysis of Bacterial Signal Peptidase in Ternary Complex with Arylomycin $A_2$ and a β-Sultam Inhibitor", *Biochemistry* 48(38), (2009), 8976-8984.
Roberts, Tucker C, et al., "Structural and Initial Biological Analysis of Synthetic Aryfomycin $A_2$", *JACS*, 129(51), (2007),15830-15838.
Roberts, Tucker C, et al., "Synthesis and Biological Characterazation of Arylomycin B Antibiotics", *J. Natural Prod.*, 74(5), (May 2011), 956-961.
Schimana, Judith, et al., "Arylomycins A and B, New Biaryl-bridged Lipopeptide Antibiotics Produced by Streptomyces sp. Tü 6075, I. Taxonomylc Fermentation, Isolation and Biological Activities", *The Journal of Antibiotics*, 55(6), (Jun. 2002), 565-570.
Smith, Peter A., et al., "In Vitro Activities of Arylomycin Naturat-Product Antibiotics against Staphylococcus epidermidis and Other Coagulase-Negative Staphylococci", *Antimicr. Agents Chemother.*, 55(3), (2011), 1130-1134.

(Continued)

*Primary Examiner* — Jeffrey E Russel
(74) *Attorney, Agent, or Firm* — Schwegman Lundberg & Woessner, P.A.

(57) ABSTRACT

Arylomycin analogs are provided, wherein the analogs can have broad spectrum bioactivity. Resistance to the antibiotic bioactivity of natural product arylomycin in a range of pathogenic bacterial species has been found to depend upon single amino acid mutations at defined positions of bacterial Signal Peptidases (SPases), wherein the presence of a proline residue confers arylomycin resistance. Arylomycin analogs are provided herein that can overcome that resistance and provide for a broader spectrum of antibiotic bioactivity than can natural product arylomycins such as arylomycin A2. Methods for determining if a bacterial strain is susceptible to narrow spectrum arylomycin antibiotics, or if a broad spectrum analog is required for treatment, is provided. Pharmaceutical compositions and methods of treatment of bacterial infections, and methods of synthesis of arylomycin analogs, are provided.

29 Claims, 13 Drawing Sheets

(56) References Cited

OTHER PUBLICATIONS

"European Application Serial No. 11825668.4, Office Action mailed Feb. 14, 2014", 1 pg.
"European Application Serial No. 11825668.4, Response filed Aug. 22, 2014 to Office Action mailed Aug. 14, 2014", 21 pgs.
Kulanthaivel, P., et al., "Novel lipoglycopeptides as inhibitors of bacterial signal peptidase I", J Biol Chem., 279(35), (Aug. 27, 2004), 36250-8.
"Chinese Application Serial No. 201180055018.6, Response filed May 28, 2014 to Office Action mailed Jan. 15, 2014", 32 pgs.
"International Application Serial No. PCT/US2011/049967, International Preliminary Report on Patentability mailed Mar. 28, 2013", 8 pgs.
"International Application Serial No. PCT/US2013/029913, International Search Report mailed Aug. 1, 2013", 5 pgs.
"International Application Serial No. PCT/US2013/029913, Invitation to Pay Additional Fees and Partial Search Report mailed Jun. 6, 2013", 12 pgs.
"International Application Serial No. PCT/US2013/029913, Written Opinion mailed Aug. 1, 2013", 7 pgs.
Roberts, T.C., et al., "Initial efforts toward the optimization of arylomycins for antibiotic activity", *J. Med. Chem.*, 54(14), (2011), 4954-4963 (24 pgs).
Smith, P. A., et al., "Broad-Spectrum Antibiotic Activity of the Arylomycin Natural Products Is Masked by Natural Target Mutations", *Chemistry & Biology*, 17, (2010), 1223-1231.
"International Application Serial No. PCT/US/2011/049967, Search Report mailed Apr. 6, 2012", 4 pgs.
"International Application Serial No. PCT/US/2011/049967, Written Opinion mailed Apr. 6, 2012", 6 pgs.
"International Application Serial No. PCT/US2011/49967, Invitation to Pay Additional Fees mailed Jan. 17, 2012", 2 pgs.
Bockstael, et al., "Evaluation of the type I Signal Peptidase as Antibacterial Target for Biofilm-Associated Infections of *Staphylococcus epidermidis*", Microbiology, 155(11), (2009), 3719-3729.
Butler, Mark S, et al., "Natural Products", The Future Scaffolds for Novel Antibiotics?, (2006), 919-929 pgs.
Clardy, et al., "New Antibiotics from Bacterial Natural products", Nature Biotechnology, 24, (2006), 1541-1550.
Dufour, et al., "Intramolecular Suzuki-Miyaura Reaction for the Total Synthesis fo Signal Peptidase Inhibitors", Arylomycins A2 and B2—A European Journal EPub, 16(34), (Jul. 23, 2010), 10523-10534.
Musial-Siwek, et al., "A Small Subset of Signal Peptidase Residues are Perturbed by Signal Peptide Binding", Chem Biol Drug Des., 72(2), (2008), 140-146.
Nilsson, et al., "A Signal Peptide with a Proline Next to the Cleavage Stie Inhibits Leader peptidase When Present in a Sec-Independent Protein.", FEBS Letters, 299(3), (1992), 243-246.
"Chinese Application Serial No. 201180055018.6, Office Action mailed Aug. 26, 2014", 20 pgs.
"Eurasian Application Serial No. 201491646, Office Action mailed Nov. 17, 2014", 3 pgs.
"European Application Serial No. 11825668.4, Examination Notification Art. 94(3) mailed Nov. 20, 2014", 7 pgs.
"International Application Serial No. PCT/US2013/029913, International Preliminary Report on Patentability mailed Sep. 25, 2014", 9 pgs.
"Japanese Application Serial No. 2015-500480, Written Amendment filed Jan. 8, 2015", 37 pgs.

\* cited by examiner

| ARYLOMYCIN | $R_1$ | $R_2$ |
|---|---|---|
| $A_1$ | H | iso-$C_{11}$ |
| $A_2$ | H | iso-$C_{12}$ |
| $A_3$ | H | n-$C_{12}$ |
| $A_4$ | H | anteiso-$C_{13}$ |
| $A_5$ | H | iso-$C_{14}$ |
| $B_1$ | $NO_2$ | iso-$C_{11}$ |
| $B_2$ | $NO_2$ | iso-$C_{12}$ |
| $B_3$ | $NO_2$ | n-$C_{12}$ |
| $B_4$ | $NO_2$ | anteiso-$C_{13}$ |
| $B_5$ | $NO_2$ | iso-$C_{13}$ |
| $B_6$ | $NO_2$ | iso-$C_{14}$ |
| $B_7$ | $NO_2$ | anteiso-$C_{15}$ |

| ORGANISM | AMINO ACID AT RESIDUE -7 FROM CATALYTIC SER |
|---|---|
| ABIOTROPHIA_DEFECTIVA | NKE |
| ACIDOTHERMUS_CELLULOLYTICUS | A |
| ACTINOMYCES_COLEOCANIS | A |
| ACTINOMYCES_ODONTOLYTICUS | V |
| ACTINOMYCES_SP_848_STR_F0332 | A |
| ACTINOMYCES_UROGENITALIS | W |
| ACTINOSYNNEMA_MIRUMDSM | W |
| ANAEROCELLUM_THERMOPHILUM | L |
| ANAEROCOCCUS_HYDROGENALIS | A |
| ANAEROCOCCUS_LACTOLYTICUS | AL |
| ANAEROCOCCUS_PREVOTII | A |
| ANAEROCOCCUS_TETRADIUS | A |
| ANAEROCOCCUS_VAGINALIS | A |
| ANAEROMYXOBACTER_DEHALOGENANS | AA |
| ANAEROMYXOBACTER_SP_FW109-5 | AA |
| ANAEROMYXOBACTER_SP_K | AA |
| ANAEROSTIPES_CACCAE | GRN |
| ANAEROTRUNCUS_COLIHOMINIS | LT |
| ARCOBACTER_BUTZLERI | A |
| ARTHROBACTER_AURESCENS | V |
| ARTHROBACTER_SP_FB24 | VA |
| ATOPOBIUM_PARVULUM | V |
| ATOPOBIUM_RIMAE | V |
| ATOPOBIUM_VAGINAE | V |
| BACILLUS_HALODURANS | S |
| BEUTENBERGIA_CAVERNAE | A |
| BIFIDOBACTERIUM_ADOLESCENTIS | F |
| BIFIDOBACTERIUM_ANGULATUM | C |
| BIFIDOBACTERIUM_ANIMALIS | M |
| BIFIDOBACTERIUM_BIFIDUM | F |
| BIFIDOBACTERIUM_BREVE | F |
| BIFIDOBACTERIUM_CATENULATUM | F |
| BIFIDOBACTERIUM_DENTIUM | F |
| BIFIDOBACTERIUM_GALLICUM | M |
| BIFIDOBACTERIUM_LONGUM | VF |
| BIFIDOBACTERIUM_PSEUDOCATENULATUM | F |
| BLAUTIA_HANSENII | SN |
| BLAUTIA_HYDROGENOTROPHICA | VNS |
| BREVIBACTERIUM_LINENS | RS |
| BUTYRATE-PRODUCING_BACTERIUM_L2-50 | TR |
| BUTYRATE-PRODUCING_BACTERIUM_M62-1 | N |
| BUTYRATE-PRODUCING_BACTERIUM_SS2-1 | RSN |

Fig. 5A

| ORGANISM | AMINO ACID AT RESIDUE −7 FROM CATALYTIC SER |
|---|---|
| BUTYRIVIBRIO_CROSSOTUS | NNK |
| CALDANAEROBACTER_SUBTERRANEUS | L |
| CALDICELLULOSIRUPTOR_SACCHAROLYTICUS | L |
| CAMINIBACTER_MEDIATLANTICUS | A |
| CAMPYLOBACTER_COLI | A |
| CAMPYLOBACTER_CONCISUS | A |
| CAMPYLOBACTER_CURVUS | A |
| CAMPYLOBACTER_FETUS | A |
| CAMPYLOBACTER_GRACILIS | A |
| CAMPYLOBACTER_HOMINIS | A |
| CAMPYLOBACTER_JEJUNI | AIM |
| CAMPYLOBACTER_LARI | A |
| CAMPYLOBACTER_RECTUS | A |
| CAMPYLOBACTER_SHOWAE | A |
| CAMPYLOBACTER_UPSALIENSIS | A |
| CAMPYLOBACTERALES_BACTERIUM_GD1 | A |
| CANDIDATUS_PROTOCHLAMYDIA | L |
| CARBOXYDIBRACHIUM_PACIFICUM | L |
| CARBOXYDOTHERMUS_HYDROGENOFORMANS | L |
| CATENULISPORA_ACIDIPHILA | VAAM |
| CELLULOMONAS_FLAVIGENA | A |
| CHLAMYDIA_MURIDARUM | L |
| CHLAMYDIA_TRACHOMATIS | L |
| CHLAMYDOPHILA_ABORTUS | L |
| CHLAMYDOPHILA_CAVIAE | L |
| CHLAMYDOPHILA_FELIS | L |
| CHLAMYDOPHILA_PNEUMONIAE | L |
| CLAVIBACTER_MICHIGANENSIS | S |
| CLOSTRIDIALESBACTERIUM1_7_47FAA | NQN |
| CLOSTRIDIALESGENOMO_SP_BVAB3 | V |
| CLOSTRIDIUM_ACETOBUTYLICUM | RT |
| CLOSTRIDIUM_ASPARAGIFORME | NQN |
| CLOSTRIDIUM_BEIJERINCKII | GANN |
| CLOSTRIDIUM_BOLTEAE | NQN |
| CLOSTRIDIUM_BOTULINUM | STN |
| CLOSTRIDIUM_BUTYRICUM | NGNN |
| CLOSTRIDIUM_CELLULOVORANS | NNN |
| CLOSTRIDIUM_HATHEWAYI | QNN |
| CLOSTRIDIUM_HYLEMONAE | IRR |
| CLOSTRIDIUM_KLUYVERI | RIT |
| CLOSTRIDIUM_LEPTUM | V |
| CLOSTRIDIUM_METHYLPENTOSUM | VN |

Fig. 5B

| ORGANISM | AMINO ACID AT RESIDUE −7 FROM CATALYTIC SER |
|---|---|
| CLOSTRIDIUM_NEXILE | RR |
| CLOSTRIDIUM_NOVYI | QQ |
| CLOSTRIDIUM_PERFRINGENS | KIKK |
| CLOSTRIDIUM_SCINDENS | FIRR |
| CLOSTRIDIUM_SPOROGENES | TK |
| CLOSTRIDIUM_TETANI | T |
| CLOSTRIDIUMSP_7_2_43FAA | KS |
| COPROCOCCUS_COMES | QR |
| COPROCOCCUS_EUTACTUS | NKR |
| CORYNEBACTERIUM_ACCOLENS | MQ |
| CORYNEBACTERIUM_AMYCOLATUM | V |
| CORYNEBACTERIUM_AURIMUCOSUM | LQL |
| CORYNEBACTERIUM_DIPHTHERIAE | V |
| CORYNEBACTERIUM_GENITALIUM | V |
| CORYNEBACTERIUM_GLUCURONOLYTICUM | I |
| CORYNEBACTERIUM_GLUTAMICUM | M |
| CORYNEBACTERIUM_JEIKEIUM | M |
| CORYNEBACTERIUM_KROPPENSTEDTII | W |
| CORYNEBACTERIUM_LIPOPHILOFLAVUM | M |
| CORYNEBACTERIUM_MATRUCHOTII | L |
| CORYNEBACTERIUM_PSEUDOGENITALIUM | MQ |
| CORYNEBACTERIUM_STRIATUM | MQ |
| CORYNEBACTERIUM_TUBERCULOSTEARICUM | QM |
| CORYNEBACTERIUM_UREALYTICUM | L |
| DELTA_PROTEOBACTERIUM_MLMS−1 | A |
| DESULFOBACTERIUM_AUTOTROPHICUM | A |
| DESULFOHALOBIUM_RETBAENSE | A |
| DESULFOMICROBIUM_BACULATUM | A |
| DESULFONATRONOSPIRA_THIODISMUTANS | A |
| DESULFOTALEA_PSYCHROPHILA | A |
| DESULFOVIBRIO_AESPOEENSIS | NA |
| DESULFOVIBRIO_DESULFURICANS | A |
| DESULFOVIBRIO_MAGNETICUS | EA |
| DESULFOVIBRIO_PIGER | A |
| DESULFOVIBRIO_SALEXIGENS | A |
| DESULFOVIBRIO_VULGARIS | A |
| DESULFURIVIBRIO_ALKALIPHILUS | A |
| DETHIOBACTER_ALKALIPHILUS | V |
| DOREA_FORMICIGENERANS | RRN |
| DOREA_LONGICATENA | RRN |
| EGGERTHELLA_LENTA | AA |

*Fig. 5C*

| ORGANISM | AMINO ACID AT RESIDUE -7 FROM CATALYTIC SER |
|---|---|
| EPULOPISCIUM_SP_NT_B | HH |
| ETHANOLIGENENS_HARBINENSE | TT |
| EUBACTERIUM_ELIGENS | NR |
| EUBACTERIUM_HALLII | RRT |
| EUBACTERIUM_RECTALE | NIG |
| EUBACTERIUM_SAPHENUM | T |
| EUBACTERIUM_SIRAEUM | V |
| EUBACTERIUM_VENTRIOSUM | N |
| FAECALIBACTERIUM_PRAUSNITZII | I |
| FINEGOLDIA_MAGNA | TI |
| FRANCISELLA_NOVICIDA | N |
| FRANCISELLA_PHILOMIRAGIA | N |
| FRANCISELLA_TULARENSIS | N |
| FRANKIA_ALNI | A |
| FRANKIA_SP_CCI3 | A |
| FRANKIA_SP_EAN1PEC | AA |
| FRANKIA_SP_EUI1 | A |
| FRANKIA_SP_EUN1F | A |
| GARDNERELLA_VAGINALIS | V |
| GEOBACTER_BEMIDJIENSIS | A |
| GEOBACTER_LOVLEYI | AAL |
| GEOBACTER_METALLIREDUCENS | A |
| GEOBACTER_SP_FRC-32 | A |
| GEOBACTER_SP_M18 | A |
| GEOBACTER_SP_M21 | A |
| GEOBACTER_SULFURREDUCENS | A |
| GEOBACTER_URANIIREDUCENS | AA |
| GORDONIA_BRONCHIALIS | Q |
| HALIANGIUM_OCHRACEUM | A |
| HALOTHERMOTHRIX_ORENII | S |
| HELICOBACTER_ACINONYCHIS | A |
| HELICOBACTER_CANADENSIS | A |
| HELICOBACTER_CINAEDI | A |
| HELICOBACTER_HEPATICUS | A |
| HELICOBACTER_MUSTELAE | A |
| HELICOBACTER_PULLORUM | A |
| HELICOBACTER_PYLORI | A |
| HELICOBACTER_SP_ATCC_43879 | G |
| HELICOBACTER_WINGHAMENSIS | A |
| HIRSCHIA_BALTICA | L |
| HYPHOMONAS_NEPTUNIUM | Q |

Fig. 5D

| ORGANISM | AMINO ACID AT RESIDUE -7 FROM CATALYTIC SER |
|---|---|
| JONESIA_DENITRIFICANS | A |
| KINEOCOCCUS_RADIOTOLERANS | SAAT |
| KOCURIA_RHIZOPHILA | GV |
| KRIBBELLA_FLAVIDA | AM |
| KYTOCOCCUS_SEDENTARIUS | AT |
| LACTOBACILLUS_ACIDOPHILUS | N |
| LACTOBACILLUS_ANTRI | I |
| LACTOBACILLUS_BREVIS | RV |
| LACTOBACILLUS_CASEI | K |
| LACTOBACILLUS_COLEOHOMINIS | N |
| LACTOBACILLUS_CRISPATUS | NN |
| LACTOBACILLUS_DELBRUECKII | N |
| LACTOBACILLUS_FERMENTUM | L |
| LACTOBACILLUS_GASSERI | NN |
| LACTOBACILLUS_HELVETICUS | NN |
| LACTOBACILLUS_INERS | N |
| LACTOBACILLUS_JENSENII | N |
| LACTOBACILLUS_JOHNSONII | NN |
| LACTOBACILLUS_PLANTARUM | MVM |
| LACTOBACILLUS_REUTERI | I |
| LACTOBACILLUS_RHAMNOSUS | K |
| LACTOBACILLUS_SALIVARIUS | V |
| LACTOBACILLUS_ULTUNENSIS | NN |
| LACTOBACILLUS_VAGINALIS | I |
| LACTOCOCCUS_LACTIS | L |
| LAWSONIA_INTRACELLULARIS | A |
| LEIFSONIA_XYLI | S |
| LEUCONOSTOC_CITREUM | L |
| LEUCONOSTOC_MESENTEROIDES | LR |
| MACROCOCCUS_CASEOLYTICUS | TS |
| MARICAULIS_MARIS | A |
| MARINEACTINO_BACTERIUM | S |
| MARVINBRYANTIA_FORMATEXIGENS | TR |
| MICROCOCCUS_LUTEUS | MVV |
| MICROMONOSPORA_AURANTIACA | TA |
| MICROMONOSPORA_CARBONACEA | TA |
| MITSUOKELLA_MULTACIDA | L |
| NAKAMURELLA_MULTIPARTITA | V |
| NATRANAEROBIUS_THERMOPHILUS | VI |
| NAUTILIA_PROFUNDICOLA | A |
| NITRATIRUPTOR_SP_SB155-2 | A |

Fig. 5E

| ORGANISM | AMINO ACID AT RESIDUE −7 FROM CATALYTIC SER |
|---|---|
| NOCARDIOIDES_SP_JS614 | A |
| NOCARDIOPSIS_DASSONVILLEI | A |
| OCEANICAULIS_ALEXANDRII | A |
| ORIBACTERIUM_SINUS | NL |
| ORIBACTERIUM_SP_F0262 | QN |
| ORIENTIA_TSUTSUGAMUSHI | L |
| PARVIMONAS_MICRA | S |
| PEDIOCOCCUS_ACIDILACTICI | I |
| PEDIOCOCCUS_PENTOSACEUS | F |
| PELOBACTER_CARBINOLICUS | A |
| PELOBACTER_PROPIONICUS | AL |
| PEPTONIPHILUS_LACRIMALIS | L |
| PROPIONIBACTERIUM_ACNES | M |
| RHODOCOCCUS_ERYTHROPOLIS | IV |
| RHODOCOCCUS_JOSTII | V |
| RHODOCOCCUS_OPACUS | V |
| RICKETTSIA_BELLII | S |
| ROSEBURIA_INTESTINALIS | RRN |
| ROSEBURIA_INULINIVORANS | NR |
| ROTHIA_MUCILAGINOSA | G |
| RUBROBACTER_XYLANOPHILUS | A |
| RUMINOCOCCUS_GNAVUS | RR |
| RUMINOCOCCUS_LACTARIS | RN |
| RUMINOCOCCUS_OBEUM | TN |
| RUMINOCOCCUS_TORQUES | NRR |
| SACCHAROMONOSPORA_VIRIDIS | V |
| SACCHAROPOLYSPORA_ERYTHRAEA | V |
| SALINISPORA_ARENICOLA | TA |
| SALINISPORA_TROPICA | TA |
| SANGUIBACTER_KEDDIEII | A |
| SELENOMONAS_FLUEGGEI | LN |
| SELENOMONAS_SPUTIGENA | L |
| SHUTTLEWORTHIA_SATELLES | RT |
| SLACKIA_EXIGUA | AA |
| SLACKIA_HELIOTRINIREDUCENS | AL |
| SORANGIUM_CELLULOSUM | AQ |
| STACKEBRANDTIA_NASSAUENSIS | SSS |
| STAPHYLOCOCCUS_CARNOSUS | S |
| STAPHYLOCOCCUS_EPIDERMIDIS | SS |
| STAPHYLOCOCCUS_HAEMOLYTICUS | SS |
| STAPHYLOCOCCUS_HOMINIS | SS |

Fig. 5F

| ORGANISM | AMINO ACID AT RESIDUE −7 FROM CATALYTIC SER |
|---|---|
| STAPHYLOCOCCUS_LUGDUNENSIS | TS |
| STREPTOCOCCUS_AGALACTIAE | FV |
| STREPTOCOCCUS_DYSGALACTIAE | A |
| STREPTOCOCCUS_MITIS | N |
| STREPTOCOCCUS_PNEUMONIAE | N |
| STREPTOCOCCUS_PYOGENES | A |
| STREPTOCOCCUS_SP_M143 | N |
| STREPTOMYCES_SP_AA4 | W |
| STREPTOSPORANGIUM_ROSEUM | ATA |
| SUBDOLIGRANULUM_VARIABILE | I |
| SULFURIMONAS_DENITRIFICANS | A |
| SULFUROSPIRILLUM_DELEYIANUM | AA |
| SULFUROVUM_SP_NBC37-1 | SI |
| SYMBIOBACTERIUM_THERMOPHILUM | VW |
| SYNTROPHOBACTER_FUMAROXIDANS | AA |
| SYNTROPHOMONAS_WOLFEI | G |
| SYNTROPHUS_ACIDITROPHICUS | A |
| THERMOANAEROBACTER_ETHANOLICUS | L |
| THERMOANAEROBACTER_MATHRANII | L |
| THERMOANAEROBACTER_PSEUDETHANOLICUS | L |
| THERMOMONOSPORA_CURVATA | A |
| TROPHERYMA_WHIPPLEI | V |
| TSUKAMURELLA_PAUROMETABOLA | Q |
| WEISSELLA_PARAMESENTEROIDES | M |
| WOLINELLA_SUCCINOGENES | A |
| XYLANIMONAS_CELLULOSILYTICA | LA |
| ALIS_PUTREDINIS | M |
| BACTEROIDES_CACCAE | SNW |
| BACTEROIDES_CAPILLOSUS | FV |
| BACTEROIDES_CELLULOSILYTICUS | STTSNS |
| BACTEROIDES_COPROCOLA | NS |
| BACTEROIDES_COPROPHILUS | SNS |
| BACTEROIDES_DOREI | SN |
| BACTEROIDES_EGGERTHII | N |
| BACTEROIDES_FINEGOLDII | N |
| BACTEROIDES_FRAGILIS | NS |
| BACTEROIDES_INTESTINALIS | TSTNT |
| BACTEROIDES_OVATUS | N |
| BACTEROIDES_PECTINOPHILUS | N |
| BACTEROIDES_PLEBEIUS | N |
| BACTEROIDES_SP_1_1_6 | SN |

Fig. 5G

| ORGANISM | AMINO ACID AT RESIDUE −7 FROM CATALYTIC SER |
|---|---|
| BACTEROIDES_SP_2_1_16 | N |
| BACTEROIDES_SP_3_1_33FAA | N |
| BACTEROIDES_SP_4_3_47FAA | SS |
| BACTEROIDES_SP_9_1_42FAA | NSS |
| BACTEROIDES_SP_D1 | N |
| BACTEROIDES_SP_D2 | N |
| BACTEROIDES_SP_D20 | SN |
| BACTEROIDES_STERCORIS | N |
| BACTEROIDES_THETAIOTAOMICRON | SN |
| BACTEROIDES_UNIFORMIS | NS |
| BACTEROIDES_VULGATUS | SN |
| CAND_AZOBACTEROIDES | H |
| CHIT_PINENSIS | IA |
| DYAD_FERMENTANS | AA |
| MICR_MARINA | AAA |
| PARA_DISTASONIS | NT |
| PARA_JOHNSONII | NSS |
| PARA_SP_D13 | TN |
| PEDO_HEPARINUS | A |
| PEDO_SP_BAL39 | A |
| PORPHYROMONAS_ENDODONTALIS | N |
| PORPHYROMONAS_GINGIVALIS | N |
| PORPHYROMONAS_UENONIS | N |
| PREVOTELLA_BERGENSIS | N |
| PREVOTELLA_BIVIA | N |
| PREVOTELLA_BUCCAE | N |
| PREVOTELLA_BUCCALIS | N |
| PREVOTELLA_COPRI | N |
| PREVOTELLA_MELANINOGENICA | N |
| PREVOTELLAORIS | N |
| PREVOTELLA_RUMINICOLA | N |
| PREVOTELLA_SP_F0039 | NF |
| PREVOTELLA_SP_F0108 | N |
| PREVOTELLA_SP_F0295 | N |
| PREVOTELLA_TANNERAE | N |
| PREVOTELLA_TIMONENSIS | N |
| PREVOTELLA_VERORALIS | N |
| RHOD_MARINUS | AL |
| SALINIBACTER_RUBER | L |
| SPHINGOBACTERIUM_SPIRITIVORUM | LA |
| SPIROSOMA_LINGUALE | AA |

Fig. 5H

BROAD SPECTRUM ANTIBIOTIC ARYLOMYCIN ANALOGS

PRIORITY CLAIM TO RELATED APPLICATIONS

This application is a national stage application under 35 U.S.C. § 371 of PCT/US2011/049967, filed Aug. 31, 2011, and published as WO 2012/036907 A2on Mar. 22, 2012, which claims priority to U.S. Provisional Application No. 61/382,988, filed Sep. 15, 2010, which applications and publication are incorporated by reference as if reproduced herein and made a part hereof in their entirety, and the benefit of priority of each of which is claimed herein.

STATEMENT OF GOVERNMENT SUPPORT

This application was made with governmental support under N00014-03-1-0126and N00014-08-1-0478 awarded by the Office of Naval Research and A1081126 awarded by the National Institutes of Health. The U.S. government has certain rights in the invention.

BACKGROUND

The arylomycin class of natural product, which includes the arylomycin A and B series, was initially discovered by the group of Hans-Peter Frielder, and described in a 2002 publication in the Journal of Antibiotics (J. Schimana, et al., *J. Antibiotics* (2002), 55(6), 565-570 and 571-577). The arylomycins, as characterized in this publication, comprise a unique structural class of natural product composed of a hexapeptide with a unique biaryl bridge between N-methyl-4-hydroxyphenylglycine–5 (MeHpg5) and tyrosine-7, and N-terminal acyl tails of various lengths. See FIG. 1 showing the structures of natural products of the arylomycin A and B classes as determined by the Frielder group.

The initial report describing the arylomycins provided data describing the antibiotic activity of these compounds again the soil bacteria, *Arthrobacter globiformis* DSM20124, *Arthrobacter oxygans* DSM 6612, *Arthrobacter pascens* DSM 20545, *Rhodococcus erythropolis* DSM 1069 (currently characterized *Rhodococcus opacus*), *Streptomyces viridochromogenes* Tu 57, and *Brevibacillus brevis* DSM 30, and against the fungus *Mucor hiemalis* Tu 179/180. The data appear to suggest and the authors conclude that the arylomycins have limited to no activity against the examined bacteria with the exception of *Rhodococcus opacus* and *Brevibacillus brevis*. Furthermore while no data is provided, the authors state that no the arylomycin lack activity against the Gram-negative bacteria *Escherichia coli* K12, *Proteus mirabilis* ATCC 35501, *Pseudomonas fluorescens* DSM 50090 and against the eukaryotic organisms *Saccharomyces cerevisiae* ATCC 9080, *Botrytis cinerea* Tu 157 and against the green algae *Chlorella fusca* and against the duckweed *Lemna minor.*

In 2004 Kulanthaivel, et al., independently discovered a subclass of the arylomycins, the lipoglycopeptides, which differ from the arylomycin A and B series via glycosylation and aromatic hydroxylation of the hydroxyphenylglycine residue as well as in the length of the N-terminal acyl tail. Kinetic evidence was provided to support the conclusion that the lipoglycopepetides inhibit the essential bacterial enzyme type I signal peptidase in vitro. However, most active members of the lipoglycopeptides displayed only moderate whole cell activity against the human pathogen *Streptococcus pnemoniae* R6, and extremely little to no activity against the human pathogens *Staphylococcus aureus* ATCC13709, *Haemophilus influenzae* ATCC49247, and *Escherichia coli* K12. Furthermore the intrinsic resistance of *E. coli* K12 to the lipoglycopeptide subclass of arylomycins was attributed to outer membrane penetrance of drug efflux based on genetic data, suggesting that the arylomycins are not suitable as antimicrobial agents against Gram-negative bacteria. See U.S. Pat. No. 6,951,840, issued Oct. 4, 2005; see also P. Kulanthaivel, et al., *J. Biol. Chem.* (2004), 279(35), 36250-36258.

The natural products as described by Frielder and Kulanthaivel are as shown in FIG. 1; the compounds termed "arylomycins" by Frielder's group, and the compounds termed "lipoglycopeptides" by the Lilly workers including Kulanthaivel.

A total synthesis of arylomycin A2 has been reported by the inventors herein, see T. Roberts, et al. (2007), *J. Am. Chem. Soc.* 129, 15830-15838.

SUMMARY

The present invention is directed to the use of analogs of the natural product arylomycin for the treatment of microbial infections, such as for the treatment of bacterial infections. In various embodiments, the invention provides classes and subclasses of chemical compounds structurally related to arylomycin for the treatment of bacterial infections. In various embodiments, the bacterial infections are resistant to treatment with the natural product arylomycin, but are susceptible to treatment with an arylomycin analog of the invention.

In various embodiments, the invention provides a compound of formula (I)

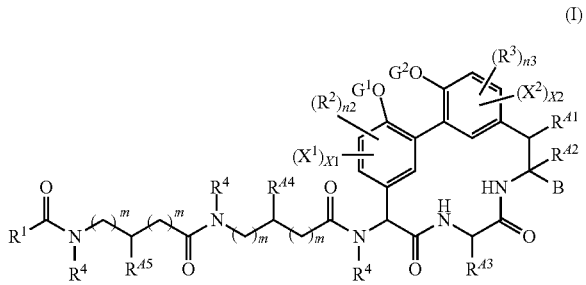

wherein

B is $CO_2H$, $CH_2CO_2H$, $C(=O)NHCH_2C(=O)H$, $CH_2C(=O)H$, $C(=O)NHCH_2B(OR^B)_2$ or $C(=O)NHCH_2P(=O)(OR^B)_2$ wherein $R^B$ is H or $(C_1-C_6)$alkyl, or B is a group of formula

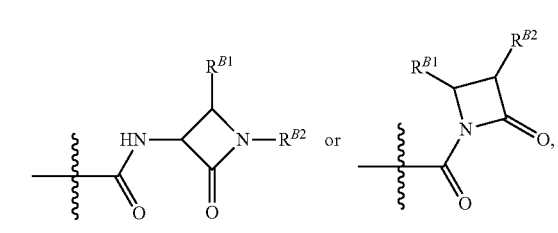

wherein $R^{B1}$ and $R^{B2}$ are each independently H, $(C_1-C_6)$ alkyl, $(C_3-C_6)$ cycloalkyl, $OR^C$, $C(=O)NR^C_2$, $OC(=O)NR^C_2$, $C(=O)OR^C$, $OC(=O)OR^C$, nitro, trifluoromethyl, trifluoromethoxy, $(C_1-C_6)$alkoxy, $(C_1-C_6)$thioalkoxy, $NR^C_2$, 5-7 membered heterocyclyl or 5-7 membered heteroaryl, or $(C_6-C_{10})$ aryl; $R^C$ is independently at each occurrence H or (C$_1$-C$_6$) alkyl, and a wavy line indicates a point of attachment of B to a carbon of formula (I) bearing B;

R$^1$ comprises a group of formula (IIA) or (IIB) or (IIC)

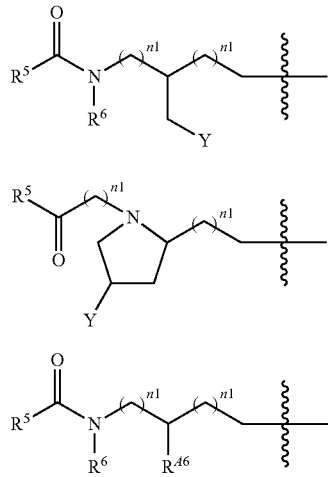

wherein each m is independently 0, 1, or 2, n1 is independently at each occurrence 0, 1, or 2; Y is (CH$_2$)$_{0-2}$H, (CH$_2$)$_{0-2}$OH, or (CH$_2$)$_{0-2}$OC(=O)(C$_1$-C$_6$)alkyl; R$^{46}$ is hydrogen, (C$_1$-C$_6$)alkyl, (C$_3$-C$_7$)cycloalkyl, 5- to 7-membered heteroaryl, 5- to 7-membered heterocyclyl, or (C$_6$-C$_{10}$) aryl, wherein any alkyl, cycloalkyl, heterocyclyl, aryl or heteroaryl may be substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, (C$_1$-C$_6$)alkoxy, (C$_1$-C$_6$)alkyl, (C$_3$-C$_7$)cycloalkyl, (C$_1$-C$_6$)-mono- or di-alkylamino, (C$_1$-C$_6$)alkoxycarbonyl, (C$_1$-C$_6$)alkylhydroxycarbonyl, (C$_1$-C$_6$) alkylaminocarbonyl, (C$_1$-C$_6$)alkylsulfonylamino, and (C$_6$-C$_{10}$)-arylsulfonylamino; and a wavy line indicates a point of attachment of R$^1$ to an atom of formula (I) bearing R$^1$; and R$^5$ is a linear or branched alkyl chain of about 1-22 carbon atoms, bonded to the carbonyl carbon to which it is attached directly or by an O or NR, to provide an amide, carbamate, or urea linkage respectively; optionally comprising within the chain or at a chain terminus, any of the following groups:

(A)

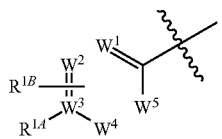

wherein W$^1$, W$^2$, W$^3$, W$^4$ and W$^5$ are each independently C or N, provided that no more than two of W$^1$, W$^2$, W$^3$, W$^4$ and W$^5$ are N; provided that when R$^{1A}$ or R$^{1B}$ is non-hydrogen, any W atom to which the R$^{1A}$ or R$^{1B}$ is respectively bonded is C, wherein there can be one or more R$^{1B}$ bonded to the ring bearing the W atoms; R$^{1A}$ is hydrogen, halogen, amino, hydroxyl, aminocarbonyl, hydroxycarbonyl, nitro, fluoroalkyl, cyano, (C$_1$-C$_6$)-thioether, fluoroalkoxy, (C$_1$-C$_6$)-alkyl, (C$_1$-C$_6$)-alkoxy, (C$_1$-C$_6$)-mono- or di-alkylamino, (C$_1$-C$_6$)-alkyl, 5- to 7-membered heteroaryl, 5- to 7-membered heterocyclyl, or (C$_6$-C$_{10}$) aryl; R$^{1B}$ is hydrogen, alkyl, halogen, amino, hydroxyl, aminocarbonyl, hydroxycarbonyl, nitro, fluoroalkyl, (C$_1$-C$_6$)-thioalkyl, fluoroalkoxy, cyano, (C$_1$-C$_6$)-alkyl, (C$_1$-C$_6$)-alkoxy, (C$_1$-C$_6$)-alkylamino, (C$_1$-C$_6$)-alkyl, 5- to 7-membered heteroaryl, 5- to 7-membered heterocyclyl, or (C$_6$-C$_{10}$) aryl; wherein any R$^{1A}$ or R$^{1B}$ can be further substituted with one to three (C$_1$-C$_{12}$)-alkyl or -alkoxy groups, which can further bear halogen, amino, hydroxyl, aminocarbonyl, hydroxycarbonyl, nitro, fluoroalkyl, (C$_1$-C$_6$)-thioalkyl, fluoroalkoxy, cyano, (C$_1$-C$_6$)-alkyl, (C$_1$-C$_6$)-alkoxy, (C$_1$-C$_6$)-alkylamino, (C$_1$-C$_6$)-alkyl, 5- to 7-membered heteroaryl, 5- to 7-membered heterocyclyl, or (C$_6$-C$_{10}$) aryl groups; wherein a wavy line indicates a point of attachment;

(B)

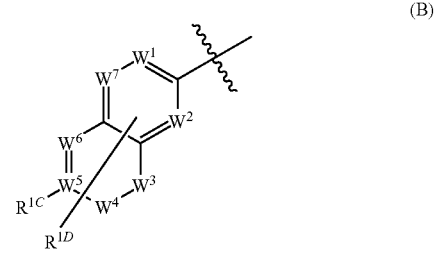

wherein W$^1$, W$^2$, W$^3$, W$^4$, W$^5$, W$^6$, and W$^7$ are each independently C or N, provided that no more than three of W$^1$, W$^2$, W$^3$, W$^4$, W$^5$, W$^6$, and W$^7$ are N; provided that when R$^{1C}$ or R$^{1D}$ is non-hydrogen, any W atom to which the R$^{1C}$ or R$^{1D}$ is respectively bonded is C, wherein either ring can bear one or more R$^{1D}$; R$^{1C}$ is hydrogen, halogen, amino, hydroxyl, aminocarbonyl, hydroxycarbonyl, nitro, fluoroalkyl, (C$_1$-C$_6$)-thioalkyl, fluoroalkoxy, cyano, (C$_1$-C$_6$)-alkyl, (C$_1$-C$_6$)-alkoxy, (C$_1$-C$_6$)-mono- or di-alkylamino, (C$_1$-C$_6$)-alkyl, 5- to 7-membered heteroaryl, 5- to 7-membered heterocyclyl, or (C$_6$-C$_{10}$) aryl; R$^{1D}$ is hydrogen, alkyl, halogen, amino, hydroxyl, aminocarbonyl, hydroxycarbonyl, nitro, fluoroalkyl, (C$_1$-C$_6$)-thioalkyl, fluoroalkoxy, cyano, (C$_1$-C$_6$)-alkyl, (C$_1$-C$_6$)-alkoxy, (C$_1$-C$_6$)-mono- or di-alkylamino, (C$_1$-C$_6$)-alkyl, 5- to 7-membered heteroaryl, 5- to 7-membered heterocyclyl, or (C$_6$-C$_{10}$) aryl; wherein any R$^{1C}$ or R$^{1D}$ can be further substituted with one to three (C$_1$-C$_{12}$)-alkyl or -alkoxy groups, which can further bear halogen, amino, hydroxyl, aminocarbonyl, hydroxycarbonyl, nitro, fluoroalkyl, (C$_1$-C$_6$) thioalkyl, fluoroalkoxy, cyano, (C$_1$-C$_6$)-alkyl, (C$_1$-C$_6$)-alkoxy, (C$_1$-C$_6$)-mono- or di-alkylamino, (C$_1$-C$_6$)-alkyl, 5- to 7-membered heteroaryl, 5- to 7-membered heterocyclyl, or (C$_6$-C$_{10}$) aryl; wherein a wavy line indicates a point of attachment;

(C)

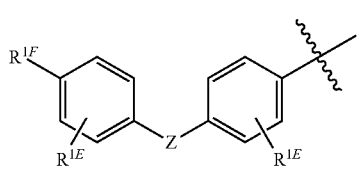

wherein Z is O, S, NH or CH$_2$; R$^{1E}$ at each occurrence is independently hydrogen, halogen, amino, hydroxyl, aminocarbonyl, hydroxycarbonyl, nitro, fluoroalkyl, (C$_1$-C$_6$)-thioalkyl, fluoroalkoxy, cyano, (C$_1$-C$_6$)-alkyl, (C$_1$-C$_6$)-alkoxy, (C$_1$-C$_6$)-mono- or di-alkylamino, (C$_1$-C$_6$)-alkyl, 5- to 7-membered heteroaryl, 5- to 7-membered heterocyclyl, or (C$_6$-C$_{10}$) aryl; R$^{1F}$ is hydrogen or alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein any $R^{1E}$ or $R^{1F}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$ thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein a wavy line indicates a point of attachment; or

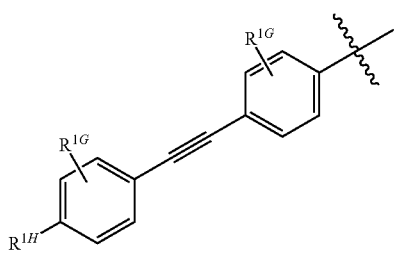

(D)

wherein $R^{1G}$ at each occurrence is independently hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; $R^{1H}$ is hydrogen or alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein any $R^{1G}$ or $R^{1H}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein a wavy line indicates a point of attachment;

$R^2$ and $R^3$ are each independently nitro, halo, cyano, hydroxy, glycosyloxy, amino, $(C_1-C_4)$alkoxy, $(C_1-C_4)$acyloxy, or $(C_1-C_4)$alkyl, wherein any carbon atom can be unsubstituted or substituted with J, wherein $n^2$ and $n^3$ are independently 0, 1, 2, or 3; or wherein two $R^2$ groups taken together, and/or two $R^3$ groups taken together, can comprise fused cycloalkyl, aryl, heterocyclyl, or heteroaryl ring or rings, any of which is substituted with 0-3 J;

$R^4$ and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl can be substituted with 1 to 3 J;

$R^{41}$, $R^{42}$, $R^{43}$, $R^{44}$, $R^{45}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl can be substituted with 1 to 3 J;

J is halogen, R', OR', CN, $CF_3$, $OCF_3$, O, S, C(O), S(O), methylenedioxy, ethylenedioxy, $(CH_2)_{0-p}N(R')_{0-9}$ $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)CH_2C(O)R'$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}OC(O)N(R')_2$, $(CH_2)_{0-p}C(S)N(R)_2$, $(CH_2)_{0-p}NH—C(O)R'$, $(CH_2)_{0-p}N(R')N(R')C(O)R'$, $(CH_2)_{0-p}N(R')N(R')C(O)OR'$, $(CH_2)_{0-p}N(R')N(R')CON(R')_2$, $(CH_2)_{0-p}N(R')SO_2R$, $(C^H_2)_{0-p}N(R')SO_2N(R)_2$, $(CH_2)_{0-p}N(R')C(O)OR'$, $(CH_2)_{0-p}N(R)C(O)R_9N(R)_2$, $(CH_2)_{0-p}N(R')C(S)R'$, $(CH_2)_{0-p}N(R)C(O)N(R)_2$, $(CH_2)_{0-p}N(R)C(S)N(R)_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$; wherein p is about 4, each R' is independently at each occurrence hydrogen, $(C_1-C_{12})$-alkyl, $(C_2-C_{12})$-alkenyl, $(C_2-C_{12})$-alkynyl, $(C_3-C_{10})$-cycloalkyl, $(C_3-C_{10})$-cycloalkenyl, $[(C_3-C_{10})$cycloalkyl or $(C_3-C_{10})$-cycloalkenyl]-[$(C_1-C_{12})$-alkyl or $(C_2-C_{12})$-alkenyl or $(C_2-C_{12})$-alkynyl], $(C_6-C_{10})$-aryl, $(C_6-C_{10})$-aryl-[$(C_1-C_{12})$-alkyl or $(C_2-C_{12})$-alkenyl or $(C_2-C_{12})$-alkynyl], mono- or bicyclic 3-10 membered heterocyclyl, mono- or bicyclic 3-10 membered heterocyclyl-[$(C_1-C_{12})$-alkyl or $(C_2-C_{12})$-alkenyl or $(C_2-C_{12})$-alkynyl], mono- or bicyclic 5-10 membered heteroaryl, or mono- or bicyclic 5-10 membered heteroaryl-[$(C_1-C_{12})$-alkyl or $(C_2-C_{12})$-alkenyl or $(C_2-C_{12})$-alkynyl], wherein R' is substituted with 0-3 substituents selected independently from J;

or, when two R' are bound to a nitrogen atom or to two adjacent nitrogen atoms, the two R' groups together with the nitrogen atom or atoms to which they are bound can form a 3- to 8-membered monocyclic heterocyclic ring, or an 8- to 20-membered, bicyclic or tricyclic, heterocyclic ring system, wherein any ring or ring system can further contain 1-3 additional heteroatoms selected from the group consisting of N, NR', O, S, S(O) and $S(O)_2$, wherein each ring is substituted with 0-3 substituents selected independently from J;

wherein, in any bicyclic or tricyclic ring system, each ring is linearly fused, bridged, or spirocyclic, wherein each ring is either aromatic or nonaromatic, wherein each ring can be fused to a $(C_6-C_{10})$aryl, mono- or bicyclic 5-10 membered heteroaryl, $(C_3-C_{10})$cycloalkyl or mono- or bicyclic 3-10 membered heterocyclyl;

$G^1$ and $G^2$ are each independently a hydrogen or a glycosyl residue, or a group cleavable under physiological conditions to provide a compound of formula (I) wherein $G^1$ or $G^2$ respectively is hydrogen;

$(X^1)_{X1}$ and $(X^2)_{X2}$ each signify that 0, 1, or 2 ring atoms of each respective ring can be nitrogen, provided that where a non-hydrogen substituent is bonded, $X^1$ or $X^2$, respectively, is C;

provided that when $G^1$ is a 6-deoxyhexopyranosyl residue, $G^2$ is H, $R^1$ is of formula (IIA), $R^2$ is hydrogen or hydroxy, $R^3$ is hydrogen, $R^{41}$ and $R^{42}$ and $R^{44}$ are H, $R^{43}$ and $R^{45}$ are methyl, and B is $CO_2H$, or when $G^1$ and $G^2$ are H, $R^1$ is of formula (IIA), $R^2$ is hydrogen, $R^3$ is hydrogen or nitro, $R^{41}$ and $R^{42}$ and $R^{44}$ are H, $R^{43}$ and $R^{45}$ are methyl, and B is $CO_2H$, then $R^5$ is not unsubstituted $(C_{10}-C_{16})$-alkyl;

or a salt thereof.

In various embodiments, the present invention relates to the use of arylomycins to treat a microbial or bacterial infection caused by a microbe (e.g., a bacterium) that encodes a type I signal peptidase bearing a specific amino acid sequence signature. In addition, in various embodiments, the present invention relates to the use of arylomycin to treat indications known to be caused predominantly by bacteria that encoded type I signal peptidases bearing a specific amino acid sequence signature.

In various embodiments, the invention is direct to the use of genetically modified organisms harboring mutations in the type I bacterial signal peptidase enzyme to screen for or to characterize the activity of type I signal peptidase inhibitors such as arylomycin analogs of the invention. In various embodiments, the invention provides methods for the use of genetically altered recombinant forms of bacterial signal peptidase protein, in which specific residues have been mutated, to screen for or characterize the activity of type I signal peptidase inhibitors, such as arylomycin analogs of the invention.

BRIEF DESCRIPTION OF THE FIGURES

FIG. 3 shows some of the physical and biochemical evidence for a mechanism of arylomycin resistance.

FIGS. 5A through 5H is a list of organisms that lack a proline residue at positions −5 and/or −7 (N-terminal) to the active site serine of the SPase encoded in their genome.

DETAILED DESCRIPTION

Definitions

Figure 1:
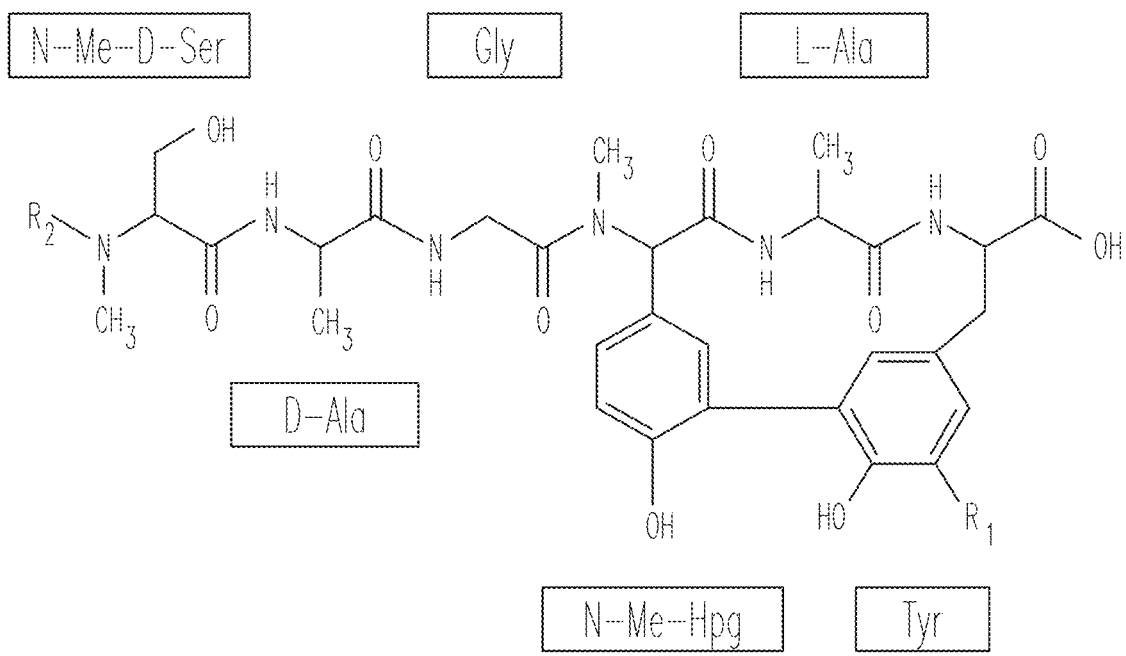
FIG. 1 shows the structures of arylomycins A and B, natural products, as characterized in J. Schimana, et al., *J. Antibiotics* (2002), 55(6), 565-570). $R^1$ refers to a substituent on the tyrosine residue, and $R^2$ refers to an acyl group of the indicated number of carbon atoms bonded to the N-methylserine nitrogen atom.

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein, "individual" (as in the subject of the treatment) means both mammals and non-mammals. Mammals include, for example, humans; non-human primates, e.g. apes and monkeys; and non-primates, e.g. dogs, cats, cattle, horses, sheep, and goats. Non-mammals include, for example, fish and birds.

The term "disease" or "disorder" or "malcondition" are used interchangeably, and are used to refer to diseases or conditions wherein a bacterial SPase plays a role in the biochemical mechanisms involved in the disease or malcondition such that a therapeutically beneficial effect can be achieved by acting on the enzyme. "Acting on" SPase can include binding to SPase and/or inhibiting the bioactivity of an SPase.

The expression "effective amount", when used to describe therapy to an individual suffering from a disorder, refers to the amount of a compound of the invention that is effective to inhibit or otherwise act on SPase in the individual's tissues wherein SPase involved in the disorder is active, wherein such inhibition or other action occurs to an extent sufficient to produce a beneficial therapeutic effect.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

"Treating" or "treatment" within the meaning herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result. A therapeutically effective amount is also one in which any toxic or detrimental effects of compounds of the invention are outweighed by the therapeutically beneficial effects.

By "chemically feasible" is meant a bonding arrangement or a compound where the generally understood rules of organic structure are not violated; for example a structure within a definition of a claim that would contain in certain situations a pentavalent carbon atom that would not exist in nature would be understood to not be within the claim. The structures disclosed herein, in all of their embodiments are intended to include only "chemically feasible" structures, and any recited structures that are not chemically feasible, for example in a structure shown with variable atoms or groups, are not intended to be disclosed or claimed herein.

When a substituent is specified to be an atom or atoms of specified identity, "or a bond", a configuration is referred to when the substituent is "a bond" that the groups that are immediately adjacent to the specified substituent are directly connected to each other in a chemically feasible bonding configuration.

All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be isolated or synthesized so as to be substantially free of their enantiomeric or diastereomeric partners, and these are all within the scope of the invention.

The inclusion of an isotopic form of one or more atoms in a molecule that is different from the naturally occurring isotopic distribution of the atom in nature is referred to as an "isotopically labeled form" of the molecule. All isotopic forms of atoms are included as options in the composition of any molecule, unless a specific isotopic form of an atom is indicated. For example, any hydrogen atom or set thereof in a molecule can be any of the isotopic forms of hydrogen, i.e., protium ($^1$H), deuterium ($^2$H), or tritium ($^3$H) in any combination. Similarly, any carbon atom or set thereof in a molecule can be any of the isotopic form of carbons, such as $^{11}$C, $^{12}$C, $^{13}$C, or $^{14}$C, or any nitrogen atom or set thereof in a molecule can be any of the isotopic forms of nitrogen, such as $^{13}$N, $^{14}$N, or $^{15}$N. A molecule can include any combination of isotopic forms in the component atoms making up the molecule, the isotopic form of every atom forming the molecule being independently selected. In a multi-molecular sample of a compound, not every individual molecule necessarily has the same isotopic composition. For example, a sample of a compound can include molecules containing various different isotopic compositions, such as in a tritium or $^{14}$C radiolabeled sample where only some fraction of the set of molecules making up the macroscopic sample contains a radioactive atom. It is also understood that many elements that are not artificially isotopically enriched themselves are mixtures of naturally occurring isotopic forms, such as $^{14}$N and $^{15}$N, $^{32}$S and $^{34}$S, and so forth. A molecule as recited herein is defined as including isotopic forms of all its constituent elements at each position in the molecule. As is well known in the art, isotopically labeled compounds can be prepared by the usual methods of chemical synthesis, except substituting an isotopically labeled precursor molecule. The isotopes, radiolabeled or stable, can be obtained by any method known in the art, such as generation by neutron absorption of a precursor nuclide in a nuclear reactor, by cyclotron reactions, or by isotopic separation such as by mass spectrometry. The isotopic forms are incorporated into precursors as required for use in any particular synthetic route. For example, $^{14}$C and $^3$H can be prepared using neutrons generated in a nuclear reactor. Following nuclear transformation, $^{14}$C and $^3$H are incorporated into precursor molecules, followed by further elaboration as needed.

The term "amino protecting group" or "N-protected" as used herein refers to those groups intended to protect an amino group against undesirable reactions during synthetic procedures and which can later be removed to reveal the amine. Commonly used amino protecting groups are disclosed in Protective Groups in Organic Synthesis, Greene, T. W.; Wuts, P. G. M., John Wiley & Sons, New York, N.Y., (3rd Edition, 1999). Amino protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; alkoxy- or aryloxy-carbonyl groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzylhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like Amine protecting groups also include cyclic amino protecting groups such as phthaloyl and dithiosuccinimidyl, which incorporate the amino nitrogen into a heterocycle. Typically, amino protecting groups include formyl, acetyl, benzoyl, pivaloyl, t-butylacetyl, phenylsulfonyl, Alloc, Teoc, benzyl, Fmoc, Boc and Cbz. It is well within the skill of the ordinary artisan to select and use the appropriate amino protecting group for the synthetic task at hand.

The term "hydroxyl protecting group" or "O-protected" as used herein refers to those groups intended to protect an OH group against undesirable reactions during synthetic procedures and which can later be removed to reveal the amine. Commonly used hydroxyl protecting groups are disclosed in Protective Groups in Organic Synthesis, Greene, T. W.; Wuts, P. G. M., John Wiley & Sons, New York, N.Y., (3rd Edition, 1999). Hydroxyl protecting groups include acyl groups such as formyl, acetyl, propionyl, pivaloyl, t-butylacetyl, 2-chloroacetyl, 2-bromoacetyl, trifluoroacetyl, trichloroacetyl, o-nitrophenoxyacetyl, α-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; acyloxy groups (which form urethanes with the protected amine) such as benzyloxycarbonyl (Cbz), p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzylhydryloxycarbonyl, t-butyloxycarbonyl (Boc), diisopropylmethoxycarbonyl, isopropyloxycarbonyl, ethoxycarbonyl, methoxycarbonyl, allyloxycarbonyl (Alloc), 2,2,2-trichloroethoxycarbonyl, 2-trimethylsilylethyloxycarbonyl (Teoc), phenoxycarbonyl, 4-nitrophenoxycarbonyl, fluorenyl-9-methoxycarbonyl (Fmoc), cyclopentyloxycarbonyl, adamantyloxycarbonyl, cyclohexyloxycarbonyl, phenylthiocarbonyl and the like; aralkyl groups such as benzyl, triphenylmethyl, benzyloxymethyl and the like; and silyl groups such as trimethylsilyl and the like. It is well within the skill of the ordinary artisan to select and use the appropriate hydroxyl protecting group for the synthetic task at hand.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, NO, NO$_2$, ONO$_2$, azido, CF$_3$, OCF$_3$, R', O (oxo), S (thiono), C(O), S(O), methylenedioxy, ethylenedioxy, N(R')$_2$, SR', SOW, SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_{0-2}$N(R')C(O)R', (CH$_2$)$_{0-2}$N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

When a substituent is monovalent, such as, for example, F or Cl, it is bonded to the atom it is substituting by a single bond. When a substituent is more than monovalent, such as O, which is divalent, it can be bonded to the atom it is substituting by more than one bond, i.e., a divalent substituent is bonded by a double bond; for example, a C substituted with O forms a carbonyl group, C=O, which can also be written as "CO", "C(O)", or "C(=O)", wherein the C and the O are double bonded. When a carbon atom is substituted with a double-bonded oxygen (=O) group, the oxygen substituent is termed an "oxo" group. When a divalent substituent such as NR is double-bonded to a carbon atom, the resulting C(=NR) group is termed an "imino" group. When a divalent substituent such as S is double-bonded to a carbon atom, the results C(=S) group is termed a "thiocarbonyl" group.

Alternatively, a divalent substituent such as O, S, C(O), S(O), or S(O)$_2$ can be connected by two single bonds to two different carbon atoms. For example, O, a divalent substituent, can be bonded to each of two adjacent carbon atoms to provide an epoxide group, or the O can form a bridging ether group, termed an "oxy" group, between adjacent or non-adjacent carbon atoms, for example bridging the 1,4-carbons of a cyclohexyl group to form a [2.2.1]-oxabicyclo system. Further, any substituent can be bonded to a carbon or other atom by a linker, such as (CH$_2$)$_n$ or (CH$_2$)$_n$ wherein n is 1, 2, 3, or more, and each R' is independently selected.

C(O) and S(O)$_2$ groups can be bound to one or two heteroatoms, such as nitrogen, rather than to a carbon atom. For example, when a C(O) group is bound to one carbon and one nitrogen atom, the resulting group is called an "amide" or "carboxamide." When a C(O) group is bound to two nitrogen atoms, the functional group is termed a urea. When a S(O)$_2$ group is bound to one carbon and one nitrogen atom, the resulting unit is termed a "sulfonamide." When a S(O)$_2$ group is bound to two nitrogen atoms, the resulting unit is termed a "sulfamate."

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups can also be substituted with alkyl, alkenyl, and alkynyl groups as defined herein.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

As to any of the groups described herein, which contain one or more substituents, it is understood, of course, that such groups do not contain any substitution or substitution patterns which are sterically impractical and/or synthetically non-feasible. In addition, the compounds of this disclosed subject matter include all stereochemical isomers arising from the substitution of these compounds.

Selected substituents within the compounds described herein are present to a recursive degree. In this context, "recursive substituent" means that a substituent may recite another instance of itself or of another substituent that itself recites the first substituent. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by of example and not limitation, physical properties such as molecular weight, solubility or log P, application properties such as activity against the intended target, and practical properties such as ease of synthesis.

Recursive substituents are an intended aspect of the disclosed subject matter. One of ordinary skill in the art of medicinal and organic chemistry understands the versatility of such substituents. To the degree that recursive substituents are present in a claim of the disclosed subject matter, the total number should be determined as set forth above.

Alkyl groups include straight chain and branched alkyl groups and cycloalkyl groups having from 1 to about 20 carbon atoms, and typically from 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, isobutyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed above, for example, amino, hydroxy, cyano, carboxy, nitro, thio, alkoxy, and halogen groups. A description herein that a group is alkyl chain "optionally comprising within the chain or at a chain terminus" a moiety, the term signifies that the moiety can be disposed between two subunits of the alkyl chain, or can be disposed at an unsubstituted end of the chain, or can be disposed between the chain and a point of attachment of the chain, for example to a carbonyl, NR, or O group. For example, an alkylbenzoyl group is an alkyl chain with a phenyl group disposed between the alkyl and a carbonyl, fitting the above description; an N-alkylphenylcarboxamido is an alkyl chain with a phenyl group disclosed between the alkyl and the aminocarbonyl group, filling within the above description.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The terms "carbocyclic," "carbocyclyl," and "carbocycle" denote a ring structure wherein the atoms of the ring are carbon, such as a cycloalkyl group or an aryl group. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N−1 substituents wherein N is the size of the carbocyclic ring with, for example, alkyl, alkenyl, alkynyl, amino, aryl, hydroxy, cyano, carboxy, heteroaryl, heterocyclyl, nitro, thio, alkoxy, and halogen groups, or other groups as are listed above. A carbocyclyl ring can be a cycloalkyl ring, a cycloalkenyl ring, or an aryl ring. A carbocyclyl can be monocyclic or polycyclic, and if polycyclic each ring can be independently be a cycloalkyl ring, a cycloalkenyl ring, or an aryl ring.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to vinyl, —CH═CH($CH_3$), —CH═C($CH_3$)$_2$, —C($CH_3$)═$CH_2$, —C($CH_3$)═CH($CH_3$), —C($CH_2CH_3$)═$CH_2$, cyclohexenyl, cyclopentenyl, cyclohexadienyl, butadienyl, pentadienyl, and hexadienyl among others.

Cycloalkenyl groups include cycloalkyl groups having at least one double bond between 2 carbons. Thus for example, cycloalkenyl groups include but are not limited to cyclohexenyl, cyclopentenyl, and cyclohexadienyl groups. Cycloalkenyl groups can have from 3 to about 8-12 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like, provided they include at least one double bond within a ring. Cycloalkenyl groups also include rings that are substituted with straight or branched chain alkyl groups as defined above.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C($CH_3$), —C≡C($CH_2CH_3$), —$CH_2$C≡CH, —$CH_2$C≡C($CH_3$), and —$CH_2$C≡C($CH_2CH_3$) among others.

The term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2CH_2$—OH, —$CH_2$—$CH_2$—NH—$CH_3$, —$CH_2$—S—$CH_2$—$CH_3$, —$CH_2CH_2$—S(═O)—$CH_3$, and —$CH_2CH_2$—O—$CH_2CH_2$—O—$CH_3$. Up to two heteroatoms may be consecutive, such as, for example, —$CH_2$—NH—$OCH_3$, or —$CH_2$—$CH_2$—S—S—$CH_3$.

A "cycloheteroalkyl" ring is a cycloalkyl ring containing at least one heteroatom. A cycloheteroalkyl ring can also be termed a "heterocyclyl," described below.

The term "heteroalkenyl" by itself or in combination with another term means, unless otherwise stated, a stable straight or branched chain monounsaturated or di-unsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH═CH—O—$CH_3$, —CH═CH—$CH_2$—OH, —$CH_2$—CH═N—$OCH_3$, —CH═CH—N($CH_3$)—$CH_3$, —$CH_2$—CH═CH—$CH_2$—SH, and —CH═CH—O—$CH_2CH_2$—O—$CH_3$.

Aryl groups are cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined above. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. Aralkenyl group are alkenyl groups as defined above in which a hydrogen or carbon bond of an alkyl group is replaced with a bond to an aryl group as defined above.

Heterocyclyl groups or the term "heterocyclyl" includes aromatic and non-aromatic ring compounds containing 3 or more ring members, of which, one or more is a heteroatom such as, but not limited to, N, O, and S. Thus a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms sums up to equal the total number of ring atoms. A heterocyclyl ring can also include one or more double bonds. A heteroaryl ring is an embodiment of a heterocyclyl group. The phrase "heterocyclyl group" includes fused ring species including those comprising fused aromatic and non-aromatic groups. For example, a dioxolanyl ring and a benzdioxolanyl ring system (methylenedioxyphenyl ring system) are both heterocyclyl groups within the meaning herein. The phrase also includes polycyclic ring systems containing a heteroatom such as, but not limited to, quinuclidyl. Heterocyclyl groups can be unsubstituted, or can be substituted as discussed above. Heterocyclyl groups include, but are not limited to, pyrrolidinyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Representative substituted heterocyclyl groups can be mono-substituted or substituted more than once, such as, but not limited to, piperidinyl or quinolinyl groups, which are 2-, 3-, 4-, 5-, or 6-substituted, or disubstituted with groups such as those listed above.

Heteroaryl groups are aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure. A heteroaryl group designated as a $C_2$-heteroaryl can be a 5-ring with two carbon atoms and three heteroatoms, a 6-ring with two carbon atoms and four heteroatoms and so forth. Likewise a $C_4$-heteroaryl can be a 5-ring with one heteroatom, a 6-ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heteroaryl groups can be unsubstituted, or can be substituted with groups as is discussed above. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group as defined above is replaced with a bond to a heterocyclyl group as defined above. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

Heteroarylalkyl groups are alkyl groups as defined above in which a hydrogen or carbon bond of an alkyl group is replaced with a bond to a heteroaryl group as defined above.

The term "alkoxy" refers to an oxygen atom connected to an alkyl group, including a cycloalkyl group, as are defined above. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structures are substituted therewith.

The terms "halo" or "halogen" or "halide" by themselves or as part of another substituent mean, unless otherwise stated, a fluorine, chlorine, bromine, or iodine atom, preferably, fluorine, chlorine, or bromine A "haloalkyl" group includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

A "haloalkoxy" group includes mono-halo alkoxy groups, poly-halo alkoxy groups wherein all halo atoms can be the same or different, and per-halo alkoxy groups, wherein all hydrogen atoms are replaced by halogen atoms, such as fluoro. Examples of haloalkoxy include trifluoromethoxy, 1,1-dichloroethoxy, 1,2-dichloroethoxy, 1,3-dibromo-3,3-difluoropropoxy, perfluorobutoxy, and the like.

The term "$(C_x$-$C_y)$perfluoroalkyl," wherein x<y, means an alkyl group with a minimum of x carbon atoms and a maximum of y carbon atoms, wherein all hydrogen atoms are replaced by fluorine atoms. Preferred is —$(C_1$-$C_6)$perfluoroalkyl, more preferred is —$(C_1$-$C_3)$perfluoroalkyl, most preferred is —$CF_3$.

The term "$(C_x$-$C_y)$perfluoroalkylene," wherein x<y, means an alkyl group with a minimum of x carbon atoms and a maximum of y carbon atoms, wherein all hydrogen atoms are replaced by fluorine atoms. Preferred is —$(C_1$-$C_6)$perfluoroalkylene, more preferred is —$(C_1$-$C_3)$perfluoroalkylene, most preferred is —$CF_2$—.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary or quaternary amino group. An "alkylamino" group includes a monoalkylamino, dialkylamino, and trialkylamino group.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —$C(O)NR_2$, and —NRC(O)R groups, respectively. Amide groups therefore include but are not limited to primary carboxamide groups (—$C(O)NH_2$) and formamide groups (—NHC(O)H). A "carboxamido" group is a group of the formula $C(O)NR_2$, wherein R can be H, alkyl, aryl, etc.

The term "azido" refers to an $N_3$ group. An "azide" can be an organic azide or can be a salt of the azide ($N_3^-$) anion. The term "nitro" refers to an $NO_2$ group bonded to an organic moiety. The term "nitroso" refers to an NO group bonded to an organic moiety. The term nitrate refers to an $ONO_2$ group bonded to an organic moiety or to a salt of the nitrate ($NO_3^-$) anion.

The term "urethane" ("carbamoyl" or "carbamyl") includes N- and O-urethane groups, i.e., —NRC(O)OR and —$OC(O)NR_2$ groups, respectively.

The term "sulfonamide" (or "sulfonamido") includes S- and N-sulfonamide groups, i.e., —$SO_2NR_2$ and —$NRSO_2R$ groups, respectively. Sulfonamide groups therefore include but are not limited to sulfamoyl groups (—$SO_2NH_2$). An organosulfur structure represented by the formula —S(O)(NR)— is understood to refer to a sulfoximine, wherein both the oxygen and the nitrogen atoms are bonded to the sulfur atom, which is also bonded to two carbon atoms.

The term "amidine" or "amidino" includes groups of the formula —$C(NR)NR_2$. Typically, an amidino group is —$C(NH)NH_2$.

The term "guanidine" or "guanidino" includes groups of the formula —$NRC(NR)NR_2$. Typically, a guanidino group is —$NHC(NH)NH_2$.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other than water replaces the water. For example, methanol or ethanol can form an "alcoholate", which can again be stoichiometic or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4.

In various embodiments, the compound or set of compounds, such as are used in the inventive methods, can be any one of any of the combinations and/or sub-combinations of the above-listed embodiments.

In various embodiments, a compound as shown in any of the Examples, or among the exemplary compounds, is provided. Provisos may apply to any of the disclosed categories or embodiments wherein any one or more of the other above disclosed embodiments or species may be excluded from such categories or embodiments.

The present invention further embraces isolated compounds according to formula (I). The expression "isolated compound" refers to a preparation of a compound of formula (I), or a mixture of compounds according to formula (I), wherein the isolated compound has been separated from the reagents used, and/or byproducts formed, in the synthesis of the compound or compounds. "Isolated" does not mean that the preparation is technically pure (homogeneous), but it is sufficiently pure to compound in a form in which it can be used therapeutically. Preferably an "isolated compound" refers to a preparation of a compound of formula (I) or a mixture of compounds according to formula (I), which contains the named compound or mixture of compounds according to formula (I) in an amount of at least 10 percent by weight of the total weight. Preferably the preparation contains the named compound or mixture of compounds in an amount of at least 50 percent by weight of the total weight; more preferably at least 80 percent by weight of the total weight; and most preferably at least 90 percent, at least 95 percent or at least 98 percent by weight of the total weight of the preparation.

The compounds of the invention and intermediates may be isolated from their reaction mixtures and purified by standard techniques such as filtration, liquid-liquid extraction, solid phase extraction, distillation, recrystallization or chromatography, including flash column chromatography, or HPLC.

Isomerism and Tautomerism in Compounds of the Invention

Tautomerism

Within the present invention it is to be understood that a compound of the formula (I) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. It is to be understood that the formulae drawings within this specification can represent only one of the possible tautomeric forms. However, it is also to be understood that the invention encompasses any tautomeric form, and is not to be limited merely to any one tautomeric form utilized within the formulae drawings. The formulae drawings within this specification can represent only one of the possible tautomeric forms and it is to be understood that the specification encompasses all possible tautomeric forms of the compounds drawn not just those forms which it has been convenient to show graphically herein. For example, tautomerism may be exhibited by a pyrazolyl group bonded as indicated by the wavy line. While both substituents would be termed a 4-pyrazolyl group, it is evident that a different nitrogen atom bears the hydrogen atom in each structure.

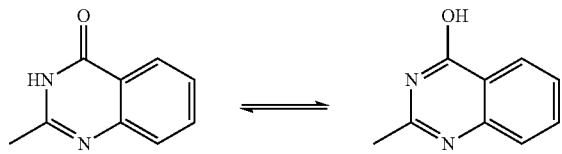

Such tautomerism can also occur with substituted pyrazoles such as 3-methyl, 5-methyl, or 3,5-dimethylpyrazoles, and the like. Another example of tautomerism is amido-imido (lactam-lactim when cyclic) tautomerism, such as is seen in heterocyclic compounds bearing a ring oxygen atom adjacent to a ring nitrogen atom. For example, the equilibrium:

is an example of tautomerism. Accordingly, a structure depicted herein as one tautomer is intended to also include the other tautomer.

Optical Isomerism

It will be understood that when compounds of the present invention contain one or more chiral centers, the compounds may exist in, and may be isolated as pure enantiomeric or diastereomeric forms or as racemic mixtures. The present invention therefore includes any possible enantiomers, diastereomers, racemates or mixtures thereof of the compounds of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. The priority of substituents is ranked based on atomic weights, a higher atomic weight, as determined by the systematic procedure, having a higher priority ranking. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the example in Scheme 14, the Cahn-Ingold-Prelog ranking is A>B>C>D. The lowest ranking atom, D is oriented away from the viewer.

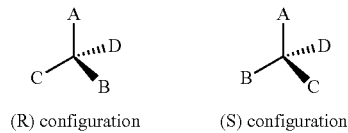

(R) configuration      (S) configuration

The present invention is meant to encompass diastereomers as well as their racemic and resolved, diastereomerically and enantiomerically pure forms and salts thereof. Diastereomeric pairs may be resolved by known separation techniques including normal and reverse phase chromatography, and crystallization.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Isolated optical isomers may be purified from racemic mixtures by well-known chiral separation techniques. According to one such method, a racemic mixture of a compound of the invention, or a chiral intermediate thereof, is separated into 99% wt. % pure optical isomers by HPLC using a suitable chiral column, such as a member of the series of DAICEL® CHIRALPAK® family of columns (Daicel Chemical Industries, Ltd., Tokyo, Japan). The column is operated according to the manufacturer's instructions.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species (see below). It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of formula (I) which are biologically active in the treatment of cancer or other proliferative disease states.

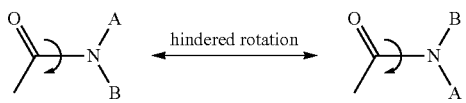

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

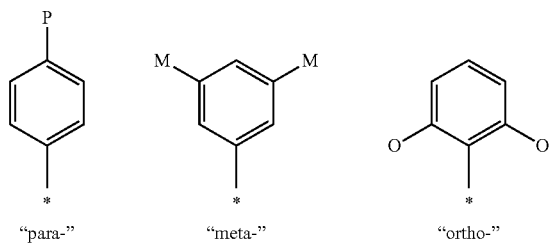

"para-"    "meta-"    "ortho-"

In various embodiments, the compound or set of compounds, such as are among the inventive compounds or are used in the inventive methods, can be any one of any of the combinations and/or sub-combinations of the above-listed embodiments.

DETAILED DESCRIPTION

The present invention, in various embodiments is directed to analogs of arylomycins A and B. By arylomycins A and B are meant, respectively, the natural products of the following structures:

The arylomycin A compounds bear a hydrogen atom in the $R_1$ position as defined in the above structure, and the arylomycin B compounds bear a nitro group in that position. The lipid tails, designated as group $R_2$ in the above structure, are n-alkyl, isoalkyl, and anteisoalkyl acyl groups with 11 to 15 total carbon atoms that form an amide bond with the N-Me-D-Ser residue. As used herein, the terms "arylomycins", "arylomycin A", "arylomycin B", "arylomycin $A_x$", "arylomycin natural products" and the like refer to these natural products, unless otherwise specified. The terms "arylomycin analogs", "arylomycin derivatives", "compounds of the invention", and the like, refer to the compounds disclosed herein that do not fit within the herein-defined structural classes of arylomycin A or arylomycin B. Compounds of the invention are distinct from the natural products as specified above.

In various embodiments, the arylomycin analogs of the invention, i.e., the novel structures disclosed and claimed herein, exhibit a broader spectrum of antibiotic activity, i.e., against a wider variety of bacterial species, than do the natural products termed arylomycins A and B.

The invention, in various embodiments, also provides methods of treatment of bacterial infections using the analogs of the invention, and using arylomycins A and B, such as against bacterial species or strains that would not be expected, based upon ordinary knowledge, to be susceptible to treatment with arylomycins A and B. In this context, the invention includes the use of the inventive arylomycin analogs and of the arylomycin A and B natural products in carrying out an inventive method as disclosed and claimed herein.

Compounds of the Invention

In various embodiments, the invention provides a compound of formula (I)

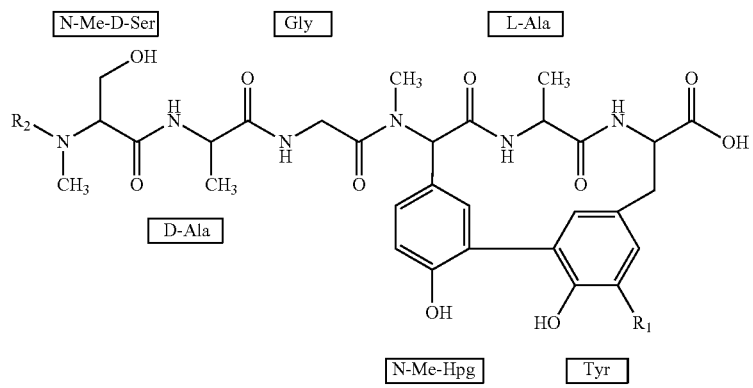

| Arylomycin | $R_1$ | $R_2$ |
|---|---|---|
| $A_1$ | H | iso-$C_{11}$ |
| $A_2$ | H | iso-$C_{12}$ |
| $A_3$ | H | n-$C_{12}$ |
| $A_4$ | H | anteiso-$C_{13}$ |
| $A_5$ | H | iso-$C_{14}$ |
| $B_1$ | $NO_2$ | iso-$C_{11}$ |
| $B_2$ | $NO_2$ | iso-$C_{12}$ |
| $B_3$ | $NO_2$ | n-$C_{12}$ |
| $B_4$ | $NO_2$ | anteiso-$C_{13}$ |
| $B_5$ | $NO_2$ | iso-$C_{13}$ |
| $B_6$ | $NO_2$ | iso-$C_{14}$ |
| $B_7$ | $NO_2$ | anteiso-$C_{13}$ |

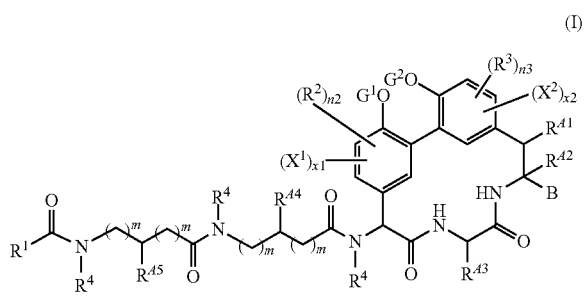

(I)

wherein

B is $CO_2H$, $CH_2CO_2H$, $C(=O)NHCH_2C(=O)H$, $CH_2C(=O)H$, $C(=O)NHCH_2B(OR^B)_2$ or $C(=O)NHCH_2P(=O)(OR^B)_2$ wherein $R^B$ is H or $(C_1-C_6)$alkyl, or B is a group of formula

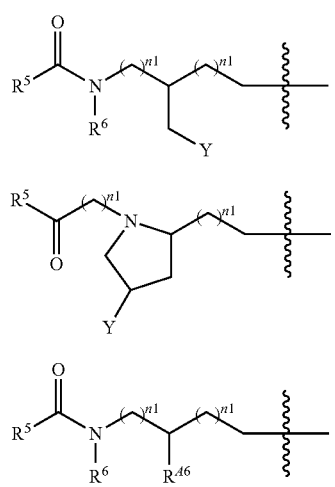

wherein $R^{B1}$ and $R^{B2}$ are each independently H, $(C_1-C_6)$ alkyl, $(C_3-C_6)$ cycloalkyl, $OR^C$, $C(=O)NR^C_2$, $OC(=O)NR^C_2$, $C(=O)OR^C$, $OC(=O)OR^C$, nitro, trifluoromethyl, trifluoromethoxy, $(C_1-C_6)$alkoxy, $(C_1-C_6)$thioalkoxy, $NR^C_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of B to a carbon of formula (I) bearing B;

$R^1$ comprises a group of formula (IIA) or (IIB) or (IIC)

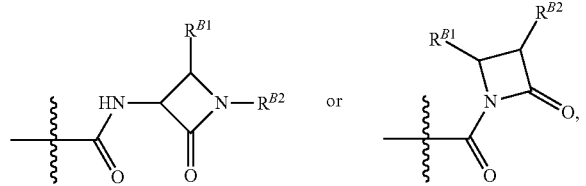

wherein each m is independently 0, 1, or 2, n1 is independently at each occurrence 0, 1, or 2; Y is $(CH_2)_{0-2}14$, $(CH_2)_{0-2}OH$, or $(CH_2)_{0-2}OC(=O)(C_1-C_6)$alkyl; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl may be substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (I) bearing $R^1$; and $R^5$ is a linear or branched alkyl chain of about 1-22 carbon atoms, bonded to the carbonyl carbon to which it is attached directly or by an O or NR, to provide an amide, carbamate, or urea linkage respectively; optionally comprising within the chain or at a chain terminus, any of the following groups:

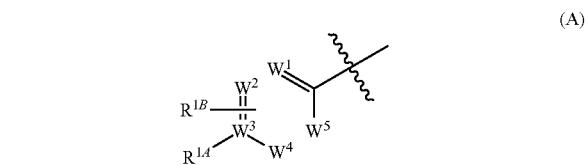

(A)

wherein $W^1$, $W^2$, $W^3$, $W^4$ and $W^5$ are each independently C or N, provided that no more than two of $W^1$, $W^2$, $W^3$, $W^4$ and $W^5$ are N; provided that when $R^{1A}$ or $R^{1B}$ is non-hydrogen, any W atom to which the $R^{1A}$ or $R^{1B}$ is respectively bonded is C, wherein there can be one or more $R^{1B}$ bonded to the ring bearing the W atoms; $R^{1A}$ is hydrogen, halogen, amino, hydroxyl, aminocarbonyl, hydroxycarbonyl, nitro, fluoroalkyl, cyano, $(C_1-C_6)$-thioether, fluoroalkoxy, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; $R^{1B}$ is hydrogen, alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-alkylamino, $(C_1-C_6)$-alkyl, 5- to 7-membered heteroaryl, 5- to 7-membered heterocyclyl, or $(C_6-C_{10})$ aryl; wherein any $R^{1A}$ or $R^{1B}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-alkylamino, $(C_1-C_6)$-alkyl, 5- to 7-membered heteroaryl, 5- to 7-membered heterocyclyl, or $(C_6-C_{10})$ aryl groups; wherein a wavy line indicates a point of attachment;

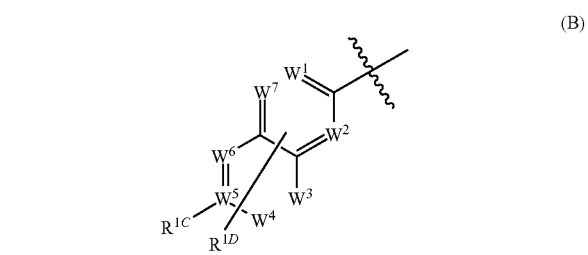

(B)

wherein $W^1$, $W^2$, $W^3$, $W^4$, $W^5$, $W^6$, and $W^7$ are each independently C or N, provided that no more than three of $W^1$, $W^2$, $W^3$, $W^4$, $W^5$, $W^6$, and $W^7$ are N; provided that when $R^{1C}$ or $R^{1D}$ is non-hydrogen, any W atom to which the $R^{1C}$ or $R^{1D}$ is respectively bonded is C, wherein either ring can bear one or more $R^{1D}$; $R^{1C}$ hydrogen, halogen, amino, hydroxyl, aminocarbonyl, hydroxycarbonyl, nitro, fluoroalkyl, $(C_1-C_6)$- thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; $R^{1D}$ is hydrogen, alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein any $R^{1C}$ or $R^{1D}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$ thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein a wavy line indicates a point of attachment;

(C)

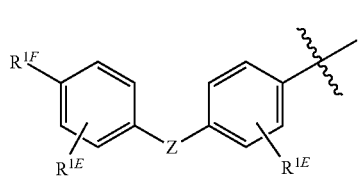

wherein Z is O, S, NH or $CH_2$; $R^E$ at each occurrence is independently hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; $R^{1F}$ is hydrogen or alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein any $R^{1E}$ or $R^{1F}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$ thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein a wavy line indicates a point of attachment; or (D)

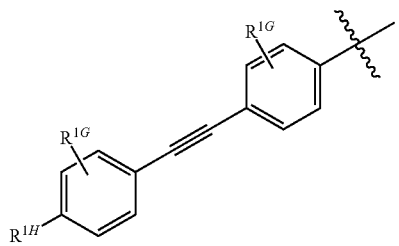

wherein $R^{1G}$ at each occurrence is independently hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; $R^{1H}$ is hydrogen or alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein any $R^{1G}$ or $R^{1H}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein a wavy line indicates a point of attachment;

$R^2$ and $R^3$ are each independently nitro, halo, cyano, hydroxy, glycosyloxy, amino, $(C_1-C_4)$alkoxy, $(C_1-C_4)$acyloxy, or $(C_1-C_4)$alkyl, wherein any carbon atom can be unsubstituted or substituted with J, wherein $n^2$ and $n^3$ are independently 0, 1, 2, or 3; or wherein two $R^2$ groups taken together, and/or two $R^3$ groups taken together, can comprise fused cycloalkyl, aryl, heterocyclyl, or heteroaryl ring or rings, any of which is substituted with 0-3 J;

$R^4$ and $R^6$ are each independently at every occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl can be substituted with 1 to 3 J;

$R^{A1}$, $R^{A2}$, $R^{A3}$, $R^{A4}$, $R^{A5}$ are independently at each occurrence hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl can be substituted with 1 to 3 J;

J is halogen, R', OR', CN, $CF_3$, $OCF_3$, O, S, C(O), S(O), methylenedioxy, ethylenedioxy, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)CH_2C(O)R'$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}OC(O)N(R')_2$, $(CH_2)_{0-p}C(S)N(R)_2$, $(CH_2)_{0-p}NH—C(O)R'$, $(CH_2)_{0-p}N(R')N(R')C(O)R'$, $(CH_2)_{0-p}N(R')N(R')C(O)OR'$, $(CH_2)_{0-p}N(R')N(R')CON(R')_2$, $(CH_2)_{0-p}N(R')SO_2R$, $(CH_2)_{0-p}N(R)SO_2N(R)_2m$ $(CH_2)_{0-p}N(R')C(O)OR'$, $(CH_2)_{0-p}N(R)C(O)R'$, $(CH_2)_{0-p}N(R')C(S)R'$, $(CH_2)_{0-p}N(R)C(O)N(R)_2$, $(CH_2)_{0-p}N(R)C(S)N(R)_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$; wherein p is about 4, each R' is independently at each occurrence hydrogen, $(C_1-C_{12})$-alkyl, $(C_2-C_{12})$-alkenyl, $(C_2-C_{12})$-alkynyl, $(C_3-C_{10})$-cycloalkyl, $(C_3-C_{10})$-cycloalkenyl, [$(C_3-C_{10})$cycloalkyl or $(C_3-C_{10})$-cycloalkenyl]-[$(C_1-C_{12})$-alkyl or $(C_2-C_{12})$-alkenyl or $(C_2-C_{12})$-alkynyl], $(C_6-C_{10})$-aryl, $(C_6-C_{10})$-aryl-[$(C_1-C_{12})$-alkyl or $(C_2-C_{12})$-alkenyl or $(C_2-C_{12})$-alkynyl], mono- or bicyclic 3-10 membered heterocyclyl, mono- or bicyclic 3-10 membered heterocyclyl-[$(C_1-C_{12})$-alkyl or $(C_2-C_{12})$-alkenyl or $(C_2-C_{12})$-alkynyl], mono- or bicyclic 5-10 membered heteroaryl, or mono- or bicyclic 5-10 membered heteroaryl-[$(C_1-C_{12})$-alkyl or $(C_2-C_{12})$-alkenyl or $(C_2-C_{12})$-alkynyl], wherein R' is substituted with 0-3 substituents selected independently from J;

or, when two R' are bound to a nitrogen atom or to two adjacent nitrogen atoms, the two R groups together with the nitrogen atom or atoms to which they are bound can form a 3- to 8-membered monocyclic heterocyclic ring, or an 8- to 20-membered, bicyclic or tricyclic, heterocyclic ring system, wherein any ring or ring system can further contain 1-3 additional heteroatoms selected from the group consisting of N, NR', O, S, S(O) and $S(O)_2$, wherein each ring is substituted with 0-3 substituents selected independently from J;

wherein, in any bicyclic or tricyclic ring system, each ring is linearly fused, bridged, or spirocyclic, wherein each ring is either aromatic or nonaromatic, wherein each ring can be fused to a ($C_6$-$C_{10}$)aryl, mono- or bicyclic 5-10 membered heteroaryl, ($C_3$-$C_{10}$)cycloalkyl or mono- or bicyclic 3-10 membered heterocyclyl;

$G^1$ and $G^2$ are each independently a hydrogen or a glycosyl residue, or a group cleavable under physiological conditions to provide a compound of formula (I) wherein $G^1$ or $G^2$ respectively is hydrogen;

$(X^1)_{X1}$ and $(X^2)_{X2}$ each signify that 0, 1, or 2 ring atoms of each respective ring can be nitrogen, provided that where a non-hydrogen substituent is bonded, $X^1$ or $X^2$, respectively, is C;

provided that when $G^1$ is a 6-deoxyhexopyranosyl residue, $G^2$ is H, $R^1$ is of formula (IIA), $R^2$ is hydrogen or hydroxy, $R^3$ is hydrogen, $R^{A1}$ and $R^{A2}$ and $R^{A4}$ are H, $R^{A3}$ and $R^{A5}$ are methyl, and B is $CO_2H$, or when $G^1$ and $G^2$ are H, $R^1$ is of formula (IIA), $R^2$ is hydrogen, $R^3$ is hydrogen or nitro, $R^{A1}$ and $R^{A2}$ and $R^{A4}$ are H, $R^{A3}$ and $R^{A5}$ are methyl, and B is $CO_2H$, then $R^5$ is not unsubstituted ($C_{10}$-$C_{16}$)-alkyl;

or a salt thereof.

In various embodiments, compounds of the invention can include atropisomeric forms due to hindered rotation about the phenyl-phenyl bond of the biphenyl (or bi-aryl or aryl-heteroaryl or bi-heteroaryl) moiety. In various embodiments, a compound of the invention can comprise the Sa atropisomer. Applicants have found that when the amide bond connecting the macrocycle to the tail is not methylated both atropisomers can be present and interconvert freely.

In various embodiments, the invention provides a compound of formula I of the invention wherein when $G^1$ is a H or a 6-deoxyhexopyranosyl residue, $G^2$ is H, $R^1$ is of formula (IIA), $R^2$ is hydrogen or hydroxy, $R^3$ is hydrogen or nitro, $R^{A1}$ and $R^{A2}$ and $R^{A4}$ are H, $R^{A3}$ and $R^{A5}$ are methyl, and B is $CO_2H$, then $R^5$ is not unsubstituted ($C_1$-$C_{22}$)alkyl.

In various embodiments, the invention provides a compound of the invention wherein the compound is of formula (IA)

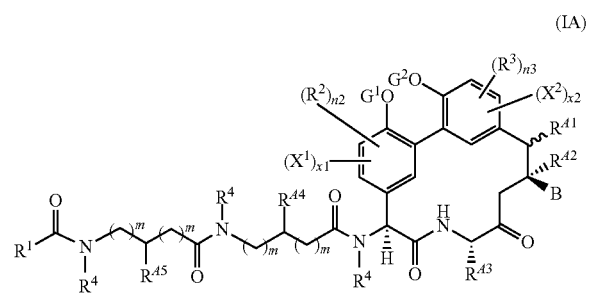

(IA)

wherein $R^1$, $R^2$, $R^3$, $R^4$, $R^5$, $R^6$, $R^{A1}$, $R^{A2}$, $R^{A3}$, $R^{A4}$, $R^{A5}$, $R^{A6}$, $R^B$, $R^{B1}$, $R^{B2}$, and $R^C$, and m, n, $n^1$, $n^2$, $n^3$, B, $G^1$, $G^2$, $(X^1)_{X1}$, $(X^2)_{X2}$, and Y, are as defined herein and a wavy line indicates a point of attachment of $R^1$ to an atom bonded to $R^1$ in formula (IA);

or a salt thereof.

In various embodiments, the invention provides a compound of the invention wherein $R^1$ is a group of formula (IIAS) or (IIBS)

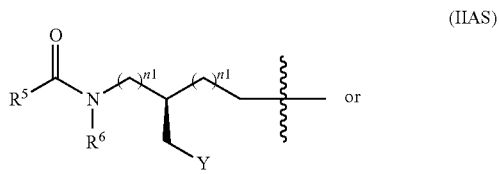

(IIAS)

(IIBS)

wherein $n^1$, $R^5$, $R^6$, and Y, are as defined herein and a wavy line indicates a point of attachment of $R^1$ to an atom bonded to $R^1$ in formula (I);

or a salt thereof.

In various embodiments, the invention provides a compound of the invention wherein $R^5$ is a ($C_1$-$C_{22}$) linear or branched alkyl.

In various embodiments, the invention provides a compound of the invention wherein $R^5$ is a ($C_1$-$C_{22}$) linear or branched alkyl comprising one or more of groups (A), (B), (C), or (D).

In various embodiments, the invention provides a compound of the invention wherein $R^5$ is a ($C_1$-$C_{22}$) linear or branched alkyl.

In various embodiments, the invention provides a compound of the invention wherein $R^5$ is a ($C_1$-$C_{22}$) linear or branched alkyl, comprising one or more of groups (A), (B), (C), or (D).

In various embodiments, the invention provides a compound of the invention wherein $R^5$ is any of the following groups

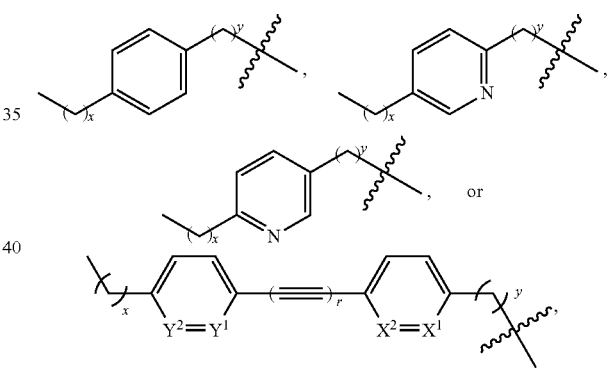

wherein x is 0-14, y is 0-14, provided that x+y≤22, and $X^1$, $X^2$, $Y^1$ and $Y^2$ are each independently C or N, provided that no more than one of $X^1$ and $X^2$, and no more than one of $Y^1$ and $Y^2$, is N, wherein a wavy line indicates a point of attachment of $R^5$ to an atom bonded to $R^5$ in formula (IIA), (IIB), or (IIC).

In various embodiments, the invention provides a compound of the invention wherein $R^5$ is any of the following: methyl, ethyl, ($C_3$-$C_{22}$)-n-alkyl, ($C_3$-$C_{22}$)-isoalkyl, ($C_4$-$C_{22}$)-anteisoalkyl, naphthyl, ($C_2$-$C_{10}$) naphthyl, naphthylmethyl, ($C_2$-$C_{10}$) naphthylmethyl, biphenyl, ($C_2$-$C_{10}$)alkylbiphenyl, biphenylmethyl, ($C_2$-$C_{10}$)alkylbiphenylmethyl, ($C_4$-$C_{12}$) phenyl, ($C_4$-$C_{12}$)benzyl, or ($C_2$-$C_{10}$)-1,2-diphenylethynyl, wherein a wavy line indicates a point of attachment of $R^5$ to an atom bonded to $R^5$ in formula (IIA), (IIB), or (IIC).

In various embodiments, the invention provides a compound of the invention wherein ring bearing one or more $X^1$ or $X^2$, respectively, is a phenyl, pyridyl, pyrazinyl, pyrimidyl, or pyridazinyl, optionally wherein $R^2$ and $R^3$ are both hydrogen.

In various embodiments, the invention provides a compound of the invention wherein at least one of $R^2$ and $R^3$ is hydrogen.

In various embodiments, the invention provides a compound of the invention wherein at least one of $R^2$ and $R^3$ is nitro, halo, hydroxy, glycosyloxy, amino, $(C_1-C_4)$alkoxy, or $(C_1-C_4)$alkyl, and $n^2$ or $n^3$ respectively, or both, is 1.

In various embodiments, the invention provides a compound of the invention wherein both G are hydrogen.

In various embodiments, the invention provides a compound of the invention wherein any of $R^{41}$, $R^{42}$ and $R^{44}$ are hydrogen, any of $R^{43}$ and $R^{45}$ are methyl, or any combination thereof.

In various embodiments, the invention provides a compound of the invention wherein $R^{43}$ is hydrogen, methyl, ethyl, n-propyl, isopropyl, n-butyl, isobutyl, 3-hydroxypropyl, 4-hydroxybutyl, or 2,2,2-trifluoroethyl.

In various embodiments, the invention provides a compound of the invention wherein all of $R^4$ and $R^6$ are independently selected hydrogen or methyl.

In various embodiments, the invention provides a compound of the invention wherein the compound is any of the following compounds of formula (III)

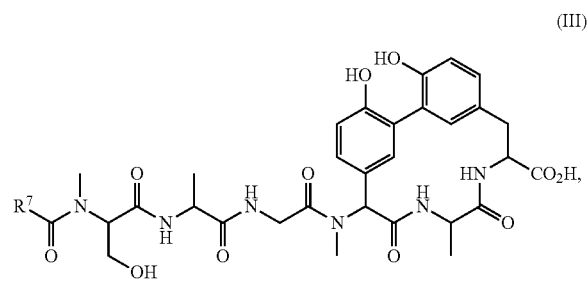

(III)

wherein $R^7$ is $(C_8-C_{18})$-n-alkyl, $(C_8-C_{18})$-isoalkyl, $(C_8-C_{18})$-anteisoalkyl, any of which includes a group (A), (B), (C), (D), or (E) of claim 1; or is 2-naphthyl, 6-$(C_2-C_{10})$-2-naphthyl, 2-naphthylmethyl, 6-$(C_2-C_{10})$-2-naphthylmethyl, 4-biphenyl, 4-biphenylmethyl, 4'-$(C_2-C_{10})$alkyl-4-biphenyl, 4'-$(C_2-C_{10})$alkyl-4-biphenylmethyl, p-$(C_4-C_{12})$phenyl, p-$(C_4-C_{12})$benzyl, or 4'-$(C_2-C_{10})$-1,2-diphenylethynyl;

or a salt thereof.

In various embodiments, the invention provides a compound of the invention wherein the compound is any of the following compounds of formula (IV)

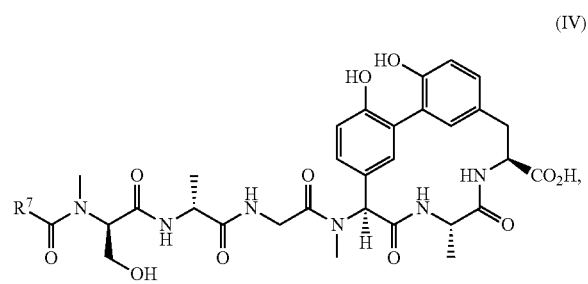

(IV)

herein $R^7$ is $(C_8-C_{18})$-n-alkyl, $(C_8-C_{18})$-isoalkyl, $(C_8-C_{18})$-anteisoalkyl, any of which includes a group (A), (B), (C), (D), or (E) of claim 1; or is 2-naphthyl, 6-$(C_2-C_{10})$-2-naphthyl, 2-naphthylmethyl, 6-$(C_2-C_{10})$-2-naphthylmethyl, 4-biphenyl, 4-biphenylmethyl, 4'-$(C_2-C_{10})$alkyl-4-biphenyl, 4'-$(C_2-C_{10})$alkyl-4-biphenylmethyl, p-$(C_4-C_{12})$phenyl, p-$(C_4-C_{12})$benzyl, or 4'-$(C_2-C_{10})$-1,2-diphenylethynyl;

or a salt thereof.

In various embodiments, the invention provides a compound comprising a hydrate, solvate, prodrug, or metabolite of a compound of the invention.

In various embodiments, the invention provides a pharmaceutical composition comprising the compound of the invention and a pharmaceutically acceptable excipient.

Methods of Treatment of Bacterial Infections Using Compounds of the Invention.

The evolution of bacteria that are resistant to multiple antibiotics poses a serious threat to human health.[1,2] Although much effort has been focused on the discovery and development of fully synthetic antibiotics,[3] most of the antibiotics used in the clinic were derived from natural products, which evolved over eons of time to penetrate bacteria, avoid efflux, and inhibit essential and highly conserved biochemical processes.[4] Unfortunately, broad-spectrum natural product antibiotics have become increasingly difficult to isolate and the more plentiful narrow-spectrum agents are limited either by unknown factors or by factors that are intrinsic to the compound, such as poor penetration or targeting proteins that are not sufficiently essential or conserved, and which are viewed as challenging to overcome by optimization.[3] In contrast, there is much precedent for re-optimizing antibiotics after their spectrum has been compromised by specific resistance mechanisms acquired during clinical use, as evidenced by the development of many "next generation" antibiotics.[5-8]

The arylomycins are a class of lipopeptide antibiotics that inhibit bacterial type I signal peptidase (SPase), an essential serine-lysine dyad protease that is anchored to the outer leaflet of the cytoplasmic membrane and that removes N-terminal signal peptides from proteins that are transported out of the cytoplasm.[9-11] Three related series of arylomycins have been identified, the arylomycins A and B and the lipoglycopeptides, which have similar core macrocycles, but different substituents and fatty acid tails (FIG. 1).[12,13] Based on their novel mechanism of action, there was originally much enthusiasm for these compounds, but despite their ability to inhibit SPase in vitro, and their in vivo activity against the soil bacteria Rhodococcus opacus and Brevibacillus brevis and the human pathogen Streptococcus pneumoniae, they were found to have no activity against a variety of other important human pathogens.[13,14] This apparently narrow spectrum is surprising considering that SPase is located on the outer leaflet of the cytoplasmic membrane and appears to be present and essential in all Eubacteria.[10,15-17] To explore the origins of their narrow spectrum, we synthesized and evaluated arylomycin $A_2$, as well as several derivatives, including arylomycin $C_{16}$ (FIG. 1).[18] Interestingly, we found that the arylomycins are as active against Staphylococcus epidermidis as the antibiotics used for its treatment, and importantly, we determined that S. epidermidis evolves resistance by introducing a Pro residue into SPase at position 29, which is located in the enzyme's P5 pocket. Remarkably, all bacteria that had been shown to be resistant to the arylomycins have a Pro at the corresponding position, and we identified a wide variety of bacteria that lack this residue and showed that the majority of them are sensitive to the arylomycins, including the Gram-positive pathogens Streptococcus pyogenes and Staphylococcus haemolyticus, and the Gram-negative pathogens Helicobacter pylori and Chlamydia trachomatis. Moreover, while the arylomycins slow the growth of Staphylococcus aureus strain 8325, they do not actually prevent it,[18] even at concentrations as high as 128 μg/ml, however, they do prevent the growth of USA300, an epidemic MRSA isolate, with an MIC of 16 μg/ml. While this might result from unique features associated with methicillin resistance, it suggests that the arylomycin scaffold has the potential for broader spectrum S. aureus activity. Importantly, we showed that the Pro residue imparts resistance by reducing the affinity with which the arylomycin binds, and that removing it is sufficient to render resistant *S. aureus*, *Escherichia coli*, and *Pseudomonas aeruginosa* highly sensitive. This data suggests that if the arylomycins could be optimized to bind SPases regardless of the resistance-conferring Pro, they would have a remarkably broad spectrum of activity.

Figure 3A:
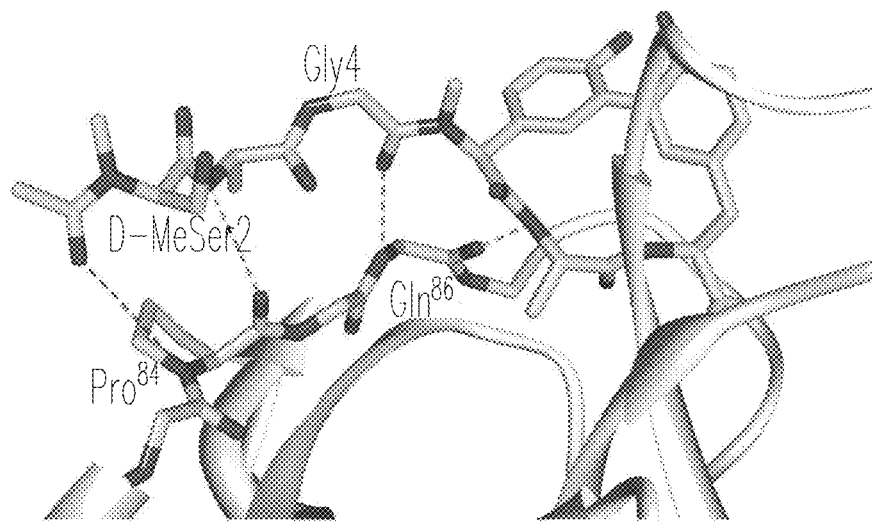
FIG. 3A shows the structure of crystalline *E. coli* SPase in complex with arylomycin A2 (PDB ID 1T7D) (see, Paetzel et al., J. Biol. Chem. 279, 30781-30790 (2004)). Hydrogen-bonds observed in the crystal structure are shown in green, while the potential hydrogen bond prevented by Pro84 is shown in red.

Despite not having activity against wild type *E. coli*, two crystal structures of arylomycin $A_2$ bound to a soluble fragment of *E. coli* SPase have been reported (FIG. 3A).[19,20] The arylomycin is seen to bind in an extended β-sheet conformation that likely mimics the binding of membrane bound preprotein substrates.[19] The C-terminal macrocycle of the arylomycin binds in a deep hydrophobic cleft and makes multiple hydrogen-bonds and hydrophobic interactions with the protein, while the C-terminal carboxyl group forms a critical salt bridge with the catalytic residues. The peptide tail extends down a shallow cleft in the surface of SPase and forms two hydrogen-bonds with backbone residues of the protein. The critical resistance-conferring residue, $Pro^{84}$, interacts with the N-terminal end of the peptidic tail and appears to preclude the formation of a hydrogen-bond to a carbonyl oxygen of the arylomycin and possibly to alter the trajectory of the lipid moiety as it enters the membrane (FIG. 3A). While the crystal structures are likely to reveal little information about the biologically relevant structure of the lipid tail due to the use of a soluble truncated fragment of SPase and the absence of a membrane bilayer, it most likely adopts an extended conformation to maximize packing within the outer leaflet of the cytoplasmic membrane.

As with a variety of other antibiotics with membrane-associated targets,[21-24] the lipopeptide tail of the arylomycins has been shown to play an important role in their activity.[13,14,21-24] Here, we report the first structure-activity relationship study of synthetic arylomycins, focusing on derivatives with altered lipopeptide tails. The activities of the arylomycin derivatives were evaluated with *S. epidermidis*, *S. aureus*, *E. coli*, and *P. aeruginosa*. With each pathogen, the derivatives were evaluated in the context of SPases with and without the critical resistance-conferring Pro, to identify the changes in activity that result from altered interactions with this resistance-conferring residue and to identify the types of modifications that might be pursued to overcome resistance and thereby instill the arylomycin scaffold with broad-spectrum antibacterial activity.

SPase and the N-terminal portion of its natural substrates are embedded within the bacterial cell membrane,[26,27] suggesting that some part of the inhibitor's lipopeptide tail must also be accommodated within the membrane. To probe this interaction, and also to determine whether a positive charge at the lipid-peptide junction of arylomycin is capable of interacting with the negatively charged head groups of the phospholipid bilayer, we synthesized a derivative of the formula shown (Compound 25 of Table 2B), wherein $R^1$ is H and $R^2$ (of FIG. 1) is a C16-n-alkyl, not an alkanoyl, chain, which serves to replace the lipid tail amide with a charged tertiary amine. This derivative has significantly reduced activity against *S. epidermidis* and sensitized *S. aureus* (MICs of 32 and 64 µg/ml, respectively), and no activity against any of the wild type or mutant Gram-negative strains examined. The decreased activity likely results from the inability of a hydrophobic environment to accommodate the charge, suggesting that this portion of the tail is embedded in the membrane or within the interface between the membrane and SPase.

Accordingly, a series of hydrophobic tail analogs of arylomycin A2, adapted to accommodate the proline residues of the resistant forms of SPase as described in the Specification and documents cited herein, were designed. Certain compounds were synthesized and tested, as shown below in the bioactivity Tables 1-4, below.

To explore the minimal tail length required for activity and to determine whether there is a limit to the tail length that can be accommodated within the cytoplasmic membranes of the different bacteria, we synthesized and characterized derivatives 2-5 (Table 1). None of these derivatives gained activity against any of the resistant bacteria relative to arylomycin $C_{16}$, but significant differences were apparent with *S. epidermidis* and the genetically sensitized strains. With the sensitive strains, the $C_8$ derivative 2 has no activity, but the $C_{10}$ derivative 3 has activity against *S. epidermidis*, *S. aureus*, and *E. coli*, while only 4 and 5 show activity against *P. aeruginosa*, revealing that at minimum a $C_{12}$ tail is required. In each case, activity increased with increasing tail length until it plateaued with the $C_{16}$ fatty acid tail (i.e. arylomycin $C_{16}$), and activity decreased slightly with the $C_{18}$ derivative 5 with all but *P. aeruginosa*.

To further explore the effects of increased hydrophobicity, we synthesized and characterized derivatives with tails that contain one or more aromatic rings (Table 1).

We first examined the series of napthyl and biphenyl derivatives 6-8. The napthyl derivative 6 shows no activity against any of the bacteria tested, while the biphenyl derivative 7 retains some activity against wild type *S. epidermidis*. We found that compound 8, which lacks the methylene spacer between the fatty acid carbonyl and the biphenyl moiety also retains some activity against *S. epidermidis*, suggesting that flexibility of the biphenyl moiety is not essential. To further explore this biphenyl architecture, we synthesized the p-alkyl substituted biphenyl derivatives 9-12. We observed an increase in activity with increasing alkyl substituent length against wild type *S. epidermidis* that plateaued with the $C_6$ and $C_8$ derivatives 11 and 12, which are also active against resistant *S. epidermidis*. Interestingly, several of the compounds in this series are also active against both sensitized and wild type *S. aureus*, with relative activities similar to those observed with *S. epidermidis*, but with absolute activities that were somewhat lower. None of the biphenyl derivatives have activity against the wild type or sensitized strains of *P. aeruginosa*, but they do maintain activity against sensitized *E. coli*, again showing trends that were similar to those observed with *S. epidermidis* and *S. aureus*. Overall, the data reveal that relative to the straight chain derivatives, the biphenyl derivatives show similar activities against *S. epidermidis* and *E. coli*, less activity against *P. aeruginosa*, but greater activity against *S. aureus*.

We next examined the series of phenyl substituted tail mimetics 13-15 (Table 1). With *S. epidermidis* and the genetically sensitized strains, we again observed an increase in activity with increasing alkyl chain length. Moreover, the decylphenyl derivative 15 has activity against wild type *S. aureus*. Because the number of carbon atoms in this derivative is similar to that of arylomycin $C_{16}$, which has no activity against wild type *S. aureus*, the data suggest that at least some of the activity is mediated by the interaction of the polarizable aromatic moiety with the membrane or with SPase.

To explore the effects of lipopeptide methylation, and to begin a more focused exploration of modifications that might overcome the deleterious effects of the resistance-conferring Pro, we synthesized and characterized derivatives with altered N-methylation at d-MeSer2 and d-Ala3 (Table 2), arylomycin residues that are proximal to this critical residue when bound to SPase (FIG. 3A). The absence of the d-MeSer2 N-methyl group in 16 results in a slight decrease in activity against both the wild type and resistant *S. epidermidis* strains, and a more pronounced loss of activity against each of the other strains that is most pronounced with *P. aeruginosa*. It is unlikely that this reduced activity results from specific deleterious interactions with the lipid membrane due to membrane fluidity, nor with SPase, as the structure of the *E. coli* SPase-arylomycin $A_2$ complex suggests that this region of the lipopeptide tail is either disordered or oriented away from the protein (although as discussed above, the N-terminally truncated form of SPase used in the structural studies renders this conclusion somewhat speculative).[19] Thus, the observed decrease in activity is likely the result of decreased hydrophobicity, outer membrane penetration, or protease resistance. The loss in activity is even more pronounced with compound 17 where methylation of d-Ala3 ablates activity against all organisms tested, likely resulting from replacement of a stabilizing H-bond with a destabilizing steric clash.

To explore the effects of lipopeptide tail rigidity, and to further explore modifications that might directly compensate for the resistance conferred by Pro29/84 of SPase, we designed the hydroxyproline derivative 18 (Table 2). In this compound, the side chain of d-MeSer2, which interacts with the sidechain and backbone of the SPase residue at position 29/84,[19] is homologated by a methylene unit and fused with the methyl group of the neighboring N-methyl amide bond. We found that this modification results in a complete loss of activity against the Gram-negative organisms but only little to moderate loss in activity against the Gram-positive organisms. Interestingly, because 18 retained full activity against resistant *S. epidermidis*, the disparity in activities against the wild type and resistant variants is greatly decreased, suggesting that at least for this organism, 18 recognizes both the Ser- and the Pro-variant SPases similarly. To explore the effects of decreased rigidity, we synthesized derivative 19 (Table 2), which lacks the peptide bond between the serine and the fatty acid tail (and thus should impart the tail with greater rotational freedom). This molecule has significantly less activity compared to arylomycin $C_{16}$ against all organisms tested, with no observable activity against *E. coli, S. aureus*, or *P. aeruginosa*, and only moderate activity against *S. epidermidis*.

To increase flexibility without introducing or deleting other peptidic functionalities that might contribute to binding SPase, we synthesized and evaluated derivatives with one or two methylene units inserted immediately N-terminal or C-terminal to the amide bond linking d-MeSer2 to d-Ala3 (20-23, Table 2). These compounds did not gain activity against either of the wild type Gram-negative bacteria. With the sensitized Gram-negative strains, activity was observed only with 20, which relative to the parent compound is 16-fold less active against *E. coli*, but only 2-fold less active against *P. aeruginosa*. The effects of methylene addition were significantly different with the Gram-positive bacteria. Relative to arylomycin $C_{16}$, derivatives 20-23 lost 8- to 16-fold activity against sensitive *S. epidermidis*, but retained activity against the resistant strain. This demonstrates that once the hydrogen-bond donor of the protein is removed (by mutation to Pro), perturbing the H-bond acceptor does not further decrease activity. The results were somewhat more complicated with *S. aureus*. As expected, relative to arylomycin $C_{16}$, addition of the methylene units decreased activity against the sensitized strain of *S. aureus*, 2- to 8-fold for 21-23, and at least 64-fold for 20. In the case of wild type *S. aureus*, however, no activity is observed with 20 or 21, but interestingly, 22 and especially 23 gain activity.

TABLE 1

MICs (µM) of selected compounds.

Arylomycin $A_2$: $R_1$ = iso-$C_{11}$, R = Me
Arylomycin $C_{16}$: $R_1$ = n-$C_{15}$, R = Me
1: $R_1$ = iso-$C_{15}$, R = Me
2: $R_1$ = iso-$C_{15}$, R = H

| Strain | Arylomycin $A_2$ | Compound 1 | Compound 2 |
|---|---|---|---|
| *E. coli* MG1655 | >128 | >128 | >128 |
| *S. aureus* 8325 | >128 | >128 | >128 |
| *S. epidermidis* ATCC 35984 | 1 | 0.5 | 1 |
| *B. anthracis* Sterne | n.d. | 32 | n.d. |
| *E. faecium* AEFA001[a] | n.d. | >64 | n.d. |

TABLE 1-continued

| | | | |
|---|---|---|---|
| E. faecalis ATCC 29212 | n.d. | >64 | n.d. |
| E. faecalis ATCC 51299 | n.d. | >64 | n.d. |

[a]Part of the Achaogen, Inc. strain collection.

TABLE 2A

Activity (MICs (μg/ml)) of arylomycin derivatives with altered fatty acid tails against strains of S. epidermidis, S. aureus, E. coli, and P. aeruginosa harboring SPase without (Sensitive) and with (Resistant) the arylomycin-resistance conferring Pro residue.

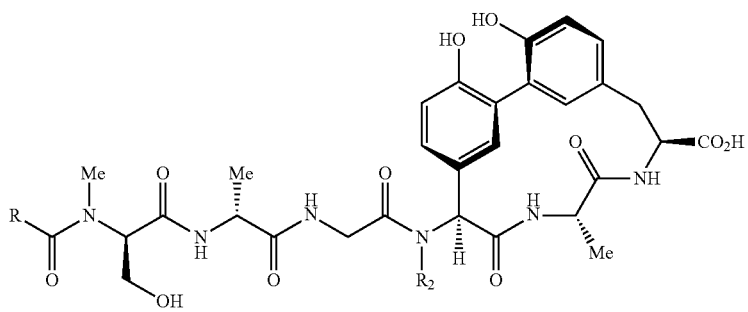

| R | | Sensitive[b] | | | | Resistant[c] | | | |
|---|---|---|---|---|---|---|---|---|---|
| | | Se | Sa | Ec | Pa | Se | Sa | Ec | Pa |
| 3 | (C9 alkyl) | >64 | >64 | >64 | >64 | >64 | >64 | >64 | >64 |
| 4 | (C11 alkyl) | 16 | 64 | 32 | >64 | >64 | >64 | >64 | >64 |
| 5 | (C13 alkyl) | 0.5 | 16 | 8 | 64 | >64 | >64 | >64 | >64 |
| —[a] | (C15 alkyl) | 0.5 | 2 | 0.5 | 8 | 8 | >64 | >64 | >64 |
| 6 | (C17 alkyl) | 1 | 4 | 2 | 8 | 16 | >64 | >64 | >64 |
| 7 | (naphthyl-neopentyl) | >64 | >64 | >64 | >64 | >64 | >64 | >64 | >64 |
| 8 | (biphenyl-neopentyl) | 32 | >64 | >64 | >64 | >64 | >64 | >64 | >64 |
| 9 | (biphenyl-methyl) | 64 | >64 | >64 | >64 | >64 | >64 | >64 | >64 |

TABLE 2A-continued

Activity (MICs (μg/ml)) of arylomycin derivatives with altered fatty acid tails against strains of *S. epidermidis*, *S. aureus*, *E. coli*, and *P. aeruginosa* harboring SPase without (Sensitive) and with (Resistant) the arylomycin-resistance conferring Pro residue.

| | | Sensitive[b] | | | | Resistant[c] | | | |
|---|---|---|---|---|---|---|---|---|---|
| | R | Se | Sa | Ec | Pa | Se | Sa | Ec | Pa |
| 10 | biphenyl-CH(Me)- | 8 | 64 | 16 | >64 | >64 | >64 | >64 | >64 |
| 11 | biphenyl-CH(propyl)- | 1 | 16 | 4 | >64 | >64 | >64 | >64 | >64 |
| 12 | biphenyl-CH(pentyl)- | 0.5 | 8 | 1 | >64 | 32 | 64 | >64 | >64 |
| 13 | biphenyl-CH(heptyl)- | 1 | 8 | 1 | >64 | 16 | 16 | >64 | >64 |
| 14 | phenyl-CH(pentyl)- | 8 | 64 | 32 | >64 | >64 | >64 | >64 | >64 |
| 15 | phenyl-CH(heptyl)- | 1 | 8 | 8 | 64 | >64 | >64 | >64 | >64 |
| 16 | phenyl-CH(nonyl)- | 0.5 | 4 | 2 | 16 | 16 | 32 | >64 | >64 |

Se = *S. epidermidis*, Sa = *S. aureus*, Ec = *E. coli*, Pa = *P. aeruginosa*

[a]Arylomycin $C_{16}$ (fourth entry) included for reference.

[b]Sensitive strains include wild type *S. epidermidis* RP62A, lepB(P29S) *S. aureus* 8325, lepB(P84L) *E. coli* MG1655, and lepB(P84L) *P. aeruginosa* PAO1.

[c]Resistant strains include spsB(S29P) *S. epidermidis* RP62A, and wild type *S. aureus* 8325, *E. coli* MG1655, and *P. aeruginosa* PAO1.

TABLE 2B
Activity (MICs (μg/ml)) of arylomycin derivatives with altered lipopeptide tails against strains of *S. epidermidis*, *S. aureus*, *E. coli*, and *P. aeruginosa* harboring SPase without (Sensitive) and with (Resistant) the arylomycin-resistance conferring Pro residue.
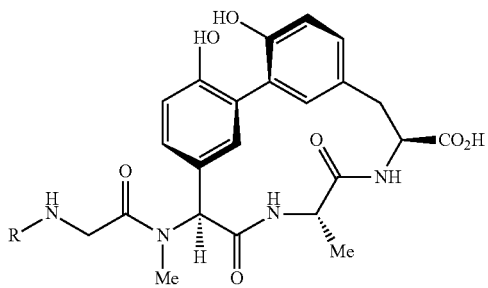
| R | Sensitive[b] | | | | Resistant[c] | | | |
|---|---|---|---|---|---|---|---|---|
| | Se | Sa | Ec | Pa | Se | Sa | Ec | Pa |
| —[a] | 0.5 | 2 | 0.5 | 8 | 8 | >64 | >64 | >64 |
| 17 | 1 | 16 | 4 | >64 | 32 | >64 | >64 | >64 |
| 18 | >64 | >64 | >64 | >64 | >64 | >64 | >64 | >64 |
| 19 | 4 | 4 | >64 | >64 | 8 | >64 | >64 | >64 |
| 20 | 8 | >64 | >64 | >64 | >64 | >64 | >64 | >64 |

TABLE 2B-continued

Activity (MICs (µg/ml)) of arylomycin derivatives with altered lipopeptide tails against strains of S. epidermidis, S. aureus, E. coli, and P. aeruginosa harboring SPase without (Sensitive) and with (Resistant) the arylomycin-resistance conferring Pro residue.

| | | Sensitive[b] | | | | Resistant[c] | | | |
|---|---|---|---|---|---|---|---|---|---|
| | R | Se | Sa | Ec | Pa | Se | Sa | Ec | Pa |
| 21 | (structure) | 8 | >64 | 8 | 16 | 16 | >64 | >64 | >64 |
| 22 | (structure) | 8 | 8 | >64 | >64 | 8 | >64 | >64 | >64 |
| 23 | (structure) | 4 | 16 | >64 | >64 | 8 | 64 | >64 | >64 |
| 24 | (structure) | 8 | 4 | >64 | >64 | 16 | 16 | >64 | >64 |

Se = S. epidermidis, Sa = S. aureus, Ec = E. coli, Pa = P. aeruginosa

[a]Arylomycin C$_{16}$ (fourth entry) included for reference.

[b]Sensitive strains include wild type S. epidermidis RP62A, lepB(P29S) S. aureus 8325, lepB(P84L) E. coli MG1655, and lepB(P84L) P. aeruginosa PAO1. See text for details.

[c]Resistant strains include spsB(S29P) S. epidermidis RP62A, and wild type S. aureus 8325, E. coli MG1655, and P. aeruginosa PAO1.

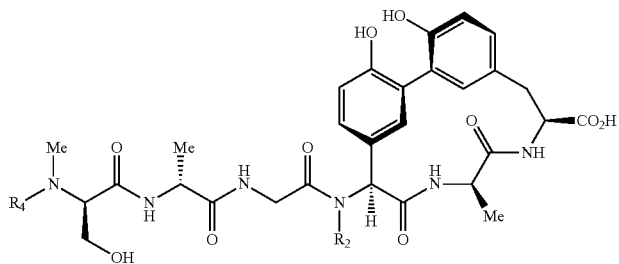

25: R$_1$ = H, R$_2$ = H
R$_3$ = H, R$_4$ = alkyl-C$_{16}$

TABLE 3

Arylomycin P3 Position Derivatives

| R | | S. epidermidis[b] | S. aureus[c] | E. coli[d] | P. aeruginosa[e] |
|---|---|---|---|---|---|
| 26 | —H | 8 | >64 | 16 | >64 |
| —[a] | —Me | 0.25 | 4 | 2 | 4 |
| 27 | —CH₂Me (ethyl) | 0.5 | 8 | 1 | 4 |
| 28 | —(CH₂)₂Me (propyl) | 1 | 8 | 2 | 8 |
| 29 | —(CH₂)₃Me (butyl) | 4 | 16 | >128 | >128 |
| 30 | —(CH₂)₄Me (pentyl) | 4 | 16 | >128 | >128 |
| 31 | —(CH₂)₂OH | >64 | >64 | >64 | >64 |
| 32 | —(CH₂)₃OH | >64 | >64 | >64 | >64 |
| 33 | —CH₂CF₃ | 8 | >64 | 16 | >64 |

TABLE 3-continued

Arylomycin P3 Position Derivatives

| R | | S. epidermidis[b] | S. aureus[c] | E. coli[d] | P. aeruginosa[e] |
|---|---|---|---|---|---|
| 34 | isopropyl (Me, Me) | 4 | 32 | 4 | 16 |
| 35 | isobutyl (CH2-CH(Me)2) | 2 | 32 | 4 | >64 |

[a]Arylomycin $C_{16}$ (fourth entry) included for reference.
[b]wild type S. epidermidis RP62A.
[c]lepB(P29S) S. aureus 8325.
[d]lepB(P84L) E. coli MG1655, and lepB(P84L)
[e]P. aeruginosa PAO1

TABLE 4

MICs of Arylomycin Derivatives (µg/mL)

| Strain | Arylomycin $C_{16}$ (R = H) | Arylomycin B-$C_{16}$ (R = $NO_2$) | 36 (R = $NH_2$) |
|---|---|---|---|
| S. epidermidis | 0.25 | 0.13 | 8 |
| S. aureus P29S | 8 | 8 | 64 |
| E. coli P84L | 2 | 2 | 16 |
| E. coli | >64 | >64 | >64 |
| P. aeruginosa P84L | 4 | 4 | 32 |
| B. brevis | >64 | >64 | >64 |
| R. equi | 16 | 32 | nd |
| R. opacus | 1 | 4 | nd |
| S. agalactiae | >128 | 8 | nd |
| S. pyogenes | 8 | 4 | nd |
| S. pneumoniae | 8 | 16 | nd |
| C. efficiens | 16 | 16 | nd |
| C. glutamicum | 2 | 2 | nd |
| L. lactis | 16 | 32 | nd |

The phenyl- and biphenyl-fatty acid tail series showed similar activities against *S. epidermidis*, *S. aureus*, and *E. coli*, with the longer p-alkyl derivatives having activity against both sensitive and resistant strains of *S. aureus*. Interestingly, *P. aeruginosa* again shows unique behavior as it is not inhibited by any of the biphenyl-modified derivatives. This is particularly noteworthy considering that it is inhibited by the $C_8$- and $C_{1-10}$-substituted phenyl analogs, which in some cases are less hydrophobic. While some of the differences may result from altered outer membrane penetration or in vivo stability, the data likely reflect suboptimal insertion of the arylomycin into the plasma membrane of *P. aeruginosa*. It is interesting to speculate that this might result from unique aspects of the phospholipids that comprise the plasma membrane of *P. aeruginosa*, such as the presence of phosphatidylcholine,[46-50] or from different constituent fatty acids.[51-54] For example, *P. aeruginosa* appears to employ a higher percentage of cis-vaccenic acid (a $C_{18}$ fatty acid) relative to palmitic and palmitoleic acids (which are $C_{16}$ fatty acids),[51-54] possibly resulting in a slightly thicker plasma membrane and possibly accounting for the generally longer fatty acid tail lengths that were observed to be required for *P. aeruginosa* inhibition. Overall, the data collected with the different tail derivatives suggest that the phenyl-modified derivatives are likely better scaffolds for arylomycin optimization than the natural, saturated fatty acid chains. This is most clearly highlighted by compound 15, which retains all of the activities of the parent compound arylomycin $C_{16}$ but also gains activity against *S. aureus*.

N-methylation is common with non-ribosomally synthesized peptides such as the arylomycins, and is generally thought to optimize hydrophobicity, hydrogen-bonding potential, conformation, and/or resistance to proteases.[55-58] The peptide portion of the arylomycin lipopeptide tail is backbone methylated at D-MeSer2 and MeHpg5, but not at D-Ala3 or Gly4. Previously, we showed that the methyl group at MeHpg5 pre-organizes the biaryl ring system for recognition of SPase.[18] When we altered the backbone methylation state of D-MeSer2 and D-Ala3, which are both proximal to the critical resistance-conferring Pro in the *E. coli* SPase-arylomycin $A_2$ complex,[19] significant activity was lost against both Gram-positive and Gram-negative bacteria. Although the specific origins of the decreased activity may differ at the two sites examined, the data suggests that natural lipopeptide tail methylation pattern is already optimized for activity.

In an effort to more directly compensate for the negative interactions introduced by the resistance-conferring Pro, we synthesized several derivatives with increased or decreased flexibility around D-MeSer2 and D-Ala3. None of the derivatives gained activity against either of the wild type Gram-negative bacteria, and while 20 retained activity against sensitized *P. aeruginosa*, it and the other derivatives lost activity against sensitized *E. coli*. The results were significantly different with the Gram-positive pathogens. Relative to arylomycin $C_{16}$, derivatives 20-23 each lost 8 to 16-fold activity against sensitive *S. epidermidis* and 2- to >32-fold activity against the genetically sensitized *S. aureus*. This trend is consistent with the modifications shifting the register of the β-sheet formed between SPase and the inhibitor such that a stabilizing H-bond is lost. However, and more importantly, 22, and especially 23, gain activity against wild type *S. aureus*. As mentioned above, the structure of the *E. coli* SPase-arylomycin $A_2$ complex suggests that Pro84 (and by inference the homologous Pro in the other bacteria) disrupts arylomycin binding by physically occluding the lipopeptide tail from a hydrophobic groove and by disrupting an otherwise stabilizing hydrogen-bond with the carbonyl group of the lipid tail. While the precise mechanism by which these derivatives gain activity against *S. aureus* remains to be determined, the data nonetheless support the possibility that the spectrum of the arylomycins may be optimized by derivatization.

Accordingly, a series of derivatives with residues of varied side chains at the position of the macrocycle of arylomycin C16 where Ala is present, adapted to compensate for binding energy lost due to the existence of the proline residues of the resistant forms of SPase as described in the specification and documents cited herein, were designed. Certain compounds were synthesized and tested, as shown below in the bioactivity Tables 3, below. The derivatives were evaluated by characterizing their minimal inhibitory concentration (MIC) against wild type *S. epidermidis* (strain RP62A), as well as mutant strains of *S. aureus* 8325, *E. coli* MG1655, and *P. aeruginosa* PAO1 that are rendered sensitive to the arylomycins via mutation of the resistance-conferring SPase Pro residue to Ser (*S. aureus*) or Leu (*E. coli*, and *P. aeruginosa*).

We initially explored the effects of removing the side chain at P3 by incorporation of Gly (26, Table 3). This compound lost significant activity against *S. epidermidis* (32-fold), *S. aureus* (>16 fold), *E. coli* (32-fold) and *P. aeruginosa* (>16-fold), suggesting that α-branching is required at this position either for packing within the hydrophobic environment of the S3 pocket and/or to help orient the backbone of the arylomycin, and thereby decrease the internal entropy of the macrocycle lost upon binding.

Having established the requirement for an α-substituent at the P3 position to maintain activity, we systematically explored the effect of increased side chain length with arylomycin derivatives 27-30. Interestingly, the data reveal that arylomycin $C_{16}$, which bears a methyl group at this position, and analogs with ethyl, or n-propyl side chain results all have indistinguishable activities against each of the bacteria tested (Table 5-1). In contrast, the derivatives and 29 with n-butyl and n-pentyl side chains, respectively, had significant effects that were somewhat different with the different bacteria examined. Relative to arylomycin $C_{16}$, both compounds 29 and 30 lost 8- to 32-fold activity against *S. epidermidis*, 32-fold against *S. aureus*, and at least 32- and 64-fold against *P. aeruginosa* and *E. coli*, respectively. The data suggest that the different SPases do not discriminate against shorter side chains at this position, but have varying abilities to tolerate increasingly longer P3 side chains.

While an inability to accommodate the longer P3 side chains is a simple explanation for the structure activity-relationships revealed with 27-30, the crystal structure of the inhibitor-bound *E. coli* peptidase reveals the presence of several crystallographically observable water molecules near the P3 pocket. Thus, it is also possible that the n-butyl and n-pentyl derivatives may have lost activity by forcing a hydrophobic methyl group proximal to these water molecules, or by forcing desolvation of the protein without compensating with any stabilizing interactions. To address these possibilities, we explored the effects of increased hydrophilicity and/or hydrogen-bonding via derivatives 31 and 32 which bear n-propanol and n-butanol side chains, respectively. All activity was lost with these compounds against all bacteria tested, suggesting that the longer alkyl or hydroxyalkyl are not accommodated due to size constraints with the S3 pocket.

To further explore how changes in the hydrophobicity of the P3 side chain impact activity we examined trifluoroethyl derivative 33. Such fluorinated derivatives are thought to be 'superhydrophobic'[24] and are often used in drug optimization.[25] We found that compound 33 is 8-fold less active against *E. coli*, at least 16-fold less active against *P. aeruginosa* and *S. aureus*, and 32-fold less active against *S. epidermidis*.

Having explored the effect of altered length and hydrophobicity within a linear side chain, we turned our attention to the Val and Leu derivatives 34 and 35, which possess β- and γ-branched side chains, respectively. While these compounds are also less active than the parent compound, the loss in activity was again organism dependent. Both 34 and 35 lost 8- to 16-fold activity against both Gram-positive bacteria, but they maintained activity against *E. coli*. Interestingly, *P. aeruginosa* more strongly differentiated between the branched derivatives, with 34 losing 4-fold activity, but 35 losing >16-fold activity. This data suggests that the S3 pocket of the *E. coli* SPase is relatively tolerant toward branching in general, that the Gram-positive SPase are less so, and that the S3 pocket of *P. aeruginosa* SPase is relatively tolerant of β-branching but intolerant of γ-branching.

In summary, we have synthesized the first series of arylomycin derivatives with substitution in the backbone of the macrocycle. We found that the side chain at the P3 position of arylomycin contributes significantly to binding. In addition, we found that the S3 pocket of SPase can accommodate up to three linear saturated carbons from the P3 position of arylomycin however, increasing the size of the substituent filling this pocket does not increase overall activity. Arylomycin derivatives with side-chains larger than three linear saturated carbons either linearly or laterally at the P3 position lose activity against most strains with larger losses of activity seen when larger substituents were present. While these derivatives did not make arylomycin more potent, they defined the limits of the S3 pocket for the inhibitor and they suggest a binding model where the arylomycins, and perhaps the recognition sequence of preproteins, are not free in solution but are bound in the lipophilic membrane before binding SPase.

To explore the effect of substituents on the aromatic ring affect binding of the arylomycin we synthesized and arylomycin B derivative arylomycin B $C_{16}$ and its amino derivative 36. They were adapted to compensate for binding energy lost due to the existence of the proline residues of the resistant forms of SPase as described in the specification and documents cited herein, were designed. Certain compounds were synthesized and tested, as shown below in the bioactivity Table 4, below.

The activity of arylomycin B—$C_{16}$ and its derivative 36 was characterized by determining the minimal inhibitory concentration (MIC) required to inhibit the growth of wild type *S. epidermidis* (strain RP62A), and *E. coli* (MG1655). The compounds were also tested against strains of *S. aureus* (8325), *E. coli* (MG1655), and *P. aeruginosa* (PAO1) that were rendered sensitive to the arylomycins by mutation of the resistance-conferring Pro to a residue that does not confer resistance (P29S in the *S. aureus* protein, and P84L in the *E. coli*, and *P. aeruginosa* proteins).

Like arylomycin $A_2$ and its derivative arylomycin $C_{16}$, arylomycin B—$C_{16}$ has potent activity against *S. epidermidis* (Table 4) and no activity against wild-type *E. coli*. In addition, similar to the arylomycin A compounds, arylomycin B—$C_{16}$ has activity against the mutant strains of *S. aureus*, *E. coli*, and *P. aeruginosa*. Thus, the activity of the B series compound is limited against natural isolates via the same mechanism as the A series compounds. In fact, the level of arylomycin B—$C_{16}$ activity against all strains tested is indistinguishable from that of arylomycin $C_{16}$ (Table 4). Surprisingly, our data contradicts the previously reported conclusion that the arylomycins have activity against *B. brevis* and that nitro substitution increases the activity of the arylomycin scaffold.[18] In our experiments, using both MHBII broth and nutrient broth (as was used in the previously reported studies) both compounds showed no activity against *B. brevis*.

Relative to the two natural products, we found that the amino derivative 36 is significantly less active against all bacteria tested and the loss in activity is slightly larger against the Gram-positive bacteria (32-fold) than against the Gram-negative pathogens (8-fold). The amino group is expected to be protonated and thus charged at physiological pH, and the inability of the SPase binding site to accommodate this charge likely explains the decreased activity.

To generate a broader assessment of the activity of the A- and B-series arylomycins, we examined representatives from a broad range of bacteria that are sensitive to arylomycin $C_{16}$[20] including *Rhodococcus equi*, *Rhodococcus opacus*, *Streptococcus agalactiae*, *Streptococcus pneumonia*, *Streptococcus pyogenes*, *Corynebacterium efficiens*, *Corynebacterium glutamicum* and *Lactococcus lactis* (Table 4). For almost all of the bacteria tested the inhibitory concentrations for arylomycin $C_{16}$ and arylomycin B—$C_{16}$ were identical or within the error of the experiment. However, *Streptococcus agalactiae* showed significant differences in MICs between the compounds with arylomycin B—$C_{16}$ having greater than 16-fold more activity than its non-nitrosylated analogue arylomycin $C_{16}$. This result is especially interesting given that the in neither of the two SPases of *S. agalactiae* is the resistance conferring Pro present and that identical activities were observed between the two compounds against the closely related organisms *Streptococcus pneumoniae*, and *Streptococcus pyogenes*. It is interesting to speculate that in the context of an arms race this species may have found an alternative method for mediating resistance to the arylomycin A series that was overcome by the installation of a nitro group in the arylomycin B series.

In conclusion, we have shown that aminated arylomycin loses significant activity relative to the nitrosylated variant. In addition, we have showed that arylomycin B—$C_{16}$ has no difference in activity against *S. epidermidis*, mutant strains of *S. aureus*, *E. coli* and *P. aeruginosa* and multiple other strains of bacteria when compared to the analogous arylomycin $C_{16}$ of the A series. Importantly, it was found that *S. agalactiae* is uniquely sensitive to the arylomycin B—$C_{16}$. In addition, closely related strains of bacteria showed no difference between the A and B series arylomycins. These results support the idea that nitrosylation of the arylomycin is important for biological activity against some bacteria and that its inclusion in the repertoire of arylomycins was possibly the result of selection on the producing organism.

Reports by other workers indicate that arylomycins (e.g., those shown in FIG. 1) have little whole cell activity against most bacterial pathogens except possibly for *Staphylococcus epidermidis*, and *Rhodococcus opacus*. See, e.g., Kulanthaivel et al., J. Biol. Chem. 279: 36250-58 (2004); Schimana et al., J. Antibiotics 55:565-70 (2002). For example, currently available reports indicate that arylomycins A and B lack activity against the Gram-negative bacteria *Escherichia coli* K12, *Proteus mirabilis* ATCC 35501, *Pseudomonas fluorescens* DSM 50090 and against the eukaryotic organisms *Saccharomyces cerevisiae* ATCC 9080, *Botrytis cinerea* Tu 157 and against the green algae *Chlorella fusca* and against the duckweed *Lemna minor*.

However, according to the invention, arylomycins actually do have activity against a variety of bacterial species. For example, the following bacterial species are susceptible to arylomycins: *Rhodococcus equi*, *Corynebacterium diphtheriae*, *Lactococcus lactis* subsp. *cremoris*, *Corynebacterium glutamicum*, *Francisella tularensis*, *Campylobacter jejuni*, Helicobacter pylori, Propionibacterium acnes, Chlamydia trachomatis, Chlamydophila pneumoniae, Staphylococcus carnosus, Staphylococcus haemolyticus, Staphylococcus hominis, Staphylococcus lugdunensis, Streptococcus agalactiae, Streptococcus dysgalactiae, Streptococcus mitis, Streptococcus oralis, and Streptococcus pyogenes, as illustrated in the following Table 5.

TABLE 5

Bacteria Predicted by sequence to be Sensitive and Confirmed Sensitive.
Predicted by sequence to be Sensitive and Confirmed Sensitive.

| Species | Aminio acid −7 from catalytic Ser[a] | MIC (µg/ml) |
| --- | --- | --- |
| Staphylococcus epidermidis | S, S | 0.25 |
| Staphylococcus haemolyticus | S, S | 2 |
| Staphylococcus hominis | S, S | 0.25 |
| Staphylococcus lugdunensis | S, T | 0.25 |
| Staphylococcus simulans | S, ? | 0.25 |
| Staphylococcus cohnii | S, ? | 8 |
| Streptococcus pneumoniae | N | 16 |
| Streptococcus pyogenes | A | 16 |
| Corynebacterium glutamicum | M | 2 |
| Rhodococcus opacus | V | 2 |
| Lactococcus lactis | L | 16, >128[b] |
| Rhodococcus equi | V, I | 16 |
| Helicobacter pylori | A | 4 |
| Chlamydia trachomatis | L | 6 |
| Francisella tularensis | N | 4-16, >64[b] |

[a]Multiple amino acids indicate where organisms express multiple SPases
[b]Range of MICs across different isolates Accordingly, another aspect of the invention is a method of treating a bacterial infection in an animal that includes administering any one or any combination of the arylomycin compounds (e.g., compounds of Formula I) to the animal, wherein the bacterial infection comprises an infection by Rhodococcus equi, Corynebacterium diphtheriae, Lactococcus lactis subsp. cremoris, Corynebacterium glutamicum, Francisella tularensis, Campylobacter jejuni, Helicobacter pylori, Propionibacterium acnes, Chlamydia trachomatis, Chlamydophila pneumoniae, Staphylococcus carnosus, Staphylococcus haemolyticus, Staphylococcus hominis, Staphylococcus lugdunensis, Streptococcus agalactiae, Streptococcus dysgalactiae, Streptococcus mitis, Streptococcus oralis, and Streptococcus pyogenes. The arylomycin compounds, including those of Formula I can be administered in a therapeutically effective amount.

As further described below, arylomycin antibiotics inhibit the bacterial type I signal peptidase (SPase) enzyme, particularly when the bacteria's SPase enzyme does not have a proline within about 10 amino acids N-terminal to the SPase catalytic serine, and especially when the bacteria's SPase enzyme does not have a proline at 5 to 7 amino acids N-terminal to the SPase catalytic serine. Thus, another aspect of the invention is a method of treating a bacterial infection in an animal that includes administering any one or any combination of arylomycin A, arylomycin B or the arylomycin compounds of Formula I to the animal, wherein the bacterial infection comprises an infection by a bacteria that encodes or expresses an SPase enzyme that does not have a proline within about 10 amino acids N-terminal to the SPase catalytic serine, or is an infection by Yersinia pestis. In some embodiments, the bacteria encodes or expresses an SPase enzyme that does not have a proline at 5 to 7 amino acids N-terminal to the SPase catalytic serine. The arylomycin A, arylomycin B and/or the compounds of Formula I can be administered in a therapeutically effective amount. Examples of organism with SPase genes that encode amino acids other than proline at residues −5 and −7 from the catalytic serine include but are not limited to Staphylococcus epidermidis, Staphylococcus haemolyticus, Staphylococcus luganensis, Staphylococcus hominis subsp. hominis, Staphylococcus hominis subsp. novobiosepticus, Staphylococcus cohnii, Streptococcus pnemoniae, Streptococcus pyogenes, Streptococcus agalactiae, Lactococcus lactis subsp. lactis, Rhodococcus opacus, Rhodococcus equi, Corynebacterium glutamicum Helicobacter pylori, Chlamydia trachomatis, and Francisella tularensis.

The following Table 6 provides a representative listing of bacterial species that do not have a proline at 5 to 7 amino acids N-terminal to the SPase catalytic serine.

TABLE 6

Bacteria Expressing a SPase enzyme that does not have a proline 5 to 7 amino acids N-terminal to the SPase catalytic serine

| Species | 8 residues N-terminal to and including catalytic Ser |
| --- | --- |
| Rhodococcus equi | VYLIPSES |
| Rhodococcus opacus | VYLIPSES |
| Corynebacterium diphtheriae | VYMIPSQS |
| Lactococcus lactis subsp. cremoris | LVVVDGHS |
| Corynebacterium glutamicum | MYMIPSGS |
| Francisella tularensis | NFLIPTAS |
| Campylobacter jejuni | AFVIPSGS |
| Helicobacter pylori | AFIIPSRS |
| Propionibacterium acnes | MFVIPSKS |
| Chlamydia trachomatis | LYEVPTGS |
| Chlamydophila pneumoniae | LYEVPTGS |
| Staphylococcus carnosus | SYTVRGDS |
| Staphylococcus haemolyticus | SYTIKGDS<br>SYTVSGSS |
| Staphylococcus epidermidis | SYSIKGDS<br>SYTVKGAS |
| Staphylococcus hominis | SYTIKGDS<br>SYTVSGSS |
| Staphylococcus lugdunensis | SYTIKGDS<br>TYSVSGDS |
| Streptococcus pneumoniae | NVRVEGHS |
| Streptococcus agalactiae | VLRIYGHS<br>FVKVDGHS |
| Streptococcus dysgalactiae | AVKVDGHS |
| Streptococcus mitis | NVRVEGHS |
| Streptococcus oralis | NVRVEGHS |
| Streptococcus pyogenes | AVKVDGHS |

While almost all bacteria that do not have a proline within about 10 amino acids N-terminal to the SPase catalytic serine are susceptible to arylomycins (including arylomycin A, arylomycin B and the compounds of Formula I), there are a few exceptions. For example, some strains of *Staphylococcus aureus*, *Staphylococcus capitis*, *Staphylococcus caprae* and *Yersinia pestis* are still susceptible to arylomycins even though they do have a proline residue within 10 amino acids N-terminal to the catalytic serine (see Table 7).

TABLE 7

Bacterial Species Susceptible to Arylomycins but with a Proline N-terminal to the SPase Catalytic Serine

| Species | Aminio acid −7 from catalytic Ser[a] | MIC (µg/ml) |
|---|---|---|
| Yersinia pestis | P | 4 |
| Staphylococcus capitis | P, S | 8 |
| Staphylococcus caprae | P, S | 8 |

[a]Multiple amino acids indicate where organisms express multiple SPases

Thus, another aspect of the invention is a method of treating a bacterial infection in an animal that includes administering arylomycin A and/or arylomycin B and/or a compound of Formula I to the animal, wherein the infection is an infection involving a bacterial species that is susceptible to arylomycin but where the bacterial species has a proline residue within 10 amino acids N-terminal to the catalytic serine (e.g., at positions −5 and/or −7 from the catalytic serine). Such organisms include certain strains of *Staphylococcus aureus*, *Staphylococcus capitis*, *Staphylococcus caprae* and *Yersinia pestis*.

For example, *Yersinia pestis* has a single SPase with a proline at position 29, but as demonstrated herein, *Yersinia pestis*, is sensitive to arylomycin compounds. *Yersinia pestis* is a significant pathogen that can infect humans and other animals—it is the causative agent of the plague. Thus, new methods of treating *Yersinia pestis* infections are highly desirable. Therefore, another aspect of the invention is a method of treating a *Yersinia pestis* infection in an animal that includes administering arylomycin A and/or arylomycin B and/or a compound of Formula I to the animal. The arylomycin A and/or arylomycin B and/or the compound of Formula I can be administered in a therapeutically effective amount.

However, according to the invention, bacterial species with a proline 5-7 amino acids N-terminal to the catalytic serine are resistance to arylomycins. Such species include those shown in Table 8.

TABLE 8

Bacterial Species with a Proline within 10 amino acids N-terminal to the SPase Catalytic Serine

| | 8 residues N-terminal to and including catalytic Ser | SEQ ID NO: |
|---|---|---|
| Escherichia coli | PFQIPSGS | 87 |
| Klebsiella pneumoniae | PFQIPSGS | 87 |
| Salmonella entericia | PFQIPSGS | 87 |
| Vibrio cholerae | PFQIPSGS | 87 |
| Pseudomonas aeruginosa | PFQIPSGS | 87 |
| Acinetobacter baumanii | PFNIPSDS | 88 |
| Neiserria meningitidis | PFQIPSSS | 89 |

TABLE 8-continued

Bacterial Species with a Proline within 10 amino acids N-terminal to the SPase Catalytic Serine

| | 8 residues N-terminal to and including catalytic Ser | SEQ ID NO: |
|---|---|---|
| Haemophilus influenzae | PFQIPSGS | 89 |
| Citrobacter koseri | PFQIPSGS | 89 |
| Shigella flexneri | PFQIPSGS | 89 |
| Bordetella pertussis | PFHIPSGS | 90 |
| Mycobacterium tuberculosis | PYLIPSES | 91 |
| Staphylococcus aurues | PYTIKGES | 92 |
| Bacillus anthracis | PSLVQGES | 93 |
| | LCKVEGKS | 94 |
| Streptococcus mutans | PVQVDGHS | 95 |
| Clostridium difficile | PSIVSGES | 96 |
| | PTIVKGES | 97 |
| | PTLVNGES | 98 |
| Enterococcus faecalis | PAAVNGSS | 99 |
| | SYPIAGQS | 100 |
| | PVVVRGHS | 101 |
| | PVRVDGHS | 102 |
| Listeria monocytogenes | PVKVEGTS | 103 |
| | PVTVNGKS | 104 |
| | PILVDGIS | 105 |

Infections of particular interest that can be treated using arylomycins include those commonly detected in humans and/or those infections that are frequently inadequately treated by other antibiotics. Examples of infections that are susceptible to arylomycin treatment include those involving *Staphylococcus epidermidis*, *Staphylococcus haemolyticus*, *Staphylococcus luganensis*, *Staphylococcus hominis* subsp. *hominis*, *Staphylococcus hominis* subsp. *novobiosepticus*, *Staphylococcus cohnii*, *Streptococcus pnemoniae*, *Streptococcus pyogenes*, *Streptococcus agalactiae*, *Lactococcus lactis* subsp. *lactis*, *Rhodococcus opacus*, *Rhodococcus equi*, *Corynebacterium glutamicum Helicobacter pylori*, *Chlamydia trachomatis*, and *Francisella tularensis*, *Rhodococcus equi*, *Corynebacterium diphtheriae*, *Lactococcus lactis* subsp. *cremoris*, *Corynebacterium glutamicum*, *Francisella tularensis*, *Campylobacter jejuni*, *Helicobacter pylori*, *Propionibacterium acnes*, *Chlamydia trachomatis*, *Chlamydophila pneumoniae*, *Staphylococcus carnosus*, *Staphylococcus haemolyticus*, *Staphylococcus hominis*, *Staphylococcus lugdunensis*, *Streptococcus agalactiae*, *Streptococcus dysgalactiae*, *Streptococcus mitis*, *Streptococcus oralis*, and *Streptococcus pyogenes*.

In one embodiment, the infection involves *Helicobacter pylori* (whose SPase has Ala29), which infection is readily identified by available procedures. Hence, when such infections are identified the infections can be treated by administering to the affected animal any one or any combination of arylomin A, arylomycin B and/or any of the arylomycin compounds of Formula I. The arylomycin A and/or arylomycin B and/or the compound of Formula I can be administered in a therapeutically effective amount.

In other embodiments, the bacterial infection does not involve *Staphylococcus epidermidis* and/or *Rhodococcus opacus*.

The animal can be any animal suspected of suffering from a bacterial infection. For example, the animal can be a human, a domesticated animal, a zoo animal or an animal under the treatment of a doctor, nurse or veterinarian. Examples of animals that can be treated include humans, dogs, cats, horses, cattle, pigs, goats, sheep, chickens, geese, turkeys, rats, mice, hamsters, ferrets, parrots, lizards and the like.

Thus, the compounds of the invention can be administered to an animal (e.g., a mammal), especially a human in need of such treatment, prevention, elimination, alleviation or amelioration of a malcondition.

The compounds of the invention are effective over a wide dosage range. For example, in the treatment of adult humans, dosages from about 0.05 to about 5000 mg, preferably from about 1 to about 2000 mg, and more preferably between about 2 and about 2000 mg per day can be used. A typical dosage is about 10 mg to about 1000 mg per day. In choosing a regimen for patients it can frequently be necessary to begin with a higher dosage and when the condition is under control to reduce the dosage. The exact dosage will depend upon the activity of the compound, mode of administration, on the therapy desired, form in which administered, the subject to be treated and the body weight of the subject to be treated, and the preference and experience of the physician or veterinarian in charge.

Generally, the compounds of the invention are dispensed in unit dosage form including from about 0.05 mg to about 1000 mg of active ingredient together with a pharmaceutically acceptable carrier per unit dosage.

Usually, dosage forms suitable for oral, nasal, pulmonal or transdermal administration include from about 125 µg to about 1250 mg, preferably from about 250 µg to about 500 mg, and more preferably from about 2.5 mg to about 250 mg, of the compounds admixed with a pharmaceutically acceptable carrier or diluent. Dosage forms can be administered daily, or more than once a day, such as twice or thrice daily. Alternatively dosage forms can be administered less frequently than daily, such as every other day, or weekly, if found to be advisable by a prescribing physician.

It is within ordinary skill to evaluate any compound disclosed and claimed herein for effectiveness in inhibition of susceptible and resistant variants of bacterial SPases, and in the various in vivo assays, using the procedures described above or found in the scientific literature. Accordingly, the person of ordinary skill can prepare and evaluate any of the claimed compounds without undue experimentation.

Any compound found to be an effective inhibitor of a bacterial SPase can likewise be tested in animal models and in human clinical studies using the skill and experience of the investigator to guide the selection of dosages and treatment regimens.

Documents Cited (1) Miller, L. G.; Kaplan, S. L. *Infect. Dis. Clin. North Am.* 2009, 23, 35-52.
(2) Pearson, A. *J Hosp Infect* 2009, 73, 296-304.
(3) Payne, D. J.; Gwynn, M. N.; Holmes, D. J.; Pompliano, D. *Nat. Rev. Drug Discov.* 2007, 6, 29-40.
(4) Clardy, J.; Fischbach, M. A.; Walsh, C. T. *Nat Biotechnol* 2006, 24, 1541-50.
(5) Gringauz, A. *Introduction to Medicinal Chemistry: How Drugs Act and Why*; Wiley-VCH: Weinheim, Germany, 1996.
(6) Schneider, P.; Hawser, S.; Islam, K. *Bioorg. Med. Chem. Lett.* 2003, 13, 4217-21.
(7) von Nussbaum, F.; Brands, M.; Hinzen, B.; Weigand, S.; Habich, D. *Angew. Chem. Int. Ed. Engl.* 2006, 45, 5072-129.
(8) Sharma, P. C.; Jain, A.; Jain, S. *Acta Pol Pharm* 2009, 66, 587-604.
(9) Carlos, J. L.; Paetzel, M.; Brubaker, G.; Karla, A.; Ashwell, C. M.; Lively, M. O.; Cao, G.; Bullinger, P.; Dalbey, R. E. *J. Biol. Chem.* 2000, 275, 38813-38822.
(10) Paetzel, M.; Dalbey, R. E.; Strynadka, N. C. *Pharmacol. Ther.* 2000, 87, 27-49.
(11) Paetzel, M.; Karla, A.; Strynadka, N. C. J.; Dalbey, R. E. *Chem. Rev.* 2002, 102, 4549-4580.
(12) Holtzel, A.; Schmid, D. G.; Nicholson, G. J.; Stevanovic, S.; Schimana, J.; Gebhardt, K.; Fiedler, H. P.; Jung, G. *The Journal of antibiotics* 2002, 55, 571-577.
(13) Kulanthaivel, P., et al. *J. Biol. Chem.* 2004, 279, 36250-8.
(14) Schimana, J.; Gebhardt, K.; Holtzel, A.; Schmid, D. G.; Sussmuth, R.; Muller, J.; Pukall, R.; Fiedler, H. P. *The Journal of antibiotics* 2002, 55, 565-570.
(15) Cragg, G. M.; Newman, D. J.; Snader, K. M. *J Nat Prod* 1997, 60, 52-60.
(16) Dalbey, R. E.; Lively, M. O.; Bron, S.; van Dijl, J. M. *Protein Sci* 1997, 6, 1129-38.
(17) Date, T. *J. Bacteriol.* 1983, 154, 76-83.
(18) Roberts, T. C.; Smith, P. A.; Cirz, R. T.; Romesberg, F. E. *J Am Chem Soc* 2007, 129, 15830-8.
(19) Paetzel, M.; Goodall, J. J.; Kania, M.; Dalbey, R. E.; Page, M. G. *J. Biol. Chem.* 2004, 279, 30781-90.
(20) Luo, C.; Roussel, P.; Dreier, J.; Page, M. G.; Paetzel, M. *Biochemistry* 2009, 48, 8976-84.
(21) Beauregard, D. A.; Williams, D. H.; Gwynn, M. N.; Knowles, D. J. *Antimicrob Agents Chemother* 1995, 39, 781-5.
(22) Breukink, E.; de Kruijff, B. *Nat Rev Drug Discov* 2006, 5, 321-32.
(23) Kim, S. J.; Schaefer, J. *Biochemistry* 2008, 47, 10155-61.
(24) Nagarajan, R. *J Antibiot (Tokyo)* 1993, 46, 1181-95.
(25) Dufour, J.; Neuville, L.; Zhu, J. P. *Synlett* 2008, 2355-2359.
(26) Heller, H.; Schaefer, M.; Schulten, K. *The Journal of Physical Chemistry* 1993, 97, 8343-8360.
(27) Wang, Y.; Bruckner, R.; Stein, R. L. *Biochemistry* 2004, 43, 265-70.
(28) Baltz, R. H. *Journal of Industrial Microbiology & Biotechnology* 2006, 33, 507-13.
(29) Martinez, J. L. *Proc. Biol. Sci.* 2009, 276, 2521-30.
(30) D'Costa, V. M.; Griffiths, E.; Wright, G. D. *Curr Opin Microbiol* 2007, 10, 481-9.
(31) Allen, H. K.; Donato, J.; Wang, H. H.; Cloud-Hansen, K. A.; Davies, J.; Handelsman, J. *Nat. Rev. Microbiol.* 2010, 8, 251-9.
(32) Laskaris, P.; Tolba, S.; Calvo-Bado, L.; Wellington, L. *Environ. Microbiol.* 2010, 12, 783-96.
(33) Czaran, T. L.; Hoekstra, R. F.; Pagie, L. *Proc. Natl. Acad. Sci. U.S.A.* 2002, 99, 786-90.
(34) Lynch, M. *Proc. Natl. Acad. Sci. U.S.A.* 2007, 104 Suppl 1, 8597-604.
(35) Allen, N. E.; LeTourneau, D. L.; Hobbs, J. N., Jr. *J Antibiot (Tokyo)* 1997, 50, 677-84.
(36) Chen, L.; Yuan, Y.; Helm, J. S.; Hu, Y.; Rew, Y.; Shin, D.; Boger, D. L.; Walker, S. *J Am Chem Soc* 2004, 126, 7462-3.
(37) Cooper, M. A.; Williams, D. H. *Chem Biol* 1999, 6, 891-9.
(38) Dong, S. D.; Oberthur, M.; Losey, H. C.; Anderson, J. W.; Eggert, U.S.; Peczuh, M. W.; Walsh, C. T.; Kahne, D. *J Am Chem Soc* 2002, 124, 9064-5.
(39) Kerns, R.; Dong, S. D.; Fukuzawa, S.; Carbeck, J.; Kohler, J.; Silver, L.; Kahne, D. *Journal of the American Chemical Society* 2000, 122, 12608-12609.

(40) Mackay, J. P.; Gerhard, U.; Beauregard, D. A.; Maplestone, R. A.; Williams, D. H. *Journal of the American Chemical Society* 1994, 116, 4573-4580.
(41) Maffioli, S. I.; Ciabatti, R.; Romano, G.; Marzorati, E.; Preobrazhenskaya, M.; Pavlov, A. *Bioorg. Med. Chem. Lett.* 2005, 15, 3801-5.
(42) Nagarajan, R.; Schabel, A. A.; Occolowitz, J. L.; Counter, F. T.; Ott, J. L. *J Antibiot (Tokyo)* 1988, 41, 1430-8.
(43) Nagarajan, R.; Schabel, A. A.; Occolowitz, J. L.; Counter, F. T.; Ott, J. L.; Felty-Duckworth, A. M. *J Antibiot (Tokyo)* 1989, 42, 63-72.
(44) Rodriguez, M. J.; Snyder, N. J.; Zweifel, M. J.; Wilkie, S. C.; Stack, D. R.; Cooper, R. D.; Nicas, T. I.; Mullen, D. L.; Butler, T. F.; Thompson, R. C. *J Antibiot (Tokyo)* 1998, 51, 560-9.
(45) Sharman, G. J.; Try, A. C.; Dancer, R. J.; Cho, Y. R.; Staroske, T.; Bardsley, B.; Maguire, A. J.; Cooper, M. A.; O'Brie, D. P.; Williams, D. H. *Journal of the American Chemical Society* 1997, 119, 12041-12047.
(46) Albelo, S. T.; Domenech, C. E. *FEMS Microbiol. Lett.* 1997, 156, 271-4.
(47) Wilderman, P. J.; Vasil, A. I.; Martin, W. E.; Murphy, R. C.; Vasil, M. L. *J. Bacteriol.* 2002, 184, 4792-9.
(48) Sohlenkamp, C.; Lopez-Lara, I. M.; Geiger, O. *Prog. Lipid Res.* 2003, 42, 115-62.
(49) Cronan, J. E.; Vagelos, P. R. *Biochim. Biophys. Acta* 1972, 265, 25-60.
(50) Brundish, D. E.; Shaw, N.; Baddiley, *J. Biochem. J.* 1967, 104, 205-11.
(51) Mechin, L.; Dubois-Brissonnet, F.; Heyd, B.; Leveau, J. Y. *J. Appl. Microbiol.* 1999, 86, 859-66.
(52) Oliver, J. D.; Colwell, R. R. *Int J Syst Bacteriol* 1973, 23, 442-458.
(53) Nielsen, L. E.; Kadavy, D. R.; Rajagopal, S.; Drijber, R.; Nickerson, K. W. *Appl. Environ. Microbiol.* 2005, 71, 5171-6.
(54) De Siervo, A. J. *J. Bacteriol.* 1969, 100, 1342-9.
(55) Chatterjee, J.; Gilon, C.; Hoffman, A.; Kessler, H. *Acc Chem Res* 2008, 41, 1331-42.
(56) Conradi, R. A.; Hilgers, A. R.; Ho, N. F.; Burton, P. S. *Pharm Res* 1992, 9, 435-9.
(57) De Zotti, M.; Biondi, B.; Formaggio, F.; Toniolo, C.; Stella, L.; Park, Y.; Hahm, K. S. *J Pept Sci* 2009, 15, 615-9.
(58) Walsh, C. T.; Chen, H.; Keating, T. A.; Hubbard, B. K.; Losey, H. C.; Luo, L.; Marshall, C. G.; Miller, D. A.; Patel, H. M. *Curr Opin Chem Biol* 2001, 5, 525-34.

Methods of Preparation

Compounds of the invention can be prepared either by semi-synthesis starting with an arylomycin compound isolated from a fermentation procedure, or by total chemical synthesis. Procedures are provided herein that, in combination with the knowledge of the synthetic organic chemist of ordinary skill in the art, can be used to prepare the full range of compounds of the invention as disclosed and claimed herein.

Total Chemical Synthesis

For total synthesis, a retrosynthetic analysis was carried out, as shown in Scheme 1.

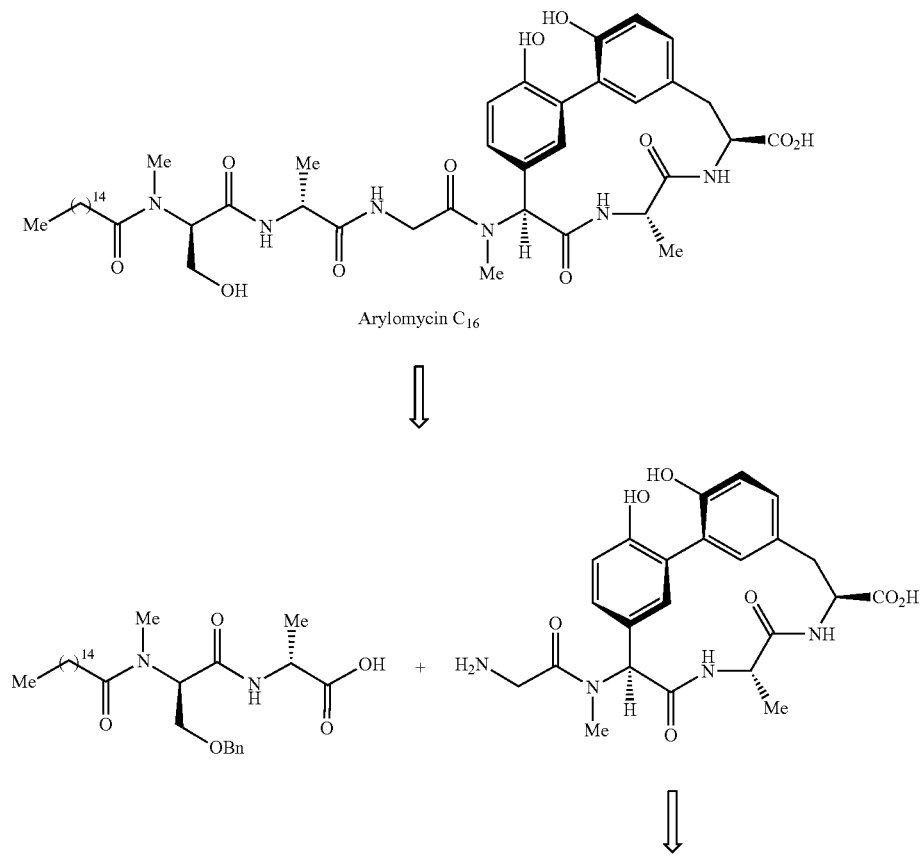

Scheme 1. Retrosynthesis of Arylomycin C16

-continued

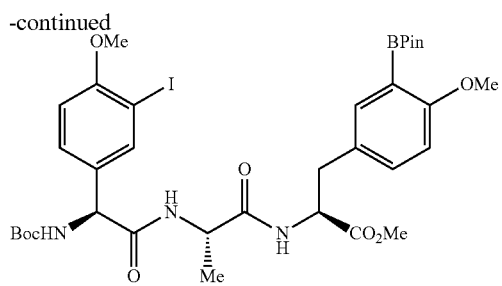

Arylomycin derivatives can be synthesized synthesized by synthesizing tripeptides by solution phase peptide couplings and then cyclization via Suzuki-Miyaura macrocyclization (the final step shown in the above retrosynthetic analysis).

Alternatively, natural product arylomycins can provide a core for further synthetic elaboration in some cases, depending upon the desired substituent pattern.

Starting with a cyclic core, for example by a total synthesis approach as shown above and exemplified in the Examples section, below, the exocyclic peptide/peptidomimetic domain, and the lipophilic tail domain, can be elaborated using approaches and methods described herein and those within the knowledge of the person of ordinary skill. See, for example, T. Roberts, et al. (2007), *J. Am. Chem. Soc.* 129, 15830-15838; Dufour, J.; Neuville, L.; Zhu, J. P. *Synlett* 2008, 2355-2359.

The various lipopeptide tails can be assembled via solution phase peptide couplings and then coupling to the macrocyclic core. The molecule can be considered to include three major domains: the cyclic core, an exocyclic peptide or peptidomimetic moiety, and a lipophilic tail moiety. In the natural product arylomycins, such as arylomycin A2, the lipophilic tail is an n-alkanoyl, isoalkanoyl, or anteisoalkanoyl acyl group; in compounds of the invention groups are introduced into the lipophilic tail that are adapted to provide a more favorable binding interaction of the inventive arylomycin analog with an SPase including a proline residue at the −5 and −7 position relative to the catalytic SPase serine residue, as shown in the X-ray crystal structure of arylomycin bound to a fragment of a resistant form of SPase, shown in FIG. 3A. As discussed above, the presence of a proline residue at one of these positions has been found by the inventors herein to provide resistance of the SPase to inhibition by natural product arylomycins such as arylomycin A2. The inventive compounds can overcome this resistance by designing the lipophilic tail to bind more effectively to SPase forms having the proline residue(s).

The $R^5$ group can be bonded to the exocyclic peptide moiety via acyl, carbamate, or urea linkages, which can be formed as described below, for the three classes of linkages.

For compounds where the $R^5$ linkage to the peptide is an amide bond, and wherein the aromatic ring is connected directly to the carbonyl group of the amide, these compounds can be synthesized by coupling of commercially available benzoic acids or heterocyclic acids that had been substituted by electrophilic or nucleophilic aromatic substitution or palladium catalyzed processes (and appropriately protected using standard protecting groups[S1]) to the N-terminus of the peptide chain. Heterocycles where the commercially available acids are not available will be synthesized via any one of a number of methods for synthesizing pyridines, pyrazines, pyrimidines or pyradizines[S2].

For compounds where the linkage of $R^5$ to the exocyclic peptide is an amide bond, and where the aromatic ring is not connected directly to the carbonyl group of the amide, these compounds can be synthesized via the scheme:

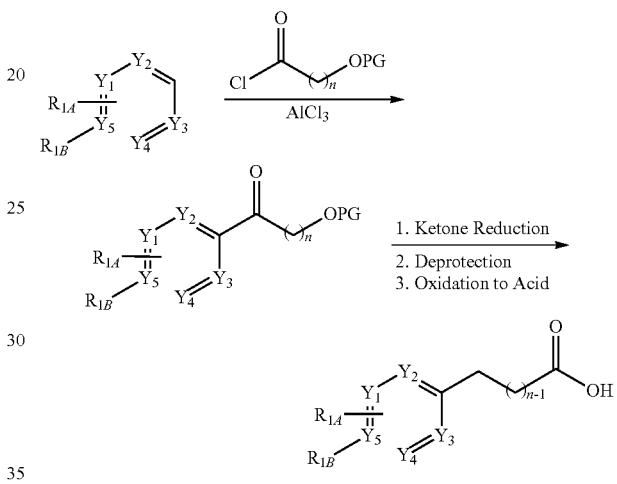

Appropriately functionalized or unfunctionalized aryl rings (appropriately protected using standard protecting groups[S1]) will be subjected to Friedel-Crafts acylation conditions with an alkyl chain bearing an acid chloride and a protected hydroxyl group. The ketone is then reduced, the protected hydroxyl group is deprotected, the hydroxyl is oxidized to an acid and the resulting acid is coupled to the N-terminus of the peptide.

For compounds where the $R^5$ linkage to the peptide is a carbamate and the aryl ring is not attached directly to the carbamate, functionalized phenols (appropriately protected using standard protecting groups[S1]) can be treated with phosgene to create the aryl carbamoyl chloride which can then be used to acylate the N-terminus of the peptide. Functionalized or unfunctionalized aryl rings will be subjected to Friedel-Crafts acylation conditions with an alkyl chain bearing an acid chloride and a protected hydroxyl group. The ketone of the resulting compound will be reduced and the protecting group will be removed. The compound will then be treated with phosgene to form the carbamoyl chloride[S3] and this compound will be used to acylate the N-terminus of the peptide as shown in the scheme:

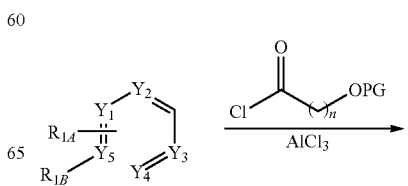

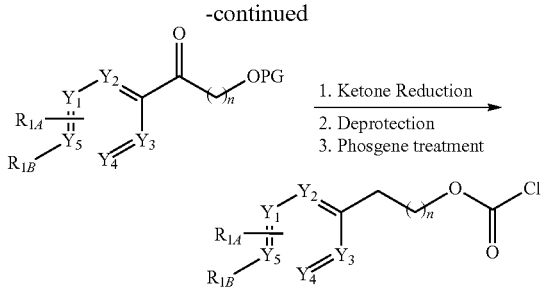

Heterocycles where Friedel-Crafts acylations are not possible will be halogenated (and appropriately protected using standard protecting groups$^{S1}$) and the appropriate length hydrocarbon chain terminated on one end with a protected alcohol and the other end with a halogen or boronic acid/ester will be attached via palladium mediated coupling.

For compounds where the $R^5$ linkage to the peptide is a urea and the aryl ring is attached directly to the nitrogen atom, functionalized aryl amines will be treated with phosgene to create the aryl ureayl chloride which will then be used to acylate the N-terminus of the peptide.

For compounds where the $R^5$ linkage to the peptide is a urea and the aryl ring is not attached directly to the carbamate, the compounds will be synthesized via the scheme:

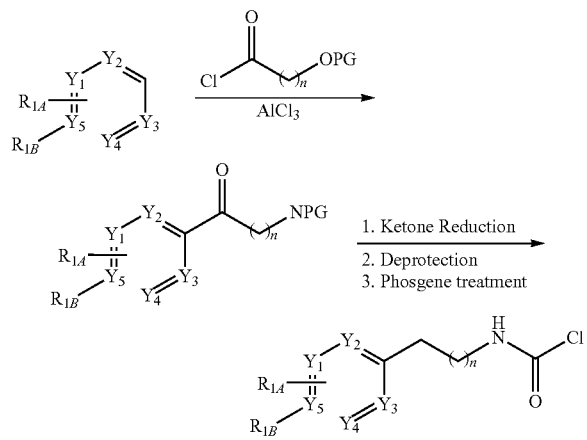

Appropriately functionalized or unfunctionalized aryl rings (and appropriately protected using standard protecting groups$^{S1}$) will be subjected to Friedel-Crafts acylation conditions with an alkyl chain bearing an acid chloride and a protected amine. The ketone of the resulting compound will be reduced and the protecting group will be removed. The compound will then be treated with phosgene to form the ureayl chloride$^{S4}$ and this compound will be used to acylate the N-terminus of the peptide. Heterocycles where Friedel-Crafts acylations are not possible are halogenated (and appropriately protected using standard protecting groups$^{S1}$) and an appropriate length hydrocarbon chain terminated on one end with a protected amine and the other end with a halogen or boronic acid/ester will be attached via palladium mediated coupling.

The various embodiments of compounds of the invention with the variants of the $R^5$ group can be synthesized using the above approaches, in conjunction with ordinary knowledge concerning the use of any protecting or blocking groups that may be necessary. See, for example, Protective Groups in Organic Synthesis, Greene, T. W.; Wuts, P. G. M., John Wiley & Sons, New York, N.Y., (3rd Edition, 1999).

In various embodiments of the invention, $R^5$ can be straight chain or branched chain alkyl, wherein the chain can include any of the following groups (A)-(E). Synthetic approaches appropriate for each class of $R^5$ group are provided.

(A)

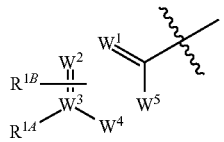

wherein $W^1$, $W^2$, $W^3$, $W^4$ and $W^5$ are each independently C or N, provided that no more than two of $W^1$, $W^2$, $W^3$, $W^4$ and $W^5$ are N; provided that when $R^{1A}$ or $R^{1B}$ is non-hydrogen, any W atom to which the $R^{1A}$ or $R^{1B}$ is respectively bonded is C, wherein there can be one or more $R^{1B}$ bonded to the ring bearing the W atoms; $R^{1A}$ is hydrogen, halogen, amino, hydroxyl, aminocarbonyl, hydroxycarbonyl, nitro, fluoroalkyl, cyano, ($C_1$-$C_6$)-thioether, fluoroalkoxy, ($C_1$-$C_6$)-alkyl, ($C_1$-$C_6$)-alkoxy, ($C_1$-$C_6$)-mono- or di-alkylamino, ($C_1$-$C_6$)-alkyl, 5- to 7-membered heteroaryl, 5- to 7-membered heterocyclyl, or ($C_6$-$C_{10}$) aryl; $R^{1B}$ is hydrogen, alkyl, halogen, amino, hydroxyl, aminocarbonyl, hydroxycarbonyl, nitro, fluoroalkyl, ($C_1$-$C_6$)-thioalkyl, fluoroalkoxy, cyano, ($C_1$-$C_6$)-alkyl, ($C_1$-$C_6$)-alkoxy, ($C_1$-$C_6$)-alkylamino, ($C_1$-$C_6$)-alkyl, 5- to 7-membered heteroaryl, 5- to 7-membered heterocyclyl, or ($C_6$-$C_{10}$) aryl; wherein any $R^{1A}$ or $R^{1B}$ can be further substituted with one to three ($C_1$-$C_{12}$)-alkyl or -alkoxy groups, which can further bear halogen, amino, hydroxyl, aminocarbonyl, hydroxycarbonyl, nitro, fluoroalkyl, ($C_1$-$C_6$)-thioalkyl, fluoroalkoxy, cyano, ($C_1$-$C_6$)-alkyl, ($C_1$-$C_6$)-alkoxy, ($C_1$-$C_6$)-alkylamino, ($C_1$-$C_6$)-alkyl, 5- to 7-membered heteroaryl, 5- to 7-membered heterocyclyl, or ($C_6$-$C_{10}$) aryl groups; wherein a wavy line indicates a point of attachment.

For compounds where the $R^5$ linkage to the peptide is an acyl group and where the aromatic ring is connected directly to the acyl group these compounds can be synthesized by peptide coupling of commercially available benzoic or heterocyclic acids that had been substituted by electrophilic aromatic substitution, nucleophilic aromatic substitution or palladium catalyzed processes (and appropriately protected using standard protecting groups$^{S1}$) to the N-terminus of the peptide chain. Heterocycles where the commercially available acids are not available can be synthesized via any one of a number of methods for synthesizing pyridines, pyrazines, pyrimidines or pyradizines$^{S2}$.

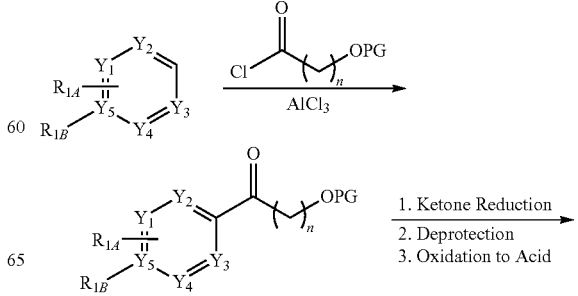

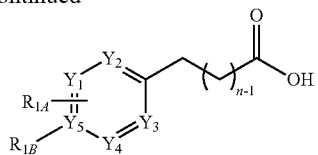

For compounds where the $R^5$ linkage to the peptide is an acyl group and where the aromatic ring is not connected directly to the acyl group, these compounds can be synthesized via the above scheme. Appropriately functionalized or unfunctionalized aryl rings (appropriately protected using standard protecting groups$^{S1}$) can be subjected to Friedel-Crafts acylation conditions with an alkyl chain bearing an acid chloride and a protected hydroxyl group. The ketone can then be reduced, the protected hydroxyl group deprotected, the hydroxyl oxidized to an acid, and the resulting acid coupled to the N-terminus of the peptide.

For compounds where the $R^5$ linkage to the peptide is a carbamate and the aryl ring is attached directly to the carbamate, functionalized phenols (appropriately protected using standard protecting groups$^{S1}$) can be treated with phosgene to create the aryl carbamoyl chloride which can then be used to acylate the N-terminus of the peptide.

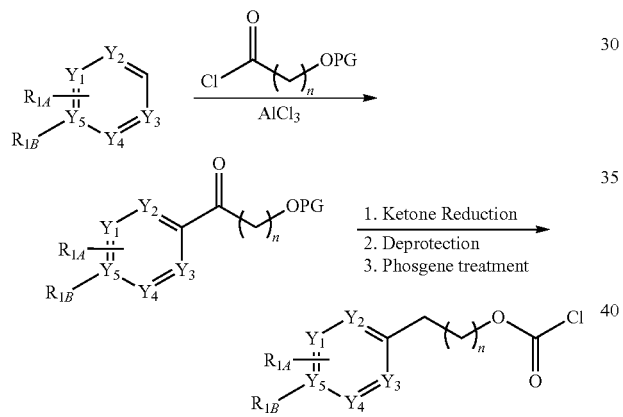

For compounds where the $R^5$ linkage to the peptide is a carbamate and the aryl ring is not attached directly to the carbamate, the compounds can be synthesized via the route shown in the above scheme. Appropriately functionalized benzenes (appropriately protected using standard protecting groups$^{S1}$) can be subjected to Friedel-Crafts acylation conditions with an alkyl chain bearing an acid chloride and a protected hydroxyl group. The ketone of the resulting compound can be reduced and the protecting group removed. The compound can then be treated with phosgene to form the carbamoyl chloride$^{S3}$ and this compound can be used to acylate the N-terminus of the peptide. Heterocycles where Friedel-Crafts acylations are not possible can be halogenated (and appropriately protected using standard protecting groups$^{S1}$) and the appropriate length hydrocarbon chain terminated on one end with a protected alcohol and the other end with a halogen or boronic acid/ester can be attached via palladium mediated coupling.

For compounds where the $R^5$ linkage to the peptide is a urea and the aryl ring is attached directly to the carbamate, functionalized aryl amines can be treated with phosgene to create the aryl ureayl chloride which can then be used to acylate the N-terminus of the peptide.

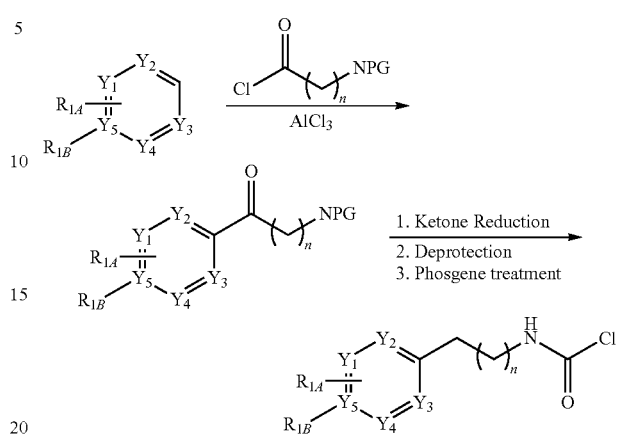

For compounds where the $R^5$ linkage to the peptide is a urea and the aryl ring is not attached directly to the carbamate, the compounds can be synthesized via the route shown in the above scheme. Appropriately functionalized can be subjected to Friedel-Crafts acylation conditions with an alkyl chain bearing an acid chloride and a protected amine. The ketone of the resulting compound can be reduced and the protecting group be removed. The compound can then be treated with phosgene to form the ureayl chloride$^{S4}$ and this compound can be used to acylate the N-terminus of the peptide. Heterocycles where Friedel-Crafts acylations are not possible can be halogenated (and appropriately protected using standard protecting groups$^{S1}$) and an appropriate length hydrocarbon chain terminated on one end with a protected amine and the other end with a halogen or boronic acid/ester attached via palladium mediated coupling.

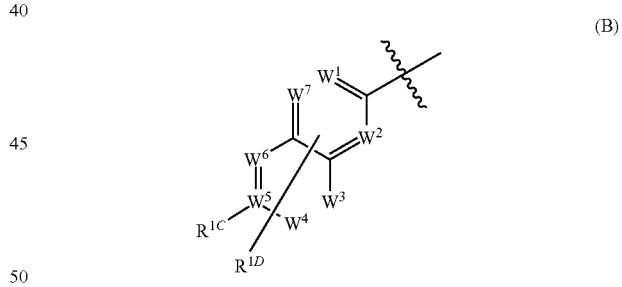

(B)

wherein $W^1$, $W^2$, $W^3$, $W^4$, $W^5$, $W^6$, and $W^7$ are each independently C or N, provided than no more than three of $W^1$, $W^2$, $W^3$, $W^4$, $W^5$, $W^6$, and $W^7$ are N; provided that when $R^{1C}$ or $R^{1D}$ is non-hydrogen, any W atom to which the $R^{1C}$ or $R^{1D}$ is respectively bonded is C, wherein either ring can bear one or more $R^{1D}$; $R^{1C}$ is hydrogen, halogen, amino, hydroxyl, aminocarbonyl, hydroxycarbonyl, nitro, fluoroalkyl, ($C_1$-$C_6$)-thioalkyl, fluoroalkoxy, cyano, ($C_1$-$C_6$)-alkyl, ($C_1$-$C_6$)-alkoxy, ($C_1$-$C_6$)-mono- or di-alkylamino, ($C_1$-$C_6$)-alkyl, 5- to 7-membered heteroaryl, 5- to 7-membered heterocyclyl, or ($C_6$-$C_{10}$) aryl; RID is hydrogen, alkyl, halogen, amino, hydroxyl, aminocarbonyl, hydroxycarbonyl, nitro, fluoroalkyl, ($C_1$-$C_6$)-thioalkyl, fluoroalkoxy, cyano, ($C_1$-$C_6$)-alkyl, ($C_1$-$C_6$)-alkoxy, ($C_1$-$C_6$)-mono- or di-alkylamino, ($C_1$-$C_6$)-alkyl, 5- to 7-membered heteroaryl, 5- to 7-membered heterocyclyl, or ($C_6$-$C_{10}$) aryl; wherein any $R^{1C}$ or $R^{1D}$ can be further substituted with one to three ($C_1$-$C_{12}$)-alkyl or -alkoxy groups, which can further bear halogen, amino, hydroxyl, aminocarbonyl, hydroxycarbonyl, nitro, fluoroalkyl, ($C_1$-$C_6$) thioalkyl, fluoroalkoxy, cyano, ($C_1$-$C_6$)-alkyl, ($C_1$-$C_6$)-alkoxy, ($C_1$-$C_6$)-mono- or di-alkylamino, ($C_1$-$C_6$)-alkyl, 5- to 7-membered heteroaryl, 5- to 7-membered heterocyclyl, or ($C_6$-$C_{10}$) aryl; wherein a wavy line indicates a point of attachment.

For compounds where the $R^5$ linkage to the peptide is an acyl group and where the aromatic rings are connected directly to the acyl group these compounds can be synthesized by peptide coupling of commercially available heterocyclic acids that are substituted by electrophilic aromatic substitution, nucleophilic aromatic substitution, heteroaryllithium formation or palladium catalyzed processes (and appropriately protected using standard protecting groups[S1]) to the N-terminus of the peptide chain. Heterocycles where the commercially available acids are not available can be synthesized via any one of a number of methods for synthesizing quinolines, isoquinolines, quinazolines, quinoxalines or 1,8-napthyridines[S2].

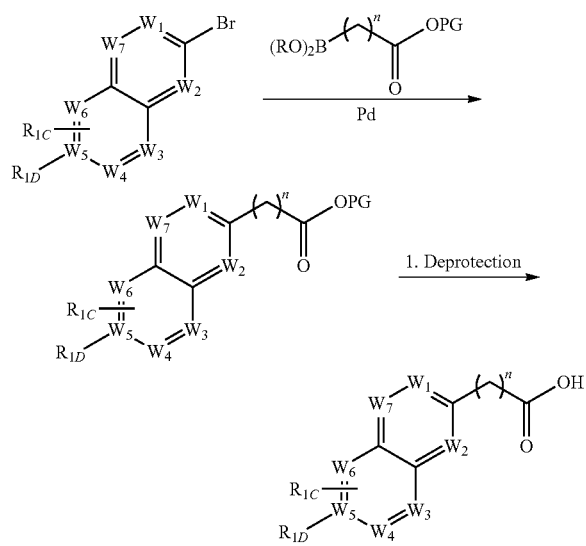

For compounds where the $R^5$ linkage to the peptide is an acyl group and where the aromatic ring is not connected directly to the acyl group, these compounds can be synthesized via the above scheme. Halogenated and appropriately functionalized or unfunctionalized aryl rings (appropriately protected using standard protecting groups[S1]) and an appropriate length hydrocarbon chain terminated on one end with a protected carboxylate and the other end with a halogen or boronic acid/ester can be attached via palladium mediated coupling For compounds where the $R^5$ linkage to the peptide is a carbamate and the aryl rings are attached directly to the carbamate, these compounds can be by peptide coupling of commercially available heterocyclic alcohols that are substituted by electrophilic aromatic substitution, nucleophilic aromatic substitution, heteroaryllithium formation or palladium catalyzed processes (and appropriately protected using standard protecting groups[S1]) to the N-terminus of the peptide chain. Heterocycles where the commercially available alcohols are not available can be synthesized via any one of a number of methods for synthesizing quinolines, isoquinolines, quinazolines, quinoxalines or 1,8-napthyridines[S2].

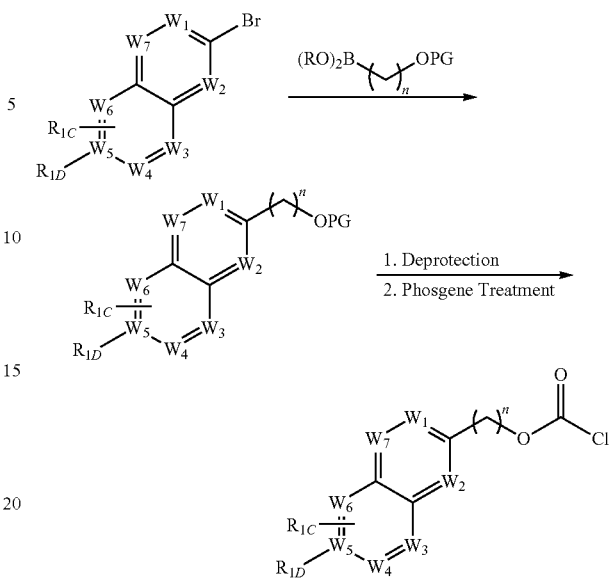

For compounds where the $R^5$ linkage to the peptide is a carbamate and the aryl rings are not attached directly to the carbamate, these compounds an be synthesized via the above scheme. Halogenated and appropriately functionalized or unfunctionalized aryl rings (appropriately protected using standard protecting groups[S1]) and an appropriate length hydrocarbon chain terminated on one end with a protected alcohol and the other end with a halogen or boronic acid/ester can be attached via palladium mediated coupling. The alcohol can then be deprotected, the compound treated with phosgene and the resulting carbamoyl chloride used to acylate the N-terminus of the peptide.

For compounds where the $R^5$ linkage to the peptide is a urea and the aryl rings are attached directly to the urea, these compounds can be synthesized by peptide coupling of commercially available heterocyclic amines that are substituted by electrophilic aromatic substitution, nucleophilic aromatic substitution, heteroaryllithium formation or palladium catalyzed processes (and appropriately protected using standard protecting groups[S1]) then treated with phosgene[S4] to the N-terminus of the peptide chain. Heterocycles where the commercially available amines are not available can be synthesized via any one of a number of methods for synthesizing quinolines, isoquinolines, quinazolines, quinoxalines or 1,8-napthyridines[S2].

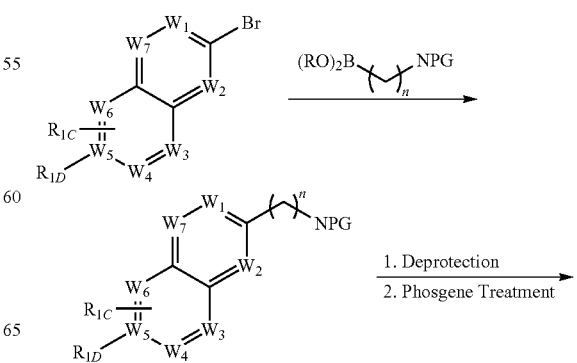

-continued

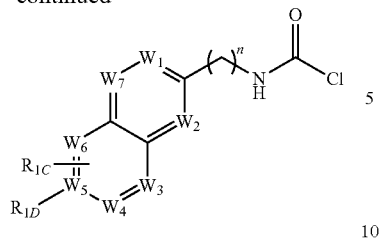

For compounds where the $R^5$ linkage to the peptide is a urea and the aryl rings are not attached directly to the urea, these compounds can be synthesized via the above scheme. Halogenated and appropriately functionalized or unfunctionalized aryl rings (appropriately protected using standard protecting groups[S1]) and an appropriate length hydrocarbon chain terminated on one end with a protected amine and the other end with a halogen or boronic acid/ester can be attached via palladium mediated coupling. The amine can then be deprotected, the compound will be treated with phosgene and the resulting carbamoyl chloride used to acylate the N-terminus of the peptide.

(C)

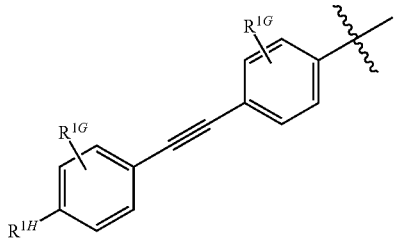

wherein Z is O, S, NH or $CH_2$; $R^E$ at each occurrence is independently hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; $R^{1F}$ is hydrogen or alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heterocyclyl, or $(C_6-C_{10})$ aryl; wherein any $R^{1E}$ or $R^{1F}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$ thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein a wavy line indicates a point of attachment.

In addition to the procedures outlined above for attachment to the peptide, compounds of this functionality are synthesized by employment of the Buchwald-Hartwig coupling conditions[S5] when Z=O or N. Where a para-halogen substituted protected benzoic acid, homologated benzoic acid or precursor is coupled with a phenol functionalized by electrophilic or nucleophilic aromatic substitution or palladium catalyzed processes (and appropriately protected using standard protecting groups[S1]). When Z=S these compounds can be formed using transition metal catalyzed couplings of a para-halogen substituted protected benzoic acid, homologated benzoic acid or precursor combined with an appropriately functionalized thiophenol.

(D)

wherein $R^{1G}$ at each occurrence is independently hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; $R^{1H}$ is hydrogen or alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein any $R^{1G}$ or $R^{1H}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein a wavy line indicates a point of attachment.

In addition to the procedures outlined above for attachment to the peptide, compounds of this functionality can be synthesized by employment of Sonagashira reaction conditions[S6] on a para-halogen substituted protected benzoic acid, homologated benzoic acid or precursor combined with the appropriately functionalized by electrophilic or nucleophilic aromatic substitution or palladium catalyzed processes (and appropriately protected using standard protecting groups[S1]) aryl acetylene as shown in the below scheme.

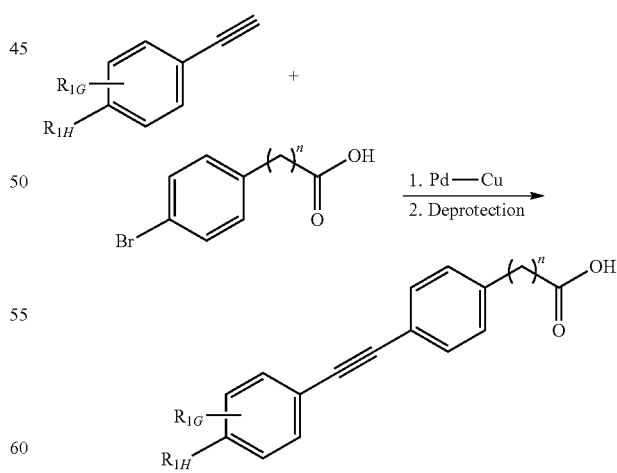

The peptidic tail can be assembled analogously to procedures described herein using standard solution or solid phase peptide couplings. Constituent amino acids containing substituents at the $R^{A3}$, $R^{A4}$, and $R^{A5}$ positions, and the groups of formulas (IIA), (IIB), and (IIC), can either be purchased commercially or synthesized via amino acid synthesis procedures described in the literature[S7-S9].

Peptidic tails where any $R^4$ or $R^6$ are not hydrogen can be assembled using literature protocols for peptide-peptoid conjugates[S10]. The monomers can be synthesized using amine alkylation protocols[S11] for example an amino acid with a protected carboxylate is protected at the amine with a nosyl group, the nosylated amine is selectively alkylated with base and an electrophile and the nosyl group is deprotected by thiolate anion.

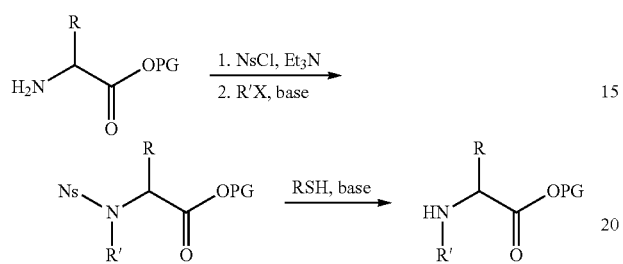

Where m, n1, or n2 are either 0 or 1, amino acids building blocks where m, n1, and n2 are equal to 1 are commercially available or can be synthesized via methods found in the literature[S12], for example from succinates where one acid is protected with a carboxyl protecting group and the other attached to a chiral auxiliary which then allows asymmetric monoalkylation. The protected carboxyl can then be deprotected and transformed into an amine via a Curtius rearrangement followed by cleavage of the chiral auxiliary with peroxide.

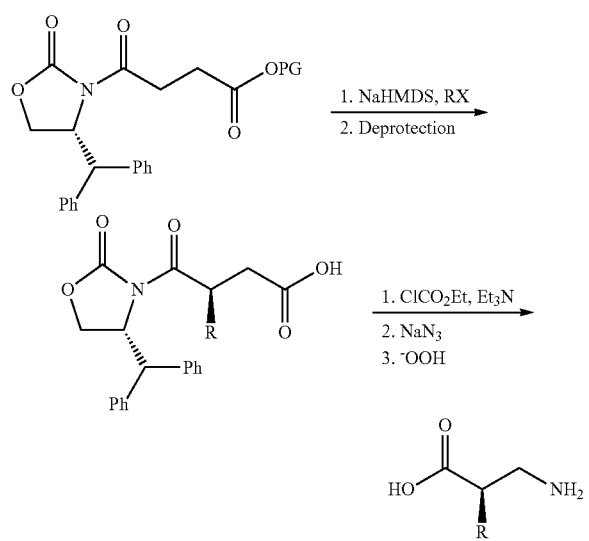

Where m, n1, and n2 are 0, 1 or 2, amino acids building blocks where m, n1, and n2 are equal to 1 or 2 can be synthesized analogously wherein the differentially protected aspartic or glutamic acid is functionalized at the free carboxylate attached to the alpha carbon by any number of strategies including but not limited to peptide coupling, reduction whereby the acid can be converted to a functionalized ketone via a Weinreb amide or reduction whereby the acid is converted to an alcohol that is subsequently converted to a tosylate and either displaced by a nucleophile or coupled to another aryl or alkyl group via a palladium mediated process:

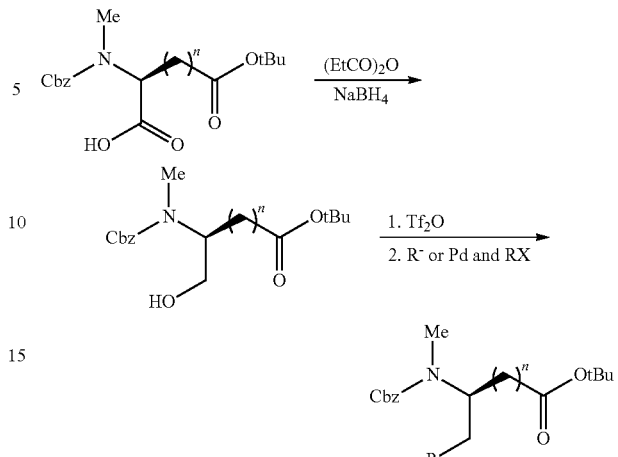

These amino acids can be synthesized via protocols found in the literature[S12-S13] for example Arndt Eistert homologation(s) as shown in the below scheme.

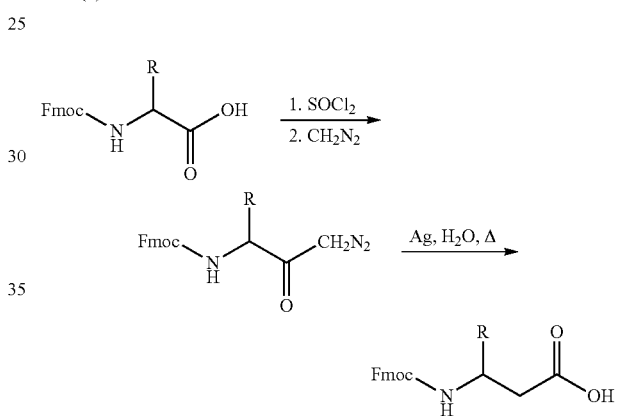

Amino acids building blocks for the synthesis of compounds where $R^2$ and $R^3$ are each independently not hydrogen can either be purchased commercially or can be synthesized via amino acid synthesis procedures described in the literatures[S7-S9,S14] and appropriately protected using standard protecting groups[S1].

Where $OG^1$ and $OG^2$ hydroxyl, O-alkyl, or O-glycosyl, compounds can be synthesized by protocols developed for synthesis of the arylomycin natural product[S15].

Where $R^{41}$ is not hydrogen can be synthesized by the methods described for the synthesis of the arylomycin macrocycle. The tyrosine derivatives required as building blocks for that synthesis can be synthesized as described by Michaux et. al.[S16] and the references described therein. A Horner Wadsworth Emmons reaction can be used, followed by halogenations of the alkene Suzuki coupling of the desired substituent and asymmetric catalytic hydrogenation to the desired tyrosine derivative.

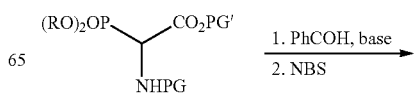

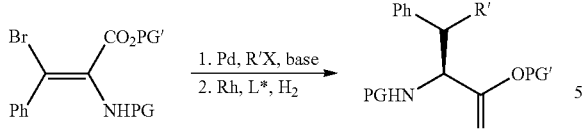

Where $R^{42}$ is not hydrogen, compounds can be synthesized using protocols for the synthesis of the natural product and protocols for peptide coupling of disubstituted amino acids[S17]. The amino acid building blocks can be synthesized by literature protocols[S18]. For example the amino and carboxyl groups of an appropriately protected tyrosine can be condensed with benzaldehyde to form an oxazolidinone which can then be asymmetrically alkylated with strong base and an electrophile and hydrolyzed to yield the substituted tyrosine derivative[S19].

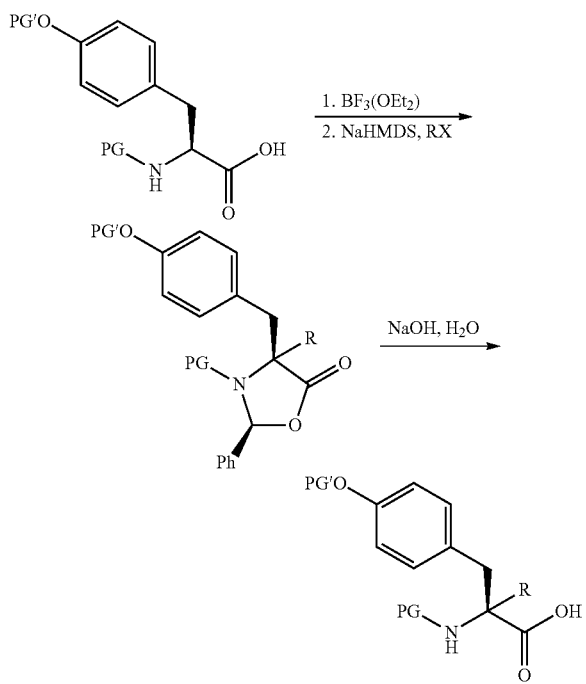

Compounds where a carbonyl group is directly attached to the scaffold at B can be synthesized from the fully deprotected arylomycin. Peptide coupling to an amino acid where the carboxylate is replaced by a protected or unprotected electrophilic moiety can install the aldehydes[S20], boronic acids/esters[S21] and phosphonates[S22]. Azetidinones that are attached to the arylomycin through an amine at the 3-position of the azetidinone ring can be synthesized via peptide coupling of the amine of the azetidinone to the carboxylate of arylomycin[S23] Azetidinones that are attached to the arylomycin through the cyclic nitrogen can be synthesized by peptide coupling of the cyclic NH to the arylomycin carboxylate[S24]. The azetidinone building blocks can be synthesized via literature protocols[S25-S26].

(S1) Wuts, P. G. M.; Greene, T. W. *Greene's protective groups in organic synthesis;* 4th ed.; Wiley-Interscience: Hoboken, N.J., 2007.

(S2) Joule, J. A.; Mills, K. *Heterocyclic chemistry;* 4th ed.; Blackwell Science: Oxford; Malden, Mass., 2000.

(S3) Shin, D.-S.; Lee, Y.-S. *Synlett* 2009, 2009, 3307.

(S4) Musser, J. H.; Chakraborty, U.; Bailey, K.; Sciortino, S.; Whyzmuzis, C.; Amin, D.; Sutherland, C. A. *Journal of Medicinal Chemistry* 1987, 30, 62.

(S5) Hartwig, J. F. *Angew Chem Int Edit* 1998, 37, 2047.

(S6) Sonogashira, K. *J Organomet Chem* 2002, 653, 46.

(S7) Nájera, C.; Sansano, J. M. *Chemical Reviews* 2007, 107, 4584.

(S8) Maruoka, K.; Ooi, T. *Chemical Reviews* 2003, 103, 3013.

(S9) Easton, C. J. *Chemical Reviews* 1997, 97, 53.

(S10) Olsen, C. A. *ChemBioChem* 2010, 11, 152.

(S11) Kan, T.; Fukuyama, T. *Chemical Communications* 2004, 353.

(S12) Liu, M.; Sibi, M. P. *Tetrahedron* 2002, 58, 7991.

(S13) Lelais, G.; Seebach, D. *Peptide Science* 2004, 76, 206.

(S14) Williams, R. M.; Hendrix, J. A. *Chemical Reviews* 1992, 92, 889.

(S15) Roberts, T. C.; Smith, P. A.; Cirz, R. T.; Romesberg, F. E. *J Am Chem Soc* 2007, 129, 15830.

(S16) Michaux, J.; Niel, G.; Campagne, J.-M. *Chemical Society Reviews* 2009, 38, 2093.

(S17) Humphrey, J. M.; Chamberlin, A. R. *Chemical Reviews* 1997, 97, 2243.

(S18) Ohfune, Y.; Shinada, T. *European Journal of Organic Chemistry* 2005, 2005, 5127.

(S19) Aberle, N.; Ovenden, S. P. B.; Lessene, G.; Watson, K. G.; Smith, B. J. *Tetrahedron Letters* 2007, 48, 2199.

(S20) Zhang, X.; Rodrigues, J.; Evans, L.; Hinkle, B.; Ballantyne, L.; Pena, M. *The Journal of Organic Chemistry* 1997, 62, 6420.

(S21) Zhu, Y.; Yao, S.; Xu, B.; Ge, Z.; Cui, J.; Cheng, T.; L1, R. *Bioorganic & Medicinal Chemistry* 2009, 17, 6851.

(S22) Sienczyk, M.; Lesner, A.; Wysocka, M.; Legowska, A.; Pietrusewicz, E.; Rolka, K.; Oleksyszyn, J. *Bioorganic & Medicinal Chemistry* 2008, 16, 8863.

(S23) Setti, E. L.; Davis, D.; Janc, J. W.; Jeffery, D. A.; Cheung, H.; Yu, W. *Bioorganic & Medicinal Chemistry Letters* 2005, 15, 1529.

(S24) Vidya, R.; Eggen, M.; Nair, S. K.; Georg, G. I.; Himes, R. H. *The Journal of Organic Chemistry* 2003, 68, 9687.

(S25) Brandi, A.; Cicchi, S.; Cordero, F. M. *Chemical Reviews* 2008, 108, 3988.

(S26) Magriotis, P. A. *Angewandte Chemie International Edition* 2001, 40, 4377.

Semisynthesis

Compounds of the invention can also be prepared by semisynthesis, that is, through synthetic conversions applied to arylomycin compounds isoloated from natural sources such as fermentation broths or in vitro biosynthesis systems.

It is known in the art that the natural product arylomycin, such as arylomycin A2, can be isolated and purified from its microbial source.[N1-N2] The natural product can then be treated with a 50:50 mixture of trifluoroacetic acid and $CH_2Cl_2$ to cleave off the n-terminal lipid and N-Me serine residue leaving a free amine, as shown below. When the arylomycin starting material is in the A series, X is hydrogen, and when the arylomycin starting material is in the B series, X is nitro.

75

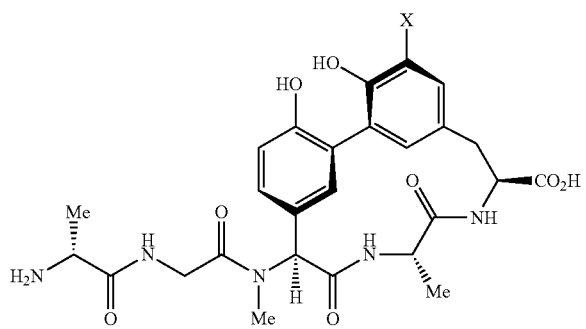

The resulting free amine can then either be coupled to a new N-alkyl amino acid and lipid tail or protected with a nosyl group, selectively methylated, denosylated[N3], acetylated and treated again with a 50:50 mixture of trifluoroacetic acid and CH$_2$Cl$_2$ to cleave off the N-terminal alanine.

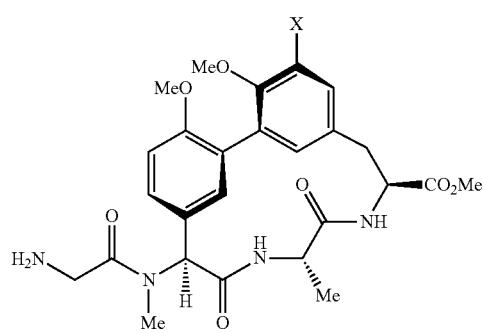

The free amine of the alanine cleaved compound can then be alkylated, if desired, then coupled to an appropriately functionalized and protected lipodipeptide tail and globally deprotected[N4] (scheme 2, below).

Scheme 2: Semisynthetic Precursor Preparation and Elaboration

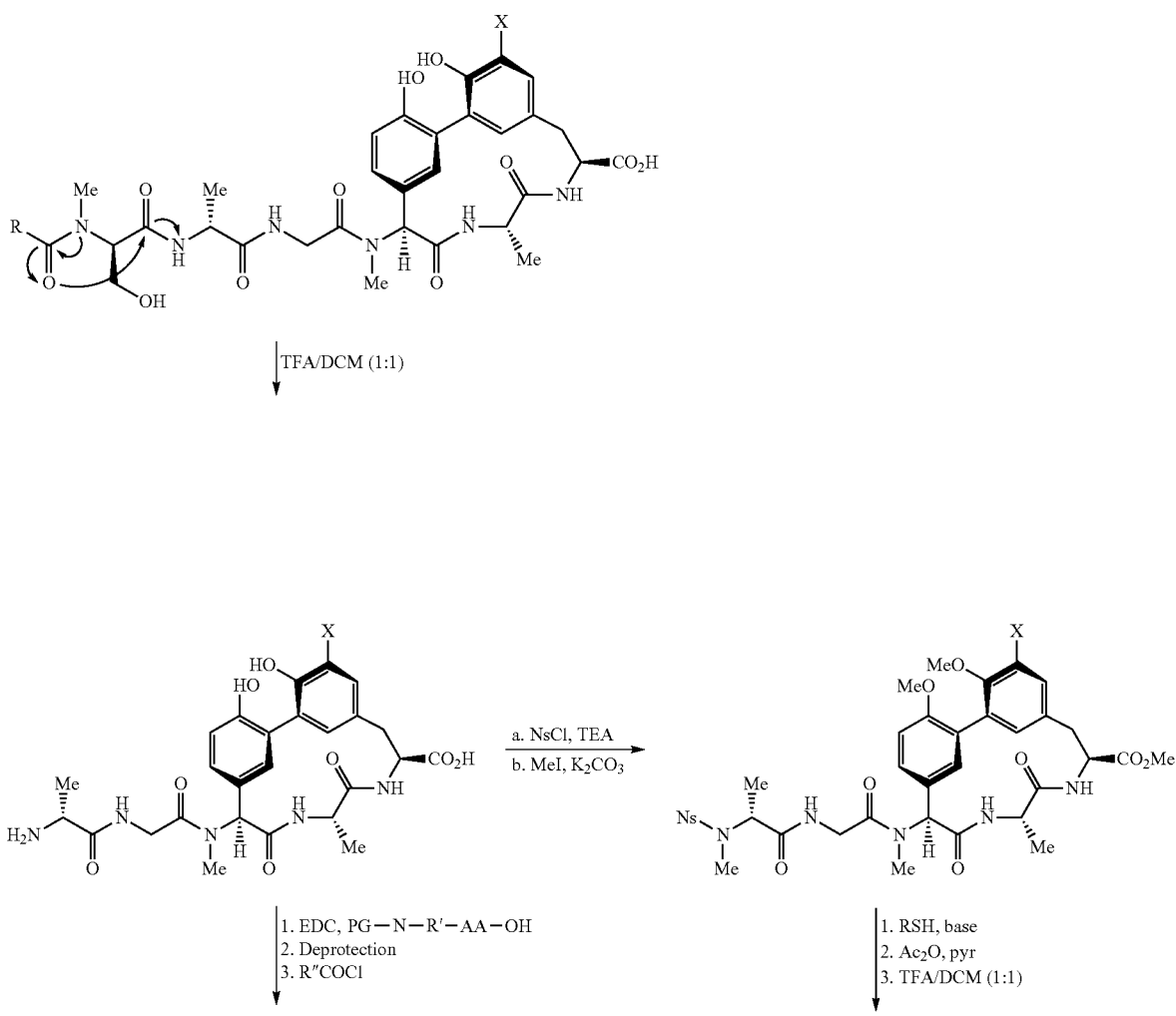

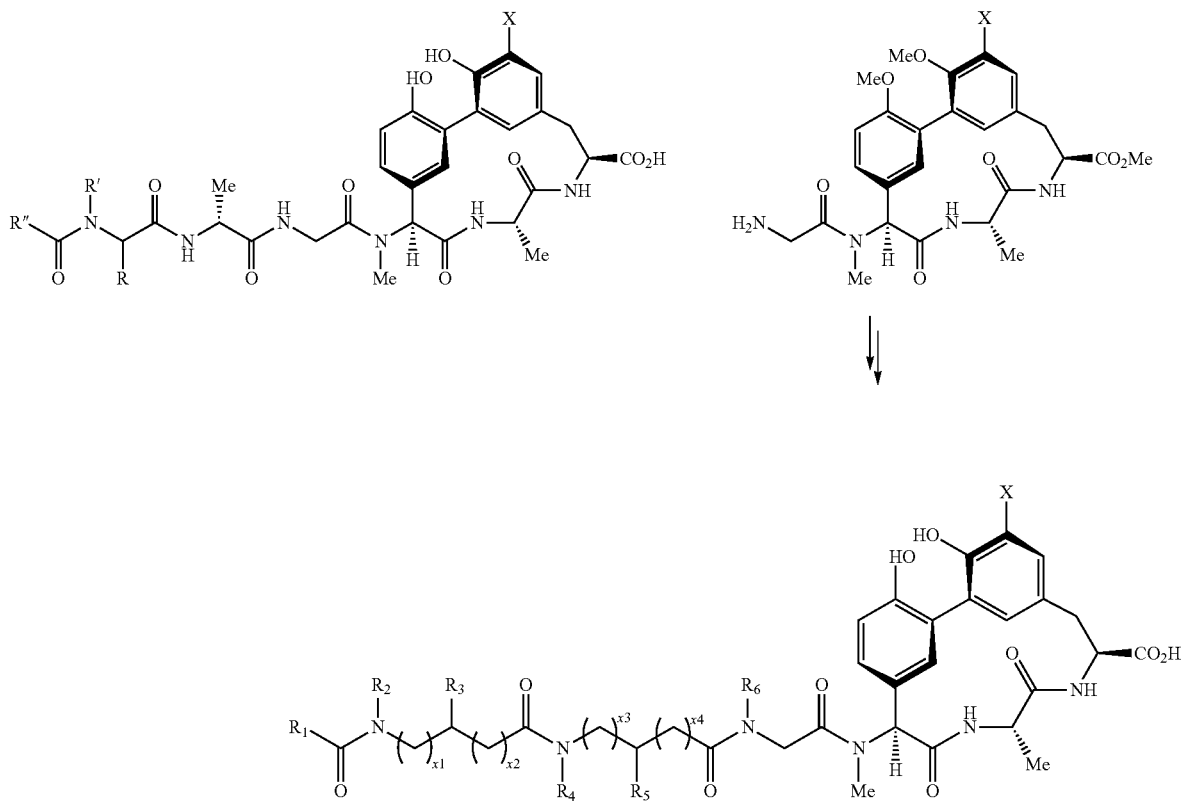

The isolated natural product of the arylomycin B series bears a nitro group on the tyrosine[N1-N2], so the free amine that is the result of TFA mediated cleavage of the lipid tail and N-terminal serine of this compound, or the free amine that is the result of cleavage of the lipid tail and the N-terminal serine and alanine residues of this compound, contain a nitro functionality that can then be used to prepare other modifications of the tyrosine ring and, due to the nitro deactivation of the tyrosine ring, of the hydroxyphenylglycine ring as well. After protection or deprotection with the appropriate protecting groups[N5] the nitro compounds of the arylomycin B derivatives can be selectively iodinated ortho to the hydroxyl of the hydroxyphenylglycine residue. This compound can then be functionalized to install numerous chemical groups selectively on the hydroxyphenylglycine ring using, for example, palladium mediated coupling[N6]. For further functionalization of the tyrosine ring, after appropriate protection or deprotection, the nitro group can be reduced to an amine and converted into a diazo salt[N7]. This compound can be subsequently functionalized via the Sandmeyer reaction[N8] to yield a variety of different functional groups. The resulting compound can then be attached to a lipopeptide tail via peptide coupling, then globally deprotected[N4] (scheme 3, below).

Documents Cited (N1) Schimana, J.; Gebhardt, K.; Holtzel, A.; Schmid, D. G.; Sussmuth, R.; Muller, J.; Pukall, R.; Fiedler, H. P. J Antibiot 2002, 55, 565.

(N2) Holtzel, A.; Schmid, D. G.; Nicholson, G. J.; Stevanovic, S.; Schimana, J.; Gebhardt, K.; Fiedler, H. P.; Jung, G. J Antibiot 2002, 55, 571.

(N3) Kan, T.; Fukuyama, T. Chemical Communications 2004, 353.

(N4) Roberts, T. C.; Smith, P. A.; Cirz, R. T.; Romesberg, F. E. J Am Chem Soc 2007, 129, 15830.

(N5) Wuts, P. G. M.; Greene, T. W. Greene's protective groups in organic synthesis; 4th ed.; Wiley-Interscience: Hoboken, N.J., 2007.

(N6) Miyaura, N.; Suzuki, A. Chem Rev 1995, 95, 2457.

(N7) Evans, D. A.; Katz, J. L.; Peterson, G. S.; Hintermann, T. Journal of the American Chemical Society 2001, 123, 12411.

(N8) Galli, C. Chem Rev 1988, 88, 765.

Scheme 3: Semisynthetic Preparation of Aryl Ring Derivatives

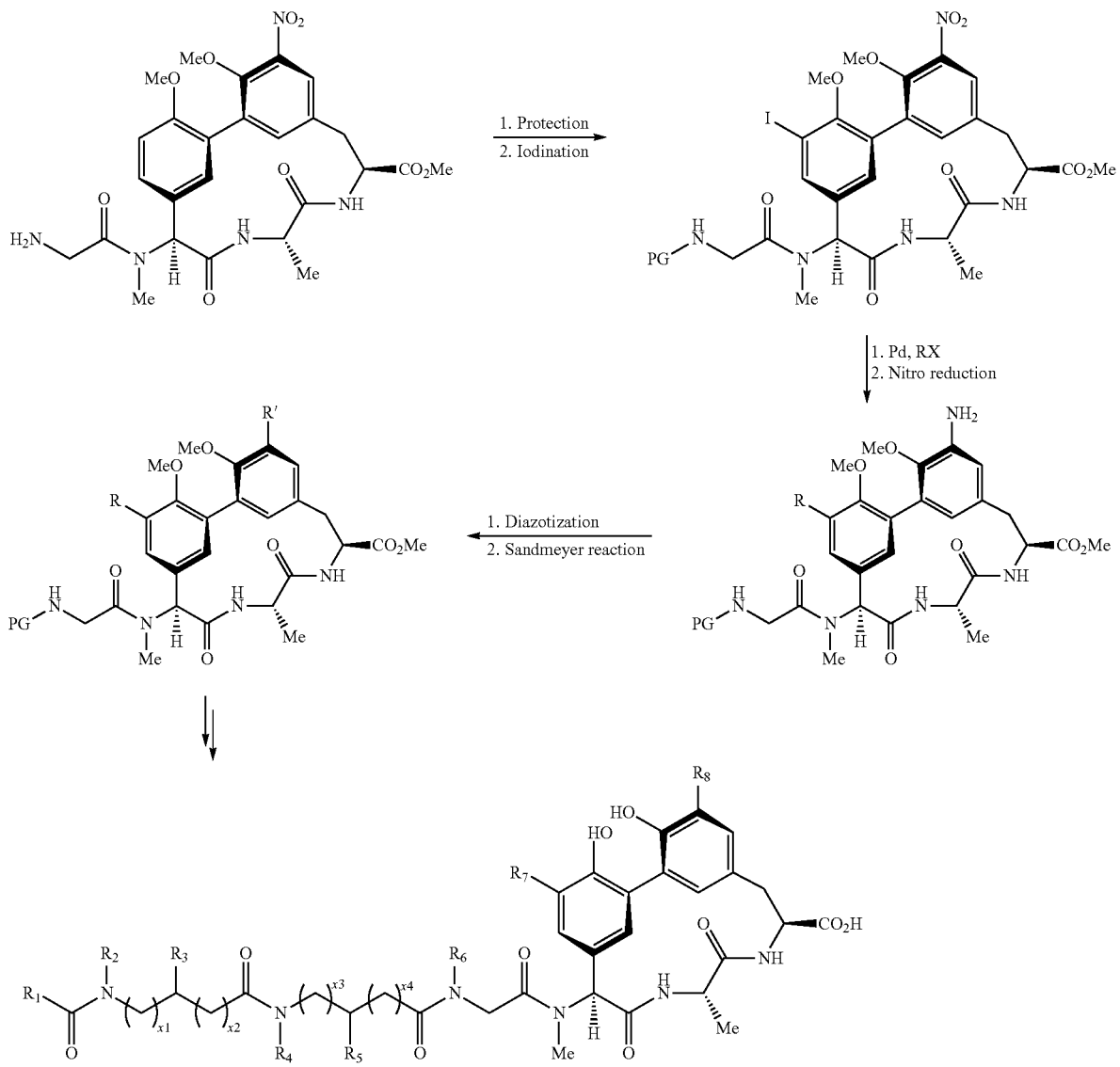

Signal Peptidase (SPase)

As described and illustrated herein, arylomycin antibiotics can inhibit the bacterial type I signal peptidase (SPase) enzyme, an essential serine-lysine dyad protease that is anchored to the outer leaflet of the bacterial cytoplasmic membrane and that removes N-terminal signal peptides from proteins that are transported out of the cytoplasm. Bacterial SPase proteases appear to be present and essential in all *Eubacteria*. However, not all *Eubacteria* are susceptible to arylomycin antibiotics.

According to the invention, the sequence of a bacterial SPase is correlated with susceptibility or resistance to arylomycin antibiotics. In particular, the presence of one or more proline residues near the catalytic serine gives rise to an arylomycin-resistant phenotype. The term "resistant" or "resistance" is used to refer to the reduced sensitivity of a strain harboring a resistance-conferring Pro relative to the isogenic strain without the Pro, and not to the absolute sensitivities of the different bacteria (e.g. resistant *S. epidermidis* is inhibited with an MIC of 8 μg/ml and is significantly more sensitive to arylomycin $C_{16}$ than the resistant mutants of the other pathogens, which are not inhibited at concentrations as high as 128 μg/ml).

Sequences for bacterial SPase nucleic acids and polypeptides are publicly available, for example, in the database maintained by the National Center for Biotechnology (ncbi.nlm nih gov) and can be used to make probes, primers and antigens useful for detecting arylomycin-susceptible or arylomycin-resistant bacteria.

For example, the *Staphylococcus epidermidis* RP62A signal peptidase IB has the following sequence (SEQ ID NO:1; see NCBI accession no. YP_188144.1, gi:57866486).

```
 1 MKKEILEWIV AIAVAIALIA IITKFVGKSY SIKGDSMDPT
41 LKDGERVVVN IIGYKLGGVE KGNVIVFHAN KKDDYVKRVI
```

```
 81 GTPGDSVEYK NDTLYVNGKK QSEPYLNYNE KRKQTEYITG

121 SFKTKNLPNA NPQSNVIPKG KYLVLGDNRE VSKDSRSFGL

161 IDKDQIVGKV SLRYWPFSEF KSNFNPNNTK N
```

The underlining shows the region of the catalytic serine, which is at position 36 in this SPase sequence. A nucleic acid sequence for the SEQ ID NO:1 *Staphylococcus epidermidis* RP62A signal peptidase IB can have the following sequence (SEQ ID NO:2, see NCBI accession no. NC_002976.3, GI:57865352).

```
  1 TTGAAAAAAG AAATTTTAGA GTGGATTGTT GCCATAGCCG

41 TTGCCATTGC ACTTATTGCC ATAATCACTA AATTTGTCGG

81 AAAATCATAT TCTATTAAAG GTGATTCAAT GGATCCTACA

121 TTAAAAGATG GGGAGCGTGT AGTGGTAAAT ATTATTGGCT

161 ATAAATTAGG TGGCGTTGAA AAAGGAAATG TCATTGTATT

201 TCATGCTAAT AAAAAAGATG ATTATGTTAA AAGAGTTATT

241 GGAACTCCAG GAGATAGTGT TGAATATAAA AATGATACAC

281 TCTATGTTAA TGGTAAAAAG CAATCAGAAC CATACTTGAA

321 CTATAATGAA AAACGTAAGC AAACTGAGTA TATCACAGGT

361 AGTTTCAAAA CAAAAAATTT ACCAAATGCT AATCCTCAAT

401 CTAATGTTAT TCCTAAAGGT AAATATTTAG TTTTGGGGGA

441 TAACCGTGAG GTAAGTAAAG ATAGTCGTTC ATTCGGTTTA

481 ATTGACAAAG ACCAAATTGT TGGAAAGGTA TCGCTCAGAT

521 ATTGGCCTTT CAGTGAATTT AAATCTAACT TTAATCCAAA

561 TAACACTAAA AATTAA
```

According to the invention, a bacterium having a mutant SPase gene is resistant to arylomycin antibiotics when one or more proline residues are present near the catalytic serine (e.g., at position 36 in SEQ ID NO:1) of the SPase polypeptide, for example, within about 10 amino acid positions on the N-terminal side of the catalytic serine of the SPase polypeptide. Thus, as illustrated herein, a bacterium with a proline between about amino acid position 28 to about amino acid position 35 of the SEQ ID NO:1 SPase amino acid sequence tends to exhibit resistance to arylomycin antibiotics. In some embodiments, the proline residue that gives rise to arylomycin resistance is present at about position −7 relative to catalytic serine. In other embodiments, the proline residue that gives rise to arylomycin resistance is present at about position −5 relative to catalytic serine. For example, in the SEQ ID NO:1 SPase sequence, a proline at position 29 or a proline at position 31 gives rise to arylomycin resistance.

One aspect of the invention therefore includes a method for detecting whether bacterial cells susceptible to arylomycin compounds are present in a test sample. Such susceptibility can be detected by detecting whether a SPase polypeptide is present that does not have a proline near the catalytic serine, for example, within about 10 amino positions on the N-terminal side of the catalytic serine and about two positions on the C-terminal side of the bacterial SPase polypeptide (e.g., within about positions 26-38 of SEQ ID NO:1). The absence of such a proline within the SPase polypeptide sequence indicates that bacterial cells within the sample are susceptible to arylomycin treatment.

In some embodiments, the method may also include detecting whether bacteria are present a test sample. The presence or absence of a proline in the Spase polypeptides can be simultaneously or subsequently detected to ascertain whether bacterial cells in the test sample are resistant or susceptible, respectively, to arylomycin compounds.

The presence of bacterial resistance to arylomycin compounds can be detected by determining whether a proline is present within about 10-12 amino acids of the catalytic serine in a SPase polypeptide. For example, an antibody that is specific for the proline-containing SPase polypeptide can be employed. Such a specific antibody binds with detectably greater affinity to a SPase polypeptide having one or more prolines than to a corresponding SPase polypeptide that does not have any such proline residues.

Conversely, the presence of susceptibility to arylomycin compounds can be detected by determining whether no proline residues are present within about 10-12 amino acids of the catalytic serine in a SPase polypeptide. An antibody specific for a SPase polypeptide that does not have a proline within about 10-12 amino acids of the catalytic serine in a SPase polypeptide can, for example, be used to detect whether a bacteria cell in a test sample is susceptible to arylomycin treatment.

Alternatively, such antibiotic resistance or susceptibility can be detected by detecting a nucleic acid encoding a SPase protein with such a proline residue. Thus, for example, nucleic acids in a test sample can be isolated using available procedures and the presence of a nucleic acid can be detected that encodes a SPase protein with or without such a proline residue. These isolated nucleic acids can be tested by available hybridization and/or nucleic acid amplification procedures to ascertain whether proline-encoding or non-proline-encoding SPase nucleic acids are present in the test sample.

Probes, primers and antigenic peptides useful for detecting the presence or absence of a proline within a SPase nucleic acid or polypeptide can readily be designed by one of ordinary skill in the art. For example, the following description illustrates how the SEQ ID NO:1 and 2 sequences can be used to design such probes, primers and/or antigenic peptides.

When the SEQ ID NO:1 and 2 sequences are aligned as illustrated below, the nucleic acid and amino acid sequences near the catalytic serine become apparent, as well as the sequences and codons that can become proline residue(s) in arylomycin resistant SPases (e.g. the underlined seauences).

```
DNA: ATGAAAAAAGAAATTTTAGAGTGGATTGTTGCCATAGCCGTTGCCATTGCA
  1: M  K  K  E  I  L  E  W  I  V  A  I  A  V  A  I  A

DNA: CTTATTGCCATAATCACTAAATTTGTCGGAAAATCATATTCTATTAAAGGT
 18: L  I  A  I  I  T  K  F  V  G  K  S  Y  S  I  K  G

DNA: GATTCAATGGATCCTACATTAAAAGATGGGGAGCGTGTAGTGGTAAATATT
 35: D  S  M  D  P  T  L  K  D  G  E  R  V  V  V  N  I

DNA: ATTGGCTATAAATTAGGTGGCGTTGAAAAAGGAAATGTCATTGTATTTCAT
```

```
+1:  I  G  Y  K  L  G  G  V  E  K  G  N  V  I  V  F  H

DNA: GCTAATAAAAAAGATGATTATGTTAAAAGAGTTATTGGAACTCCAGGAGAT
+1:  A  N  K  K  D  D  Y  V  K  R  V  I  G  T  P  G  D

DNA: AGTGTTGAATATAAAAATGATACACTCTATGTTAATGGTAAAAAGCAATCA
+1:  S  V  E  Y  K  N  D  T  L  Y  V  N  G  K  K  Q  S

DNA: GAACCATACTTGAACTATAATGAAAAACGTAAGCAAACTGAGTATATCACA
+1:  E  P  Y  L  N  Y  N  E  K  R  K  Q  T  E  Y  I  T

DNA: GGTAGTTTCAAAACAAAAAATTTACCAAATGCTAATCCTCAATCTAATGTT
+1:  G  S  F  K  T  K  N  L  P  N  A  N  P  Q  S  N  V

DNA: ATTCCTAAAGGTAAATATTTAGTTTTGGGGGATAACCGTGAGGTAAGTAAA
+1:  I  P  K  G  K  Y  L  V  L  G  D  N  R  E  V  S  K

DNA: GATAGTCGTTCATTCGGTTTAATTGACAAAGACCAAATTGTTGGAAAGGTA
+1:  D  S  R  S  F  G  L  I  D  K  D  Q  I  V  G  K  V

DNA: TCGCTCAGATATTGGCCTTTCAGTGAATTTAAATCTAACTTTAATCCAAAT
+1:  S  L  R  Y  W  P  F  S  E  F  K  S  N  F  N  P  N

DNA: AACACTAAAAATTAA
+1:  N  T  K  N  *
```

As described herein, when position −7 or position −5 from the catalytic serine is occupied by a proline rather than a serine, bacteria containing such a SPase enzyme are arylomycin resistant. When no such proline is present in the SPase enzyme, the bacteria are arylomycin susceptible. In the SEQ ID NO:1 SPase amino acid sequence, the −7 position is at position 29 and the −5 position is at position 31-serine is typically present in both positions within the wild type, arylomycin-susceptible SEQ ID NO:1 sequence.

Examples of shorter SPase peptide and nucleotide sequences from SEQ ID NO:1 and 2 that are correlated with arylomycin resistance or susceptibility include the following, where the position of the mutation in the nucleotide sequence is noted with a small arrow.

```
DNA: GTCGGAAAATCATATTCTATTAAAGGTGATTCA   Arylomycin
                                        Susceptible
 28: V  G  K  S  Y  S  I  K  G  D  S    SEQ ID NOs: 3 and 4

↓
DNA: GTCGGAAAACCATATTCTATTAAAGGTGATTCA   Arylomycin
                                        Resistant
 28: V  G  K  P  Y  S  I  K  G  D  S    SEQ ID NOs: 5 and 6

↓ ↓
DNA: GTCGGAAAACCGTATTCTATTAAAGGTGATTCA   Arylomycin
                                        Resistant
 28: V  G  K  P  Y  S  I  K  G  D  S    SEQ ID NOs: 7 and 6

↓ ↓
DNA: GTCGGAAAACCCTATTCTATTAAAGGTGATTCA   Arylomycin
                                        Resistant
 28: V  G  K  P  Y  S  I  K  G  D  S    SEQ ID NOs: 8 and 6

↓ ↓
DNA: GTCGGAAAACCTTATTCTATTAAAGGTGATTCA   Arylomycin
                                        Resistant
 28: V  G  K  P  Y  S  I  K  G  D  S    SEQ ID NOs: 9 and 6

↓
DNA: GTCGGAAAATCATATCCTATTAAAGGTGATTCA   Arylomycin
                                        Resistant
 28: V  G  K  S  Y  P  I  K  G  D  S    SEQ ID NOs: 10 and
                                        11

↓ ↓
DNA: GTCGGAAAATCATATCCCATTAAAGGTGATTCA   Arylomycin
                                        Resistant
 28: V  G  K  S  Y  P  I  K  G  D  S    SEQ ID NOs: 12 and
                                        11
```

-continued

```
                     ↓ ↓
DNA: GTCGGAAAATCATATCCAATTAAAGGTGATTCA   Arylomycin
Resistant
 28: V  G  K  S  Y  P  I  K  G  D  S     SEQ ID NOs: 13 and
 11

↓ ↓
DNA: GTCGGAAAATCATATCCGATTAAAGGTGATTCA   Arylomycin
Resistant
 28: V  G  K  S  Y  P  I  K  G  D  S     SEQ ID NOs: 14 and
 11
```

The first set of nucleotide and peptide sequences are just short sequences taken from the wild type, arylomycin susceptible SEQ ID NO:1 and 2 SPase sequences. Note that proline is encoded by four different codons (CCT, CCC, CCA, CCG), so four different SPase nucleotide sequences (e.g., SEQ ID NOs: 5, 7, 8 and 9) can exist for each proline-containing SPase polypeptide (e.g., a SPase polypeptide containing SEQ ID NO:6).

Primers and probes can readily be designed that are complementarity to nucleic acids encoding SPase-susceptible (non-proline containing) or SPase-resistant (proline-encoding) polypeptides. Such primers and probes can be designed to have sufficient sequence identity and/or sufficient complementary sequence identity to selectively hybridize with bacterial nucleic acids that encode SPase-susceptible (non-proline containing) or SPase-resistant (proline-encoding) polypeptides, and thereby permit detection of whether bacteria are arylomycin susceptible or arylomycin resistant. For example, to detect whether *S. epidermidis* bacteria in a test sample are arylomycin susceptible or arylomycin resistant primers or probes are designed to selectively hydridize to regions of nucleic acids that include any of SEQ ID NOs:3, 5, 7-10, 12, 13 or 14. Further information is provided below on selective hybridization and on the selection of probes and primers to detect bacterial nucleic acids that encode SPase-susceptible (non-proline containing) or SPase-resistant (proline-encoding) polypeptides, and thereby permit detection of whether bacteria are arylomycin susceptible or arylomycin resistant. For example, the Examples provide specific primer sequences that can be used to detect an/or isolate SPase nucleic acids.

One of skill in the art can also readily generate antibodies that selectively bind to bacterial SPase-susceptible (non-proline containing) polypeptides or SPase-resistant (proline-encoding) polypeptides, and to use those antibodies to detect whether bacteria are arylomycin susceptible or arylomycin resistant. For example, peptides or polypeptides that contain any of SEQ ID NOs:4, 6 or 11 can be used to generate such antibodies. These antibodies can be screened to identify antibody preparations that selectively bind to bacterial SPase-susceptible (non-proline containing) polypeptides or SPase-resistant (proline-encoding) polypeptides. Further information is provided below on making and using antibodies for detecting SPase-susceptible (non-proline containing) or SPase-resistant (proline-encoding) polypeptides, to thereby detect whether bacteria with such polypeptides are arylomycin susceptible or arylomycin resistant.

Primers and/or probes can be made from other bacterial SPase polypeptide and nucleic acid sequences, for example, any of those described herein or available in sequence databases. For example, the *Staphylococcus epidermidis* RP62A signal peptidase I has the following sequence, where the catalytic serine is identified in bold and with underlining (SEQ ID NO:15; see NCBI accession no. YP_187624.1, gi:57865986).

```
  1 MKKEIIEWIV AIIVAIVIVT LVQKFLFASY TVKGASMHPT

41 FENREKVIVS RIAKTLDHID TGDVVIFHAN AKQDYIKRLI

81 GKPGDSVEYK KDQLYLNGKK VDEPYLSENK KHKVGEYLTE

121 NFKSRDLKGT NGNMKIPSGK YLVLGDNRQN SIDSRMDEVG

161 LLDKNQVVGK VVLRYWPFNR WGGSFNPGTF PN
```

The nucleotide sequence for the SEQ ID NO:15 *Staphylococcus epidermidis* RP62A signal peptidase I has the following sequence (SEQ ID NO:16; see NCBI accession no. NC_002976.3 GI:57865352).

```
  1 ATGAAGAAAG AAATAATAGA ATGGATTGTA GCCATAATCG

41 TTGCAATTGT TATCGTCACA CTTGTGCAAA AGTTTTTATT

81 TGCTTCTTAT ACAGTCAAAG GAGCATCTAT GCATCCAACA

121 TTTGAAAATC GAGAAAAAGT GATAGTAAGT CGTATAGCAA

161 AAACGCTTGA TCATATTGAT ACAGGAGATG TAGTGATTTT

201 TCATGCTAAC GCGAAGCAAG ATTATATTAA GCGACTTATT

241 GGTAAACCAG GTGATTCAGT AGAATATAAA AAAGATCAAC

281 TATATTTAAA CGGTAAAAAA GTAGATGAGC CTTATTTAAG

321 TGAAAATAAA AAACATAAAG TTGGAGAATA TCTAACGGAA

361 AACTTTAAGT CTAGAGATCT TAAGGGTACG AATGGCAATA

401 TGAAAATTCC TAGTGGTAAA TACTTGGTTT TAGGTGATAA

441 TCGTCAAAAC AGTATTGACA GTCGCATGGA TGAAGTAGGT

481 CTTTTAGATA AAAATCAAGT TGTTGGAAAA GTAGTTTTGA

521 GATACTGGCC ATTTAATCGG TGGGGCGGTA GTTTTAATCC

561 TGGAACATTT CCTAACTAA
```

Additional bacterial SPase sequences are available, for example, in the NCBI sequence database.

Genetically Modified Bacterial Signal Peptidases

Another aspect of the invention is a modified bacterial SPase and/or a bacterial host cell that includes a modified bacterial SPase. Such modified SPases are useful for identifying arylomycin compounds that can inhibit the activity of modified and/or naturally occurring SPases. For example, when a proline is present within about 10 amino acids N-terminal to the catalytic serine, the SPase does not effectively bind an arylomycin and the arylomycin does not effectively inhibit the activity of the SPase. The presence of the proline reduces arylomycin binding to such an extent that the effects of structural changes in the arylomycin compound structure cannot readily be detected.

According to the invention, one way to detect improved arylomycin structures during structure-activity studies is to observe the binding of a test arylomycin compound to an SPase that has been modified by replacement of the proline at position 5 to 7 N-terminal to the catalytic serine with another amino acid (e.g., a serine or other amino acid). Alternatively, improved arylomycin structures can be identified by observing the binding of a test arylomycin compound to an SPase that has been modified by replacement of a naturally occurring amino acid at position 5 to 7 N-terminal to the catalytic serine with a proline (thereby converting an arylomycin-susceptible SPase into an arylomycin-resistant SPase). These types of modified SPase enzymes therefore permit evaluation of test compounds against non-proline containing "arylomycn resistant" SPase sequences so that secondary sites of potential (minor) resistance can be identified and the arylomycin structure can be modified to addressany such secondary sites of resistance. Similarly, SPases that are naturally resistant to arylomycin, due to the absence of a proline within about 10 amino acids of the catalytic serine, are modified by substitution to place a proline at −5 to −7 postions N-terminal to the catalytic serine so that the test compounds can be identified that effectively bind and inhibit such an SPase even though there is a proline in what is otherwise an"arylomycin-susceptible" SPase structure.

Therefore, another aspect of the invention is a method of identifying a compound that can bind to and/or inhibit the activity of a bacterial SPase that involves contacting a modified SPase with a test compound and observing whether the test compound binds to and/or inhibits the activity of the modified SPase, wherein the modified SPase has a natural bacterial SPase amino acid sequence that has been modified at position −5 to −7 relative to the catalytic serine by substitution or replacement of a proline that position. In some embodiments, a proline at position −5 and/or at position −7 is replaced with another amino acid (e.g., a serine). In other embodiments, the amino acid that is naturally present at position −5 and/or at position −7 is replaced with a proline. Test compounds that bind and/or inhibit the activity of the modified SPase are compounds of interest.

In another embodiment, test compounds that have antibiotic activity against bacteria are identified by contacting a culture of bacteria with the test compound and identifying whether the test compound inhibits the growth of the bacteria, wherein the bacteria express a modified SPase that has a natural bacterial SPase amino acid sequence that has been modified at position −5 to −7 relative to the catalytic serine by substitution or replacement of a proline that position. In some embodiments, a proline at position −5 and/or at position −7 is replaced with another amino acid (e.g., a serine). In other embodiments, the amino acid that is naturally present at position −5 and/or at position −7 is replaced with a proline. Test compounds that inhibit the growth of a bacterium expressing such modified SPase have antibiotic activity.

The bacteria can be modified by recombinant techniques available to those of skill in the art so that the bacteria express a modified SPase. Such techniques can include removal, replacement or mutation of an endogenous SPase gene so that endogenous SPase gene is not expressed, thereby allowing expression of only the modified SPase enzyme. Such "knock-out" procedures for removal, replacement and/or mutation of an endogenous gene in a bacterium are available in the art, and can readily be employed to generate bacterial populations that express a selected modified SPase enzyme.

Examples of procedures for generating such modified SPase enzymes and modified bacterial populations are provided, for example, in the Examples and in the art. A "knockout cassette" can be employed. Such a knockout cassette refers to a fragment of native chromosomal DNA having a foreign DNA piece that may provide a selectable marker. In one embodiment "knock-out mutation cassettes" are created by interrupting a fragment of genomic DNA with a foreign piece of DNA, and replacing the wild-type chromosomal copy of the sequence with the knock-out cassette. In this embodiment, the knock-out protocol involves cloning a modified SPase DNA segment into a target DNA such that "tails" comprising the target site DNA remain at the 5' and 3' ends of the knock-out cassette. The tails may be at least 50 base pairs and preferably greater than 200 to 500 base pairs for efficient recombination and/or gene conversion. For convenience, the foreign DNA cloned into the target DNA also provides a selectable marker, for example, an antibiotic resistance gene. Where the target DNA is disrupted with a marker antibiotic resistance gene, selection of transformants is carried out on agar plates containing suitable levels of an appropriate antibiotic. Following transformation, a fraction of cells that have taken up the knockout cassette will have undergone homologous recombination or gene conversion across the genomic DNA tails of the cassette, resulting in replacement of the wild-type genomic sequence by the knock-out cassette. Knock-out recombination events are easily confirmed by, for example, Southern blot hybridization, or by PCR.

Detection and/or Amplification of SPase Nucleic Acids

The presence of bacterial species susceptible or resistant to arylomycin antibiotics can be detected by detecting SPase nucleic acids in a test sample suspected of containing bacteria. As described and illustrated herein arylomycin antibiotic resistance or susceptibility can be detected by detecting a nucleic acid encoding a SPase protein with a proline residue near the catalytic serine residue.

Nucleic acids in a test sample can be isolated using available procedures. For example, bacterial nucleic acids can be isolated from a test sample by lysing the bacterial cells using detergents, heat, proteases and/or phenol extraction and alcohol preceiptitation.

The presence of a nucleic acid can be detected that encodes a SPase protein with or without such a proline residue by employing available hybridization, single nucleotide polymorphism and/or nucleic acid amplification procedures to ascertain whether proline-encoding or non-proline-encoding SPase nucleic acids are present in the test sample. In general, selective hybridization conditions are employed to facilitate detection of the proline-encoding and/or non-proline-encoding SPase nucleic acids and these procedures.

The term "selectively hybridize" includes hybridization, under stringent hybridization conditions, of a nucleic acid sequence to a specified nucleic acid target sequence (e.g., SEQ ID NO:2 or any SPase nucleic acid) to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, or 60-90% sequence identity, or 90-95% sequence identity, or 90-99% sequence identity, or 95-97% sequence identity, or 98-99% sequence identity, or 100% sequence identity (or complementarity) with each other. In some embodiments, a selectively hybridizing sequence has about at least about 70% sequence identity with SEQ ID NO:2. Note that if a value of a variable that is necessarily an integer, e.g., the number of nucleotides or amino acids in a nucleic acid or protein, is described as a range, e.g., or 90-99% sequence identity, or 100% sequence identity, what is meant is that the value can be any integer between 90 and 99 inclusive, i.e., 90, 91, 92, 93, 94, 95, 96, 97, 98 or 99.

The probes and primers of the invention include those with about 10-100 of the same nucleotides as either strand of a bacterial SPase DNA or RNA (e.g., SEQ ID NOs:2), or about 12-50, or about 13-40, or about 14-30 of the same nucleotides as either strand of a bacterial SPase DNA or RNA (e.g., SEQ ID NO:2). The probes and primers of the invention also include those with about 10-30 of the same nucleotides as either strand of any of SEQ ID NOs: 2, 5, 7, 8, 9 or the other SPase nucleic acids disclosed herein or available in a public data. The identical nucleotides or amino acids can be distributed throughout the nucleic acid or the protein, and need not be contiguous. Based on such methodologies, a person skilled in the art can readily design primers in suitable regions 5' and 3' to the signal peptidase segment that may encode the proline.

The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified which can be up to 100% complementarity to the probe (homologous probing). Alternatively, stringency conditions can be adjusted to allow some mismatching in sequences so that lower degrees of similarity are detected (heterologous probing).

A probe or primer can vary in length. For example, a probe can be approximately 20-500 nucleotides in length, but can vary greatly in length from about 15, or about 16, or about 17, or about 18 nucleotides to equal to the entire length of the target sequence.

In some embodiments, the probe is about 10-50 nucleotides in length, or about 15-40 nucleotides in length, or about 18-50 nucleotides in length, or about 18-100 nucleotides in length.

In some embodiments, primers are shorter than probes. For example, a primer may be about 12 to 50 nucleotides in length, or about 13 to 40 nucleotides in length, or about 14 to 35 nucleotides in length.

In some embodiments, stringent hybridization conditions and procedures are employed. Typically, stringent conditions will be those where the salt concentration is less than about 1.5 M Na ion, typically about 0.01 to 1.0 M Na ion concentration (or other salts) at pH 7.0 to 8.3 and the temperature is at least about 30° C. for short probes or primers (e.g., 10 to 50 nucleotides) and at least about 60° C. for long probes (e.g., greater than 50 nucleotides). Stringent conditions may also be achieved with the addition of destabilizing agents such as formamide or Denhardt's. Exemplary low stringency conditions include hybridization with a buffer solution of 30 to 35% formamide, 1M NaCl, 1% SDS (sodium dodecyl sulphate) at 37° C., and a wash in 1×SSC to 2×SSC (where 20×SSC is 3.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated from the equation of Meinkoth and Wahl (Anal. Biochem. 138:267-84 (1984)):

$T_m$=81.5° C.+16.6 (log M)+0.41 (% GC)−0.61 (% formamide)−500/L where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired identity. For example, if sequences with greater than or equal to 90% sequence identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or a wash at 1, 2, 3 or 4° C. lower than the thermal melting point ($T_m$). Moderately stringent conditions can utilize a hybridization and/or a wash at 6, 7, 8, 9 or 10° C. lower than the thermal melting point ($T_m$). Low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill can identify and isolate nucleic acids with sequences related to SEQ ID NO:1. Those of skill in the art also understand how to vary the hybridization and/or wash solutions. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, part 1, chapter 2, "Overview of principles of hybridization and the strategy of nucleic acid probe assays," Elsevier, N.Y. (1993); and Current Protocols in Molecular Biology, chapter 2, Ausubel, et al., eds, Greene Publishing and Wiley-Interscience, New York (1995). Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

Therefore hybridization procedures can be used to detect the presence or absence of an encoded proline in bacterial signal peptidase nucleic acids. In addition, the presence or absence of such an encoded proline can be detected by nucleic acid amplification, single nucleotide polymorphism (SNP), sequencing and other procedures available to one of skill in the art.

Amplification methods available in the art can be utilized, including polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, and isothermal amplification methods such as nucleic acid sequence based amplification (NASBA), and self-sustained sequence replication (Guatelli et al., Proc. Natl. Acad. Sci. USA 87: 1874, 1990).

A variety of single nucleotide polymorphism (SNP) genotyping methods are available including those described in Chen et al., "Single nucleotide polymorphism genotyping: biochemistry, protocol, cost and throughput", Pharmacogenomics J. 2003; 3(2):77-96; Kwok et al., "Detection of single nucleotide polymorphisms", Curr Issues Mol. Biol. 2003 April; 5(2):43-60; Shi, "Technologies for individual genotyping: detection of genetic polymorphisms in drug targets and disease genes", Am J. Pharmacogenomics. 2002; 2(3):197-205; and Kwok, "Methods for genotyping single nucleotide polymorphisms", Annu Rev Genomics Hum Genet. 2001; 2:235-58; see also, U.S. Patent Application Publication No. 20100216154, contents of which publications are incorporated by reference in their entireties. Exemplary techniques for high-throughput SNP genotyping are described in Marnellos, "High-throughput SNP analysis for genetic association studies", Curr Opin Drug Discov Devel. 2003 May; 6(3):317-21, which is incorporated herein by reference in its entirety. Common SNP genotyping methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA (U.S. Pat. No. 4,988,167, which is incorporated herein by reference in its entirety), multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

Various methods for detecting polymorphisms include, but are not limited to, methods in which protection from cleavage agents is used to detect mismatched bases in RNA/RNA or RNA/DNA duplexes (Myers et al., Science 230:1242 (1985); Cotton et al., PNAS 85:4397 (1988); and Saleeba et al., Meth. Enzymol. 217:286-295 (1992)), comparison of the electrophoretic mobility of variant and wild type nucleic acid molecules (Orita et al., PNAS 86:2766 (1989); Cotton et al., Mutat. Res. 285:125-144 (1993); and Hayashi et al, Genet. Anal. Tech. Appl. 9:73-79 (1992)), and assaying the movement of polymorphic or wild-type fragments in polyacrylamide gels containing a gradient of denaturant using denaturing gradient gel electrophoresis (DGGE) (Myers et al., Nature 313:495 (1985)); the contents of which publications are incorporated herein by reference in their entirety. Sequence variations at specific locations can also be assessed by nuclease protection assays such as RNase and 51 protection or chemical cleavage methods.

For example, in some embodiments, SNP genotyping is performed using the TaqMan assay, which is also known as the 5' nuclease assay (U.S. Pat. Nos. 5,210,015 and 5,538,848, which are incorporated herein by reference in their entirety). The TaqMan assay detects the accumulation of a specific amplified product during PCR. The TaqMan assay utilizes an oligonucleotide probe labeled with a fluorescent reporter dye and a quencher dye. The reporter dye is excited by irradiation at an appropriate wavelength, it transfers energy to the quencher dye in the same probe via a process called fluorescence resonance energy transfer (FRET). When attached to the probe, the excited reporter dye does not emit a signal. The proximity of the quencher dye to the reporter dye in the intact probe maintains a reduced fluorescence for the reporter. The reporter dye and quencher dye may be at the 5' most and the 3' most ends, respectively, or vice versa. Alternatively, the reporter dye may be at the 5' or 3' most end while the quencher dye is attached to an internal nucleotide, or vice versa. In yet another embodiment, both the reporter and the quencher may be attached to internal nucleotides at a distance from each other such that fluorescence of the reporter is reduced.

In another aspect of the invention, the signal peptidase sequences of various bacterial species are determined and compared to generate bacterial phylogenetic profiles of drug resistance useful for identifying drugs that can readily be modified to overcome such drug resistance.

To generate such drug resistance phylogenetic profiles, the degree of sequence similarity and difference is determined. The following terms are used to describe the sequence relationships between two or more nucleic acids or nucleic acids or polypeptides: (a) "reference sequence," (b) "comparison window," (c) "sequence identity," (d) "percentage of sequence identity" and (e) "substantial identity." As used herein, "reference sequence" is a defined sequence used as a basis for sequence comparison. The reference sequence can be a nucleic acid sequence (e.g., SEQ ID NO:2) or an amino acid sequence (e.g., SEQ ID NO:1). A reference sequence may be a subset or the entirety of a specified sequence. For example, the reference sequence can be an entire SPase DNA, RNA or polypeptide sequence, or a segment of a full-length SPase DNA, RNA or polypeptide sequence, or a peptide, DNA or RNA including/encoding just the region of the catalytic serine and/or a region that is N-terminal to catalytic serine (e.g., from about amino acid position −10 to about amino acid +2 relative to the catalytic serine).

As used herein, "comparison window" means includes reference to a contiguous and specified segment of a nucleic acid or an amino acid sequence, wherein the nucleic acid/amino acid sequence may be compared to a reference sequence and wherein the portion of the nucleic acid/amino acid sequence in the comparison window may comprise additions or deletions (i.e., gaps) compared to the reference sequence (which does not comprise additions or deletions) for optimal alignment of the two sequences. The comparison window can vary for nucleic acid and polypeptide sequences. Generally, for nucleic acids, the comparison window is at least 20 contiguous nucleotides in length, and optionally can be 22, 25, 30, 35, 40, 50, 100 or more nucleotides. For amino acid sequences, the comparison window is at least about 10 to 15 amino acids, and can optionally be 20, 22, 25, 30, 35, 40, 50, 100 or more amino acids. Those of skill in the art understand that to avoid a high similarity to a reference sequence due to inclusion of gaps in the nucleic acid or amino acid sequence a gap penalty is typically introduced and is subtracted from the number of matches.

Methods of alignment of nucleotide and amino acid sequences for comparison are well known in the art. The local homology algorithm (BESTFIT) of Smith and Waterman, (1981) Adv. Appl. Math 2:482, may conduct optimal alignment of sequences for comparison; by the homology alignment algorithm (GAP) of Needleman and Wunsch, (1970) J. Mol. Biol. 48:443-53; by the search for similarity method (Tfasta and Fasta) of Pearson and Lipman, (1988) Proc. Natl. Acad. Sci. USA 85:2444; by computerized implementations of these algorithms, including, but not limited to: CLUSTAL in the PC/Gene program by Intelligenetics, Mountain View, Calif., GAP, BESTFIT, BLAST, FASTA and TFASTA in the Wisconsin Genetics Software Package, Version 8 (available from Genetics Computer Group (GCG™ programs (Accelrys, Inc., San Diego, Calif.)). The CLUSTAL program is well described by Higgins and Sharp, (1988) Gene 73:237-44; Higgins and Sharp, (1989) CABIOS 5:151-3; Corpet, et al., (1988) Nucleic Acids Res. 16:10881-90; Huang, et al., (1992) Computer Applications in the Biosciences 8:155-65 and Pearson, et al., (1994) Meth. Mol. Biol. 24:307-31. The preferred program to use for optimal global alignment of multiple sequences is PileUp (Feng and Doolittle, (1987) J. Mol. Evol., 25:351-60 which is similar to the method described by Higgins and Sharp, (1989) CABIOS 5:151-53 and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., eds., Greene Publishing and Wiley-Interscience, New York (1995).

GAP uses the algorithm of Needleman and Wunsch, (1970) J. Mol. Biol. 48:443-53, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. Thus, for example, the gap creation and gap extension penalties can be 0, 1, 2, 3, 4, 5, 6, 7, 8, 9, 10, 15, 20, 30, 40, 50 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see, Henikoff and Henikoff, (1989) Proc. Natl. Acad. Sci. USA 89:10915).

Unless otherwise stated, sequence identity/similarity values provided herein refer to the value obtained using the BLAST 2.0 suite of programs using default parameters (Altschul, et al., (1997) Nucleic Acids Res. 25:3389-402). As those of ordinary skill in the art will understand, BLAST searches assume that proteins can be modeled as random sequences. However, many real proteins comprise regions of nonrandom sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, (1993) Comput. Chem. 17:149-63) and XNU (C.sub.1-ayerie and States, (1993) Comput. Chem. 17:191-201) low-complexity filters can be employed alone or in combination.

Anti-SPase Antibodies

Another aspect of the invention is an antibody that can distinguish between a SPase that contains or does not contain a proline within about 10-12 amino acids of the catalytic serine in the SPase polypeptide. Thus, in some embodiments, the antibody binds with specificity to a bacterial SPase epitope that contains a proline within about 10-12 amino acids of the catalytic serine in the SPase polypeptide. In other emdoiments, the antibody binds with specificity to a bacterial SPase epitope that does not contain a proline within about 10-12 amino acids of the catalytic serine in the SPase polypeptide.

Antibodies that selectively bind to a SPase polypeptide can be isolated using conventional methods. Such antibodies can be polyclonal or monoclonal antibodies. In some embodiments, the anti-SPase antibodies are monoclonal antibodies.

For example, antibodies of the invention can be obtained from the blood or spleen of a animal that has been immunized with an SPase peptide or polypeptide that contains a selected amino acid sequence (e.g., SPase that contains or does not contain a proline within about 10-12 amino acids of the catalytic serine in the SPase polypeptide). The SPase polypeptide can be obtained using conventional methods, for example, as described in the Examples. Peptides from SPase polypeptides can be obtained by proteolytic cleavage of a SPase polypeptide or by recombinant expression of the SPase peptide. The animal can be, for example, a rabbit, goat, rat, horse or mouse. At the appropriate time after immunization, antibody molecules can be isolated from the animal, e.g. from the blood, spleen or other fluid of the animal, and further purified using standard techniques that include, without limitation, precipitation using ammonium sulfate, gel filtration chromatography, ion exchange chromatography or affinity chromatography using protein A. Antibodies that bind to SPase-specific antigens, can be identified using ELISA. Antibodies that bind to proline-containing epitopes on SPase proteins, but do not bind to non-proline-containing epitopes (or vice cersa) can be identified by screening methods available in the art.

Antibodies specific for proline-containing and non-proline-containing SPase polypeptides can also be obtained using various methods. Non-limiting examples include: (1) the generation of an antibody from an antibody-producing cell of a animal that has been immunized with a SPase polypeptide or peptide using single human B cell RT-PCR and expression vector cloning; (2) isolation from immortalized antibody-secreting B cells; and (3) isolation from an antibody-producing hybridoma generated by fusion of an antibody-producing cell with a myeloma cell. These techniques are known in the art. See, for example, Kohler & Milstein, *Nature* 256:495-97 (1975); Kozbor et al. *Immunol Today* 4: 72 (1983); Tiller et al., *J Immunol Methods* 329:112-124 (2008) and Traggiai et al., *Nat Med* 10:871-875(2004).

Antibodies specific for proline-containing and non-proline-containing SPase polypeptides can also be prepared using other methods known in the art, such as, for example, screening of a recombinant combinatorial immunoglobulin library such as an antibody phage display library using antigenic epitope of the SPase polypeptide. See, for example, Barbas, C. F. et al., PHAGE DISPLAY—A LABORATORY MANUAL (2001) Cold Spring Harbor, New York: Cold Spring Harbor Laboratory Press; and Kontermann & Dubel, ANTIBODY ENGINEERING (2001) Berlin, Heidelberg: Springer-Verlag.

Nucleic acids encoding antibodies specific for the SPase polypeptides of the invention can be derived from an animal immunized with the SPase polypeptide or a peptide fragment thereof by generating an expression library using the RNA of the animal's B cells or plasma cells and then screening for antibody-coding sequences. See, for example, in Antibodies, A Laboratory Manual, by Harlow and Lane, Cold Spring Harbor Laboratory Press, Cold Spring Harbor, N.Y., 1988, and in Molecular Cloning, A Laboratory Manual by Sambrook, et al., Cold Spring Harbor Laboratory Press, Cold Spring Harbor, N.Y. 1989, the disclosures of which are incorporated herein by reference.

For example, antibodies can be used that specifically detect any of the following peptides, where the proline(s) that give rise to arylomycin-resistance are shown as a P within a box (i.e., P) and the catalytic serine is shown at the C-terminus

TABLE 9

Peptide Epitopes

| Bacterial Strain | Mutant or Wild type | SPase peptide sequence | SEQ ID NO: |
|---|---|---|---|
| S. epidermidis RP62A | WT | VGKSYSIKGDS | 17 |
| S. epidermidis PAS9001 | S29P | VGK P YSIKGDS | 18 |
| S. epidermidis PAS9002 | S31P | VGKSY P IKGDS | 19 |
| S. aureus NTCT 8325 | WT | VAKPYTVKGDS | 20 |
| S. aureus PAS8001 | P29S | VAK S YTVKGDS | 21 |
| E. coli MG1655 | WT | IYEPFQIPSGS | 22 |
| E. coli PAS0232 | P84S | IYE S FQIPSGS | 23 |
| P. aeruginosa PAO1 | WT | LFEPFQIPSGS | 24 |
| P. aeruginosa PAS2006 | P84S | LFE S FQIPSGS | 25 |

Compositions and Combinations

Another aspect of an embodiment of the invention provides compositions of the compounds of the invention, alone or in combination with another medicament. As set forth herein, compounds of the invention include stereoisomers, tautomers, solvates, prodrugs, pharmaceutically acceptable salts and mixtures thereof. Compositions containing a compound of the invention can be prepared by conventional techniques, e.g. as described in Remington: The Science and Practice of Pharmacy, 19th Ed., 1995, or later versions thereof, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents that do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

Moreover, the compositions can include other therapeutic agents such as analgesics, other antibiotics, antihistamines, anti-inflammatory agents and the like. In some embodiments, the compositions include a second type of antibiotic, for example, a non-arylomycin antibiotic.

The route of administration can be any route which effectively transports the active compound of the invention to the appropriate or desired site of action, such as oral, nasal, pulmonary, buccal, subdermal, intradermal, transdermal, topical or parenteral, e.g., rectal, depot, subcutaneous, intravenous, intraurethral, intramuscular, intranasal, ophthalmic solution or an ointment, the oral route being preferred. In some embodiments, the compositions containing any of the compounds described herein are administered topically. For example, compositions containing arylomycon A and/or arylomycin B (with or without some of the compounds of formula I may advantageously be administered topically.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet that can be prepared by conventional tabletting techniques can contain:

| Core: | |
|---|---|
| Active compound (as free compound or salt thereof) | 250 mg |
| Colloidal silicon dioxide (Aerosil) ® | 1.5 mg |
| Cellulose, microcryst. (Avicel) ® | 70 mg |
| Modified cellulose gum (Ac-Di-Sol) ® | 7.5 mg |
| Magnesium stearate | Ad. |
| Coating: | |
| HPMC approx. | 9 mg |
| *Mywacett 9-40 T approx. | 0.9 mg |

*Acylated monoglyceride used as plasticizer for film coating.

A typical capsule for oral administration contains compounds of the invention (250 mg), lactose (75 mg) and magnesium stearate (15 mg). The mixture is passed through a 60 mesh sieve and packed into a No. 1 gelatin capsule. A typical injectable preparation is produced by aseptically placing 250 mg of compounds of the invention into a vial, aseptically freeze-drying and sealing. For use, the contents of the vial are mixed with 2 mL of sterile physiological saline, to produce an injectable preparation.

The following non-limiting Examples illustrate aspects of the invention.

EXAMPLES

Example 1

General Chemical Methods $^1$H and $^{13}$C NMR spectra were recorded on Bruker AMX 400, Bruker DRX 500, or Bruker DRX 600 spectrometers. Chemical shifts are reported relative to either chloroform (δ 7.26), methanol (δ 3.31), or dimethylsulfoxide (DMSO) (δ 2.50) for $^1$H NMR and either chloroform (δ 77.16), methanol (δ 49.00), or DMSO (δ 39.52) for $^{13}$C NMR. IR measurements were taken using a Nicolet 6700 ATR FT-IR. High resolution mass spectra were measured at the Scripps Center for Mass Spectrometry. All assigned structures are consistent with spectral data obtained.

Optical rotations were measured on a Perkin Elmer model 341 polarimeter. Yields refer to chromatographically and spectroscopically pure compounds unless otherwise stated. Reactions were magnetically stirred, and monitored by thin layer chromatography (TLC) with 0.25 mm Whatman precoated silica gel (with fluorescence indicator) plates. Flash chromatography was performed with silica gel (particle size 40-63 μm, EMD chemicals). Acetone was dried over anhydrous potassium carbonate, and all other dry solvents were purchased from Acros. H-D-Ser(Bzl)-OH and H-Ala-OBzl HCl were purchased from Bachem.

4-Nitrobenzenesulfonylchloride, and 1,1'-bis(diphenylphosphino)ferrocene palladium(II) chloride complex with dichloromethane (PdCl$_2$(dppf) were purchased from Alfa Aesar and Strem Chemicals, respectively. Boc-Gly-OH was purchased from Novabiochem. Anhydrous 1-hydroxybenzotriazole (HOBT) was purchased from Chem-Impex. Diazomethane was prepared according to Arndt, F. Org. Synth. 1934, 2:165. All other chemicals were purchased from Fisher/Acros or Aldrich. Abbreviations: THF, tetrahydrofuran; EtOH, ethanol; MeOH, methanol; AcOH, acetic acid; DCM, dichloromethane; DMF, N,N-dimethylformamide; EDC, 1-(3-dimethylaminopropyl)-3-ethylcarbodiimide hydrochloride; EtOAc, ethyl acetate; Ar, argon; DBU, 1,8-diazabicyclo [5.4.0]undec-7-ene; TFA, trifluoroacetic acid.

All preparative reverse phase chromatography was performed using Dynamax SD-200 pumps connected to a Dynamax UV-D II detector (monitoring at 220 nm). The column used was a Phenomenex Jupiter C$_{18}$ (10 □m, 2.12×25 cm, 300 Å pore size). All solvents contained 0.1% TFA; Solvent A, H$_2$O; Solvent B, acetonitrile with 10% H$_2$O. All samples were loaded onto the column at 0% B and the column was allowed to equilibrate for ~10 min before a linear gradient was started. Retention values are reported according to the linear gradient used and the % B at the time the sample eluted.

Procedures and Characterization

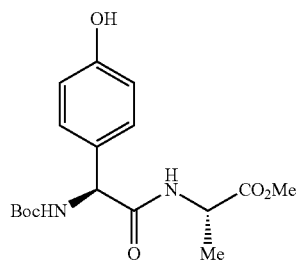

6

To a solution of 4-hydroxyphenylglycine (12 g, 71.8 mmol) in a 1:1 mixture of acetone and water was added di-tert-butyldicarbonate (16.5 mL, 71.8 mmol, 1 eq) and sodium bicarbonate (6.03 g, 0.11 mol, 1.5 eq). The solution was allowed to stir overnight, and then was quenched with the addition of citric acid (pH 3) to pH 4. The aqueous layer was then extracted 2× with EtOAc and the combined organic layers were washed with brine, dried over Na$_2$SO$_4$ and concentrated to a white foam. The crude material (18.43 g, 69 mmol (assumed)) was used without further purification by dissolving it in anhydrous DMF and treating sequentially with triethylamine (12.6 mL, 75.9 mmol, 1.3 eq), HOBT (9.32 g, 69 mmol, 1 eq) and Ala-OMe HCl (9.63 g, 69 mmol, 1 eq). The solution was then cooled to 0° C. and EDC (19.55 g, 0.1 mol, 1.5 eq) was added in one portion. The reaction was allowed to warm to room temperature and stirred overnight. Water and EtOAc were added, the aqueous layer was extracted 3×, and the combined organic layers were washed with brine, dried over $Na_2SO_4$ and concentrated. The residue was purified by flash chromatography (6% MeOH, 0.6% AcOH in DCM) to give a clear residue (17.82 g, 71% yield). $R_f$=0.39 (7% MeOH in DCM). $^1$H NMR ($CDCl_3$, 600 MHz) δ (ppm) 7.11 (d, J=8.4 Hz, 2H), 6.64 (d, J=8.4 Hz, 2H), 6.51 (br d, J=6.6 Hz, 1H), 5.71 (br s, 1H), 5.07 (br s, 1H), 4.57-4.52 (m, 1H), 3.69 (s, 3H), 1.42-1.40 (m, 12H). $^{13}$C NMR ($CDCl_3$, 600 MHz) δ (ppm) 173.2, 170.5, 156.6, 155.4, 129.0, 128.7 (2C), 116.1 (2C), 80.5, 58.2, 52.7, 48.5, 28.4 (3C), 18.4. IR (film) $v_{max}$=1655, 1512, 1450, 1365, 1215, 1157, 1049 $cm^{-1}$. ESI HRMS calcd for $[(M+Na)^+]$ $C_{17}H_{24}N_2O_6$: 375.1526. found: 375.1532.

MeOH in DCM)). To a solution of the crude compound (16.68 g, 45.6 mmol (assumed)) in MeOH (607 mL) was added $AgSO_4$ (14.9 g, 47.8 mmol, 1.05 eq) and $I_2$ (12.1 g, 47.8 mmol, 1.05 eq) consecutively. The reaction was stirred vigorously until TLC analysis (starting material stains with cerium(IV)sulfate; product does not) showed no remaining starting material (~30 min) solid $Na_2S_2O_3$ (large excess) was then added. The solids were filtered, the filtrate was concentrated, and the crude residue was purified via flash column chromatography (2% MeOH in DCM). The product was a white solid (21.19 g, 76% yield). $R_f$=0.50 (3% MeOH in DCM). $^1$H NMR ($CDCl_3$, 600 MHz) δ (ppm) 7.76 (d, J=1.8 Hz, 1H), 7.33 (d, J=7.8 Hz, 1H), 6.78 (d, J=8.4 Hz, 1H), 6.31 (d, J=7.2 Hz, 1H), 5.69 (br s, 1H), 5.07 (br s, 1H), 4.56-4.51 (m, 1H), 3.86 (s, 3H), 3.70 (s, 3H), 1.41-1.40 (m, 12H). $^{13}$C NMR ($CDCl_3$, 600 MHz) δ (ppm) 172.9 (2C), 169.5, 158.3, 138.3, 132.2, 128.9, 111.1, 86.6, 80.4, 57.4, 56.5, 52.7, 48.6, 28.4 (3C), 18.4. IR (film) $v_{max}$=1655, 1489, 1363, 1248, 1155, 1047, 1016, 548 $cm^{-1}$. ESI HRMS calcd for $C_{18}H_{25}IN_2O_6$ $[(M+H)^+]$ 493.0830. found 493.0829.

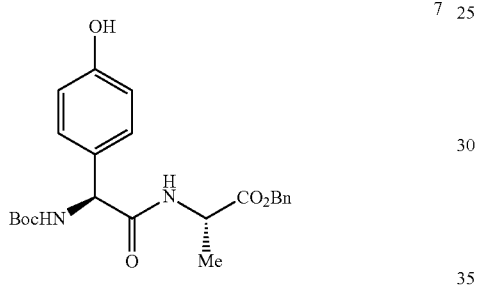

7

Compound 7 was synthesized in the same manner as compound 6. $R_f$=0.3 (4.5% MeOH in DCM). $^1$H NMR ($CDCl_3$, 600 MHz) δ (ppm) 7.38-7.31 (m, 3H), 7.29-7.26 (m, 2H), 7.11 (d, J=8.5 Hz, 2H), 6.63 (d, J=8.3 Hz, 2H), 6.44-6.38 (m, 2H), 5.69 (br s, 1H), 5.15-4.99 (m, 3H), 4.59 (p, J=7.2 Hz, 1H), 1.44-1.39 (m, 12H). $^{13}$C NMR ($CDCl_3$, 600 MHz) δ (ppm) 172.5, 170.4, 162.8, 156.4, 135.2, 128.8 (2C), 128.7, 128.6 (2C), 128.3 (2C), 116.1 (2C), 99.7, 67.5, 48.7, 36.7, 31.7, 28.5 (3C), 18.5. IR (film) $v_{max}$=1655, 1510, 1209, 1153, 1045, 696 $cm^{-1}$. ESI HRMS calcd for $C_{23}H_{28}N_2O_6$ $[(M+H)^+]$ 429.2020. found 429.2025.

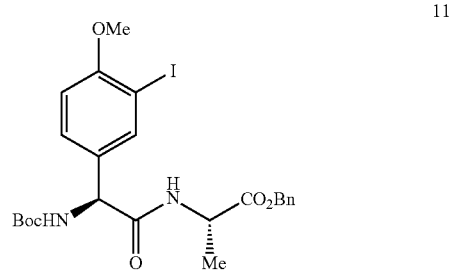 [SMILES: COC(=O)[C@H](C)NC(=O)[C@@H](NC(=O)OC(C)(C)C)c1ccc(OC)c(I)c1]

11

Compound 11 was synthesized in the same manner as compound 10. $R_f$=0.59 (2% MeOH in DCM). $^1$H NMR ($CDCl_3$, 600 MHz) δ (ppm) 7.76 (s, 1H), 7.38-7.23 (m, 6H), 6.72 (d, J=8.4 Hz, 1H), 6.32 (d, J=6.6 Hz, 1H), 5.68 (s, 1H), 5.16-5.02 (m, 3H), 4.61-4.55 (m, 1H), 3.84 (s, 3H), 1.45-1.35 (m, 12H). $^{13}$C NMR (MeOD, 600 MHz) δ (ppm) 173.5, 172.4, 159.5, 157.3, 139.6, 137.1, 133.1, 129.9, 129.5 (2C), 129.1, 129.0 (2C), 114.9, 111.9, 86.3, 80.9, 67.8, 58.1, 56.8, 28.7 (3C), 17.3. IR (film) $v_{max}$=1655, 1489, 1246, 1153, 1045, 735, 696 $cm^{-1}$. ESI HRMS calcd for $C_{24}H_{29}IN_2O_6$ $[(M+H)^+]$ 569.1143. found 569.1149.

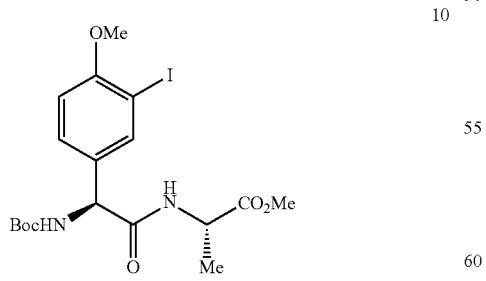

10

A mixture of 6 (20.6 g, 58 mmol) dissolved in dry acetone (390 mL) and potassium carbonate (40.4 g, 0.29 mol, 5 eq) under Ar was treated with iodomethane (25.4 mL, 0.41 mol, 7 eq) and heated to reflux. After 17 h, the solution was cooled, filtered and concentrated to the crude product ($R_f$=0.35 (2%

17

To a mixture of compound 11 (200 mg, 350 μmol), compound 15 (198 mg, 420 μmol, 1.2 eq) and $K_2CO_3$ (243 mg, 1.35 mmol, 5 eq) under Ar was added an Ar sparged suspension of PdCl$_2$(dppf) (57.5 mg, 70 μmol, 0.2 eq) in DMSO (3.5 mL) via cannula. The reaction was allowed to stir at 80° C. for 36 hrs. then was cooled and dilute NH$_4$Cl$_{(aq)}$ and EtOAc were added. The aqueous layer was extracted 2× with EtOAc and the combined organic fractions were dried over Na$_2$SO$_4$ and concentrated. Purification by flash column chromatography (30% EtOAc in hexanes) yielded compound 17 (99.9 mg, 36% yield). R$_f$=0.14 (35% EtOAc in hexanes). $^1$H NMR (CDCl$_3$, 600 MHz) multiple isomers. $^{13}$C NMR (CDCl$_3$, 600 MHz) multiple isomers. IR (film) $v_{max}$=1707, 1666, 1500, 1452, 1242, 1209, 1151, 1049, 1022, 742, 696 cm$^{-1}$. ESI HRMS calcd for C$_{43}$H$_{49}$N$_3$O$_{11}$ [(M+H)$^+$] 783.3440. found 783.3444.

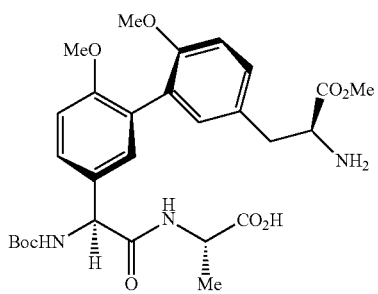

3

A solution of compound 17 (51.3 mg, 66 μmol) in 95% EtOH (16 mL) was treated with 10% Pd/C (17 mg) and allowed to stir until the presence of starting material could no longer be detected by TLC (~3 hrs). The reaction mixture was filtered through Celite, washed with ethyl acetate, and concentrated. The product was taken forward with no further purification. $^1$H NMR (MeOD, 600 MHz) multiple isomers. IR (film) $v_{max}$=1497, 1246, 1155, 1132, 1045, 1024 cm$^{-1}$. ESI HRMS calcd for C$_{28}$H$_{37}$N$_3$O$_9$ [(M+H)$^+$] 560.2602. found 560.2597.

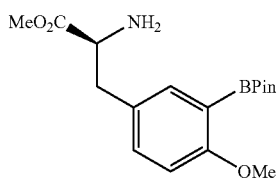

16

Compound 15 could not be purified completely due to instability on silica gel. A solution of semi-pure compound 15 (646 mg, 1.38 mmol) in 95% EtOH (70 mL) was treated with 10% Pd/C (215 mg) and allowed to stir until the presence of starting material could no longer be detected by TLC (35% EtOAc in Hex) (~4 hrs). The reaction mixture was filtered through Celite, washed with ethyl acetate, and concentrated. The product, a yellow oil, was taken forward with no further purification (431 mg, 93% yield). $^1$H NMR (CDCl$_3$, 400 MHz) δ (ppm) 7.48 (d, J=2.3 Hz, 1H), 7.21 (dd, J=8.4, 2.3 Hz, 1H), 6.80 (d, J=8.5 Hz, 1H), 3.81 (s, 3H), 3.76-3.68 (m, 4H), 3.03 (dd, J=13.7, 4.9 Hz, 1H), 2.78 (dd, J=13.6, 8.1 Hz, 1H), 1.39-1.32 (m, 12H) $^{13}$C NMR (CDCl$_3$, 600 MHz) δ (ppm) 175.6, 163.4, 137.6, 133.4, 128.5, 110.8, 83.6 (2C), 83.2, 56.1, 56.0, 52.1, 40.2, 25.0 (3C). IR (film) $v_{max}$=1605, 1493, 1417, 1335, 1248, 1142, 1070, 1022, 852, 796, 673, 538 cm$^{-1}$. ESI HRMS calcd for C$_{17}$H$_{26}$BNO$_5$ [(M+H)$^+$] 336.1977. found 336.1973.

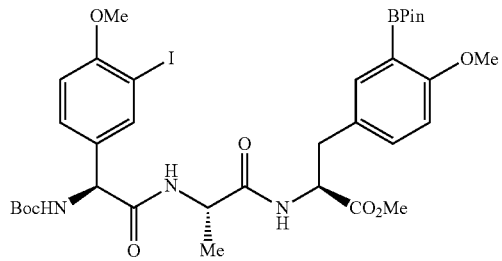

4

To a solution of compound 10 (1 g, 2.0 mmol) in THF (100 mL) was added 17 mL of 0.2 M LiOH$_{(aq)}$ (3.4 mmol, 1.7 eq). The reaction was allowed to stir until TLC indicated all starting material had been consumed. The reaction was then quenched by the addition of 5% NH$_4$Cl and most of the THF was blown off under a stream of nitrogen. Water and EtOAc were added and the aqueous phase was extracted 2× with EtOAc. The combined organic layers were then washed with brine, dried over Na$_2$SO$_4$, and concentrated. Compound 19 (1.9 g, 4.36 mmol) was dissolved in a 2.2:1 mixture of acetonitrile and DMF (25.7 mL). The compound was then treated sequentially with NaHCO$_3$ (catalytic), HOBT (1.5 g, 10.9 mmol, 2.5 eq), compound 16 (1.61 g, 4.8 mmol, 1.1 eq), and EDC (1.8 g, 9.59 mmol, 2.2 eq) and stirred under Ar overnight. The volatiles were evaporated, the residue was taken up in ethyl acetate and washed with 5% NaHCO$_{3(aq)}$, citric acid $_{(aq)}$, water, and brine. The organic layer was dried over Na$_2$SO$_4$ and concentrated. Abbreviated column chromatography (2.5% MeOH in DCM) yielded a semi-pure product as a yellow foam (1.22 g, 79% yield). The product could not be purified further due to instability upon prolonged exposure to silica gel or a C$_{18}$ HPLC column. Crude spectra were used to characterize the compound. R$_f$=0.32 (3% MeOH in DCM). $^1$H NMR (CDCl$_3$, 600 MHz) δ (ppm) 7.85 (s, 1H), 7.30 (d, J=10.8 Hz, 1H), 7.11 (d, J=8.2 Hz, 1H), 6.81-6.71 (m, 3H), 6.23 (br s, 1H), 5.81 (br s, 1H), 5.15 (br s, 1H), 4.74-4.68 (m, 1H), 4.58-4.51 (m, 1H), 3.87 (s, 3H), 3.85 (s, 3H), 3.73 (s, 3H), 3.05-3.02 (m, 1H), 2.87-2.80 (m, 1H), 1.52-1.36 (m, 24H) $^{13}$C NMR (CDCl$_3$, 600 MHz) δ (ppm) 171.5, 171.0, 169.9, 163.5, 158.2, 155.1, 138.1, 137.7, 133.4, 132.3, 128.5, 127.0, 111.3, 110.8, 86.7, 83.9 (2C), 80.3, 57.4, 56.5, 56.0, 53.5, 52.4, 49.0, 36.8, 28.4 (3C), 25.2 (4C), 18.2 (no signal was observed for the carbon attached to the boron). IR (film) $v_{max}$=1645, 1489, 1344, 1248, 1144, 1072, 1047, 1018, 854, 656, 550 cm$^{-1}$. ESI HRMS calcd for [(M+H)$^+$] C$_{34}$H$_{47}$BIN$_3$O$_{10}$: 796.2472. found: 796.2465.

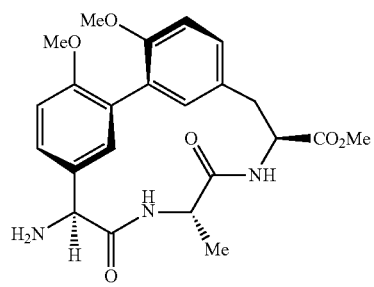

20

A solution of compound 4 (100 mg, 126 μmol) and K$_2$CO$_3$ (174 mg, 1.26 mmol, 10 eq) in acetonitrile (1.9 mL, 20 mM final) was stirred in a sealed vial and purged extensively with Ar. The mixture was then treated via syringe with a suspension of PdCl$_2$(dppf) (10.3 mg, 12.6 µmol, 10 mol %) in acetonitrile (1.3 mL, 5 mM) that had been sparged with Ar. The vial was then heated to 80° C., and allowed to stir for 21 hrs. The reaction mixture was cooled, EtOAc and dilute NH$_4$Cl$_{(aq)}$ were added. The aqueous phase was extracted 2× with EtOAc and the combined organic phases were washed with brine, dried over Na$_2$SO$_4$, and concentrated. The crude residue was then filtered through an abbreviated silica column (4% MeOH in DCM) to remove palladium species yielding a semipure residue. A solution of crude compound 18 (R$_f$=0.36 (4% MeOH in DCM)) was then taken up in anhydrous CH$_2$Cl$_2$ (2 mL) under Ar and treated dropwise with trifluoroacetic acid (0.5 mL). The reaction was allowed to stir until TLC indicated complete disappearance of starting material (~50 min). The volatiles were then evaporated under a stream of nitrogen, the crude material was purified via column chromatography (9.5% MeOH in DCM with trace triethylamine) and the purified material was filtered through basic alumina to give compound 20 (26 mg, 48% yield). R$_f$=0.44 (10% MeOH in DCM with 1 drop of TEA/10 mL). $^1$H NMR (MeOD, 600 MHz) multiple isomers. $^{13}$C NMR (MeOD, 600 MHz) multiple isomers. IR (film) v$_{max}$=1624, 1508, 1269, 1246, 1176, 1022, 795, 582 cm$^{-1}$. ESI HRMS calcd for C$_{23}$H$_{27}$N$_3$O$_6$ [(M+H)$^+$] 442.1973. found 442.1966.

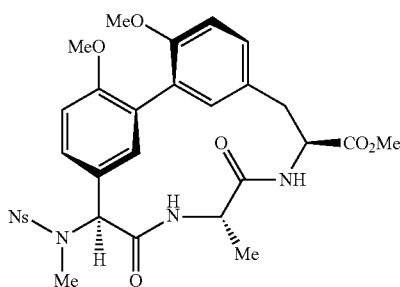

22

A solution of compound 20 (94 mg, 223 µmol) in acetonitrile (3 mL) was treated with nosyl chloride (76 mg, 335 µmol, 1.5 eq) and triethylamine (91 µL, 669 µmol, 3 eq). After stirring for 2 hrs all starting material was consumed as determined by TLC and a white precipitate had formed. The solvent was then evaporated, purged with Ar, and crude compound 21 (R$_f$=0.36 (7% MeOH in DCM)) was taken up in dry acetone (4 mL). The dissolved material was treated with K$_2$CO$_3$ (314 mg, 2.3 mmol 10 eq), the reaction tube was sealed, and iodomethane (129 µL, 2.3 mmol, 10 eq) was added. The mixture was stirred at 65° C. overnight then cooled, filtered, and concentrated. The residue was then subjected to flash column chromatography (2.5% MeOH in DCM) yielding compound 22 (54 mg, 37% yield). R$_f$=0.32 (2.5% MeOH in DCM). $^1$H NMR (CDCl$_3$, 600 MHz) δ (ppm) 8.34 (d, J=7.2 Hz, 1H), 8.02 (d, J=7.2 Hz, 1H), 7.38 (d, J=8.3 Hz, 1H), 6.94 (d, J=8.2 Hz, 1H), 6.82 (d, J=8.2 Hz, 1H), 6.67-6.59 (m, 2H), 6.56 (s, 1H), 6.24 (d, J=4.8 Hz, 1H), 5.81 (s, 1H), 4.85-4.80 (m, 1H), 4.52-4.44 (m, 1H), 3.84-3.76 (m, 9H), 3.44 (d, J=15.3 Hz, 1H), 2.99 (dd, J=15.5, 5.7 Hz, 1H), 2.83 (s, 3H), 1.30 (d, J=5.3 Hz, 3H) $^{13}$C NMR (CDCl$_3$, 600 MHz) δ (ppm) 172.0, 171.8, 169.0, 157.4, 156.1, 150.1, 145.1, 134.5, 134.5, 129.7, 128.9, 128.7 (2C), 128.6, 128.3, 127.0, 125.1, 124.2 (2C), 112.3, 111.8, 62.6, 56.1 (2C), 53.0, 49.8, 34.5, 32.0, 19.9. IR (film) v$_{max}$=1645, 1527, 1504, 1348, 1269, 1173, 1146, 735, 606 cm$^{-1}$. ESI HRMS calcd for C$_{30}$H$_{32}$N$_4$O$_{10}$S [(M+Na)$^+$]: 663.1731. found: 663.1724.

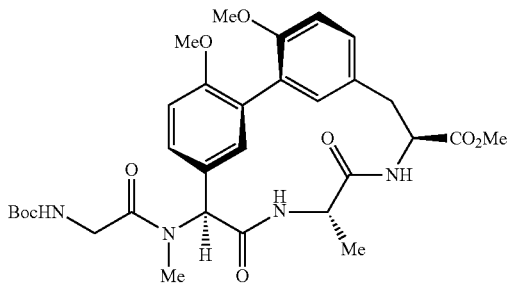

23

To a solution of compound 22 (20 mg, 31.3 µmol) in acetonitrile (1 mL) under Ar was added sequentially 2-mercaptoacetic acid (6.5 µL, 94 µmol, 3 eq) and DBU (23 µL, 157 µmol, 5 eq). The reaction was monitored by TLC for the disappearance of starting material and the volatiles were evaporated under a stream of nitrogen when the starting material had been completely consumed (~30 min). The residue was taken up in EtOAc and 1 N HCl was added. The organic layer was extracted 2× with 1 N HCl and the combined aqueous layers were basified with saturated NaHCO$_3$. The aqueous layer was then extracted 2× with EtOAc and the combined organic layers were dried over sodium sulfate and concentrated. The product (R$_f$=0.29 (8% MeOH in DCM with 1 drop of TEA/10 mL)) was not further purified and was taken directly to the next reaction. A solution of the crude material in CH$_2$Cl$_2$:DMF (3:1, 1 mL) was treated sequentially with HoBT (11.1 mg, 82.5 µmol, 3.3 eq), Boc-Gly-OH (4.8 mg, 27.5 µmol, 1.1 eq), and EDC (14.4 mg, 75 µmol, 3 eq). The reaction was stirred overnight, then the volatiles were evaporated and EtOAc and water were added. The aqueous layer was extracted (2×) with EtOAc and the combined organic layers were washed with brine, dried over Na$_2$SO$_4$ and concentrated. The crude material was purified via column chromatography (4% MeOH in DCM) to yield a white foam (14.1 mg, 74% yield). R$_f$=0.32 (5% MeOH in DCM). $^1$H NMR (CDCl$_3$, 600 MHz) δ (ppm) 7.15 (d, J=7.9 Hz, 1H), 6.99 (d, J=7.1 Hz, 1H), 6.93 (d, J=8.3 Hz, 1H), 6.86 (d, J=8.3 Hz, 1H), 6.80 (s, 1H), 6.71 (s, 1H), 6.44-6.26 (m, 3H), 5.57 (s, 1H), 4.96-4.89 (m, 1H), 4.74-4.66 (m, 1H), 4.13 (d, J=16.3 Hz, 1H), 4.00 (d, J=16.7 Hz, 1H), 4.86-4.80 (m, 9H), 4.13 (d, J=16.3 Hz, 1H), 4.00 (d, J=16.7 Hz, 1H), 3.54 (d, J=15.9 Hz, 1H), 3.04 (dd, J=15.7, 7.0 Hz, 1H), 2.79 (s, 3H), 1.46 (s, 9H), 1.38 (d, J=6.53 Hz, 3H) $^{13}$C NMR (CDCl$_3$, 600 MHz) δ (ppm) 172.3, 172.0, 170.2, 170.0, 157.2, 156.1, 156.0, 135.3, 134.3, 129.9, 129.0, 129.0, 128.4, 127.2, 125.9, 112.1, 111.8, 79.7, 60.3, 56.1, 53.0, 52.7, 49.9, 46.0, 42.9, 34.5, 31.7, 28.5 (3C), 19.7. IR (film) v$_{max}$=1639, 1508, 1269, 1246, 1163, 1024 cm$^{-1}$. ESI HRMS calcd for C$_{31}$H$_{40}$N$_4$O$_9$ [(M+H)$^+$]: 613.2868. found: 613.2860.

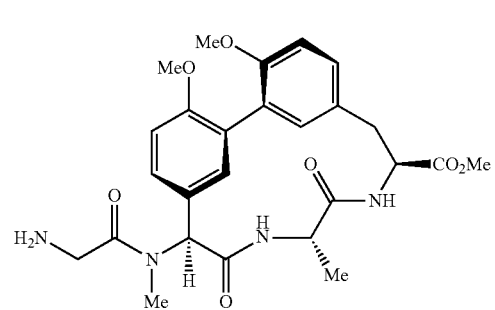

1

A solution of compound 23 (29.2 mg, 47.7 μmol) in CH$_2$Cl$_2$ (0.66 mL) was treated with TFA (0.33 mL) while stirring at 0° C. in a sealed vial. After 30 min, the reaction was found to be complete by TLC analysis, the vial was warmed to room temperature, a small amount of ethyl acetate was added, and the volatiles were evaporated under a stream of dry N$_2$ gas and dried in vacuo. The residue was then taken up in ethyl acetate and K$_2$CO$_3$ solid was added. The mixture was then filtered, concentrated, and purified by column chromatography (10% MeOH in DCM w/trace TEA). The product was obtained as a white residue (69 mg, 96% yield). R$_f$=0.33 (14% MeOH in DCM with 1 drop of TEA/10 mL). $^1$H NMR (MeOD, 400 MHz) multiple isomers, see page S34. $^{13}$C NMR (CDCl$_3$, 600 MHz) δ (ppm) 172.3, 172.0, 170.5, 157.1, 156.1, 135.3, 134.4, 129.8, 128.9, 128.9, 128.4, 127.3, 126.3, 112.1, 111.8, 60.4, 56.1, 56.1, 53.0, 52.7, 49.8, 43.6, 34.5, 31.6, 19.6. IR (film) ν$_{max}$=1639, 1506, 1269, 1202, 1175, 1128, 1022, 800, 719 cm$^{-1}$. ESI HRMS calcd for C$_{26}$H$_{32}$N$_4$O$_7$ [(M+H$^{-1}$)$^+$]: 513.2344. found: 513.2340.

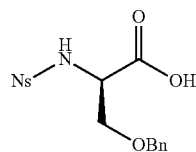

25

A solution of D-Ser-(OBzl)-OH (1.47 g, 15.4 mmol) in 1 N NaOH (14.7 mL) was treated dropwise with 4-nitrobenzenesulfonyl chloride (1.85 g, 7.9 mmol, 1.05 eq) in THF (1.4 mL). The solution was allowed to stir overnight then neutralized with citric acid (pH-3.5) and extracted with ethyl acetate (3×). The organic layers were combined, dried over Na$_2$SO$_4$, and concentrated. Flash column chromatography (6% MeOH in DCM w/trace AcOH) gave compound 25 as an off-white powder (62% yield). R$_f$=0.42 (7% MeOH in DCM w/1 drop/ 10 mL AcOH). $^1$H NMR (CDCl$_3$, 600 MHz) δ (ppm) 8.24 (d, J=11.0 Hz, 2H), 7.98 (d, J=11.0 Hz, 2H), 7.32-7.19 (m, 5H), 5.82 (d, J=11.0 Hz, 1H), 4.50-4.43 (m, 2H), 4.23 (m, 1H), 3.85 (dd, J=14.4 Hz, J=4.5 Hz, 1H), 3.65 (dd, J=14.4 Hz, J=4.5 Hz, 1H). $^{13}$C NMR (CDCl$_3$, 600 MHz) δ (ppm) 173.3, 150.2, 146.0, 136.7, 128.7 (2C), 128.4, 128.4 (2C), 128.0 (2C), 124.4 (2C), 73.8, 70.1, 56.0.

IR (film) ν$_{max}$=1740, 1529, 1350, 1173, 1086, 856, 737, 656, 609, 554 cm$^{-1}$. ESI HRMS calcd for C$_{16}$H$_{16}$N$_2$O$_7$S [(M+Na)$^+$]: 403.0570. found: 403.0566.

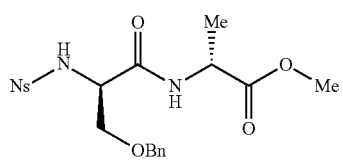

26

A solution of D-Ala-OMe HCl (147 mg, 1.05 mmol) in a 3:1 mixture of dichloromethane and DMF (30 mL) under Ar at 0° C. was treated sequentially with NaHCO$_3$ (88 mg, 1.05 mmol, 1 eq), anhydrous HoBT (468 mg, 3.5 mmol, 3.3 eq.), compound 25 (400 mg, 1.05 mmol, 1 eq.), and EDC (604 mg, 3.15 mmol, 3 eq.). The solution was allowed to warm to room temperature and stirred overnight. All volatiles were then evaporated, and the mixture was diluted with EtOAc and water. The aqueous layer was extracted (2×) and the combined organic layers were dried over Na$_2$SO$_4$ and concentrated. Flash column chromatography (1% MeOH in DCM) afforded the product in 88% yield. R$_f$=0.20 (1% MeOH in DCM with 1 drop of AcOH/10 mL). $^1$H NMR (CDCl$_3$, 500 MHz) δ (ppm) 8.27 (d, J=8.9 Hz, 2H), 7.99 (d, J=8.9 Hz, 2H), 7.37-7.30 (m, 3H), 7.28-7.23 (m, 2H), 7.18 (d, J=7.3 Hz, 1H), 5.85 (d, J=5.7 Hz, 1H), 4.51 (s, 1H), 4.47-4.40 (m, 1H), 3.89-3.83 (m, 2H), 3.72 (s, 3H), 3.54-3.49 (m, 1H), 1.29 (d, J=7.2 Hz, 1H) $^{13}$C NMR (CDCl$_3$, 600 MHz) δ (ppm) 172.7, 168.1, 150.3, 145.1, 136.8, 128.8 (2C), 128.7 (2C), 128.5, 128.2 (2C), 124.5 (2C), 73.9, 70.1, 55.4, 52.7, 48.6, 18.2. IR (film) ν$_{max}$=1645, 1525, 1450, 1348, 1310, 1165, 1119, 1092, 852, 733, 617, 546, 525 cm$^{-1}$. ESI HRMS calcd for C$_{20}$H$_{23}$N$_3$O$_8$S [(M+Na)$^+$]: 488.1098. found: 488.1095.

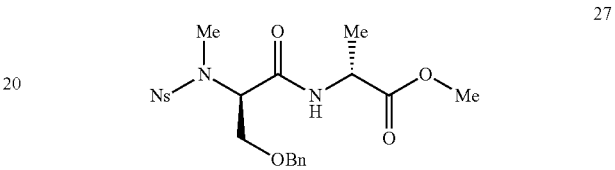

27

A solution of compound 26 (417 mg, 0.90 mmol) in dry CH$_2$Cl$_2$ (15 mL) under Ar was treated with diazomethane (0.66 M in ether, 16.3 mL, 12 eq, 11 mmol). The solution was monitored by TLC and when all starting material had been consumed, the volatiles were evaporated under a stream of dry nitrogen. Flash column chromatography (1% MeOH in DCM) yielded the product (86 mg, 90% yield). R$_f$=0.57 (2% MeOH in DCM). $^1$H NMR (CDCl$_3$, 400 MHz) δ (ppm) 8.05 (d, J=9 Hz, 2H), 7.92 (d, J=9 Hz, 2H), 7.30-7.26 (m, 3H), 7.12-7.02 (m, 3H), 4.50 (p, J=7 Hz, 1H), 4.29 (dd, J=40.0 Hz, 11.0 Hz, 2H), 3.90-3.84 (m, 1H), 3.78-3.70 (m, 4H), 2.89 (s, 3H), 1.41 (d, J=7.2 Hz, 3H). $^{13}$C NMR (CDCl$_3$, 600 MHz) δ (ppm) 172.8, 167.6, 149.9, 144.4, 136.7, 128.9 (2 C), 128.6 (2C), 128.5, 128.3 (2C), 123.9 (2C), 73.9, 67.1, 59.7, 52.8, 48.4, 30.7, 18.2. IR (film) ν$_{max}$=1740, 1670, 1525, 1346, 1153, 1107, 1086, 854, 741, 604 cm$^{-1}$. ESI HRMS calcd for C$_{21}$H$_{25}$N$_3$O$_8$S [(M+H)$^+$]: 480.1435. found 480.1445.

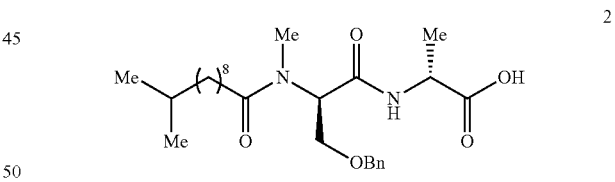

2

A solution of compound 27 (86.2 mg, 180 μmol) in anhydrous acetonitrile under Ar was treated sequentially with 2-mercaptoacetic acid (38 μL, 540 μmol, 3 eq) and DBU (135 μL, 900 μmol, 5 eq). The compound was allowed to stir until TLC indicated all of the starting material had been consumed. At this point, HCl (0.5 N) and EtOAc were added, the aqueous layer was extracted and then basified with saturated NaHCO$_3$. The aqueous layer was then extracted again with EtOAc (2×) and the combined organic layers from this extraction were pooled, dried over Na$_2$SO$_4$, and concentrated yielding compound 28. A 9% NaHCO$_3$ solution was then added to the crude material and stirred. In a separate reaction, isolauric acid (34 mg, 170 mmol) in anhydrous CH$_2$Cl$_2$ (1.5 mL) was treated with SOCl$_2$ (148 μL, 2.0 mmol, 12 eq) and refluxed for ~45 min. The volatiles were then blown off under a stream of N$_2$ and pumped off in vacuo. The resulting white film was taken up in 2 mL of anhydrous CH$_2$Cl$_2$ and this solution was added to the freshly deprotected compound 28 in 9% NaHCO$_3$. This mixture was stirred vigorously for ~5 hrs. The organic layer was removed and the water layer was extracted 2× with additional CH$_2$Cl$_2$. The combined organic layers were then dried over Na$_2$SO$_4$ and concentrated. This crude material was then dissolved in THF (2 mL), treated with 0.2 N LiOH (0.98 ml, 1.15 eq) and allowed to stir for 3 hrs. Then 5% NH$_4$Cl$_{(aq)}$ and EtOAc were added the aqueous phase was extracted 2× with EtOAc, the combined organic layers were dried over Na$_2$SO$_4$, and concentrated. The crude material was purified using column chromatography (8% MeOH in DCM w/trace AcOH) yielding compound 2 (15.2 mg, 19% yield). R$_f$=0.35 (8% MeOH in DCM with 1 drop of AcOH/10 mL). $^1$H NMR (CDCl$_3$, 600 MHz) multiple isomers, see page S42. IR (film) v$_{max}$=2924, 2850, 1726, 1624, 1529, 1454, 1402, 1205, 1105, 733, 696 cm$^{-1}$. ESI HRMS calcd for C$_{26}$H$_{42}$N$_2$O$_5$ [(M+H)$^+$] 463.3166. found 463.3158.

To a solution of compound 29 (8 mg, 8.4 μmol) in ethanethiol (0.4 mL) under Ar was added AlBr$_3$ in a 1.0 M solution of CH$_2$Br$_2$ (0.21 mL, 25 eq) via syringe. The reaction was then heated to 50° C. for 4 hrs. Upon cooling, water and EtOAc were added and the aqueous layer was extracted (2×) with EtOAc. The aqueous layer was then extracted (2×) with acetonitrile and the combined organic layers were dried over Na$_2$SO$_4$ and concentrated. The residue was then taken up in 100% B (1 mL) and this solution and the aqueous layer were purified by HPLC column (linear gradient, 0.5% B per minute, product eluted at 58.3% B) to yield a white powder after lyophilization (7.2 mg, 46% yield). $^1$H NMR (MeOD, 600 MHz) δ (ppm) multiple isomers, see page S45. $^{13}$C NMR (MeOD, 600 MHz) multiple isomers. IR (film) v.=1630, 1506, 1408, 1230, 810 cm$^{-1}$. ESI HRMS calcd for C$_{42}$H$_{60}$N$_6$O$_{11}$ [(M+H)$^+$] 825.4393. found 825.4397. [α]$^{20}_D$ (c 3.4, MeOH): +85.1°.

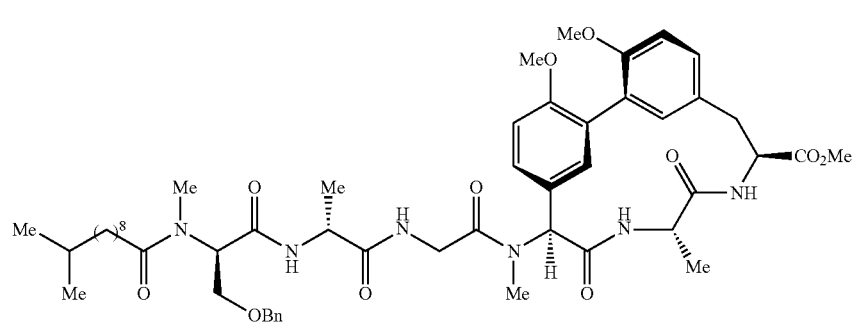

29

To a solution of compound 1 (16.5 mg, 0.03 mmol) in a 2.2:1 mixture of AcCN and DMF (1.5 mL) was added sequentially HOBT (13.5 mg, 0.1 mmol, 3.1 eq), compound 2 (14.9 mg, 0.03 mmol, 1 eq) and EDC (18.5 mg, 0.97 mmol, 3 eq) under Ar. The reaction was allowed to stir overnight. Water and EtOAc were then added and the aqueous layer was extracted 2× with EtOAc. The combined organic layers were then washed with brine, dried over Na$_2$SO$_3$, and concentrated. Flash column chromatography (4.5% MeOH in DCM) afforded the product (19.5 mg, 63% yield). R$_f$=0.25 (3% MeOH in DCM). $^1$H NMR (CDCl$_3$, 600 MHz) multiple isomers. $^{13}$C NMR (CDCl$_3$, 600 MHz) multiple isomers. IR (film) v.=1630, 1506, 1265, 1103, 1026, 798, 696 cm$^{-1}$. ESI HRMS calcd for C$_{52}$H$_{72}$N$_6$O$_{11}$ [(M+H)$^+$] 957.5332. found 957.5334.

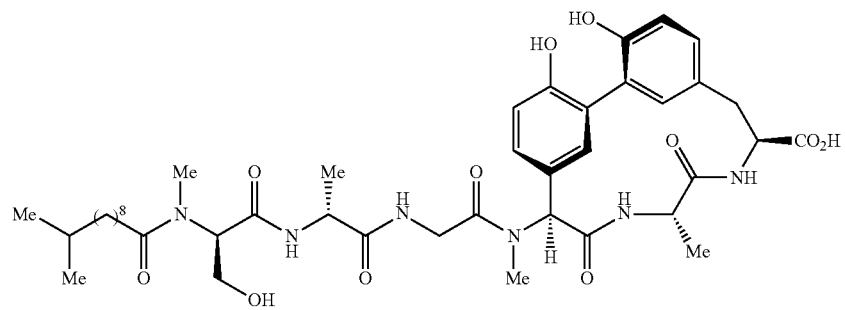

Arylomycin A$_2$

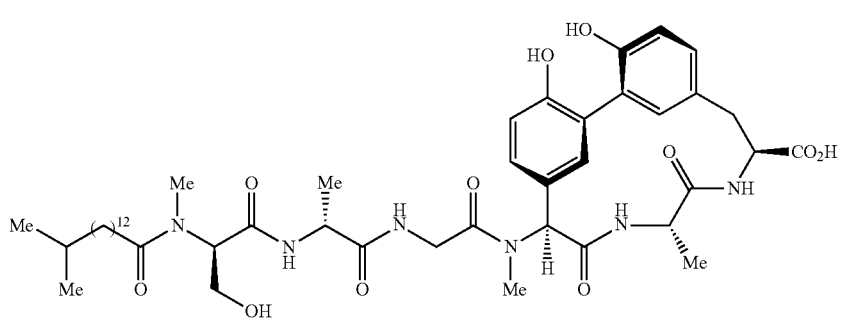

37

Compound 37 was synthesized in the same manner as arylomycin A$_2$. $^1$H NMR (MeOD, 600 MHz) δ (ppm) multiple isomers. $^{13}$C NMR (MeOD, 600 MHz) δ (ppm) multiple isomers. IR (film) v.=3275, 2922, 2852, 1632, 1506, 1410, 1230, 810 cm$^{-1}$. ESI HRMS calcd for C$_{46}$H$_{68}$N$_6$O$_{11}$ [(M+H)$^+$] 881.5019. found 881.5025. [α]$^{20}$$_D$ (c 1.8, MeOH): +64.9°.

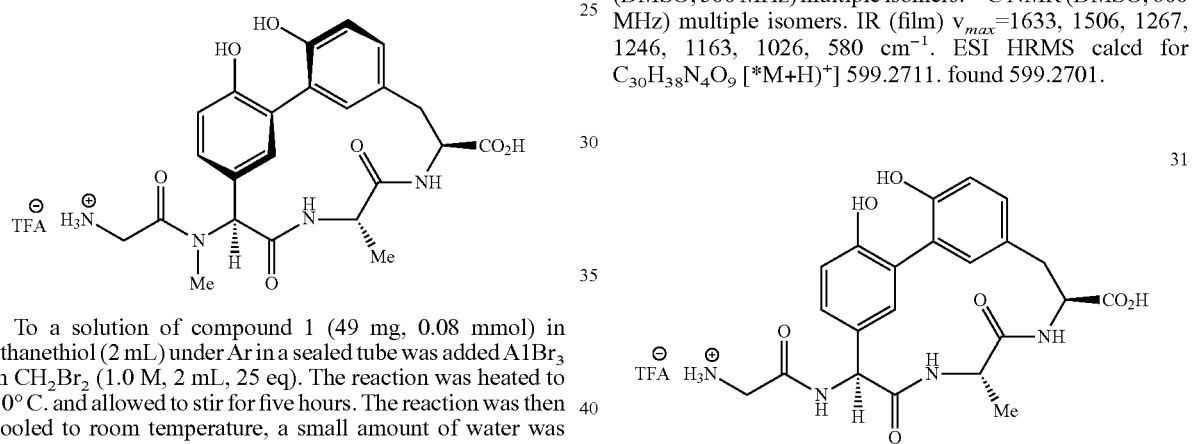

30

To a solution of compound 1 (49 mg, 0.08 mmol) in ethanethiol (2 mL) under Ar in a sealed tube was added AlBr$_3$ in CH$_2$Br$_2$ (1.0 M, 2 mL, 25 eq). The reaction was heated to 50° C. and allowed to stir for five hours. The reaction was then cooled to room temperature, a small amount of water was added, and the volatiles were evaporated under a stream of nitrogen. Additional water was added, followed by EtOAc, and the aqueous layer was extracted, filtered through a 0.22 μm syringe filter and purified by HPLC (linear gradient, 0.5% B per minute, product eluted at 17.9% B). Lyophilization afforded the product as the TFA salt. (30 mg, 63% yield). $^1$H NMR (DMSO, 500 MHz) multiple isomers. $^{13}$C NMR (DMSO, 600 MHz) multiple isomers. IR (film) v.=1639, 1509, 1416, 1184, 1134, 798, 721, 511 cm$^{-1}$. ESI HRMS calcd for C$_{23}$H$_{26}$N$_4$O$_7$ [(M+H)$^+$] 471.1874. found 471.1880.

32

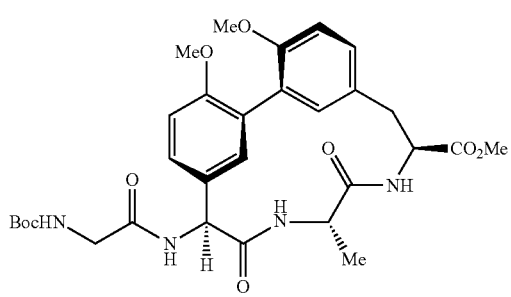

To a solution of compound 17 (30 mg, 0.073 mmol) in AcCN:DMF (2:1, 1.5 mL) under Ar was added consecutively HOBT (30 mg, 0.22 mmol, 3 eq), Boc-Gly-OH (14 mg, 0.08 mmol, 1.1 eq), and EDC (42 mg, 0.22 mmol, 3 eq). The reaction was stirred overnight then water and EtOAc were added. The water layer was extracted (2×), and the combined organic layers were washed with brine, dried over Na$_2$SO$_4$, and concentrated. Flash column chromatography (5.5% MeOH in DCM) yielded the product as a white flaky solid (30 mg, 68% yield). R$_f$=0.37 (7% MeOH in DCM). $^1$H NMR (DMSO, 500 MHz) multiple isomers. $^{13}$C NMR (DMSO, 600 MHz) multiple isomers. IR (film) v$_{max}$=1633, 1506, 1267, 1246, 1163, 1026, 580 cm$^{-1}$. ESI HRMS calcd for C$_{30}$H$_{38}$N$_4$O$_9$ [*M+H)$^+$] 599.2711. found 599.2701.

31

To a solution of compound 32 (15 mg, 0.025 mmol) in ethanethiol (0.6 mL) under Ar in a sealed tube was added AlBr$_3$ in CH$_2$Br$_2$ (1.0 M, 0.6 mL, 25 eq). The reaction was heated to 50° C. and allowed to stir for five hours. The reaction was then cooled to room temperature, a small amount of water was added and the volatiles were blown off under a stream of nitrogen. Additional water was added and the aqueous layer was extracted with EtOAc, the aqueous layer was filtered through a 0.22 μm syringe filter and purified by HPLC (linear gradient =0.67% B per minute, product eluted at 17.9% B). Lyophilization afforded the product as the TFA salt. (5.8 mg, 52% yield). $^1$H NMR (MeOD, 600 MHz) δ (ppm) 7.24 (dd, J=8.4, 2.2 Hz, 1H), 7.15-7.10 (m, 2H), 7.06 (d, J=2.00 Hz, 1H), 6.92 (d, J=8.41 Hz, 1H), 6.86 (d, J=8.26 Hz, 1H), 5.80 (s, 1H), 4.97-4.92 (m, 1H), 4.74 (dd, J=10.96, 2.27 Hz, 1H), 3.84-3.76 (m, 2H), 3.35-3.30 (m, 1H), 3.02 (dd, J=15.82, 11.05 Hz, 1H), 1.37 (d, J=6.83 Hz, 3H) ($^{13}$C NMR (DMSO, 600 MHz) δ (ppm) 182.8, 181.1, 179.0, 175.9, 163.2, 162.4, 141.3, 140.9, 139.1, 138.7, 138.3, 136.0, 135.9, 135.8, 125.6, 63.9, 62.6, 58.2, 57.8, 50.1, 43.9, 28.8. IR (film) v$_{max}$=3271 (br), 1633, 1543, 1500, 1236, 1188, 1136, 798, 683, 563 cm$^{-1}$. ESI HRMS calcd for C$_{22}$H$_{24}$N$_4$O$_7$ [(M+H)$^+$] 457.1718. found 457.1721.

39

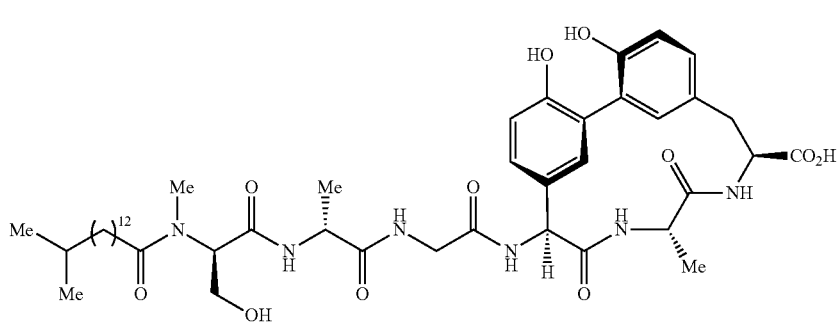

Compound 29 was synthesized in the same manner as arylomycin A₂. $^1$H NMR (MeOD, 600 MHz) δ (ppm) multiple isomers. $^{13}$C NMR (MeOD, 600 MHz) δ (ppm) multiple isomers. ESI HRMS calcd for $C_{45}H_{66}N_6O_{11}$ [(M+H)⁺] 867.4862. found 867.4853.

4.11

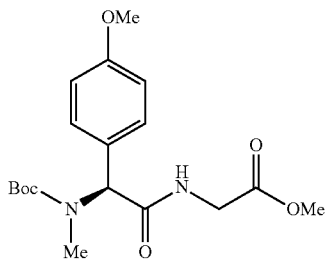

To a solution of H-Gly-OMe HCl (40 mg, 0.32 mmol, 1 eq) in DMF (3 mL) was added sequentially Boc-N-Me-Hydroxyphenylglycine (122 mg, 1.35 eq), HOBT (43 mg, 1 eq), EDC (67 mg, 1.1 eq) and TEA (49 μL, 1.1 eq). The solution was allowed to stir overnight then dilute NaHCO₃(aq) and EtOAc, the aqueous phase was extracted 3× with EtOAc and the combined organic fractions were washed with 5% citric acid (pH–3), water and brine. The organics were dried over sodium sulfate, concentrated then the crude was taken on directly without further purification. The crude residue (113 mg) was taken up in acetone (3.5 mL), treated with MeI (139 μL, 7 eq) and K₂CO₃ (221 mg, 5 eq) and heated at reflux in a sealed vial overnight. The reaction was then allowed to warm to room temperature, the volatiles were blown off and water and EtOAc were added. The aqueous layer was extracted 3× with EtOAc and the combined organic layers were dried over sodium sulfate and concentrated. Column chromatography (3% MeOH in DCM) yielded the product (64.3 mg, 55% yield over two steps). $^1$H NMR (CDCl₃, 500 MHz) δ (ppm) 7.27 (d, J=8.5 Hz, 2H), 6.89 (d, J=8.5 Hz, 2H), 6.49 (br s, 1H), 5.84 (br s, 1H), 4.09-4.08 (m, 2H), 3.80 (s, 3H), 3.75 (s, 3H), 2.71 (s, 3H), 1.47 (s, 9H) $^{13}$C NMR (CDCl₃, 500 MHz) δ (ppm) 170.6, 170.2, 159.6, 130.6, 127.2, 114.1, 80.6, 55.3, 52.4, 41.3, 31.5, 32.1, 28.4. MS (ESI) m/z 389.2 (M+Na⁺).

4.12

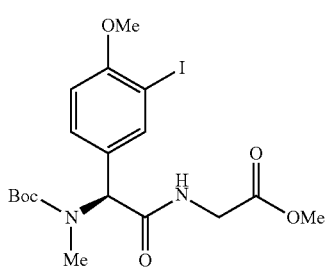

To a solution of Compound 4.11 (63 mg, 0.17 mmol, 1 eq) in MeOH (2 mL) was added sequentially AgSO₄ (56 mg, 1.05 eq) and I₂ (46 mg, 1.05 eq). The reaction mixture was allowed to stir for 2 hrs then an excess of solid sodium thiosulfate was added, the reaction was filtered through glass wool and concentrated by rotary evaporation. The crude material was purified via column chromatography (2% MeOH in DCM) to yield the product (74 mg, 88% yield). $^1$H NMR (CDCl₃, 500 MHz) δ (ppm) 7.72 (d, J=2.0 Hz, 1H), 7.30 (dd, J=8.5 Hz, J=1.5 Hz, 1H), 6.78 (d, J=8.5 Hz, 1H), 6.54 (br s, 1H), 5.78 (br s, 1H), 4.06-4.05 (m, 2H), 3.85 (s, 3H), 3.74 (s, 3H), 2.70 (s, 3H), 1.45 (s, 9H). $^{13}$C NMR (CDCl₃, 500 MHz) δ (ppm) 170.1, 170.0, 158.1, 140.2, 130.6, 129.3, 110.7, 86.1, 80.9, 56.5, 52.5, 41.3, 31.7, 28.4. MS (ESI) m/z XX (M+H⁺).

4.13

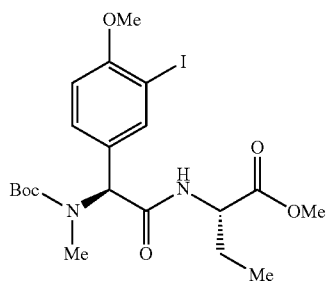

To a solution of Boc-N-Me-3-Iodo-Hydroxyphenylglycine (150 mg, 0.37 mmol, 1 eq) in DMF (3.5 mL) was added sequentially L-2-aminobutyric acid HCl (48 mg, 1.1 eq), HOBT (50 mg, 1 eq), EDC (78 mg, 1.1 eq) and NaHCO₃ (34 mg, 1.1 eq). The solution was allowed to stir overnight then was diluted with NaHCO₃(aq) and EtOAc. The aqueous phase was extracted 3× with EtOAc and the combined organic layers were washed with 5% citric acid (pH–3), water and brine. The organics were then dried over sodium sulfate then concentrated. TLC analysis of the crude mixture showed one major product so the crude material (105 mg, 0.20 mmol (assumed), 1 eq) was taken up in acetone (2.5 mL) and treated with MeI (63 μL, 5 eq) and K₂CO₃ (138 mg, 5 eq). The reaction was stirred for 1.5 h at reflux in a sealed tube then the acetone was blown off under a stream of nitrogen. To the residue was added water and EtOAc and the aqueous was extracted 3× with EtOAc. The combined organic layers were then dried over sodium sulfate, concentrated and the crude material was purified via column chromatography (1% MeOH in DCM) to give the product (58 mg, 29% yield over 2 steps). $^1$H NMR (CDCl₃, 500 MHz) δ (ppm) 7.73-7.71 (m, 1H), 7.32-7.28 (m, 1H), 6.45-6.37 (m, 1H), 5.76 (br s, 1H), 4.61-4.55 (m, 1H), 3.87 (s, 3H), 3.74 (s, 3H), 2.71-2.70 (m, 3H), 1.93-1.88 (m, 1H), 1.74-1.69 (m, 1H), 1.47-1.46 (m, 9H), 0.93-0.87 (m, 3H) $^{13}$C NMR (CDCl₃, 500 MHz) δ (ppm)

172.5, 169.5, 158.1, 140.2, 130.5, 129.3, 110.8, 86.1, 80.9, 56.5, 53.6, 52.5, 31.6, 28.5, 25.5, 9.8. MS (ESI) m/z 543.1 (M+Na$^+$).

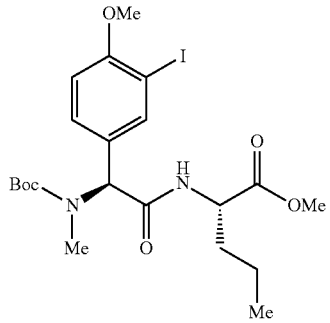

4.14

Compound 4.14 was synthesized identically to compound 4.13 giving the product (47 mg, 15% yield over 2 steps). $^1$H NMR (MeOD, 600 MHz) δ (ppm) 7.72 (s, 1H), 7.33 (d, J=8.4 Hz, 1H), 6.98 (d, J=8.4 Hz, 1H), 5.77 (br s, 1H), 4.45-4.42 (m, 1H), 3.88 (s, 3H), 3.75 (s, 3H), 2.64 (s, 3H), 1.80-1.78 (m, 1H), 1.69-1.67 (m, 1H), 1.53-1.29 (m, 11H), 0.95 (t, J=7.2 Hz, 3H) $^{13}$C NMR (MeOD, 600 MHz) δ (ppm) 174.0, 172.7, 159.7, 157.6, 141.2, 131.9, 130.7, 111.9, 86.3, 81.8, 62.5, 56.9, 53.7, 52.8, 34.2, 32.1, 28.7, 20.2, 13.9. MS (ESI) m/z 557.1 (M+Na$^+$).

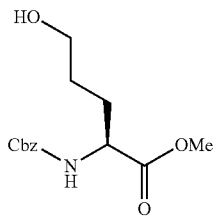

4.15

To a solution of Z-Glu-OMe (268 mg, 0.91 mmol, 1 eq) in THF (3 mL) at 0° C. was added ethyl chloroformate (174 μL, 2 eq), and TEA (253 μL, 2 eq). The mixture was allowed to stir for 45 min then filtered through glass wool (washing with THF) and the filtrate was treated with NaBH$_4$ (151 mg, 4.4 eq) in H$_2$O (1.5 mL) at 0° C. This reaction was allowed to stir for 45 min then it was warmed to rt. Next, saturated NaHCO$_3$, water and EtOAc were added and the aqueous phase was extracted 3× with EtOAc. The combined organic layers were washed with 5% citric acid and brine then dried over sodium sulfate and concentrated. Column chromatography (4% MeOH in DCM) yielded the product (106 mg, 41% yield). $^1$H NMR (CDCl$_3$, 600 MHz) δ (ppm) 7.36-7.28 (m, 5H), 5.08 (s, 2H), 4.21-4.19 (m, 1H), 3.70 (s, 3H), 3.56-3.54 (m, 2H), 1.93-1.87 (m, 1H), 1.74-1.68 (m, 1H), 1.65-1.55 (m, 2H).). $^{13}$C NMR (CDCl$_3$, 500 MHz) δ (ppm) 174.6, 158.6, 138.1, 129.4, 129.0, 128.8, 67.6, 62.1, 55.3, 52.6, 29.8, 29.1. MS (ESI) m/z 304.1 (M+Na$^+$).

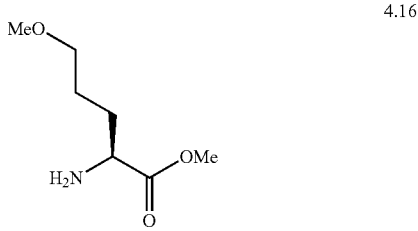 [SMILES: COCCC[C@H](N)C(=O)OC]

4.16

To a solution of compound 4.15 (104 mg, 0.37 mmol, 1 eq) in DCM (2.0 mL) was added 50% HBF$_{4(aq)}$ (23 μL, 1 eq) and 2M TMSCH$_2$N$_2$ in diethyl ether (370 μL, 2 eq) dropwise over 15 min at 0° C. The reaction was monitored by TLC for disappearance of starting material. TMSCH$_2$N$_2$ (190 μL, 1 eq) was added every (~45 min) four times over the course of 3 hrs. along with 50% HBF$_{4(aq)}$ (12 μL, 0.5 eq). The reaction was allowed to stir for an additional 30 min then the volatiles were evaporated, water was added and the aqueous layer was washed with EtOAc 3×. The combined organic layers were dried over sodium sulfate concentrated and purified via column chromatography (35% EtOAc in Hex). This material (55 mg, R$_f$ 0.35 in 35% EtOAc in Hex) was dissolved in MeOH, to it was added 10% Pd/C (20 mg, ⅓ by weight) and the mixture was placed under an atmosphere of H$_2$ (1 atm). When TLC indicated a complete consumption of starting material the mixture was filtered through Celite and concentrated. The resulting Cbz deprotected material (30 mg, 50% yield) was used directly in the next step of the synthesis.

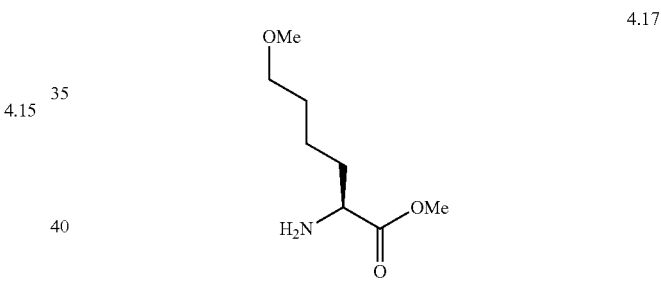

4.17

To a solution of Boc-L-6-hydroxynorleucine (500 mg, 2 mmol, 1 eq) in a 9:1 mixture of toluene:MeOH (5 mL) was added TMSCH$_2$N$_2$ (1.15 mL, 1.15 eq) and the solution was allowed to stir for 1.5 hrs. The volatiles were then evaporated and the crude was purified via column chromatography (4% MeOH in DCM) to yield the product (472 mg). This material (418 mg, 1.6 mmol) was then dissolved in DCM (7 mL) and treated with 50% HBF$_{4(aq)}$ (200 μL, 1 eq) and TMSCH$_2$N$_2$ in hexanes (1.6 mL, 2 eq) at 0° C. After 0.5 hr the solution was treated with TMSCH$_2$N$_2$ in Hexanes (0.5 eq, 0.4 mL) and after a further 15 min the solution was treated with 50% HBF$_{4(aq)}$ (50 μL, 1 eq) and TMSCH$_2$N$_2$ in Hexanes (0.5 eq, 0.4 mL). The reaction was allowed to stir for another 40 min then dilute NaHCO$_3$ was added and the aqueous layer was extracted 3× with DCM. The combined organic layers were dried over sodium sulfate and concentrated. The crude material was purified via column chromatography (1.5% MeOH in DCM) to give the product (255 mg, 52% over 2 steps). $^1$H NMR (CDCl$_3$, 400 MHz) δ (ppm) 5.05 (d, J=8.0 Hz, 1H), 4.27-4.21 (m, 1H), 3.68 (s, 3H), 3.31 (t, J=6.4 Hz, 2H), 3.26 (s, 3H), 1.81-1.72 (m, 1H), 1.64-1.34 (m, 14H). $^{13}$C NMR (CDCl$_3$, 400 MHz) δ (ppm) 173.4, 155.4, 79.8, 72.4, 58.6, 53.4, 52.2, 32.5, 29.2, 28.4, 22.1. MS (ESI) m/z 176.2 (M+H$^+$). The preceding compound (136 mg, 0.49 mmol) was dissolved in DCM (3 mL) and treated with TFA (0.75 mL). The reaction was allowed to run for 1.5 hrs then the volatiles were evaporated under a stream of nitrogen and the crude was taken up in EtOAc and treated with dilute NaHCO₃. The aqueous phase was extracted 9× with EtOAc then the combined organic layers were dried over sodium sulfate and concentrated to give compound 4.17 (75 mg, 87%) which was used in the following step without purification.

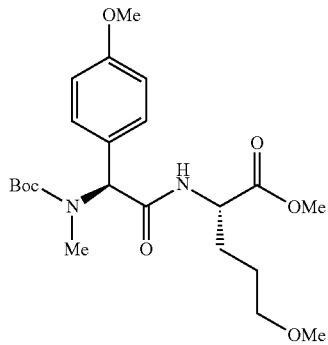

4.18

Boc-N-Me-Hydroxyphenylglycine (71 mg, 0.19 mmol, 1 eq) was dissolved in DMF (1.0 mL) and treated sequentially with compound 4.16 (30 mg, 1 eq), HOBT (26 mg, 1 eq), EDC (37 mg, 1 eq) and TEA (catalytic). The reaction was allowed to stir overnight under Ar then water and EtOAc were added. The aqueous layer was extracted 3× with EtOAc then the combined organic layers were washed with dilute NaHCO₃(aq) and brine. The organics were dried over sodium sulfate, concentrated and the crude was used without further purification. This material (75 mg, 0.18 mmol (assumed), 1 eq) was dissolved in acetone (2 mL), treated with MeI (77 μL, 7 eq) and K₂CO₃ (124 mg, 5 eq) and heated to reflux in a sealed vial overnight. The reaction mixture was then cooled to room temperature and the acetone was evaporated under a stream on nitrogen. Water and EtOAc were added, the aqueous phase was extracted 3× with EtOAc, and the combined organic layers were dried over sodium sulfate. After concentrating, the crude material was purified via column chromatography (3% MeOH in DCM) to yield the product (68 mg, 81% over two steps). ¹H NMR (CDCl₃, 400 MHz) δ (ppm) 7.28 (d, J=8.4 Hz, 2H), 6.88 (d, J=8.8 Hz, 2H), 6.56 (d, J=7.2 Hz, 1H), 5.82 (br s, 1H), 4.63-4.58 (m, 1H), 3.79 (s, 3H), 3.72 (s, 3H), 3.34 (t, J=6.0 Hz, 2H) 3.22 (s, 3H), 2.67 (s, 3H) 1.94-1.79 (m, 2H), 1.63-1.42 (m, 11H) ¹³C NMR (CDCl₃, 400 MHz) δ (ppm) 172.7, 170.2, 159.6, 130.8, 127.4, 114.1, 80.5, 71.9, 58.6, 55.4, 52.4, 52.2, 31.4, 29.0, 28.5, 28.5, 25.6. MS (ESI) m/z 461.5 (M+Na⁺).

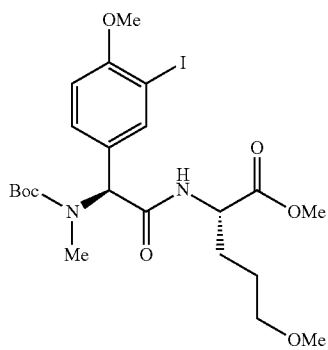

4.19

To a solution of compound 4.18 (67 mg, 0.15 mmol, 1 eq) in MeOH (3.5 mL) was added sequentially AgSO₄ (50 mg, 1.05 eq) and I₂ (41 mg, 1.05 eq). The reaction mixture was allowed to stir for 2.5 hrs then the proportion of product to starting material was checked by mass spectrometry. Seeing that starting material remained AgSO₄ (5.0 mg, 0.1 eq) and I₂ (4.0 mg, 0.1 eq). This process was repeated every 2-3 hrs for 6 hrs then 10% sodium thiosulfate was added and some of the volatiles were blown off under a stream of nitrogen. EtOAc was added, the aqueous layer was extracted 3× with EtOAc then the combined organic layers were washed with brine, dried over sodium sulfate and concentrated by rotary evaporation. The crude material was purified via column chromatography (2% MeOH in DCM) to yield the product (44 mg, 52% yield). Some NMR resonances appeared broadened or doubled (with one isomer in large excess to the other) due to slow rotation about the N-Me amide. ¹H NMR (CDCl₃, 600 MHz) δ (ppm) 7.74 (s, 1H), 7.33 (d, J=7.8, 1H), 6.80 (d, J=8.4 Hz, 1H), 6.67-6.66 (m, 1H), 5.77 (br s, 1H), 4.60-4.57 (m, 1H), 3.87 (s, 3H), 3.72 (s, 3H), 3.39 (t, J=6.0 Hz, 2H), 3.23 (s, 3H), 2.68 (s, 3H), 1.96-1.77 (m, 2H), 1.61-1.47 (m, 11H). ¹³C NMR (CDCl₃, 600 MHz) δ (ppm) 172.5, 169.6, 158.1, 140.3, 140.2, 130.7, 129.5, 129.4, 121.6, 110.7, 86.0, 80.8, 71.9, 58.6, 56.5, 52.5, 52.3, 31.5, 28.9, 28.5, 27.8, 25.5. MS (ESI) m/z 587.2 (M+Na⁺).

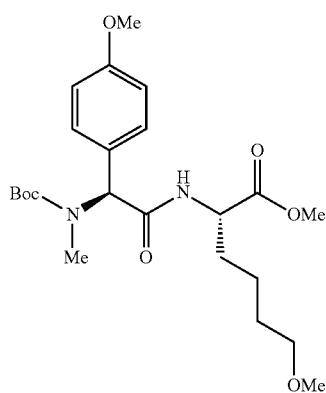

4.20

Boc-N-Me-Hydroxyphenylglycine (39 mg, 0.14 mmol, 1 eq) was dissolved in DMF (1.5 mL) and treated sequentially with compound 4.17 (25 mg, 1 eq), HOBT (19 mg, 1 eq), EDC (30 mg, 1 eq) and TEA (catalytic). The reaction was allowed to stir overnight under Ar then water and EtOAc were added. The aqueous layer was extracted 3× with EtOAc then the combined organic layers were washed with dilute NaHCO₃(aq) and brine. The organics were dried over sodium sulfate, concentrated and the crude was used without further purification. This material (61 mg, 0.14 mmol (assumed), 1 eq) was dissolved in acetone (1.5 mL), treated with MeI (88 μL, 10 eq) and K₂CO₃ (58 mg, 3 eq) and heated to reflux in a sealed vial overnight. The reaction mixture was then cooled to room temperature and the acetone was evaporated under a stream on nitrogen. Water and EtOAc were added, the aqueous phase was extracted 3× with EtOAc, and the combined organic layers were dried over sodium sulfate. After concentrating, the crude material was purified via column chromatography (2.5% MeOH in DCM) to yield the product (46 mg, 72% over two steps). ¹H NMR (CDCl₃, 500 MHz) δ (ppm) 7.27 (d, J=8.5 Hz, 2H), 6.89 (d, J=8.5 Hz, 2H), 6.33 (d, J=8.0 Hz, 1H), 5.81 (br s, 1H), 4.64-4.60 (m, 1H), 3.80 (s, 3H), 3.73 (s, 3H), 3.34 (t, J=6.5 Hz, 2H) 3.29 (s, 3H), 2.69 (s, 3H) 1.89-1.84 (m, 1H), 1.72-1.65 (m, 1H), 1.61-1.34 (m, 13H) ¹³C NMR (CDCl₃, 500 MHz) δ (ppm) 172.7, 170.1, 159.6, 130.7, 127.2, 114.1, 80.5, 72.4, 58.6, 55.4, 52.4, 52.4, 32.0, 31.4, 29.1, 28.5, 22.3. MS (ESI) m/z 475.2 (M+Na⁺).

4.21

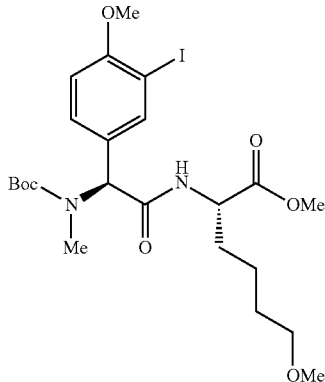

To a solution of compound 4.20 (44 mg, 0.097 mmol, 1 eq) in MeOH (1.5 mL) was added sequentially AgSO₄ (32 mg, 1.05 eq) and I₂ (26 mg, 1.05 eq). The reaction mixture was allowed to stir for 2.5 hrs then the proportion of product to starting material was checked by mass spectrometry. Seeing that starting material remained AgSO₄ (3.0 mg, 0.1 eq) and I₂ (3.0 mg, 0.1 eq). This process was repeated every 2-3 hrs for 6 hrs then 10% sodium thiosulfate was added and some of the volatiles were blown off under a stream of nitrogen. EtOAc was added, the aqueous layer was extracted 3× with EtOAc then the combined organic layers were washed with brine, dried over sodium sulfate and concentrated by rotary evaporation. The crude material was purified via column chromatography (2.5% MeOH in DCM) to yield the product (46 mg, 81% yield). Some NMR resonances appeared broadened or doubled (with one isomer in large excess to the other) due to slow rotation about the N-Me amide. ¹H NMR (CDCl₃, 500 MHz) δ (ppm) 7.73 (d, J=1.5 Hz, 1H), 7.31 (d, J=8.5, 1H), 6.79 (d, J=8.5 Hz, 1H), 6.38 (d, J=7.5 Hz, 1H), 5.74 (br s, 1H), 4.61-4.57 (m, 1H), 3.86 (s, 3H), 3.73 (s, 3H), 3.33 (t, J=6.5 Hz, 2H), 3.27 (s, 3H), 2.69 (s, 3H), 1.90-1.85 (m, 1H), 1.72-1.65 (m, 1H), 1.58-1.34 (m, 13H). ¹³C NMR (CDCl₃, 500 MHz) δ (ppm) 172.6, 169.5, 158.1, 140.3, 130.6, 129.3, 110.8, 86.1, 80.8, 72.4, 58.6, 56.5, 52.5, 52.5, 32.0, 31.6, 29.1, 28.5, 22.3. MS (ESI) m/z 601.2 (M+Na⁺).

4.22

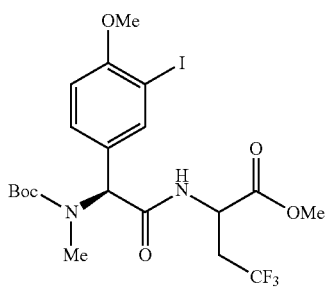

Boc-N-Me-3-Iodo-Hydroxyphenylglycine (116 mg, 0.28 mmol, 1 eq) was dissolved in a 3:1 mixture of DCM:DMF (2.8 mL) and treated sequentially with racemic 2-amino-4,4,4-trifluoro-butyric acid hydrochloride (59 mg, 1 eq), HOBT (38 mg, 1 eq), DIC (49 µL, 1.1 eq) and TEA (40 µL, 1 eq). The reaction was allowed to stir overnight under Ar then the DCM was blown off and dilute NaHCO₃(aq) and EtOAc were added. The aqueous layer was extracted 3× with EtOAc then the combined organic layers were washed with 5% citric acid (pH−3), water and brine. The organics were dried over sodium sulfate, concentrated and purified via column chromatography (4% MeOH in DCM) to yield an oil. This material (81 mg, 0.145 mmol (assumed), 1 eq) was dissolved in acetone (2 mL), treated with MeI (45 µL, 5 eq) and K₂CO₃ (100 mg, 5 eq) and heated to reflux in a sealed vial overnight. The reaction mixture was then cooled to room temperature and the acetone was evaporated under a stream on nitrogen. Water and EtOAc were added, the aqueous phase was extracted 3× with EtOAc, and the combined organic layers were dried over sodium sulfate. After concentrating, the crude material was purified via column chromatography (1.8% MeOH in DCM) to yield the product as a foam (47 mg, 15% over two steps). ¹H NMR (MeOD, 600 MHz) δ (ppm) 7.70 (s, 1H), 7.32-7.29 (m, 1H), 6.99-6.97 (m, 1H), 5.78 (br s, 1H), 4.82-4.68 (m, 1H), 3.88 (s, 3H), 3.80-3.79 (m, 3H), 2.94-2.86 (m, 1H), 2.74-2.66 (m, 5H), 1.49 (s, 1H) ¹³C NMR (MeOD, 600 MHz) δ (ppm) 172.4, 172.2, 171.4, 171.3, 159.8, 141.2, 132.0, 131.9, 130.4, 128.3, 128.3, 126.5, 126.4, 112.0, 112.0, 86.3, 86.3, 82.0, 62.8, 56.9, 53.5, 53.4, 35.6, 35.4, 35.4, 35.2, 31.9, 28.6. MS (ESI) m/z 597.1 (M+Na⁺).

4.23

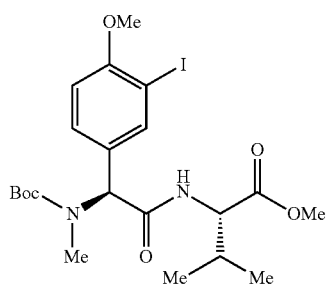

Compound 4.23 was synthesized in a manner identical to compound 4.13 (53% yield).

4.24

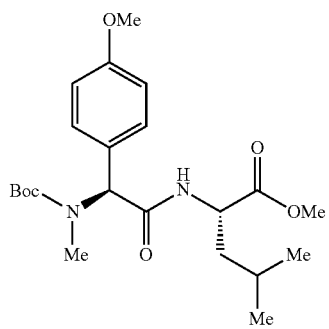

Boc-N-Me-Hydroxyphenylglycine (124 mg, 0.44 mmol, 1 eq) dissolved in DMF (2.0 mL) was added sequentially H-Leu-OMe (80 mg, 1 eq), HOBT (59 mg, 1 eq), EDC (93 mg, 1.1 eq) and TEA (67 µL, 1.1 eq). The reaction was allowed to stir overnight then dilute NaHCO₃(aq) and EtOAc, the aqueous phase was extracted 3× with EtOAc and the combined organic fractions were washed with 5% citric acid (pH−3), water and brine. The organics were then dried over sodium sulfate, concentrated and the crude was used without further purification. The crude material (170 mg, 0.42 mmol (assumed), 1 eq) was taken up in acetone (2 mL) and treated with MeI (260 µL, 10 eq) and K₂CO₃ (172 mg, 3 eq). The reaction was stirred for overnight at reflux in a sealed tube then the acetone was blown off under a stream of nitrogen. To the residue was added water and EtOAc and the aqueous was extracted 3× with EtOAc. The combined organic layers were then dried over sodium sulfate, concentrated and the crude material was purified via column chromatography (1.5% MeOH in DCM) to give the product (130 mg, 70% yield over 2 steps). $^1$H NMR (CDCl$_3$, 500 MHz) δ (ppm) 7.26 (d, J=8.5 Hz, 2H), 6.88 (d, J=8.5 Hz, 2H), 6.49 (d, J=8.0 Hz 1H), 5.81 (br s, 1H), 4.68-4.63 (m, 2H), 3.79 (s, 3H), 3.72 (s, 3H), 1.66-1.63 (s, 2H), 1.54-1.46 (m, 10H), 0.93 (t, J=6.0 Hz, 3H) $^{13}$C NMR (CDCl$_3$, 500 MHz) δ (ppm) 173.3, 170.1, 159.6, 130.7, 127.2, 114.2, 80.5, 55.4, 52.4, 51.0, 41.5, 31.4, 28.5, 25.0, 22.9, 22.0. MS (ESI) m/z 445.2 (M+Na$^+$).

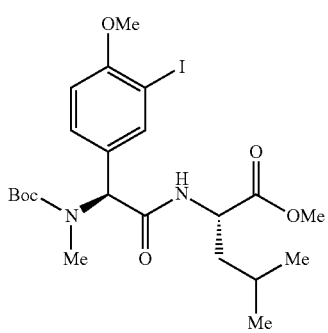

4.25

To a solution of compound 4.24 (129 mg, 0.31 mmol, 1 eq) in MeOH (2 mL) was added sequentially AgSO$_4$ (101 mg, 1.05 eq) and I$_2$ (81 mg, 1.05 eq). The reaction mixture was allowed to stir for 2.5 hrs then 10% sodium thiosulfate and some of the volatiles were blown off under a stream of nitrogen. EtOAc was added, the aqueous layer was extracted 3× with EtOAc then the combined organic layers were washed with brine, dried over sodium sulfate and concentrated by rotary evaporation. The crude material was purified via column chromatography (1% MeOH in DCM) to yield the product (135 mg, 80% yield). $^1$H NMR (CDCl$_3$, 500 MHz) δ (ppm) 7.72 (d, J=2.0 Hz, 1H), 7.30 (dd, J=8.5 Hz, J=1.5 Hz, 1H), 6.78 (d, J=8.5 Hz, 1H), 6.23 (br s, 1H), 5.74 (br s, 1H), 4.65-4.60 (m, 2H), 3.85 (s, 3H), 3.72 (s, 3H), 2.68 (s, 3H), 1.65-1.63 (m, 2H), 1.53-1.45 (m, 10H), 0.92 (t, J=6 Hz, 6H). $^{13}$C NMR (CDCl$_3$, 500 MHz) δ (ppm) 173.1, 169.5, 158.1, 140.2, 130.5, 129.2, 110.7, 86.0, 80.8, 56.5, 52.4, 41.3, 31.6, 28.4, 24.9, 22.9, 21.9. MS (ESI) m/z XX (M+H$^+$).

General Procedure A

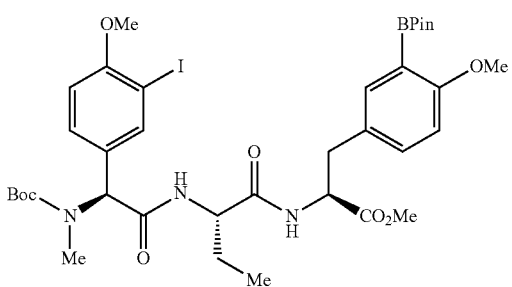

4.26

To a solution of compound 4.13 (57 mg, 0.11 mmol, 1 eq) in THF (1.3 mL) was added a 0.2 M LiOH solution (1.1 mL, 2 eq). The solution was allowed to stir until all starting material had been consumed by TLC analysis then the reaction was quenched by the addition of citric acid (pH–3) and THF was blown off under a stream of nitrogen. The aqueous layer was extracted 3× with EtOAc and the combined organic layers were washed with brine, dried over sodium sulfate and concentrated. The resulting crude material (55 mg) was used without further purification. To a solution of this crude material (52 mg, 0.1 mmol, 1 eq) and compound XX in a 1:1 mixture of AcCN:DMF (2.6 mL) was added sequentially HOBT (24 mg, 2.5 eq) and EDC (42 mg, 2.2 eq). The reaction was allowed to stir overnight then dilute NaHCO$_{3(aq)}$ was added and the aqueous phase was extracted 3× with EtOAc. The combined organic layers were washed with 5% citric acid (pH–3), water and brine then dried over sodium sulfate and concentrated. The crude material was purified via abbreviated column chromatography (2.5% MeOH in DCM) due to its instability in the presence of silica gel. The purification yielded a semi-pure residue (65 mg, 77% yield). $^1$H NMR (CDCl$_3$, 600 MHz) δ (ppm) $^{13}$C NMR (CDCl$_3$, 600 MHz) δ (ppm) 171.8, 171.5, 171.0, 170.9, 170.8, 169.7, 163.7, 163.5, 163.4, 158.2, 158.1, 158.0, 140.4, 140.2, 137.8, 137.6, 133.4, 133.3, 130.7, 130.3, 130.2, 130.0, 129.2, 127.8, 127.0, 114.2, 114.1, 110.9, 110.8, 110.8, 110.6, 110.0, 86.2, 86.1, 83.7, 83.7, 81.1, 80.9, 62.2, 56.5, 56.5, 56.4, 55.9, 55.7, 55.3, 54.5 (2C), 54.4, 53.8, 53.6 (2C), 53.2, 52.5 (2C), 52.4, 37.0, 36.8, 36.6, 32.1, 28.5, 25.5, 25.0, 24.9 (2C), 10.1, 9.9 (2C), 9.8. MS (ESI) m/z 846.3 (M+Na$^+$).

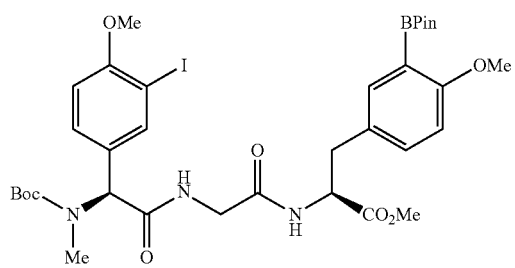

4.27

Compound 4.27 was synthesized via general procedure A starting from compound 4.12 (66% yield). R$_f$-0.28 (4% MeOH in DCM). $^1$H NMR (CDCl$_3$, 600 MHz) δ (ppm) 7.70-7.68 (m, 1H), 7.45-7.33 (m, 1H), 7.23-7.22 (m, 1H), 7.15-7.10 (m, 1H), 6.75-6.66 (m, 4H), 5.61 (br s, 1H), 4.79-4.73 (m, 1H), 4.03-3.96 (m, 1H) 3.84-3.67 (m, 9H), 3.11-2.95 (m, 2H), 2.70-2.69 (m, 3H), 1.45-1.44 (m, 9H) 1.31-1.30 (m, 10H). $^{13}$C NMR (CDCl$_3$, 600 MHz) δ (ppm) 171.8, 171.8, 171.6, 170.1, 168.4, 163.6, 163.4, 163.3, 158.1, 158.1, 140.3, 140.3, 140.2, 137.7, 137.6, 133.2, 134.8, 130.5, 129.2, 127.0, 110.8, 110.7, 110.6, 86.1, 83.6, 80.9, 62.4, 56.5, 56.4, 56.4, 55.9, 55.8, 55.6, 53.7, 53.5, 52.5, 52.4, 52.4, 43.0, 43.0, 36.7, 36.6, 32.2, 28.4, 27.7, 25.0, 24.9, 24.9, 24.8. MS (ESI) m/z 818.3 (M+H$^+$).

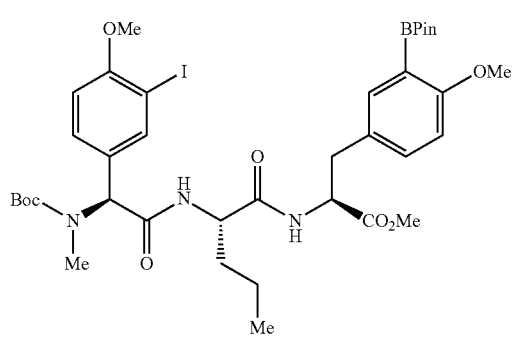

4.28

Compound 4.28 was synthesized via general procedure A using compound 4.14 (81% yield). $^1$H NMR (MeOD, 600 MHz) δ (ppm) 7.69-7.64 (m, 1H), 7.45 (s, 1H), 7.29-7.26 (m, 1H), 7.16-7.07 (m, 1H), 6.97-6.81 (m, 2H), 5.68-5.64 (m, 1H), 4.62-4.59 (m, 1H), 4.45-4.43 (m, 1H) 3.87-3.67 (m, 9H), 3.09-3.06 (m, 1H), 2.89-2.93 (m, 1H), 2.66-2.64 (m, 3H), 1.75-1.69 (m, 1H) 1.62-1.27 (m, 24H), 0.95-0.88 (s, 3H). $^{13}$C NMR (MeOD, 600 MHz) δ (ppm) 174.0, 173.3, 172.2, 164.8, 164.8, 141.3, 141.2, 138.7, 138.6, 134.8, 134.8, 132.0, 131.6, 131.3, 130.6, 129.3, 114.9, 112.1, 112.0, 111.7, 111.6, 86.5, 86.3, 84.8, 81.9, 57.0, 56.9, 55.9, 55.8, 55.7, 55.6, 54.3, 52.7, 52.6, 37.6, 37.4, 35.2, 32.4, 28.7, 28.7, 25.2, 25.1, 20.0, 19.9, 14.1. MS (ESI) m/z 860.3 (M+Na$^+$).

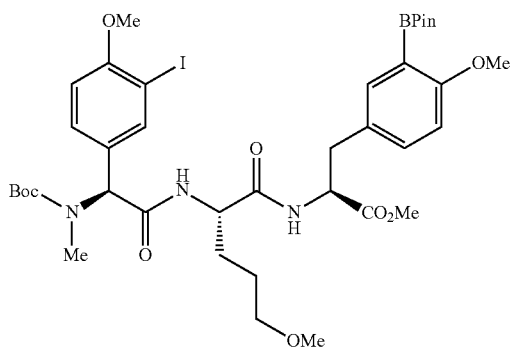

Compound 4.29 was synthesized via general procedure A using compound 4.19 (72% yield). $^1$H NMR (CDCl$_3$, 400 MHz) δ (ppm) 7.70-7.69 (s, 1H), 7.43-7.37 (m, 1H), 7.24-7.07 (m, 2H), 7.00-6.98 (m, 1H), 6.78-6.67 (m, 3H), 5.66-5.62 (m, 1H), 4.76-4.71 (m, 1H), 4.57-4.51 (m, 1H) 3.86-3.68 (m, 9H), 3.44-3.39 (m, 2H), 3.28-3.18 (m, 3H), 3.06-2.95 (m, 2H), 2.75-2.68 (m, 3H), 1.85-1.71 (m, 2H), 1.62-1.41 (m, 11H) 1.37-1.23 (m, 12H). $^{13}$C NMR (CDCl$_3$, 400 MHz) δ (ppm) 171.9, 171.0, 169.7, 163.4, 158.0, 140.2, 137.6, 133.2, 130.3, 129.4, 127.2, 110.8, 110.7, 86.1, 83.6, 80.8, 72.8, 62.2, 58.7, 56.5, 55.9, 53.8, 52.7, 52.3, 36.9, 32.0, 30.5, 28.5, 25.3, 25.0, 24.9. MS (ESI) m/z 890.3 (M+Na$^+$).

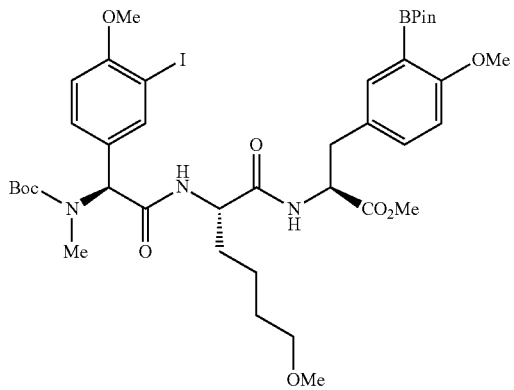

Compound 4.30 was synthesized via general procedure A using compound 4.21 (65% yield). R$_f$-0.26 (4% MeOH in DCM). $^1$H NMR (CDCl$_3$, 600 MHz) δ (ppm) 7.74-7.70 (s, 1H), 7.42-7.33 (m, 1H), 7.22-7.16 (m, 1H), 7.11-7.10 (m, 1H), 6.78-6.69 (m, 2H), 6.63-6.53 (m, 1H), 6.42-6.40 (m, 1H), 5.66-5.61 (m, 1H), 4.77-4.74 (m, 1H), 4.49-4.40 (m, 1H) 3.87-3.69 (m, 9H), 3.34-3.26 (m, 5H), 3.06-2.98 (m, 2H), 2.76-2.68 (m, 3H), 2.05-2.03 (m, 1H), 1.91-1.86 (m, 1H), 1.61-1.24 (m, 25H). $^{13}$C NMR (CDCl$_3$, 600 MHz) δ (ppm) 171.8, 171.0, 169.7, 163.4, 158.1, 140.2, 137.6, 133.3, 130.3, 129.2, 127.0, 110.9, 110.6, 86.2, 83.7, 83.6, 80.9, 72.5, 62.2, 58.6, 56.5, 55.9, 53.7, 53.2, 52.3, 36.9, 32.1, 32.0, 29.0, 28.5, 25.0, 24.9, 24.8, 22.2. MS (ESI) m/z 904.3 (M+Na$^+$).

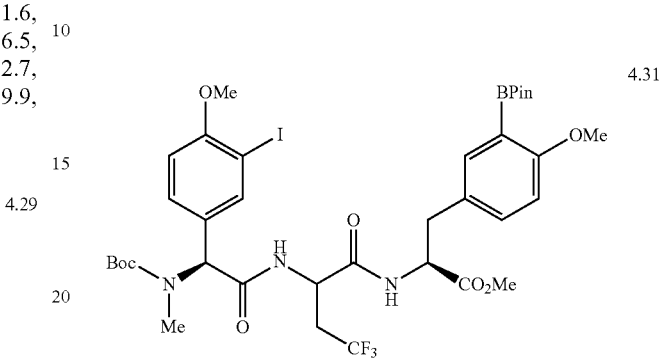

Compound 4.31 was synthesized via general procedure A using compound 4.22 (68% yield). $^1$H NMR (MeOD, 600 MHz) δ (ppm) 7.69-7.64 (m, 1H), 7.49-7.46 (m, 1H), 7.31-7.06 (m, 2H), 6.95-6.80 (m, 2H), 5.66-5.56 (m, 1H), 4.87-4.83 (m, 1H), 4.66-4.56 (m, 1H) 3.87-3.68 (m, 9H), 3.14-3.08 (m, 1H), 2.99-2.96 (m, 1H), 2.66-2.43 (m, 5H), 1.49-1.47 (m, 9H), 1.33 (s, 11H). $^{13}$C NMR (MeOD, 600 MHz) δ (ppm) 173.1 (2C), 173.0, 172.3, 172.1, 171.9, 171.5, 171.3, 171.1, 171.0, 164.9, 164.8, 164.8, 164.7, 159.9, 159.8, 159.7, 141.5, 141.4, 141.3, 141.2, 138.8, 138.7, 138.6, 134.8, 134.8, 132.0, 131.7, 131.7, 130.4, 130.0, 129.3, 129.2, 129.1, 128.3, 126.4, 118.5, 115.0, 112.1 (3C), 111.9, 111.8, 111.7, 111.7, 86.5, 86.4, 86.3, 84.8, 82.0, 63.7, 63.7, 63.2, 57.0, 56.9, 56.0, 55.9, 55.9, 55.9, 52.9, 52.8, 52.8, 52.7, 37.6, 37.5, 28.7, 28.7, 28.6, 25.2, 25.1, 25.1. MS (ESI) m/z 900.3 (M+Na$^+$).

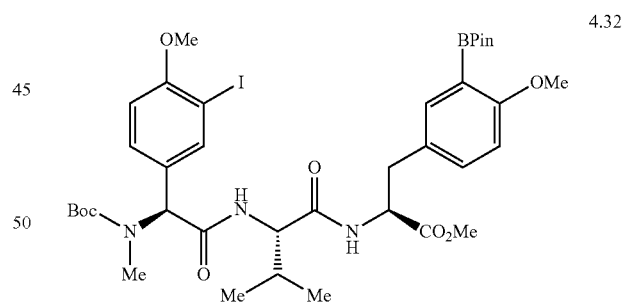

Compound 4.32 was synthesized via general procedure A using compound 4.23 (68% yield). $^1$H NMR (CDCl$_3$, 600 MHz) δ (ppm) $^{13}$C NMR (CDCl$_3$, 600 MHz) δ (ppm) 171.8, 171.8, 170.6, 170.5, 170.5, 169.9, 169.6, 163.5, 163.4, 158.8, 158.1, 158.0, 156.1, 140.4, 140.0, 137.7, 137.6, 137.5, 133.4, 133.3, 130.7, 130.3, 130.2, 130.1, 129.2, 129.1, 127.1, 118.0, 114.1, 114.1, 110.8, 110.8, 110.8, 110.6, 86.1, 86.0 (2C), 83.6, 83.6, 83.5, 80.9, 62.5, 58.4, 58.3, 58.3, 56.5 (2C), 55.9, 55.9, 53.7, 53.6, 53.5, 52.4, 52.4, 52.4, 52.3, 36.9, 36.9, 36.8, 30.8, 28.4, 24.9 (3C), 24.8, 19.3 (3C), 19.2, 17.8. MS (ESI) m/z 860.3 (M+Na$^+$).

4.33

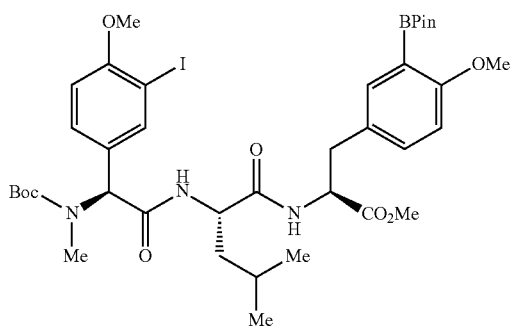

Compound 4.33 was synthesized via general procedure A starting from compound 4.25 (69% yield). R$_f$-0.41 (4% MeOH in DCM). $^1$H NMR (CDCl$_3$, 600 MHz) δ (ppm) 7.68 (s, 1H), 7.33-7.31 (m, 1H), 7.20-7.17 (m, 1H), 7.11-7.06 (m, 1H), 6.77-6.59 (m, 3H), 6.30 (d, J=7.8 Hz, 1H), 5.64-5.56 (m, 1H), 4.76-4.72 (m, 1H), 4.53-4.50 (m, 1H) 3.86-3.68 (m, 9H), 3.06-2.97 (m, 2H), 2.72-2.67 (m, 3H), 1.69-1.60 (m, 2H), 1.46-1.45 (m, 10H) 1.32-1.27 (m, 11H) 0.90-0.85 (m, 3H). $^{13}$C NMR (CDCl$_3$, 600 MHz) δ (ppm) 171.8, 171.4, 169.7, 163.3, 158.0, 140.1, 137.6, 133.3, 130.1, 129.1, 128.6, 127.0, 110.8, 110.5, 86.2, 83.6, 81.0, 80.8, 56.4, 55.8, 53.6, 52.3, 51.7, 40.8, 36.8, 28.4, 25.0, 24.9, 24.8, 24.8, 23.1, 21.8. MS (ESI) m/z 874.3 (M+Na$^+$).

General Procedure B 4.34

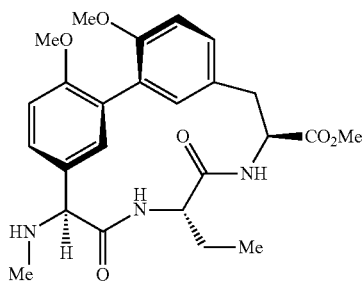

A solution of compound 4.26 (50 mg, 61 μmol, 1 eq) and NaHCO$_3$ (49 mg, 10 eq) in DMF (1.75 mL) was purged several times via cycling with vacuum and Ar and sealed with a crimped septa. To this solution was added a solution of PdCl$_2$(dppf) (9.9 mg, 0.2 eq) in DMF (1.2 mL) that had been sparged with Ar for ~15 minutes via syringe. The resulting mixture was submitted to several more cycles of vacuum and Ar then heated to 80° C. The mixture was cooled to room temperature and water was added. The aqueous phase was extracted with EtOAc 3× then washed with water and brine, dried over sodium sulfate and concentrated. The crude material wassubjected to abbreviated column chromatography (4% MeOH in DCM) to remove most of the Pd species then used without further purification. The resulting semi-pure material (16 mg) was taken up in DCM (1.5 mL) and treated with TFA (0.3 mL). The reaction was monitored via TLC and when starting material was no longer present the volatiles were blown off under a stream of nitrogen. DCM was added and blown off under nitrogen twice more and the crude residue was dissolved EtOAc. The organic layer was washed with saturated NaHCO$_3$, dried over sodium sulfate and concentrated. The crude material was purified via pipette column chromatography (7.5% MeOH in DCM) to give the product (7.5 mg, 26% yield). MS (ESI) m/z 470.2 (M+H$^+$).

4.35

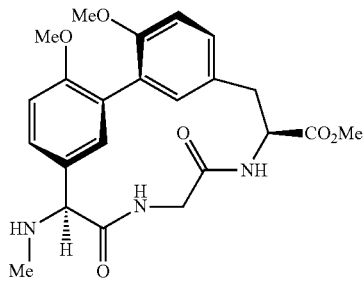

Compound 4.35 was synthesized via general procedure B starting from compound 4.27 (22% yield). MS (ESI) m/z 442.2 (M+H$^+$).

4.36

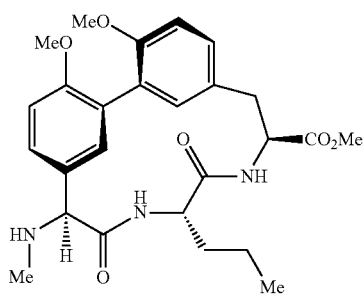

Compound 4.36 was synthesized via general procedure B starting from compound 4.28 (29% yield). MS (ESI) m/z 484.2 (M+H$^+$).

4.37

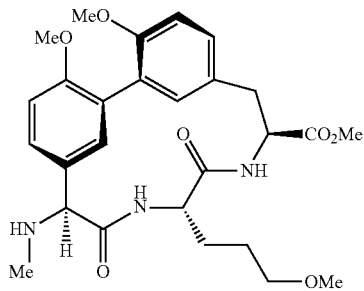

Compound 4.37 was synthesized via general procedure B starting from compound 4.29 (44% yield).

4.38

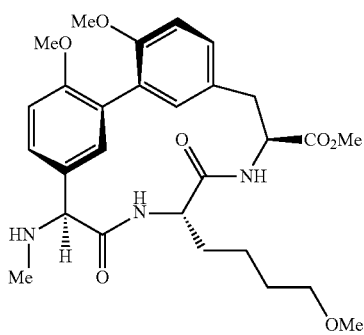

Compound 4.38 was synthesized via general procedure B starting from compound 4.30 (32% yield). MS (ESI) m/z 528.3 (M+H$^+$).

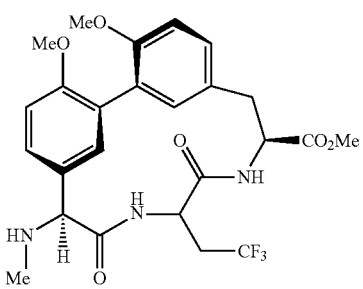

4.39

Compound 4.39 was synthesized via general procedure B starting from compound 4.31 (26% yield). MS (ESI) m/z 524.2 (M+H⁺).

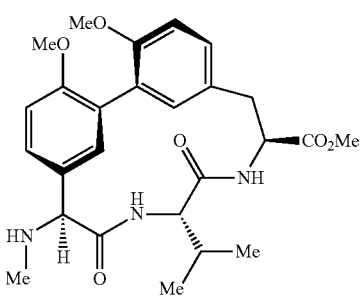

4.40

Compound 4.40 was synthesized via general procedure B starting from compound 4.32 (32% yield). MS (ESI) m/z 484.2 (M+H⁺).

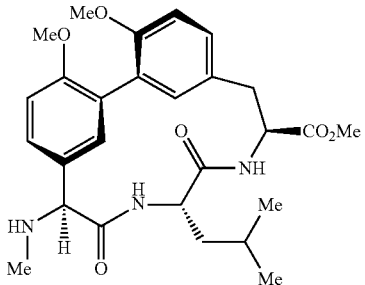

4.41

Compound 4.41 was synthesized via general procedure B starting from compound 4.33 (39% yield). MS (ESI) m/z 498.2 (M+H⁺).

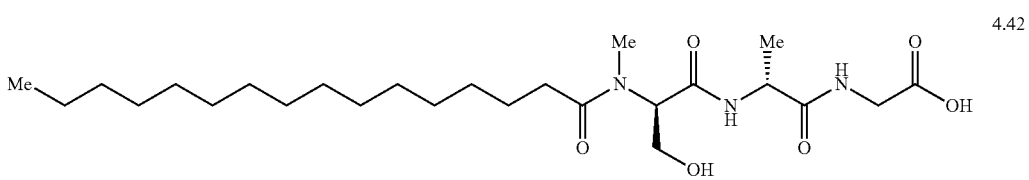 [SMILES: CCCCCCCCCCCCCCCC(=O)N(C)[C@H](CO)C(=O)N[C@H](C)C(=O)NCC(=O)O]

4.42

Compound 4.42 was synthesized via standard Fmoc/piperidine solid phase peptide synthesis. Fmoc-Gly-OH was loaded onto chlorotrityl chloride resin with DIEA, then the constituent amino acids, Fmoc-d-Ala-OH and Fmoc-N-Me-d-Ser-OH were coupled to the resin using HCTU/HOBT/DIEA in DMF followed by palmitic acid coupling with HCTU/HOBT/DIEA in DMF and enough DCM to completely dissolve the acid. Cleavage from the resin was achieved using 1% TFA in DCM using protocols detailed in the Novabiochem catalogue. The product was purified via HPLC (linear gradient, 0.66% B per minute, product eluted at 97% B).

General Procedure C

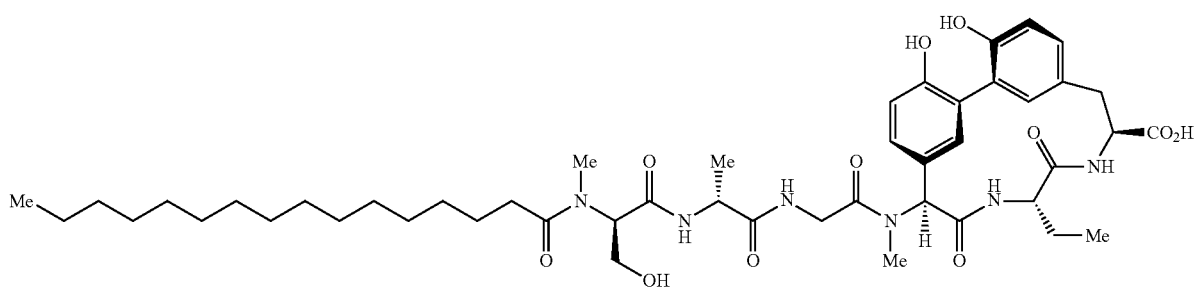

4.2

To a solution of Compound 4.34 (7.0 mg, 14.9 μmol) and compound 4.42 (12.8 mg, 1.5 eq) in THF (0.5 mL) at 0° C. was added DEPBT (7.0 mg, 1.6 eq) and NaHCO$_3$ (1.3 mg, 1 eq). The reaction was then allowed to warm to room temperature and stirred overnight. The THF was blown off under a stream of nitrogen and the reaction was dried under vacuum. The crude reaction mixture was taken up in EtOAc, washed 2× with saturated NaHCO$_3$, then brine, dried over sodium sulfate and concentrated. The crude was purified via pipette column chromatography (3% MeOH in DCM then 4.5% MeOH in DCM) to give the intermediate product. The intermediate product (6.6 mg, 6.4 μmol, 1 eq) was dissolved in ethanethiol (300 μL), treated with 1.0 M AlBr$_3$ in CH$_2$Br$_2$ (128 μL, 20 eq) and heated to 50° C. for 5 hrs. The reaction was allowed to cool to room temperature, quenched by the addition of MeOH and the volatiles were blown off under a stream of nitrogen. The crude was taken up in MeOH and dried twice more to remove lingering ethanethiol then it was dissolved in MeOH centrifuged and purified via HPLC (linear gradient, 0.67% B per minute, product eluted at 82% B) to give the final product (1.8 mg, 13% yield). ESI HRMS calcd for C$_{47}$H$_{70}$N$_6$O$_{11}$ [(M+H)$^+$] 895.5175. found 895.5165.

4.1

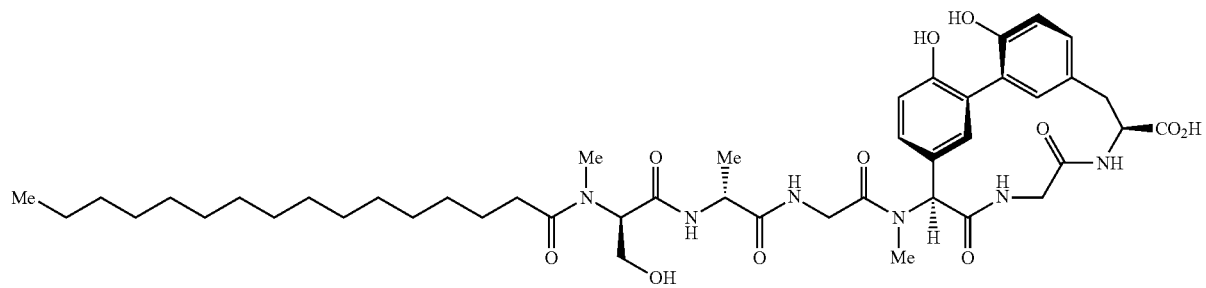

Compound 4.1 was synthesized via general procedure C starting from compound 4.35 (31% yield). ESI HRMS calcd for C$_{45}$H$_{66}$N$_6$O$_{11}$ [(M+H)$^+$] 867.4862. found 867.4860.

4.3

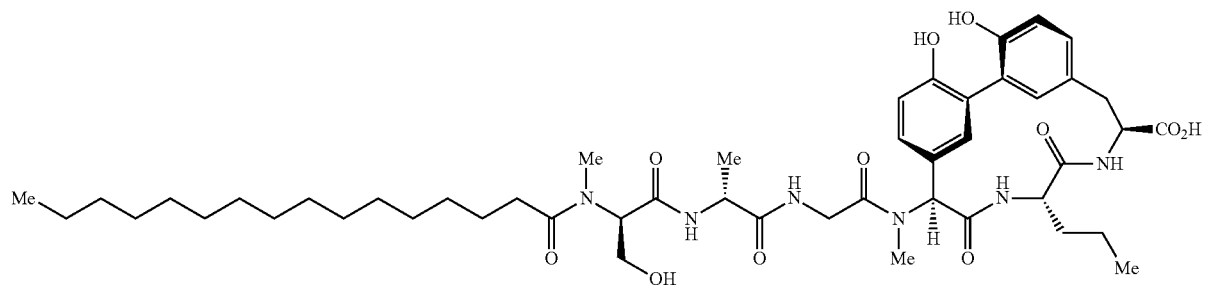

Compound 4.3 was synthesized via general procedure C starting from compound 4.36 (27% yield). ESI HRMS calcd for C$_{48}$H$_{72}$N$_6$O$_{11}$ [(M+H)$^+$] 909.5332. found 909.5336.

4.6

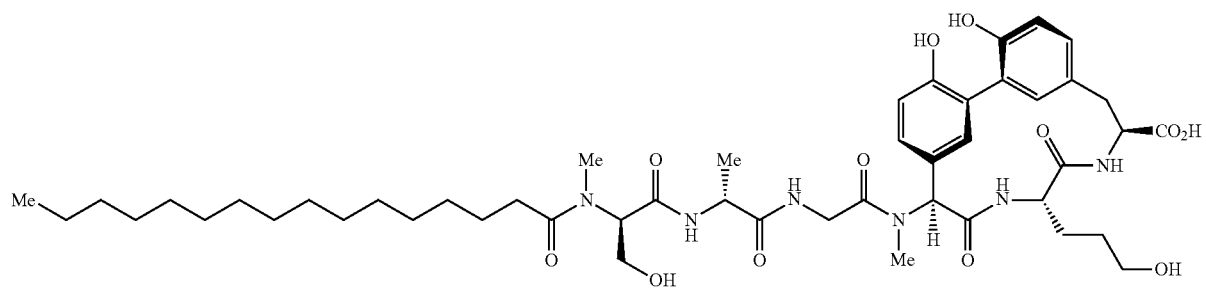

Compound 4.6 was synthesized via general procedure C starting from compound 4.37 (31% yield). ESI HRMS calcd for $C_{48}H_{72}N_6O_{12}$ [(M+H)$^+$] 925.5281. found 925.5275.

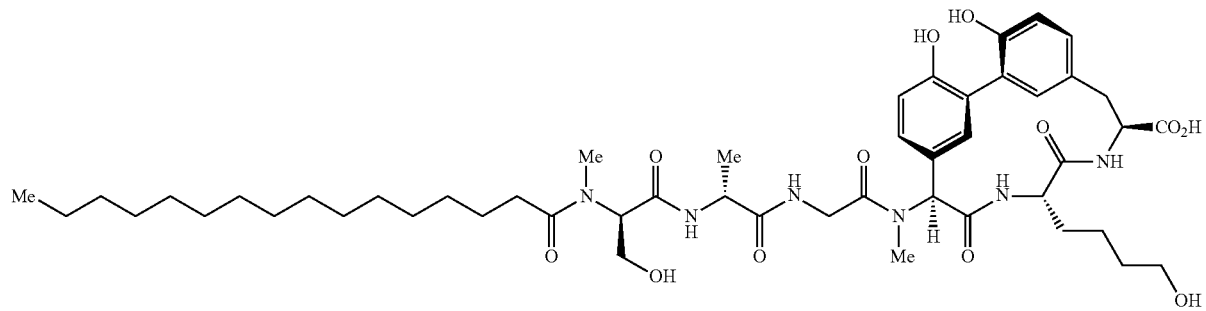

4.7

Compound 4.7 was synthesized via general procedure C starting from compound 4.38 (35% yield). ESI HRMS calcd for $C_{49}H_{74}N_6O_{12}$ [(M+H)$^+$] 939.5437. found 939.5459.

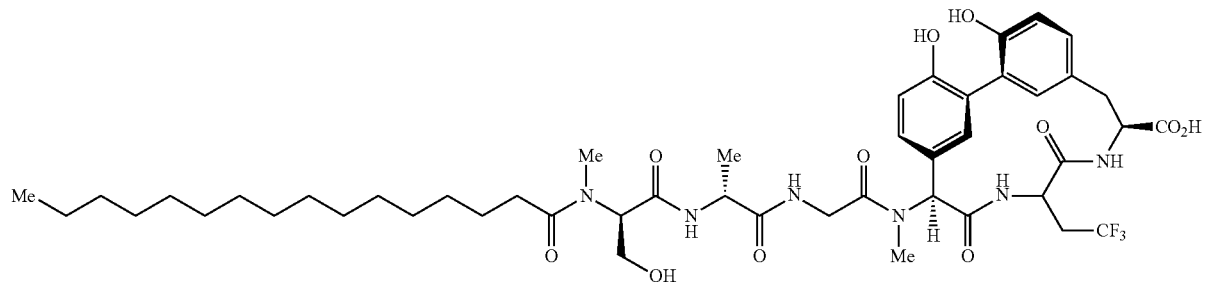

4.8

Compound 4.8 was synthesized via general procedure C starting from compound 4.39 (24% yield). ESI HRMS calcd for $C_{47}H_{67}N_6O_{11}$ [(M+H)$^+$] 949.4892. found 949.4886.

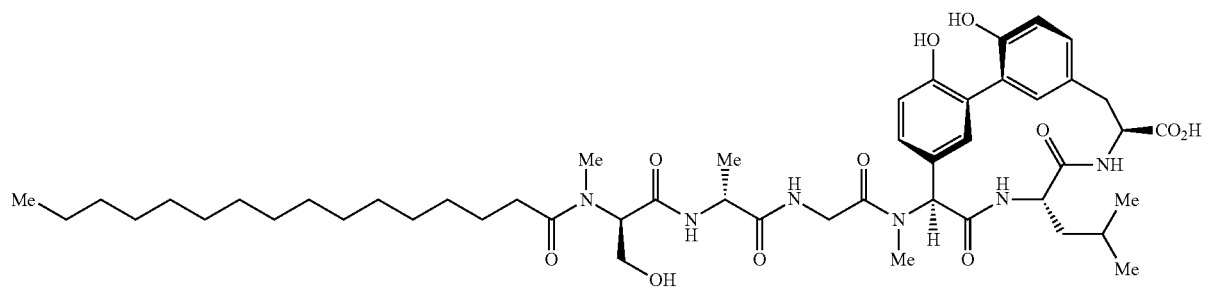

4.10

Compound 4.10 was synthesized via general procedure C starting from compound 4.40 (36% yield). ESI HRMS calcd for $C_{49}H_{74}N_6O_{11}$ [(M+Na)$^+$] 945.5307. found 945.5306.

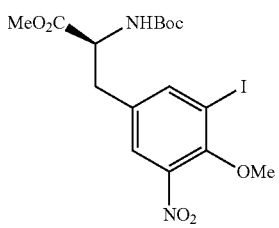

5.4

A solution of 3-nitro-tyrosine (1 g, 4.4 mmol, 1 eq) was dissolved in acetone:H$_2$O (1:1, 10 mL) and treated with NaHCO$_3$ (554 mg, 1.5 eq) and Boc$_2$O (946 μL, 1 eq) and allowed to stir overnight. The reaction was acidified with 5% citric acid (pH ~3) and extracted 3× with EtOAc then the combined organic fractions were washed with brine, dried over sodium sulfate and concentrated. The crude (1.37 g, 4.2 mmol, 1 eq) was taken up in a 5:2 mixture of DCM:MeOH (56 mL), treated with BTMA-ICl$_2$ (1.6 g, 1.1 eq) and NaHCO$_3$ (2.47 g, 7 eq) and allowed to stir overnight. The solid NaHCO$_3$ was then filtered, the filtrate was concentrated and acidified with 5% citric acid (pH ~3). The aqueous layer was extracted 3× with EtOAc and the combined organic layers were dried over sodium sulfate and concentrated. The crude material (1.89 g, 4.19 mmol, 1 eq) was dissolved in acetone, and treated with K$_2$CO$_3$ (2.9 g, 5 eq) and MeI (1.3 mL, 5 eq) and heated to reflux over two days. The reaction mixture was then allowed to cool to room temperature, the reaction was quenched with a small amount of water and the volatiles were evaporated. 5% citric acid (pH ~3) and EtOAc were added then separated and the aqueous layer was extracted 2× with EtOAc. The combined organic layers were washed with brine, dried over sodium sulfate and concentrated. The crude material was purified via column chromatography (0-0.5% MeOH in DCM) to yield compound 5.4 (1.67 g, 82% yield over 3 steps). $^1$H NMR (CDCl$_3$, 500 MHz) δ (ppm) 7.80 (d, J=1.5 Hz, 1H), 7.56 (d, J=1.5 Hz, 1H), 5.12 (d, J=6.5 Hz, 1H), 4.54-4.53 (m, 1H), 3.94 (s, 3H), 3.76 (s, 3H), 3.18 (dd, J=5.0 Hz, J=14.0 Hz, 1H) 2.98 (dd, J=6.5 Hz, J=14.0 Hz, 1H) 1.41 (s, 9H) $^{13}$C NMR (CDCl$_3$, 500 MHz) δ (ppm) 171.5, 155.0, 152.1, 144.9, 143.8, 135.1, 126.4, 94.3, 80.5, 62.8, 54.2, 52.8, 37.0, 28.4. MS (ESI) m/z 503.0 (M+Na$^+$). Compound 5.4 (127 mg, 0.27 mmol, 1 eq) was then dissolved in DCM (2.5 mL) and treated with TFA (0.5 mL). When TLC analysis indicated the complete consumption of starting material the volatiles were blown off and the residue was diried under vacuum. The residue was then taken up in EtOAc and saturated NaHCO$_3$, the aqueous layer was extracted 3× with EtOAc, the combined organic layers were dried over sodium sulfate and concentrated. The resulting compound 5.6 (101 mg) was used without further purification.

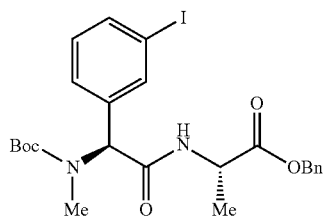

5.8

To a solution of compound 5.7 (300 mg, 0.74 mmol, 1 eq) in DMF (7.4 mL) was added sequentially H-Ala-OBn HCl (160 mg, 1 eq), EDC (170 mg, 1.2 eq), HOBt (100 mg, 1 eq) and NaHCO$_3$ (71 mg, 1.15 eq) and the reaction was allowed to stir overnight. Dilute NaHCO$_3$ was added and the aqueous phase was extracted 3× with EtOAc. The combined organic layers were washed with 5% citric acid (pH~3), water and brine then dried over sodium sulfate and concentrated. The crude material (353 mg, 0.62 mmol, 1 eq) was taken up in acetone (6.2 mL) and to this solution was added K$_2$CO$_3$ (428 mg, 5 eq) and MeI (386 μL, 10 eq). The mixture was allowed to stir overnight at reflux in a sealed vial then the solvent was evaporated, water was added and the aqueous phase was extracted 3× with EtOAc. The combined organic layers were washed with brine, dried over sodium sulfate and concentrated. The crude material was purified via column chromatography (0.75% MeOH in DCM) to give the product (189 mg, 44% yield over 2 steps). $^1$H NMR (CDCl$_3$, 600 MHz) δ (ppm) 7.80 (s, 1H), 7.37-7.29 (m, 6H), 6.74 (d, J=8.4 Hz, 1H), 6.30 (d, J=7.2 Hz, 1H), 5.74 (br s, 1H), 5.22-5.15 (m, 2H), 4.70-4.66 (m, 1H) 3.87 (s, 3H) 2.70 (s, 3H) 1.48 (s, 9H), 1.44 (d, J=7.2 Hz, 3H). $^{13}$C NMR (CDCl$_3$, 600 MHz) δ (ppm) 172.6, 169.3, 158.2, 140.4, 135.4, 130.6, 129.3, 128.8, 128.6, 128.4, 114.2, 110.7, 86.2, 80.9, 67.4, 56.6, 55.4, 53.6, 48.5, 31.7, 28.5, 18.3. MS (ESI) m/z 605.1 (M+Na$^+$).

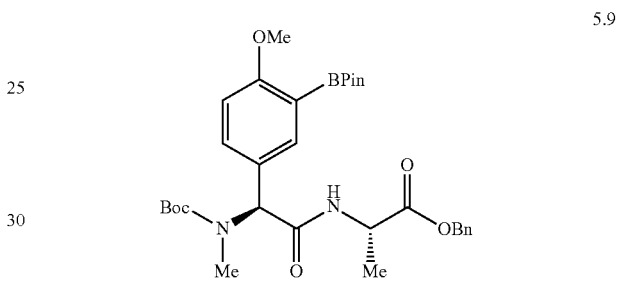

5.9

To a solution of compound 5.8 (185 mg, 0.36 mmol, 1 eq) in DMSO (7 mL) under Ar was added sequentially bispinacolatodiboron (95 mg, 1.05 eq), potassium acetate (353 mg, 10 eq) and PdCl$_2$(dppf) (15 mg, 0.05 eq). The mixture was allowed to stir for 2.5 hrs at 80° C. then cooled to room temperature diluted with water and extracted 3× with EtOAc. The combined organic layers were washed with brine dried over sodium sulfate and concentrated. The crude material was purified by abbreviated (to minimize the time of the compounds exposure to silica) column chromatography (35% EtOAc in Hex) giving compound 5.9 as a mixture of boronic acid and ester (118 mg, 64% yield). NMR spectra showed two sets of overlapping signals in a 3:1 ratio. $^1$H NMR (CDCl$_3$, 600 MHz) δ (ppm) 7.61-7.59 (m, 1H), 7.37-7.31 (m, 5H), 6.81-6.76 (m, 1H), 6.31-6.18 (m, 1H), 5.74 (br, s), 5.20-5.12 (m, 2H), 4.73-4.66 (m, 1H), 3.83-3.80 (m, 3H), 2.68-2.67 (m, 3H) 1.47-1.40 (m, 12H), 1.34-1.33 (m, 9H). MS (ESI) m/z 605.3 (M+Na$^+$).

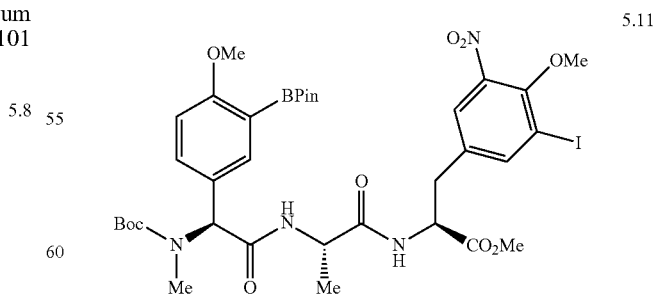

5.11

Compound 5.9 (118 mg, 0.19 mmol, 1 eq) was taken up in 95% EtOH (2 mL), 10% Pd/C (38 mg, ⅓ by weight) was added and the mixture was placed under an atmosphere of H$_2$. The reaction was allowed to proceed until TLC analysis indicated the complete consumption of starting material. The mixture was then filtered through celite and concentrated to yield compound 5.11. To a solution of this crude material (94 mg, 0.19 mmol, 1 eq) and compound 5.6 (101 mg, 0.27 mmol, 1.4 eq) in AcCN:DMF (2.2:1, 2 mL) was added sequentially HOBt (64 mg, 2.5 eq) and EDC (80 mg, 2.2 eq) and the reaction was allowed to stir overnight. Dilute NaHCO$_{3(aq)}$ was then added to the reaction and the aqueous phase was extracted 3× with EtOAc. The combined organic layers were washed with 5% citric acid, water and brine then dried over sodium sulfate and concentrated. The crude material was purified via abbreviated column chromatography (3% MeOH in DCM) to give a semi-pure product (130 mg, 80%). MS (ESI) m/z 877.2 (M+Na$^+$).

A solution of compound 5.11 (118 mg, 0.14 mol, 1 eq) and NaHCO$_3$ (118 mg, 10 eq) in DMF (4.2 mL) was purged several times via cycling with vacuum and Ar and sealed with a crimped septa. To this solution was added, via syringe, a solution of PdCl$_2$(dppf) (23.0 mg, 0.2 eq) in DMF (2.8 mL) that had been sparged with Ar for ~15 minutes. The resulting mixture was submitted to several more cycles of vacuum and Ar then heated to 80° C. The mixture was cooled to room temperature and water was added. The aqueous phase was extracted with EtOAc 3× then washed with water and brine, dried over sodium sulfate and concentrated. The crude material was subjected to abbreviated column chromatography (4% MeOH in DCM) to remove most of the Pd species then used without further purification. The resulting semi-pure material (83 mg) was taken up in DCM (4.0 mL) and treated with TFA (0.8 mL). The reaction was monitored via TLC and when starting material was no longer present the volatiles were blown off under a stream of nitrogen. DCM was added and blown off under nitrogen twice more and the crude residue was dissolved EtOAc. The organic layer was washed with saturated NaHCO$_3$, dried over sodium sulfate and concentrated. The crude material was purified via pipette column chromatography (9% MeOH in DCM) to give the product (29.7 mg, 42% yield). MS (ESI) m/z 501.1 (M+H$^+$).

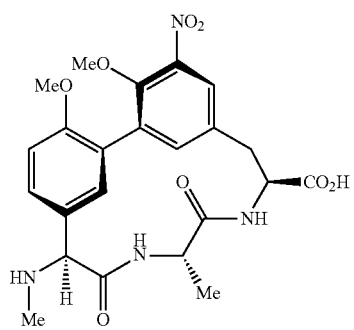

5.12

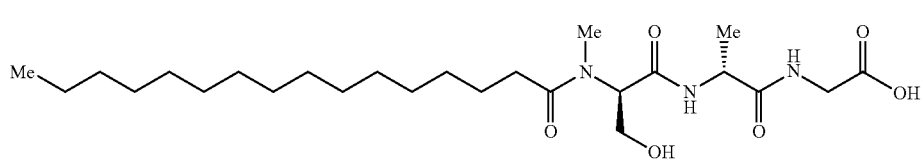

5.12

Compound 5.12 was synthesized via standard Fmoc/piperidine solid phase peptide synthesis. Fmoc-Gly-OH was loaded onto chlorotrityl chloride resin with DIEA, then the constituent amino acids, Fmoc-d-Ala-OH and Fmoc-N-Me-d-Ser-OH were coupled to the resin using HCTU/HOBT/DIEA in DMF followed by palmitic acid coupling with HCTU/HOBT/DIEA in DMF and enough DCM to completely dissolve the acid. Cleavage from the resin was achieved using 1% TFA in DCM using protocols detailed in the Novabiochem catalogue. The product was purified via HPLC (linear gradient, 0.66% B per minute, product eluted at 97% B).

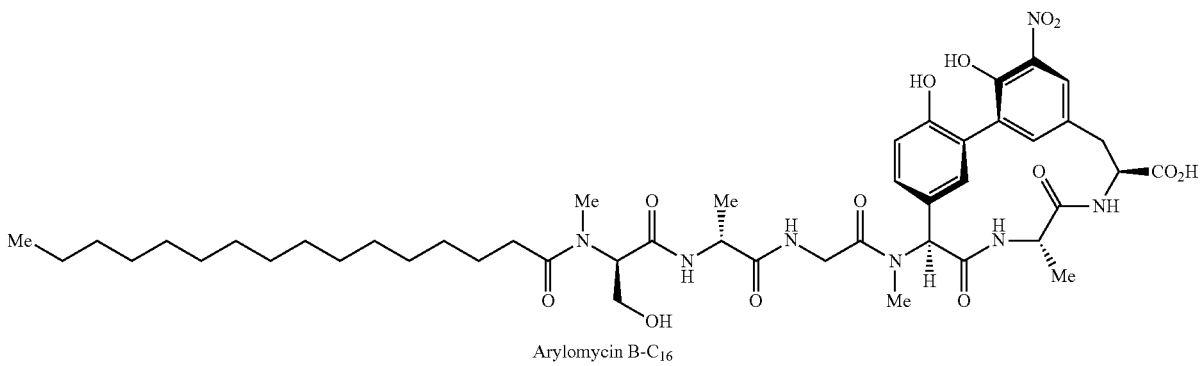

Arylomycin B-C$_{16}$

To a solution of Compound 5.12 (29.2 mg, 58.4 μmol) and compound 5.12 (50 mg, 1.5 eq) in THF (0.5 mL) at 0° C. was added DEPBT (28.0 mg, 1.6 eq) and NaHCO$_3$ (5.0 mg, 1 eq). The reaction was then allowed to warm to room temperature and stirred overnight. The THF was then blown off under a stream of nitrogen and the reaction was dried under vacuum. The crude reaction mixture was taken up in EtOAc, washed 2× with saturated NaHCO$_3$, then brine, dried over sodium sulfate and concentrated. The crude was purified via column chromatography (3% MeOH in DCM then 4.5% MeOH in DCM) to give the protected arylomycin. The protected arylomycin (10.0 mg, 9.4 μmol, 1 eq) was dissolved in CHCl$_3$ (2 mL) treated with ethanethiol (180 μL, 250 eq) and 1.0 M AlBr$_3$ in CH$_2$Br$_2$ (189 μL, 20 eq) and stirred in a vial open to air for 6 hrs. The reaction was quenched by the addition of MeOH and the volatiles were blown off under a stream of nitrogen. The crude was taken up in MeOH and dried twice more to remove lingering ethanethiol then it was dissolved in MeOH centrifuged and purified via HPLC (linear gradient, 1.0% B per minute, product eluted at 82% B) to give the product (5.8 mg, 67% yield). ESI HRMS calcd for C$_{47}$H$_{70}$N$_6$O$_{11}$ [(M+H)$^+$] 926.4869. found 926.4873.

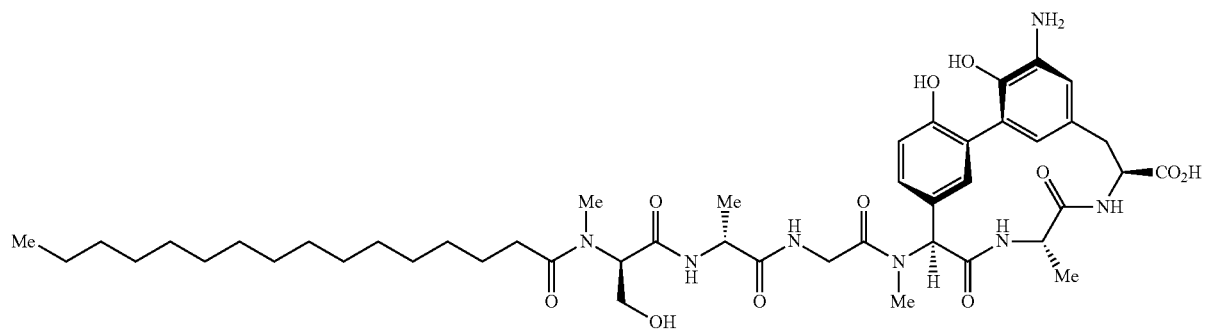

5.1

The protected arylomycin (6.3 mg, 6.0 μmol, 1 eq) was dissolved in ethanethiol (300 μL) and 1.0 M AlBr$_3$ in CH$_2$Br$_2$ (120 μL, 20 eq) and stirred in a vial for 5 hrs under Ar. The reaction was quenched by the addition of MeOH and the volatiles were blown off under a stream of nitrogen. The crude was taken up in MeOH and dried twice more to remove lingering ethanethiol then it was dissolved in MeOH centrifuged and purified via HPLC (linear gradient, 1.0% B per minute, product eluted at 75% B) to give the product (1.0 mg, 19% yield). ESI HRMS calcd for C$_{47}$H$_{70}$N$_6$O$_{11}$ [M+H)$^+$] 896.5128. found 896.5123.

General Procedure D: Macrocycle and Tail Coupling, Example—Arylomycin C16

Compound 52 (80 mg, 0.16 mmol) was taken up in AcCN (7.2 mL) and DMF (3.2 mL) and treated sequentially with HOBT (64 mg, 3 eq), compound 51 (81.3 mg, 1 eq) and EDC (90.3 mg, 3 eq). The reaction was allowed to stir overnight, after which water, saturated NaHCO$_3$, and EtOAc were added, the aqueous phase was extracted 3× with EtOAc and the combined organic layers were washed with 5% citric acid (pH−3) and brine. The organics were dried over sodium sulfate and concentrated. The crude was purified by column chromatography (5.5% MeOH in DCM) to give the product 53 (72.4 mg, 45% yield).

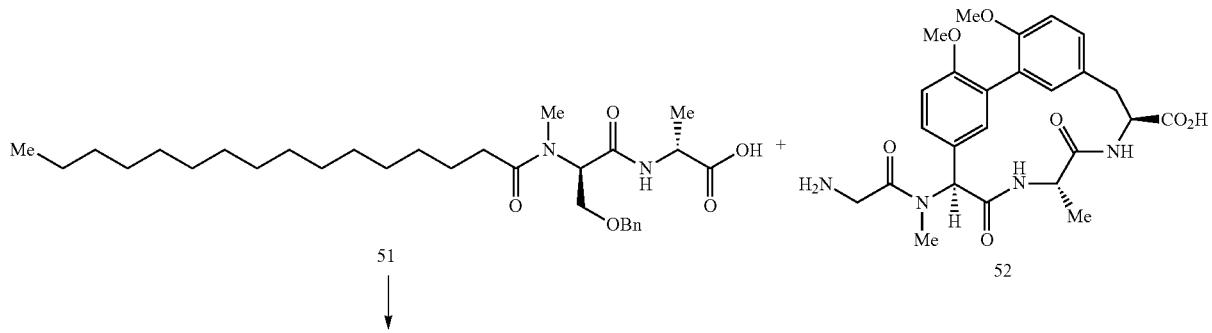

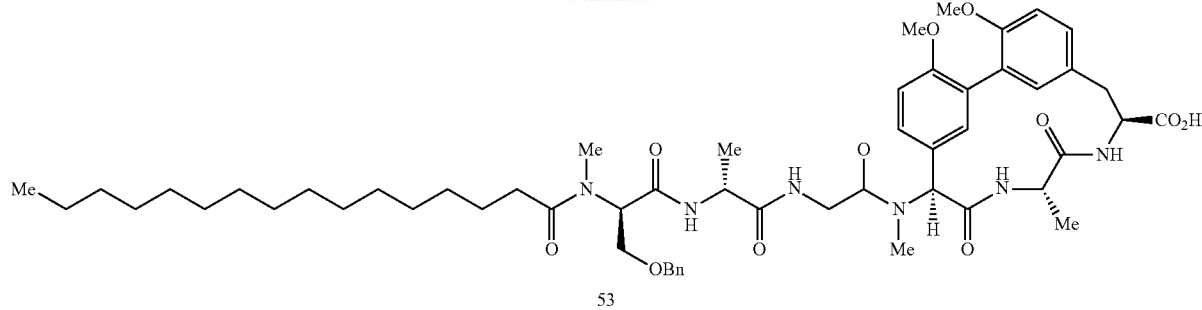

53

General Procedure E: Global Deprotection, Example—Arylomycin C16

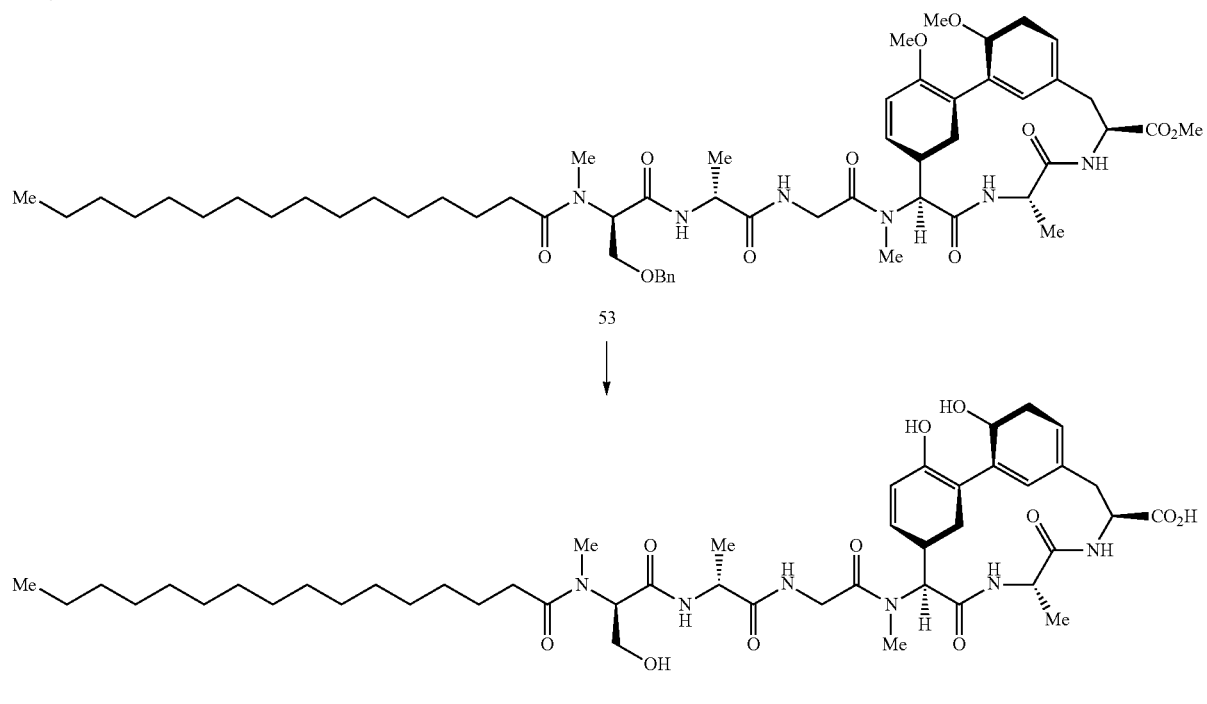

53

↓

Arylomycin C16

Compound 53 (72.4 mg, 72 mmol, 1 eq) was dissolved in ethanethiol (2 mL) under Ar and treated with 1.0 M AlBr$_3$ in CH$_2$Br$_2$ (1.79 mL, 25 eq). The reaction vial was sealed and heated to 50° C. and stirred for 4 h. The reaction was cooled to room temperature, MeOH was added (0.5 mL) and the volatiles were blown off under a stream of nitrogen. MeOH was added again and was blown off under a stream of nitrogen and the crude product was dried under vacuum. The crude product was then dissolved in MeOH and purified by HPLC (linear gradient, 0.67% B/min, product eluted at 80% B) to give Arylomycin C16. (32.6 mg, 51% yield). ESI HRMS calcd for C46H69N6O11 [(M+H)+]: 881.5019. found: 881.5021

General Procedure F: Macrocycle and Tail Coupling Example—Compound 56:

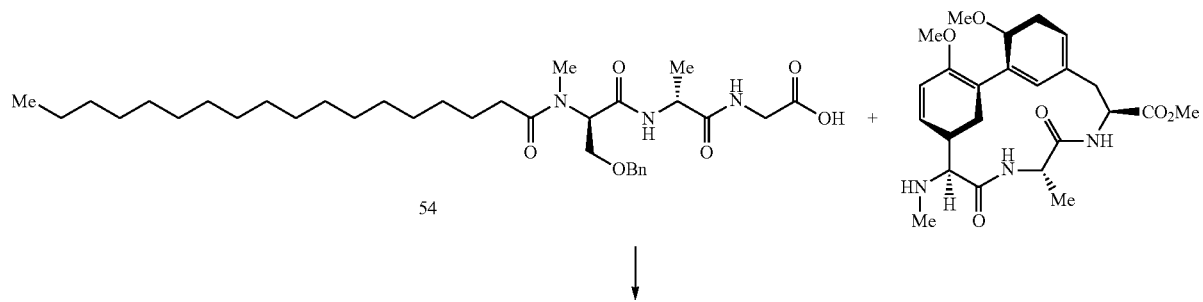

54

↓

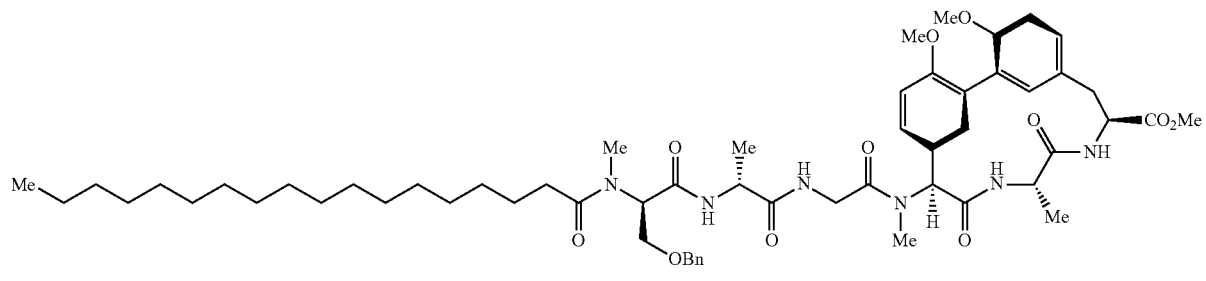

56

This procedure is based on the conditions previously reported.9 Compound 53 (23.5 mg, 52 mot, 1 eq) and compound 54 (70 mg, 2.2 eq) were dissolved in THF (2 mL) under Ar and treated with TEA (7 μL, 1 eq) and DEPBT (39 mg, 2.5 eq). The reaction was allowed to stir overnight then the volatiles were blown off under a stream of nitrogen, the residue was dried under vacuum, and EtOAc and saturated NaHCO₃ were added. The aqueous layer was extracted, then the organic layer was washed with 0.1N HCl, dried over sodium sulfate and concentrated.

Compound 1 was synthesized using general procedures D and E.

ESI HRMS calcd for C46H70N6O10 [M+H]+: 867.5226. found: 867.5207.

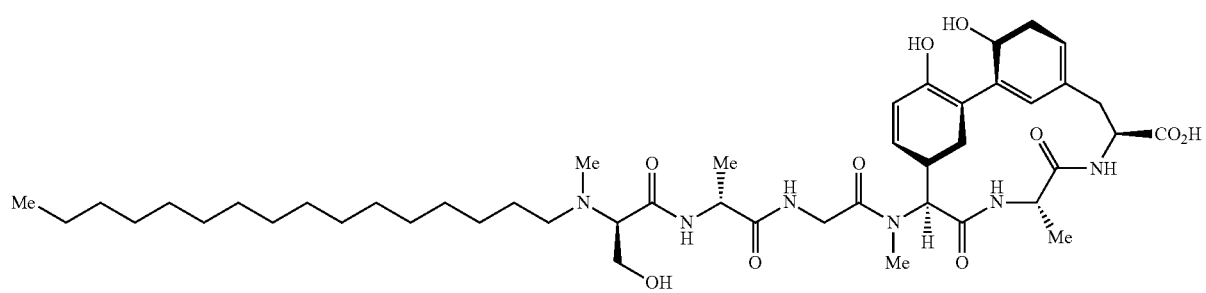

1

Compound 2 was synthesized using general procedures D and E.

ESI HRMS calcd for C38H53N6O11 [M+H]+: 769.3767. found: 769.3770.

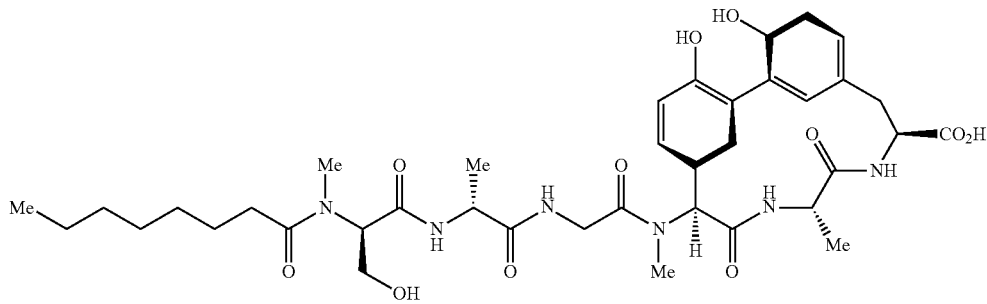

2

Compound 3 was synthesized using general procedures D and E.
ESI HRMS calcd for C40H57N6O11 [M+H)+]: 797.408. found: 797.4070
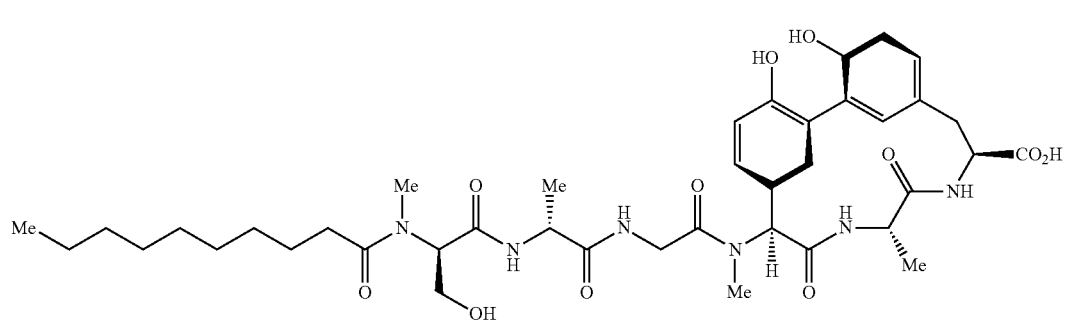
3
Compound 4 was synthesized using general procedures D and E.
ESI HRMS calcd for C42H61N6O11 [M+H)+]: 825.4393. found: 825.4386
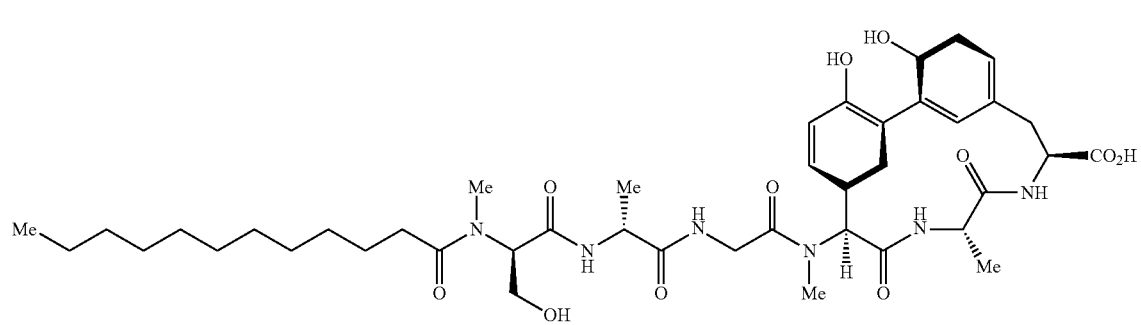
4
Compound 5 was synthesized as shown above then subjected to general procedure F to give the product (20.6 mg, 58% yield).
ESI HRMS calcd for C48H72N6O11 [M+H)+]: 909.5332. found: 909.5328.
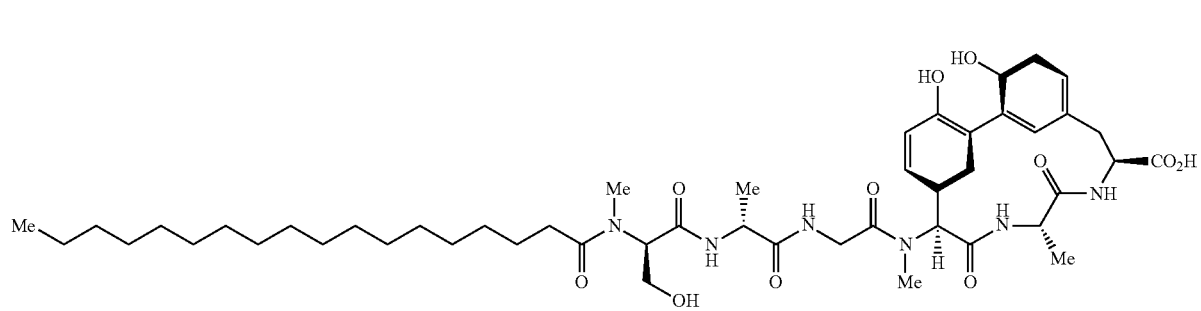
5

Compound 6 was synthesized using general procedures D and E. ESI HRMS calcd for $C_{43}H_{54}N_6O11$ [M+H]+: 811.3297. found: 811.3300
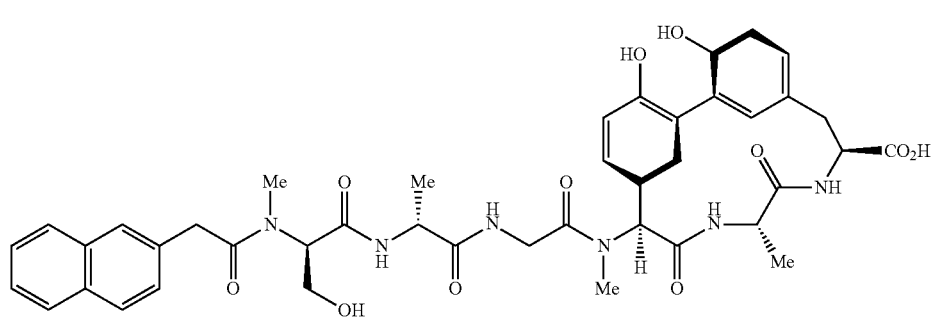
6
Compound 7 was synthesized using general procedures D and E. ESI HRMS calcd for $C44H48N_6O11$ [M+H]+: 837.3454. found: 837.3443
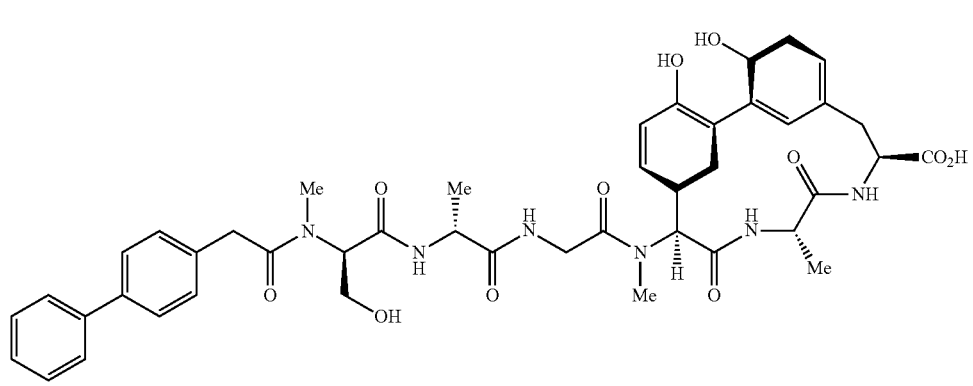
7
Compound 8 was synthesized using general procedures D and E.
ESI HRMS calcd for $C43H46N_6O11$ [M+H]+: 823.3297. found: 823.3296
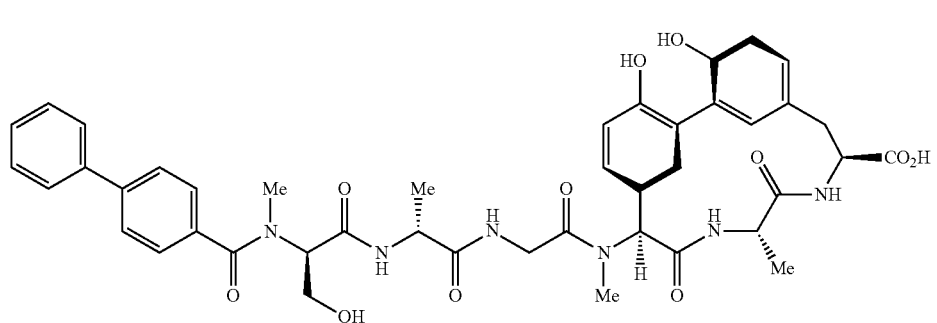
8

Compound 9 was synthesized using general procedures D and E.
ESI HRMS calcd for C45H50N6O11 [M+H)+]: 851.361. found: 851.359
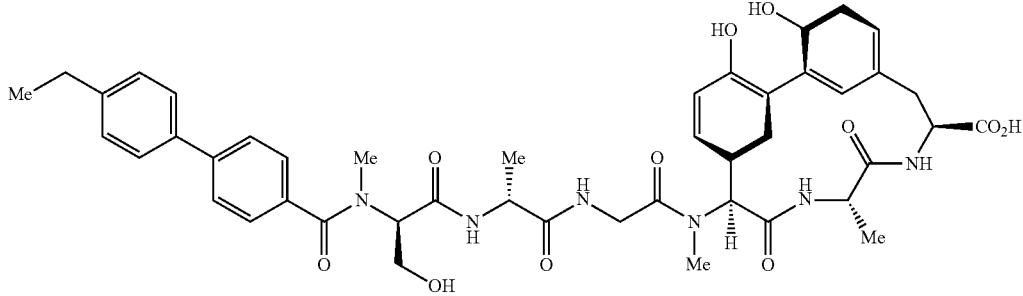
9
Compound 10 was synthesized using general procedures D and E.
ESI HRMS calcd for C47H54N6O11 [M+H)+]: 879.3923. found: 879.3924
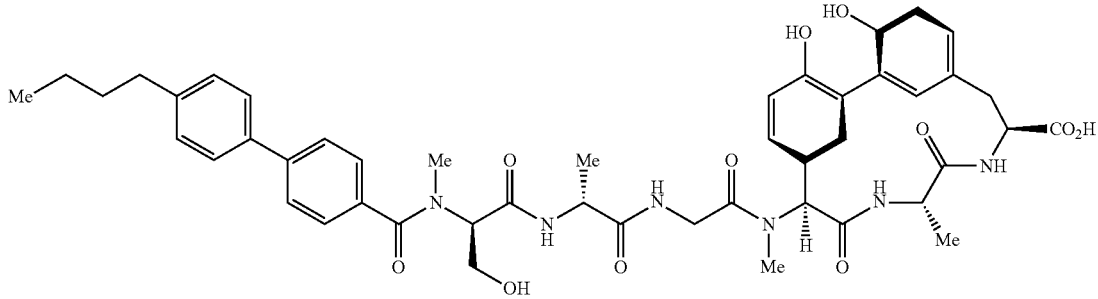
10
Compound 11 was synthesized using general procedures D and E.
ESI HRMS calcd for C49H58N6O11 [M+H)+]: 907.4236. found: 907.4246
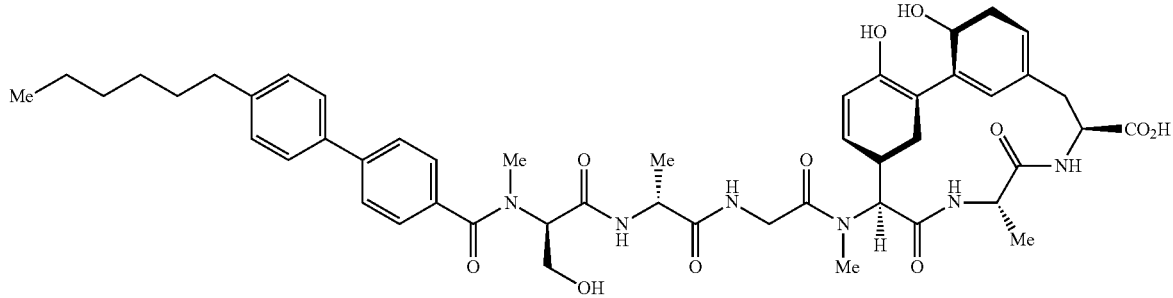
11

Compound 12 was synthesized using general procedures D and E.
ESI HRMS calcd for C51H62N6O11 [M+H)+]: 935.4549. found: 935.4548
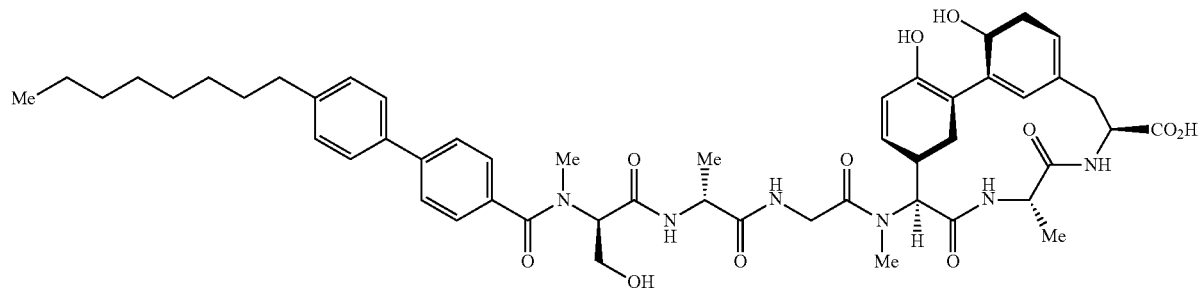
12
Compound 13 was synthesized using general procedures D and E. ESI HRMS calcd for C43H54N6O11 [M+H)+]: 831.3923. found: 831.3917
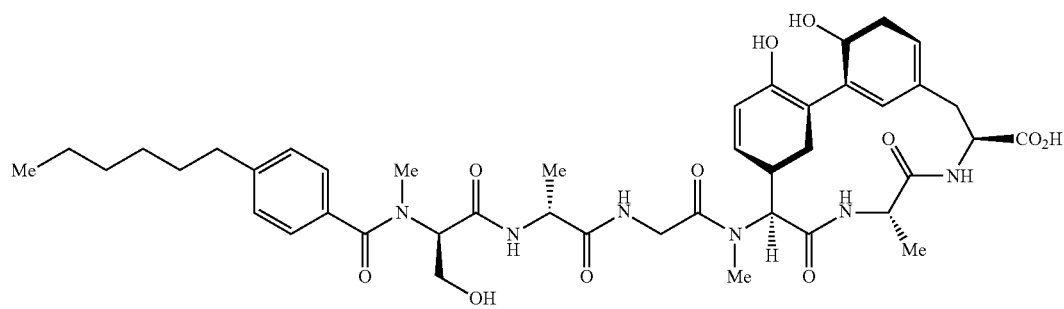
13
Compound 14 was synthesized using general procedures D and E.
ESI HRMS calcd for C45H58N6O11 [M+H)+]: 859.4236. found: 859.4231
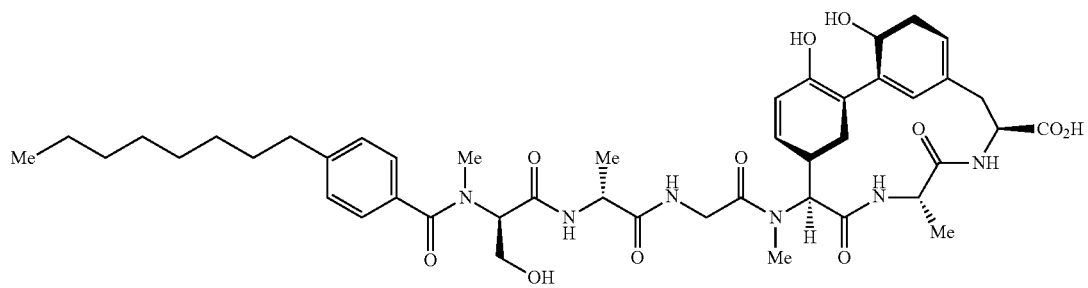
14

Compound 15 was synthesized using general procedures D and E.
ESI HRMS calcd for C47H62N6O11 [M+H)+]: 887.4549. found: 887.4539
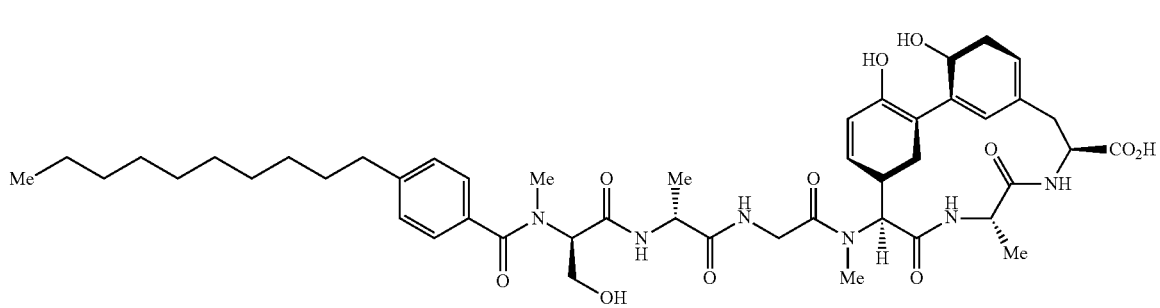
15
Compound 16 was synthesized using general procedures D and E.
ESI HRMS calcd for C45H66N6O11 [M+H)+]: 867.4862. found: 867.4873
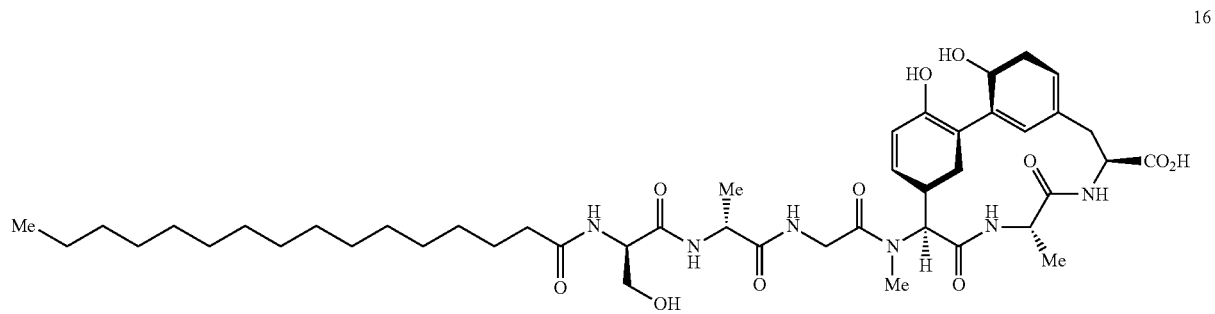
16
Compound 17 was synthesized using general procedures D and E.
ESI HRMS calcd for C47H70N6O10 [M+H)+]: 895.5175. found: 895.5190
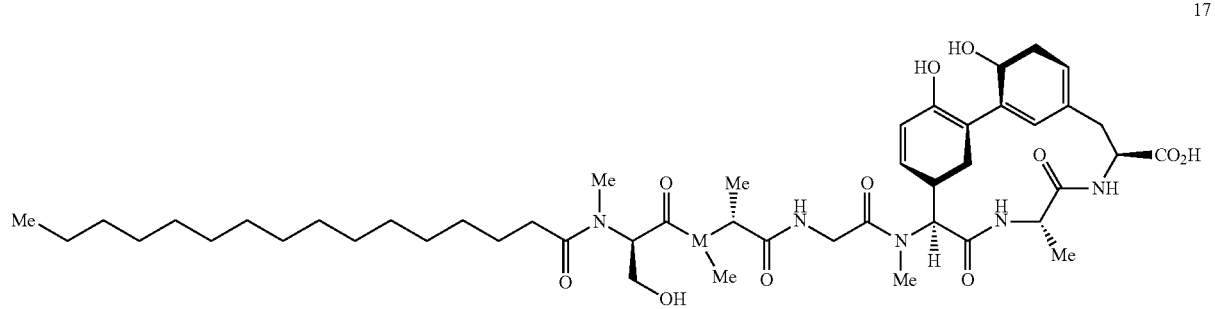
17

Compound 18 was synthesized using general procedures D and E.
ESI HRMS calcd for C47H68N6O11 [M+H]+: 893.5019. found: 893.5014
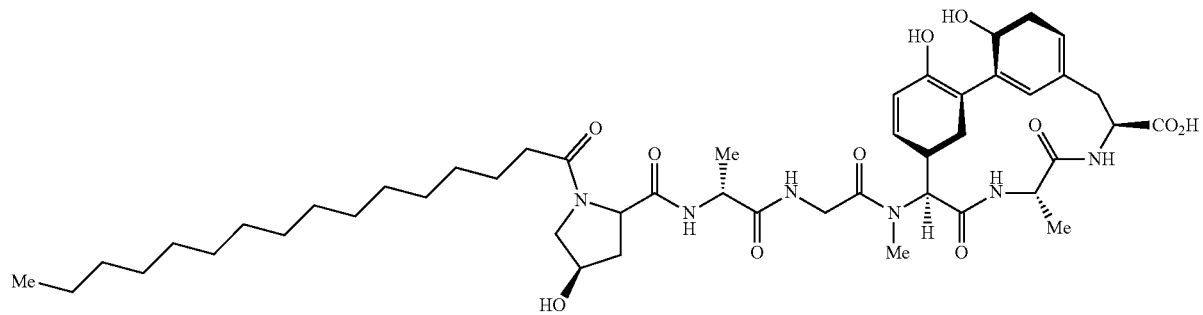
18
Diastereomer A of compound 19 was synthesized using general procedures D and E.
ESI HRMS calcd for C43H63N5O9 [M+H]+: 794.4698. found: 794.4705
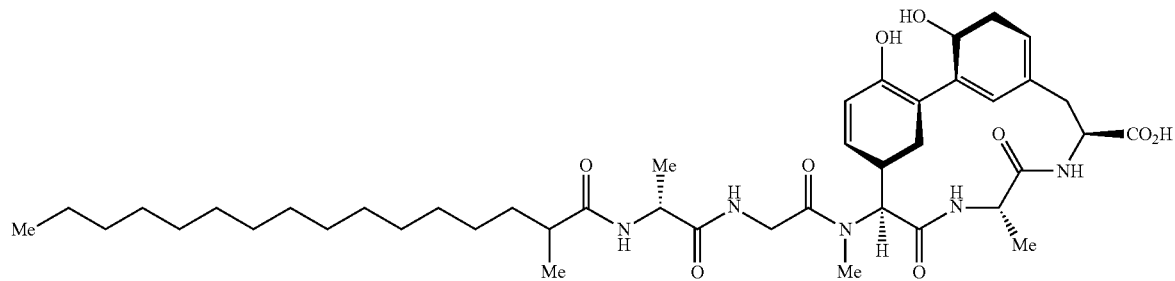
19
Diastereomer B of compound 19 was synthesized using general procedures D and E.
ESI HRMS calcd for C43H63N5O9 [M+H]+: 794.4698. found: 794.4689
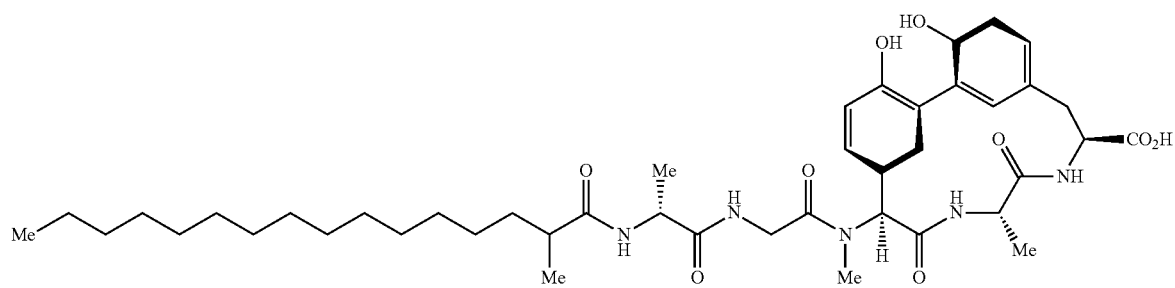
19

Compound 20 was synthesized racemically using general procedures E and F.
ESI HRMS calcd for C47H70N6O11 [M+H)+]: 895.5175. found: 895.5180
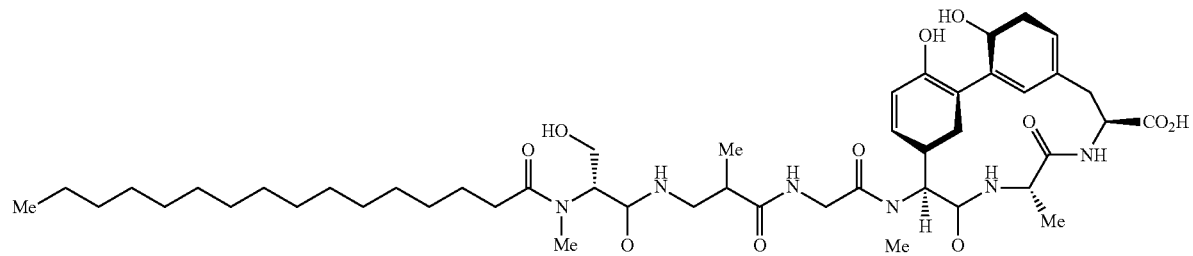
20
Compound 21 was synthesized racemically using general procedures E and F. ESI
HRMS calcd for C48H72N6O11 [M+H)+]: 909.5332. found: 909.5334
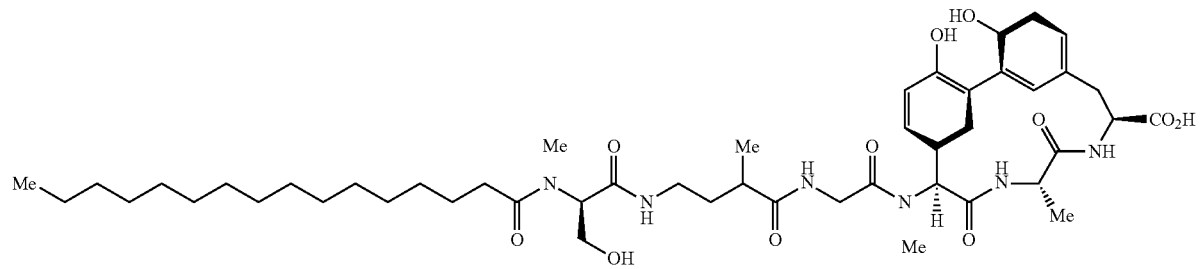
21
Compound 22 was synthesized using general procedures D and E.
ESI HRMS calcd for C47H70N6O11 [M+H)+]: 895.5175. found: 895.5178
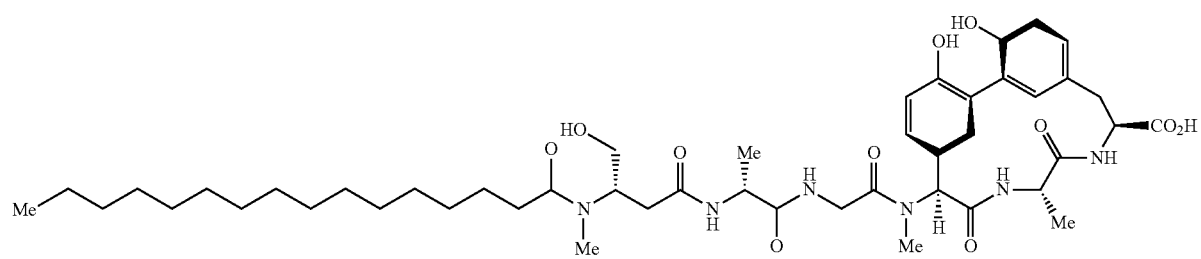
22

Compound 23 was synthesized using general procedures D and E.

ESI HRMS calcd for C48H72N6O11 [M+H]+: 909.5332. found: 909.5305.

Broth II (MHBII) at 37° C. *Rhodococcus opacus* DSM 1069, *Corynebacterium glutamicum* DSM 44475, *Brevibacillus brevis* ATCC 8246, and *Bacillus subtilis* 168 were grown in Mueller Hinton Broth II at 28° C. *Francisella* tularensis (19

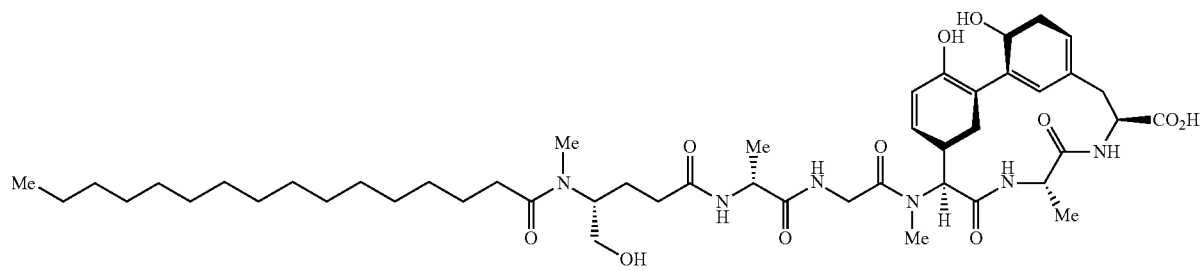

23

Example 2

Bacteriological Materials and Methods

This Example illustrates procedures for testing and manipulating the response of bacteria to arylomycins.

Strains and Culture Conditions

Standard methods were used to culture bacteria for all experiments and to construct mutant strains. *Escherichia coli* MG1655, *Pseudomonas aeruginosa* PAO1, and *Klebsiella pneumoniae* ATCC 43816 were grown in Luria-Bertani (LB) broth at 37° C. *Yersinia pestis* Kim+6 was grown in LB broth at 28° C. *Staphylococcus epidermidis* RP62A, *Staphylococcus haemolyticus*, a clinical isolate obtained from the London Health Services Centre, London, Ontario, Canada, *Staphylococcus aureus* NCTC 8325, and *Corynebacterium efficiens* DSM 44549 were grown in trypicase soy broth (TSB) at 37° C. *Streptococcus pneumoniae* R800, was grown in Todd Hewitt broth without shaking at 37° C. *Streptococcus agalactiae* COH-1 and *Streptococcus pyogenes* M1-5448 were grown in Brain-Heart Infusion (BHI) broth at 37° C. *Lactobacillus gasseri* ATCC 19992, *Lactobacillus acidophilus* ATCC 4356, and *Lactobacillus plantarum* ATCC 8014 were grown at 37° C. on Man-Rogosa-Sharp agar in a sealed candle jar to provide a CO2 enriched atmosphere. *Lactococcus Lactis* subsp. *lactis* ATCC 11454 and *Lactococcus Lactis* subsp. *cremoris* ATCC 19257 were grown in Trypticase Soy Yeast broth at 37° C. and 28° C. respectively. *Rhodococcus equi* ATCC 6939 was grown in cation-adjusted Mueller Hinton strains including Types A and B) were grown on chocolatized 9% sheep blood (CHAB) at 37° C. in a BSL level 3 facility. *Clostridia difficile* WAL14572, *Clostridia bolteae* WAL16351, *Clostridia perfringens* WAL 14572, *Bacteroides fragilis* ATCC 25285 and *Prevotella copris* WAL16310 were grown on reinforced clostridial medium (Oxoid CM149) under anaerobic conditions at 37° C. *Helicobacter pylori* SS1 was grown in BHI broth supplemented with 5% fetal bovine serum in 10% CO2 at 37° C. *Chlamydia trachomatis* was propagated and titered in HeLa229 cells grown in Dulbecco's modified Eagle's medium (high glucose; Invitrogen, Carlsbad, Calif.) as described previously (Lad et al., 2007). All liquid cultures were grown with 275 rpm shaking, and all media was obtained from Difco™.

Selection of Arylomycin Resistant *S. epidermidis* and Sequencing of Signal Peptidase Genes

*S. epidermidis* (~1×109 cfu) were plated on tryptic soy agar (TSA) containing 2 µg/ml arylomycin C16. Resistant colonies visible at 24 hours were re-streaked onto TSA containing 2 µg/ml arylomycin C16 to confirm the resistant phenotype.

Isolation of genomic DNA and sequencing of SPases genes was performed using available procedures. In particular, genomic DNA was obtained by lysing *S. epidermidis* with lysostaphin (Sigma), followed by Proteinase K (Roche) treatment, and heat lysis at 95° C. Signal peptidase genes were amplified using the primer pairs Se_SpsIB_F/Se_SpsIB_R and Se_SpsI_F/Se_SpsI_R (see Table 10 of Primers, below). Sequencing was performed using primers Se_SpsIB_R and Se_SpsI_F.

TABLE 10

Primers for Detecting and Synthesizing Bacterial Spase Nucleic Acids

| Primer Name | Primer Sequence 5' --> 3' | SEQ ID NO: |
|---|---|---|
| Ec_lepB_usNF | TCCCGTTCGCTGGCTGCCTGTG | 26 |
| Ec_lepB_CR_Kan | CGGCGGCTTTGTTGAATAAATCGTTAATGGATGCCGCCAATGCG | 27 |
| Ec_lepB_CF_Kan | GAGACACAACGTGGCTTTCCCATTAATAGCCATCTTCGTTCACG | 28 |
| Ec_lepB_dsCR | TTGGTTTCTAGACCAGCGTATTGCCACGGACC | 29 |

TABLE 10-continued

Primers for Detecting and Synthesizing Bacterial Spase Nucleic Acids

| Primer Name | Primer Sequence 5' --> 3' | SEQ ID NO: |
|---|---|---|
| Ec_lepB_Nconf | TTGGTTTCTAGACTTTATCGACACCCCGG | 30 |
| Kan_ICF2 | GGTTGTAACACTGGCAGAGC | 31 |
| Ec_lepB_QC_P84A_F | CGTTCGTTTATTTATGAAGCGTTCCAGATCCCGTCAGGT | 32 |
| Ec_lepB_QC_P84A_R | ACCTGACGGGATCTGGAACGCTTCATAAATAAACGAACG | 33 |
| Ec_lepB_QC_P84C_F | CGTTCGTTTATTTATGAATGCTTCCAGATCCCGTCAGGT | 34 |
| Ec_lepB_QC_P84C_R | ACCTGACGGGATCTGGAAGCATTCATAAATAAACGAACG | 35 |
| Ec_lepB_QC_P84D_F | CGTTCGTTTATTTATGAAGATTTCCAGATCCCGTCAGGT | 36 |
| Ec_lepB_QC_P84D_R | ACCTGACGGGATCTGGAAATCTTCATAAATAAACGAACG | 37 |
| Ec_lepB_QC_P84E_F | CGTTCGTTTATTTATGAAGAGTTCCAGATCCCGTCAGGT | 38 |
| Ec_lepB_QC_P84E_R | ACCTGACGGGATCTGGAACTCTTCATAAATAAACGAACG | 39 |
| Ec_lepB_QC_P84F_F | CGTTCGTTTATTTATGAATTCTTCCAGATCCCGTCAGGT | 40 |
| Ec_lepB_QC_P84F_R | ACCTGACGGGATCTGGAAGAATTCATAAATAAACGAACG | 41 |
| Ec_lepB_QC_P84G_F | CGTTCGTTTATTTATGAAGGCTTCCAGATCCCGTCAGGT | 42 |
| Ec_lepB_QC_P84G_R | ACCTGACGGGATCTGGAAGCCTTCATAAATAAACGAACG | 43 |
| Ec_lepB_QC_P84H_F | CGTTCGTTTATTTATGAACATTTCCAGATCCCGTCAGGT | 44 |
| Ec_lepB_QC_P84H_R | ACCTGACGGGATCTGGAAATGTTCATAAATAAACGAACG | 45 |
| Ec_lepB_QC_P84I_F | CGTTCGTTTATTTATGAAATCTTCCAGATCCCGTCAGGT | 46 |
| Ec_lepB_QC_P84I_R | ACCTGACGGGATCTGGAAGATTTCATAAATAAACGAACG | 47 |
| Ec_lepB_QC_P84K_F | CGTTCGTTTATTTATGAAAAATTCCAGATCCCGTCAGGT | 48 |
| Ec_lepB_QC_P84K_R | ACCTGACGGGATCTGGAATTTTTCATAAATAAACGAACG | 49 |
| Ec_lepB_QC_P84L_F | CGTTCGTTTATTTATGAACTGTTCCAGATCCCGTCAGGT | 50 |
| Ec_lepB_QC_P84L_R | ACCTGACGGGATCTGGAACAGTTCATAAATAAACGAACG | 51 |
| Ec_lepB_QC_P84M_F | CGTTCGTTTATTTATGAAATGTTCCAGATCCCGTCAGGT | 52 |
| Ec_lepB_QC_P84M_R | ACCTGACGGGATCTGGAACATTTCATAAATAAACGAACG | 53 |
| Ec_lepB_QC_P84N_F | CGTTCGTTTATTTATGAAAACTTCCAGATCCCGTCAGGT | 54 |
| Ec_lepB_QC_P84N_R | ACCTGACGGGATCTGGAAGTTTTCATAAATAAACGAACG | 55 |

TABLE 10-continued

Primers for Detecting and Synthesizing Bacterial Spase Nucleic Acids

| Primer Name | Primer Sequence 5' --> 3' | SEQ ID NO: |
|---|---|---|
| Ec_lepB_QC_P84Q_F | CGTTCGTTTATTTATGAACAGTTCCAGA TCCCGTCAGGT | 56 |
| Ec_lepB_QC_P84Q_R | ACCTGACGGGATCTGGAACTGTTCATA AATAAACGAACG | 57 |
| Ec_lepB_QC_P84R_F | CGTTCGTTTATTTATGAACGGTTCCAGA TCCCGTCAGGT | 58 |
| Ec_lepB_QC_P84R_R | ACCTGACGGGATCTGGAACCGTTCATA AATAAACGAACG | 59 |
| Ec_lepB_QC_P84S_F | GTGCGTTCGTTTATTTATGAATCGTTCC AGATCCCGTCAGGTTCG | 60 |
| Ec_lepB_QC_P84S_R | CGAACCTGACGGGATCTGGAACGATTC ATAAATAAACGAACGCAC | 61 |
| Ec_lepB_QC_P84T_F | CGTTCGTTTATTTATGAAACCTTCCAGA TCCCGTCAGGT | 62 |
| Ec_lepB_QC_P84T_R | ACCTGACGGGATCTGGAAGGTTTCATA AATAAACGAACG | 63 |
| Ec_lepB_QC_P84V_F | CGTTCGTTTATTTATGAAGTGTTCCAGA TCCCGTCAGGT | 64 |
| Ec_lepB_QC_P84V_R | ACCTGACGGGATCTGGAACACTTCATA AATAAACGAACG | 65 |
| Ec_lepB_QC_P84W_F | CGTTCGTTTATTTATGAATGGTTCCAGA TCCCGTCAGGT | 66 |
| Ec_lepB_QC_P84W_R | ACCTGACGGGATCTGGAACCATTCATA AATAAACGAACG | 67 |
| Ec_lepB_QC_P84Y_F | CGTTCGTTTATTTATGAATATTTCCAGA TCCCGTCAGGT | 68 |
| Ec_lepB_QC_P84Y_R | ACCTGACGGGATCTGGAAATATTCATA AATAAACGAACG | 69 |
| Pa_lepB_usNF3_BamHI | TTGGTTGGATCCTGGTGCTCGACTTCTT CGATCG | 70 |
| Pa_lepB_dsCR_SpeI | TTGGTTACTAGTGTCGGACCTCATGTCA GTGTAG | 71 |
| Pa_lepB_QC_P84S_F | CGTTCCTTCCTGGTCGAGAGCTTCCAGA TTCCCTCGGGG | 72 |
| Pa_lepB_QC_P84S_R | CCCCGAGGGAATCTGGAAGCTCTCGAC CAGGAAGGAACG | 73 |
| Pa_lepB_seqF | GTGGCGATCCAGGCAGCCATC | 74 |
| Sa_spsB_usNF_EcoRI | TTGGTTGAATTCGATCTGTAAACGATTG GTGAACAC | 75 |
| Sa_spsB_dsCR_EcoRI | TTGGTTGAATTCGTTCGCTATAACTACC AACTTCTTGG | 76 |
| Sa_spsB_QC_P29S_F | GTAGGTAAATTTATTGTTACGTCATATA CAATTAAAGGTGAATC | 77 |
| Sa_spsB_QC_P29S_R | GATTCACCTTTAATTGTATATGACGTAA CAATAAATTTACCTAC | 78 |
| Se_spsI_F | CAAGGAAAGCGTGTCGTTGTTGTACC | 79 |
| Se_spsI_R | CCAATCATTCTTGCTGCAGTAGGTCTAA CG | 80 |
| Se_spsIB_F | TGATGGTGATACGATTCCACCGGGAGC | 81 |

TABLE 10-continued

Primers for Detecting and Synthesizing Bacterial Spase Nucleic Acids

| Primer Name | Primer Sequence 5' --> 3' | SEQ ID NO: |
|---|---|---|
| Se_spsIB_R | GCATGGCTGTTGACTTTCCTGTACCTGC | 82 |
| Ec_lepB_A2_75_NF_NcoI | GGTTCCATGGTGCGTTCGTTTATTTATGAAC | 83 |
| Ec_lepB_CR_BamHI | TTGGTTGGATCCTGGCATTTAATGGATGCCGCCAATGC | 84 |
| Sa_spsIB_NF_KpnI | TTGGTTGGTACCTTGAAAAAGAAATATTGGAATGG | 85 |
| Sa_spsIB_CR_XhoI | TTGGTTCTCGAGTTAATTTTTAGTATTTTCAGGATTGAAAT | 86 |

Construction of Mutant Strains.

E. coli with a kanamycin marked lepB gene was constructed using allelic exchange methods described by Cirz et al. (PLoS Biol. 3, e176 (2005)) and the following primers: Ec_lepB_usNF, Ec_lepB_CRKan, Ec_lepB_CF-Kan, Ec_lepB_dsCR, Ec_lepB_Nconf, and Kan_ICF$_2$. The kanamycin marked SPase gene was moved into wild type MG1655 by P1 phage transduction. Point mutations at codon 84 of SPase were introduced by amplifying a pair of overlapping DNA fragments from the cassette used for construction of the wild type cassette using primer pairs Ec_lepB_usNF/Ec_lepB_QC_P83X_R and Ec_lepB_QC_P83X_F/Ec_lepB_dsCR. Overlapping PCR of the two fragments yielded the complete SPase/kanamycin resistance cassette containing the desired mutation. P. aeruginosa mutants were constructed using the allelic exchange plasmid pKNG101 using methods described by Kaniga et al. (Gene 109, 137-141 (1991)) and the primers Pa_lepB_usNF3-BamHI and Pa_lepB_dsCR-SpeI. Point mutations were introduced using overlap PCR as described for E. coli with primer pairs Pa_lepB_usNF3-BamHI/Pa_lepB_QC_P84S_R and Pa_lepB_dsCRSpeI/Pa_lepB_QC_P84S_F. S. aureus mutants were constructed using the allelic exchange vector pMAD as described by Arnaud et al. (Appl. Environ. Microbiol. 70, 6887-6891 (2004)) and the primers Sa_spsB_usNF_EcoRI and Sa_spsB_dsCR_EcoRI. Point mutations were introduced using overlap PCR as described for E. coli with primer pairs Sa_spsB_usNF_EcoRI/Sa_spsB_QC_P29S_R and a_spsB_dsCR_EcoRI/Sa_spsB_QC_P29S_F.

Growth Curves.

For each of the twenty strains of E. coli, each harboring one of the twenty amino acids at SPase residue 84, saturated overnight cultures were diluted 100-fold into fresh LB broth and grown to an OD600 nm of 0.4-0.6. These cultures were diluted into pre-warmed LB to a final density of OD600 nm 0.001 (106 cfu/mL). Growth was measured by plating serial dilutions of the cultures at 30 min intervals for three hours and counting the resulting colonies. Doubling times were determined from the exponential curve of viable cells versus time. Averages and standard deviations were determined for three independent growth curves.

S. aureus and S. epidermidis Competitive Growth Experiments.

Competitive growth experiments were run in triplicate by diluting equal volumes of saturated S. epidermidis SpsIB (WT) and S. epidermidis SpsIB(S29P) cultures 2000-fold into TSB and growing the resulting culture overnight to saturation (~10 doublings). This saturated culture was diluted 1000-fold and grown overnight to saturation an additional three to four times for a total of 40 to 50 doublings. Serial dilutions of each saturated culture were plated onto TSA and onto TSA containing 2 ng/mL arylomycin C16 to quantify the number of total cells and arylomycin C16 resistant cells respectively. Similar experiments were performed between wild type S. epidermidis and the S. epidermidis SpsIB (S31P) mutant and between wild type S. aureus and the S. aureus SpsB(P29S) mutant.

Minimum Inhibitory Concentration (MIC) Experiments

With the exception of C. trachomatis and H. pylori, minimum inhibitory concentrations (MICs) of arylomycin C16 were determined by a modified Clinical and Laboratory Standards Institute (CLSI) micro-broth dilution method in 100 µL of media containing 2-fold dilutions of arylomycin C16. Inocula were formed by resuspending bacteria growing on solid media into the same broth used in the MIC experiment and diluted a final concentration of $1 \times 10^7$ colony forming units/ml. 5u1 of this suspension was added wells containing 100u1 of media and arylomycin C16. MICs of E. coli, P. aeruginosa, K. pneumoniae and Y. pestis were determined in LB. MICs of S. aureus, S. epidermidis, S. haemolyticus, R. equi, R. opacus, C. glutamicum, C. efficiens, B. brevis, B. subtilis, F. tularensis, were determined in Cation-adjusted Mueller Hinton broth. MICs of S. pyogenes, S. agalactiae, and S. pneumoniae were determined in Todd Hewitt broth. MICs of both L. lactis strains were determined in TSYE broth. MICs of arylomycin C16 for L. gasseri, L. acidophilus, and L. plantarum were determined in cation-adjusted Mueller Hinton broth supplemented with 10% Man-Rogosa-Sharpe broth adjusted to pH 6.7 (Klare et al., 2005), and the 96-well plates were incubated a sealed in a jar containing a lit candle to provide a $CO_2$ enriched atmosphere. MICs of arylomycin for strains of Clostridia and Bacteroidetes were determined using the CLSI approved Wadsworth agar dilution technique. Unless noted otherwise MIC experiments were performed at the optimal growth temperatures of each strain and the MIC determined after 24 hours of growth.

MICs were defined as the lowest arylomycin C16 concentrations yielding no increase in $OD_{590nm}$ above background after 24 hours of incubation. If the MIC breakpoint was uncertain by OD measurement, viable cells were determined by plating serial dilutions, and MIC was defined as the lowest concentration at which less than 5-fold outgrowth occurred by 24 hours. The MIC of arylomycins C16 for *H. pylori* were determined by diluting a culture at ~108 cfu 200-fold into fresh media containing 2-fold dilutions of arylomycin C16. After 24 hours, serial dilutions were plated onto Columbia agar with 5% lysed horse blood and viable cells determined after 5 days of growth. The MIC was defined as the amount of arylomycin C16 required to achieve a 1000-fold decrease in viable cells. To determine MIC of arylomycin C16 for *C. trachomatis*, HeLa 229 cells were grown to 30% confluence, transferred to 12-well plates treated with 2.0 µg/ml fibronectin, and allowed to adhere overnight. Adherent cells were treated with one infectivity unit of *C. trachomatis* L2 cells (see, Lad et al., J. Bacteriol. 189: 6619-25 (2007)) and with various concentrations of arylomycin C16. After 24 hours cells were fixed with 3% paraformaldehyde and visualized by fluorescence microscopy using monoclonal antibodies to the chlamydial major outer membrane protein (MOMP) provided by L. M. de la Maza. The MIC was defined as the lowest concentration of arylomycin C16 that resulted in no increase in fluorescence relative to background at 24 hours.

The minimal inhibitory concentration (MIC) of each derivative was determined using a standard broth dilution method. Test strains included wild type *S. epidermidis* (strain RP62A), as well as mutant strains of *S. aureus* (strain 8325), *E. coli* (strain MGI655), and *P. aeruginosa* (strain PAGI) that were rendered sensitive to the arylomycins by mutation of the resistance-conferring Pro to a residue that does not confer resistance (P29S in the *S. aureus* protein, and P84L in the *E. coli*, and *P. aeruginosa* proteins). MICs were also determined with the isogenic wild type strains of *S. aureus, E. coli*, and *P. aeruginosa*, as well as an isogenic mutant strain of *S. epidermidis* where the resistance-conferring Pro has been introduced (S29P).

Cloning for Protein Expression.

Plasmids for expression of the A2-75 variant of *E. coli* SPase were constructed by amplifying genomic DNA encoding the A2-75 variant of WT and (P83S) *E. coli* SPase from the
corresponding *E. coli* strains with primers Ec_lepB_A2_75_NF_NcoI and
Ec_lepB_CR_BamHI and cloning the resulting ORFs into pET15b (Novagen) at the NcoI and BamHI restriction sites, yielding plasmids pET15blepBTrunc and pET15b-lepB-Trunc(P83S). The plasmid pET23-lepB for the expression of full length His 6x tagged *E. coli* SPase protein was kindly provided by Dr. Mark Paetzel (Simon Fraser University). To express the P83S variant of *E. coli* SPase, the LepB(P83S) mutation was introduced into pET23-lepB using QuikChange site directed mutagenesis (Stratagene) with the primers described above yielding plasmid pET23-lepB(P83S). Plasmids for expression of the His6x-tagged *S. aureus* SPase were constructed by amplifying the genomic DNA encoding SpsB from *S. aureus* NCTC 8325 and the corresponding SpsB (P29S) chromosomal mutant using primers Sa-SPase-KpnI-F and Sa-SPase-XhoI-R and cloning the resulting DNA was into the plasmid pCDF1 (Novagen) at the KpnI and XhoI restriction sites resulting in the addition of an N-terminal His 6x-Tag to the spsB open reading frame.

Protein Expression.

The *E. coli* A 2-75 SPase proteins were expressed in and purified from BL21(DE3)
harboring pET15b-lepBTrunc or pET15b-lepBTrunc(P83S) and stored in a manner similar to that described by Paetzel et al. (Proteins 23, 122-125 (1995)). Full length His-tagged *E. coli* SPase proteins were expressed in BL21(DE3) containing the plasmid pET23-lepB or pET23-lepB(P83S) and purified as described by Klenotic et al. (J. Biol. Chem. 275, 6490-6498 (2000)), with the exception the Q-column step was omitted and that 1% Elugent (Calbiochem) was used in place of Triton X-100 as the detergent while washing and eluting from the Ni-NTA Superflow resin (Qiagen). Full length His-tagged *S. aureus* SPase proteins were expressed in and purified from BL21(DE3) containing the plasmid pCDF1-SaSpsB or pCDF1-SaSpsB(P29S) in a manner analogous to the purification of *Streptococcus pneumoniae* SPase described by Peng et al. (J. Bacteriol. 183, 621-627 (2001)), with the following exceptions. SPase protein was solubilized using 300 mM NaCl, 20 mM Tris pH 8.06, 5 mM imidazole, 10% glycerol, 1% Triton X-100, prior to purification in Ni-NTA Superflow resin and resin bound protein was washed in a similar buffer containing 1% Elugent in place of Triton X-100 prior to protein eluted in wash buffer supplemented with 300 mM imidazole. SDS-PAGE followed by Coomassie staining revealed a single band of approximately 21 kD. All protein concentrations were determined by BCA assay.

In Vitro KD Measurements

Construction of expression vectors and the subsequent production of the various SPase variants used in this study are described above. Steady state binding of arylomycin C16 was determined by measuring the previously described increase in arylomycin fluorescence ($\lambda$ex=320 nm, $\lambda$em=410 nm) upon binding *E. coli* $\Delta$2-75 SPase (see, Paetzel et al., J. Biol. Chem. 279, 30781-30790 (2004)). The binding buffer for full length and truncated *E. coli* proteins was as follows: 100 mM NaCl, 20 mM Tris-HCl pH 7.4, 1 mM EDTA, 1% n-octyl-β-glucopyranoside (Anatrace). This buffer was supplemented with 10% glycerol for experiments with *S. aureus* SPase protein.

SPase Sequence Analysis

The amino acid sequences of the SPases from *E. coli, S. aureus, B. fragilis* and *C. efficiens* were concatenated and used as the query sequence in a BLAST against all of the fully sequenced genomes of Bacteriodetes, Actinobacteria, Firmicutes, Proteobacteria, and Chlamydiae/Verrucomicrobia available in the NCBI Microbial Genome Database. The amino acid sequence of BLAST hits with an E-value less than 0.1 were aligned using MUSCLE (Edgar, Nucleic Acids Res. 32, 1792-1797 (2004)), and all sequences lacking the catalytic Ser or Lys residues were removed. Poorly aligned regions were removed using the "Block Mapping and Gathering using Entropy" program found at http://mobyle.pasteur.fr/cgi-bin/portal.py, with Gap Rate Cutoff 0.3 and the Entropy Cutoff of 0.7. Phylogenetic analysis was conducted using PhyML with SPR branch improvement (Guindon and Gascuel, Syst. Biol. 52, 696-704 (2003)). SPases from Gram-positive and Gram-negative organisms were kept separate during alignment and phylogenetic analysis to improve the quality of these analyses.

Also several SPases from the Gram-negative Proteobacteria were removed prior to analysis of SPase phylogeny, since they did not show an obvious relation to any of the other Gram-negative or Grampositive SPases examined. Phylogenetic trees were displayed using the Interactive Tree of Life (Letunic and Bork, Bioinformatics 23, 127-128 (2007)).

Conservation of Residue 29

A single alignment of SPases from all of the Gram-negative and Gram-Positive genomes examined was made using MUSCLE, and poorly aligned regions were removed using "Block Mapping and Gathering using Entropy" with a gap cutoff of 0.3 and an entropy cutoff of 0.7. The resulting alignment was primarily within the previously described Boxes A-E (Dalbey et al., Protein Sci. 6: 1129-38 (1997)), which are highly conserved across all bacterial SPases. Aligned and trimmed sequences were then grouped by the Phylum of the organisms in which they are found. Each alignment (one for each of the five Phyla) was submitted to the "Score Sequence Conservation" program (Capra and Singh, Bioinformatics 23, 1875-1882 (2007); compbio.cs.princeton.edu/conservation/score.html), and the sequence conservation was scored using the Jensen-Shannon divergence method with weighted sequences and a window size of 1. The per residue conservation scores were averaged across the entire alignment, across each set of residues comprising Boxes B-E, and across the regions five amino acids centered on residue 29.

16sRNA Sequence Analysis

Aligned 16sRNA sequences were analyzed were obtained from the Ribosomal Database Project (Cole et al., Nucleic Acids Res. 37, D141-145 (2009)). The "Block Mapping and Gathering using Entropy" program was used with a Gap Rate Cutoff of 0.7 and an Entropy Cutoff of 0.7 to remove poorly aligned regions. Phylogenetic analysis was performed using PhyML 3.0, with the HKY85 substitution model and SPR tree improvement, and the resulting tree was displayed using the Interactive Tree of Life.

Example 3

The Antibiotic Activity of Arylomycins is Masked by SPase Mutations

The Example describes experimental results demonstrating that many strains of bacteria have naturally developed SPase mutations that confer resistance to arylomycins.

Point Mutations in SPase Confer Arylomycin Resistance

S. epidermidis is atypical in its sensitivity to the arylomycins (Roberts et al., J. Am. Chem. Soc. 129: 15830-15838 (2007)). To investigate whether S. epidermidis lacks specific resistance mechanisms inherent to other bacteria, selection experiments were performed to isolate mutants that were able to grow in the presence of 2 µg/ml arylomycin C16 (8×MIC). Mutants were obtained at a frequency of 4 per 109 viable cells and fell into two phenotypic classes: the majority (~75%) had a 32-fold elevated MIC compared to the wild type strain, and the remainder had a greater than 256-fold elevated MIC. Consistent with this low frequency of resistance, arylomycin resistance was correlated with either of two mutations in SpsIB, one of the two SPases found in S. epidermidis. The 32-fold increase in resistance was associated with a Ser to Pro mutation at position 29 (10/11 clones sequenced); while the >256-fold increase in resistance was associated with a Ser to Pro mutation at position 31 (9/11 clones sequenced). None of the resistant mutants in either class exhibited growth defects under the standard laboratory conditions employed (data not shown).

These data indicate that the whole cell antibiotic activity of the arylomycins results from their inhibition of SPase and also that mutations in SPase are the dominant mechanism whereby S. epidermis evolves resistance.

To investigate whether naturally resistant bacteria harbor the same mutations that confer resistance in S. epidermidis, the amino acid sequences of SPases were examined in the closely related organism S. aureus, as well as in the more distantly related Gram-negative organisms E. coli and P. aeruginosa (Table 11).

TABLE 11

Resistance to Arylomycin A2 C16 Correlates with Proline at Position-5 and/or -7 in Bacterial SPase*

| Bacterial Strain | SPase Type | SPase Alignment | MIC (µg/mL) | SEQ ID NO: |
|---|---|---|---|---|
| S. epidermidis RP62A | WT | VGKSYSIKGDS | 0.25 | 17 |
| S. epidermidis PAS9001 | S29P | VGK[P]YSIKGDS | 8 | 18 |
| S. epidermidis PAS9002 | S31P | VGKSY[P]IKGDS | >128 | 19 |
| S. aureus NTCT 8325 | WT | VAKPYTVKGDS | >128 | 20 |
| S. aureus PAS8001 | P29S | VAK[S]YTVKGDS | 2 | 21 |
| E. coli MG1655 | WT | IYEPFQIPSGS | >128 | 22 |
| E. coli PAS0232 | P84S | IYE[S]FQIPSGS | 2 | 23 |
| P. aeruginosa PAO1 | WT | LFEPFQIPSGS | >128 | 24 |
| P. aeruginosa PAS2006 | P84S | LFE[S]PFQIPSGS | 8 | 25 |

*Mutations are shown in boxes (e.g., as [P] or [S]), and the catalytic serine is shown at the C-terminal end of the peptide sequence.

As shown in Table 11, at the position corresponding to the S. epidermidis SPase residue 29, Pro is found in the single SPase of S. aureus, in the single SPase of E. coli, and in one of the two SPases of P. aeruginosa (Pro29 in S. aureus, Pro84 in E. coli and P. aeruginosa). However, at the position corresponding to SPase residue 31 in S. epidermidis, Pro is not found in any of these S. aureus, E. coli, and P. aeruginosa SPase sequences. Moreover, an E. coli strain with Pro at Spase position 31 could not be constructed, suggesting that SPase position 31 mutations are not tolerated in some organisms.

To determine whether the innate arylomycin resistance observed in E. coli, P. aeruginosa, and S. aureus results from the identified Pro residues, mutant strains of these bacteria were constructed in which the Pro was replaced by Ser (the corresponding residue in wild type S. epidermidis SpsIB). In each organism, mutation of Pro to Ser conferred a high degree of sensitivity to arylomycin C16 (Table 11). No growth defects were apparent in the mutant strains (FIG. 2), suggesting that the increased sensitivity does not result from decreased fitness or compromised SPase activity.

The sensitivity of the E. coli and P. aeruginosa serine mutants to arylomycin C16 indicates that the presence of the Pro residue correlates with arylomycin resistance and that the arylomycins penetrate the formidable outer-membrane of Gram-negative bacteria. Consistent with efficient outer-membrane penetration, experiments demonstrated that permeabilizing these bacteria with polymyxin B nonapeptide had only a negligible effect on the MIC values (≤4-fold decrease).

Figure 2:
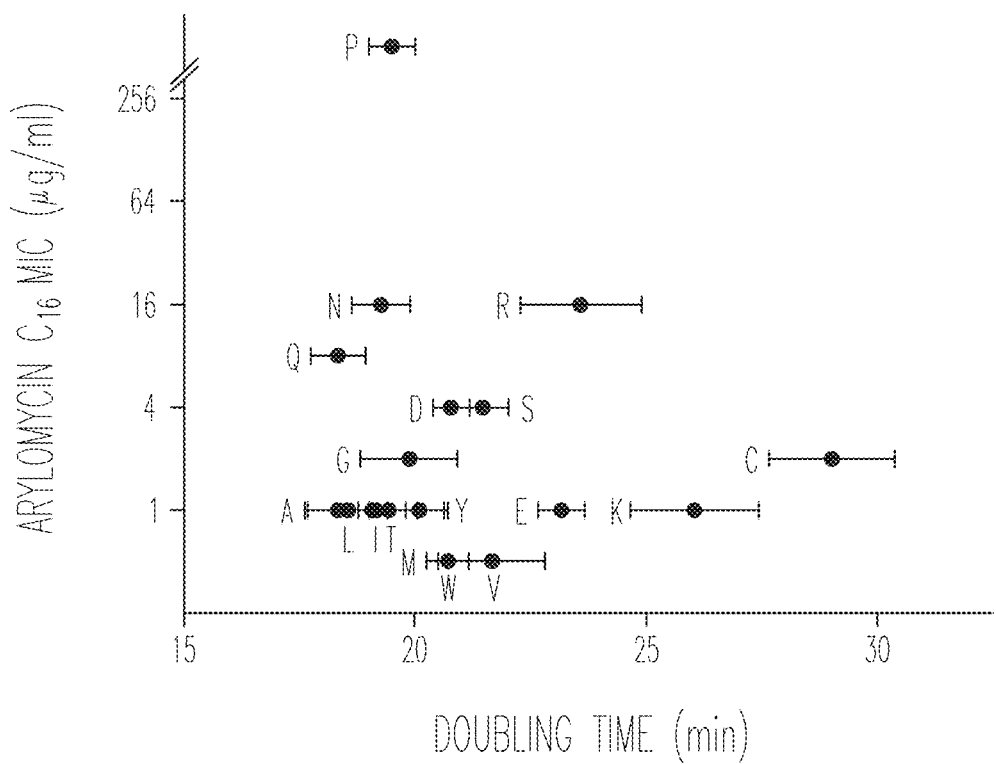
FIG. 2 graphically correlates the doubling time and the minimum inhibitory concentrations (MICs) of arylomycin C16 observed for *E. coli* strains harboring the indicated amino acid at SPase residue 84. Horizontal bars indicate standard deviation of doubling times from three independent experiments. MIC values varied less than 2-fold between experiments. The His (MIC 4 µg/ml) and Phe or His (MIC 2 µg/ml) variants have a temperature sensitive phenotype and therefore not shown. For Pro29, the MIC exceeded the detection limit of 256 µg/ml.

To determine whether the identified Pro is unique in its ability to confer arylomycin resistance, mutant strains of E. coli were constructed in which each of the other 19 amino acids was introduced into the E. coli SPase at the same position (residue 84). Based on the growth rates observed in arylomycin-free media, most amino acids at this position were well tolerated (FIG. 2), indicating that the nature of the amino acid at residue 84 does not generally affect fitness under the conditions employed, although a minor growth defect was observed when Arg, Lys, Glu, and Cys was present at position 84 and a temperature sensitive phenotype was observed when His and Phe were present at position 84. In contrast, when arylomycin C16 was added to the media, the MIC values observed are highly dependent on the identity of the amino acid at residue 84, but Pro was the only amino acid that imparted high-level arylomycin resistance (MIC >256 µg/ml) (FIG. 2). All of the other amino acids lead to arylomycin sensitivity (MIC values of ≤16 µg/ml), with the hydrophobic amino acids conferring somewhat greater sensitivities.

Resistance-Conferring Mutations Reduce the Affinity of Arylomycin for SPase

Based on the previously reported crystal structure of the *E. coli* SPase complex (Paetzel et al., J. Biol. Chem. 279, 30781-30790 (2004)) arylomycin A2 binds in a manner that mimics that proposed for natural peptide substrates, and the resistance-conferring Pro residue (Pro84), is positioned within the *E. coli* SPase substrate binding pocket, but distal to the catalytic residues (FIG. 3A). To test whether the resistance-conferring mutations directly interfere with arylomycin C16 binding in vitro, equilibrium binding constants were determined using recombinant SPase enzymes reconstituted in micelles that mimic a lipid bilayer environment. The affinities of arylomycin C16 were measured for a truncated wild type *E. coli* SPase that lacks the N-terminal membrane helices but that still associates with micelles, and for a P84S variant of this truncated *E. coli* SPase enzyme, (Kuo et al., Arch. Biochem. Biophys. 303, 274-280 (1993)). FIG. 3D shows the binding affinity of arylomycin C16 for the wild type and P84S variants of the soluble N-terminally truncated *E. coli* SPase. Arylomycin C16 bound the truncated wild type protein with a KD of 979±69 nM, which is similar to the value reported for arylomycin A2 (Paetzel et al., Biol. Chem. 279, 30781-30790 (2004)). In contrast, a significantly lower KD of 39±15 nM was observed for the serine-containing P84S variant of this *E. coli* SPase.

Figure 3B:
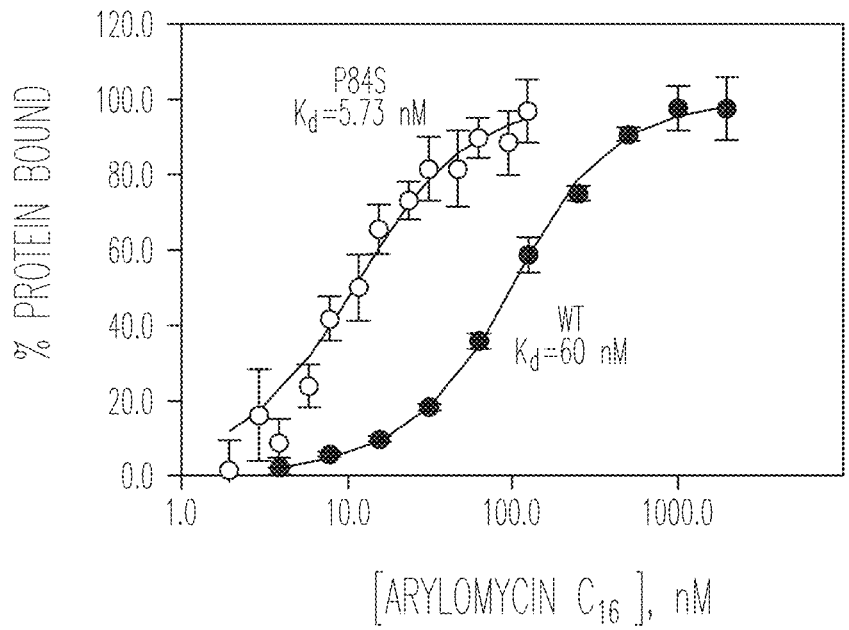
FIGS. 3B-3C show the equilibrium binding affinities of arylomycin for Pro- and Ser- variants of *E. coli* (FIG. 3B) and *S. aureus* (FIG. 3C) SPases. Data points and bars represent average values and standard deviations within a single experiment. KD values shown are the average of three independent experiments.

To control for artifacts associated with deletion of the N-terminal helices, which might interact with the lipid tail of the inhibitor or help to co-localize the protein and the inhibitor within the membrane-like micellular environment, the affinities of arylomycin C16 for the wild type and P84S variants of a detergent-solubilized full-length *E. coli* SPase were determined (FIG. 3B). While arylomycin C16 bound the full-length proteins with higher affinities than the corresponding soluble fragments, the affinity of arylomycin for the full-length Ser-variant (KD=5.7±1.0 nM) was again an order-of-magnitude higher than that for the corresponding Pro-variant (KD=60±16 nM).

Figure 3C:
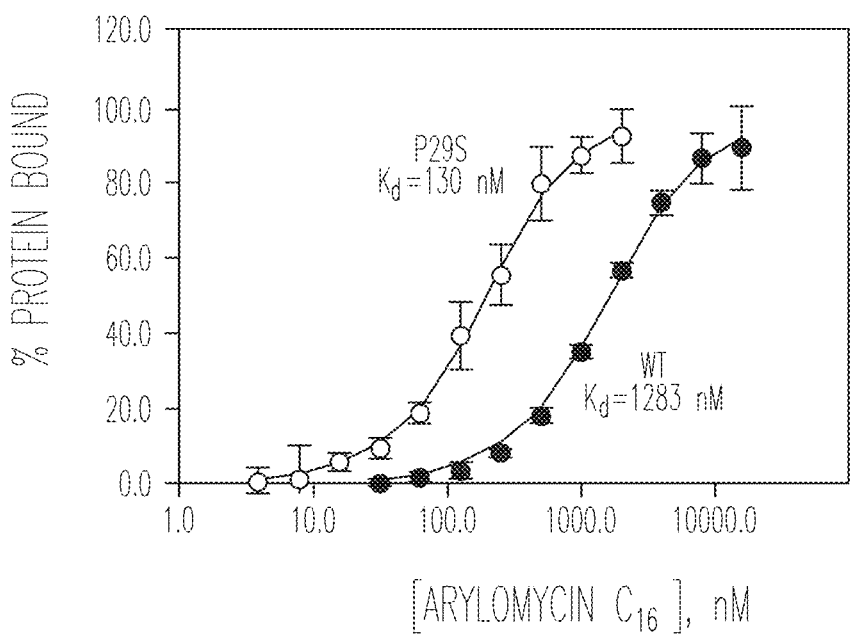
Figure 3D:
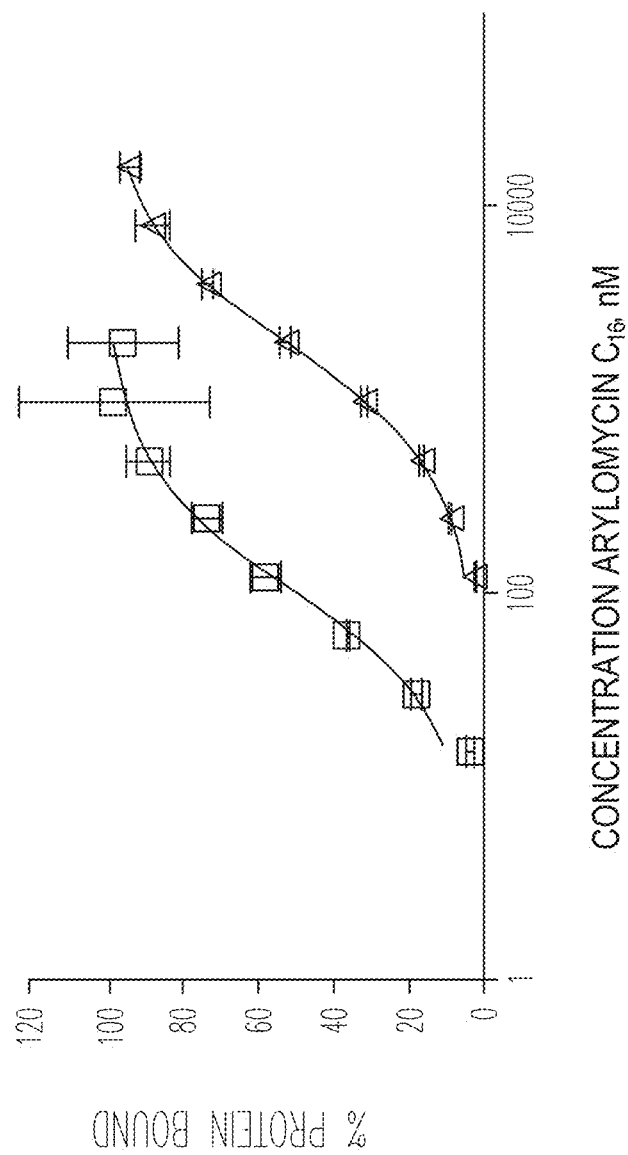
FIG. 3D shows the affinity of arylomycin C16 for the soluble N-terminally truncated *E. coli* SPase. The steady state binding affinities of arylomycin C16 for WT (open diamonds) and P84S (open square) variants of the soluble N-terminally truncated *E. coli* SPase are shown as a function of Arylomycin C concentration.

Lastly, to characterize a representative Gram-positive SPase, the affinity of arylomycin C16 for the full-length wild type and P29S mutant of *S. aureus* SPase was measured (FIG. 3C). As with the *E. coli* SPase, arylomycin C16 bound the Ser-variant of *S. aureus* SPase an order-of-magnitude more tightly than the Pro-variant, with KD values of 130±53 and 1283±278 nM, respectively. Thus, the Pro residues responsible for resistance in *E. coli* and *S. aureus* appear to act by interfering with arylomycin binding.

Distribution of Resistance-Conferring Residues in Nature

To better understand the distribution of this resistance determinant in nature, the phylogenetic relationship of the fully sequenced bacteria from five phyla was determined, as reflected by their 16S rRNA sequences. This phylogeny was then compared to the number of SPases in each organism and to the presence or absence of Pro at the position corresponding to residue 29 in *S. epidermidis* (unless otherwise specified, *S. epidermidis* numbering is used hereafter). In general, Gram-negative bacteria from the Chlamydiae/Verrucomicrobia, Proteobacteria, and Bacteroidetes phyla have a single SPase, and in each phylum, Pro29 is present in the SPases of a subset of organisms (FIG. 5).

Accordingly, almost all of the sequenced α-, β-, γ-Proteobacteria have SPases with Pro29 (115/123, 64/65, and 178/183 of the sequenced organisms, respectively), whereas most of the sequenced δ- and ε-Proteobacteria have SPases with Ala29 (32/35 and 27/29, respectively). Similarly, within the Bacteroidetes phylum, each of the sequenced Flavobacteria has one SPase where Pro is always present at position 29, whereas each of the Bacteroidia typically has an SPase with Asn29 and sometimes a second SPase with Ser29. Finally, among the few Chlamydiae/Venucomicrobia that have been sequenced, each of the *Chlamydia* has one SPase with Leu29 (7/7), while each of the Verrucomicrobia has at least one SPase with Pro29 (8/8). The phylogeny of the SPase genes themselves largely minors that of the 16S rRNA sequences, indicating that relatively little horizontal transfer of SPase genes has occurred and confirming that Pro29 was installed independently into the SPases of these lineages. Interestingly, horizontal gene transfer is responsible for the scattered instances of Proteobacteria that do encode multiple SPases, including the second SPase of *P. aeruginosa* that has at Leu29. These additional SPases are not closely related to any of the sequenced SPases examined in this analysis, and they may not be functionally equivalent to the other Proteobacterial SPases.

In contrast to the Gram-negative bacteria, the Gram-positive Firmicutes and Actinobacteria commonly encode multiple SPases, and comparison of the 16S rRNA and SPase phylogenies indicates that duplication of SPase genes has occurred multiple times in these lineages (FIG. 5). The distribution of Pro29 is also more irregular, which appears to have resulted from reduced conservation leading to the frequent introduction and removal of Pro at this position.

Moreover, the region defined by residues 27-31 appears to be poorly conserved within the Gram-positive SPases relative to the same region in the Gram-negative proteins or to the regions that comprise the core and active site of the protein (Table 12). Table 13 shows the relative conservation of regions of SPase genes from five bacterial phyla as reflected by the average Jensen-Shannon divergence score of the comprising residues (Capra and Singh, Bioinformatics 23, 1875-1882 (2007)). Boxes B-E were defined previously as the conserved regions that form the substrate binding site and active site (Dalbey et al., Protein Sci. 6: 1129-38 (1997)). The rank of residue 29 indicates the degree of conservation at this position relative each the other 137 residues used in the SPase sequence alignment, where 1 indicates the most conserved residue.

TABLE 12

Conservation of Regions of SPase genes from Five Bacterial Phyla

| Bacterial Phyla | Entire Aligned Sequence | Box B | Box C | Box D | Box E | Residues 27-31 | Rank Residue 29 |
|---|---|---|---|---|---|---|---|
| Actinobacteria | 0.473 | 0.572 | 0.464 | 0.632 | 0.602 | 0.416 | 76/137 |
| Firmicutes | 0.431 | 0.491 | 0.370 | 0.626 | 0.587 | 0.248 | 134/137 |

TABLE 12-continued

Conservation of Regions of SPase genes from Five Bacterial Phyla

| Bacterial Phyla | Entire Aligned Sequence | Box B | Box C | Box D | Box E | Residues 27-31 | Rank Residue 29 |
|---|---|---|---|---|---|---|---|
| Bacteroidetes | 0.516 | 0.615 | 0.529 | 0.645 | 0.594 | 0.431 | 98/137 |
| Chlamydia/ Verrucomicrobia | 0.553 | 0.681 | 0.599 | 0.636 | 0.616 | 0.567 | 47/137 |
| Proteobacteria | 0.534 | 0.629 | 0.585 | 0.654 | 0.664 | 0.568 | 30/137 |

Figure 4:
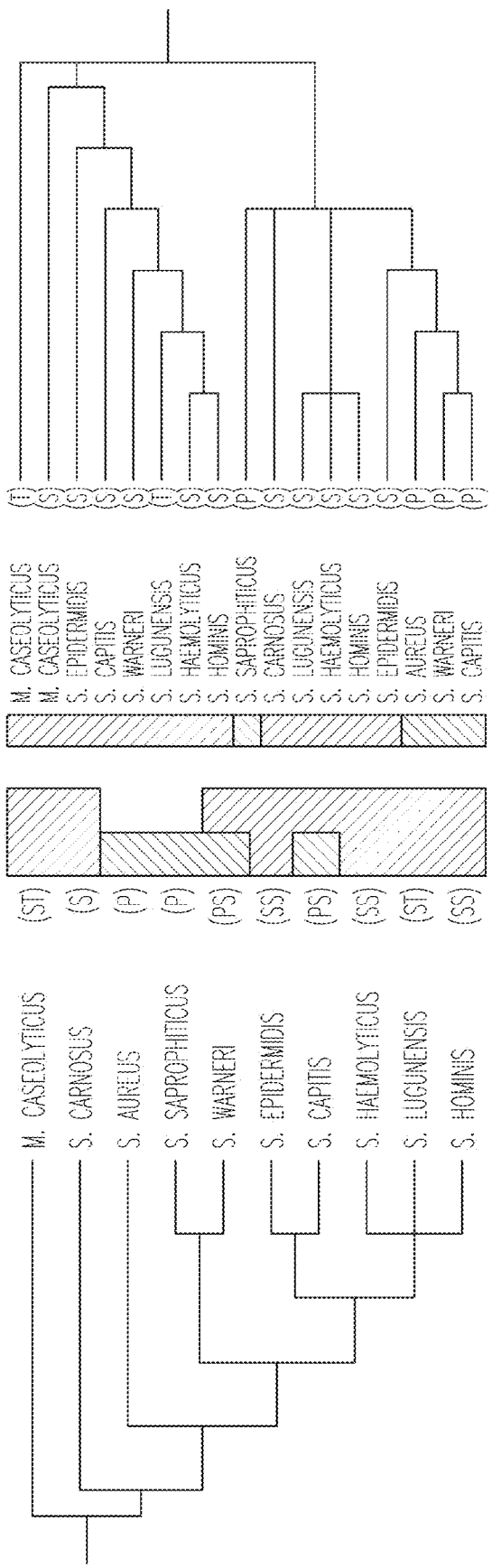
FIG. 4 shows a phylogenetic reconstruction of the evolution of Pro29 within Staphylococcaceae SPases. The left side shows the phylogeny of Staphylococcaceae based on 16S RNA sequences. For each species, color bars indicate the number of SPases and presence or absence of Pro at residue 29; the amino acid(s) at residue(s) 29 is/are parenthetically noted in single letter code following the species name. The right side shows the phylogenetic relationship of SPase sequences from the indicated species. For each gene, the amino acid at residue 29 is parenthetically noted in single letter code following the name of the species in which the gene is found. Red and Blue branches represent the evolution of two distinct SPase lineages present in the common ancestor of sequenced Staphylococcaceae. Branches with an alternative likelihood ratio test support of less than 50% are collapsed.

As shown in Table 12, the region defined by residues 27-31 appears to be poorly conserved within the Gram-positive SPases relative to the same region in the Gram-negative proteins. However, Pro29 is particularly common among the SPases of a subset of the Gram-positive bacteria Bacilli, including the genres Bacillus, Listeria, and Staphylococcus. Interestingly, although SPases with Pro29 appear to have been present and maintained during speciation of the Bacillus and Listeria, the common Staphylococci ancestor appears to have had two SPases each with Ser29, as is still the case with S. epidermidis. S. aureus appears to have deleted one SPase and introduced Pro29 into the other (FIG. 4).

The Arylomycins have a Broad Spectrum of Antibiotic Activity

To further explore the spectrum of arylomycins and to test the contribution of the Pro29 to arylomycin resistance in a wider range of bacteria, the arylomycin susceptibilities were determined of representative organisms from the above phylogenetic analysis (Table 13). Bacteria from all five phyla were sampled, and when possible important human pathogens were included.

TABLE 13

Associations between arylomycin C16 sensitivity and SPase genotype(s) among different wild type bacteria

| Species | Reside 29 | MIC (μg/ml) |
|---|---|---|
| Staphylococcus epidermidis | S, S | 0.25 |
| Staphylococcus haemolyticus | S, S | 2 |
| Rhodococcus opacus | V | 2 |
| Corynebacterium glutamicum | M | 2 |
| Helicobacter pylori | A | 4 |
| Yersinia pestis | P | 4 |
| Chlamydia trachomatis | L | 6 |
| Francisella tularensis | N | 4-16, >64* |
| Streptococcus pneumoniae | N | 16 |
| Streptococcus pyogenes | A | 16 |
| Lactococcus lactis | L | 16, >128* |
| Rhodococcus erythropolis | V, I | 16 |
| Corynebacterium efficiens | P | >64 |
| Staphylococcus aureus | P | 16-32, >128* |
| Brevibacillus brevis | P, P, P, P, V | >64 |
| Enterococcus faecalis | P, P, P, S | >64 |
| Bacillus subtilis | P, P, P, D | >128 |
| Streptococcus agalactiae | F, V | >128 |
| Escherichia coli | P | >128 |
| Pseudomonas aeruginosa | P, L | >128 |
| Klebsiella pneumoniae | P | >128 |
| Lactobacillus gasseri | N, N | >128 |
| Lactobacillus acidophilus | N | >128 |
| Lactobacillus plantarum | M, M, V | >128 |
| Clostridium difficile | P, P, P | >16 |
| Clostridium bolteae | N, N, Q | >16 |
| Clostridium perfringens | K, K, K, I | >16 |
| Bacteroides fragilis | S, N | >16 |
| Prevotella copris | N | >16 |

*Multiple values indicate heterogeneity within different strains of a species, as discussed in the text.

As shown in Table 13, arylomycin C16 is active against the ε-Proteobacteria H. pylori (whose SPase has Ala29) with an MIC of 4 μg/ml. Similarly, the intracellular Gram-negative pathogen C. trachomatis (Leu29) is eradicated from human HeLa 229 cells with an MIC of 6 μg/ml. Notably, no adverse effects on the human cells were observed up to 20 μg/ml of arylomycin, the highest concentrations examined. Francisella tularensis (Asn29) is a potential biological warfare agent and a member of the only genera of γ-Proteobacteria that does not have Pro29. Nineteen clinical isolates of Francisella tularensis (Asn29) were examined and it was determined that 8 were inhibited with MICs of 4 to 16 μg/ml, one with an MIC of 32 μg/ml, and the remainder with MICs in excess of 64 μg/ml. Klebsiella pneumoniae encodes a single SPase that has Pro29 and is resistant to the arylomycins. Interestingly, although it has a single SPase with a Pro29, Yersinia pestis, the causative agent of plague, is sensitive to arylomycin C16.

The Gram-positive Firmicutes Streptococcus pneumoniae, Streptococcus pyogenes, and Staphylococcus haemolyticus are all human pathogens that lack SPases with Pro29. Each of these species is sensitive to arylomycin C16. However, B. subtilis and E. faecalis, Firmicutes with multiple SPases having Pro29, are resistant. In contrast, the Gram-positive Actinobacteria Rhodococcus equi and Rhodococcus opacus (Schimana et al., J. Antibiot. (Tokyo) 55, 565-570 (2002)) lack Pro29 and are each sensitive to arylomycin C16. While the actinobacteria Corynebacterium glutamicum has a single SPase with Met29 and an arylomycin C16 MIC of 2 μg/ml, the related actinobacteria Corynebacterium efficiens has a single SPase with Pro29 and an MIC of 16 μg/ml.

However, while Lactococcus lactis spp. cremonis, which has one SPase with Leu29, is sensitive to arylomycin C16, the highly related Lactococcus lactis spp. lactii also has a single SPase with Leu29 and is resistant. Additionally, a variety of other Lactobacillales, and all investigated Clostridia and Bacteriodetes, are resistant to the arylomycins despite the fact that many lack SPases with Pro29 (MIC >64 μg/ml for the Lactobacillales and >16 μg/ml for the Clostridia and Bacteriodetes). Finally, a broader survey of S. aureus strains revealed that two strains, despite a prediction of arylomycin-resistance because they have SPases with Pro29, are actually arylomycin-sensitive: COL a tetracycline and penicillin resistant strain (MIC=12 μg/ml), and Rosenbach 328, an MRSA strain (Pantosti and Venditti, Eur. Respir. J. 34, 1190-1196 (2009)) (MIC=25 μg/ml).

Table 14 shows the activity of arylomycin A-$C_{16}$ and arylomycin B—$C_{16}$ against Streptococcus pnemoniae, Streptococcus pyogenes, and Streptococcus agalactiae.

TABLE 14

| Strain | MIC (μg/ml) Arylomycin A-C16 | MIC (μg/ml) Arylomycin B-C16 |
|---|---|---|
| S. pneumoniae | 8 | 16 |
| S. pyogenes | 8 | 4 |
| S. agalactiae | >128 | 8 |

Representative SPase Sequences of Arylomycin-Susceptible
Bacteria
1_Rhodococcus equi ATCC 33707_GI# 296036237_Catalytic Ser
Residue 69

(SEQ ID NO: 106)
VADAPQDPDVTPDETEQEQTGGRSRRRRGKDKKPRSFWREIPILIVVALLLSFLLQTFI
ARVYLIPSESMEPTLHGCPGCTGDRIVVEKISYRFGDPKPGDVVVFRGPESWSEGYSST
RSDNVVVRGLQEVGSLVGVVPPDENDLVKRVIATGGQTVECCDDQGRVLVDGKPLDEPY
ITMDFPFIPGVQTCDTAVKSGRCFGPVTVPDGHLWVMGDNRSNSADSRYHVSDEMQGTI
PVDNVIGKATFIVLPPGRWGSISSPDIRQQ*

1_Rhodococcus equi ATCC 33707_GI# 296036237_Catalytic Ser
nucleotides 205-207

(SEQ ID NO: 107)
GTGGCAGATGCACCGCAGGACCCCGGACGTGACGCCGGACGAGACCGAGCAGGAGCAGAC
CGGGGGACGGTCCCGCAGGCGCAGGGGGAAGGACAAGAAACCTCGATCGTTCTGGCGTG
AGATCCCGATCCTCATCGTCGTCGCCTTGCTGTTGAGTTTCCTGCTGCAGACGTTCATC
GCCCGGGTCTACCTCATTCCGTCCGAGTCGATGGAGCCGACGCTGCACGGTTGCCCCGG
GTGCACCGGTGACCGCATCGTCGTCGAGAAGATCAGTTACCGATTCGGCGACCCGAAGC
CCGGCGACGTCGTGGTCTTCCGCGGCCCGGAGTCGTGGTCCGAGGGATATTCGTCGACA
CGCTCGGACAACGTGGTGGTCCGCGGTCTGCAGGAGGTCGGCTCGCTCGTCGGTGTCGT
GCCGCCGGACGAGAACGATCTCGTCAAACGCGTCATCGCGACGGGTGGGCAGACCGTCG
AGTGCTGCGACGACCAGGGCCGTGTCCTGGTCGACGGAAAGCCGCTCGACGAGCCGTAC
ATCACGATGGACTTCCCTTTCATCCCCGGCGTGCAGACGTGTGACACCGCCGTGAAGTC
CGGACGCTGCTTCGGACCCGTCACGGTTCCCGATGGGCACCTGTGGGTGATGGGCGACA
ACCGCAGCAATTCCGCGGATTCGCGGTACCACGTCTCCGACGAGATGCAGGGCACGATT
CCGGTGGACAATGTGATCGGTAAGGCGACCTTCATCGTCCTGCCCCCCGGGCCGGTGGGG
ATCGATCTCGTCTCCCGACATCCGGCAGCAGTGA

2_Rhodococcus opacus B4_GI# 226366004_Catalytic Ser Residue
72

(SEQ ID NO: 108)
VTDSSKERALSSESESETTGDSAATSAVNGGAAETEKKPRSFLRELPILILVALVLSFLLQ
TFVARVYLIPSESMEPTLHGCAGCTGDRIVVEKIGYRFGDPQPGDVIVFRGPDSWSQDF
VSTRSSNVVIRGAQEVGSLVGLVPPDENDLVKRVIATGGQTVECCDDQGRILVDGQPID
EPYVVMDFPFVPGSQACDTALKSARCFGPVTVPEGHLWVMGDNRSNSADSRYHVGDDMQ
GTIPLDNVIGKAVFIALPPSRMGTISSPDIQGK*

2_Rhodococcus opacus B4_GI# 226366004_Catalytic Ser
nucleotides 214-216

(SEQ ID NO: 109)
GTGACAGATTCTTCGAAGGAGCGGGCATTGTCGTCGGAATCCGAGACCACCGGCGATTC
GGCCGCCACCTCCGCAGTGAACGGCGGTGCGGCGGAGACCGAGAAGAAACCCCGCTCCT
TCCTCCGCGAGTTGCCGATCCTGATCCTGGTCGCGCTCGTCCTGAGTTTCCTGCTGCAG
ACGTTCGTCGCCCGCGTGTATCTCATTCCGTCGGAGTCGATGGAACCGACGCTGCACGG
GTGCGCGGGCTGCACCGGCGACCGCATCGTGGTCGAGAAGATCGGCTACCGTTTCGGGG
ACCCGCAACCCGGTGACGTCATCGTGTTCCGCGGGCCCGACTCGTGGTCACAGGATTTC
GTCTCCACCCGTTCCTCCAACGTGGTGATCCGCGGTGCGCAGGAAGTCGGTTCCCTCGT
CGGACTCGTCCCGCCGGACGAGAACGACCTCGTCAAGCGTGTGATCGCCACCGGCGGTC
AGACCGTCGAATGCTGCGACGACCAGGGCCGCATCCTGGTGGACGGACAACCGATCGAC
GAGCCCTACGTCGTCATGGACTTCCCCTTCGTCCCCGGCTCCCAGGCCTGCGACACGGC
GCTGAAGTCGGCGCGCTGCTTCGGTCCCGTCACCGTCCCCGAGGGGCACCTGTGGGTGA
TGGGCGACAACCGCAGCAACTCCGCGGACTCCCGCTACCACGTCGGCGACGACATGCAA
GGCACCATCCCGCTCGACAACGTGATCGGCAAGGCGGTCTTCATCGCGTTGCCGCCGTC
GCGAATGGGCACGATCAGTTCACCCGATATCCAGGGCAAGTGA

3_Corynebacterium diphtheriae NCTC 13129_GI#
38234095_Catalytic Ser Residue 90

(SEQ ID NO: 110)
MKRSVFSFCMMQQASLGVFHSMAETAARVLKVSSANNETVSPTEGVETHDKEKKQLPWF
VEIPVVVVTLLVITLLQTFVGRVYMIPSQSMEPTLHGCAGCTGDRIYVDKLAYRFGEP
EAGDVVVFAGTESWNTGFTTSRSENPLVRGIQNAGAFVGLVAPDENDLVKRIVATGGQT
VQCLEGDEGVKVDGKVIDSSYTLMPPAYPVDQTTGSEACGGFYFGPIKVPEGNYFMMGD
NRTNSADSRYHIGDQYQGTIPKENLKGKVQFKIFPFNRIGAVEDYDIQQ*

3_Corynebacterium diphtheriae NCTC 13129_GI#
38234095_Catalytic Ser nucleotides 268-270

(SEQ ID NO: 111)
ATGAAGCGCTCAGTTTTCTCTTTTTGTATGATGCAGCAAGCGTCGCTGGGCGTTTTTCA
TTCGATGGCTGAAACAGCTGCTAGAGTTCTCAAAGTGAGTTCAGCTAATAACGAGACTG
TGTCCCCCACGGAAGGCGTCGAAACGCACGACAAGGAAAAGAAGCAACTGCCATGGTTT
GTGGAAATCCCTGTCGTCGTAGTGGTGACCCTTCTTGTGATCACCTTGCTTCAAACGTT
CGTTGGACGGGTCTATATGATCCCAAGTCAGTCAATGGAGCCGACACTTCATGGATGTG
CAGGGTGTACCGGAGACCGAATTTATGTAGATAAGCTGGCTTATCGTTTTGGTGAACCA
GAAGCCGGCGACGTTGTAGTTTTTGCAGGTACAGAATCATGGAACACCGGATTTACCAC
TTCACGGTCAGAAAATCCTCTGGTTCGTGGAATACAAAATGCGGGTGCTTTCGTCGGAT
TAGTAGCACCAGACGAAAACGACCTTGTAAAACGCATCGTAGCAACAGGGGGTCAAACG
GTGCAGTGCCTTGAAGGCGATGAAGGTGTCAAAGTAGACGGTAAAGTCATCGACTCGTC
ATATACTCTGATGCCACCAGCGTATCCGGTCGACCAGACCACAGGATCAGAGGCGTGCG
GCGGCTTTTACTTCGGACCTATCAAGGTACCTGAAGGAAATTACTTCATGATGGGCGAT
AACCGGACAAACTCCGCGGATTCTCGTTACCACATTGGTGATCAGTATCAAGGCACCAT

-continued
CCCTAAAGAAAACCTCAAGGGGAAAGTTCAGTTCAAGATTTTCCCATTTAACCGTATTG
GTGCAGTCGAGGATTACGATATCCAACAGTGA 4_Lactococcus lactis subsp. cremoris MG1363_GI#
125625303_Catalytic Ser Residue 35
(SEQ ID NO: 112)
MMKFLKEWGLFIFIIAAVLLSRVFIWSLVVVDGHSMDPTLADKERLVIVRTTKINRFDI
VVAKENAADGSTKDIVKRVVGMPGDTIKFDHDQLTINNKVYPENYLKDYQKQLADGQLE
KTYGNYPLTKALTDQNRSLFVSLAQSTKAFTTDSTGNPTFTVKVPDGQYFLMGDNRVVS
QDSRAVGSFKRSAIIGEAKLRVWPLNKISFF*

4_Lactococcus lactis subsp. cremoris MG1363_GI#
125625303_Catalytic Ser nucleotides 103-105
(SEQ ID NO: 113)
ATGATGAAATTTTTAAAAGAATGGGGATTATTTATCTTTATAATTGCCGCTGTCCTTCT
CTCGCGCGTCTTTATTTGGTCACTAGTTGTCGTTGATGGCCATTCAATGGACCCTACTT
TAGCCGATAAAGAAAGACTTGTAATTGTTAGAACGACAAAAATTAATCGTTTTGATATT
GTAGTTGCTAAAGAAAACGCGGCTGATGGTTCAACCAAAGATATTGTCAAACGTGTCGT
TGGGATGCCTGGGGACACTATAAAATTCGACCATGACCAACTTACTATCAATAATAAGG
TTTATCCAGAAACTATCTCAAAGACTATCAAAAACAATTGGCTGATGGTCAATTGGAA
AAAACTTACGGGAACTATCCTTTGACAAAAGCATTAACTGATCAAATCGTAGTTTATT
TGTAAGCTTAGCTCAGAGCACCAAAGCTTTTACAACGGATAGTACTGGTAATCCAACCT
TTACAGTCAAAGTCCCTGACGGACAATACTTCTTGATGGGAGATAATCGTGTTGTGTCT
CAAGATAGCCGAGCAGTTGGAAGTTTCAAACGTTCAGCGATTATTGGTGAAGCCAAATT
ACGAGTTTGGCCACTCAATAAAATTTCTTTCTTTTAA 5_Corynebacterium glutamicum ATCC 13032_GI#
19553237_Catalytic Ser Residue 67
(SEQ ID NO: 114)
VTDFSSASNADDSTQDGRPGRRAGKSKKESKPTPWYIEIPVVVVLTLALIFVLQTFVGR
MYMIPSGSMEPTLHGCEGCTGDRILVEKVSYYFTDPEPGDVVVFKGTDSWNVGFTTQRS
DNSVIRGLQNLGSYVGLVAPDENDLVKRIIATGGQTVSCQAGDPGIMVDGKEVDDSYTL
QPAQFPIDETSGSTECGGNYFGPITVPGGNYFMMGDNRTNSMDSRYHLGDQYQGTIPEE
NIKGKVQAIILPFSRIGGVDDPAIKG*

5_Corynebacterium glutamicum ATCC 13032_GI#
19553237_Catalytic Ser nucleotides 199-201
(SEQ ID NO: 115)
GTGACTGATTTTTCTAGTGCTTCAAATGCTGACGATTCCACGCAGGACGGTCGTCCTGG
TCGACGTGCTGGAAAGTCTAAGAAGGAATCGAAGCCAACTCCGTGGTACATCGAAATTC
CAGTGGTTGTGGTTTTGACCCTCGCGCTGATTTTCGTGCTCCAGACGTTTGTCGGACGC
ATGTACATGATTCCGAGTGGTTCGATGGAACCTACTTTGCACGGATGTGAGGGCTGCAC
GGGTGACCGCATCCTGGTGGAGAAGGTTTCTTACTACTTCACGGATCCAGAGCCGGGCG
ATGTTGTGGTGTTCAAGGGTACTGATTCCTGGAACGTTGGATTCACTACGCAGCGTTCC
GATAATTCGGTGATCCGCGGCCTGCAGAACCTGGGTTCTTACGTGGGTCTTGTCGCACC
TGATGAAAATGACCTGGTCAAGCGCATTATCGCCACCGGCGGTCAGACTGTTTCGTGCC
AAGCCGGTGATCCTGGAATCATGGTTGACGGCAAGGAAGTCGATGACAGCTACACGCTG
CAACCTGCGCAATTCCCCATCGATGAGACCTCCGGTTCCACCGAATGCGGCGGCAACTA
TTTCGGCCCCATCACCGTGCCTGGCGGCAACTACTTCATGATGGGTGACAACCGCACCA
ACTCCATGGATTCCCGCTACCACCTGGGCGATCAGTACCAAGGAACCATCCCTGAGGAA
AACATCAAGGGCAAAGTTCAAGCAATTATCCTGCCATTTAGCCGAATCGGTGGCGTCGA
CGACCCTGCCATCAAAGGCTAG 6_Francisella tularensis subsp. holarctica_GI#
89255957_Catalytic Ser Residue 99
(SEQ ID NO: 116)
MEILNYILNLSFTFWLLFLTIASGLIYIIDFVFFQKSRLAAYTDELKGLSKKQKRQFYK
DRGLKAPFIADQARSLFSVFFVVFLLRTFLIGNFLIPTASMTPTLPVGDFIFVNKTAYG
IRAPFTNETLIKVGEPKRGDIVVFHFPVNPNVDFVKRVIGLPGDVISYKDKMLTINGKK
LEYTNCNRDAMNYYNQSLAAGSGDTVCTENLDGVKHEVDWIESIKGTDFENLKVPAGQY
FVMGDNRDNSEDSRYWGFVPDKDLVGKAKVVWMSWDKIDKKVRWDEIGKVF*

6_Francisella tularensis subsp. holarctica_GI#
89255957_Catalytic Ser nucleotides 295-297
(SEQ ID NO: 117)
ATGGAAATCTTAAACTATATTTTAAACTTGAGCTTTACTTTTTGGCTTTTATTCTTAAC
CATTGCCAGTGGTTTAATTTATATTATTGATTTTGTGTTCTTCCAAAAATCAAGATTAG
CAGCATATACAGATGAATTAAAAGGTCTTTCTAAGAAGCAAAAACGTCAGTTCTATAAA
GATAGAGGATTAAAAGCACCTTTTATTGCTGATCAGGCGAGATCTTTATTTAGTGTATT
TTTTGTAGTTTTTCTACTTAGAACCTTCTTGATTGGTAATTTTTTAATTCCAACTGCAT
CAATGACACCAACACTTCCAGTTGGTGATTTTATTTTTGTCAATAAAACTGCTTATGGT
ATCAGAGCACCATTTACCAATGAGACTTTAATAAAAGTTGGTGAACCCAAAAGAGGTGA
TATTGTAGTATTTCATTTTCCAGTTAATCCTAATGTTGATTTTGTAAAACGAGTGATCG
GTTTGCCTGGCGATGTAATTTCGTATAAAGACAAAATGTTGACAATAAATGGTAAAAAA
CTTGAATATACTAATTGTAATCGTGATGCAATGAACTATTATAATCAGTCTTTAGCTGC
TGGTAGTGGCGATACAGTATGTACGGAAAACCTTGATGGAGTTAAACATGAGGTTGATT
GGATAGAGTCTATAAAGGGAACTGATTTTGAAAACCTTAAAGTCCCAGCAGGTCAATAC
TTTGTCATGGGAGATAATCGTGATAATAGTGAAGATAGTCGTTATTGGGGTTTTGTACC
TGACAAAGATCTAGTTGGTAAAGCAAAAGTTGTTTGGATGAGCTGGGATAAGATAGATA
AAAAGGTTCGCTGGGATGAAATTGGTAAGGTCTTTTAA 7_Campylobacter jejuni RM1221_GI# 57237697_Catalytic Ser
Residue 38

(SEQ ID NO: 118)

MEILKKLYKFSQSWTGTVVIVLLVIFFFIQAFVIPSGSMKNTLLVGDFLFVKKFSYGIP
TPHIPWLEIPVLPDFNKDGHLIKAQGSQRGDIVVFRNPRNEKEHFVKRCVGTGGDRIVY
ANKTLYVRMHEGDEFMKEHYPNDLVTLGGQIYVKEPYKQKGIHYDPKKDIESDILRFLS
IGDFAMSPTYIKELGNHIGFSGGNAYVFDVPENEYFMMGDNRDYSYDSRFWGSVPYRLI
VGKPWFVYFSWDKDKNVRWERIGRFVDTLENDEQYIHDHDDEDKLS*

7_Campylobacter jejuni RM1221_GI# 57237697_Catalytic Ser
nucleotides 112-114

(SEQ ID NO: 119)

ATGGAAATTTTAAAGAAATTATATAAATTTTCACAGTCTTGGACTGGAACTGTAGTTAT
TGTTCTTTTGGTGATTTTTTTCTTTATACAAGCTTTTGTTATTCCTTCTGGTTCTATGA
AAAACACCTTATTGGTAGGGGATTTTTTATTTGTTAAAAAATTTAGCTATGGTATCCCA
ACTCCTCATATTCCTTGGTTGGAAATTCCTGTTTTGCCAGATTTCAATAAAGATGGGCA
TTTGATAAAAGCACAAGGGTCACAAAGAGGAGATATAGTTGTTTTTAGAAATCCTAGAA
ATGAAAAGAACACTTTGTAAAGCGTTGTGTAGGCACAGGAGGAGATAGGATAGTTTAT
GCAAATAAAACACTTTATGTAAGAATGCATGAGGGTGATGAATTTATGAAAGAACATTA
TCCGAATGATCTTGTTACTCTTGGAGGGCAAATTTATGTAAAAGAACCTTATAAACAAA
AAGGTATTCATTATGATCCAAAAAAGATATAGAAAGCGATATTTTACGCTTTCTTAGC
ATAGGTGATTTTGCTATGTCTCCAACTTATATTAAAGAACTTGGAAATCATATAGGTTT
TAGCGGCGGAAATGCTTATGTTTTTGATGTGCCTGAAAATGAGTATTTCATGATGGGTG
ATAATCGCGATTATTCTTATGATAGTCGTTTTTGGGGTTCTGTTCCTTATAGGTTGATA
GTAGGTAAACCTTGGTTTGTATATTTCTCTTGGGATAAAGATAAAAATGTTCGCTGGGA
AAGGATAGGGCGTTTTGTTGATACCTTGGAAAATGATGAACAATATATCCATGATCATG
ATGATGAGGATAAATTAAGCTAA

8_Helicobacter pylori HPAG1_GI# 108562981_Catalytic Ser
Residue 38

(SEQ ID NO: 120)

MKFLRSVYAFCSSWVGTIVIVLLVIFFVAQAFIIPSRSMVGTLYEGDMLFVKKFSYGIP
IPKIPWIELPIMPDFKNNGHLIEGDRPKRGEVVVFIPPHEKKSYYVKRNFAIGGDEVLF
TNEGFYLHPFESGNDKDYIAKHYPNAMTKEFMGKIFVLNPYKSKHPGIHYQKDNETFHL
MEQLATQGAEANISMQLIQMEGEKVFYKKINSDEFFMIGDNRDNSSDSRFWGSVAYKNI
VGSPWFVYFSLSLKNSLEMDAENNPKKRYLVRWERMFKSVEGLEKIIKKEKATH*

8_Helicobacter pylori HPAG1_GI# 108562981_Catalytic Ser
nucleotides 112-114

(SEQ ID NO: 121)

ATGAAATTTTTACGCTCTGTTTATGCATTTTGCTCCAGTTGGGTAGGGACGATTGTTAT
TGTGCTGTTGGTATCTTTTTTGTTGCGCAAGCTTTCATCATTCCCTCTCGCTCTATGG
TAGGCACGCTCTATGAGGGCGACATGCTCTTTGTCAAAAAATTTTCTTACGGCATACCC
ATTCCTAAAATCCCATGGATTGAGCTTCCTATTATGCCTGATTTTAAAAATAACGGGCA
TTTGATAGAGGGGGATCGCCCTAAGCGCGGCGAAGTGGTCGTATTTATCCCCCCCCATG
AAAAAAAATCTTACTATGTCAAAAGGAATTTTGCCATTGGGGCGATGAGGTGCTATTC
ACTAATGAGGGGTTTTATTTGCACCCTTTTGAGAGCGGCAACGATAAGGATTTATATTGC
TAAACATTACCCTAACGCCATGACTAAAGAATTTATGGGTAAAATTTTTGTTTTAAACC
CTTATAAAAGTAAGCATCCGGGTATCCATTACCAAAAAGACAATGAAACCTTCCACTTA
ATGGAGCAGTTAGCCACTCAAGGTGCGGAAGCTAATATCAGCATGCAACTCATTCAAAT
GGAGGGCGAAAAGGTGTTTTACAAGAAAATCAATAGCGATGAATTTTTCATGATCGGCG
ATAACAGAGACAATTCTAGCGACTCGCGCTTTTGGGGGAGTGTGGCTTATAAAAACATC
GTGGGTTCGCCATGGTTTGTTTATTTCAGTTTGAGTTTAAAAAATAGCCTGGAAATGGA
TGCAGAAAACAACCCCAAAAAACGCTATTTGGTGCGTTGGGAACGCATGTTTAAAAGCG
TTGAAGGCTTAGAAAAAATCATTAAAAAAGAAAAAGCAACGCATTAA

9_Propionibacterium acnes J139_GI# 282854577_Catalytic Ser
Residue 69

(SEQ ID NO: 122)

VADDYRARRAANGDTRDSDDATARGEQASGWQRFRSGAIEVVLIVVGALIISAVLRGFV
AQMFVIPSKSMQNTLQVGDRVIAVKAADFHRGDVVVFKDTEHWLPAVQDRRSVPGQILE
FVGLLPNKSSNYLIKRVIGMPGDTVACCNVNGQVTVNGKALDERSYLYSENGEMVKPSA
MEFRVTVPRGRMFVLGDHRNASGDSRYHLQDLDPGEYTGAPAFVPLDDVVGPAKAILMP
LNRIEGLGTPNTFRGIPDRSSSAPAKARICVGNTCCPK*

9_Propionibacterium acnes J139_GI# 282854577_Catalytic Ser
nucleotides 205-207

(SEQ ID NO: 123)

GTGGCGGATGACTACCGGGCGAGGCGGGCTGCAAACGGCGACACCAGGGACTCTGACGA
TGCAACAGCACGTGGGGAACAGGCGTCTGGGTGGCAGCGCTTTCGGTCGGGGGCCATCG
AAGTTGTTCTCATCGTCGTTGGTGCCCTCATCATCTCAGCTGTGCTGCGTGGTTTCGTC
GCTCAGATGTTTGTCATCCCGTCGAAGTCCATGCAAAACACCTTGCAGGTGGGTGACCG
CGTGATCGCGGTGAAAGCCGCCGATTTTCATCGGGGCGACGTCGTCGTGTTCAAAGACA
CCGAACATTGGTTACCTGCTGTTCAGGATCGCCGCTCTGTTCCAGGACAGATCCTCGAA
TTCGTCGGGTTGTTGCCTAACAAGAGCTCGAACTACCTCATTAAGCGAGTGATCGGCAT
GCCTGGGGACACCGTTGCCTGCTGCAACGTCAACGGCCAGGTGACCGTCAACGGTAAGG
CGCTTGACGAGCGGTCATACCTGTACTCCGAAAATGGTGAAATGGTTAAACCCTCGGCG
ATGGAATTCCGGGTCACTGTTCCTCGGGGGCGGATGTTCGTCTTGGGGGACCATCGCAA
TGCCTCGGGTGACTCGCGCTATCACCTCCAAGACCTTGATCCGGGTGAGTATACGGGCG
CTCCTGCGTTTGTGCCGCTCGATGACGTCGTTGGGCCGGCAAAGGCCATTCTTATGCCT

```
CTCAATCGCATTGAGGGACTGGGGACTCCTAACACTTTCCGGGGAATCCCGGATAGGTC
GTCGTCAGCTCCAGCCAAGGCGCGCATCTGCGTCGGTAACACGTGCTGCCCTAAGTGA
```

10_Chlamydia trachomatis 434/Bu_GI# 166154241_Catalytic Ser Residue 113

(SEQ ID NO: 124)

```
MTSSYMSRLYSLNKSRRILHSSFRLLKSTKMLSHPETQKELQEVLKQLEEAILDQNRED
ASLFAKQAQAIQKRFPKSKLRATFDLIYALTFAAILAFLIRQFWFELYEVPTGSMRPTI
LEQDRILVSKTTFGLRLPFSNRSIGYTPEAITRGELVVFTVGDLPIPNADTKYFGIIPG
KKRYIKRCMGKPGDTVYFYGGKIYGIDCDGEPIFPQNTENLYHVPYISFDGTPEILTHS
EEQTDVIFNQFHTPCGKISLPQQASYGQFFYKNAWHNDTPYALKDPHNEPVSYADLFGI
KNFAMVRILTKKQAALTHVLPSPLSDTYLEIAHTPNVSYPHPHLRPFETQLIPTIEPMK
TLLPLRKEHIHLIRNNLTTSRFTVVDGYAYKYQPAPMNTSGMVRMFALPMPNIPDGCYE
FSKGDVFKINMGGFRTKLKQPHPLTQLSNSQVIDLFNCGISFHTIYIPKNPQYAPFPNR
YAFFNQGNLFVMDSPVFIDSDPALQKFIVSEEEKELQSSEDKPYIAFIDRGPPPESTEE
FVSFITNFGLKIPEGHVLVLGDNCPMSADSRDFGFVPVENLLGSPVGIFWPINRLGLLS
SNITPLSLPGYLVNGLALGAFLYCIGLWYYRKNHRLFP*
```

10_Chlamydia trachomatis 434/Bu_GI# 166154241_Catalytic Ser nucleotides 337-339

(SEQ ID NO: 125)

```
ATGACGAGCAGTTACATGAGTCGCTTATATTCCCTGAATAAGAGTCGTCGCATTCTTCA
TTCTTCCTTTAGATTGCTGAAAAGCACAAAAATGCTCTCTCATCCGGAAACTCAAAAAG
AACTACAAGAAGTCTTGAAACAGCTTGAAGAGGCTATTTTGGATCAGAATAGGGAAGAT
GCTTCCCTTTTTGCTAAGCAAGCTCAAGCCATACAAAAAGATTCCCTAAATCCAAACT
CCGAGCTACTTTTGATCTTATCTATGCTTTGACGTTTGCTGCCATTCTTGCTTTTTTAA
TCCGCCAGTTCTGGTTTGAGCTATATGAAGTTCCTACAGGATCTATGCGGCCTACTATT
CTTGAACAAGATCGTATTCTTGTTTCCAAAACAACATTTGGACTCCGGCTACCTTTTAG
TAACAGAAGTATTGGCTATACACCTGAGGCTATCACTCGAGGAGAACTGGTAGTCTTCA
CTGTTGGAGATCTTCCTATCCCTAATGCCGACACTAAGTATTTTGGAATCATCCCTGGG
AAAAAACGCTATATAAAACGGTGCATGGGTAAACCTGGAGATACCGTATATTTTTATGG
AGGGAAAATTTATGGGATCGATTGCGACGGAGAGCCCATCTTCCCCCAAAATACAGAGA
ATCTCTACCACGTCCCCTATATTTCTTTTGACGGAACTCCAGAAATTCTTACCCATTCA
GAAGAGCAAACAGATGTGATCTTTAACCAATTTCACACACCTTGTGGAAAGATTTCTCT
CCCTCAACAGGCTTCTTATGGACAATTTTTCTATAAGAATGCTTGGCATAATGATACTC
CCTATGCTTTAAAAGATCCTCATAATGAGCCTGTTAGCTATGCCGATCTATTCGGAATA
AAAAATTTTGCAATGGTTCGCATCCTTACCAAAAAACAAGCTGCTCTTACTCATGTCCT
TCCCTCTCCTCTTTCGGACACCTACCTAGAAATTGCCCACACTCCTAATGTTTCCTATC
CTCACCCTCACTTACGTCCATTTGAAACACAGCTTATTCCTACTATCGAACCTATGAAA
ACCTTGCTTCCTTTAAGGAAGGAACATATTCATTTGATTCGTAATAACCTCACAACATC
CCGTTTTACAGTTGTAGATGGATATGCTTACAAGTACCAACCTGCTCCCATGAATACCT
CAGGCATGGTCAGGATGTTTGCCCTACCTATGCCAAATATTCCTGACGGATGTTATGAA
TTTTCTAAAGGAGACGTGTTTAAAATCAATATGGGTGGCTTTCGAACAAAACTCAAACA
GCCGCATCCTTTAACGCAATTAAGCAATTCTCAGGTCATTGACTTATTTAATTGCGGCA
TTAGTTTCCACACGATCTATATTCCTAAAAACCCTCAATATGCTCCGTTCCCTAATCGC
TATGCATTTTTCAATCAAGGGAACCTGTTCGTTATGGATTCTCCAGTTTTTATTGATAG
CGATCCTGCCTTACAGAAATTCATTGTGTCTGAAGAGGAAAAAGAACTTCAATCATCTG
AAGACAAACCTTACATCGCATTTATTGACAGAGGTCCTCCTCCAGAATCTACAGAGGAA
TTTGTTTCCTTTATTACTAATTTCGGTCTTAAAATTCCGGAAGGCCACGTGCTTGTCTT
AGGAGATAATTGTCCTATGAGCGCTGATAGCCGTGATTTTGGTTTTGTTCCCGTTGAAA
ATCTTTTGGGATCTCCTGTTGGGATCTTCTGGCCTATTAATCGTCTAGGATTGTTATCT
TCCAATATAACGCCCTTGAGTTTACCTGGCTACCTCGTAAATGGATTGGCTCTAGGAGC
TTTTCTTTACTGCATAGGATTATGGTACTATCGAAAAAACCATAGGCTATTCCCTTAA
```

11_Chlamydophila pneumoniae CWL029_GI# 15618034_Catalytic Ser Residue 108

(SEQ ID NO: 126)

```
MKQHYSLNKSRHILRSTYKLLKSKKLAHSPADKKQLQELLEQLEEAIFEHDQETASDLA
QQALAFSNRYPNSFGRKTYELIKALLFAGVVAFLVRQFWFELYEVPTGSMRPTILEQDR
ILVSKTTFGLHCPFAKKPLAFNPESVTRGGLVVFTVGDLPIPDADTKYFGLIPGKKRYI
KRCMGRPGDFLYFYGGKIYGLDDAGKRIEFPSVHGLENLYHVPYISFDGTTSSHTEGQK
TIIDFKQFNQSYGRLIFPQTSMYGQFFDHKEWHQDEPNKLKDPHLSPVSYADLFGMGNY
AMVRILTEHQARTSHLLPNPGSPTKVYLEICHTANLSYPKPLLRHYEHQLSPAIQPMKT
LLPLRKEHLHLIRNNLTTSRFIVAQGCAYKYHQFKINTSGIAKAYAILLPKVPDGCYEY
SKGEAYQIGFEIRYKLKSSHPLTQLNDKQVIELFNCGINFSSIYNPVNPLQAPLPNRY
AFFNQGNLYIMDSPVFIKNDPTLQKFVTSETEKQEGSSETQPYIAFVDKGLPPEDFKEF
VEFIHNFGIQVPKGHVLVLGDNYPMSADSREFGFVPMENLLGSPLCTFWPIGRMGRLTG
VSAPTTLSGYLVSGIALATGLSLIGYVYYQKRRRLFPKKEEKNHKK*
```

11_Chlamydophila pneumoniae CWL029_GI# 15618034_Catalytic Ser nucleotides 322-324

(SEQ ID NO: 127)

```
ATGAAACAACACTATTCTCTAAATAAAAGTCGTCATATCCTTCGCAGTACTTATAAGCT
TTTAAAAAGTAAAAAACTCGCCCATTCCCCTGCAGATAAAAAGCAACTGCAAGAACTAC
TAGAACAACTAGAAGAGGCTATCTTTGAACATGATCAAGAAACTGCAAGCGACTTAGCT
CAGCAAGCATTAGCATTTTCCAACCGTTATCCTAATTCCTTCGGACGCAAAACCTATGA
GCTTATCAAGGCCCTTCTTTTTGCTGGTGTTGTAGCCTTCTTAGTTCGGCAATTTTGGT
TTGAACTTTATGAAGTGCCTACAGGATCCATGAGGCCTACAATTTTAGAACAGGATCGG
ATTCTTGTATCCAAAACAACATTTGGTCTCCATTGCCCTTTTGCTAAGAAACCACTTGC
CTTCAATCCTGAATCCGTAACTCGCGGGGGTCTTGTTGTTTCACTGTAGGCGACCTCC
CTATCCCAGATGCTGATACAAAGTACTTCGGATTGATTCCAGGAAAAAAGCGTTACATT
```

```
-continued
AAACGTTGCATGGGAAGACCTGGGGACTTCTTATATTTCTATGGAGGAAAAATTTATGG
TCTTGATGATGCAGGTAAACGCATAGAGTTTCCTTCTGTCCATGGTTTAGAAAACTTAT
ATCACGTCCCCTATATATCCTTTGATGGCACTACCAGCAGCCATACAGAAGGGCAGAAA
ACAATTATAGATTTTAAGCAGTTCAATCAAAGTTATGGTCGGCTGATTTTCCCTCAAAC
CTCCATGTATGGACAATTCTTTGACCATAAAGAATGGCATCAAGACGAGCCTAATAAAT
TAAAAGATCCTCATCTTTCGCCAGTCAGCTATGCCGATCTTTTTGGTATGGGTAACTAT
GCTATGGTGCGCATCTTAACAGAACATCAGGCACGAACATCCCATCTACTTCCGAATCC
AGGAAGTCCAACTAAAGTCTACTTAGAAATTTGCCATACAGCGAACCTTTCCTACCCAA
AGCCTCTGTTGCGTCACTATGAGCATCAGCTCTCGCCTGCGATTCAACCTATGAAGACT
TTACTTCCTTTGCGTAAGGAACATTTGCACTTAATTCGGAACAATCTTACTACCTCTCG
TTTTATTGTTGCTCAAGGATGTGCGTATAAATACCATCAATTCAAGATTAACACTTCAG
GAATTGCCAAAGCTATGCAATTCTCCTGCCCAAGGTCCCTGATGGTTGTTATGAATAT
TCTAAAGGCGAAGCGTATCAAATTGGCTTTGGAGAGATTCGTTATAAGCTAAATCTTC
TCACCCCCTTACTCAGCTCAATGATAAGCAAGTGATTGAACTTTTTAACTGCGGGATCA
ACTTTAGTTCTATTTATAATCCTGTGAATCCGCTGCAAGCACCTTTACCTAACCGTTAT
GCATTCTTTAACCAAGGGAATCTTTATATCATGGATTCTCCTGTATTTATAAAGAATGA
TCCAACTCTGCAAAATTTGTGACTTCTGAAACGGAAAAGCAAGAGGGGTCTTCAGAGA
CACAACCCTATATAGCTTTTGTTGACAAGGGACTCCCTCCAGAAGATTTTAAAGAATTC
GTGGAGTTTATACATAATTTTGGTATTCAAGTTCCTAAAGGTCATGTTCTCGTCTTGGG
AGATAACTACCCTATGAGTGCGGATAGTCGAGAATTTGGCTTTGTTCCTATGGAAAATC
TCTTAGGATCTCCTCTATGTACATTCTGGCCTATTGGACGCATGGGACGGTTAACTGGA
GTTTCTGCTCCAACAACACTCTCAGGTTATCTTGTTAGTGGGATAGCATTAGCGACGGG
TCTCTCTCTCATTGGATATGTCTACTATCAAAAACGACGCAGACTCTTTCCTAAGAAAG
AGGAGAAAAACCACAAGAAATAA 12_Staphylococcus carnosus subsp. carnosus TM300_GI#
224476066_Catalytic Ser Residue 36
                                  (SEQ ID NO: 128)
VKKEIKEWIIAIAIALVLVLVITNFIAKSYTVRGDSMYPTLKDGEKVIVNMIGFKTGGL
EKGNVIVFHATKNSDYVKRVIGMPGDSIEYKHDQLYVNGKKVKEPYLDYNEKHKSYDEI
TGSFKVKNLPNANGSNTIPKNKLLVLGDNREVSKDSRSFGLIDEDQVVGKVSLRYWPFT
SFKVNFNPDTKY*

12_Staphylococcus carnosus subsp. carnosus TM300_GI#
224476066_Catalytic Ser nucleotides 106-108
                                  (SEQ ID NO: 129)
GTGAAGAAAGAAATTAAAGAGTGGATAATAGCCATAGCAATAGCTTTGGTATTAGTTCT
AGTCATAACAAATTTCATTGCGAAATCATATACGGTTCGTGGTGATTCAATGTATCCAA
CGCTAAAAGACGGAGAAAAAGTTATCGTTAATATGATTGGATTTAAAACTGGCGGTTTA
GAAAAAGGTAATGTGATTGTATTCCACGCTACTAAAAACAGCGACTACGTTAAACGTGT
TATCGGTATGCCTGGTGACAGTATTGAATATAAACATGATCAATTGTATGTTAATGGTA
AAAAAGTGAAAGAACCTTATTTAGATTATAATGAAAAACATAAAAGCTATGATGAAATT
ACAGGTAGCTTTAAAGTGAAAAATTTACCTAATGCAAATGGTTCAAACACAATTCCTAA
AAACAAACTTCTTGTATTAGGAGATAACCGTGAAGTCAGTAAAGACAGCCGTTCATTCG
GTTTAATTGATGAAGATCAAGTTGTTGGTAAAGTAAGCTTGCGTTATTGGCCGTTTACA
TCTTTCAAAGTAAACTTTAATCCGGATACAAAATATTAA 13_Staphylococcus haemolyticus JCSC1435_GI#
70726986_Catalytic Ser Residue 36
                                  (SEQ ID NO: 130)
LKKEIVEWIVAIAVGLLLVWVMVNFVAKSYTIKGDSMDPTLKDGEHVMVNILGYKVGDI
KKGNVIVFHANQQDDYVKRVIGVPGDNVIYKNDKLYVNGKKINEPYLDYNEKRKQGEYI
TGSFETKDLLNANPKSNIIPKGKYLVLGDNREVSKDSRAFGLIDRDQIVGKVSFRFWPF
SEFKFNFNPDNEK*

13_Staphylococcus haemolyticus JCSC1435_GI#
70726986_Catalytic Ser nucleotides 106-108
                                  (SEQ ID NO: 131)
TTGAAGAAAGAAATAGTTGAATGGATTGTTGCCATAGCGGTAGGTTTATTACTTGTATG
GGTAATGGTTAACTTCGTAGCTAAATCATATACTATAAAAGGCGATTCAATGGATCCAA
CACTAAAAGATGGCGAACACGTCATGGTTAACATTCTAGGATATAAAGTTGGAGACATA
AAAAAAGGTAATGTAATCGTATTTCATGCGAATCAACAAGACGATTATGTTAAACGTGT
CATTGGTGTACCTGGCGATAACGTTATTTATAAAAATGATAAACTATATGTTAATGGTA
AAAAGATAAATGAACCTTATCTTGATTACAATGAAAAACGTAAACAAGGTGAATATATT
ACGGGTTCATTTGAAACTAAAGATTTACTAAATGCAAATCCTAAATCAAATATCATACC
AAAAGGTAAATACTTAGTTTTAGGTGATAACAGAGAAGTCAGTAAGGATAGTAGGGCGT
TTGGTTTAATTGATAGAGATCAAATTGTTGGTAAAGTATCATTTAGATTTTGGCCATTC
AGTGAATTTAAGTTTAATTTTAATCCAGATAATGAAAAATAA 14_Staphylococcus haemolyticus JCSC1435_GI#
70727661_Catalytic Ser Residue 36
                                  (SEQ ID NO: 132)
LKKEIIEWIVAIGGALLIVGIVLKFIGTSYTVSGSSMYPTFQDRNKVIVSKISKTLNHI
DNGDVVVFHEDAQRDFIKRVIGTPGDKVEYEGDQLYVNDKKVSEPYLDYNKKHKQGKYL
TGTFKTSQVNGANGKNKIPKDKYLVLGDNRQNSVDSRLAEVGLVDKQLVGKVVLRYWP
FNKWEAGFNPGTF*
```

14_Staphylococcus haemolyticus JCSC1435_GI#
70727661_Catalytic Ser nucleotides 106-108

(SEQ ID NO: 133)
```
TTGAAAAAAGAGATAATTGAATGGATTGTAGCCATTGGTGGCGCACTCTTAATTGTAGG
TATTGTATTAAAGTTTATTGGAACATCATACACAGTATCAGGTTCATCGATGTATCCAA
CTTTCCAAGATAGAAATAAAGTGATAGTTAGTAAGATTTCGAAAACATTGAACCACATT
GATAATGGTGATGTCGTTGTCTTCCATGAAGATGCACAACGTGATTTTATTAAGCGTGT
GATTGGTACGCCAGGTGATAAAGTTGAGTATGAAGGTGATCAATTATATATGTTAATGACA
AAAAGGTATCAGAGCCTTATTTAGATTATAATAAGAAGCATAAACAAGGTAAGTATTTA
ACAGGTACATTTAAAACAAGCCAAGTGAACGGAGCAAATGGTAAAAATAAAATTCCTAA
AGATAAGTATTTAGTTTTAGGTGATAACAGACAAAATAGTGTAGATAGCCGTTTGGCTG
AAGTTGGTTTAGTAGATAAAGACCAACTTGTAGGTAAAGTTGTTTTAAGATATTGGCCA
TTTAATAAATGGGAAGCAGGTTTTAACCCAGGCACATTTTAG
```

15_Staphylococcus epidermidis ATCC 12228_GI#
27467580_Catalytic Ser Residue 36

(SEQ ID NO: 134)
```
LKKEILEWIVAIAVAIALIAIITKFVGKSYSIKGDSMDPTLKDGERVVVNIIGYKLGGV
EKGNVIVFHANKKDDYVKRVIGTPGDSVEYKNDTLYVNGKKQSEPYLNYNEKRKQTEYI
TGSFKTKNLPNANPQSNVIPKGKYLVLGDNREVSKDSRSFGLIDKDQIVGKVSLRYWPF
SEFKSNFNPNNTKN*
```

15_Staphylococcus epidermidis ATCC 12228_GI#
27467580_Catalytic Ser nucleotides 106-108

(SEQ ID NO: 135)
```
TTGAAAAAAGAAATTTTAGAGTGGATTGTTGCCATAGCCGTTGCCATTGCACTTATTGC
CATAATCACTAAATTTGTCGGAAAATCATATTCTATTAAAGGTGATTCAATGGATCCTA
CATTAAAAGATGGGGAGCGTGTAGTGGTAAATATTATTGGCTATAAATTAGGTGGCGTT
GAAAAAGGAAATGTCATTGTATTTCATGCTAATAAAAAAGATGATTATGTTAAAAGAGT
TATTGGAACTCCAGGAGATAGTGTTGAATATAAAAATGATACACTCTATGTTAATGGTA
AAAAGCAATCAGAACCATACTTGAACTATAATGAAAAACGTAAGCAAACTGAGTATATC
ACAGGTAGTTTCAAAACAAAAAATTTACCAAATGCTAATCCTCAATCTAATGTTATTCC
TAAAGGTAAATATTTAGTTTTGGGGGATAACCGTGAGGTAAGTAAAGATAGTCGTTCAT
TCGGTTTAATTGACAAAGACCAAATTGTTGGAAAGGTATCGCTCAGATATTGGCCTTTC
AGTGAATTTAAATCTAACTTTAATCCAAATAACACTAAAAATTAA
```

16_Staphylococcus epidermidis ATCC 12228_GI#
27469315_Catalytic Ser Residue 36

(SEQ ID NO: 136)
```
MKKEIIEWIVAIIVAIVIVTLVQKFLFASYTVKGASMHPTFENREKVIVSRIAKTLDHI
DTGDVVIFHANAKQDYIKRLIGKPGDSVEYKKDQLYLNGKKVDEPYLSENKKHKVGEYL
TENFKSKDLKGTNGNMKIPSGKYLVLGDNRQNSIDSRMDEVGLLDKNQVVGKVVLRYWP
FNRWGGSFNPGTFPN*
```

16_Staphylococcus epidermidis ATCC 12228_GI#
27469315_Catalytic Ser nucleotides 106-108

(SEQ ID NO: 137)
```
ATGAAGAAAGAAATAATAGAATGGATTGTAGCCATAATCGTTGCAATTGTTATCGTCAC
ACTTGTGCAAAAGTTTTTATTTGCTTCTTATACAGTCAAAGGAGCGTCTATGCATCCAA
CATTTGAAAATAGAGAAAAAGTGATAGTAAGTCGTATAGCAAAAACACTTGATCATATT
GATACAGGAGATGTAGTGATTTTTCATGCTAACGCGAAGCAAGATTATATTAAGCGACT
TATTGGTAAACCAGGTGATTCAGTAGAATATAAAAAAGATCAACTATATTTAAACGGTA
AAAAAGTAGATGAGCCTTATTTAAGTGAAAATAAAAAACATAAAGTTGGAGAATATCTA
ACGGAAAACTTTAAGTCTAAAGATCTTAAGGGTACGAATGGCAATATGAAAATTCCTAG
TGGTAAATACTTGGTTTTAGGTGATAATCGTCAAAACAGTATTGACAGTCGCATGGATG
AAGTAGGTCTTTTAGATAAAAATCAAGTTGTTGGAAAAGTAGTTTTGAGATACTGGCCA
TTTAATCGGTGGGGCGGTAGTTTTAATCCTGGAACATTTCCTAACTAA
```

17_Staphylococcus hominis SK119_GI# 228474322_Catalytic Ser
Residue 36

(SEQ ID NO: 138)
```
LKKEITEWIVAIAVGLLLVWLVVTFVAKSYTIKGDSMDPTLKDGQHVMVNILGYKVGNI
KKGNVIVFHANQSDDYVKRVIGVPGDSVTYKKDQLYINGKKVNEPYLDYNEKHKQGEYI
TGSFETKDLLNAHPNSNVIPKNKYLVLGDNREVSKDSRAFGLIDKQQIVGKVSFRFWPL
NNFKFNFNPDK*
```

17_Staphylococcus hominis SK119_GI# 228474322_Catalytic Ser
nucleotides 106-108

(SEQ ID NO: 139)
```
TTGAAAAAAGAAATAACAGAATGGATTGTTGCGATAGCTGTAGGTTTATTGCTCGTATG
GCTTGTAGTCACTTTTGTTGCCAAATCCTATACAATAAAAGGTGACTCAATGGATCCAA
CATTAAAAGATGGGCAACATGTGATGGTTAACATTTTAGGTTATAAGGTAGGAAACATA
AAAAAAGGAAATGTTATTGTCTTCCATGCTAATCAATCTGATGACTATGTTAAAAGAGT
AATAGGCGTACCAGGAGATAGTGTGACATATAAAAAGATCAGCTATATATTAATGGGA
AAAAGGTAAATGAGCCTTACTTAGACTATAATGAAAAACATAAACAAGGAGAGTACATT
ACTGGATCTTTTGAAACTAAGGATCTTCTTAATGCTCATCCTAACTCTAACGTTATTCC
TAAAAATAAATACTTAGTATTAGGAGATAACCGTGAAGTTAGTAAAGATAGTAGAGCGT
TTGGATTAATAGATAAACAACAAATCGTCGGTAAAGTATCATTTAGATTTTGGCCATTA
AATAATTTTAAATTTAATTTTAATCCAGATAAGTAG
```

18_Staphylococcus lugdunensis HKU09-01_GI#
289551204_Catalytic Ser Residue 36

(SEQ ID NO: 140)

VKKELTEWLIAIAVGIILVILIINFVAKSYTIKGDSMNPTLKDGDHVLVNIIGYKVGTV
KKGNVIVFHANQKDDYVKRVIGTPGDKVYYRDDQLIINGKKVKEPYLEYNMKRKQGEYI
TGSLDIKDLAGAKHNSNVIPQHKYLVLGDNREVSKDSRAFGLIDEKQIVGKVSLRFWPL
TDFKFNFNPDMS*

18_Staphylococcus lugdunensis HKU09-01_GI#
289551204_Catalytic Ser nucleotides 106-108

(SEQ ID NO: 141)

GTGAAAAAGGAATTGACAGAATGGTTAATAGCTATAGCGGTAGGTATTATTTTAGTCAT
ACTAATCATTAATTTTGTAGCGAAATCATATACCATTAAAGGAGACTCAATGAATCCAA
CATTAAAAGATGGCGATCATGTTCTGGTCAATATTATCGGCTATAAAGTAGGCACTGTG
AAAAAGGGGAATGTCATTGTCTTCCATGCTAACCAAAAGGATGATTATGTTAAACGCGT
TATAGGCACACCAGGTGACAAAGTATACTATCGAGATGATCAACTTATTATAAACGGAA
AAAAAGTAAAAGAACCTTATCTCGAATACAATATGAAACGTAAGCAAGGAGAGTATATT
ACTGGATCTTTAGATATAAAAGATTTGGCCGGTGCAAAACATAATTCTAATGTCATACC
TCAACATAAATACCTCGTGTTAGGAGACAATCGTGAGGTAAGTAAAGATAGCCGTGCTT
TTGGCCTTATCGATGAAAAGCAAATTGTCGGTAAAGTGTCTTTAAGATTTTGGCCATTA
ACTGATTTTAAATTTAATTTTAACCCTGATATGAGCTAA

19_Staphylococcus lugdunensis HKU09-01_GI#
289551814_Catalytic Ser Residue 36

(SEQ ID NO: 142)

VKKEILEWIVSIAVALIIVGIVVKFIGVTYSVSGDSMYPTFKDREKVVVSKISKTLDHI
DNGDIVVFKEDKDRDFIKRLIGKPGDKVEYKGDQLYVNNKKIDEPYLKYNKEHKNGKYL
TGSFKSSDLQNANGETKIPKDKYLVLGDNRQNSLDSRFPQVGLIDKEQIVGKVVLRFWP
FGEWTTKFNPGTFDK*

19_Staphylococcus lugdunensis HKU09-01_GI#
289551814_Catalytic Ser nucleotides 106-108

(SEQ ID NO: 143)

GTGAAAAAAGAGATCTTAGAGTGGATTGTGTCTATAGCAGTTGCACTTATCATTGTAGG
TATAGTTGTTAAATTTATTGGAGTTACATATTCAGTTTCGGGAGATTCAATGTATCCAA
CATTTAAAGATAGAGAAAAAGTAGTAGTGAGTAAATTTCCAAAACGTTAGACCATATT
GATAATGGTGATATCGTTGTCTTTAAAGAAGATAAAGATAGAGACTTTATTAAACGTTT
AATTGGTAAACCTGGAGACAAAGTTGAGTATAAAGGTGACCAACTATATGTTAATAATA
AAAAAATTGATGAGCCTTATTTAAAATATAACAAAGAGCATAAAAATGGTAAGTATCTG
ACAGGTTCTTTCAAATCGAGTGATTTGCAAAATGCTAATGGTGAGACGAAGATTCCTAA
AGACAAATATTTAGTGTTAGGTGATAATCGTCAAAACAGTTTAGATAGTCGTTTTCCAC
AGGTAGGGCTTATTGATAAAGAACAAATTGTAGGTAAAGTTGTGTTACGTTTCTGGCCA
TTTGGTGAGTGGACAACAAAATTTAATCCTGGAACATTTGATAAGTAA

20_Streptococcus agalactiae COH1_GI# 77408620_Catalytic Ser
Residue 58

(SEQ ID NO: 144)

MKRQISSDKLSQELDRVTYQKRFWSVIKNTIYILMAVASIAILIAVLWLPVLRIYGHSM
NKTLSAGDVVFTVKGSNFKTGDVVAFYYNNKVLVKRVIAESGDWVNIDSQGDVYVNQHK
LKEPYVIHKALGNSNIKYPYQVPDKKIFVLGDNRKTSIDSRSTSVGDVSEEQIVGKISF
RIWPLGKISSIN*

20_Streptococcus agalactiae COH1_GI# 77408620_Catalytic Ser
nucleotides 172-174

(SEQ ID NO: 145)

ATGAAAAGACAGATTAGTTCAGATAAAATTATCTCAAGAACTGGATCGCGTAACTTATCA
GAAACGCTTTTGGAGTGTCATTAAAAATACCATATACATCTTGATGGCGGTTGCCTCAA
TAGCCATTTTAATTGCGGTTTTATGGTTGCCTGTATTAAGAATCTACGGACATTCAATG
AATAAGACTTTAAGTGCAGGTGATGTAGTCTTTACAGTAAAAGGTTCAAATTTTAAAAC
TGGAGACGTTGTCGCGTTTTACTACAATAATAAGGTCCTAGTCAAGCGGGTTATTGCAG
AGTCAGGAGACTGGGTTAATATTGATTCTCAAGGGGATGTTTACGTGAATCAACATAAG
TTGAAAGAACCATATGTTATTCATAAAGCACTCGGTAATAGTAATATAAAATACCCATA
TCAAGTACCTGATAAAAAAATTTTTGTATTAGGAGACAACCGAAAAACTTCAATTGATT
CTCGAAGTACTTCTGTAGGAGATGTTTCAGAAGAACAAATTGTAGGTAAAATTTCTTTC
AGAATATGGCCTCTAGGTAAGATTAGTAGTATCAATTAA

21_Streptococcus agalactiae COH1_GI# 77409453_Catalytic Ser
Residue 35

(SEQ ID NO: 146)

MKEFIKEWGVFILILSLFLLSRIFLWQFVKVDGHSMDPTLADKEQLVVLKQTKINRFDI
VVANEEEGGQKKKIVKRVIGMPGDVIKYKNDTLTINNKKTEEPYLKEYTKLFKKDKLQE
KYSYNPLFQDLAQSSTAFTTDSNGSSEFTTVVPKGHYYLVGDDRIVSKDSRAVGSFKKS
TIVGEVKFRFWPIRRFGTIN*

21_Streptococcus agalactiae COH1_GI# 77409453_Catalytic Ser
nucleotides 103-105

(SEQ ID NO: 147)

ATGAAAGAATTTATTAAAGAATGGGGTGTCTTTATCCTCATCCTCTCACTTTTTTTACT
ATCGCGTATCTTTTTATGGCAATTCGTTAAAGTTGACGGACACTCCATGGATCCAACTT
TAGCTGACAAGGAACAGCTAGTAGTTCTCAAACAAACAAAAATCAATCGATTCGATATT
GTAGTGGCTAACGAAGAAGAAGGCGGCCAAAAGAAAAAAATTGTTAAACGTGTCATTGG

```
TATGCCAGGTGATGTCATCAAATATAAAAATGACACCTTAACTATTAACAATAAAAAAA
CAGAAGAACCTTACCTCAAGGAATATACTAAATTATTTAAAAAGGATAAATTACAGGAA
AAATATTCGTATAACCCACTTTTCCAAGACCTAGCACAAAGCTCTACCGCTTTCACCAC
TGACAGCAATGGCAGCAGCGAATTTACTACTGTCGTGCCTAAAGGCCACTACTATCTTG
TTGGTGATGACCGAATTGTCTCTAAAGATAGTCGTGCCGTCGGTTCCTTCAAAAAATCA
ACGATTGTGGGAGAGGTTAAATTCCGCTTCTGGCCAATTCGTCGTTTTGGAACTATCAA
CTAA

22_Streptococcus dysgalactiae subsp. equisimilis
GGS_124_GI# 251783284_Catalytic Ser Residue 35
                                                (SEQ ID NO: 148)
MKHFIKEWGPFTLFLILFGLSRLFLWQAVKVDGHSMDPTLAHGERLIVLNQARIDRFDI
VVAREEENGQKKEIVKRVVGMPGDTIAYNDDTLYINGKKTDEPYLVNYLKEFKKDKLQK
TYAYNSLFQQLAETSDAFTTNAEGQTRFEISVPEGEYLLLGDDRIVSRDSREVGSFKKE
KLIGEVKARFWPLNKMTLFK*
22_Streptococcus dysgalactiae subsp. equisimilis
GGS_124_GI# 251783284_Catalytic Ser nucleotides 103-105
                                                (SEQ ID NO: 149)
ATGAAACATTTTATTAAAGAATGGGGCCCATTTACCCTCTTTCTCATCCTCTTCGGTTT
ATCTCGTCTTTTCTTGTGGCAAGCTGTTAAAGTTGATGGCCACTCCATGGACCCTACGT
TAGCCCATGGGGAACGTCTCATTGTTTTAAACCAAGCTAGAATTGACCGTTTCGATATT
GTCGTTGCCCGTGAGGAAGAAAATGGGCAGAAAAAAGAAATTGTCAAACGAGTTGTCGG
CATGCCAGGTGATACCATTGCCTACAACGATGATACGCTTTACATTAATGGTAAAAAAA
CAGATGAGCCTTACCTAGTTAACTACCTTAAAGAGTTCAAAAAGGACAAGCTTCAAAAG
ACTTACGCTTACAATAGTCTATTTCAGCAATTAGCTGAAACATCGGATGCCTTCACCAC
TAATGCTGAAGGTCAAACACGTTTTGAAATCAGTGTACCGAAGGTGAATACCTCCTTC
TTGGAGATGACCGAATTGTCTCACGCGACAGCCGTGAAGTTGGTAGTTTTAAAAAAGAA
AAACTTATCGGTGAAGTCAAGGCTCGCTTCTGGCCACTCAATAAAATGACTCTTTTTAA
GTAA 23_Streptococcus mitis B6_GI# 289168569_Catalytic Ser
Residue 38
                                                (SEQ ID NO: 150)
MNSFKNFLKEWGLFLLILSLLALSRIFFWSNVRVEGHSMDPTLADGEILFVVKHLPIDR
FDIVVAHEEDGNKDIVKRVIGMPGDTIRYENDKLYINDKETDEPYLADYIKRFKDDKLQ
STYSGKGFEGNKGTFFFRSIAEKAQAFTVDVNYNTNFSFTVPEGEYLLLGDDRLVSSDSR
HVGTFKAKDITGEAKFRFWPITRIGTF*

23_Streptococcus mitis B6_GI# 289168569_Catalytic Ser
nucleotides 112-114
                                                (SEQ ID NO: 151)
ATGAATTCATTTAAAAATTTCCTAAAAGAGTGGGGATTGTTCCTCCTGATTCTGTCATT
ACTAGCTTTGAGCCGTATCTTTTTTTGGAGTAATGTCCGCGTAGAAGGGCATTCCATGG
ATCCGACCCTAGCGGATGGCGAAATTCTCTTCGTTGTCAAACACCTTCCTATTGACCGT
TTTGATATCGTGGTGGCCCATGAGGAAGATGGCAATAAGGACATCGTCAAGCGCGTGAT
TGGAATGCCTGGCGATACTATCCGTTACGAAAACGATAAACTTTACATCAATGATAAAG
AGACGGACGAACCTTACCTAGCTGACTATATCAAACGTTTCAAGGATGACAAACTCCAA
AGCACCTACTCAGGCAAGGGCTTTGAAGGAAATAAAGGAACCTTCTTTAGAAGTATTGC
GGAAAAAGCTCAAGCCTTCACAGTTGATGTCAACTATAACACCAACTTTAGCTTTACTG
TTCCAGAAGGAGAATACCTTCTCCTCGGAGACGACCGCTTGGTTTCTAGCGACAGCCGT
CACGTAGGTACCTTCAAAGCAAAAGATATCACAGGGGAAGCTAAATTCCGCTTCTGGCC
AATCACCCGTATCGGAACATTTTAA 24_Streptococcus oralis ATCC 35037_GI# 293364826_Catalytic
Ser Residue 38
                                                (SEQ ID NO: 152)
MNSFKTFLKEWGVFFLIIALVGLSRIFLWSNVRVEGHSMDPTLADGEVLFVVKHLPIDR
FDIVVAHEEDGNKDIVKRVIGMPGDTIRYENDKLFINGEETNEPYLAEYLNLFKTEKLQ
NTYTGKGFEGNKGVYFRELAQKAQAFTVDVNSNTRFSFTVPQGEYLLLGDDRLVSSDSR
HVGTFKASDIKGEAKFRFWPLNRIGTF*

24_Streptococcus oralis ATCC 35037_GI# 293364826_Catalytic
Ser nucleotides 112-114
                                                (SEQ ID NO: 153)
ATGAATTCGTTTAAAACATTTCTAAAAGAATGGGGAGTTTTCTTCCTGATTATCGCACT
GGTCGGTCTTAGCCGCATCTTTCTTTGGAGCAATGTCCGTGTGGAAGGACACTCTATGG
ACCCTACCCTAGCTGACGGAGAAGTTCTCTTCGTTGTTAAACACCTCCCAATTGACCGC
TTCGACATCGTGGTTGCGCATGAGGAAGACGGAAATAAAGACATTGTCAAAAGGGTTAT
CGGTATGCCTGGTGATACCATCCGCTACGAAAATGACAAACTCTTTATCAACGGTGAAG
AAACGAATGAACCCTACCTAGCTGAGTACCTCAACTTGTTCAAAACAGAAAAGTTGCAA
AACACCTATACTGGAAAAGGATTTGAAGGCAATAAGGGAGTTTACTTTAGAGAACTTGC
TCAAAAAGCACAAGCCTTTACGGTCGATGTCAATTCCAACACCAGATTCAGCTTTACTG
TCCCTCAAGGCGAATACCTTCTCCTTGGTGACGATCGTCTAGTCTCTAGCGACAGCCGC
CATGTCGGTACCTTCAAGGCCAGCGATATCAAAGGCGAAGCAAAATTCCGTTTCTGGCC
ACTTAACCGTATCGGAACTTTTTAA 25_Streptococcus pneumoniae R6_GI# 15902408_Catalytic Ser
Residue 38
                                                (SEQ ID NO: 154)
MNLFKNFLKEWGLFLLILSLLALSRIFFWSNVRVEGHSMDPTLADGEILFVVKHLPIDR
FDIVVAHEEDGNKDIVKRVIGMPGDTIRYENDKLYINDKETDEPYLADYIKRFKDDKLQ
```

-continued

STYSGKGFEGNKGTFFRSIAQKAQAFTVDVNYNTNFSFTVPEGEYLLLGDDRLVSSDSR
HVGTFKAKDITGEAKFRFWPITRIGTF*

25_Streptococcus pneumoniae R6_GI# 15902408_Catalytic Ser
nucleotides 112-114

(SEQ ID NO: 155)
ATGAATTTATTTAAAAATTTCTTAAAAGAGTGGGGATTATTCCTCCTGATTCTGTCATT
ACTAGCTTTGAGCCGTATCTTTTTTTGGAGCAATGTTCGCGTAGAAGGACATTCCATGG
ATCCGACCCTAGCGGATGGTGAAATCCTCTTTGTTGTTAAGCACCTCCCTATTGACCGT
TTTGATATCGTGGTGGCCCATGAGGAAGATGGCAATAAGGACATCGTCAAGCGCGTGAT
TGGAATGCCTGGCGACACCATTCGTTACGAAAATGATAAACTCTACATCAATGACAAAG
AAACGGACGAGCCTTATCTAGCAGACTATATCAAACGCTTCAAGGATGACAAACTCCAA
AGCACTTACTCAGGCAAGGGCTTTGAAGGAAATAAAGGAACTTTCTTTAGAAGTATCGC
TCAAAAAGCCCAAGCCTTCACAGTTGATGTCAACTACAACACCAACTTTAGCTTTACTG
TTCCAGAAGGAGAATACCTTCTCCTCGGAGATGACCGCTTGGTTTCGAGCGACAGCCGC
CACGTAGGTACCTTCAAAGCAAAAGATATCACAGGGGAAGCTAAATTCCGCTTCTGGCC
AATCACCCGTATCGGAACATTTTAA

26_Streptococcus pyogenes M1 GAS_GI# 15675668_Catalytic Ser
Residue 35

(SEQ ID NO: 156)
MKQFIKEWGPFTLFLILFGLSRLFLWQAVKVDGHSMDPTLAHGERLIVFNQARIDRFDI
VVAQEEENGQKKEIVKRVIGLPGDTISYNDDTLYINGKKTVEPYLAEYLKQFKNDKLQK
TYAYNTLFQQLAETSDAFTTNSEGQTRFEMSVPKGEYLLLGDDRIVSRDSREVGSFKKE
NLIGEVKARFWPLNKMTVFN*

26_Streptococcus pyogenes M1 GAS_GI# 15675668_Catalytic Ser
nucleotides 103-105

(SEQ ID NO: 157)
ATGAAACAGTTTATTAAAGAATGGGGCCCATTCACTCTCTTTTTAATTCTCTTTGGTCT
ATCTCGTCTTTTTTTGTGGCAGGCTGTTAAAGTAGACGGCCATTCTATGGACCCAACTC
TAGCTCATGGCGAACGCCTTATCGTTTTTAATCAAGCTAGAATTGATCGCTTTGATATT
GTAGTTGCTCAGGAAGAAGAAAACGGACAAAAGAAAGAAATCGTAAAAAGAGTTATTGG
ATTGCCAGGCGATACCATTTCTTATAATGATGACACACTTTATATTAATGGTAAAAAAA
CAGTTGAGCCGTATTTGGCTGAGTATCTAAAACAATTTAAAAACGATAAACTCCAAAAA
ACTTACGCCTATAATACCCTATTCCAACAGTTAGCAGAAACATCTGATGCTTTTACAAC
TAATTCTGAGGGACAAACACGCTTTGAGATGAGTGTTCCAAAAGGAGAATACCTTCTTC
TTGGTGATGATCGTATTGTTTCCAGGGATAGTCGCGAAGTTGGTAGTTTCAAAAAAGAA
AACCTTATCGGTGAAGTGAAAGCTCGTTTTTGGCCACTCAATAAAATGACCGTTTTTAA
TTAG

SPase Sequences of Arylomycin-Resistant Bacteria

1_Escherichia coli str. K-12 substr. MG1655_GI#
16130493_Catalytic Ser Residues 91

(SEQ ID NO: 158)
MANMFALILVIATLVTGILWCVDKFFFAPKRRERQAAAQAAAGDSLDKATLKKVAPKPG
WLETGASVFPVLAIVLIVRSFIYEPFQIPSGSMMPTLLIGDFILVEKFAYGIKDPIYQK
TLIETGHPKRGDIVVFKYPEDPKLDYIKRAVGLPGDKVTYDPVSKELTIQPGCSSGQAC
ENALPVTYSNVEPSDFVQTFSRRNGGEATSGFFEVPKNETKENGIRLSERKETLGDVTH
RILTVPIAQDQVGMYYQQPGQQLATWIVPPGQYFMMGDNRDNSADSRYWGFVPEANLVG
RATAIWMSFDKQEGEWPTGLRLSRIGGIH*

1_Escherichia coli str. K-12 substr. MG1655_GI#
16130493_Catalytic Ser nucleotides 271-273

(SEQ ID NO: 159)
ATGGCGAATATGTTTGCCCTGATTCTGGTGATTGCCACACTGGTGACGGGCATTTTATG
GTGCGTGGATAAATTCTTTTTCGCACCTAAACGGCGGGAACGTCAGGCAGCGGCGCAGG
CGGCTGCCGGGGACTCACTGGATAAAGCAACGTTGAAAAAGGTTGCGCCGAAGCCTGGC
TGGCTGGAAACCGGTGCTTCTGTTTTTCCGGTACTGGCTATCGTATTGATTGTGCGTTC
GTTTATTTATGAACCGTTCCAGATCCCGTCAGGTTCGATGATGCCGACTCTGTTAATTG
GTGATTTTATTCTGGTAGAGAAGTTTGCTTATGGCATTAAAGATCCTATCTACCAGAAA
ACGCTGATCGAAACCGGTCATCCGAAACGCGGCGATATCGTGGTCTTTAAATATCCGGA
AGATCCAAAGCTTGATTACATCAAGCGCGCGGTGGGTTTACCGGGCGATAAAGTCACTT
ACGATCCGGTCTCAAAAGAGCTGACGATTCAACCGGGATGCAGTTCCGGCCAGGCGTGT
GAAAACGCGCTGCCGGTCACCTACTCAAACGTGGAACCGAGCGATTTCGTTCAGACCTT
CTCACGCCGTAATGGTGGGGAAGCGACCAGCGGATTCTTTGAAGTGCCGAAAAACGAAA
CCAAAGAAAATGGAATTCGTCTTTCCGAGCGTAAAGAGACACTGGGTGATGTGACGCAC
CGCATTCTGACAGTGCCGATTGCGCAGGATCAGGTGGGGATGTATTACCAGCAGCCAGG
GCAACAACTGGCAACCTGGATTGTTCCTCCGGGACAATACTTCATGATGGGCGACAACC
GCGACAACAGCGCGGACAGCCGTTACTGGGGCTTTGTGCCGGAAGCGAATCTGGTCGGT
CGGGCAACGGCTATCTGGATGAGCTTCGATAAGCAAGAAGGCGAATGGCCGACTGGTCT
GCGCCTTAAGTCGCATTGGCGGCATCCATTAA

2_Salmonella enterica subsp. enterica serovar Typhi str.
CT18_GI# 16761494_Catalytic Ser Residues 91

(SEQ ID NO: 160)
MANMFALILVIATLVTGILWCVDKFVFAPKRRARQAAAQTASGDALDNATLNKVAPKPG
WLETGASVFPVLAIVLIVRSFLYEPFQIPSGSMMPTLLIGDFILVEKFAYGIKDPIYQK
TLIETGHPKRGDIVVFKYPEDPKLDYIKRAVGLPGDKITYDPVAKEVTIQPGCSSGQAC
ENALPVTYSNVEPSDFVQTFARRNGGEATSGFFEVPLNETKENGIRLTERKETLGDVTH
RILMVPIAQDQLGMYYQQPGQPLATWVVPPGQYFMMGDNRDNSADSRYWGFVPEANLVG
KAVAIWMSFDKQEGEWPTGVRLSRIGGIH*

2_Salmonella enterica subsp. *enterica* serovar *Typhi* str.
CT18_GI# 16761494_Catalytic Ser nucleotides 271-273
(SEQ ID NO: 161)
ATGGCGAACATGTTTGCCCTGATTCTGGTGATAGCCACACTGGTGACGGGCATTTTATG
GTGCGTTGATAAGTTTGTTTTCGCGCCAAAACGTCGGGCGCGCCAGGCTGCCGCGCAAA
CGGCGTCGGGAGATGCGCTGGATAACGCTACGCTCAATAAAGTGGCGCCTAAGCCGGGC
TGGCTGGAGACCGGGGCGTCGGTTTTCCCGGTTCTGGCGATCGTTCTGATCGTTCGTTC
ATTTCTTTATGAACCCTTTCAGATCCCGTCAGGCTCAATGATGCCGACACTGCTTATCG
GCGATTTTATTCTGGTGGAAAAATTTGCCTACGGCATTAAAGATCCGATCTACCAGAAA
ACCCTGATTGAAACCGGTCATCCAAAGCGCGGGGATATTGTGGTATTTAAATATCCGGA
AGATCCTAAGTTAGATTACATCAAACGCGCCGTCGGTTTGCCGGGCGATAAAATCACTT
ATGATCCGGTTGCGAAAGAGGTGACGATTCAGCCTGGCTGTAGCTCCGGTCAGGCGTGC
GAAAATGCGCTGCCGGTTACCTACTCTAACGTTGAGCCGAGCGATTTTGTACAGACCTT
TGCCCGCCGTAACGGCGGAGAAGCGACCAGCGGTTTCTTTGAGGTTCCGCTAAACGAGA
CAAAAGAAAACGGCATTCGCCTGACCGAACGTAAAGAGACGTTAGGCGATGTGACCCAC
CGCATCCTGATGGTGCCGATAGCCCAGGATCAGTTGGGCATGTATTACCAACAGCCAGG
ACAACCGCTGGCGACCTGGGTTGTACCGCCGGGGCAATATTTCATGATGGGCGACAACC
GCGATAACAGCGCGGATAGTCGTTACTGGGGATTTGTTCCGGAAGCGAATCTGGTCGGT
AAAGCGGTCGCTATCTGGATGAGCTTTGACAAGCAGGAAGGGGAGTGGCCGACAGGCGT
ACGCCTGAGTCGTATCGGCGGTATTCACTAA 3_Klebsiella pneumoniae subsp. *pneumoniae* MGH 78578_GI#
152971424_Catalytic Ser Residues 91
(SEQ ID NO: 162)
MANMFALILVIATLVTGVLWCLDKFIFAPKRRERQAAAQAATGEQLDKKTLKKVGPKPG
WLETGASVFPVLAIVLVVRSFIYEPFQIPSGSMMPTLLIGDFILVEKFAYGIKDPIYQK
TLIETGHPKRGDIVVFKYPEDPRLDYIKRAVGLPGDKVTYDPVAKQVTIQPGCSSGQAC
GNALPVTYSNVEPSDFVQTFSRSNGGEASSGFWQLPKGETKADGIRLTERQETLGDVTH
RILMVPIAQDQVGMYYHQSGLPLATWIVPPGQYFMMGDNRDNSADSRYWGFVPEANLVG
KATAIWMSFEKQEGEWPTGVRLSRIGGIH*

3_Klebsiella pneumoniae subsp. *pneumoniae* MGH 78578_GI#
152971424_Catalytic Ser nucleotides 271-273
(SEQ ID NO: 163)
ATGGCGAACATGTTTGCCCTGATCCTGGTGATTGCAACCCTGGTGACGGGCGTTTTATG
GTGCCTGGACAAGTTCATTTTTGCACCGAAACGTCGTGAACGTCAGGCCGCTGCTCAGG
CAGCGACCGGCGAGCAACTGGACAAGAAGACGCTGAAGAAAGTCGGCCCGAAACCGGGC
TGGCTGGAAACCGGCGCATCGGTTTTCCCGGTGCTGGCGATCGTTCTGGTGGTACGTTC
ATTTATTTATGAGCCTTTCCAGATCCCCTTCAGGTTCGATGATGCCAACGCTGCTCATCG
GCGATTTTATTCTGGTGGAGAAATTTGCCTACGGCATTAAAGATCCTATCTACCAGAAA
ACGCTGATCGAGACCGGCCATCCGAAGCGCGGCGACATCGTGGTATTTAAATATCCGGA
AGACCCGCGTCTGGACTACATTAAGCGCGCGGTGGGGTTACCGGGTGATAAGGTCACCT
ACGATCCGGTTGCCAAACAGGTCACTATTCAGCCGGGCTGCAGTTCCGGACAGGCCTGC
GGCAACGCGCTGCCGGTGACCTATTCCAACGTGGAGCCGAGCGATTTTGTTCAGACCTT
CTCCCGCAGCAACGGCGGCGAAGCGAGCAGCGGTTTCTGGCAGTTGCCGAAGGGCGAAA
CCAAAGCCGACGGCATTCGTCTTACCGAGCGTCAGGAGACATTGGGCGACGTGACGCAC
CGAATTCTGATGGTGCCGATTGCCCAGGATCAGGTTGGGATGTACTACCATCAGTCCGG
TCTGCCGCTGGCCACCTGGATTGTGCCGCCCGGTCAGTACTTCATGATGGGCGACAACC
GGGATAACAGCGCCGACAGCCGGTACTGGGGCTTTGTGCCGGAAGCCAACCTGGTCGGA
AAAGCAACCGCTATCTGGATGAGTTTTGAAAAGCAGGAAGGTGAATGGCCGACCGGCGT
GCGGTTATCGCGCATTGGTGGAATTCATTAA 4_Mycobacterium tuberculosis H37Rv_GI# 15610040_Catalytic
Ser Residues 96
(SEQ ID NO: 164)
VTETTDSPSERQPGPAEPELSSRDPDIAGQVFDAAPFDAAPDADSEGDSKAAKTDEPRP
AKRSTLREFAVLAVIAVVLYYVMLTFVARPYLIPSESMEPTLHGCSTCVGDRIMVDKLS
YRFGSPQPGDVIVFRGPPSWNVGYKSIRSHNVAVRWVQNALSFIGFVPPDENDLVKRVI
AVGGGQTVQCRSDTGLTVNGRPLKEPYLDPATMMADPSIYPCLGSEFGPVTVPPGRVWVM
GDNRTHSADSRAHCPLLCTDDPLPGTVPVANVIGKARLIVWPPSRWGVVRSVNPQQGR*

4_Mycobacterium tuberculosis H37Rv_GI# 15610040_Catalytic
Ser nucleotides 286-288
(SEQ ID NO: 165)
GTGACCGAAACCACGGACTCCCCATCGGAGCGCCAGCCGGGTCCGGCAGAGCCGGAGCT
CTCCTCCCGGGACCCGGACATTGCCGGCCAGGTCTTCGACGCAGCCCCGTTCGACGCAG
CCCCGGATGCGGACTCCGAAGGCGACTCCAAGGCGGCCAAAACGGACGAGCCGCGGCCC
GCGAAGCGATCAACGCTGCGGGAGTTCGCGGTGCTGGCGGTGATTGCTGTGGTGCTCTA
CTACGTCATGCTGACGTTTGTCGCGCGCCCTTATCTGATTCCGTCGGAATCGATGGAAC
CCACGTTGCACGGGTGTTCGACGTGCGTCGGCGACCGCATCATGGTGGACAAACTCAGC
TACCGCTTCGGCTCACCGCAACCTGGCGACGTCATCGTCTTCAGGGGACCGCCGTCGTG
GAACGTTGGTTACAAGTCGATCCGTTCGCACAACGTCGCCGTGCGCTGGGTGCAGAACG
CGTTGTCGTTCATCGGTTTCGTGCCTCCCGACGAGAACGACCTGGTCAAGCGTGTCATC
GCGGTCGGCGGACAGACGGTTCAATGCCGGTCCGACACCGGCCTGACGGTCAACGGCAG
GCCACTGAAGGAGCCATACCTGGATCCGGCCACCATGATGGCCGACCCGTCGATATACC
CGTGCCTGGGCAGCGAGTTCGGGCCGGTCACCGTCCCGCCCGGGCGTGTCTGGGTGATG
GGCGACAACCGCACCCATTCGGCGGATTCCCGCGCTCACTGCCCGTTGCTATGTACTGA
CGATCCGCTACCGGGGACCGTGCCGGTGGCCAACGTCATCGGTAAGGCCAGGTTGATCG
TGTGGCCGCCGTCGCGTTGGGGTGTTGTGCGTTCGGTGAATCCCCAGCAAGGTCGGTAG 5_Yersinia pestis KIM 10_GI# 22123922_Catalytic Ser
Residues 98

(SEQ ID NO: 166)
MANMFALILAIATLLTGIIWCFERFKWGPARQAKIAAVNAQTAEIKAQTGCAVDNKTLA
QAAKQPGWIETCASIFPVLALVFIVRSFIYEPFQIPSGSMMPTLLIGDFILVEKFAYGI
KDPITQTTLIPTGKPNRGDIAVFKYPLDPRLDYIKRVVGLPGDRVIYNPISKEVTVQPS
CNTGTSCDSALAITYSTSEPSEFVQTFRYSGNGESSAGFFPIPLNQAVPDGGVRLRERT
ESLGPVAHHILTVPGRQDPLGSYYQQPDQPLGVWVVPEGHYFMMGDNRDNSADSRFWGF
VPERNLVGKATAIWMSFEKQEGEWPTGVRLSRIGGIH*

5_Yersinia pestis KIM 10_GI# 22123922_Catalytic Ser nucleotides 292-294

(SEQ ID NO: 167)

ATGGCTAACATGTTTGCTTTGATTCTGGCAATAGCAACGCTGTTGACGGGGATTATCTG
GTGCTTCGAGCGGTTTAAATGGGGGCCAGCCCGTCAGGCAAAAATTGCGGCAGTTAATG
CACAAACTGCGGAAATCAAGGCCCAAACCGGGTGTGCCGTAGATAATAAAACCTTAGCC
CAAGCTGCAAAGCAACCGGGTTGGATCGAGACATGTGCCTCTATCTTCCCGGTGCTGGC
CTTGGTCTTTATCGTGCGTTCGTTTATTTACGAGCCTTTCCAGATCCCTTCTGGTTCGA
TGATGCCAACGCTGCTTATCGGTGATTTTATTTTGGTTGAGAAATTTGCTTATGGGATT
AAAGATCCCATTACTCAGACCACATTAATTCCAACAGGTAAGCCAAACCGCGGTGACAT
TGCGGTGTTTAAATATCCGTTGGATCCACGTTTGGATTATATCAAGCGTGTGGTGGGGC
TGCCGGGGGATCGGGTAATTTATAACCCGATAAGTAAAGAAGTCACGGTACAACCGTCA
TGTAATACCGGTACTTCTTGTGATAGTGCGTTGGCCATCACTTACAGCACGTCTGAGCC
AAGTGAGTTTGTGCAGACATTCCGTTATAGCGGTAATGGCGAAAGCTCCGCAGGGTTCT
TCCCAATCCCGCTAAATCAGGCAGTACCTGATGGCGGTGTCCGGTTACGTGAGCGTACT
GAAAGCCTCGGCCCGGTAGCGCATCACATTCTGACCGTCCCAGGGCGGCAGGATCCGTT
AGGCTCTTATTATCAGCAACCCGATCAACCGTTAGGGGTTTGGGTGGTACCGGAAGGCC
ATTACTTTATGATGGGTGATAACCGGGATAACAGTGCAGATAGCCGCTTCTGGGGTTTT
GTACCAGAACGTAATCTGGTAGGTAAGGCTACGGCTATTTGGATGAGTTTTGAAAAGCA
AGAAGGTGAATGGCCAACGGGTGTGCGTTTAAGCCGAATTGGTGGAATTCACTAA

6_Staphylococcus aureus subsp. *aureus* COL_GI# 57651657_Catalytic Ser Residues 39

(SEQ ID NO: 168)

VSKLKKEILEWIISIAVAFVILFIVGKFIVTPYTIKGESMDPTLKDGERVAVNIVGYKT
GGLEKGNVVVFHANKNDDYVKRVIGVPGDKVEYKNDTLYVNGKKQDEPYLNYNLKHKQG
DYITGTFQVKDLPNANPKSNVIPKGKYLVLGDNREVSKDSRAFGLIDEDQIVGKVSFRF
WPFSEFKHNFNPENTKN*

6_Staphylococcus aureus subsp. *aureus* COL_GI# 57651657_Catalytic Ser nucleotides 115-117

(SEQ ID NO: 169)

GTGTCAAAATTGAAAAAAGAAATATTGGAATGGATTATTTCAATTGCAGTCGCTTTTGT
CATTTTATTTATAGTAGGTAAATTTATTGTTACGCCATATACAATTAAAGGTGAATCAA
TGGATCCAACTTTGAAAGATGGCGAGCGAGTAGCTGTAAACATTGTTGGATATAAAACA
GGTGGTTTGGAAAAAGGTAATGTAGTTGTCTTCCATGCAAACAAAAATGATGACTATGT
TAAACGTGTCATCGGTGTTCCTGGTGATAAAGTAGAATACAAAAATGATACATTATATG
TCAATGGTAAAAAACAAGATGAACCATATTTAAACTACAATTTAAAACATAAACAAGGT
GATTACATTACTGGGACTTTCCAAGTTAAAGATTTACCGAATGCGAATCCTAAATCAAA
TGTCATTCCAAAAGGTAAATATTTAGTGCTTGGAGATAATCGTGAAGTAAGTAAAGATA
GCCGTGCGTTTGGCCTCATTGATGAAGACCAAATTGTTGGTAAAGTTTCATTTAGGTTC
TGGCCATTTAGTGAATTTAAACATAATTTCAATCCTGAAAATACTAAAAATTAA

7_Vibrio cholerae O1 biovar El Tor str. N16961_GI# 15642458_Catalytic Ser Residues 90

(SEQ ID NO: 170)

MANTFSLILVIVTLVTGIVWTLEKLVWAKKRQQKQAHLQAQTPDMPASALDKVVAQPWW
IENSVSIFPVIAFVLVLRSFIYEPFQIPSGSMMPTLLVGDFILVEKYAYGLKDPVWRTQ
LVETGKPERGDIVVFKYPVNPEIDYIKRVVGMPGDTVRYSAGKELCIQHQGESECQAVK
LSNVQESEFYQNEIPLIQLNEQLGKVEHNILVNPLSIDNVANYRPRSGVNEWVVPQGHY
FVMGDNRDNSADSRFWGFVPEQNLVGKAVAIWISFEFERAEDSVLPRWIPTGVRFNRVG
GIH*

7_Vibrio cholerae O1 biovar El Tor str. N16961_GI# 15642458_Catalytic Ser nucleotides 268-270

(SEQ ID NO: 171)

ATGGCGAACACATTCTCACTGATTTTGGTGATCGTAACTCTGGTCACCGGTATCGTCTG
GACACTGGAAAAGCTGGTGTGGGCGAAAAAACGCCAACAGAAACAAGCTCATTTACAGG
CGCAAACGCCCGATATGCCAGCCTCAGCGCTGGATAAAGTCGTGGCTCAGCCGTGGTGG
ATTGAAAACAGTGTCTCGATTTTCCCTGTTATTGCTTTTGTGCTGGTACTGCGCTCGTT
CATTTATGAACCGTTCCAAATTCCATCCGGTTCGATGATGCCGACTCTGCTGGTCGGGG
ATTTTATTCTGGTTGAGAAATACGCTTACGGCTTGAAAGATCCTGTATGGCGCACTCAG
TTAGTGGAAACGGGTAAACCTGAGCGTGGTGATATTGTGGTGTTCAAATACCCAGTGAA
CCCTGAGATCGACTACATCAAACGTGTGGTGGGGATGCCCGGAGATACCGTACGTTACA
GCGCAGGTAAAGAGCTGTGTATTCAGCACCAAGGCGAGAGCGAATGCCAAGCAGTTAAA
CTCTCTAACGTGCAAGAGAGCGAGTTTTACCAAAATGAGATCCCCCTGATCCAGCTGAA
CGAACAGCTAGGTAAGGTTGAGCACAATATTTTGGTTAACCCATTGAGCATTGATAACG
TGGCGAATTATCGCCCACGCAGTGGCGTGAATGAATGGGTTGTACCACAAGGGCACTAT
TTTGTGATGGGTGATAACCGTGACAACAGTGCTGACAGCCGTTTCTGGGGCTTTGTGCC
AGAGCAGAATCTGGTCGGAAAAGCTGTGGCTATCTGGATCAGTTTCGAGTTTGAACGCG

-continued

CTGAAGACAGCGTACTTCCACGCTGGATTCCTACCGGAGTACGATTCAATCGTGTTGGT
GGGATCCACTAA

8_Haemophilus influenzae 86-028NP_GI# 68248566_Catalytic
Ser Residues 115

(SEQ ID NO: 172)

MSNLFFVILLAVGFGVWKVLDYFQLPNTFSILLLILTALSGVLWCYHRFVVLPKRHRQV
ARAEQRSGKTLSEEEKAKIEPISEASEFLSSLFPVLAVVFLVRSFLFEPFQIPSGSMES
TLRVGDFLVVNKYAYGVKDPIFQNTIIEGEKPQRGDVIVFKAPQQALIRTGLGATRAAF
AENLALSSKDNMSGVDYIKRIVGKGGDRIIFDVEQKTLKIVYGKDGKPCEVDCETKAFE
YTQNPTNPAFPNELELTEKGDVTHNVLIGEYRRYSDLEFFPQEGMQTAEWLVPEGQYFV
MGDHRDHSDDSRFWGFVPEKNIVGKATYIWMSLEKEANEWPTGFRFDRFFTAIK*

8_Haemophilus influenzae 86-028NP_GI# 68248566_Catalytic
Ser nucleotides 343-345

(SEQ ID NO: 173)

ATGTCAAATTTATTTTTTGTGATTTTATTGGCTGTCGGCTTTGGTGTGTGGAAAGTTTT
AGATTATTTTCAGTTGCCAAATACTTTTAGTATTTTGTTACTAATTTTGACCGCACTTT
CTGGCGTATTATGGTGTTATCATCGTTTTGTGGTGCTGCCAAAACGTCATCGTCAAGTG
GCACGTGCAGAACAACGTTCTGGTAAAACCTTAAGTGAGGAAGAAAAAGCCAAAATTGA
ACCGATTTCTGAGGCTTCAGAATTTTTGTCTTCACTTTTTCCTGTGCTTGCAGTGGTAT
TTTTGGTTCGTTCTTTTTTGTTTGAACCGTTTCAAATTCCCTCTGGCTCAATGGAGTCC
ACTTTACGCGTTGGCGATTTTTTAGTTGTGAATAAATATGCTTATGGTGTGAAAGATCC
GATTTTCCAAAACACCATTATTGAGGGCGAAAAACCACAACGTGGCGATGTGATTGTGT
TTAAAGCACCACAACAAGCGTTAATTCGTACTGGTCTTGGGGCTACTCGAGCGGCTTTT
GCAGAAAATTTAGCGTTAAGTTCAAAAGATAATATGTCTGGTGTGGATTATATTAAGCG
TATTGTTGGAAAGGGCGGAGATCGCATCATTTTTGATGTGGAACAAAAAACATTAAAAA
TTGTATATGGCAAAGATGGTAAACCTTGTGAAGTTGATTGCGAAACCAAGGCGTTTGAA
TATACACAAAATCCAACAAATCCTGCTTTTCCGAATGAATTAGAATTGACTGAAAAAGG
CGATGTAACACATAACGTGTTAATTGGTGAGTATCGTCGTTATTCAGACCTTGAATTTT
TCCCACAAGAGGGAATGCAAACTGCAGAATGGCTTGTGCCAGAGGGGCAGTATTTTGTG
ATGGGGGATCATCGCGATCACAGCGATGACAGTCGTTTTTGGGGCTTTGTGCCTGAAAA
AAATATTGTGGGAAAGCCACTTATATTTGGATGAGCTTAGAAAAAGAAGCGAATGAAT
GGCCAACAGGTTTCCGTTTTGATCGCTTCTTTACAGCAATAAAATAA

9_Pseudomonas aeruginosa PA01_GI# 15595965_Catalytic Ser
Residues 90

(SEQ ID NO: 174)

MTLNFPLLLVIAVAVCGALALVDLVLFAPRRRAAISSYEGQVNEPDPAVLEKLNKEPLL
VEYGKSFFPVLFIVLVLRSFLVEPFQIPSGSMKPTLEVGDFILVNKFAYGIRLPVLDTK
VIPIGDPQRGDVMVFRYPSEPNINYIKRVVGLPGDTVRYTKEKRLYVNGELVAEKLVGE
EPGTLGSVTLYQEKLGQAEHLIRKEMSRYRIEPDRQWTIPAGHYFMMGDNRDNSNDSRY
WNDPKIPKDLLGMVPDRNIVGKAFAVWMSWPDPKMSNLPNFSRVGVIH*

9_Pseudomonas aeruginosa PA01_GI# 15595965_Catalytic Ser
nucleotides 268-270

(SEQ ID NO: 175)

ATGACACTCAATTTCCCGTTGTTGCTGGTCATCGCCGTGGCTGTATGCGGCGCCCTGGC
CCTGGTCGACCTGGTGCTGTTCGCGCCGCGTCGGCGGGCCGCGATCTCTTCCTACGAAG
GGCAGGTGAACGAGCCCGATCCGGCAGTGCTGGAGAAGCTCAACAAGGAACCGCTGCTG
GTGGAGTACGGCAAGTCGTTCTTCCCGGTGCTGTTCATCGTGCTGGTGCTGCGTTCCTT
CCTGGTCGAGCCGTTCCAGATTCCCTCGGGGTCGATGAAACCTACCCTCGAGGTCGGCG
ATTTCATCCTGGTCAACAAGTTCGCCTACGGTATCCGCCTGCCGGTGCTGGACACCAAG
GTGATCCCGATCGGTGATCCGCAGCGCGGCGATGTCATGGTGTTCCGCTATCCCAGCGA
ACCGAACATCAACTACATCAAGCGCGTGGTCGGCCTGCCCGGCGACACCGTGCGCTACA
CCAAGGAAAAGCGCCTGTACGTCAACGGCGAGCTGGTGGCGGAGAAACTGGTCGGCGAG
GAACCGGGCACCCTGGGCAGCGTGACCCTGTACCAGGAGAAGCTGGGCCAGGCCGAGCA
CCTGATCCGCAAGGAAATGAGCCGCTATCGCATCGAGCCCGACCGCCAGTGGACCATTC
CCGCCGGCCACTACTTCATGATGGGCGACAACCGCGACAACTCCAACGACAGCCGCTAC
TGGAACGATCCGAAGATCCCCAAGGATCTGCTGGGCATGGTTCCGGACCGCAATATCGT
CGGCAAGGCCTTCGCCGTGTGGATGAGCTGGCCCGATCCGAAGATGAGCAACCTGCCGA
ACTTCTCCCGGGTCGGCGTGATTCACTGA

10_Acinetobacter baumannii ATCC 19606_GI#
260556580_Catalytic Ser Residues 72

(SEQ ID NO: 176)

VDFDFNLILVPVTLILFAVWLLDKLVFKQRANKGRENENFVITWAYDFWPVLAVVLVLR
SFLYEPFNIPSDSMVPTLETGDFILVNKFDYGVRLPIVNKKVIDVGEPKRGDVIVFRYP
PQPTISYIKRVIGLPGDHIVYDHGQLIINGQKIPKVPTQFSREKDALDTPTSIYHKETI
GDHTFTMRELEGVNVARQAPFINYVDNGKYANQDGLYWEVTVPKGHYFAMGDNRDQSAD
SRFWGFVPEENLTGRAFYVWMHKEPGFHLPSFNRNGKID*

10_Acinetobacter baumannii ATCC 19606_GI#
260556580_Catalytic Ser nucleotides 214-216

(SEQ ID NO: 177)

GTGGATTTTGATTTTAATTTAATTCTTGTTCCTGTTACGCTGATTTTATTTGCAGTGTG
GTTGCTAGATAAGCTTGTTTTTAAACAGCGTGCAAATAAGGGCGAGAGAACGAAAATT
TTGTTATTACATGGGCCTATGACTTTTGGCCGGTTTTAGCTGTTGTGCTTGTACTTCGC
TCATTTCTTTATGAACCATTTAATATTCCATCAGACTCTATGGTTCCGACCTTAGAGAC
TGGCGATTTTATTTTAGTTAATAAATTTGACTATGGTGTCCGTTTACCTATCGTCAATA
AAAAAGTGATTGATGTCGGTGAACCGAAACGTGGTGATGTCATTGTATTCCGTTATCCA

-continued

CCACAACCTACTATTAGTTATATTAAACGTGTAATTGGCTTACCTGGTGACCATATTGT
TTATGATCATGGACAATTGATTATTAATGGTCAAAAAATTCCTAAAGTACCAACACAGT
TTAGTCGCGAAAAAGATGCTTTAGATACACCAACTTCTATTTATCATAAAGAAACAATT
GGTGATCATACTTTTACGATGCGTGAGCTTGAAGGCGTAAATGTTGCGCGTCAGGCGCC
ATTTATCAACTATGTTGATAATGGTAAATATGCAAACCAAGACGGTTTATATTGGGAAG
TAACAGTTCCGAAAGGACATTACTTTGCAATGGGGGATAACCGTGATCAAAGTGCTGAC
AGTCGTTTCTGGGGCTTCGTACCTGAAGAAAATTTAACAGGCCGAGCTTTCTATGTCTG
GATGCATAAAGAACCTGGTTTCCACCTGCCAAGCTTTAACCGAAATGGGAAAATAGATT
AA

11_Bacillus anthracis str. Ames_GI# 30263049_Catalytic Ser
Residues 40
(SEQ ID NO: 178)
MKENTKKELFSWAKTIGFTLVLIAIIRGVLFTPSLVQGESMMPTLENNERVLVNKIGYS
ISGLERFDIIVFPHGKEGYDLVKRVIGLPGDTVEYKNDVLYVNGKAMEEPYLKEFKEKAA
GRVLTPDFTLEQITGKTKVPEGQVFVLGDNREVSKDGRMFGFISEDEIVGKGQAVFWPL
KQVRAL*

11_Bacillus anthracis str. Ames_GI# 30263049_Catalytic Ser
nucleotides 118-120
(SEQ ID NO: 179)
ATGAAGGAAAATACGAAGAAAGAATTATTCTCATGGGCGAAAACGATAGGATTTACCCT
TGTATTAATCGCAATTATTCGCGGTGTTTTATTTACACCGTCATTAGTACAAGGCGAAT
CGATGATGCCGACTTTAGAAAATAACGAACGAGTTCTCGTCAATAAGATTGGTTATAGT
ATAAGTGGATTAGAACGCTTTGATATTATCGTTTTCCATGGAAAAGAAGGATATGATTT
AGTAAAACGAGTAATTGGTTTACCAGGCGATACAGTTGAGTATAAAAATGATGTTTTAT
ATGTAAACGGCAAAGCGATGGAAGAACCATATTTAAAAGAGTTTAAAGAAAAAGCAGCA
GGTCGTGTATTAACTCCAGACTTTACGTTAGAACAAATTACAGGAAAAACGAAAGTGCC
AGAAGGCCAAGTGTTTGTATTAGGTGATAATCGTGAAGTTTCTAAAGACGGTCGTATGT
TTGGATTTATTTCAGAAGATGAAATTGTCGGAAAAGGACAAGCTGTTTTCTGGCCGTTG
AAACAAGTAAGAGCGCTATAA 12_Neisseria meningitidis MC58_GI# 15676663_Catalytic Ser
Residues 123
(SEQ ID NO: 180)
MNTMLMSGAAAALLAGIILYFKSDKKRQENGEWSSGLEYAYILTAVGVFAALSLFMSFT
AVFLIFVVLCGTAWGVYKYRLKTHPEISESSHFGDYFGSFFPTVLVLFLIRSFIAEPFQ
IPSSSMRPGLIKGDFILVGKFSYGLRVPVLNNIFIPTGKIERGDVVVFNYPLQPEMTYI
KRIVGIPGDVVEYRDKILTVNGKPTSDIPDGTYRYPDDTDPSEIHNTDMFRSGLDGKSF
NILKKEGQPAVSLPVLGKYTSDIMSENGYSIEQSGLEHCQYADDGSGFVCKVPEGRYFA
MGDNRDNSADSRYWGFVDDKLVVGKAMFILMNFGDFGRSGTAIR*

12_Neisseria meningitidis MC58_GI# 15676663_Catalytic Ser
nucleotides 367-369
(SEQ ID NO: 181)
ATGAACACAATGCTAATGTCGGGCGCGGCTGCCGCGCTGCTTGCCGGCATCATCCTTTA
TTTCAAAAGCGACAAGAAGCGGCAGGAAAACGGGGAATGGAGTTCCGGCCTTGAATACG
CCTATATCCTGACAGCGGTCGGCGTGTTTGCCGCTTTGTCCCTGTTTATGAGCTTTACC
GCCGTTTTCCTGATTTTCGTTGTATTGTGCGGTACGGCTTGGGGGGTATATAAATACCG
CCTGAAGACTCATCCCGAAATCTCGGAAAGCAGCCACTTCGGCGATTATTTCGGCAGTT
TCTTCCCTACCGTTTTGGTATTGTTCCTCATCCGGTCGTTTATCGCCGAACCGTTCCAA
ATCCCGTCCAGCTCGATGCGCCCGGGCCTGATCAAGGGCGATTTCATTTTGGTCGGCAA
ATTTTCCTACGGCCTGCGCGTACCCGTTTTAAACAATATATTTATTCCTACAGGCAAAA
TCGAACGGGGCGATGTCGTTGTTTTTAATTATCCTCTGCAGCCGGAGATGACCTACATC
AAGCGTATTGTCGGCATTCCGGGCGATGTGGTCGAATATCGGGATAAGATTTTGACGGT
AAATGGCAAACCCACTTCCGACATTCCTGACGGCACATACCGTTATCCCGACGACACCG
ACCCTTCCGAAATCCACAACCGGATATGTTCCGCAGCGGTCTAGACGGCAAATCCTTC
AATATTCTGAAAAAGAAGGACAGCCTGCCGTTTCCCTGCCCGTATTGGGCAAATATAC
CTCCGATATTATGTCTGAAAACGGATATTCCATAGAGCAAAGCGGTTTGAACACTGCC
AATATGCCGACGACGGCAGCGGTTTCGTGTGCAAAGTTCCCGAAGGACGCTATTTCGCT
ATGGGCGACAACCGCGACAACAGTGCCGATTCGCGCTACTGGGGATTTGTGGATGACAA
GCTGGTTGTCGGCAAGGCAATGTTCATTTTGATGAACTTCGGCGATTTCGGCAGGTCCG
GTACGGCAATCCGTTAG 13_Bacillus anthracis str. Ames_GI# 30263037_Catalytic Ser
Residues 35
(SEQ ID NO: 182)
MKQEIKRGWGKYILFVFVLVVAYHSFTLCKVEGKSMQPTLYEEDYVFVNKAAVHFSDLE
HGEIVIIKEEDESKYYVKRVIGLPGDVINITNGSVYVNDKKQEEPYTNKDLFNNTQVFY
NFQKTKIPPNKLFVMGDNRELSRDSRNGLGYIEEDNIIGKVEFVYYPFSKMKIIE*

13_Bacillus anthracis str. Ames_GI# 30263037_Catalytic Ser
nucleotides 103-105
(SEQ ID NO: 183)
ATGAAACAGGAGATTAAAAGAGGTTGGGGGAAATATATACTCTTCGTGTTTGTTTTGGT
AGTAGCTTATCATTCTTTTACTTTATGTAAAGTGGAAGGGAAATCAATGCAACCGACTT
TATATGAAGAAGACTACGTATTTGTAAATAAAGCAGCAGTACATTTTTCCGATTTAGAG
CATGGAGAAATTGTCATTATAAAGGAAGAGGATGAATCGAAATATTATGTAAAACGAGT
AATAGGACTTCCTGGTGACGTAATTAACATAACGAATGGATCTGTATATGTAAATGATA
AAAAACAAGAAGAACCGTATACAAATAAAGATTTATTCAATAATACGCAAGTGTTTTAT
AACTTTCAAAAGACAAAAATCCCACCAAATAAATTATTTGTAATGGGAGATAATCGTGA 14_Streptococcus mutans UA159_GI# 24380230_Catalytic Ser
Residues 35

(SEQ ID NO: 184)

MKRFLKEWGLFLVIIFALLLPRLFIWFPVQVDGHSMDPTLANGEHLIVVRTTSIKHFDI
VVAAEGNKNIVKRVIGMPGDTITYENDMLSINGKKVNETYLKQYKDKFAKDKLQKTYAY
NQYFQELASQSTAFTTDEQGNASFTIKVPKGRYLLLGDDRIVSKDSRHVGTFAKNKIVG
EVKFRFWPLNAIRFISNK*

14_Streptococcus mutans UA159_GI# 24380230_Catalytic Ser
nucleotides 103-105

(SEQ ID NO: 185)

ATGAAAAGATTTTAAAAGAATGGGGCCTTTTCTTGGTCATCATTTTCGCATTGCTACT
CCCGCGTCTCTTTATCTGGTTTCCTGTCCAAGTAGATGGACATTCAATGGATCCTACCT
TAGCCAATGGGGAGCATCTCATTGTCGTCAGGACAACTTCTATCAAACATTTTGACATT
GTTGTTGCTGCTGAAGGCAATAAAAATATTGTCAAACGTGTGATTGGCATGCCCGGTGA
TACCATTACCTATGAAAATGATATGCTTTCTATTAATGGGAAAAAAGTCAATGAAACTT
ATCTCAAGCAATACAAGGATAAATTTGCCAAGGACAAACTCCAAAAGACTTATGCCTAC
AATCAGTATTTCCAAGAATTAGCCTCACAATCAACAGCTTTCACAACAGACGAACAAGG
AAACGCCAGCTTTACGATTAAAGTACCAAAAGGACGTTACCTGCTTTTAGGTGATGATC
GCATTGTCTCTAAAGACAGCCGCCATGTTGGAACTTTTGCTAAGAATAAAATTGTTGGT
GAAGTTAAATTCCGCTTTTGGCCTTTAAACGCTATTCGTTTCATTTCAAATAAATAA

15_Shigella flexneri 2a str. 301_GI# 24113910_Catalytic Ser
Residues 91

(SEQ ID NO: 186)

MANMFALILVIATLVTGILWCVDKFFFAPKRRERQAAAQAAAGDSLDKATLKKVAPKPG
WLETGASVFPVLAIVLIVRSFIYEPFQIPSGSMMPTLLIGDFILVEKFAYGIKDPIYRK
TLIETGHPKRGDIVVFKYPEDPKLDYIKRAVGLPGDKVTYDPVSKELTIQPGCSSGQAC
ENALPVTYSNVEPSDFVQTFSRRNGGEATSGFFEVPKNETKENGIRLSERKETLGDVTH
RILTVPIAQDQVGMYYQQPGQQLATWIVPPGQYFMMGDNRDNSADSRYWGFVPEANLVG
RATAIWMSFDKQEGEWPTGVRLSRIGGIH*

15_Shigella flexneri 2a str. 301_GI# 24113910_Catalytic Ser
nucleotides 271-273

(SEQ ID NO: 187)

ATGGCGAATATGTTTGCCCTGATTCTGGTGATTGCCACACTGGTGACGGGCATTTTATG
GTGCGTGGATAAATTCTTTTTCGCACCTAAACGGCGGGAACGTCAGGCAGCGGCGCAGG
CGGCTGCCGGTGACTCACTGGATAAAGCAACGTTGAAAAAGGTTGCACCGAAGCCTGGC
TGGCTGGAAACCGGAGCTTCTGTTTTTCCGGTGCTGGCTATCGTATTGATTGTACGTTC
GTTTATTTATGAACCGTTCCAGATCCCGTCAGGTTCGATGATGCCGACTCTGTTAATCG
GTGATTTTATTCTGGTAGAGAAGTTTGCTTATGGCATTAAAGATCCTATCTACCAGAAA
ACGCTGATCGAAACCGGTCATCCGAAACGCGGCGATATCGTGGTCTTTAAATATCCGGA
AGATCCAAAGCTTGATTACATCAAGCGCGCGGTGGGTTTACCGGGCGATAAAGTCACTT
ACGATCCGGTCTCAAAAGAGCTGACGATTCAACCGGGATGCAGTTCCGGCCAGGCGTGT
GAAAACGCGCTGCCGGTCACCTACTCAAACGTGGAACCGAGCGATTTCGTTCAGACCTT
CTCACGCCGTAATGGTGGGGAAGCGACCAGCGGATTCTTTGAAGTGCCGAAAAACGAAA
CCAAAGAAAATGGAATTCGTCTTTCCGAGCGTAAAGAGACACTGGGTGATGTGACGCAC
CGAATTCTGACAGTGCCGATTGCGCAGGACCAGGTGGGGATGTATTACCAGCAGCCAGG
GCAACAACTGGCAACCTGGATTGTTCCGCCGGGACAATACTTCATGATGGGCGACAACC
GCGACAACAGCGCGGACAGCCGTTACTGGGGCTTTGTGCCTGAAGCGAATCTGGTCGGT
CGGGCCACGGCTATCTGGATGAGCTTCGATAAGCAAGAAGGCGAATGGCCGACTGGTGT
GCGCTTAAGTCGCATTGGCGGCATCCATTAA

16_Citrobacter koseri ATCC BAA-895_GI# 157144497_Catalytic
Ser Residues 91

(SEQ ID NO: 188)

MANMFALILVIATLVTGILWCVDKFIFAPKRRERQAAAQAAAGDSLDKATLKKVAPKPG
WLETGASVFPVLAIVLVVRSFIYEPFQIPSGSMMPTLLIGDFILVEKFAYGIKDPIYQK
TLIETGHPKRGDIVVFKYPEDPRLDYIKRAVGLPGDKVTYDPVAKEVTVQPGCRSGQAC
ENALPVTYSDVQPSDFVQTFARRNGGEASSGFFEVPLNETKDNGIRLAERKETLGDVTH
RILTVPIAQDQAGMYYRQPGQQLATWIVPPGQYFMMGDNRDNSADSRYWGFVPEANLVG
KATAIWMSFDKQEGEWPTGVRLSRIGGIH*

16_Citrobacter koseri ATCC BAA-895_GI# 157144497_Catalytic
Ser nucleotides 271-273

(SEQ ID NO: 189)

ATGGCGAATATGTTTGCCCTGATTCTGGTGATTGCCACACTGGTGACGGGCATTTTATG
GTGCGTTGATAAATTTATCTTCGCGCCAAAACGTCGGGAACGTCAGGCAGCGGCACAGG
CCGCTGCGGGTGATTCACTGGATAAAGCCACGTTGAAAAAGGTGGCGCCTAAGCCGGGC
TGGCTGGAAACAGGGGCTTCGGTTTTTCCGGTACTGGCGATTGTGCTGGTGGTGCGCTC
ATTTATCTATGAACCTTTCCAGATCCCGTCGGGTTCGATGATGCCGACGCTGTTAATCG
GTGACTTTATTCTGGTGGAGAAATTCGCCTATGGAATTAAAGATCCGATTTACCAGAAA
ACGTTGATTGAAACGGGTCATCCGAAACGCGGTGATATCGTGGTCTTTAAATACCCGGA
AGATCCGCGCCTGGACTACATTAAACGCGCTGTCGGCCTGCCGGGTGACAAAGTGACGT
ACGATCCGGTAGCCAAAGAGGTTACTGTACAGCCAGGATGCCGTTCCGGTCAGGCGTGT
GAAAACGCGCTGCCGGTGACTTACTCTGACGTTCAGCCCAGCGATTTCGTGCAGACCTT
TGCCCGCCGTAATGGGGGAGAAGCCAGCAGTGGGTTCTTCGAAGTGCCGTTAAACGAAA
CGAAAGATAACGGCATTCGTCTGGCGGAGCGTAAAGAGACGCTGGGAGACGTAACCCAC

```
CGTATTCTGACCGTACCGATCGCGCAGGATCAGGCGGGGATGTATTACCGTCAGCCGGG
GCAGCAACTGGCGACCTGGATCGTACCGCCAGGACAATACTTCATGATGGGTGATAACC
GCGATAACAGCGCGGACAGCCGTTACTGGGGATTTGTACCGGAAGCGAATCTGGTTGGT
AAAGCGACCGCGATCTGGATGAGTTTCGACAAACAGGAAGGTGAATGGCCGACCGGCGT
ACGCTTAAGCCGTATTGGTGGGATCCATTAA
```

17_Bordetella pertussis Tohama I_GI# 33593416_Catalytic Ser
Residues 101

(SEQ ID NO: 190)
```
MSWNFALILFVLLVITGVIWGLDLALFRKRRERRAQAAAAQVDAAGITDAEQAGRERRE
AIDAARRAPWWIEYAVSFFPVILFVFVLRSFVVEPFHIPSGSMLPTLQSGDLILVNKFS
YGIRLPIIDRKIIETGSLERGDVVVFRYPVDTDVDYIKRIVGLPGDQVAYLDKKLYING
KLVPHERDGDYFEPDRVSYIAQYKEKLGEVEHKILLDEQKIQDFGPIWKFPSIQNCQYA
RNGVRCTVPPGHYFAMGDNRDNSADSRYWGFVPDGNIVGKAFFVWMNFSDLSRIGRFH*
```

17_Bordetella pertussis Tohama I_GI# 33593416_Catalytic Ser
nucleotides 301-303

(SEQ ID NO: 191)
```
ATGAGTTGGAACTTTGCCCTGATACTTTTTGTACTGCTGGTGATTACCGGCGTTATCTG
GGGATTGGATCTGGCGCTGTTTCGCAAGCGACGCGAACGGCGGGCCCAGGCGGCGGCCG
CGCAAGTGGACGCCGCCGGCATCACGGATGCCGAGCAGGCCGGCCGCGAGCGGCGCGAG
GCCATCGACGCGGCGCGCCGCGCCCTGGTGGATCGAGTATGCGGTCAGCTTCTTCCC
GGTGATCCTGTTCGTGTTCGTGCTGCGCTCGTTCGTGGTCGAGCCGTTTCACATTCCGT
CGGGGTCCATGCTGCCCACGCTGCAATCGGGCGACCTGATCCTGGTGAACAAGTTCAGC
TACGGCATCCGCCTGCCCATCATCGATCGCAAGATCATCGAGACGGGCTCGCTGGAGCG
TGGCGACGTGGTGGTGTTCCGCTACCCGGTCGATACGGATGTCGACTACATCAAGCGCA
TCGTGGGTCTGCCGGGCGACCAGGTGGCCTACCTGGACAAGAAGCTGTACATCAACGGA
AAATTGGTGCCGCATGAACGCGACGGGGATTATTTCGAGCCCGATCGCGTGTCCTATAT
TGCGCAATACAAGGAAAAACTGGGCGAAGTGGAGCATAAGATCCTGCTTGATGAGCAGA
AAATACAGGATTTCGGCCCCATCTGGAAATTTCCCAGTATCCAGAACTGCCAGTACGCC
CGCAACGGCGTGCGCTGTACCGTCCCCCCCGGCCATTATTTCGCCATGGGAGACAACCG
TGACAATAGTGCGGACAGCCGCTACTGGGGATTCGTGCCAGACGGTAATATCGTGGGA
AGGCATTTTTTGTCTGGATGAACTTCAGCGATTTGAGCCGCATTGGCCGCTTCCATTGA
```

18_Clostridium difficile 630_GI# 126698930_Catalytic Ser
Residues 37

(SEQ ID NO: 192)
```
MSVKKEIFDWIKSIAMAIVLAFVILQFIIPSIVSGESMYPTLDDKDYLILNRISYKVGK
PEKGDIVVFKTNLVDGETGKKKDLIKRVIATEGDRIKISNSKVYVNGKLLNEPYIHNNY
TSGDIDTVVPKGKLFAMGDNRENSNDSRFPDVGMVDEDEVLGKVMVRLLPLDNIGKVD*
```

18_Clostridium difficile 630_GI# 126698930_Catalytic Ser
nucleotides 109-111

(SEQ ID NO: 193)
```
ATGAGTGTTAAAAAAGAAATATTTGATTGGATTAAGTCAATAGCTATGGCTATTGTACT
TGCATTTGTAATTCTACAATTTATAATACCTTCTATTGTAAGTGGAGAATCAATGTATC
CTACTTTAGATGATAAAGATTATCTGATTTTAAATAGGATATCATACAAGGTTGGTAAA
CCTGAAAAAGGCGATATTGTAGTTTTTAAAACCAATTTAGTTGATGGAGAAACAGGAAA
GAAAAAAGACTTAATAAAAAGAGTTATAGCTACTGAAGGTGACAGAATAAAAATATCAA
ATTCTAAAGTGTATGTAAATGGAAAATTATTAAATGAACCATATATACACAATAACTAT
ACTTCTGGAGATATAGATACTGTTGTTCCAAAAGGTAAACTATTTGCAATGGGAGATAA
TAGAGAAAATAGTAATGATAGTAGATTCCCTGATGTAGGTATGGTTGATGAAGATGAAG
TTCTTGGTAAGGTTATGGTGAGACTATTACCTCTTGATAATATTGGGAAAGTAGACTAA
```

19_Clostridium difficile 630_GI# 126698133_Catalytic Ser
Residues 39

(SEQ ID NO: 194)
```
VGEAVKKEVVEWIKVIVIALVLAFAITRFIVPTIVKGESMYPTLVERDYLIVNRIAYKV
GEPKYKDIIVFKTDLTEENGKKKDLVKRVIGVPGDHVKIQDSKVYVNDKLLDETSYIHN
NRTDGDIDIVVPEGKLFAMGDNREKSLDSRYDEVGLVDEHTILGKVLVRLYPFSKIGTI
D*
```

19_Clostridium difficile 630_GI# 126698133_Catalytic Ser
nucleotides 115-117

(SEQ ID NO: 195)
```
GTGGGTGAAGCAGTTAAAAAAGAAGTTGTAGAATGGATAAAAGTGATTGTCATAGCTCT
TGTTTTGGCATTTGCAATAACTCGTTTTATAGTGCCAACAATAGTCAAAGGAGAATCAA
TGTATCCTACATTAGTTGAACGTGATTATTTGATAGTTAACGAATTGCGTACAAGGTA
GGAGAGCCAAAATACAAAGATATAATAGTATTCAAAACCGACTTAACAGAGGAAATGG
AAAGAAAAAGATTTAGTAAAAAGAGTTATCGGGGTTCCTGGTGACCATGTAAAAATAC
AAGACTCCAAGGTATATGTAAATGATAAGTTGTTAGATGAGACTTCCTATATACATAAT
AATCGTACTGATGGAGATATTGATATCGTAGTTCCAGAAGGAAAATTATTTGCAATGGG
AGATAATAGAGAAAAAAGTTTAGATAGTAGATACGATGAGGTTGGATTGGTCGACGAGC
ATACCATTTTAGGAAAGGTTCTAGTCAGATTGTATCCATTTTCTAAGATAGGAACTATT
GACTAA
```

20_Clostridium difficile 630_GI# 126698134_Catalytic Ser
Residues 39

(SEQ ID NO: 196)
```
MNETIKEEIVEWIKIIITALFFAFIITRFIKPTLVNGESMYPTLKSHDYLVANRMTYKL
SEPKCGDIMIFKTDLLQENGRKKELVKRVIGVPGDHLKIKDSKVYINGKLLNEVSYIHD
```

-continued

NYTEGDIDMVIPKGKVFAMGDNREVSLDSRYKEVGLVDEENIKGKVILRVFPFTDIGIF
E*

20_Clostridium difficile 630_GI# 126698134_Catalytic Ser
nucleotides 115-117

(SEQ ID NO: 197)
ATGAATGAAACTATTAAAGAAGAGATTGTAGAGTGGATAAAAATAATTATTACTGCACT
TTTTTTTGCATTTATTATAACTCGTTTTATAAAACCAACATTAGTAAATGGAGAATCAA
TGTACCCAACACTTAAATCACATGATTATTTGGTAGCAAACAGGATGACATATAAGTTA
TCAGAACCAAAATGTGGAGATATAATGATATTTAAGACTGATTTATTACAAGAGAATGG
AAGGAAAAAGAGCTTGTAAAAGGGTTATAGGTGTTCCTGGTGACCATCTAAAAATTA
AGGATTCTAAGGTTTATATAAATGGTAAGTTATTAAATGAAGTTTCATATATACATGAT
AATTATACTGAAGGCGATATTGATATGGTGATTCCTAAGGGAAAAGTATTTGCGATGGG
AGACAATAGAGAAGTTAGTTTAGCAGTAGATATAAAGAAGTGGGATTAGTAGATGAAG
AAAATATTAAAGGAAAAGTTATTTTAAGAGTATTTCCTTTTACAGATATAGGTATTTTT
GAGTAG

21_Enterococcus faecalis V583_GI# 29377531_Catalytic Ser
Residues 35

(SEQ ID NO: 198)
MSSLLKRLVQLVLLVVAVLLIRHYVFSPAAVNGSSMEPTLHNNDRLWVTSIKKPQRFDI
IAFPSPRNGQRVAKRLIGLPGETVEYRDDTLYINGVSLSEDYLASAKRNVSKNENYTQD
FTLETLEATQSLTVPEGMYFVLGDNRPRSDDSRYFGFVKQASVEGVLTFRYYPLDKIGF
P*

21_Enterococcus faecalis V583_GI# 29377531_Catalytic Ser
nucleotides 103-105

(SEQ ID NO: 199)
ATGTCCTCATTATTAAAACGATTGGTTCAGTTGGTTTTGTTAGTCGTCGCTGTCTTGCT
GATTCGACACTATGTTTTCTCCCCTGCTGCGGTGAACGGCTCTTCAATGGAACCAACAC
TTCATAACAACGACCGTTTATGGGTGACCTCGATTAAAAAACCACAGCGCTTTGATATT
ATCGCTTTCCCTAGTCCTCGCAACGGCCAACGAGTAGCCAAACGTTTAATTGGTTTACC
TGGCGAAACAGTCGAGTATCGCGATGATACCCTTTATATTAATGGTGTATCACTCAGTG
AAGATTACTTAGCAAGTGCTAAACGAAATGTCTCTAAAAATGAAAATTATACCCAAGAT
TTTACGCTAGAGACCTTAGAAGCCACCCAATCCCTGACCGTTCCAGAAGGCATGTATTT
TGTCTTGGGGGATAATCGCCCGCGCTCAGACGACAGTCGTTATTTTGGCTTTGTTAAAC
AAGCGAGTGTGGAAGGTGTTTTGACTTTTCGTTATTATCCATTAGATAAAATTGGCTTT
CCATAA

22_Enterococcus faecalis V583_GI# 29375442_Catalytic Ser
Residues 101

(SEQ ID NO: 200)
MRTIRHIKRAFLKQKLPATYQLKKQKANTAMEYLLEQTDNHQSIRGPKRKMTAEEIKKK
RQAYQKKQRVQVVKFFMPAILFAIFVFFFVLKTSSYPIAGQSMKPTLNAGERVLVQRTK
QVARYDVIAFKAPLASKGTYVKRIIGVPGDRIWVNEGKLYLSEEPIASDNEALPENASR
FDLSEEAAAQLRLFQKIPAGHYFVLGDNRTHSSDSRTFGFVEIQAIEGIVVFKMAPFKE
IGKVK*

22_Enterococcus faecalis V583_GI# 29375442_Catalytic Ser
nucleotides 301-303

(SEQ ID NO: 201)
ATGCGAACAATTCGCCACATTAAGCGCGCCTTCTTGAAGCAAAAGTTGCCTGCGACATA
TCAGCTAAAAAAGCAAAAGGCTAACACAGCAATGGAATATTTGCTTGAGCAAACAGATA
ACCATCAATCAATAAGAGGACCGAAAAGAAAAATGACCGCTGAAGAGATTAAAAAAAAG
CGGCAAGCCTACCAAAAGAAACAACGCGTCCAAGTCGTTAAATTTTTTATGCCAGCTAT
TCTTTTTCGCCATTTTTGTGTTCTTTTTTGTGTTAAAGACATCTAGCTACCCAATTGCTG
GGCAATCCATGAAGCCGACACTTAACGCAGGGGAACGAGTCTTAGTACAACGGACGAAG
CAAGTAGCAAGGTACGATGTGATTGCATTTAAAGCACCGCTAGCTAGCAAAGGTACGTA
CGTCAAGCGAATCATCGGGGTTCCTGGTGATCGAATTTGGGTAAACGAGGGAAAACTTT
ATCTTTCAGAAGAACCTATAGCAAGCGATAATGAGGCACTGCCTGAGAATGCCAGTCGT
TTTGACTTATCAGAAGAAGCGGCAGCCCAACTTCGCCTGTTTCAGAAGATTCCAGCTGG
TCATTACTTTGTCTTAGGGGACAATCGTACGCATTCAAGTGATAGTCGTACGTTCGGCT
TTGTCGAGATACAAGCGATTGAAGGAATCGTGGTATTTAAAATGGCGCCGTTTAAGGAA
ATAGGGAAAGTAAAATAA

23_Enterococcus faecalis V583_GI# 29375687_Catalytic Ser
Residues 39

(SEQ ID NO: 202)
MSLKSKELIKTVVFFACLALGLFLLRQFVFTPVVVRGHSMDPTLADGERVITLKNTEIN
RFDIITFPAPDEPDKNYIKRVIGLPGDTIAYKDDTLYINGKEVDEPYLDEFKKALTDGQ
PLTGDFSLKEKVPADSYFVLGDNRRNSKDGRVIGFIHKKDILGEVKFVMWPFSRFGPIP
EVSKQ*

23_Enterococcus faecalis V583_GI# 29375687_Catalytic Ser
nucleotides 115-117

(SEQ ID NO: 203)
ATGAGTTTGAAATCAAAAGAATTAATTAAAACAGTCGTCTTTTTTGCCTGTTTAGCTTT
GGGTCTGTTTTTACTGAGACAATTTGTATTTACGCCTGTCGTAGTGAGAGGTCATTCAA
TGGATCCAACGTTAGCAGATGGTGAACGGGTAATTACGTTAAAAAACACAGAAATTAAT
CGTTTCGATATTATTACTTTCCCAGCGCCAGATGAACCAGATAAAAATTATATTAAACG
TGTGATTGGTTTACCTGGAGATACAATTGCGTACAAGGATGATACGTTGTACATCAATG

```
GAAAAGAAGTTGACGAACCCTATTTAGATGAATTTAAAAAAGCCTTAACAGATGGTCAA
CCTTTGACAGGCGATTTTTCATTAAAAGAAAAAGTACCAGCAGATAGCTACTTTGTTTT
AGGTGATAATCGACGGAATTCAAAAGACGGTCGTGTCATTGGTTTTATTCATAAAAAAG
ATATTTTGGGTGAAGTGAAATTTGTGATGTGGCCATTCTCACGGTTTGGTCCAATACCA
GAAGTGTCAAAACAATAA
```

24_Enterococcus faecalis V583_GI# 29376232_Catalytic Ser
Residues 42

(SEQ ID NO: 204)
```
LKKKRDYVGYLMYFLKILVPAIVAVFILRGFFLIPVRVDGHSMQKTLNQGDMIVMEKFS
AIKRFDVVVFKTDTGSILIKRVIGLPGEAVRYENDQLYVNNQPIAEPYLTKNRKKDHET
MPYTTNFDSKELLMQEKLPKDSYFVLGDNRRMSKDSRSFGAIHADQILGKAQFVYYPLT
HMKIIPK*
```

24_Enterococcus faecalis V583_GI# 29376232_Catalytic Ser
nucleotides 124-126

(SEQ ID NO: 205)
```
TTGAAGAAGAAACGTGATTATGTTGGGTATTTAATGTACTTTCTGAAAATTTTAGTACC
AGCAATCGTAGCCGTTTTTATTTTAAGAGGATTTTTCCTGATTCCTGTTCGGGTGGATG
GCCATTCTATGCAAAAAACCTTGAATCAAGGAGATATGATTGTGATGGAAAAATTCTCC
GCCATTAAACGGTTTGATGTGGTGGTCTTTAAAACAGATACAGGATCGATTCTGATTAA
ACGTGTGATTGGTTTACCAGGAGAAGCTGTGCGTTACGAAAACGATCAATTATATGCA
ATAATCAGCCAATCGCTGAACCGTATTTAACTAAAAACAGAAAAAAAGATCATGAAACG
ATGCCTTACACTACGAATTTTGATTCAAAAGAATTGTTAATGCAAGAAAAATTACCTAA
AGATAGCTATTTTGTGCTTGGTGATAATCGCCGTATGTCCAAAGACAGCCGTTCTTTTG
GTGCAATACATGCAGATCAAATCTTAGGGAAAGCACAATTTGTTTATTACCCACTCACT
CATATGAAGATCATTCCTAAATAA
```

25_Listeria monocytogenes str. 4b F2365_GI#
46907497_Catalytic Ser Residues 49

(SEQ ID NO: 206)
```
MTDQYDKKPKKKSGAHQLLSWVLVIVAALAIALVIRNFVVAPVKVEGTSMVPTYQDGDR
IFIEKISKPDRFDIIVFDEPPMIGSGEHFIKRVIGLPGDKIAFKNGELYLNGKRKVENY
LPEGTLTLWNPDPTQKPYIADYTLEDMTGESTVPKGKLFVLGDNRGGSSDSRVFGFIDD
SMVNGTVIQFGK*
```

25_Listeria monocytogenes str. 4b F2365_GI#
46907497_Catalytic Ser nucleotides 145-147

(SEQ ID NO: 207)
```
ATGACAGATCAATATGACAAAAAGCCCAAGAAAAAAAGCGGGGCGCACCAATTATTAAG
CTGGGTGCTAGTTATCGTTGCAGCGCTTGCAATTGCACTTGTGATTCGTAACTTTGTAG
TTGCACCAGTAAAAGTAGAAGGAACATCTATGGTTCCAACATATCAAGATGGCGATAGA
ATTTTCATTGAAAAAATTTCCAAGCCTGATCGTTTCGACATTATCGTGTTTGATGAACC
TCCAATGATTGGTTCAGGAGAGCATTTCATCAAGCGAGTGATTGGTTTGCCGGGAGATA
AAATAGCATTTAAAAACGGTGAATTATATTTAAATGGAAAACGAAAAGTAGAAAATTAC
TTGCCAGAAGGAACATTAACCCTTTGGAATCCAGATCCAACGCAAAAACCATACATAGC
GGATTATACGCTGGAGGATATGACAGGCGAAAGTACTGTTCCGAAAGGGAAACTATTTG
TACTTGGAGATAATCGCGGCGGGAGTTCAGATAGTCGCGTTTTCGGATTTATTGATGAT
TCCATGGTAAACGGTACAGTGATACAATTTGGAAAATAA
```

26_Listeria monocytogenes str. 4b F2365_GI#
46907496_Catalytic Ser Residues 42

(SEQ ID NO: 208)
```
MKSENKFFSGAFGWIKIILIALILAFGIRYFLISPVTVNGKSMDPTLHDGEHLFINKVS
DPKRFDIIVFPAPDEENAEYIKRVIGLPGDKVEYKEDQLYINGKKYDEPYLDSEKEALK
NGYLTTDAEGDPNFTMADIPNSDGSLTVPKGELFVLGDNRQVSKDSRYIGFISQDTVLG
KVISFGKSLER*
```

26_Listeria monocytogenes str. 4b F2365_GI#
46907496_Catalytic Ser nucleotides 124-126

(SEQ ID NO: 209)
```
ATGAAAAGTGAAAACAAATTTTTTTCTGGGGCATTTGGATGGATAAAAATAATTCTCAT
CGCGCTTATACTTGCTTTTGGTATTCGCTATTTTTTAATTTCTCCAGTTACTGTTAATG
GGAAATCAATGGACCCAACACTTCATGATGGGGAACATTTATTTATTAACAAGGTATCA
GATCCGAAGCGTTTTGACATTATTGTATTTCCTGCGCCTGATGAGGAAAATGCAGAGTA
CATTAAACGCGTCATTGGCCTTCCAGGAGATAAAGTGGAGTACAAAGAAGATCAACTTT
ATATTAATGGAAAAAAATATGATGAACCTTATTTAGATTCAGAAAAAGAAGCTCTAAAA
AACGGTTATTTAACCACTGATGCAGAAGGCGATCCTAATTTTACGATGGCAGACATTCC
AAACTCTGACGGCTCTCTCACTGTCCCTAAAGGAGAACTTTTTGTTTTAGGAGATAATC
GTCAAGTAAGTAAAGATAGTCGCTACATTGGCTTTATATCACAGGATACCGTGCTTGGA
AAAGTAATTTCATTTGGAAAATCCTTAGAACGTTAA
```

27_Listeria monocytogenes str. 4b F2365_GI#
46907498_Catalytic Ser Residues 40

(SEQ ID NO: 210)
```
LKEKNLKRLWSWIWAAVLAVLIAVIIRFYLFVPILVDGISMMPTLHSDDRVIINRFGNV
DRFDVIVFRESDGKEYIKRVIGLPGDTVEYKEDQLYINGKKYNEPYLDTYKEKLKDGYL
TDDYSSKDQLDGGKIPKDTYFVLGDNRRASKDSRIIGPIPFSKVLGTTPICYWPIEDAK
LID*
```

-continued

```
27_Listeria monocytogenes str. 4b F2365_GI#
46907498_Catalytic Ser nucleotides 118-120
                                                         (SEQ ID NO: 211)
TTGAAGGAGAAGAATTTAAAACGGTTATGGTCATGGATTTGGGCGGCTGTTCTAGCAGT
GTTAATAGCTGTTATAATCCGTTTTTATTTATTTGTCCCTATTCTCGTCGATGGGATAT
CAATGATGCCTACACTTCATAGCGATGACCGTGTAATTATAAATCGCTTCGGAAATGTA
GATCGTTTCGATGTGATTGTTTTCCGAGAATCAGATGGAAAAGAATACATCAAGCGAGT
GATCGGTTTGCCGGGTGATACAGTAGAATACAAAGAAGACCAACTTTACATCAATGGTA
AAAAGTATAATGAACCATATTTGGATACTTACAAAGAAAAGTTAAAAGATGGCTATTTA
ACAGATGATTACAGTTCGAAAGATCAACTAGATGGTGGCAAAATTCCAAAAGATACTTA
TTTTGTTTTAGGTGACAATCGAAGAGCAAGCAAAGACAGTCGGATAATTGGGCCAATTC
CATTTAGCAAGGTGTTAGGAACAACACCGATTTGTTACTGGCCGATTGAAGATGCCAAA
CTTATAGATTAG
```

Embodiments of the Invention
1. A compound of formula (I)

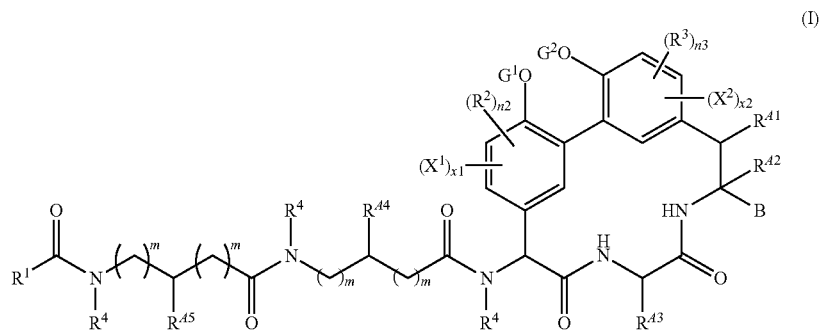

wherein

B is $CO_2H$, $CH_2CO_2H$, $C(=O)NHCH_2C(=O)H$, $CH_2C(=O)H$, $C(=O)NHCH_2B(OR^B)_2$ or $C(=O)NHCH_2P(=O)(OR^B)_2$ wherein $R^B$ is H or $(C_1-C_6)$alkyl, or B is a group of formula

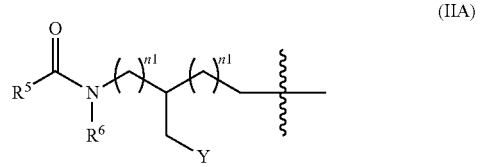

wherein $R^{B1}$ and $R^{B2}$ are each independently H, $(C_1-C_6)$ alkyl, $(C_3-C_6)$ cycloalkyl, $OR^C$, $C(=O)NR^C_2$, $OC(=O)NR^C_2$, $C(=O)OR^c$, $OC(=O)OR^c$, nitro, trifluoromethyl, trifluoromethoxy, $(C_1-C_6)$alkoxy, $(C_1-C_6)$thioalkoxy, $NR^C_2$, 5-7 membered heterocyclyl or 5-7 membered heteroaryl, or $(C_6-C_{10})$ aryl; $R^C$ is independently at each occurrence H or $(C_1-C_6)$ alkyl, and a wavy line indicates a point of attachment of B to a carbon of formula (I) bearing B;

$R^1$ comprises a group of formula (IIA) or (IIB) or (IIC)

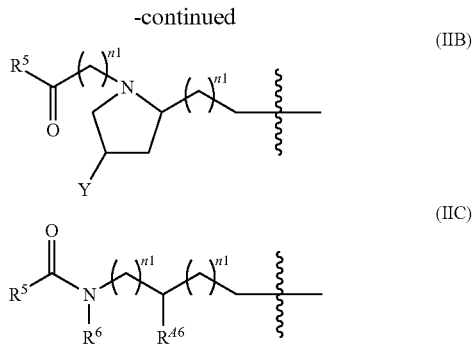

wherein each m is independently 0, 1, or 2, n1 is independently at each occurrence 0, 1, or 2; Y is $(CH_2)_{0-2}14$, $(CH_2)_{0-2}OH$, or $(CH_2)_{0-2}OC(=O)(C_1-C_6)$alkyl; $R^{46}$ is hydrogen, $(C_1-C_6)$alkyl, $(C_3-C_7)$cycloalkyl, 5- to 7-membered heteroaryl, 5- to 7-membered heterocyclyl, or $(C_6-C_{10})$ aryl, wherein any alkyl, cycloalkyl, heterocyclyl, aryl or heteroaryl may be substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7-membered heterocyclyl, $(C_1-C_6)$alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylaminocarbonyl, $(C_1-C_6)$alkylsulfonylamino, and $(C_6-C_{10})$-arylsulfonylamino; and a wavy line indicates a point of attachment of $R^1$ to an atom of formula (I) bearing $R^1$; and $R^5$ is a linear or branched alkyl chain of about 1-22 carbon atoms, bonded to the carbonyl carbon to which it is attached directly or by an O or NR, to provide an amide, carbamate, or urea linkage respectively; optionally comprising within the chain or at a chain terminus, any of the following groups:

(A)

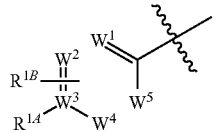

wherein $W^1$, $W^2$, $W^3$, $W^4$ and $W^5$ are each independently C or N, provided that no more than two of $W^1$, $W^2$, $W^3$, $W^4$ and $W^5$ are N; provided that when $R^{1A}$ or $R^{1B}$ is non-hydrogen, any W atom to which the $R^{1A}$ or $R^{1B}$ is respectively bonded is C, wherein there can be one or more $R^{1B}$ bonded to the ring bearing the W atoms; $R^{1A}$ is hydrogen, halogen, amino, hydroxyl, aminocarbonyl, hydroxycarbonyl, nitro, fluoroalkyl, cyano, $(C_1-C_6)$-thioether, fluoroalkoxy, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; $R^{1B}$ is hydrogen, alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-alkylamino, $(C_1-C_6)$-alkyl, 5- to 7-membered heteroaryl, 5- to 7-membered heterocyclyl, or $(C_6-C_{10})$ aryl; wherein any $R^{1A}$ or $R^{1B}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-alkylamino, $(C_1-C_6)$-alkyl, 5- to 7-membered heteroaryl, 5- to 7-membered heterocyclyl, or $(C_6-C_{10})$ aryl groups; wherein a wavy line indicates a point of attachment;

(B)

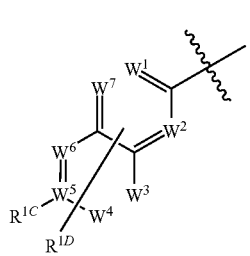

wherein $W^1$, $W^2$, $W^3$, $W^4$, $W^5$, $W^6$, and $W^7$ are each independently C or N, provided that no more than three of $W^1$, $W^2$, $W^3$, $W^4$, $W^5$, $W^6$, and $W^7$ are N; provided that when $R^{1C}$ or $R^{1D}$ is non-hydrogen, any W atom to which the $R^{1C}$ or $R^{1D}$ is respectively bonded is C, wherein either ring can bear one or more $R^{1D}$; $R^{1C}$ is hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; $R^{1D}$ is hydrogen, alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein any $R^{1C}$ or $R^{1D}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$ thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein a wavy line indicates a point of attachment;

(C)

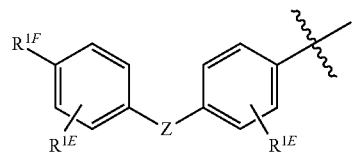

wherein Z is O, S, NH or $CH_2$; $R^E$ at each occurrence is independently hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; $R^{1F}$ is hydrogen or alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein any $R^{1E}$ or $R^{1F}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$ thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein a wavy line indicates a point of attachment; or (D)

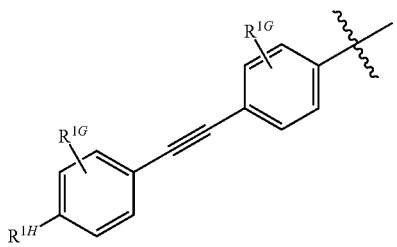

wherein $R^{1G}$ at each occurrence is independently hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; $R^{1H}$ is hydrogen or alkyl, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or $(C_6-C_{10})$ aryl; wherein any $R^{1G}$ or $R^{1H}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$thioalkyl, fluoroalkoxy, cyano, $(C_1-C_6)$-alkyl, $(C_1-C_6)$-alkoxy, $(C_1-C_6)$-mono- or di-alkylamino, $(C_1-C_6)$-alkyl, 5- to 7-membered heteroaryl, 5- to 7-membered heterocyclyl, or ($C_6$-$C_{10}$) aryl; wherein a wavy line indicates a point of attachment;

$R^2$ and $R^3$ are each independently nitro, halo, cyano, hydroxy, glycosyloxy, amino, ($C_1$-$C_4$)alkoxy, ($C_1$-$C_4$)acyloxy, or ($C_1$-$C_4$)alkyl, wherein any carbon atom can be unsubstituted or substituted with J, wherein $n^2$ and $n^3$ are independently 0, 1, 2, or 3; or wherein two $R^2$ groups taken together, and/or two $R^3$ groups taken together, can comprise fused cycloalkyl, aryl, heterocyclyl, or heteroaryl ring or rings, any of which is substituted with 0-3 J;

$R^4$ and $R^6$ are each independently at every occurrence hydrogen, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl can be substituted with 1 to 3 J;

$R^{A1}$, $R^{A2}$, $R^{A3}$, $R^{A4}$, $R^{A5}$ are independently at each occurrence hydrogen, ($C_1$-$C_6$)alkyl, ($C_3$-$C_7$)cycloalkyl, 5- to 7-membered heteroaryl, 5- to 7-membered heterocyclyl, or ($C_6$-$C_{10}$) aryl, wherein any alkyl, cycloalkyl, heterocyclyl, aryl or heteroaryl can be substituted with 1 to 3 J;

J is halogen, R', OR', CN, $CF_3$, $OCF_3$, O, S, C(O), S(O), methylenedioxy, ethylenedioxy, $(CH_2)_{0-p}N(R')_2$, $(CH_2)_{0-p}SR'$, $(CH_2)_{0-p}S(O)R'$, $(CH_2)_{0-p}S(O)_2R'$, $(CH_2)_{0-p}S(O)_2N(R')_2$, $(CH_2)_{0-p}SO_3R'$, $(CH_2)_{0-p}C(O)R'$, $(CH_2)_{0-p}C(O)$ $CH_2C(O)R'$, $(CH_2)_{0-p}C(S)R'$, $(CH_2)_{0-p}C(O)OR'$, $(CH_2)_{0-p}OC(O)R'$, $(CH_2)_{0-p}C(O)N(R')_2$, $(CH_2)_{0-p}OC(O)N(R')_2$, $(CH_2)_{0-p}C(S)N(R)_2$, $(CH_2)_{0-p}NH—C(O)R'$, $(CH_2)_{0-p}N(R')N(R')C(O)R'$, $(CH_2)_{0-p}N(R')N(R')C(O)OR'$, $(CH_2)_{0-p}N(R')N(R')CON(R')_2$, $(CH_2)_{0-p}N(R')SO_2R$, $(CH_2)_{0-p}N(R)SO_2N(R)_2$, $(CH_2)_{0-p}N(R')C(O)OR'$, $(CH_2)_{0-p}N(R)C(O)R_9$ $(CH_2)_{0-p}N(R')C(S)R'$, $(CH_2)_{0-p}N(R)C(O)N(R)_2$, $(CH_2)_{0-p}N(R)C(S)N(R)_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R'$; wherein p is about 4, each R' is independently at each occurrence hydrogen, ($C_1$-$C_{12}$)-alkyl, cycloalkyl, ($C_3$-$C_{10}$) ($C_2$-$C_{12}$)-alkenyl, ($C_2$-$C_{12}$)-alkynyl, ($C_3$-$C_{10}$)-cycloalkenyl, [($C_3$-$C_{10}$)cycloalkyl or ($C_3$-$C_{10}$)-cycloalkenyl]-[($C_1$-$C_{12}$)-alkyl or ($C_2$-$C_{12}$)-alkenyl or ($C_2$-$C_{12}$)$^{alkynyl}$], ($C_6$-$C_{10}$)-aryl, ($C_6$-$C_{10}$)-aryl-[($C_1$-$C_{12}$)-alkyl or ($C_2$-$C_{12}$)-alkenyl or ($C_2$-$C_{12}$)-alkynyl], mono- or bicyclic 3-10 membered heterocyclyl, mono- or bicyclic 3-10 membered heterocyclyl-[($C_1$-$C_{12}$)-alkyl or ($C_2$-$C_{12}$)-alkenyl or ($C_2$-$C_{12}$)-alkynyl], mono- or bicyclic 5-10 membered heteroaryl, or mono- or bicyclic 5-10 membered heteroaryl-[($C_1$-$C_{12}$)-alkyl or ($C_2$-$C_{12}$)-alkenyl or ($C_2$-$C_{12}$)-alkynyl], wherein R' is substituted with 0-3 substituents selected independently from J;

or, when two R' are bound to a nitrogen atom or to two adjacent nitrogen atoms, the two R' groups together with the nitrogen atom or atoms to which they are bound can form a 3- to 8-membered monocyclic heterocyclic ring, or an 8- to 20-membered, bicyclic or tricyclic, heterocyclic ring system, wherein any ring or ring system can further contain 1-3 additional heteroatoms selected from the group consisting of N,NR', O, S, S(O) and $S(O)_2$, wherein each ring is substituted with 0-3 substituents selected independently from J;

wherein, in any bicyclic or tricyclic ring system, each ring is linearly fused, bridged, or spirocyclic, wherein each ring is either aromatic or nonaromatic, wherein each ring can be fused to a ($C_6$-$C_{10}$)aryl, mono- or bicyclic 5-10 membered heteroaryl, ($C_3$-$C_{10}$)cycloalkyl or mono- or bicyclic 3-10 membered heterocyclyl;

$G^1$ and $G^2$ are each independently a hydrogen or a glycosyl residue, or a group cleavable under physiological conditions to provide a compound of formula (I) wherein $G^1$ or $G^2$ respectively is hydrogen;

$(X^1)_{X1}$ and $(X^2)_{X2}$ each signify that 0, 1, or 2 ring atoms of each respective ring can be nitrogen, provided that where a non-hydrogen substituent is bonded, $X^1$ or $X^2$, respectively, is C;

provided that when $G^1$ is a 6-deoxyhexopyranosyl residue, $G^2$ is H, $R^1$ is of formula (IIA), $R^2$ is hydrogen or hydroxy, $R^3$ is hydrogen, $R^{A1}$ and $R^{A2}$ and $R^{A4}$ are H, $R^{A3}$ and $R^{A5}$ are methyl, and B is $CO_2H$, or when $G^1$ and $G^2$ are H, $R^1$ is of formula (IIA), $R^2$ is hydrogen, $R^3$ is hydrogen or nitro, $R^{A1}$ and $R^{A2}$ and $R^{A4}$ are H, $R^{A3}$ and $R^{A5}$ are methyl, and B is $CO_2H$, then $R^5$ is not unsubstituted ($C_{10}$-$C_{16}$)-alkyl;

or a salt thereof.

2. The compound of formula I of embodiment 1 wherein when $G^1$ is a H or a 6-deoxyhexopyranosyl residue, $G^2$ is H, $R^1$ is of formula (IIA), $R^2$ is hydrogen or hydroxy, $R^3$ is hydrogen or nitro, $R^{A1}$ and $R^{A2}$ and $R^{A4}$ are H, $R^{A3}$ and $R^{A5}$ are methyl, and B is $CO_2H$, then $R^5$ is not unsubstituted ($C_1$-$C_{22}$)alkyl.

3. The compound of embodiment 1 or 2 wherein the compound is of formula (IA)

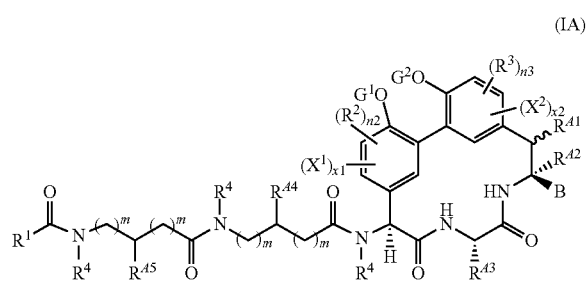

(IA)

wherein $R^1$, $R^2$, $R^3$, $R^4$, $R^5$, $R^6$, $R^{A1}$, $R^{A2}$, $R^{A3}$, $R^{A4}$, $R^{A5}$, $R^B$, $R^{B1}$, $R^{B2}$, and $R^C$, and m, n, $n^2$, $n^3$, p, B, $G^1$, $G^2$, $(X^1)_{X1}$, $(X^2)_{X2}$, and Y, are as defined in embodiment 1 and a wavy line indicates a point of attachment of $R^1$ to an atom bonded to $R^1$ in formula (IA);

or a salt thereof.

4. The compound of any one embodiments 1-3 wherein $R^1$ is a group of formula (IIAS) or (IIBS)

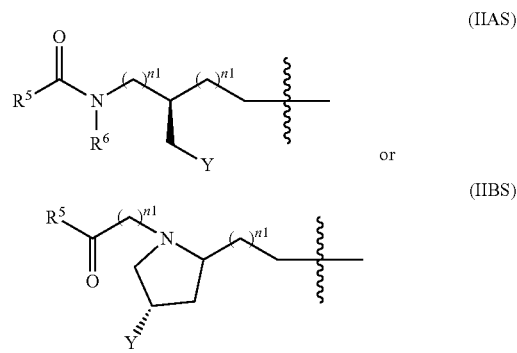

(IIAS)

or (IIBS)

wherein $n^1$, $n^2$, p, $R^5$, $R^6$, and Y, are as defined in embodiment 1 and a wavy line indicates a point of attachment of $R^1$ to an atom bonded to $R^1$ in formula (I);

or a salt thereof.

5. The compound of embodiment 1 or 2 wherein $R^5$ is a ($C_1$-$C_{22}$) linear or branched alkyl.

6. The compound of embodiment 1 or 2 wherein $R^5$ is a ($C_1$-$C_{22}$) linear or branched alkyl comprising one or more of groups (A), (B), (C), or (D), of embodiment 1.

7. The compound of embodiment 3 or 4 wherein $R^5$ is a $(C_1-C_{22})$ linear or branched alkyl.
8. The compound of embodiment 3 or 4 wherein $R^5$ is a $(C_1-C_{22})$ linear or branched alkyl, comprising one or more of groups (A), (B), (C), or (D), of embodiment 1.
9. The compound of any one of embodiments 1-7 wherein $R^5$ is any of the following groups

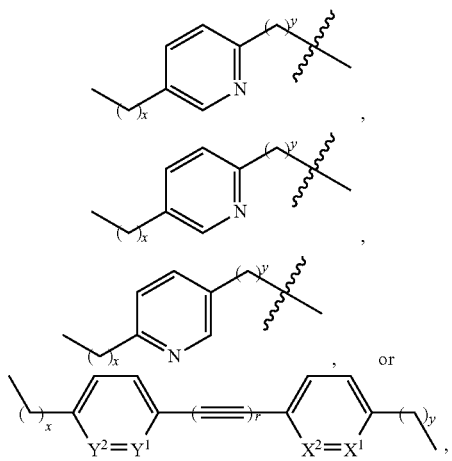

wherein x is 0-14, y is 0-14, provided that x+y≤22, and $X^1$, $X^2$, $Y^1$ and $Y^2$ are each independently C or N, provided that no more than one of $X^1$ and $X^2$, and no more than one of $Y^1$ and $Y^2$, is N, wherein a wavy line indicates a point of attachment of $R^5$ to an atom bonded to $R^5$ in formula (IIA), (IIB), or (IIC).

10. The compound of any one of embodiments 1-7 wherein $R^5$ is any of the following: methyl, ethyl, $(C_3-C_{22})$-n-alkyl, $(C_3-C_{22})$-isoalkyl, $(C_4-C_{22})$-anteisoalkyl, naphthyl, $(C_2-C_{10})$ naphthyl, naphthylmethyl, $(C_2-C_{10})$ naphthylmethyl, biphenyl, $(C_2-C_{10})$ alkylbiphenyl, biphenylmethyl, $(C_2-C_{10})$alkylbiphenylmethyl, $(C_4-C_{12})$phenyl, $(C_4-C_{12})$benzyl, $(C_2-C_{10})$-1,2-diphenylethynyl, or (Z)— or (E)-$(C_2-C_{10})$-1,2-diphenylethenyl, wherein a wavy line indicates a point of attachment of $R^5$ to an atom bonded to $R^5$ in formula (IIA), (IIB), or (IIC).
11. The compound of embodiment 1 wherein ring bearing one or more $X^1$ or $X^2$, respectively, is a phenyl, pyridyl, pyrazinyl, pyrimidyl, or pyridazinyl, optionally wherein $R^2$ and $R^3$ are both hydrogen.
12. The compound of any of embodiments 1-7 wherein at least one of $R^2$ and $R^3$ is hydrogen.
13. The compound of any of embodiments 1-7 wherein at least one of $R^2$ and $R^3$ is nitro, halo, cyano, hydroxy, glycosyloxy, amino, $(C_1-C_4)$alkoxy, or $(C_1-C_4)$alkyl, and $n^2$ or $n^3$ respectively, or both, is 1.
14. The compound of any one of embodiments 1-7 wherein both G are hydrogen.
15. The compound of any one of embodiments 1-7 wherein any of $R^{41}$, $R^{42}$ and $R^{44}$ are hydrogen, any of $R^{43}$ and $R^{45}$ are methyl, or any combination thereof.
16. The compound of any one of embodiments 1-7 wherein $R^{43}$ is hydrogen, methyl, ethyl, n-propyl, isopropyl, n-butyl, isobutyl, 3-hydroxypropyl, 4-hydroxybutyl, or 2,2,2-trifluoroethyl.
17. The compound of any one of embodiments 1-7 wherein all of $R^4$ and $R^6$ are independently selected hydrogen or methyl.
18. The compound of embodiment 1 wherein the compound is any of the following compounds of formula (III)

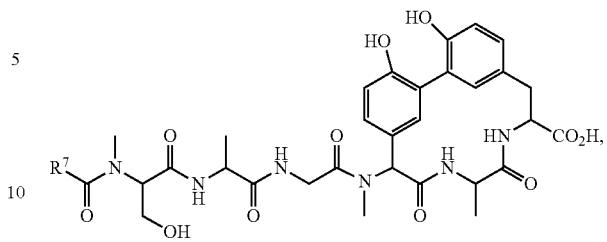

wherein $R^7$ is $(C_8-C_{18})$-n-alkyl, $(C_8-C_{18})$-isoalkyl, $(C_8-C_{18})$-anteisoalkyl, any of which includes a group (A), (B), (C), (D), or (E) of embodiment 1; or is 2-naphthyl, 6-$(C_2-C_{10})$-2-naphthyl, 2-naphthylmethyl, 6-$(C_2-C_{10})$-2-naphthylmethyl, 4-biphenyl, 4-biphenylmethyl, 4'-$(C_2-C_{10})$alkyl-4-biphenyl, 4'-$(C_2-C_{10})$alkyl-4-biphenylmethyl, p-$(C_4-C_{12})$phenyl, p-$(C_4-C_{12})$benzyl, or 4'-$(C_2-C_{10})$-1,2-diphenylethynyl;
or a salt thereof.
19. The compound of embodiment 3 wherein the compound is any of the following compounds of formula (IV)

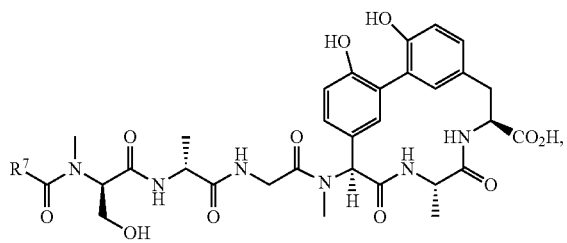

herein $R^7$ is $(C_8-C_{18})$-n-alkyl, $(C_8-C_{18})$-isoalkyl, $(C_8-C_{18})$-anteisoalkyl, any of which includes a group (A), (B), (C), (D), or (E) of embodiment 1; or is 2-naphthyl, 6-(C2-$C_{10}$)-2-naphthyl, 2-naphthylmethyl, 6-$(C_2-C_{10})$-2-naphthylmethyl, 4-biphenyl, 4-biphenylmethyl, 4'-$(C_2-C_{10})$alkyl-4-biphenyl, 4'-$(C_2-C_{10})$alkyl-4-biphenylmethyl, p-$(C_4-C_{12})$phenyl, p-$(C_4-C_{12})$benzyl, or 4'-$(C_2-C_{10})$-1,2-diphenylethynyl;
or a salt thereof.
20. A compound comprising a hydrate, solvate, prodrug, or metabolite of a compound of any one of embodiments 1-19.
21. A pharmaceutical composition comprising the compound of any one of embodiments 1-20 and a pharmaceutically acceptable excipient.
22. Use of a compound of any one of embodiments 1-20 for preparation of a medicament for treatment of a bacterial infection in a patient.
23. A method of treatment of a bacterial infection in an animal, comprising administering an effective amount of a compound of any one of embodiments 1-20 to the animal at a frequency and for a duration sufficient to provide a beneficial effect to the animal.
24. The method of embodiment 23 wherein a causative bacterial species of the bacterial infection is of a genotype resistant to treatment with arylomycin A2.
25. The method of embodiment 23, wherein the bacterial infection is an infection involving *Corynebacterium diphtheriae*, *Corynebacterium glutamicum*, *Campylobacter jejuni*, *Chlamydia trachomatis*, *Chlamydophila pneumo-* niae, *Francisella tularensis, Helicobacter pylori, Lactococcus lactis* subsp. *cremoris, Lactococcus lactis* subsp. *lactis, Propionibacterium acnes, Rhodococcus equi, Rhodococcus opacus, Staphylococcus capitis, Staphylococcus caprae, Staphylococcus carnosus, Staphylococcus cohnii, Staphylococcus epidermidis, Staphylococcus haemolyticus, Staphylococcus hominis, Staphylococcus hominis* subsp. *hominis, Staphylococcus hominis* subsp. *novobiosepticus, Staphylococcus lugdunensis, Streptococcus agalactiae, Streptococcus dysgalactiae, Streptococcus mitis, Streptococcus oralis, Streptococcus pyogenes, Streptococcus pnemoniae*, and/or *Yersinia pestis*.

26. The method of any of embodiments 23-25, wherein the bacterial infection is an infection involving a gram negative bacteria.

27. A method of treating a bacterial infection in an animal that includes administering arylomycin A and/or arylomycin B and/or a compound of any of embodiments 1-20 to the animal, wherein the infection involves a microbial species that expresses a signal peptidase without a proline residue within 10 amino acids N-terminal to the signal peptidase catalytic serine.

28. The method of embodiment 27, wherein the bacterial species encodes or expresses an SPase enzyme without a proline residue 5 to 7 amino acids N-terminal to the SPase catalytic serine.

29. The method of embodiment 27 or 28, wherein the bacterial infection is an infection involving *Corynebacterium diphtheriae, Corynebacterium glutamicum, Campylobacter jejuni, Chlamydia trachomatis, Chlamydophila pneumoniae, Francisella tularensis, Helicobacter pylori, Lactococcus lactis* subsp. *cremoris, Lactococcus lactis* subsp. *lactis, Propionibacterium acnes, Rhodococcus equi, Staphylococcus carnosus, Staphylococcus cohnii, Staphylococcus haemolyticus, Staphylococcus hominis, Staphylococcus hominis* subsp. *hominis, Staphylococcus hominis* subsp. *novobiosepticus, Staphylococcus lugdunensis, Streptococcus agalactiae, Streptococcus dysgalactiae, Streptococcus mitis, Streptococcus oralis, Streptococcus pyogenes*, and/or *Streptococcus pnemoniae*.

30. The method of any of embodiments 27-29, wherein the bacterial infection is an infection involving a gram negative bacteria.

31. The method of any of embodiments 27-30, wherein administering comprises topical administration.

32. A method of treating a bacterial infection in an animal comprising administering to the animal any one or any combination of the compounds of any of embodiments 1-20, wherein the bacterial infection comprises an infection by a bacteria that encodes or expresses an SPase enzyme that has a proline within about 10 amino acids N-terminal to the SPase catalytic serine.

33. The method of embodiment 32, wherein the bacteria encodes or expresses an SPase enzyme that does not have a proline 5 to 7 amino acids N-terminal to the SPase catalytic serine.

34. The method of embodiment 32 or 33, wherein the bacterial infection involves *Staphylococcus capitis, Staphylococcus caprae* and/or *Yersinia pestis*.

35. A method of treating a bacterial infection in an animal comprising administering to the animal arylomycin A or arylomycin B, wherein the microbial infection is an infection involving *Corynebacterium diphtheriae, Corynebacterium glutamicum, Campylobacter jejuni, Chlamydia trachomatis, Chlamydophila pneumoniae, Francisella tularensis, Helicobacter pylori, Lactococcus lactis* subsp. *cremoris, Lactococcus lactis* subsp. *lactis, Propionibacterium acnes, Rhodococcus equi, Staphylococcus capitis, Staphylococcus caprae, Staphylococcus carnosus, Staphylococcus cohnii, Staphylococcus haemolyticus, Staphylococcus hominis, Staphylococcus hominis* subsp. *hominis, Staphylococcus hominis* subsp. *novobiosepticus, Staphylococcus lugdunensis, Streptococcus agalactiae, Streptococcus dysgalactiae, Streptococcus mitis, Streptococcus oralis, Streptococcus pyogenes, Streptococcus pnemoniae*, and/or *Yersinia pestis*.

36. The method of embodiment 35, wherein administering comprises topical administration.

37. The method of any of embodiments 23-36 further comprising administering a second therapeutic agent.

38. The method of embodiment 37, wherein the second therapeutic agent is a non-arylomycin antibiotic.

39. The method of embodiment 38, wherein the non-arylomycin antibiotic is an aminoglycoside antibiotic, fluoroquinolone antibiotic, penicillin antibiotic, cephalosporin antibiotic, macrolide antibiotic, glycopeptide antibiotic, rifampicin, chloramphenicol, fluoramphenicol, colistin, mupirocin, bacitracin, daptomycin, or linezolid.

40. A method of detecting whether a test sample contains a bacterium sensitive to an arylomycin antibiotic comprising detecting whether a bacterial signal peptidase is present in the test sample, wherein the bacterial signal peptidase does not have a proline within about 10 amino acids N-terminal to the bacterial signal peptidase's catalytic serine.

41. The method of embodiment 40, furthering comprising detecting whether a test sample contains *Yersinia pestis*.

42. The method of embodiment 40, wherein the bacterial signal peptidase nucleic acid or the bacterial signal peptidase polypeptide is detected.

43. The method of any of embodiments 40-42, further comprising contacting the test sample with an anti-signal peptidase antibody and detecting whether the antibody forms a complex with a bacterial signal peptidase in the test sample.

44. The method of embodiment 43, wherein the antibody selectively binds to a signal peptidase that does not contain a proline with about 10 amino acids N-terminal to the bacterial signal peptidase's catalytic serine.

45. The method of any of embodiments 40-44, further comprising contacting the test sample with an anti-signal peptidase antibody that selectively binds to a signal peptidase that does contain a proline with about 10 amino acids N-terminal to the bacterial signal peptidase catalytic serine and detecting whether the antibody forms a complex with a bacterial signal peptidase in the test sample.

46. The method of embodiment 40-42, further comprising contacting a nucleic acid isolated from the test sample with a probe or primer that selectively hybridizes to a DNA encoding a bacterial signal peptidase that does not contain a proline with about 10 amino acids N-terminal to the bacterial signal peptidase's catalytic serine.

47. The method of embodiment 46, wherein the probe or the primer hybridizes to the DNA under stringent hybridization conditions.

48. The method of embodiment 46 or 47, wherein the probe or primer hybridizes to the signal peptidase DNA encoding a region comprising about 4 to about 15 amino acids of the bacterial signal peptidase that includes the catalytic serine.

49. The method of embodiment 40-42, 46-48, wherein detecting comprises nucleic acid amplication, nucleic acid sequencing, or single nucleotide polymorphism detection.

50. The method of any of embodiments 40-49, wherein the signal peptidase does not have a proline seven amino acids N-terminal to the bacterial signal peptidase' catalytic serine.

51. The method of any of embodiments 40-50, wherein the signal peptidase does not have a proline five amino acids N-terminal to the bacterial signal peptidase' catalytic serine.

52. The method of any of embodiments 40-51, wherein the bacterium is a *Eubacteria*, and/or the antibody selectively binds to the signal peptidase from a selected species of *Eubacteria* and/or the probe or primer selectively hybridizes to a DNA encoding a signal peptidase from a selected species of *Eubacteria*.

53. A bacterium genetically engineered to encode and/or express a signal peptidase with a proline at 5 to 7 amino acids N-terminal to the signal peptidase's catalytic serine, wherein the bacterium is selected from the group consisting of *Corynebacterium diphtheriae, Corynebacterium glutamicum, Campylobacter jejuni, Chlamydia trachomatis, Chlamydophila pneumoniae, Francisella tularensis, Helicobacter pylori, Lactococcus lactis* subsp. *cremoris, Lactococcus* lactis subsp. *lactis, Propionibacterium acnes, Rhodococcus equi, Rhodococcus opacus, Staphylococcus carnosus, Staphylococcus cohnii, Staphylococcus epidermidis, Staphylococcus haemolyticus, Staphylococcus hominis, Staphylococcus hominis* subsp. *hominis, Staphylococcus hominis* subsp. *novobiosepticus, Staphylococcus lugdunensis, Streptococcus agalactiae, Streptococcus dysgalactiae, Streptococcus mitis, Streptococcus oralis, Streptococcus pyogenes*, and *Streptococcus* pnemoniae.

54. A bacterium genetically engineered to encode and/or express a signal peptidase without a proline at 5 to 7 amino acids N-terminal to the signal peptidase's catalytic serine, wherein the bacterium is *Escherichia coli, Klebsiella pneumonia, Salmonella entericia, Vibrio cholera, Pseudomonas aeruginosa, Acinetobacter baumanii, Neiserria meningitides, Haemophilus influenza, Citrobacter koseri, Shigella flexneri, Bordetella pertussis, Mycobacterium tuberculosis, Staphylococcus aurues, Bacillus anthracis, Streptococcus mutans, Clostridium difficile, Enterococcus faecalis* and/or *Listeria monocytogenes*.

55. A mutant signal peptidase with a *Corynebacterium diphtheriae, Corynebacterium glutamicum, Campylobacter jejuni, Chlamydia trachomatis, Chlamydophila pneumoniae, Francisella tularensis, Helicobacter pylori, Lactococcus lactis* subsp. *cremoris, Lactococcus lactis* subsp. *lactis, Propionibacterium acnes, Rhodococcus equi, Rhodococcus opacus, Staphylococcus carnosus, Staphylococcus cohnii, Staphylococcus epidermidis, Staphylococcus haemolyticus, Staphylococcus hominis, Staphylococcus hominis* subsp. *hominis, Staphylococcus hominis* subsp. *novobiosepticus, Staphylococcus lugdunensis, Streptococcus agalactiae, Streptococcus dysgalactiae, Streptococcus mitis, Streptococcus oralis, Streptococcus pyogenes*, or *Streptococcus* pnemoniae signal peptidase amino acid sequence that is modified to have a proline substitution at a position 5 or at a position 7 amino acids N-terminal to the signal peptidase's catalytic serine.

56. A mutant signal peptidase with a *Escherichia coli, Klebsiella pneumonia, Salmonella entericia, Vibrio cholera, Pseudomonas aeruginosa, Acinetobacter baumanii, Neiserria meningitides, Haemophilus influenza, Citrobacter koseri, Shigella flexneri, Bordetella pertussis, Mycobacterium tuberculosis, Staphylococcus aurues, Bacillus anthracis, Streptococcus mutans, Clostridium difficile, Enterococcus faecalis* or *Listeria monocytogenes* signal peptidase amino acid sequence that is modified by replacement of a proline with a selected amino acid, wherein the proline was at 5 to 7 amino acids N-terminal to the signal peptidase's catalytic serine.

57. The mutant signal peptidase of embodiment 56, wherein the selected amino acid is a serine.

58. A method of identifying an antibiotic effective for treating a bacterial infection involving an arylomycin-resistant bacterial species, comprising contacting the arylomycin-resistant bacteria with a test agent and observing whether the test agent inhibits growth of the arylomycin-resistant bacteria, wherein the arylomycin-resistant bacteria encodes or expresses a signal peptidase enzyme that has a proline residue 5 to 7 amino acids N-terminal to the signal peptidase catalytic serine.

59. A method of identifying a compound that has antibiotic activity against bacteria comprising contacting a culture of bacteria with the test compound and identifying whether the test compound inhibits growth of the bacteria, wherein the bacteria in the culture expresses a modified SPase that has a natural bacterial SPase amino acid sequence modified at position −5 to −7 relative to the catalytic serine by substitution or replacement of an amino acid at that position.

60. The method of embodiment 59, wherein an amino acid at position −5 and/or at position—7 relative to the catalytic serine is replaced with a proline.

61. The method of embodiment 59, wherein the amino acid at position −5 and/or at position −7 relative to the catalytic serine is a proline replaced by a selected amino acid.

62. The method of embodiment 61, wherein the selected amino acid is a serine.

63. The method of embodiments 58 to 62, wherein the test compound that inhibits the growth of the bacteria has antibiotic activity.

All patents and publications referred to herein are incorporated by reference herein to the same extent as if each individual publication was specifically and individually indicated to be incorporated by reference in its entirety.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A compound of formula (I)

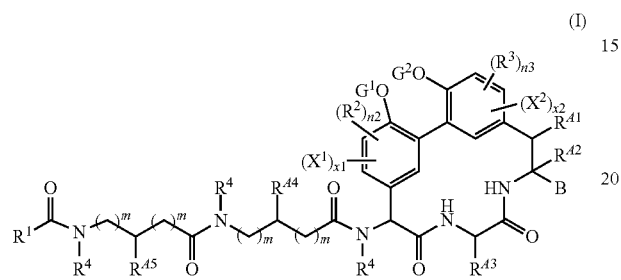

(I)

wherein

B is $CO_2H$, $CH_2CO_2H$, $C(=O)NHCH_2C(=O)H$, $CH_2C(=O)H$, $C(=O)NHCH_2B(OR^B)_2$ or $C(=O)NHCH_2P(=O)(OR^B)_2$ wherein $R^B$ is H or $(C_1-C_6)$ alkyl, or B is a group of formula

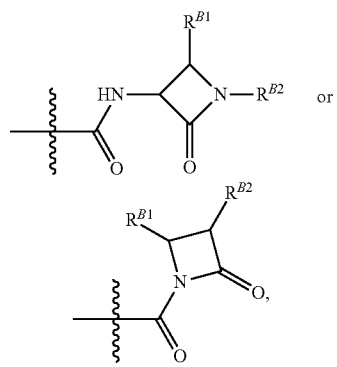

wherein $R^{B1}$ and $R^{B2}$ are each independently H, $(C_1-C_6)$ alkyl, $(C_3-C_6)$ cycloalkyl, $OR^C$, $C(=O)NR^C$, $OC(=O)NR^C_2$, $C(=O)OR^C$, $OC(=O)OR^C$, nitro, trifluoromethyl, trifluoromethoxy, $(C_1-C_6)$alkoxy, $(C_1-C_6)$thioalkoxy, $NR^C_2$, 5-7 membered heterocyclyl, 5-7 membered heteroaryl, or $(C_6-C_{10})$ aryl; $R^C$ is independently at each occurrence H or $(C_1-C_6)$ alkyl, and a wavy line indicates a point of attachment of B to a carbon of formula (I) bearing B;

each m is independently 0, 1, or 2;

$R^1$ comprises a group of formula (IIA) or (IIB) or (IIC)

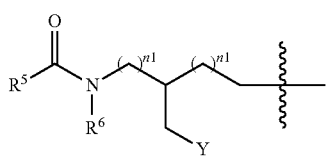

(IIA)

-continued

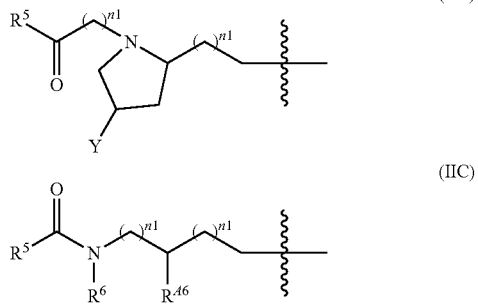

(IIB)

(IIC)

wherein n1 is independently at each occurrence 0, 1, or 2; Y is $(CH_2)_{0-2}H$, $(CH_2)_{0-2}OH$, or $(CH_2)_{0-2}OC(=O)(C_1-C_6)$alkyl; $R^{46}$ is hydrogen, $(C_1-C_6)$alkyl, $(C_3-C_7)$cycloalkyl, 5- to 7-membered heteroaryl, 5- to 7- membered heterocyclyl, or $(C_6-C_{10})$ aryl, wherein any alkyl, cycloalkyl, heterocyclyl, aryl or heteroaryl may be substituted with 1 to 3 substituents, wherein each substituent is independently selected from the group consisting of halogen, amino, hydroxyl, aminocarbonyl, hydroxycarbonyl, nitro, cyano, trifluoromethyl, trifluoromethoxy, 5- to 7- membered heterocyclyl, $(C_1-C_6)$ alkoxy, $(C_1-C_6)$alkyl, $(C_3-C_7)$cycloalkyl, $(C_1-C_6)$-mono- or di-alkylamino, $(C_1-C_6)$alkoxycarbonyl, $(C_1-C_6)$alkylhydroxycarbonyl, $(C_1-C_6)$alkylamino carbonyl, $(C_1-C_6)$alkylsulfonylamino , and $(C_6-C_{10})$-arylsulfonylamino;

and a wavy line indicates a point of attachment of $R^1$ to an atom of formula (I) bearing $R^1$; and $R^5$ is a linear or branched alkyl chain of about 1-22 carbon atoms, bonded to the carbonyl carbon to which it is attached directly or by an O or NR, to provide an amide, carbamate, or urea linkage respectively; optionally comprising within the chain or at a chain terminus, any of the following groups (A) through (D):

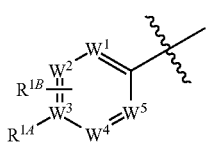

(A)

wherein $W^{1'}$, $W^{2'}$, $W^{3'}$, $W^{4'}$ and $W^{5'}$ are each independently C or N, provided that no more than two of $W^{1'}$, $W^{2'}$, $W^{3'}$, $W^{4'}$ and $W^{5'}$ are N; provided that when $R^{1A}$ or $R^{1B}$ is non-hydrogen, any $W^{1'}$, $W^{2'}$, $W^{3'}$, $W^{4'}$ and $W^{5'}$ to which $R^{1A}$ or $R^{1B}$ is respectively bonded is C, wherein at least two $R^{1B}$ are bonded to the ring bearing $W^{1'}$, $W^{2'}$, $W^{3'}$, $W^{4'}$ and $W^{5'}$;

$R^{1A}$ is hydrogen, halogen, amino, hydroxyl, aminocarbonyl, hydroxycarbonyl, nitro, fluoroalkyl, cyano, $(C_1-C_6)$-thioether, fluoroalkoxy, $(C_1-C_6)$-alkyl, $(C_1-C_6)$-alkoxy, $(C_1-C_6)$-mono- or di-alkylamino, 5- to 7-membered heteroaryl, 5- to 7-membered heterocyclyl, or $(C_6-C_{10})$ aryl;

$R^{1B}$ is hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-alkylamino, 5- to 7- membered heteroaryl, 5- to 7- membered heterocyclyl, or $(C_6-C_{10})$ aryl;

wherein any non-hydrogen $R^{1A}$ or $R^{1B}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-alkylamino, 5- to 7- membered heteroaryl, 5- to 7- membered heterocyclyl, or $(C_6-C_{10})$ aryl groups;

wherein a wavy line indicates a point of attachment:

(B)

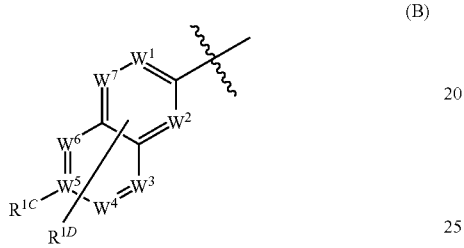

wherein $W^1$, $W^2$, $W^3$, $W^4$, $W^5$, $W^6$, and $W^7$ are each independently C or N, provided that no more than three of $W^1$, $W^2$, $W^3$, $W^4$, $W^5$, $W^6$, and $W^7$ are N; provided that when $R^{1C}$ or $R^{1D}$ is non-hydrogen, any W atom to which the $R^{1C}$ or $R^{1D}$ is respectively bonded is C, wherein at least three $R^{1D}$ are bonded to the rings bearing $W^1$, $W^2$, $W^3$, $W^4$, $W^5$, $W^6$, and $W^7$;

$R^{1C}$ is hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, 5- to 7- membered heteroaryl, 5- to 7-membered heterocyclyl, or $(C_6-C_{10})$ aryl;

$R^{1D}$ is hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, 5- to 7- membered heteroaryl, 5- to 7-membered heterocyclyl, or $(C_6-C_{10})$ aryl;

wherein any non-hydrogen $R^{1C}$ or $R^{1D}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$thioalkyl, fluoroalkoxy, cyano, $(C_1-C_6)$-alkyl, $(C_1-C_6)$-alkoxy, $(C_1-C_6)$-mono- or di-alkylamino, 5- to 7- membered heteroaryl, 5- to 7- membered heterocyclyl, or $(C_6-C_{10})$ aryl;

wherein a wavy line indicates a point of attachment;

(C)

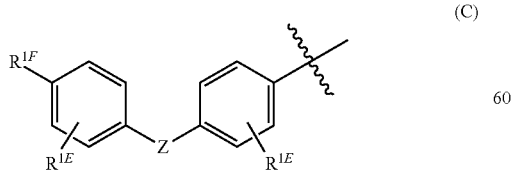

wherein Z is O, S, NH or $CH_2$;

$R^{1E}$ at each occurrence is independently hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, 5- to 7- membered heteroaryl, 5- to 7- membered heterocyclyl, or $(C_6-C_{10})$ aryl;

$R^{1F}$ is hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, 5- to 7- membered heteroaryl, 5- to 7-membered heterocyclyl, or $(C_6-C_{10})$ aryl;

wherein any non-hydrogen $R^{1E}$ or $R^{1F}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$thioalkyl, fluoroalkoxy, cyano, $(C_1-C_6)$-alkyl, $(C_1-C_6)$-alkoxy, $(C_1-C_6)$-mono- or di-alkylamino, 5- to 7- membered heteroaryl, 5- to 7- membered heterocyclyl, or $(C_6-C_{10})$ aryl;

wherein a wavy line indicates a point of attachment; or (D)

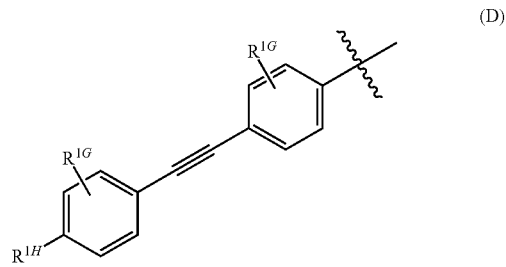

wherein $R^{1G}$ at each occurrence is independently hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, 5- to 7- membered heteroaryl, 5- to 7- membered heterocyclyl, or $(C_6-C_{10})$ aryl;

$R^{1H}$ is hydrogen, halogen, amino, hydroxyl, aminocarbonyl, hydroxycarbonyl, nitro, fluoroalkyl, $(C_1-C_6)$-thioalkyl, fluoroalkoxy, cyano, $(C_1-C_6)$-alkyl, $(C_1-C_6)$-alkoxy, $(C_1-C_6)$-mono- or di-alkylamino, 5- to 7- membered heteroaryl, 5- to 7-membered heterocyclyl, or $(C_6-C_{10})$ aryl;

wherein any non-hydrogen $R^{1G}$ or $R^{1H}$ can be further substituted with one to three $(C_1-C_{12})$-alkyl or -alkoxy groups, which can further bear halogen, amino, hydroxyl, aminocarbonyl, hydroxycarbonyl, nitro, fluoroalkyl, $(C_1-C_6)$thioalkyl, fluoroalkoxy, cyano, $(C_1-C_6)$-alkyl, $(C_1-C_6)$-alkoxy, $(C_1-C_6)$-mono- or di-alkylamino, 5- to 7- membered heteroaryl, 5- to 7- membered heterocyclyl, or $(C_6-C_{10})$ aryl;

wherein a wavy line indicates a point of attachment;

$R^2$ and $R^3$ are each independently nitro, halo, cyano, hydroxy, glycosyloxy, amino, $(C_1-C_4)$alkoxy, $(C_1-C_4)$ acyloxy, or $(C_1-C_4)$alkyl, wherein any carbon atom can be unsubstituted or substituted with J, wherein n2 and n3 are independently 0, 1, 2, or 3; or wherein two $R^2$ groups taken together, and/or two $R^3$ groups taken together, can comprise fused cycloalkyl, aryl, heterocyclyl, or heteroaryl ring or rings, any of which is substituted with 0-3 J;

$R^4$ and $R^6$ are each independently at every occurrence hydrogen, $(C_1-C_6)$alkyl, $(C_3-C_7)$cycloalkyl, 5- to 7- membered heteroaryl, 5- to 7- membered heterocyclyl, or $(C_6-C_{10})$ aryl,
wherein any alkyl, cycloalkyl, heterocyclyl, aryl or heteroaryl can be substituted with 1 to 3 J;

$R^{41}$, $R^{42}$, $R^{43}$, $R^{44}$, and $R^{45}$ are independently at each occurrence hydrogen, $(C_1-C_6)$alkyl, $(C_3-C_7)$cycloalkyl, 5- to 7- membered heteroaryl, 5- to 7- membered heterocyclyl, or $(C_6-C_{10})$ aryl,
wherein any alkyl, cycloalkyl, heterocyclyl, aryl or heteroaryl can be substituted with 1 to 3 J;

J is halogen, OR', CN, $CF_3$, $OCF_3$, O, S, C(O), S(O), methylenedioxy, ethylenedioxy, $(CH_2)_{0-p}N(R')_2$, $(CH_2)_{0-p}SR'(CH_2)_{0-p}S(O)R'(CH_2)_{0-p}S(O)_2R'(CH_2)_{0-p}S(O)_2N(R')_2(CH_2)_{0-p}SO_3R'(CH_2)_{0-p}C(O)R'(CH_2)_{0-p}C(O)CH_2C(O)R'(CH_2)_{0-p}C(S)R'(CH_2)_{0-p}C(O)OR'(CH_2)_{0-p}OC(O)R'(CH_2)_{0-p}C(O)N(R')_2(CH_2)_{0-p}OC(O)N(R')_2(CH_2)_{0-p}C(S)N(R')_2$, $(CH_2)_{0-p}NH—C(O)R'$, $(CH_2)_{0-p}N(R')N(R')C(O)R'$, $(CH_2)_{0-p}N(R')N(R')C(O)OR'$, $(CH_2)_{0-p}N(R')N(R')CON(R')_2$, $(CH_2)_{0-p}N(R')SO_2R'$, $(CH_2)_{0-p}N(R')SO_2N(R')_2$, $(CH_2)_{0-p}N(R')C(O)OR'$, $(CH_2)_{0-p}N(R')C(O)R'$, $(CH_2)_{0-p}N(R')C(S)R'$, $(CH_2)_{0-p}N(R')C(O)N(R')_2$, $(CH_2)_{0-p}N(R')C(S)N(R')_2$, $(CH_2)_{0-p}N(COR')COR'$, $(CH_2)_{0-p}N(OR')R'$, $(CH_2)_{0-p}C(=NH)N(R')_2$, $(CH_2)_{0-p}C(O)N(OR')R'$, or $(CH_2)_{0-p}C(=NOR')R$;
wherein p is about 4, each R' is independently at each occurrence hydrogen, $(C_1-C_{12})$-alkyl, $(C_2-C_{12})$-alkenyl, $(C_2-C_{12})$-alkynyl, $(C_3-C_{10})$-cycloalkyl, $(C_3-C_{10})$-cycloalkenyl, $[(C_3-C_{10})$cycloalkyl or $(C_3-C_{10})$-cycloalkenyl]-$[(C_1-C_{12})$-alkyl or $(C_2-C_{12})$-alkenyl or $(C_2-C_{12})$-alkynyl], $(C_6-C_{10})$-aryl, $(C_6-C_{10})$-aryl-$[(C_1-C_{12})$-alkyl or $(C_2-C_{12})$-alkenyl or $(C_2-C_{12})$-alkynyl], mono- or bicyclic 3-10 membered heterocyclyl, mono- or bicyclic 3-10 membered heterocyclyl-$[(C_1-C_{12})$-alkyl or $(C_2-C_{12})$-alkenyl or $(C_2-C_{12})$-alkynyl], mono- or bicyclic 5-10 membered heteroaryl, or mono- or bicyclic 5-10 membered heteroaryl-$[(C_1-C_{12})$-alkyl or $(C_2-C_{12})$-alkenyl or $(C_2-C_{12})$-alkynyl];

or, when two R' are bound to a nitrogen atom or to two adjacent nitrogen atoms, the two R' groups together with the nitrogen atom or atoms to which they are bound can form a 3- to 8-membered monocyclic heterocyclic ring, or an 8- to 20-membered, bicyclic or tricyclic, heterocyclic ring system, wherein any ring or ring system can further contain 1-3 additional heteroatoms selected from the group consisting of N, O, S, S(O) and $S(O)_2$;

wherein, in any bicyclic or tricyclic ring system, each ring is linearly fused, bridged, or spirocyclic,
wherein each ring can be fused to a $(C_6-C_{10})$aryl, mono- or bicyclic 5-10 membered heteroaryl, $(C_3-C_{10})$cycloalkyl or mono- or bicyclic 3-10 membered heterocyclyl;

$G^1$ and $G^2$ are each independently a hydrogen or a glycosyl residue, or a group cleavable under physiological conditions to provide a compound of formula (I) wherein $G^1$ or $G^2$ respectively is hydrogen;

$(X^1)_{x1}$ and $(X^2)_{x2}$ each signify that 0, 1, or 2 ring atoms of each respective ring can be nitrogen, provided that where a non-hydrogen substituent is bonded, $X^1$ or $X^2$, respectively, is C;

provided that when $G^1$ is a 6-deoxyhexopyranosyl residue, $G^2$ is H, $R^1$ is of formula (IIA), n2 is 0 or n2 is 1 and $R^2$ is hydroxy, n3 is 0, $R^{41}$ and $R^{42}$ and $R^{44}$ are H, $R^{43}$ and $R^{45}$ are methyl, and B is $CO_2H$, or when $G^1$ and $G^2$ are H, $R^1$ is of formula (IIA), n2 is 0, n3 is 0 or n3 is 1 and $R^3$ is nitro, $R^{41}$ and $R^{42}$ and $R^{44}$ are H, $R^{43}$ and $R^{45}$ are methyl, and B is $CO_2H$, then $R^5$ is not a linear or branched unsubstituted $(C_{10}-C_{16})$- alkyl;

or a salt thereof.

2. The compound of claim 1 wherein the compound is of formula (IA)

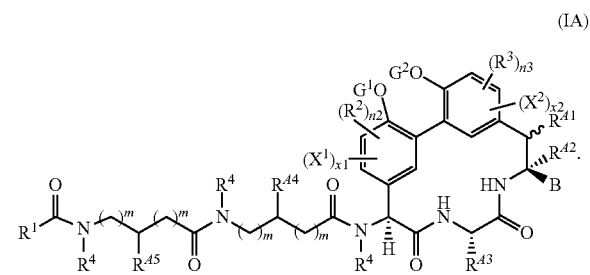

(IA)

3. The compound of claim 1 wherein $R^1$ is a group of formula (IIAS) or (IIBS)

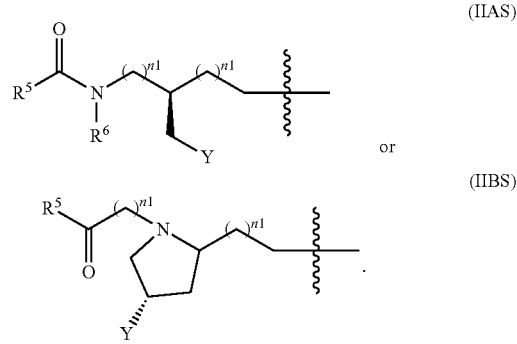

4. The compound of claim 1 wherein $R^5$ is a $(C_1-C_{22})$ linear or branched alkyl.

5. The compound of claim 2 wherein $R^5$ is a $(C_1-C_{22})$ linear or branched alkyl.

6. The compound of claim 1 wherein $R^5$ is a $(C_1-C_{22})$ linear or branched alkyl, comprising one or more of groups (A), (B), (C), or (D), of claim 1.

7. The compound of claim 1 wherein $R^5$ is any of the following groups

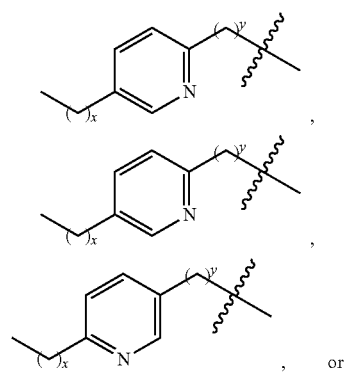

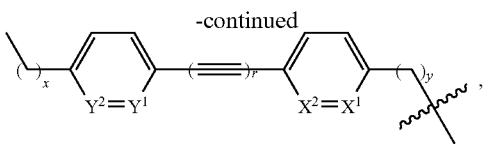

wherein x is 0-14, y is 0-14, provided that x+y<22, and $X^1, X^2, Y^1$ and $Y^2$ are each independently C or N, provided that no more than one of $X^1$ and $X^2$, and no more than one of $Y^1$ and $Y^2$, is N, wherein a wavy line indicates a point of attachment of $R^5$ to an atom bonded to $R^5$ in formula (IIA), (IIB), or (IIC).

8. The compound of claim 1 wherein $R^5$ is any of the following:

methyl, ethyl, $(C_3-C_{22})$-n-alkyl, $(C_3-C_{22})$-isoalkyl, $(C_4-C_{22})$-anteisoalkyl, naphthyl, naphthylmethyl, biphenyl, $(C_2-C_{10})$alkylbiphenyl, biphenylmethyl, or $(C_2-C_{10})$alkylbiphenylmethyl.

9. The compound of claim 1 wherein at least one of n2 and n3 is 0.

10. The compound of claim 1 wherein at least one of $R^2$ and $R^3$ is nitro, halo, cyano, hydroxy, glycosyloxy, amino, $(C_1-C_4)$alkoxy, or $(C_1-C_4)$alkyl, and n2 or n3 respectively, or both, is 1.

11. The compound of claim 1 wherein both G are hydrogen.

12. The compound of claim 1 wherein any of $R^{A1}$, $R^{A2}$ and $R^{A4}$ are hydrogen, any of $R^{A3}$ and $R^{A5}$ are methyl, or any combination thereof.

13. The compound of claim 1 wherein $R^{A3}$ is hydrogen, methyl, ethyl, n-propyl, isopropyl, n-butyl, isobutyl, 3-hydroxypropyl, 4-hydroxybutyl, or 2,2,2-trifluoroethyl.

14. The compound of claim 1 wherein all of $R^4$ and $R^6$ are independently selected hydrogen or methyl.

15. The compound of claim 1 wherein the compound is any of the following compounds of formula (III)

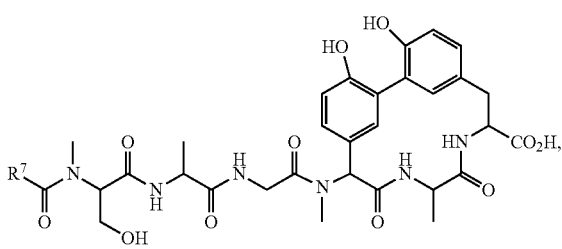

(III)

wherein $R^7$ is $(C_8-C_{18})$-n-alkyl, $(C_8-C_{18})$-isoalkyl, $(C_8-C_{18})$-anteisoalkyl, any of which includes a group (A), (B), (C), or (D), of claim 1; or is 2-naphthyl, 6-$(C_2-C_{10})$alkyl-2-naphthyl, 2-naphthylmethyl, 6-$(C_2-C_{10})$alkyl-2-naphthylmethyl, 4-biphenyl, 4-biphenylmethyl, 4'-$(C_2-C_{10})$alkyl-4-biphenyl, 4'-$(C_2-C_{10})$alkyl-4-biphenylmethyl, p-$(C_4-C_{12})$alkyl-phenyl, or p-$(C_4-C_{12})$alkyl-benzyl;

or a salt thereof.

16. The compound of claim 1 wherein the compound is any of the following compounds of formula (IV)

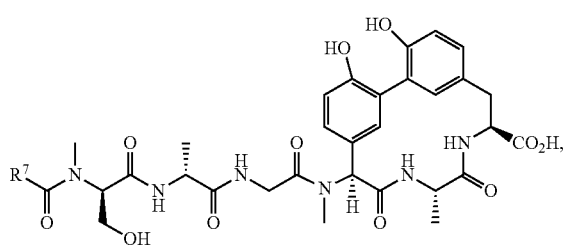

(IV)

wherein $R^7$ is $(C_8-C_{18})$-n-alkyl, $(C_8-C_{18})$-isoalkyl, $(C_8-C_{18})$-anteisoalkyl, any of which includes a group (A), (B), (C), or (D), of claim 1; or is 2-naphthyl, 6-$(C_2-C_2)$alkyl-2-naphthyl, 2-naphthylmethyl, 6-$(C_2-C_{10})$alkyl-2-naphthylmethyl, 4-biphenyl, 4-biphenylmethyl, 4'-$(C_2-C_{10})$alkyl-4-biphenyl, 4'-$(C_2-C_{10})$alkyl-4-biphenylmethyl, p-$(C_4-C_{12})$alkyl-phenyl, or p-$(C_4-C_{12})$alkyl-benzyl;

or a salt thereof.

17. A pharmaceutical composition comprising the compound of claim 1, or a salt thereof, and a pharmaceutically acceptable excipient.

18. A method of treatment of a bacterial infection in an animal, comprising administering an effective amount of a compound of claim 1, or a salt thereof, to the animal at a frequency and for a duration sufficient to provide a beneficial effect to the animal.

19. The method of claim 18 wherein a causative bacterial species of the bacterial infection is of a genotype resistant to treatment with arylomycin A2.

20. The method of claim 18, wherein the bacterial infection is an infection involving *Corynebacterium diphtheriae, Corynebacterium glutamicum, Campylobacter jejuni, Chlamydia trachomatis, Chlamydophila pneumoniae, Francisella tularensis, Helicobacter pylori, Lactococcus lactis* subsp. *cremoris, Lactococcus lactis* subsp. *lactis, Propionibacterium acnes, Rhodococcus equi, Rhodococcus opacus, Staphylococcus capitis, Staphylococcus caprae, Staphylococcus carnosus, Staphylococcus cohnii, Staphylococcus epidermidis, Staphylococcus haemolyticus, Staphylococcus hominis, Staphylococcus hominis* subsp. *hominis, Staphylococcus hominis* subsp. *novobiosepticus, Staphylococcus lugdunensis, Streptococcus agalactiae, Streptococcus dysgalactiae, Streptococcus mitis, Streptococcus oxalis, Streptococcus pyogenes, Streptococcus pnemoniae*, and/or *Yersinia pestis*.

21. The method of claim 18, wherein the bacterial infection is an infection involving a gram negative bacteria.

22. A method of treating a bacterial infection in an animal comprising administering to the animal any one or any combination of the compounds of claim 1, or a salt thereof, wherein the bacterial infection comprises an infection by a bacteria that encodes or expresses an SPase enzyme that has a proline within about 10 amino acids N-terminal to the SPase catalytic serine.

23. The method of claim 22, wherein the bacteria encodes or expresses an SPase enzyme that does not have a proline 5 to 7 amino acids N-terminal to the SPase catalytic serine.

24. The method of claim 22, wherein the bacterial infection involves *Staphylococcus capitis, Staphylococcus caprae* and/or *Yersinia pestis*.

25. The method of claim 18 further comprising administering a second therapeutic agent.

26. The method of claim 25, wherein the second therapeutic agent is a non-arylomycin antibiotic.

27. The method of claim 26, wherein the non-arylomycin antibiotic is an aminoglycoside antibiotic, fluoroquinolone antibiotic, penicillin antibiotic, cephalosporin antibiotic, macrolide antibiotic, glycopeptide antibiotic, rifampicin, chloramphenicol, fluoramphenicol, colistin, mupirocin, bacitracin, daptomycin, or linezolid.

28. A compound having the structure:

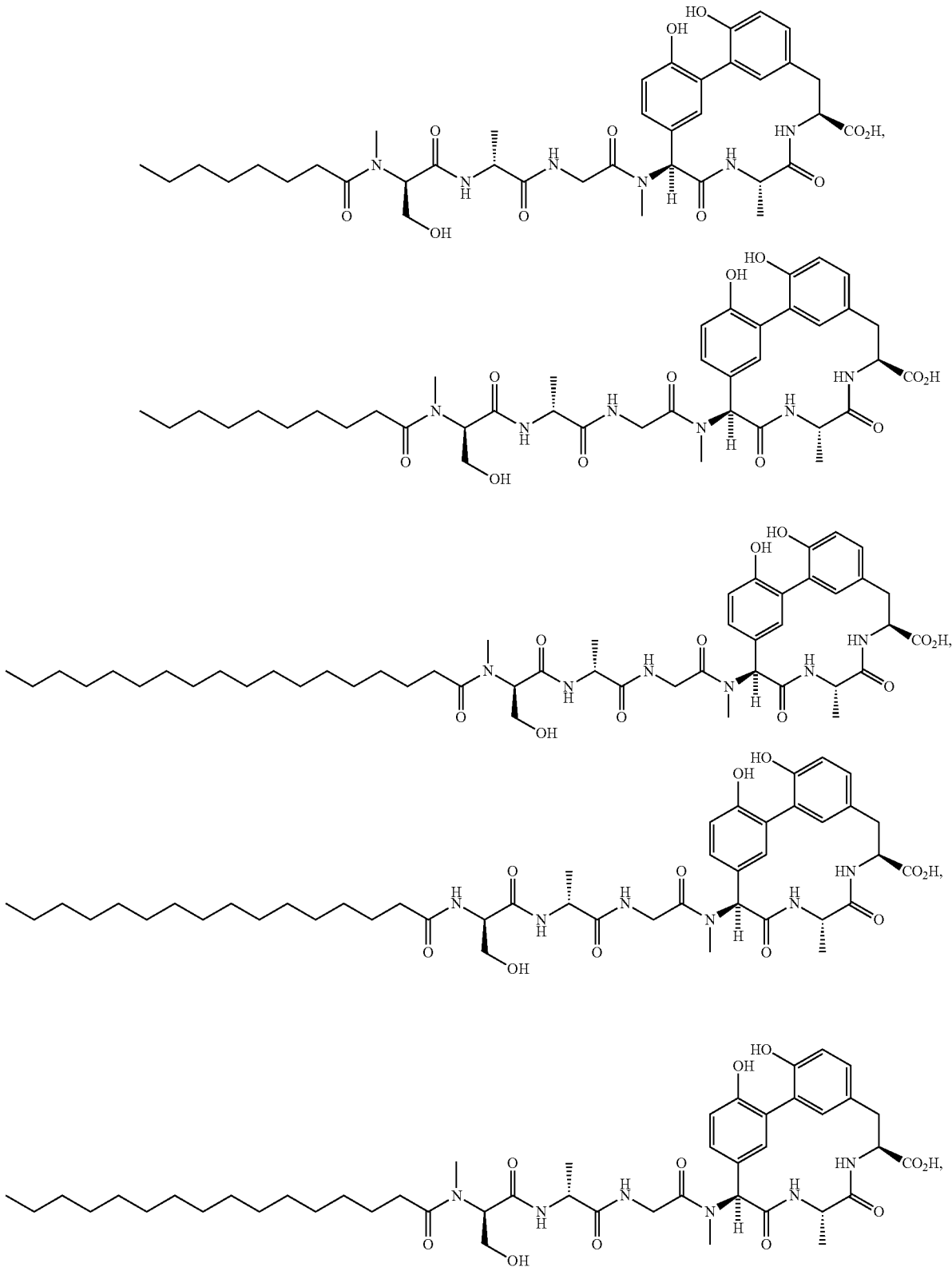

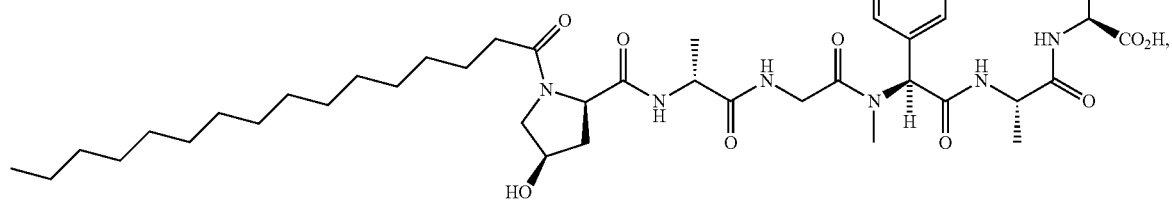
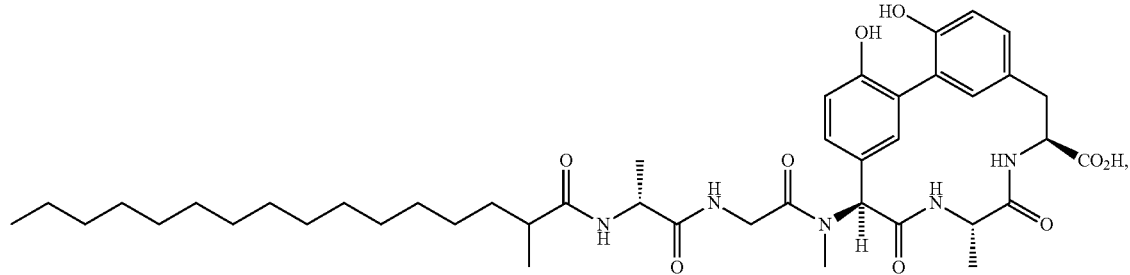
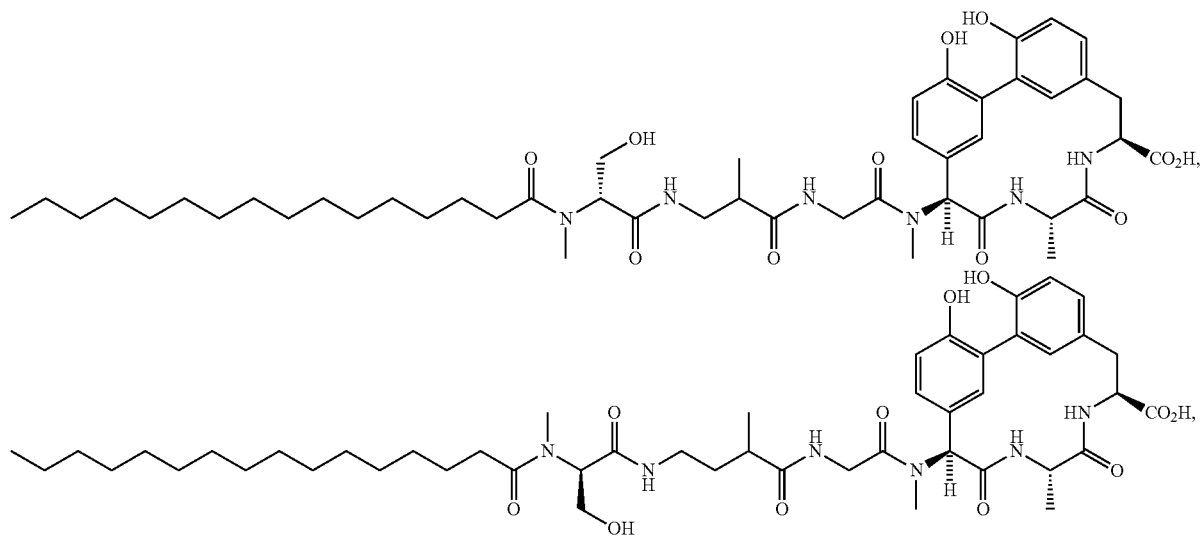
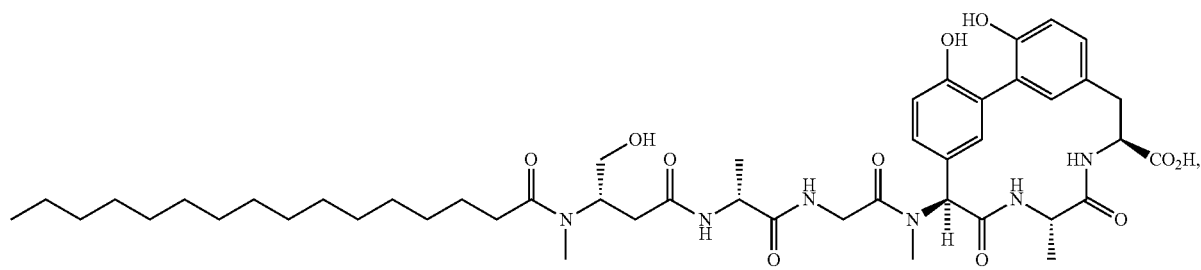

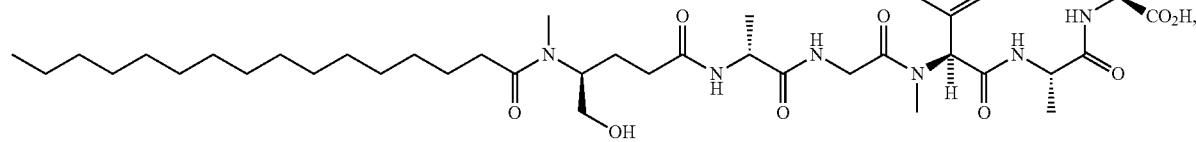
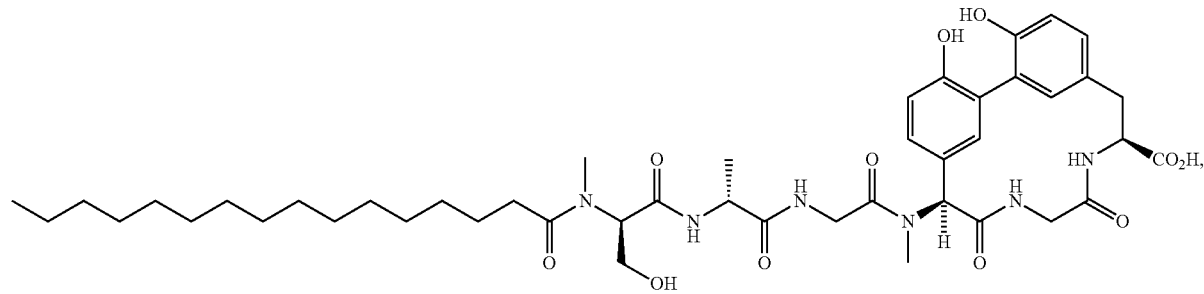
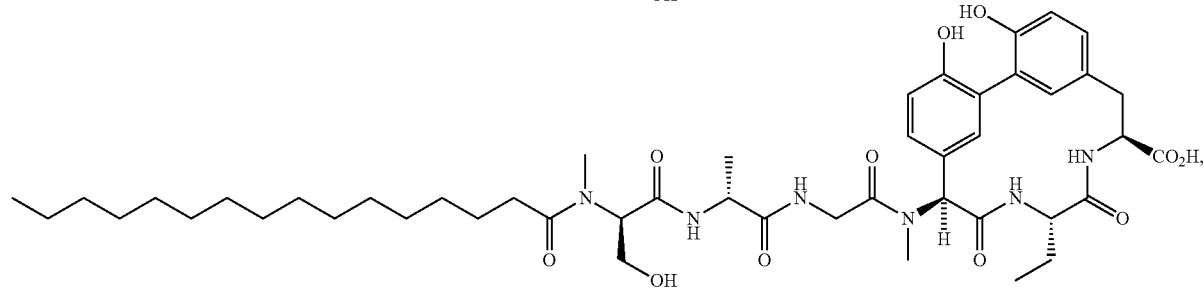
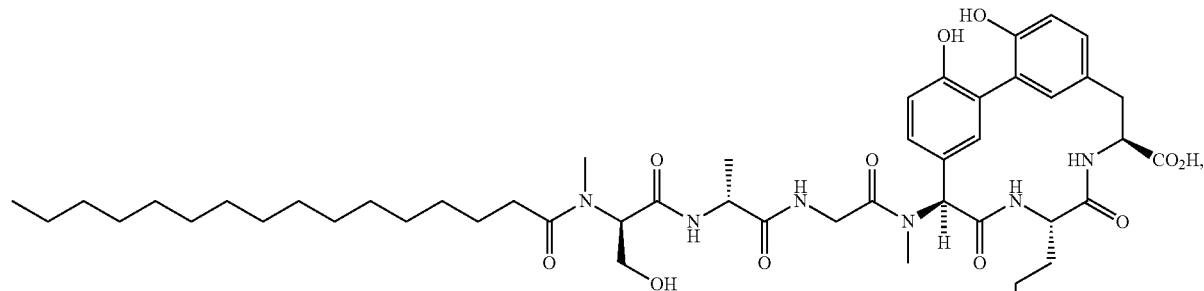
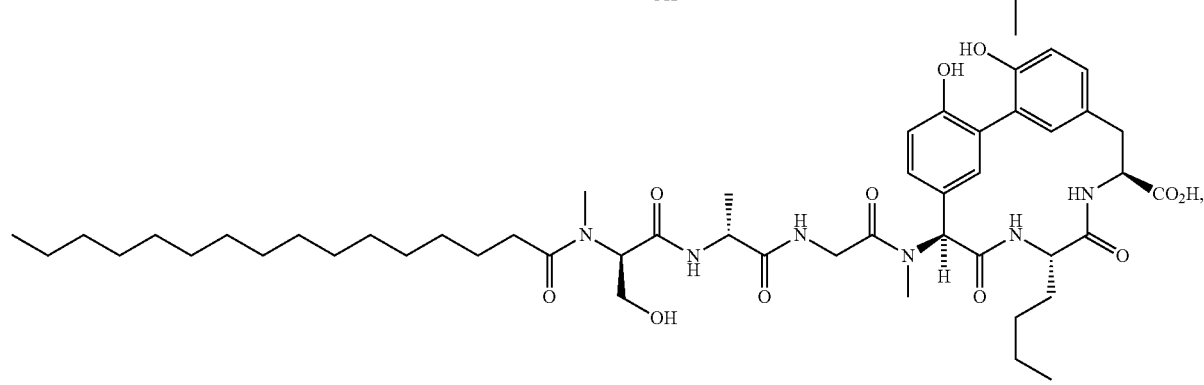

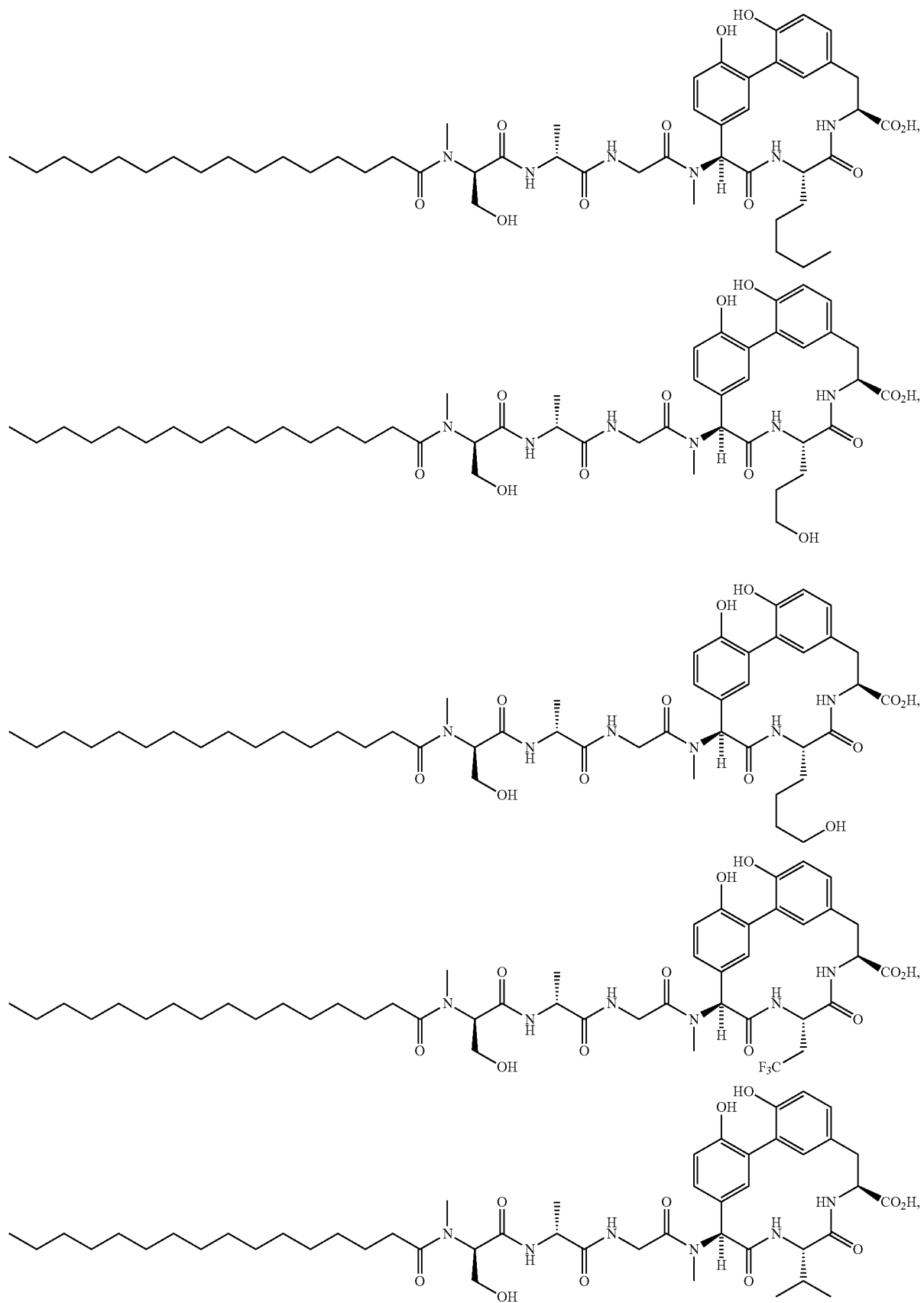

387                                            388
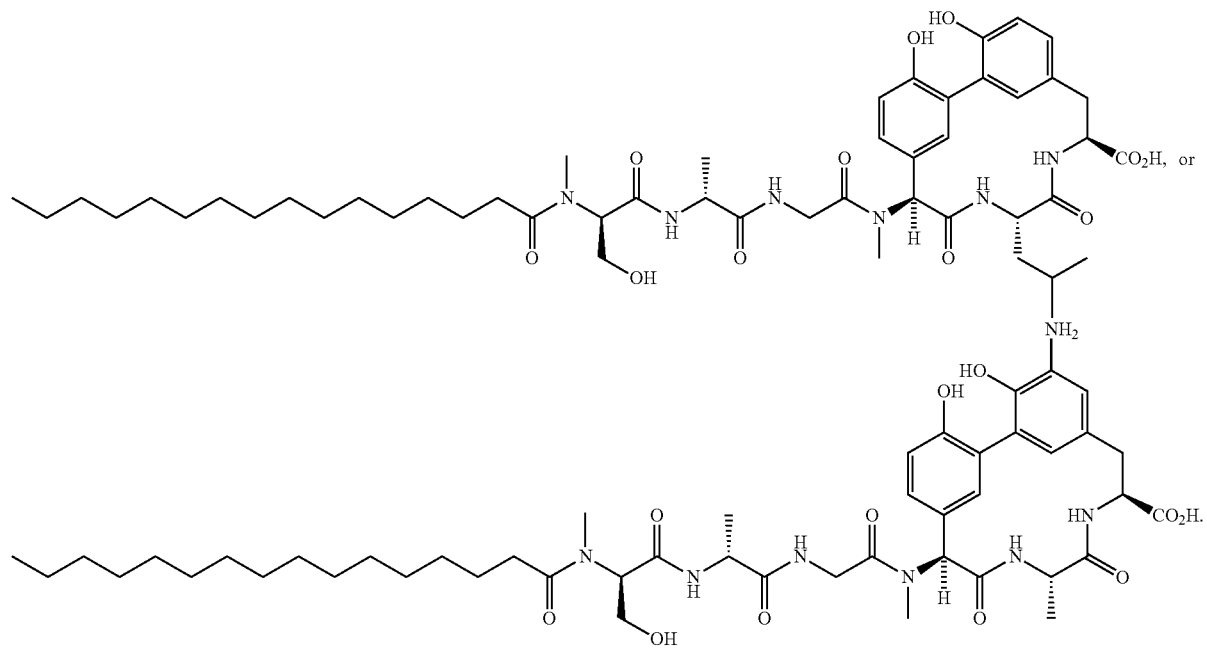
29. A compound having the structure:
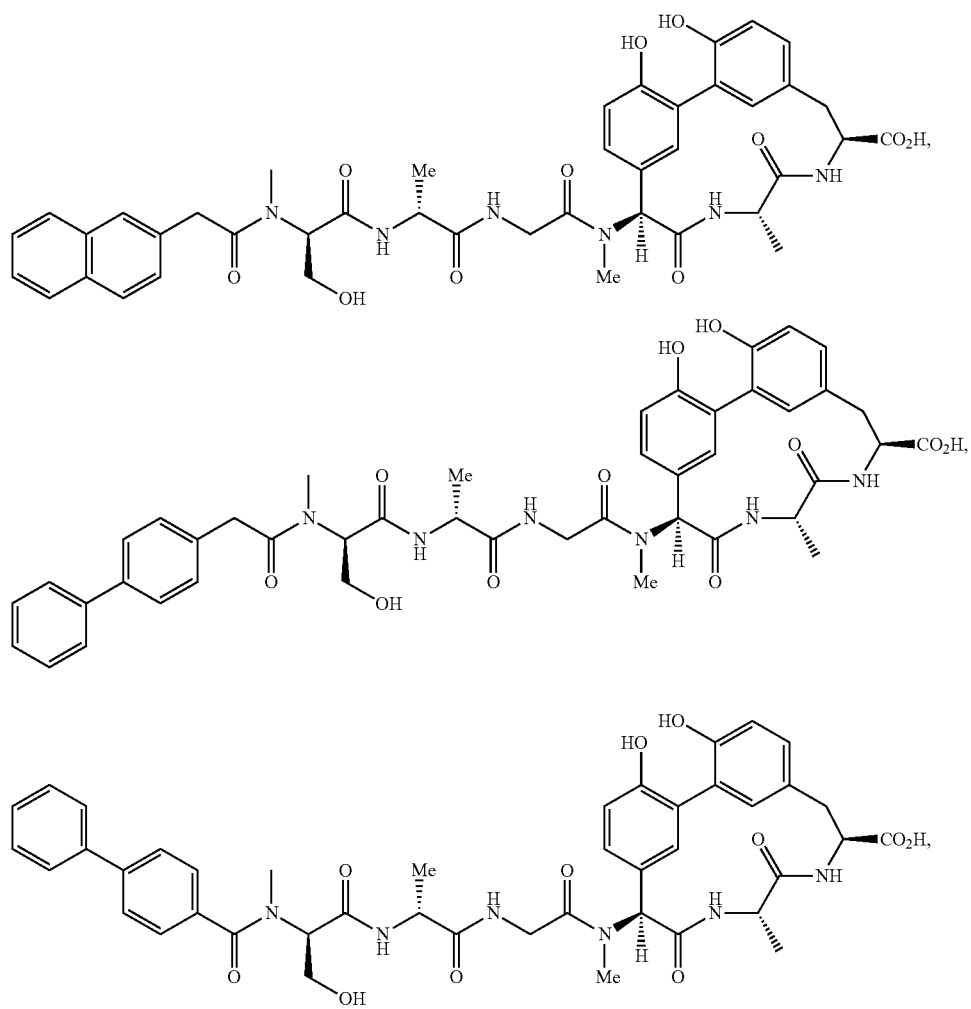

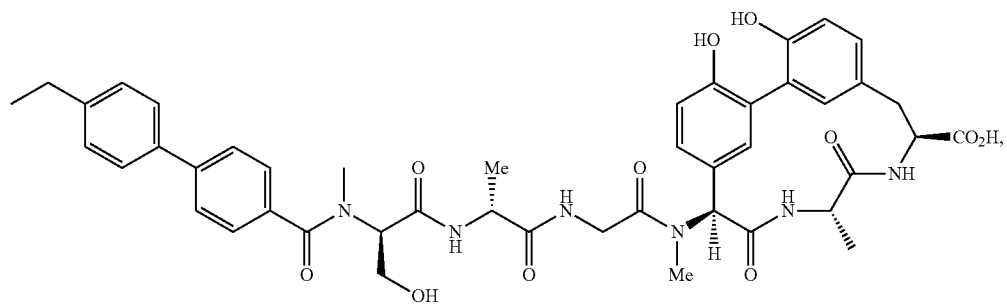
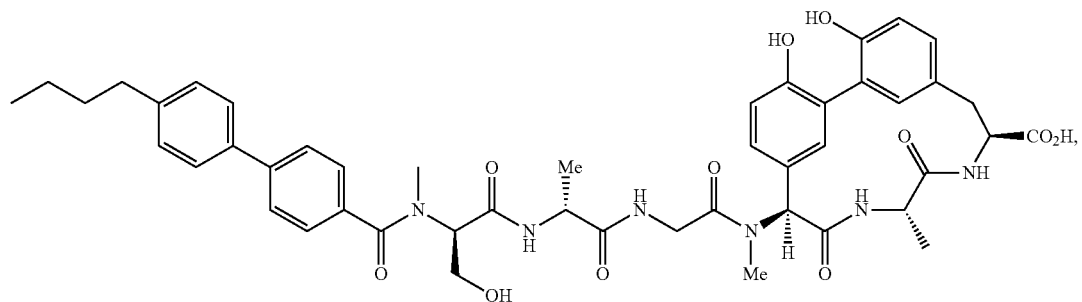
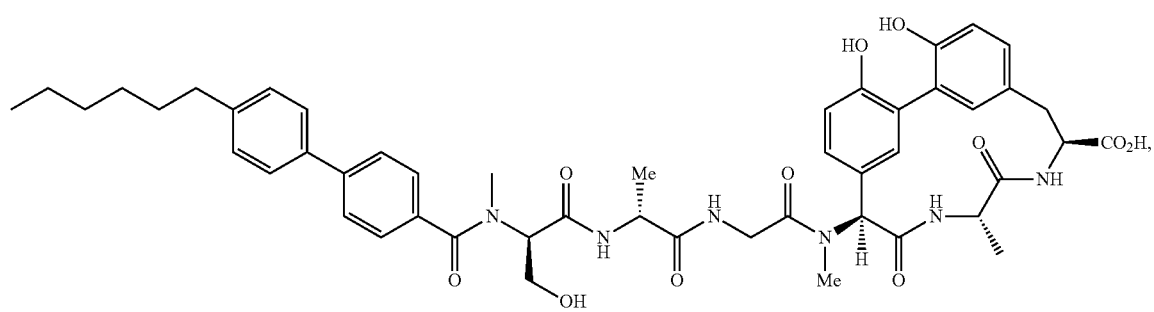
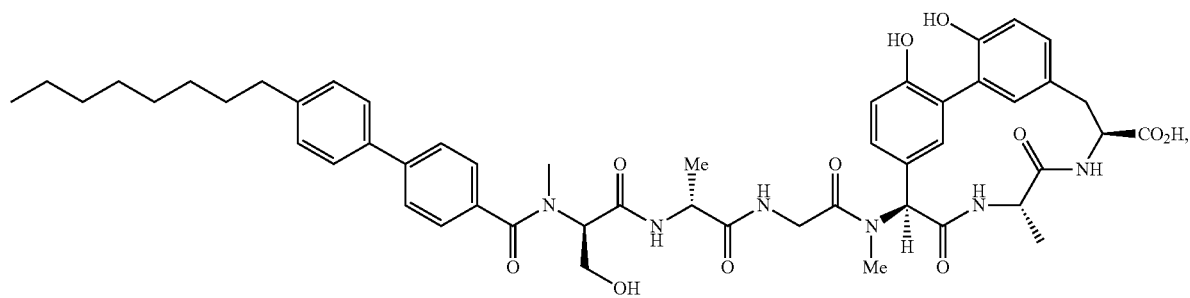
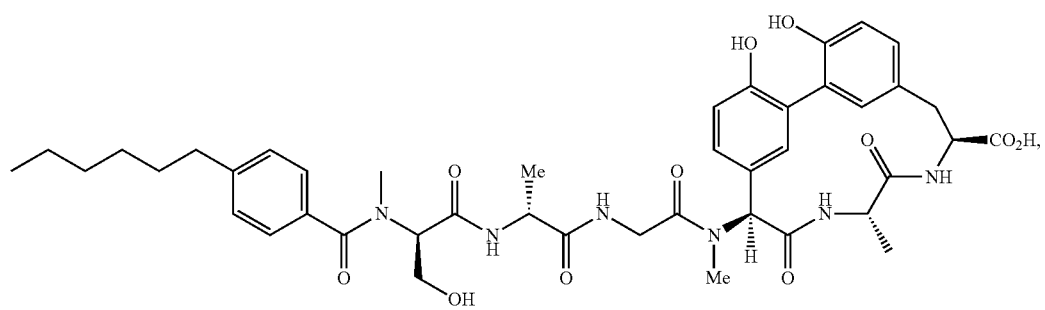

391                                   392
-continued
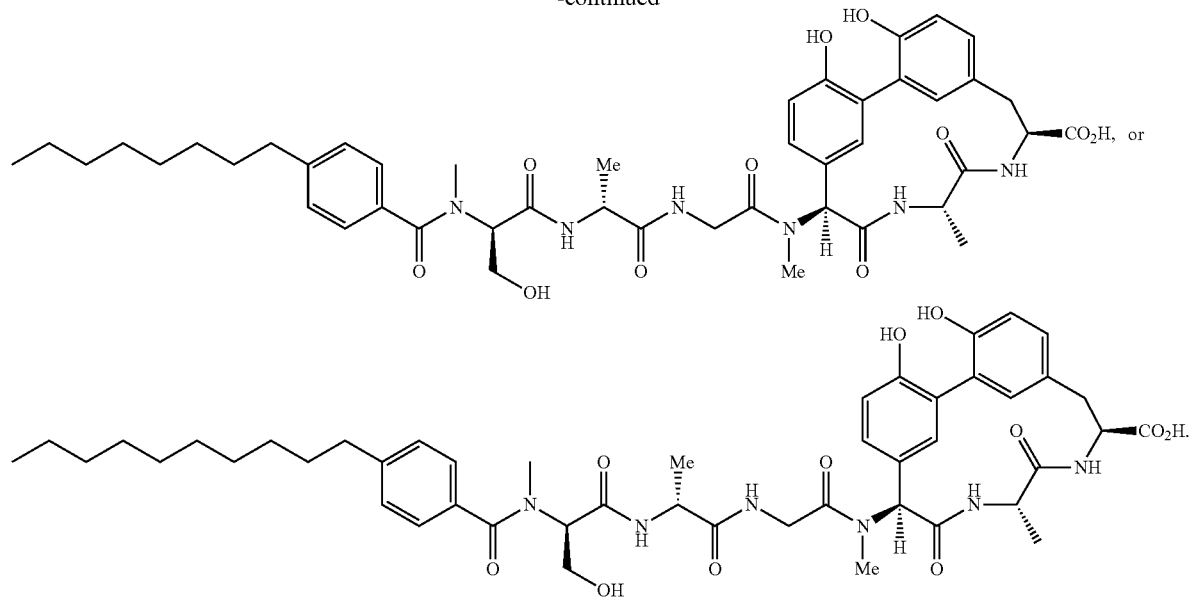
* * * * *

UNITED STATES PATENT AND TRADEMARK OFFICE
CERTIFICATE OF CORRECTION

| | | |
|---|---|---|
| PATENT NO. | : 9,187,524 B2 | Page 1 of 16 |
| APPLICATION NO. | : 13/821195 | |
| DATED | : November 17, 2015 | |
| INVENTOR(S) | : Romesberg et al. | |

It is certified that error appears in the above-identified patent and that said Letters Patent is hereby corrected as shown below:

Title page

Item (57), in "Abstract", in column 2, line 10, delete "A2." and insert --$A_2$.--, therefor On page 2, in column 2, under "Other Publications", line 11, delete "A2." and insert --$A_2$.--, therefor On page 2, in column 2, under "Other Publications", line 12, delete "B2" and insert --$B_2$--, therefor Specification In column 1, line 9, delete "A2on" and insert --A2 on--, therefor In column 1, line 19, delete "N00014-03-1-0126and" and insert --N00014-03-1-0126 and--, therefor In column 1, line 33-34, delete "N-methyl-4-hydroxyphenylglycine-5" and insert --N-methyl-4-hydroxyphenylglycine5--, therefor In column 1, line 67, delete "R6," and insert --$R^6$,--, therefor In column 2, line 15, delete "A2" and insert --$A_2$--, therefor In column 5, line 65, delete "$(CH_2)_{0-p}N(R')_{0-9}$" and insert --$(CH_2)_{0-p}N(R')_2$,--, therefor In column 6, line 3, delete "$(CH_2)_{0-p}C(S)N(R)_2$," and insert --$(CH_2)_{0-p}C(S)N(R')_2$,--, therefor In column 6, line 5, delete "$(CH2)_{0-p}N(R')SO_2R, (C^H{}_2)_{0-p}N(R)SO_2$" and insert --$(CH_2)_{0-p}N(R')SO_2R', (CH_2)_{0-p}N(R')SO_2$--, therefor Signed and Sealed this
Twenty-eighth Day of June, 2016

Michelle K. Lee
*Director of the United States Patent and Trademark Office*

CERTIFICATE OF CORRECTION (continued)
U.S. Pat. No. 9,187,524 B2

In column 6, line 6, delete "$(CH_2)_{0-p}N(R)C(O)R_9$" and insert --$(CH_2)_{0-p}N(R')C(O)R'$,--, therefor In column 6, line 7-8, after "$(CH_2)_{0-p}N(R)C(O)N(R)_2, (CH_2)_{0-p}N(R)C(S)N(R)_2$," and insert --$(CH_2)_{0-p}N(R')C(O)N(R')_2, (CH_2)_{0-p}N(R')C(S)N(R')_2$,--, therefor In column 7, line 21, delete "C16" and insert --$C_{16}$--, therefor In column 7, line 33, delete "A2" and insert --$A_2$--, therefor In column 7, line 42, delete "C16" and insert --$C_{16}$--, therefor In column 7, line 44, delete "C16" and insert --$C_{16}$--, therefor In column 10, line 18, delete "benzylhydryloxycarbonyl," and insert --benzhydryloxycarbonyl,--, therefor In column 11, line 21, delete "SOW," and insert --SOR',--, therefor In column 11, line 56, delete "$(CH_2)_n$" and insert --$(CR'_2)_n$--, therefor In column 17, line 19, after "bromine", insert --.--, therefor In column 18, line 8, after "like", insert --.--, therefor In column 25, line 62, delete "$(CH_2)_{0-2}14$," and insert --$(CH_2)_{0-2}H$,--, therefor In column 26, line 66, before "hydrogen,", insert --is--, therefor In column 27, line 29, delete "$R^E$" and insert --$R^{1E}$--, therefor In column 29, line 51, delete "$n^1, n^2, n^3$," and insert --n1, n2, n3,--, therefor In column 30, line 10, delete "$n^1$," and insert --n1,--, therefor In column 31, line 4, delete "$n^2$ or $n^3$" and insert --n2 or n3--, therefor In column 33, line 61, delete "C16-n-alkyl," and insert --$C_{16}$-n-alkyl,--, therefor In column 49, line 8, delete "$C_{1-10}$-substituted" and insert --$C_{10}$-substituted--, therefor In column 50, line 9, delete "C16" and insert --$C_{16}$--, therefor In column 51, line 38, delete "B $C_{16}$" and insert --B-$C_{16}$--, therefor In column 60, Scheme 1, line 1, delete "C16" and insert --$C_{16}$--, therefor In column 60, Scheme 1, line 3, delete " 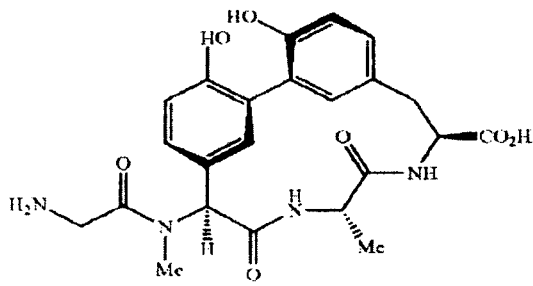 " and insert -- 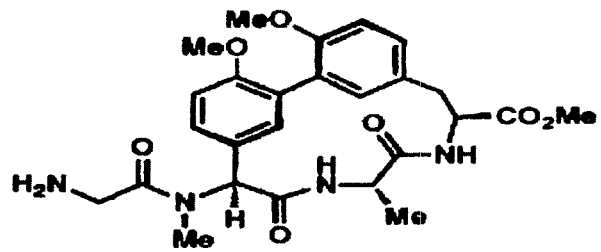 --, therefor In column 61, line 35, delete "A2," and insert --$A_2$,-- therefor In column 61, line 47, delete "A2." and insert --$A_2$.-- therefor In column 66, line 62, delete "RID" and insert --$R^{1D}$-- therefor In column 67, line 55, after "coupling", insert --.-- therefor In column 74, line 12, delete "(S 10)" and insert --(S10)-- therefor In column 74, line 36, delete "L1," and insert --Li,-- therefor In column 74, line 60, delete "A2," and insert --$A_2$,-- therefor In column 80, line 56, delete "(ncbi.nlm nih gov)" and insert --(ncbi.nlm.nih.gov)-- therefor In column 82, line 55, delete "seauences)." and insert --sequences).-- therefor In column 89, line 51, delete "30° C." and insert --30 °C.-- therefor In column 89, line 52, delete "60° C." and insert --60 °C.-- therefor In column 89, line 58, delete "37° C.," and insert --37 °C.,-- therefor In column 89, line 59-60, delete "55° C." and insert --55 °C.-- therefor In column 89, line 62, delete "37° C.," and insert --37 °C.,-- therefor

CERTIFICATE OF CORRECTION (continued)
U.S. Pat. No. 9,187,524 B2

In column 89, line 62, delete "60° C." and insert --60 °C.--, therefor

In column 89, line 64, delete "37° C.," and insert --37 °C.,--, therefor

In column 89, line 65, delete "65° C." and insert --65 °C.--, therefor

In column 90, line 4, delete "$T_m$=81.5° C.+16.6" and insert --$T_m$=81.5 °C.+16.6--, therefor In column 90, line 13, delete "1° C." and insert --1 °C.--, therefor In column 90, line 17, delete "10° C." and insert --10 °C.--, therefor In column 90, line 18, delete "5° C." and insert --5 °C.--, therefor In column 90, line 22, delete "4° C." and insert --4 °C.--, therefor In column 90, line 24, delete "10° C." and insert --10 °C.--, therefor In column 90, line 27, delete "20° C." and insert --20 °C.--, therefor In column 90, line 33, delete "45° C." and insert --45 °C.--, therefor In column 90, line 33, delete "32° C." and insert --32 °C.--, therefor In column 90, line 48, delete "65° C.," and insert --65 °C.,--, therefor In column 90, line 48, delete "65° C." and insert --65 °C.--, therefor In column 91, line 54, delete "51" and insert --S1--, therefor In column 95, line 19, delete "(i.e., [P] " and insert --i.e., [P] --, therefor In column 95, line 19, delete "C-terminus" and insert --C-terminus.--, therefor In column 98, line 22, delete "$PdCl_2$(dppf)" and insert --($PdCl_2$(dppf))--, therefor In column 99, line 5, delete "0° C." and insert --0 °C.--, therefor In column 99, line 21, delete "375.1526." and insert --375.1526,--, therefor In column 99, line 47, delete "429.2020." and insert --429.2020,--, therefor In column 100, line 7, delete "(-30 min)" and insert --(~30 min)--, therefor In column 100, line 22, delete "493.0830." and insert --493.0830,-- therefor In column 100, line 49, delete "569.1143." and insert --569.1143,-- therefor In column 101, line 2, delete "80° C." and insert --80 °C.-- therefor In column 101, line 12, delete "783.3440." and insert --783.3440,-- therefor In column 101, line 37, delete "560.2602." and insert --560.2602,-- therefor In column 101, line 55, delete "(-4 hrs)." and insert --(~4 hrs).-- therefor In column 101, line 66, delete "336.1977." and insert --336.1977,-- therefor In column 102, line 49, delete "796.2472." and insert --796.2472,-- therefor In column 103, line 4, delete "80° C.," and insert --80 °C.,-- therefor In column 103, line 16, delete "(-50 min)." and insert --(~50 min).-- therefor In column 103, line 25, delete "442.1973." and insert --442.1973,-- therefor In column 103, line 51, delete "65° C." and insert --65 °C.-- therefor In column 103, line 67, delete "663.1731." and insert --663.1731,-- therefor In column 104, line 21, delete "(-30 min)." and insert --(~30 min).-- therefor In column 104, line 31, delete "HoBT", and insert --HOBT-- therefor In column 104, line 53, delete "613.2868." and insert --613.2868,-- therefor In column 105, line 3, delete "0° C." and insert --0 °C.-- therefor In column 105, line 18-19, delete "[(M+H$^{-1}$)$^+$]: 513.2344." and insert --[(M+H)$^+$]: 513.2344,-- therefor In column 105, line 48, delete "403.0570." and insert --403.0570,-- therefor In column 105, line 61, delete "0° C." and insert --0 °C.-- therefor In column 106, line 14, delete "488.1098." and insert --488.1098,-- therefor In column 106, line 37, delete "(2 C)," and insert --(2C),-- therefor In column 106, line 41, delete "480.1435." and insert --480.1435,-- therefor In column 107, line 18, delete "463.3166." and insert --463.3166,--, therefor In column 107, line 48, delete "v.=1630," and insert --$v_{max}$=1630,--, therefor In column 107, line 49, delete "957.5332." and insert --957.5332,--, therefor In column 108, line 2, delete "A1Br$_3$" and insert --AlBr$_3$--, therefor In column 108, line 4, delete "50° C." and insert --50 °C.--, therefor In column 108, line 14, delete "v.=1630," and insert --$v_{max}$=1630,--, therefor In column 108, line 16 (Approx.), delete "825.4393." and insert --825.4393,--, therefor In column 109, line 19, delete "v.=3275," and insert --$v_{max}$=3275,--, therefor In column 109, line 21, delete "881.5019." and insert --881.5019,--, therefor In column 109, line 38, delete "A1Br$_3$" and insert --AlBr$_3$--, therefor In column 109, line 40, delete "50° C." and insert --50 °C.--, therefor In column 109, line 50, delete "471.1874." and insert --471.1874,--, therefor In column 110, line 28, delete "[*M+H)$^+$] 599.2711." and insert --[(M+H)$^+$] 599.2711,--, therefor In column 110, line 46, delete "A1Br$_3$" and insert --AlBr$_3$--, therefor In column 110, line 47, delete "50° C." and insert --50 °C.--, therefor In column 110, line 67, delete "457.1718." and insert --457.1718,--, therefor In column 111, line 20, delete "867.4862." and insert --867.4862,--, therefor In column 113, line 49, delete "0° C." and insert --0 °C.--, therefor In column 113, line 53, delete "0° C." and insert --0 °C.--, therefor In column 114, line 15, delete "0° C." and insert --0 °C.--, therefor In column 114, line 17, delete "(-45 min)" and insert --(~45 min)--, therefor In column 114, line 51, delete "0° C." and insert --0 °C.--, therefor In column 123, line 53, delete "80° C." and insert --80 °C.--, therefor In column 123, line 57, delete "wassubjected" and insert --was subjected--, therefor In column 127, line 1, delete "Compound" and insert --compound--, therefor In column 127, line 2, delete "0° C." and insert --0 °C.--, therefor In column 128, line 2, delete "A1Br$_3$" and insert --AlBr$_3$--, therefor In column 128, line 3, delete "50° C." and insert --50 °C.--, therefor In column 128, line 15, delete "867.4862." and insert --867.4862,--, therefor In column 128, line 19, delete "909.5332." and insert --909.5332,--, therefor In column 129, line 3, delete "925.5281." and insert --925.5281,--, therefor In column 129, line 28, delete "939.5437." and insert --939.5437,--, therefor In column 129, line 51, delete "949.4892." and insert --949.4892,--, therefor In column 131, line 3, delete "945.5307." and insert --945.5307,--, therefor In column 132, line 38, delete "80° C." and insert --80 °C.--, therefor In column 134, line 10, delete "80° C." and insert --80 °C.--, therefor In column 135, line 2, delete "0° C." and insert --0 °C.--, therefor In column 136, line 3, delete "A1Br$_3$" and insert --AlBr$_3$--, therefor In column 136, line 41, delete "C16" and insert --C$_{16}$--, therefor In column 136, line 54-60 (Approx.), delete " 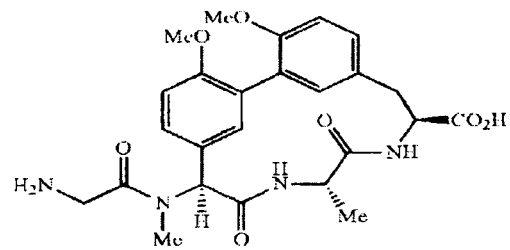 " and insert -- 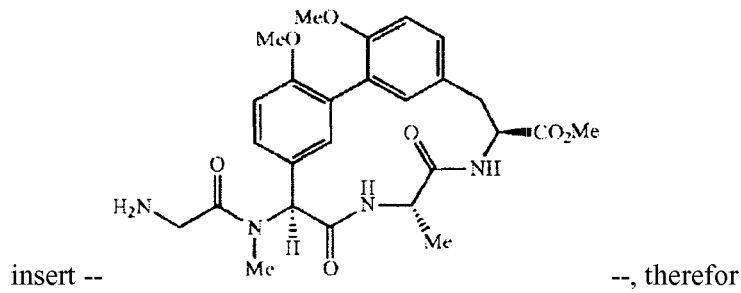 --, therefor In column 137, line 16, delete "C16" and insert --$C_{16}$--, therefor In column 137, line 46, delete "mmol," and insert --µmol,--, therefor In column 137, line 49, delete "50° C." and insert --50 °C.--, therefor In column 138, line 48, delete "C16." and insert --$C_{16}$.--, therefor In column 138, line 49, delete "C46H69N6O11 [(M+H)+]" and insert --$C_{46}H_{69}N_6O_{11}$ [(M+H)$^+$]--, therefor In column 138, line 49, delete "881.5019." and insert --881.5019,--, therefor In column 138, line 50, after "881.5021", insert --.--, therefor In column 139, line 21, delete "reported.9" and insert --reported.$^9$--, therefor In column 139, line 21, delete "52 mot," and insert --52 µmol,--, therefor In column 140, line 26, delete "C46H70N6O10 [M+H)+]:" and insert --$C_{46}H_{70}N_6O_{10}$ [(M+H)$^+$]:--, therefor In column 140, line 26, delete "867.5226." and insert --867.5226,--, therefor In column 140, line 33 (Approx.), delete "C38H53N6O11 [M+H)+]" and insert --$C_{38}H_{53}N_6O_{11}$ [(M+H)$^+$]--, therefor In column 140, line 33 (Approx.), delete "769.3767." and insert --769.3767,--, therefor In column 142, line 1, delete "C40H57N6O11 [M+H)+]" and insert --$C_{40}H_{57}N_6O_{11}$ [(M+H)$^+$]--, therefor In column 142, line 1, delete "797.408." and insert --797.408,--, therefor In column 142, line 2, after "797.4070", insert --,--, therefor In column 142, line 6, delete "C42H61N6O11 [M+H)+]" and insert --$C_{42}H_{61}N_6O_{11}$ $[(M+H)^+]$--, therefor In column 142, line 6, delete "825.4393." and insert --825.4393,--, therefor In column 142, line 7, after "825.4386", insert --.--, therefor In column 142, line 12, delete "C48H72N6O11 [M+H)+]" and insert --$C_{48}H_{72}N_6O_{11}$ $[(M+H)^+]$--, therefor In column 142, line 12, delete "909.5332." and insert --909.5332,--, therefor In column 143, line 2, delete "C₄₃H₅₄N₆O₁₁ [M+H)+]:" and insert --$C_{43}H_{54}N_6O_{11}$ $[(M+H)^+]$:--, therefor In column 143, line 3, delete "811.3297." and insert --811.3297,--, therefor In column 143, line 3, after "811.3300", insert --.--, therefor In column 143, line 6, delete "C44H48N6O11 [M+H)+]:" and insert --$C_{44}H_{48}N_6O_{11}$ $[(M+H)^+]$:--, therefor In column 143, line 7, delete "837.3454." and insert --837.3454,--, therefor In column 143, line 7, after "837.3443", insert --.--, therefor In column 143, line 9, delete "C43H46N6O11 [M+H)+]:" and insert --$C_{43}H_{46}N_6O_{11}$ $[(M+H)^+]$:--, therefor In column 143, line 9, delete "823.3297." and insert --823.3297,--, therefor In column 143, line 10, after "823.3296", insert --.--, therefor In column 146, line 1, delete "C45H50N6O11 [M+H)+]:" and insert --$C_{45}H_{50}N_6O_{11}$ $[(M+H)^+]$:--, therefor In column 146, line 2, delete "851.361." and insert --851.361,--, therefor In column 146, line 1, after "851.359", insert --.--, therefor In column 146, line 7, delete "C47H54N6O11 [M+H)+]:" and insert --$C_{47}H_{54}N_6O_{11}$ $[(M+H)^+]$:--, therefor In column 146, line 7, delete "879.3923." and insert --879.3923,--, therefor In column 146, line 8, after "879.3924", insert --.--, therefor In column 146, line 48, delete "C49H58N6O11 [M+H)+]:" and insert --$C_{49}H_{58}N_6O_{11}$ [(M+H)$^+$]:--, therefor In column 146, line 48, delete "907.4236." and insert --907.4236,--, therefor In column 146, line 49, after "907.4246", insert --.--, therefor In column 148, line 1, delete "C51H62N6O11 [M+H)+]:" and insert --$C_{51}H_{62}N_6O_{11}$ [(M+H)$^+$]:--, therefor In column 148, line 1, delete "935.4549." and insert --935.4549,--, therefor In column 148, line 2, after "935.4548", insert --.--, therefor In column 148, line 5, delete "C43H54N6O11 [M+H)+]:" and insert --$C_{43}H_{54}N_6O_{11}$ [(M+H)$^+$]:--, therefor In column 148, line 6, delete "831.3923." and insert --831.3923,--, therefor In column 148, line 6, after "831.3917", insert --.--, therefor In column 148, line 10, delete "C45H58N6O11 [M+H)+]:" and insert --$C_{45}H_{58}N_6O_{11}$ [(M+H)$^+$]:--, therefor In column 148, line 10, delete "859.4236." and insert --859.4236,--, therefor In column 148, line 11, after "859.4231", insert --.--, therefor In column 150, line 1, delete "C47H62N6O11 [M+H)+]:" and insert --$C_{47}H_{62}N_6O_{11}$ [(M+H)$^+$]:--, therefor In column 150, line 1, delete "887.4549." and insert --887.4549,--, therefor In column 150, line 2, after "887.4539", insert --.--, therefor In column 150, line 6, delete "C45H66N6O11 [M+H)+]:" and insert --$C_{45}H_{66}N_6O_{11}$ [(M+H)$^+$]:--, therefor In column 150, line 6, delete "867.4862." and insert --867.4862,--, therefor In column 150, line 7, after "867.4873", insert --.--, therefor In column 150, line 48, delete "C47H70N6O10 [M+H)+]:" and insert --$C_{47}H_{70}N_6O_{10}$ [(M+H)$^+$]:--, therefor In column 150, line 48, delete "895.5175." and insert --895.5175,--, therefor In column 150, line 49, after "895.5190", insert --.--, therefor In column 152, line 1, delete "C47H68N6O11 [M+H)+]:" and insert --$C_{47}H_{68}N_6O_{11}$ [(M+H)$^+$]:--, therefor In column 152, line 1, delete "893.5019." and insert --893.5019,--, therefor In column 152, line 2, after "893.5014", insert --.--, therefor In column 152, line 26, delete "C43H63N5O9 [M+H)+]" and insert --$C_{43}H_{63}N_5O_9$ [(M+H)$^+$]--, therefor In column 152, line 26, delete "794.4698." and insert --794.4698,--, therefor In column 152, line 27, after "794.4705", insert --.--, therefor In column 152, line 31, delete "C43H63N5O9 [M+H)+]:" and insert --$C_{43}H_{63}N_5O_9$ [(M+H)$^+$]:--, therefor In column 152, line 31, delete "794.4698." and insert --794.4698,--, therefor In column 152, line 32, after "794.4689", insert --.--, therefor In column 154, line 1, delete "C47H70N6O11 [M+H)+]" and insert --$C_{47}H_{70}N_6O_{11}$ [(M+H)$^+$]--, therefor In column 154, line 1, delete "895.5175." and insert --895.5175,--, therefor In column 154, line 2, after "895.5180", insert --.--, therefor In column 154, line 6, delete "C48H72N6O11 [M+H)+]:" and insert --$C_{48}H_{72}N_6O_{11}$ [(M+H)$^+$]:--, therefor In column 154, line 6, delete "909.5332." and insert --909.5332,--, therefor In column 154, line 7, after "909.5334", insert --.--, therefor In column 154, line 11, delete "C47H70N6O11 [M+H)+]:" and insert --$C_{47}H_{70}N_6O_{11}$ [(M+H)$^+$]:--, therefor In column 154, line 11, delete "895.5175." and insert --895.5175,--, therefor In column 154, line 12, after "895.5178", insert --.--, therefor In column 155, line 3, delete "C48H72N6O11 [M+H)+]:" and insert --$C_{48}H_{72}N_6O_{11}$ $[(M+H)^+]$:--, therefor In column 155, line 3, delete "909.5332." and insert --909.5332,--, therefor In column 155, line 33, delete "37° C." and insert --37 °C.--, therefor In column 155, line 34, delete "28° C." and insert --28 °C.--, therefor In column 155, line 38-39, delete "37° C." and insert --37 °C.--, therefor In column 155, line 40, delete "37° C." and insert --37 °C.--, therefor In column 155, line 42, delete "37° C." and insert --37 °C.--, therefor In column 155, line 45, delete "37° C." and insert --37 °C.--, therefor In column 155, line 46, delete "CO2" and insert --$CO_2$--, therefor In column 155, line 49, delete "37° C." and insert --37 °C.--, therefor In column 155, line 49, delete "28° C." and insert --28 °C.--, therefor In column 156, line 1, delete "37° C." and insert --37 °C.--, therefor In column 156, line 4, delete "28° C." and insert --28 °C.--, therefor In column 156, line 21, delete "37° C." and insert --37 °C.--, therefor In column 156, line 26, delete "37° C." and insert --37 °C.--, therefor In column 156, line 28, delete "CO2 at 37° C." and insert --$CO_2$ at 37 °C.--, therefor In column 156, line 37, delete "(-1×109 cfu)" and insert --(~1×109 cfu)--, therefor In column 156, line 38, delete "C16" and insert --$C_{16}$.--, therefor In column 156, line 40, delete "C16" and insert --$C_{16}$--, therefor In column 156, line 46, delete "95° C." and insert --95 °C.--, therefor

CERTIFICATE OF CORRECTION (continued)
U.S. Pat. No. 9,187,524 B2

In column 161, line 26, delete "Kan_ICF$_2$" and insert --Kan_ICF2.--, therefor

In column 161, line 32, delete "Ec_lepB_usNF/Ec_lepB_QC_P83X_R" and insert --Ec_lepB_usNF/Ec_lepB_QC_P83x_R--, therefor In column 161, line 33, delete "Ec_lepB_QC_P83X_F/Ec_lepB_dsCR." and insert --Ec_lepB_QC_P83x_F/Ec_lepB_dsCR.--, therefor In column 162, line 27, delete "ng/mL" and insert --µg/mL--, therefor In column 162, line 27, delete "C16" and insert --$C_{16}$--, therefor In column 162, line 28, delete "C16" and insert --$C_{16}$--, therefor In column 162, line 35, delete "C16" and insert --$C_{16}$--, therefor In column 162, line 38, delete "C16." and insert --$C_{16}$.--, therefor In column 162, line 42, delete "5u1" and insert --5ul--, therefor In column 162, line 43, delete "100u1" and insert --100ul--, therefor In column 162, line 43, delete "C16." and insert --$C_{16}$.--, therefor In column 162, line 51, delete "C16" and insert --$C_{16}$--, therefor In column 162, line 62, delete "C16" and insert --$C_{16}$--, therefor In column 163, line 1, delete "C16" and insert --$C_{16}$--, therefor In column 163, line 3, delete "C16." and insert --$C_{16}$.--, therefor In column 163, line 7, delete "C16" and insert --$C_{16}$--, therefor In column 163, line 8, delete "C16" and insert --$C_{16}$--, therefor In column 163, line 14, delete "C16." and insert --$C_{16}$.--, therefor In column 163, line 19, delete "C16" and insert --$C_{16}$--, therefor In column 163, line 35, delete "A2-75" and insert --Δ2-75--, therefor In column 163, line 37, delete "A2-75" and insert --Δ2-75--, therefor In column 163, line 38, after "the", delete "¶", therefor In column 163, line 39-40, delete "Ec_lepB_A2_75_NF NcoI" and insert --Ec_lepB_Δ_75_NF NcoI--, therefor In column 163, line 61, after "BL21(DE3)", delete "¶", therefor In column 164, line 22, delete "C16" and insert --$C_{16}$--, therefor In column 164, line 55, delete "Grampositive" and insert --Gram-positive--, therefor In column 164, line 60, delete "Gram-Positive" and insert --Gram-positive--, therefor In column 165, line 42, delete "C16" and insert --$C_{16}$--, therefor In column 166, Table 11, line 1, delete "A2" and insert --$A_2$--, therefor In column 166, Table 11, line 1, delete "C16" and insert --$C_{16}$--, therefor In column 166, line 47, delete "C16" and insert --$C_{16}$--, therefor In column 166, line 52, delete "C16" and insert --$C_{16}$--, therefor In column 166, line 61, after "arylomycin", delete "¶", therefor In column 162, line 5, delete "C16" and insert --$C_{16}$--, therefor In column 162, line 17, delete "A2" and insert --$A_2$--, therefor In column 162, line 22, delete "C16" and insert --$C_{16}$--, therefor In column 162, line 26, delete "C16" and insert --$C_{16}$--, therefor In column 162, line 33, delete "C16" and insert --$C_{16}$--, therefor In column 162, line 35, delete "A2" and insert --$A_2$--, therefor In column 162, line 42, delete "C16" and insert --$C_{16}$--, therefor In column 162, line 44, delete "C16" and insert --$C_{16}$--, therefor In column 162, line 50, delete "C16" and insert --$C_{16}$--, therefor In column 162, line 52, delete "C16" and insert --$C_{16}$--, therefor In column 169, Table 13, line 36, delete "C16" and --$C_{16}$--, therefor

CERTIFICATE OF CORRECTION (continued)
U.S. Pat. No. 9,187,524 B2

In column 169, line 66, delete "C16" and insert --$C_{16}$--, therefor

In column 170, line 28, delete "C16." and insert --$C_{16}$.--, therefor

In column 170, line 32, delete "C16." and insert --$C_{16}$.--, therefor

In column 170, line 37, delete "C16." and insert --$C_{16}$.--, therefor

In column 170, line 39, delete "C16" and insert --$C_{16}$--, therefor

In column 170, line 43, delete "C16," and insert --$C_{16}$,--, therefor

In column 170, Table 14, line 62, delete "A-C16" and insert --A-$C_{16}$--, therefor In column 170, Table 14, line 62, delete "B-C16" and insert --B-$C_{16}$--, therefor In column 205, line 51, delete "C(=O)ORc, OC(=O)ORc," and insert --C(=O)O$R^C$, OC(=O)O$R^C$,--, therefor In column 206, line 49, delete "$(CH_2)_{0-2}14$" and insert --$(CH_2)_{0-2}H$--, therefor In column 208, line 16, delete "$R^E$" and insert --$R^{1E}$--, therefor In column 209, line 6, delete "$n^2$ and $n^3$" and insert --n2 and n3--, therefor In column 209, line 37, delete "cycloalkyl, ($C_3$-$C_{10}$)" and insert --cycloalkyl ($C_3$-$C_{10}$)--, therefor In column 209, line 40, delete "$(C_2$-$C_{12})^{alkynyl], (C}{}_{6-C10})$ -aryl," and insert --($C_2$-$C_{12}$)-alkynyl], ($C_6$-$C_{10}$)-aryl,--, therefor In column 210, line 35, delete "$n^2$, $n^3$," and insert --n2, n3,--, therefor In column 210, line 59, delete "$n^1$, $n^2$," and insert --n1, n2,--, therefor In column 211, line 6, delete "1-7" and insert --1-4--, therefor In column 211, line 48, delete "1-7" and insert --1-4--, therefor In column 211, line 50, delete "1-7" and insert --1-4--, therefor In column 211, line 54, delete "1-7" and insert --1-4--, therefor In column 211, line 56, delete "1-7" and insert --1-4--, therefor In column 211, line 59, delete "1-7" and insert --1-4--, therefor In column 211, line 63, delete "1-7" and insert --1-4--, therefor In column 212, line 41-42, delete "6-(C2-$C_{10}$)-2-naphthyl," and insert --6-($C_2$-$C_{10}$)-2-naphthyl,--, therefor In column 212, line 63, delete "A2." and insert --$A_2$.--, therefor In column 216, line 28, delete "position-7" and insert --position --7--, therefor

Claims

In column 371, line 48, in Claim 1, delete "C(=O)$NR^C$," and insert --C(=O)$NR^C_2$,--, therefor In column 372, line 37-38, in Claim 1, delete "c arbonyl, ($C_1$-$C_6$)alkylsulfonylamino ," and insert --carbonyl, ($C_1$-$C_6$)alkylsulfonylamino,--, therefor In column 373, line 15, in Claim 1, delete "attachment:" and insert --attachment;--, therefor In column 373, line 29, in Claim 1, delete "$W^i$," and insert --$W^1$,--, therefor In column 375, line 7, in Claim 1, delete "$R^{A2}$,$R^{A3}$,$R^M$," and insert --$R^{A2}$, $R^{A3}$, $R^{A4}$,--, therefor In column 375, line 27, in Claim 1, delete "(=NOR')R;" and insert --(=NOR')R';--, therefor In column 375, line 45, in Claim 1, delete "20-membered$_7$" and insert --20-membered--, therefor In column 375, line 59, in Claim 1, delete "$(X^1)xi$" and insert --$(X^1)_{x1}$--, therefor In column 376, line 23, in Claim 2, delete "(HAS)" and insert --(IIAS)--, therefor In column 377, line 9, in Claim 7, delete "$X^1$,$X^2$," and insert --$X^1$, $X^2$,--, therefor In column 378, line 17, in Claim 16, delete "(D)," and insert --(D)--, therefor In column 378, line 18, in Claim 16, delete "6-($C_2$-$C_2$)alkyl-2-naphthyl," and insert --6-($C_2$-$C_{10}$)alkyl-2-naphthyl,--, therefor In column 378, line 34, in Claim 19, delete "A2." and insert --$A_2$.--, therefor In column 378, line 48, in Claim 20, delete "oxalis," and insert --oralis,--, therefor

SEQUENCE LISTING

```
<160> NUMBER OF SEQ ID NOS: 211

<210> SEQ ID NO 1
<211> LENGTH: 191
<212> TYPE: PRT
<213> ORGANISM: Staphylococcus epidermidis

<400> SEQUENCE: 1

Met Lys Lys Glu Ile Leu Glu Trp Ile Val Ala Ile Ala Val Ala Ile
1               5                   10                  15
```

```
Ala Leu Ile Ala Ile Ile Thr Lys Phe Val Gly Lys Ser Tyr Ser Ile
         20                  25                  30

Lys Gly Asp Ser Met Asp Pro Thr Leu Lys Asp Gly Glu Arg Val Val
         35                  40                  45

Val Asn Ile Ile Gly Tyr Lys Leu Gly Gly Val Glu Lys Gly Asn Val
 50                  55                  60

Ile Val Phe His Ala Asn Lys Lys Asp Asp Tyr Val Lys Arg Val Ile
 65                  70                  75                  80

Gly Thr Pro Gly Asp Ser Val Glu Tyr Lys Asn Asp Thr Leu Tyr Val
                 85                  90                  95

Asn Gly Lys Lys Gln Ser Glu Pro Tyr Leu Asn Tyr Asn Glu Lys Arg
                100                 105                 110

Lys Gln Thr Glu Tyr Ile Thr Gly Ser Phe Lys Thr Lys Asn Leu Pro
                115                 120                 125

Asn Ala Asn Pro Gln Ser Asn Val Ile Pro Lys Gly Lys Tyr Leu Val
            130                 135                 140

Leu Gly Asp Asn Arg Glu Val Ser Lys Asp Ser Arg Ser Phe Gly Leu
145                 150                 155                 160

Ile Asp Lys Asp Gln Ile Val Gly Lys Val Ser Leu Arg Tyr Trp Pro
                165                 170                 175

Phe Ser Glu Phe Lys Ser Asn Phe Asn Pro Asn Asn Thr Lys Asn
                180                 185                 190

<210> SEQ ID NO 2
<211> LENGTH: 576
<212> TYPE: DNA
<213> ORGANISM: Staphylococcus epidermidis

<400> SEQUENCE: 2
ttgaaaaaag aaattttaga gtggattgtt gccatagccg ttgccattgc acttattgcc      60
ataatcacta aatttgtcgg aaaatcatat tctattaaag gtgattcaat ggatcctaca     120
ttaaaagatg gggagcgtgt agtggtaaat attattggct ataaattagg tggcgttgaa     180
aaaggaaatg tcattgtatt tcatgctaat aaaaaagatg attatgttaa aagagttatt     240
ggaactccag gagatagtgt tgaatataaa aatgatacac tctatgttaa tggtaaaaag     300
caatcagaac catacttgaa ctataatgaa aaacgtaagc aaactgagta tatcacaggt     360
agtttcaaaa caaaaaattt accaaatgct aatcctcaat ctaatgttat tcctaaaggt     420
aaatatttag ttttggggga taaccgtgag gtaagtaaag atagtcgttc attcggttta     480
attgacaaag accaaattgt tggaaaggta tcgctcagat attggccttt cagtgaattt     540
aaatctaact ttaatccaaa taacactaaa aattaa                              576

<210> SEQ ID NO 3
<211> LENGTH: 33
<212> TYPE: DNA
<213> ORGANISM: Staphylococcus epidermidis

<400> SEQUENCE: 3
gtcggaaaat catattctat taaaggtgat tca                                   33

<210> SEQ ID NO 4
<211> LENGTH: 11
<212> TYPE: PRT
<213> ORGANISM: Staphylococcus epidermidis

<400> SEQUENCE: 4
```

-continued

Val Gly Lys Ser Tyr Ser Ile Lys Gly Asp Ser
1               5                   10

<210> SEQ ID NO 5
<211> LENGTH: 33
<212> TYPE: DNA
<213> ORGANISM: Staphylococcus epidermidis

<400> SEQUENCE: 5
gtcggaaaac catattctat taaaggtgat tca                              33

<210> SEQ ID NO 6
<211> LENGTH: 11
<212> TYPE: PRT
<213> ORGANISM: Staphylococcus epidermidis

<400> SEQUENCE: 6

Val Gly Lys Pro Tyr Ser Ile Lys Gly Asp Ser
1               5                   10

<210> SEQ ID NO 7
<211> LENGTH: 33
<212> TYPE: DNA
<213> ORGANISM: Staphylococcus epidermidis

<400> SEQUENCE: 7
gtcggaaaac cgtattctat taaaggtgat tca                              33

<210> SEQ ID NO 8
<211> LENGTH: 33
<212> TYPE: DNA
<213> ORGANISM: Staphylococcus epidermidis

<400> SEQUENCE: 8
gtcggaaaac cctattctat taaaggtgat tca                              33

<210> SEQ ID NO 9
<211> LENGTH: 33
<212> TYPE: DNA
<213> ORGANISM: Staphylococcus epidermidis

<400> SEQUENCE: 9
gtcggaaaac cttattctat taaaggtgat tca                              33

<210> SEQ ID NO 10
<211> LENGTH: 33
<212> TYPE: DNA
<213> ORGANISM: Staphylococcus epidermidis

<400> SEQUENCE: 10
gtcggaaaat catatcctat taaaggtgat tca                              33

<210> SEQ ID NO 11
<211> LENGTH: 11
<212> TYPE: PRT
<213> ORGANISM: Staphylococcus epidermidis

<400> SEQUENCE: 11

Val Gly Lys Ser Tyr Pro Ile Lys Gly Asp Ser
1               5                   10

<210> SEQ ID NO 12
<211> LENGTH: 33

```
<212> TYPE: DNA
<213> ORGANISM: Staphylococcus epidermidis

<400> SEQUENCE: 12
gtcggaaaat catatcccat taaaggtgat tca                                33

<210> SEQ ID NO 13
<211> LENGTH: 33
<212> TYPE: DNA
<213> ORGANISM: Staphylococcus epidermidis

<400> SEQUENCE: 13
gtcggaaaat catatccaat taaaggtgat tca                                33

<210> SEQ ID NO 14
<211> LENGTH: 33
<212> TYPE: DNA
<213> ORGANISM: Staphylococcus epidermidis

<400> SEQUENCE: 14
gtcggaaaat catatccgat taaaggtgat tca                                33

<210> SEQ ID NO 15
<211> LENGTH: 192
<212> TYPE: PRT
<213> ORGANISM: Staphylococcus epidermidis

<400> SEQUENCE: 15
```

Met Lys Lys Glu Ile Ile Glu Trp Ile Val Ala Ile Ile Val Ala Ile
 1               5                  10                  15

Val Ile Val Thr Leu Val Gln Lys Phe Leu Phe Ala Ser Tyr Thr Val
                20                  25                  30

Lys Gly Ala Ser Met His Pro Thr Phe Glu Asn Arg Glu Lys Val Ile
            35                  40                  45

Val Ser Arg Ile Ala Lys Thr Leu Asp His Ile Asp Thr Gly Asp Val
        50                  55                  60

Val Ile Phe His Ala Asn Ala Lys Gln Asp Tyr Ile Lys Arg Leu Ile
65                  70                  75                  80

Gly Lys Pro Gly Asp Ser Val Glu Tyr Lys Lys Asp Gln Leu Tyr Leu
                85                  90                  95

Asn Gly Lys Lys Val Asp Glu Pro Tyr Leu Ser Glu Asn Lys Lys His
            100                 105                 110

Lys Val Gly Glu Tyr Leu Thr Glu Asn Phe Lys Ser Arg Asp Leu Lys
        115                 120                 125

Gly Thr Asn Gly Asn Met Lys Ile Pro Ser Gly Lys Tyr Leu Val Leu
    130                 135                 140

Gly Asp Asn Arg Gln Asn Ser Ile Asp Ser Arg Met Asp Glu Val Gly
145                 150                 155                 160

Leu Leu Asp Lys Asn Gln Val Val Gly Lys Val Val Leu Arg Tyr Trp
                165                 170                 175

Pro Phe Asn Arg Trp Gly Gly Ser Phe Asn Pro Gly Thr Phe Pro Asn
            180                 185                 190

```
<210> SEQ ID NO 16
<211> LENGTH: 579
<212> TYPE: DNA
<213> ORGANISM: Staphylococcus epidermidis

<400> SEQUENCE: 16
```

```
atgaagaaag aaataataga atggattgta gccataatcg ttgcaattgt tatcgtcaca    60
cttgtgcaaa agttttatt tgcttcttat acagtcaaag gagcatctat gcatccaaca   120
tttgaaaatc gagaaaaagt gatagtaagt cgtatagcaa aaacgcttga tcatattgat   180
acaggagatg tagtgatttt tcatgctaac gcgaagcaag attatattaa gcgacttatt   240
ggtaaaccag gtgattcagt agaatataaa aaagatcaac tatatttaaa cggtaaaaaa   300
gtagatgagc ttatttaag tgaaataaa aaacataaag ttggagaata tctaacggaa   360
aactttaagt ctagagatct taagggtacg aatggcaata tgaaaattcc tagtggtaaa   420
tacttggttt taggtgataa tcgtcaaaac agtattgaca gtcgcatgga tgaagtaggt   480
cttttagata aaaatcaagt tgttggaaaa gtagtttga gatactggcc atttaatcgg   540
tggggcggta gttttaatcc tggaacattt cctaactaa                          579
```

```
<210> SEQ ID NO 17
<211> LENGTH: 11
<212> TYPE: PRT
<213> ORGANISM: Staphylococcus epidermidis

<400> SEQUENCE: 17

Val Gly Lys Ser Tyr Ser Ile Lys Gly Asp Ser
1               5                   10

<210> SEQ ID NO 18
<211> LENGTH: 11
<212> TYPE: PRT
<213> ORGANISM: Staphylococcus epidermidis

<400> SEQUENCE: 18

Val Gly Lys Pro Tyr Ser Ile Lys Gly Asp Ser
1               5                   10

<210> SEQ ID NO 19
<211> LENGTH: 11
<212> TYPE: PRT
<213> ORGANISM: Staphylococcus epidermidis

<400> SEQUENCE: 19

Val Gly Lys Ser Tyr Pro Ile Lys Gly Asp Ser
1               5                   10

<210> SEQ ID NO 20
<211> LENGTH: 11
<212> TYPE: PRT
<213> ORGANISM: S. aureus

<400> SEQUENCE: 20

Val Ala Lys Pro Tyr Thr Val Lys Gly Asp Ser
1               5                   10

<210> SEQ ID NO 21
<211> LENGTH: 11
<212> TYPE: PRT
<213> ORGANISM: S. aureus

<400> SEQUENCE: 21

Val Ala Lys Ser Tyr Thr Val Lys Gly Asp Ser
1               5                   10

<210> SEQ ID NO 22
<211> LENGTH: 11
<212> TYPE: PRT
```

<213> ORGANISM: E. coli

<400> SEQUENCE: 22

Ile Tyr Glu Pro Phe Gln Ile Pro Ser Gly Ser
1               5                   10

<210> SEQ ID NO 23
<211> LENGTH: 11
<212> TYPE: PRT
<213> ORGANISM: E. coli

<400> SEQUENCE: 23

Ile Tyr Glu Ser Phe Gln Ile Pro Ser Gly Ser
1               5                   10

<210> SEQ ID NO 24
<211> LENGTH: 11
<212> TYPE: PRT
<213> ORGANISM: P. aeruginosa

<400> SEQUENCE: 24

Leu Phe Glu Pro Phe Gln Ile Pro Ser Gly Ser
1               5                   10

<210> SEQ ID NO 25
<211> LENGTH: 11
<212> TYPE: PRT
<213> ORGANISM: P. aeruginosa

<400> SEQUENCE: 25

Leu Phe Glu Ser Phe Gln Ile Pro Ser Gly Ser
1               5                   10

<210> SEQ ID NO 26
<211> LENGTH: 22
<212> TYPE: DNA
<213> ORGANISM: Artificial Sequence
<220> FEATURE:
<223> OTHER INFORMATION: A synthetic primer

<400> SEQUENCE: 26
tcccgttcgc tggctgcctg tg                                           22

<210> SEQ ID NO 27
<211> LENGTH: 44
<212> TYPE: DNA
<213> ORGANISM: Artificial Sequence
<220> FEATURE:
<223> OTHER INFORMATION: A synthetic primer

<400> SEQUENCE: 27
cggcggcttt gttgaataaa tcgttaatgg atgccgccaa tgcg                   44

<210> SEQ ID NO 28
<211> LENGTH: 44
<212> TYPE: DNA
<213> ORGANISM: Artificial Sequence
<220> FEATURE:
<223> OTHER INFORMATION: A synthetic primer

<400> SEQUENCE: 28
gagacacaac gtggctttcc cattaatagc catcttcgtt cacg                   44

<210> SEQ ID NO 29
<211> LENGTH: 32

```
<212> TYPE: DNA
<213> ORGANISM: Artificial Sequence
<220> FEATURE:
<223> OTHER INFORMATION: A synthetic primer

<400> SEQUENCE: 29
ttggtttcta gaccagcgta ttgccacgga cc                              32

<210> SEQ ID NO 30
<211> LENGTH: 29
<212> TYPE: DNA
<213> ORGANISM: Artificial Sequence
<220> FEATURE:
<223> OTHER INFORMATION: A synthetic primer

<400> SEQUENCE: 30
ttggtttcta gactttatcg acaccccgg                                  29

<210> SEQ ID NO 31
<211> LENGTH: 20
<212> TYPE: DNA
<213> ORGANISM: Artificial Sequence
<220> FEATURE:
<223> OTHER INFORMATION: A synthetic primer

<400> SEQUENCE: 31
ggttgtaaca ctggcagagc                                            20

<210> SEQ ID NO 32
<211> LENGTH: 39
<212> TYPE: DNA
<213> ORGANISM: Artificial Sequence
<220> FEATURE:
<223> OTHER INFORMATION: A synthetic primer

<400> SEQUENCE: 32
cgttcgttta tttatgaagc gttccagatc ccgtcaggt                       39

<210> SEQ ID NO 33
<211> LENGTH: 39
<212> TYPE: DNA
<213> ORGANISM: Artificial Sequence
<220> FEATURE:
<223> OTHER INFORMATION: A synthetic primer

<400> SEQUENCE: 33
acctgacggg atctggaacg cttcataaat aaacgaacg                       39

<210> SEQ ID NO 34
<211> LENGTH: 39
<212> TYPE: DNA
<213> ORGANISM: Artificial Sequence
<220> FEATURE:
<223> OTHER INFORMATION: A synthetic primer

<400> SEQUENCE: 34
cgttcgttta tttatgaatg cttccagatc ccgtcaggt                       39

<210> SEQ ID NO 35
<211> LENGTH: 39
<212> TYPE: DNA
<213> ORGANISM: Artificial Sequence
<220> FEATURE:
<223> OTHER INFORMATION: A synthetic primer

<400> SEQUENCE: 35
```
acctgacggg atctggaagc attcataaat aaacgaacg        39

<210> SEQ ID NO 36
<211> LENGTH: 39
<212> TYPE: DNA
<213> ORGANISM: Artificial Sequence
<220> FEATURE:
<223> OTHER INFORMATION: A synthetic primer

<400> SEQUENCE: 36
cgttcgttta tttatgaaga tttccagatc ccgtcaggt        39

<210> SEQ ID NO 37
<211> LENGTH: 39
<212> TYPE: DNA
<213> ORGANISM: Artificial Sequence
<220> FEATURE:
<223> OTHER INFORMATION: A synthetic primer

<400> SEQUENCE: 37
acctgacggg atctggaaat cttcataaat aaacgaacg        39

<210> SEQ ID NO 38
<211> LENGTH: 39
<212> TYPE: DNA
<213> ORGANISM: Artificial Sequence
<220> FEATURE:
<223> OTHER INFORMATION: A synthetic primer

<400> SEQUENCE: 38
cgttcgttta tttatgaaga gttccagatc ccgtcaggt        39

<210> SEQ ID NO 39
<211> LENGTH: 39
<212> TYPE: DNA
<213> ORGANISM: Artificial Sequence
<220> FEATURE:
<223> OTHER INFORMATION: A synthetic primer

<400> SEQUENCE: 39
acctgacggg atctggaact cttcataaat aaacgaacg        39

<210> SEQ ID NO 40
<211> LENGTH: 39
<212> TYPE: DNA
<213> ORGANISM: Artificial Sequence
<220> FEATURE:
<223> OTHER INFORMATION: A synthetic primer

<400> SEQUENCE: 40
cgttcgttta tttatgaatt cttccagatc ccgtcaggt        39

<210> SEQ ID NO 41
<211> LENGTH: 39
<212> TYPE: DNA
<213> ORGANISM: Artificial Sequence
<220> FEATURE:
<223> OTHER INFORMATION: A synthetic primer

<400> SEQUENCE: 41
acctgacggg atctggaaga attcataaat aaacgaacg        39

<210> SEQ ID NO 42
<211> LENGTH: 39
<212> TYPE: DNA
<213> ORGANISM: Artificial Sequence
<220> FEATURE:
<223> OTHER INFORMATION: A synthetic primer

<400> SEQUENCE: 42
cgttcgttta tttatgaagg cttccagatc ccgtcaggt                                39

<210> SEQ ID NO 43
<211> LENGTH: 39
<212> TYPE: DNA
<213> ORGANISM: Artificial Sequence
<220> FEATURE:
<223> OTHER INFORMATION: A synthetic primer

<400> SEQUENCE: 43
acctgacggg atctggaagc cttcataaat aaacgaacg                                39

<210> SEQ ID NO 44
<211> LENGTH: 39
<212> TYPE: DNA
<213> ORGANISM: Artificial Sequence
<220> FEATURE:
<223> OTHER INFORMATION: A synthetic primer

<400> SEQUENCE: 44
cgttcgttta tttatgaaca tttccagatc ccgtcaggt                                39

<210> SEQ ID NO 45
<211> LENGTH: 39
<212> TYPE: DNA
<213> ORGANISM: Artificial Sequence
<220> FEATURE:
<223> OTHER INFORMATION: A synthetic primer

<400> SEQUENCE: 45
acctgacggg atctggaaat gttcataaat aaacgaacg                                39

<210> SEQ ID NO 46
<211> LENGTH: 39
<212> TYPE: DNA
<213> ORGANISM: Artificial Sequence
<220> FEATURE:
<223> OTHER INFORMATION: A synthetic primer

<400> SEQUENCE: 46
cgttcgttta tttatgaaat cttccagatc ccgtcaggt                                39

<210> SEQ ID NO 47
<211> LENGTH: 39
<212> TYPE: DNA
<213> ORGANISM: Artificial Sequence
<220> FEATURE:
<223> OTHER INFORMATION: A synthetic primer

<400> SEQUENCE: 47
acctgacggg atctggaaga tttcataaat aaacgaacg                                39

<210> SEQ ID NO 48
<211> LENGTH: 39
<212> TYPE: DNA
<213> ORGANISM: Artificial Sequence
<220> FEATURE:
<223> OTHER INFORMATION: A synthetic primer

<400> SEQUENCE: 48
cgttcgttta tttatgaaaa attccagatc ccgtcaggt                                39

<210> SEQ ID NO 49
<211> LENGTH: 39
<212> TYPE: DNA
<213> ORGANISM: Artificial Sequence
<220> FEATURE:
<223> OTHER INFORMATION: A synthetic primer

<400> SEQUENCE: 49
acctgacggg atctggaatt tttcataaat aaacgaacg             39

<210> SEQ ID NO 50
<211> LENGTH: 39
<212> TYPE: DNA
<213> ORGANISM: Artificial Sequence
<220> FEATURE:
<223> OTHER INFORMATION: A synthetic primer

<400> SEQUENCE: 50
cgttcgttta tttatgaact gttccagatc ccgtcaggt             39

<210> SEQ ID NO 51
<211> LENGTH: 39
<212> TYPE: DNA
<213> ORGANISM: Artificial Sequence
<220> FEATURE:
<223> OTHER INFORMATION: A synthetic primer

<400> SEQUENCE: 51
acctgacggg atctggaaca gttcataaat aaacgaacg             39

<210> SEQ ID NO 52
<211> LENGTH: 39
<212> TYPE: DNA
<213> ORGANISM: Artificial Sequence
<220> FEATURE:
<223> OTHER INFORMATION: A synthetic primer

<400> SEQUENCE: 52
cgttcgttta tttatgaaat gttccagatc ccgtcaggt             39

<210> SEQ ID NO 53
<211> LENGTH: 39
<212> TYPE: DNA
<213> ORGANISM: Artificial Sequence
<220> FEATURE:
<223> OTHER INFORMATION: A synthetic primer

<400> SEQUENCE: 53
acctgacggg atctggaaca tttcataaat aaacgaacg             39

<210> SEQ ID NO 54
<211> LENGTH: 39
<212> TYPE: DNA
<213> ORGANISM: Artificial Sequence
<220> FEATURE:
<223> OTHER INFORMATION: A synthetic primer

<400> SEQUENCE: 54
cgttcgttta tttatgaaaa cttccagatc ccgtcaggt             39

<210> SEQ ID NO 55
<211> LENGTH: 39
<212> TYPE: DNA
<213> ORGANISM: Artificial Sequence
<220> FEATURE:
<223> OTHER INFORMATION: A synthetic primer

<400> SEQUENCE: 55
acctgacggg atctggaagt tttcataaat aaacgaacg          39

<210> SEQ ID NO 56
<211> LENGTH: 39
<212> TYPE: DNA
<213> ORGANISM: Artificial Sequence
<220> FEATURE:
<223> OTHER INFORMATION: A synthetic primer

<400> SEQUENCE: 56
cgttcgttta tttatgaaca gttccagatc ccgtcaggt          39

<210> SEQ ID NO 57
<211> LENGTH: 39
<212> TYPE: DNA
<213> ORGANISM: Artificial Sequence
<220> FEATURE:
<223> OTHER INFORMATION: A synthetic primer

<400> SEQUENCE: 57
acctgacggg atctggaact gttcataaat aaacgaacg          39

<210> SEQ ID NO 58
<211> LENGTH: 39
<212> TYPE: DNA
<213> ORGANISM: Artificial Sequence
<220> FEATURE:
<223> OTHER INFORMATION: A synthetic primer

<400> SEQUENCE: 58
cgttcgttta tttatgaacg gttccagatc ccgtcaggt          39

<210> SEQ ID NO 59
<211> LENGTH: 39
<212> TYPE: DNA
<213> ORGANISM: Artificial Sequence
<220> FEATURE:
<223> OTHER INFORMATION: A synthetic primer

<400> SEQUENCE: 59
acctgacggg atctggaacc gttcataaat aaacgaacg          39

<210> SEQ ID NO 60
<211> LENGTH: 45
<212> TYPE: DNA
<213> ORGANISM: Artificial Sequence
<220> FEATURE:
<223> OTHER INFORMATION: A synthetic primer

<400> SEQUENCE: 60
gtgcgttcgt ttatttatga atcgttccag atcccgtcag gttcg          45

<210> SEQ ID NO 61
<211> LENGTH: 45
<212> TYPE: DNA
<213> ORGANISM: Artificial Sequence
<220> FEATURE:
<223> OTHER INFORMATION: A synthetic primer

<400> SEQUENCE: 61
cgaacctgac gggatctgga acgattcata aataaacgaa cgcac          45

<210> SEQ ID NO 62

```
<211> LENGTH: 39
<212> TYPE: DNA
<213> ORGANISM: Artificial Sequence
<220> FEATURE:
<223> OTHER INFORMATION: A synthetic primer

<400> SEQUENCE: 62
cgttcgttta tttatgaaac cttccagatc ccgtcaggt                39

<210> SEQ ID NO 63
<211> LENGTH: 39
<212> TYPE: DNA
<213> ORGANISM: Artificial Sequence
<220> FEATURE:
<223> OTHER INFORMATION: A synthetic primer

<400> SEQUENCE: 63
acctgacggg atctggaagg tttcataaat aaacgaacg                39

<210> SEQ ID NO 64
<211> LENGTH: 39
<212> TYPE: DNA
<213> ORGANISM: Artificial Sequence
<220> FEATURE:
<223> OTHER INFORMATION: A synthetic primer

<400> SEQUENCE: 64
cgttcgttta tttatgaagt gttccagatc ccgtcaggt                39

<210> SEQ ID NO 65
<211> LENGTH: 39
<212> TYPE: DNA
<213> ORGANISM: Artificial Sequence
<220> FEATURE:
<223> OTHER INFORMATION: A synthetic primer

<400> SEQUENCE: 65
acctgacggg atctggaaca cttcataaat aaacgaacg                39

<210> SEQ ID NO 66
<211> LENGTH: 39
<212> TYPE: DNA
<213> ORGANISM: Artificial Sequence
<220> FEATURE:
<223> OTHER INFORMATION: A synthetic primer

<400> SEQUENCE: 66
cgttcgttta tttatgaatg gttccagatc ccgtcaggt                39

<210> SEQ ID NO 67
<211> LENGTH: 39
<212> TYPE: DNA
<213> ORGANISM: Artificial Sequence
<220> FEATURE:
<223> OTHER INFORMATION: A synthetic primer

<400> SEQUENCE: 67
acctgacggg atctggaacc attcataaat aaacgaacg                39

<210> SEQ ID NO 68
<211> LENGTH: 39
<212> TYPE: DNA
<213> ORGANISM: Artificial Sequence
<220> FEATURE:
<223> OTHER INFORMATION: A synthetic primer

<400> SEQUENCE: 68
```
cgttcgttta tttatgaata tttccagatc ccgtcaggt    39

<210> SEQ ID NO 69
<211> LENGTH: 39
<212> TYPE: DNA
<213> ORGANISM: Artificial Sequence
<220> FEATURE:
<223> OTHER INFORMATION: A synthetic primer

<400> SEQUENCE: 69
acctgacggg atctggaaat attcataaat aaacgaacg    39

<210> SEQ ID NO 70
<211> LENGTH: 34
<212> TYPE: DNA
<213> ORGANISM: Artificial Sequence
<220> FEATURE:
<223> OTHER INFORMATION: A synthetic primer

<400> SEQUENCE: 70
ttggttggat cctggtgctc gacttcttcg atcg    34

<210> SEQ ID NO 71
<211> LENGTH: 34
<212> TYPE: DNA
<213> ORGANISM: Artificial Sequence
<220> FEATURE:
<223> OTHER INFORMATION: A synthetic primer

<400> SEQUENCE: 71
ttggttacta gtgtcggacc tcatgtcagt gtag    34

<210> SEQ ID NO 72
<211> LENGTH: 39
<212> TYPE: DNA
<213> ORGANISM: Artificial Sequence
<220> FEATURE:
<223> OTHER INFORMATION: A synthetic primer

<400> SEQUENCE: 72
cgttccttcc tggtcgagag cttccagatt ccctcgggg    39

<210> SEQ ID NO 73
<211> LENGTH: 39
<212> TYPE: DNA
<213> ORGANISM: Artificial Sequence
<220> FEATURE:
<223> OTHER INFORMATION: A synthetic primer

<400> SEQUENCE: 73
ccccgaggga atctggaagc tctcgaccag gaaggaacg    39

<210> SEQ ID NO 74
<211> LENGTH: 21
<212> TYPE: DNA
<213> ORGANISM: Artificial Sequence
<220> FEATURE:
<223> OTHER INFORMATION: A synthetic primer

<400> SEQUENCE: 74
gtggcgatcc aggcagccat c    21

<210> SEQ ID NO 75
<211> LENGTH: 36
<212> TYPE: DNA

```
<213> ORGANISM: Artificial Sequence
<220> FEATURE:
<223> OTHER INFORMATION: A synthetic primer

<400> SEQUENCE: 75
ttggttgaat tcgatctgta aacgattggt gaacac                                36

<210> SEQ ID NO 76
<211> LENGTH: 38
<212> TYPE: DNA
<213> ORGANISM: Artificial Sequence
<220> FEATURE:
<223> OTHER INFORMATION: A synthetic primer

<400> SEQUENCE: 76
ttggttgaat tcgttcgcta taactaccaa cttcttgg                              38

<210> SEQ ID NO 77
<211> LENGTH: 44
<212> TYPE: DNA
<213> ORGANISM: Artificial Sequence
<220> FEATURE:
<223> OTHER INFORMATION: A synthetic primer

<400> SEQUENCE: 77
gtaggtaaat ttattgttac gtcatataca attaaaggtg aatc                       44

<210> SEQ ID NO 78
<211> LENGTH: 44
<212> TYPE: DNA
<213> ORGANISM: Artificial Sequence
<220> FEATURE:
<223> OTHER INFORMATION: A synthetic primer

<400> SEQUENCE: 78
gattcacctt taattgtata tgacgtaaca ataaatttac ctac                       44

<210> SEQ ID NO 79
<211> LENGTH: 26
<212> TYPE: DNA
<213> ORGANISM: Artificial Sequence
<220> FEATURE:
<223> OTHER INFORMATION: A synthetic primer

<400> SEQUENCE: 79
caaggaaagc gtgtcgttgt tgtacc                                           26

<210> SEQ ID NO 80
<211> LENGTH: 30
<212> TYPE: DNA
<213> ORGANISM: Artificial Sequence
<220> FEATURE:
<223> OTHER INFORMATION: A synthetic primer

<400> SEQUENCE: 80
ccaatcattc ttgctgcagt aggtctaacg                                       30

<210> SEQ ID NO 81
<211> LENGTH: 27
<212> TYPE: DNA
<213> ORGANISM: Artificial Sequence
<220> FEATURE:
<223> OTHER INFORMATION: A synthetic primer

<400> SEQUENCE: 81
tgatggtgat acgattccac cgggagc                                          27
```

<210> SEQ ID NO 82
<211> LENGTH: 28
<212> TYPE: DNA
<213> ORGANISM: Artificial Sequence
<220> FEATURE:
<223> OTHER INFORMATION: A synthetic primer

<400> SEQUENCE: 82
gcatggctgt tgactttcct gtacctgc                                     28

<210> SEQ ID NO 83
<211> LENGTH: 33
<212> TYPE: DNA
<213> ORGANISM: Artificial Sequence
<220> FEATURE:
<223> OTHER INFORMATION: A synthetic primer

<400> SEQUENCE: 83
ttggttccat ggtgcgttcg tttatttatg aac                               33

<210> SEQ ID NO 84
<211> LENGTH: 38
<212> TYPE: DNA
<213> ORGANISM: Artificial Sequence
<220> FEATURE:
<223> OTHER INFORMATION: A synthetic primer

<400> SEQUENCE: 84
ttggttggat cctggcattt aatggatgcc gccaatgc                          38

<210> SEQ ID NO 85
<211> LENGTH: 36
<212> TYPE: DNA
<213> ORGANISM: Artificial Sequence
<220> FEATURE:
<223> OTHER INFORMATION: A synthetic primer

<400> SEQUENCE: 85
ttggttggta ccttgaaaaa agaaatattg gaatgg                            36

<210> SEQ ID NO 86
<211> LENGTH: 41
<212> TYPE: DNA
<213> ORGANISM: Artificial Sequence
<220> FEATURE:
<223> OTHER INFORMATION: A synthetic primer

<400> SEQUENCE: 86
ttggttctcg agttaatttt tagtattttc aggattgaaa t                      41

<210> SEQ ID NO 87
<211> LENGTH: 8
<212> TYPE: PRT
<213> ORGANISM: E. coli

<400> SEQUENCE: 87

Pro Phe Gln Ile Pro Ser Gly Ser
 1               5

<210> SEQ ID NO 88
<211> LENGTH: 8
<212> TYPE: PRT
<213> ORGANISM: Acinetobacter baumanii

<400> SEQUENCE: 88

Pro Phe Asn Ile Pro Ser Asp Ser
1               5

<210> SEQ ID NO 89
<211> LENGTH: 8
<212> TYPE: PRT
<213> ORGANISM: Neiserria meningitidis

<400> SEQUENCE: 89

Pro Phe Gln Ile Pro Ser Ser Ser
1               5

<210> SEQ ID NO 90
<211> LENGTH: 8
<212> TYPE: PRT
<213> ORGANISM: Bordetella pertussis

<400> SEQUENCE: 90

Pro Phe His Ile Pro Ser Gly Ser
1               5

<210> SEQ ID NO 91
<211> LENGTH: 8
<212> TYPE: PRT
<213> ORGANISM: Mycobacterium tuberculosis

<400> SEQUENCE: 91

Pro Tyr Leu Ile Pro Ser Glu Ser
1               5

<210> SEQ ID NO 92
<211> LENGTH: 8
<212> TYPE: PRT
<213> ORGANISM: S. aurues

<400> SEQUENCE: 92

Pro Tyr Thr Ile Lys Gly Glu Ser
1               5

<210> SEQ ID NO 93
<211> LENGTH: 8
<212> TYPE: PRT
<213> ORGANISM: Bacillus anthracis

<400> SEQUENCE: 93

Pro Ser Leu Val Gln Gly Glu Ser
1               5

<210> SEQ ID NO 94
<211> LENGTH: 8
<212> TYPE: PRT
<213> ORGANISM: Bacillus anthracis

<400> SEQUENCE: 94

Leu Cys Lys Val Glu Gly Lys Ser
1               5

<210> SEQ ID NO 95
<211> LENGTH: 8
<212> TYPE: PRT
<213> ORGANISM: Streptococcus mutans

<400> SEQUENCE: 95

Pro Val Gln Val Asp Gly His Ser

```
<210> SEQ ID NO 96
<211> LENGTH: 8
<212> TYPE: PRT
<213> ORGANISM: Clostridium difficile

<400> SEQUENCE: 96

Pro Ser Ile Val Ser Gly Glu Ser
1               5

<210> SEQ ID NO 97
<211> LENGTH: 8
<212> TYPE: PRT
<213> ORGANISM: Clostridium difficile

<400> SEQUENCE: 97

Pro Thr Ile Val Lys Gly Glu Ser
1               5

<210> SEQ ID NO 98
<211> LENGTH: 8
<212> TYPE: PRT
<213> ORGANISM: Clostridium difficile

<400> SEQUENCE: 98

Pro Thr Leu Val Asn Gly Glu Ser
1               5

<210> SEQ ID NO 99
<211> LENGTH: 8
<212> TYPE: PRT
<213> ORGANISM: Enterococcus faecalis

<400> SEQUENCE: 99

Pro Ala Ala Val Asn Gly Ser Ser
1               5

<210> SEQ ID NO 100
<211> LENGTH: 8
<212> TYPE: PRT
<213> ORGANISM: Enterococcus faecalis

<400> SEQUENCE: 100

Ser Tyr Pro Ile Ala Gly Gln Ser
1               5

<210> SEQ ID NO 101
<211> LENGTH: 8
<212> TYPE: PRT
<213> ORGANISM: Enterococcus faecalis

<400> SEQUENCE: 101

Pro Ala Ala Val Asn Gly Ser Ser
1               5

<210> SEQ ID NO 102
<211> LENGTH: 8
<212> TYPE: PRT
<213> ORGANISM: Enterococcus faecalis

<400> SEQUENCE: 102

Pro Val Arg Val Asp Gly His Ser
1               5
```

```
<210> SEQ ID NO 103
<211> LENGTH: 8
<212> TYPE: PRT
<213> ORGANISM: Listeria monocytogenes

<400> SEQUENCE: 103

Pro Val Lys Val Glu Gly Thr Ser
1               5

<210> SEQ ID NO 104
<211> LENGTH: 8
<212> TYPE: PRT
<213> ORGANISM: Listeria monocytogenes

<400> SEQUENCE: 104

Pro Val Thr Val Asn Gly Lys Ser
1               5

<210> SEQ ID NO 105
<211> LENGTH: 8
<212> TYPE: PRT
<213> ORGANISM: Listeria monocytogenes

<400> SEQUENCE: 105

Pro Ile Leu Val Asp Gly Ile Ser
1               5

<210> SEQ ID NO 106
<211> LENGTH: 266
<212> TYPE: PRT
<213> ORGANISM: Rhodococcus equi

<400> SEQUENCE: 106

Val Ala Asp Ala Pro Gln Asp Pro Asp Val Thr Pro Asp Glu Thr Glu
1               5                   10                  15

Gln Glu Gln Thr Gly Gly Arg Ser Arg Arg Arg Gly Lys Asp Lys
            20                  25                  30

Lys Pro Arg Ser Phe Trp Arg Glu Ile Pro Ile Leu Ile Val Val Ala
        35                  40                  45

Leu Leu Leu Ser Phe Leu Leu Gln Thr Phe Ile Ala Arg Val Tyr Leu
    50                  55                  60

Ile Pro Ser Glu Ser Met Glu Pro Thr Leu His Gly Cys Pro Gly Cys
65                  70                  75                  80

Thr Gly Asp Arg Ile Val Val Glu Lys Ile Ser Tyr Arg Phe Gly Asp
                85                  90                  95

Pro Lys Pro Gly Asp Val Val Phe Arg Gly Pro Glu Ser Trp Ser
            100                 105                 110

Glu Gly Tyr Ser Ser Thr Arg Ser Asp Asn Val Val Arg Gly Leu
        115                 120                 125

Gln Glu Val Gly Ser Leu Val Gly Val Pro Pro Asp Glu Asn Asp
    130                 135                 140

Leu Val Lys Arg Val Ile Ala Thr Gly Gly Gln Thr Val Glu Cys Cys
145                 150                 155                 160

Asp Asp Gln Gly Arg Val Leu Asp Gly Lys Pro Leu Asp Glu Pro
                165                 170                 175

Tyr Ile Thr Met Asp Phe Pro Phe Ile Pro Gly Val Gln Thr Cys Asp
            180                 185                 190

Thr Ala Val Lys Ser Gly Arg Cys Phe Gly Pro Val Thr Val Pro Asp
            195                 200                 205
```

```
Gly His Leu Trp Val Met Gly Asp Asn Arg Ser Asn Ser Ala Asp Ser
    210                 215                 220
Arg Tyr His Val Ser Asp Glu Met Gln Gly Thr Ile Pro Val Asp Asn
225                 230                 235                 240
Val Ile Gly Lys Ala Thr Phe Ile Val Leu Pro Pro Gly Arg Trp Gly
                245                 250                 255
Ser Ile Ser Ser Pro Asp Ile Arg Gln Gln
            260                 265
```

<210> SEQ ID NO 107
<211> LENGTH: 801
<212> TYPE: DNA
<213> ORGANISM: Rhodococcus equi

<400> SEQUENCE: 107

```
gtggcagatg caccgcagga cccggacgtg acgccggacg agaccgagca ggagcagacc      60
ggggacggt cccgcaggcg caggggaag gacaagaaac ctcgatcgtt ctggcgtgag      120
atcccgatcc tcatcgtcgt cgccttgctg ttgagtttcc tgctgcagac gttcatcgcc      180
cgggtctacc tcattccgtc cgagtcgatg agccgacgc tgcacggttg ccccgggtgc      240
accggtgacc gcatcgtcgt cgagaagatc agttaccgat cggcgaccc gaagcccggc      300
gacgtcgtgg tcttccgcgg cccggagtcg tggtccgagg atattcgtc gacacgctcg      360
gacaacgtgg tggtccgcgg tctgcaggag gtcggctcgc tcgtcggtgt cgtgccgccg      420
gacgagaacg atctcgtcaa cgcgtcatc gcgacgggtg ggcagaccgt cgagtgctgc      480
gacgaccagg gccgtgtcct ggtcgacgga aagccgctcg acgagccgta catcacgatg      540
gacttcccctt tcatcccgg cgtgcagacg tgtgacaccg ccgtgaagtc cggacgctgc      600
ttcggacccg tcacggttcc cgatgggcac ctgtgggtga tgggcgacaa ccgcagcaat      660
tccgcggatt cgcggtacca cgtctccgac gagatgcagg gcacgattcc ggtggacaat      720
gtgatcggta aggcgacctt catcgtcctg ccccgggcc ggtggggatc gatctcgtct      780
cccgacatcc ggcagcagtg a                                              801
```

<210> SEQ ID NO 108
<211> LENGTH: 269
<212> TYPE: PRT
<213> ORGANISM: Rhodococcus opacus

<400> SEQUENCE: 108

```
Val Thr Asp Ser Ser Lys Glu Arg Ala Leu Ser Glu Ser Glu Thr
1               5                   10                  15
Thr Gly Asp Ser Ala Ala Thr Ser Ala Val Asn Gly Gly Ala Ala Glu
                20                  25                  30
Thr Glu Lys Lys Pro Arg Ser Phe Leu Arg Glu Leu Pro Ile Leu Ile
            35                  40                  45
Leu Val Ala Leu Val Leu Ser Phe Leu Leu Gln Thr Phe Val Ala Arg
        50                  55                  60
Val Tyr Leu Ile Pro Ser Glu Ser Met Glu Pro Thr Leu His Gly Cys
65                  70                  75                  80
 Ala Gly Cys Thr Gly Asp Arg Ile Val Val Glu Lys Ile Gly Tyr Arg
                85                  90                  95
Phe Gly Asp Pro Gln Pro Gly Asp Val Ile Val Phe Arg Gly Pro Asp
                100                 105                 110
Ser Trp Ser Gln Asp Phe Val Ser Thr Arg Ser Ser Asn Val Val Ile
```

```
             115                 120                 125
Arg Gly Ala Gln Glu Val Gly Ser Leu Val Gly Leu Val Pro Pro Asp
        130                 135                 140

Glu Asn Asp Leu Val Lys Arg Val Ile Ala Thr Gly Gly Gln Thr Val
145                 150                 155                 160

Glu Cys Cys Asp Asp Gln Gly Arg Ile Leu Val Asp Gly Gln Pro Ile
                165                 170                 175

Asp Glu Pro Tyr Val Val Met Asp Phe Pro Phe Val Pro Gly Ser Gln
            180                 185                 190

Ala Cys Asp Thr Ala Leu Lys Ser Ala Arg Cys Phe Gly Pro Val Thr
        195                 200                 205

Val Pro Glu Gly His Leu Trp Val Met Gly Asp Asn Arg Ser Asn Ser
210                 215                 220

Ala Asp Ser Arg Tyr His Val Gly Asp Asp Met Gln Gly Thr Ile Pro
225                 230                 235                 240

Leu Asp Asn Val Ile Gly Lys Ala Val Phe Ile Ala Leu Pro Pro Ser
                245                 250                 255

Arg Met Gly Thr Ile Ser Ser Pro Asp Ile Gln Gly Lys
            260                 265

<210> SEQ ID NO 109
<211> LENGTH: 810
<212> TYPE: DNA
<213> ORGANISM: Rhodococcus opacus

<400> SEQUENCE: 109
gtgacagatt cttcgaagga gcgggcattg tcgtcggaat ccgagaccac cggcgattcg      60
gccgccacct ccgcagtgaa cggcggtgcg gcggagaccg agaagaaacc ccgctccttc     120
ctccgcgagt tgccgatcct gatcctggtc gcgctcgtcc tgagtttcct gctgcagacg     180
ttcgtcgccc gcgtgtatct cattccgtcg gagtcgatgg aaccgacgct gcacgggtgc     240
gcgggctgca ccggcgaccg catcgtggtc gagaagatcg gctaccgttt cggggacccg     300
caacccggtg acgtcatcgt gttcgcgggg cccgactcgt ggtcacagga tttcgtctcc     360
acccgttcct ccaacgtggt gatccgcggt gcgcaggaag tcggttccct cgtcggactc     420
gtcccgccgg acgagaacga cctcgtcaag cgtgtgatcg ccaccggcgg tcagaccgtc     480
gaatgctgcg acgaccaggg ccgcatcctg gtggacggaa aaccgatcga cgagccctac     540
gtcgtcatgg acttccccct cgtccccggc tcccaggcct gcgacacggc gctgaagtcg     600
gcgcgctgct cggtcccgt caccgtcccc gaggggcacc tgtgggtgat gggcgacaac     660
cgcagcaact ccgcggactc ccgctaccac gtcggcgacg acatgcaagg caccatcccg     720
ctcgacaacg tgatcggcaa ggcggtcttc atcgcgttgc cgccgtcgcg aatgggcacg     780
atcagttcac ccgatatcca gggcaagtga                                      810

<210> SEQ ID NO 110
<211> LENGTH: 285
<212> TYPE: PRT
<213> ORGANISM: Corynebacterium diphtheriae

<400> SEQUENCE: 110

Met Lys Arg Ser Val Phe Ser Phe Cys Met Met Gln Gln Ala Ser Leu
1               5                   10                  15

Gly Val Phe His Ser Met Ala Glu Thr Ala Ala Arg Val Leu Lys Val
            20                  25                  30
```

```
Ser Ser Ala Asn Asn Glu Thr Val Ser Pro Thr Glu Gly Val Glu Thr
        35                  40                  45

His Asp Lys Glu Lys Lys Gln Leu Pro Trp Phe Val Glu Ile Pro Val
    50                  55                  60

Val Val Val Val Thr Leu Leu Val Ile Thr Leu Leu Gln Thr Phe Val
65                  70                  75                  80

Gly Arg Val Tyr Met Ile Pro Ser Gln Ser Met Glu Pro Thr Leu His
                85                  90                  95

Gly Cys Ala Gly Cys Thr Gly Asp Arg Ile Tyr Val Asp Lys Leu Ala
            100                 105                 110

Tyr Arg Phe Gly Glu Pro Glu Ala Gly Asp Val Val Val Phe Ala Gly
        115                 120                 125

Thr Glu Ser Trp Asn Thr Gly Phe Thr Thr Ser Arg Ser Glu Asn Pro
    130                 135                 140

Leu Val Arg Gly Ile Gln Asn Ala Gly Ala Phe Val Gly Leu Val Ala
145                 150                 155                 160
Pro Asp Glu Asn Asp Leu Val Lys Arg Ile Val Ala Thr Gly Gly Gln
                165                 170                 175
Thr Val Gln Cys Leu Glu Gly Asp Glu Gly Val Lys Val Asp Gly Lys
            180                 185                 190
Val Ile Asp Ser Ser Tyr Thr Leu Met Pro Pro Ala Tyr Pro Val Asp
        195                 200                 205
Gln Thr Thr Gly Ser Glu Ala Cys Gly Gly Phe Tyr Phe Gly Pro Ile
    210                 215                 220
Lys Val Pro Glu Gly Asn Tyr Phe Met Met Gly Asp Asn Arg Thr Asn
225                 230                 235                 240
Ser Ala Asp Ser Arg Tyr His Ile Gly Asp Gln Tyr Gln Gly Thr Ile
                245                 250                 255
Pro Lys Glu Asn Leu Lys Gly Lys Val Gln Phe Lys Ile Phe Pro Phe
            260                 265                 270
Asn Arg Ile Gly Ala Val Glu Asp Tyr Asp Ile Gln Gln
        275                 280                 285
```

<210> SEQ ID NO 111
<211> LENGTH: 858
<212> TYPE: DNA
<213> ORGANISM: Corynebacterium diphtheriae

<400> SEQUENCE: 111

```
atgaagcgct cagttttctc tttttgtatg atgcagcaag cgtcgctggg cgtttttcat     60
tcgatggctg aaacagctgc tagagttctc aaagtgagtt cagctaataa cgagactgtg    120
tcccccacgg aaggcgtcga aacgcacgac aaggaaaaga agcaactgcc atggtttgtg    180
gaaatccctg tcgtcgtagt ggtgaccctt cttgtgatca ccttgcttca aacgttcgtt    240
ggacgggtct atatgatccc aagtcagtca atggagccga cacttcatgg atgtgcaggg    300
tgtaccggag accgaattta tgtagataag ctggcttatc gttttggtga accagaagcc    360
ggcgacgttg tagtttttgc aggtacagaa tcatggaaca ccggatttac cacttcacgg    420
tcagaaaatc ctctggttcg tggaatacaa aatgcgggtg ctttcgtcgg attagtagca    480
ccagacgaaa acgaccttgt aaaacgcatc gtagcaacag gggtcaaac ggtgcagtgc     540 cttgaaggcg atgaaggtgt caaagtagac ggtaaagtca tcgactcgtc atatactctg    600
atgccaccag cgtatccggt cgaccagacc acaggatcag aggcgtgcgg cggcttttac    660
ttcggaccta tcaaggtacc tgaaggaaat tacttcatga tgggcgataa ccggacaaac    720
```

```
tccgcggatt ctcgttacca cattggtgat cagtatcaag gcaccatccc taaagaaaac      780
ctcaagggga agttcagtt caagattttc ccatttaacc gtattggtgc agtcgaggat       840
tacgatatcc aacagtga                                                    858
```

<210> SEQ ID NO 112
<211> LENGTH: 208
<212> TYPE: PRT
<213> ORGANISM: Lactococcus lactis

<400> SEQUENCE: 112

```
Met Met Lys Phe Leu Lys Glu Trp Gly Leu Phe Ile Phe Ile Ile Ala
1               5                   10                  15

Ala Val Leu Leu Ser Arg Val Phe Ile Trp Ser Leu Val Val Val Asp
            20                  25                  30

Gly His Ser Met Asp Pro Thr Leu Ala Asp Lys Glu Arg Leu Val Ile
        35                  40                  45

Val Arg Thr Thr Lys Ile Asn Arg Phe Asp Ile Val Ala Lys Glu
    50                  55                  60

Asn Ala Ala Asp Gly Ser Thr Lys Asp Ile Val Lys Arg Val Gly
65                  70                  75                  80

Met Pro Gly Asp Thr Ile Lys Phe Asp His Asp Gln Leu Thr Ile Asn
                85                  90                  95

Asn Lys Val Tyr Pro Glu Asn Tyr Leu Lys Asp Tyr Gln Lys Gln Leu
            100                 105                 110

Ala Asp Gly Gln Leu Glu Lys Thr Tyr Gly Asn Tyr Pro Leu Thr Lys
        115                 120                 125

Ala Leu Thr Asp Gln Asn Arg Ser Leu Phe Val Ser Leu Ala Gln Ser
    130                 135                 140

Thr Lys Ala Phe Thr Thr Asp Ser Thr Gly Asn Pro Thr Phe Thr Val
145                 150                 155                 160

Lys Val Pro Asp Gly Gln Tyr Phe Leu Met Gly Asp Asn Arg Val Val
                165                 170                 175

Ser Gln Asp Ser Arg Ala Val Gly Ser Phe Lys Arg Ser Ala Ile Ile
            180                 185                 190

Gly Glu Ala Lys Leu Arg Val Trp Pro Leu Asn Lys Ile Ser Phe Phe
        195                 200                 205
```

<210> SEQ ID NO 113
<211> LENGTH: 627
<212> TYPE: DNA
<213> ORGANISM: Lactococcus lactis

<400> SEQUENCE: 113

```
atgatgaaat ttttaaaaga atggggatta tttatcttta taattgccgc tgtccttctc      60
tcgcgcgtct ttatttggtc actagttgtc gttgatggcc attcaatgga ccctactta     120 gccgataaag aaagacttgt aattgttaga acgacaaaaa ttaatcgttt tgatattgta    180
gttgctaaag aaaacgcggc tgatggttca accaaagata ttgtcaaacg tgtcgttggg    240
atgcctgggg acactataaa attcgaccat gaccaactta ctatcaataa taaggtttat    300
ccagaaaact atctcaaaga ctatcaaaaa caattggctg atggtcaatt ggaaaaaact    360
tacgggaact atcctttgac aaaagcatta actgatcaaa atcgtagttt atttgtaagc    420
ttagctcaga gcaccaaagc ttttacaacg gatagtactg gtaatccaac ctttacagtc    480
aaagtccctg acggacaata cttcttgatg ggagataatc gtgttgtgtc tcaagatagc    540
```
cgagcagttg gaagtttcaa acgttcagcg attattggtg aagccaaatt acgagtttgg      600
ccactcaata aaatttcttt cttttaa                                          627

<210> SEQ ID NO 114
<211> LENGTH: 262
<212> TYPE: PRT
<213> ORGANISM: Corynebacterium glutamicum

<400> SEQUENCE: 114

Val Thr Asp Phe Ser Ser Ala Ser Asn Ala Asp Ser Thr Gln Asp
 1               5                  10                  15

Gly Arg Pro Gly Arg Arg Ala Gly Lys Ser Lys Lys Glu Ser Lys Pro
                20                  25                  30

Thr Pro Trp Tyr Ile Glu Ile Pro Val Val Val Leu Thr Leu Ala
            35                  40                  45

Leu Ile Phe Val Leu Gln Thr Phe Val Gly Arg Met Tyr Met Ile Pro
    50                  55                  60

Ser Gly Ser Met Glu Pro Thr Leu His Gly Cys Glu Gly Cys Thr Gly
65                  70                  75                  80

Asp Arg Ile Leu Val Glu Lys Val Ser Tyr Tyr Phe Thr Asp Pro Glu
                85                  90                  95

Pro Gly Asp Val Val Phe Lys Gly Thr Asp Ser Trp Asn Val Gly
            100                 105                 110

Phe Thr Thr Gln Arg Ser Asp Asn Ser Val Ile Arg Gly Leu Gln Asn
    115                 120                 125

Leu Gly Ser Tyr Val Gly Leu Val Ala Pro Asp Glu Asn Asp Leu Val
    130                 135                 140

Lys Arg Ile Ile Ala Thr Gly Gly Gln Thr Val Ser Cys Gln Ala Gly
145                 150                 155                 160

Asp Pro Gly Ile Met Val Asp Gly Lys Glu Val Asp Asp Ser Tyr Thr
                165                 170                 175

Leu Gln Pro Ala Gln Phe Pro Ile Asp Glu Thr Ser Gly Ser Thr Glu
            180                 185                 190

Cys Gly Gly Asn Tyr Phe Gly Pro Ile Thr Val Pro Gly Gly Asn Tyr
        195                 200                 205

Phe Met Met Gly Asp Asn Arg Thr Asn Ser Met Asp Ser Arg Tyr His
    210                 215                 220

Leu Gly Asp Gln Tyr Gln Gly Thr Ile Pro Glu Glu Asn Ile Lys Gly
225                 230                 235                 240

Lys Val Gln Ala Ile Ile Leu Pro Phe Ser Arg Ile Gly Gly Val Asp
                245                 250                 255

Asp Pro Ala Ile Lys Gly
            260

<210> SEQ ID NO 115
<211> LENGTH: 789
<212> TYPE: DNA
<213> ORGANISM: Corynebacterium glutamicum

<400> SEQUENCE: 115
gtgactgatt tttctagtgc ttcaaatgct gacgattcca cgcaggacgg tcgtcctggt      60
cgacgtgctg gaaagtctaa gaaggaatcg aagccaactc cgtggtacat cgaaattcca     120
gtggttgtgg ttttgaccct cgcgctgatt ttcgtgctcc agacgtttgt cggacgcatg     180
tacatgattc cgagtggttc gatggaacct actttgcacg gatgtgaggg ctgcacgggt     240

-continued

```
gaccgcatcc tggtggagaa ggtttcttac tacttcacgg atccagagcc gggcgatgtt    300
gtggtgttca agggtactga ttcctggaac gttggattca ctacgcagcg ttccgataat    360
tcggtgatcc gcggcctgca gaacctgggt tcttacgtgg gtcttgtcgc acctgatgaa    420
aatgacctgg tcaagcgcat tatcgccacc ggcggtcaga ctgtttcgtg ccaagccggt    480
gatcctggaa tcatggttga cggcaaggaa gtcgatgaca gctacacgct gcaacctgcg    540
caattcccca tcgatgagac ctccggttcc accgaatgcg gcggcaacta tttcggcccc    600
atcaccgtgc ctggcggcaa ctacttcatg atgggtgaca accgcaccaa ctccatggat    660
tcccgctacc acctgggcga tcagtaccaa ggaaccatcc ctgaggaaaa catcaagggc    720
aaagttcaag caattatcct gccatttagc cgaatcggtg gcgtcgacga ccctgccatc    780
aaaggctag                                                            789
```

<210> SEQ ID NO 116
<211> LENGTH: 287
<212> TYPE: PRT
<213> ORGANISM: Francisella tularensis

<400> SEQUENCE: 116

```
Met Glu Ile Leu Asn Tyr Ile Leu Asn Leu Ser Phe Thr Phe Trp Leu
 1               5                  10                  15

Leu Phe Leu Thr Ile Ala Ser Gly Leu Ile Tyr Ile Ile Asp Phe Val
             20                  25                  30

Phe Phe Gln Lys Ser Arg Leu Ala Ala Tyr Thr Asp Glu Leu Lys Gly
         35                  40                  45

Leu Ser Lys Lys Gln Lys Arg Gln Phe Tyr Lys Asp Arg Gly Leu Lys
     50                  55                  60

Ala Pro Phe Ile Ala Asp Gln Ala Arg Ser Leu Phe Ser Val Phe Phe
 65                  70                  75                  80

Val Val Phe Leu Leu Arg Thr Phe Leu Ile Gly Asn Phe Leu Ile Pro
                 85                  90                  95

Thr Ala Ser Met Thr Pro Thr Leu Pro Val Gly Asp Phe Ile Phe Val
            100                 105                 110

Asn Lys Thr Ala Tyr Gly Ile Arg Ala Pro Phe Thr Asn Glu Thr Leu
        115                 120                 125

Ile Lys Val Gly Glu Pro Lys Arg Gly Asp Ile Val Val Phe His Phe
    130                 135                 140

Pro Val Asn Pro Asn Val Asp Phe Val Lys Arg Val Ile Gly Leu Pro
145                 150                 155                 160

Gly Asp Val Ile Ser Tyr Lys Asp Lys Met Leu Thr Ile Asn Gly Lys
                165                 170                 175

Lys Leu Glu Tyr Thr Asn Cys Asn Arg Asp Ala Met Asn Tyr Tyr Asn
            180                 185                 190

Gln Ser Leu Ala Ala Gly Ser Gly Asp Thr Val Cys Thr Glu Asn Leu
        195                 200                 205

Asp Gly Val Lys His Glu Val Asp Trp Ile Glu Ser Ile Lys Gly Thr
    210                 215                 220

Asp Phe Glu Asn Leu Lys Val Pro Ala Gly Gln Tyr Phe Val Met Gly
225                 230                 235                 240

Asp Asn Arg Asp Asn Ser Glu Asp Ser Arg Tyr Trp Gly Phe Val Pro
                245                 250                 255

Asp Lys Asp Leu Val Gly Lys Ala Lys Val Val Trp Met Ser Trp Asp
            260                 265                 270
```

Lys Ile Asp Lys Lys Val Arg Trp Asp Glu Ile Gly Lys Val Phe
        275                 280                 285

<210> SEQ ID NO 117
<211> LENGTH: 864
<212> TYPE: DNA
<213> ORGANISM: Francisella tularensis

<400> SEQUENCE: 117
atggaaatct taaactatat tttaaacttg agctttactt tttggctttt attcttaacc      60
attgccagtg gtttaattta tattattgat tttgtgttct tccaaaaatc aagattagca     120
gcatatacag atgaattaaa aggtctttct aagaagcaaa acgtcagtt ctataaagat      180 agaggattaa aagcaccctt tattgctgat caggcgagat ctttatttag tgtatttttt     240
gtagtttttc tacttagaac cttcttgatt ggtaattttt taattccaac tgcatcaatg     300
acaccaacac ttccagttgg tgattttatt tttgtcaata aaactgctta tggtatcaga     360
gcaccattta ccaatgagac tttaataaaa gttggtgaac ccaaaagagg tgatattgta     420
gtatttcatt ttccagttaa tcctaatgtt gatttttgtaa acgagtgat cggtttgcct     480 ggcgatgtaa tttcgtataa agacaaaatg ttgacaataa atggtaaaaa acttgaatat     540
actaattgta atcgtgatgc aatgaactat tataatcagt ctttagctgc tggtagtggc     600
gatacagtat gtacgaaaaa ccttgatgga gttaaacatg aggttgattg atagagtct      660 ataagggaa ctgattttga aaaccttaaa gtcccagcag gtcaatactt tgtcatggga      720
gataatcgtg ataatagtga agatagtcgt tattggggtt ttgtacctga caaagatcta     780
gttggtaaag caaagttgt ttggatgagc tgggataaga tagataaaaa ggttcgctgg      840
gatgaaattg gtaaggtctt ttaa                                            864

<210> SEQ ID NO 118
<211> LENGTH: 282
<212> TYPE: PRT
<213> ORGANISM: Campylobacter jejuni

<400> SEQUENCE: 118

Met Glu Ile Leu Lys Lys Leu Tyr Lys Phe Ser Gln Ser Trp Thr Gly
 1               5                  10                  15

Thr Val Ile Val Leu Leu Val Ile Phe Phe Ile Gln Ala Phe
            20                  25                  30

Val Ile Pro Ser Gly Ser Met Lys Asn Thr Leu Leu Val Gly Asp Phe
        35                  40                  45

Leu Phe Val Lys Lys Phe Ser Tyr Gly Ile Pro Thr Pro His Ile Pro
    50                  55                  60

Trp Leu Glu Ile Pro Val Leu Pro Asp Phe Asn Lys Asp Gly His Leu
65                  70                  75                  80

Ile Lys Ala Gln Gly Ser Gln Arg Gly Asp Ile Val Val Phe Arg Asn
                85                  90                  95

Pro Arg Asn Glu Lys Glu His Phe Val Lys Arg Cys Val Gly Thr Gly
            100                 105                 110

Gly Asp Arg Ile Val Tyr Ala Asn Lys Thr Leu Tyr Val Arg Met His
        115                 120                 125

Glu Gly Asp Glu Phe Met Lys Glu His Tyr Pro Asn Asp Leu Val Thr
    130                 135                 140

Leu Gly Gly Gln Ile Tyr Val Lys Glu Pro Tyr Lys Gln Lys Gly Ile
145                 150                 155                 160

His Tyr Asp Pro Lys Lys Asp Ile Glu Ser Asp Ile Leu Arg Phe Leu
                165                 170                 175

Ser Ile Gly Asp Phe Ala Met Ser Pro Thr Tyr Ile Lys Glu Leu Gly
            180                 185                 190

Asn His Ile Gly Phe Ser Gly Gly Asn Ala Tyr Val Phe Asp Val Pro
        195                 200                 205

Glu Asn Glu Tyr Phe Met Met Gly Asp Asn Arg Asp Tyr Ser Tyr Asp
    210                 215                 220

Ser Arg Phe Trp Gly Ser Val Pro Tyr Arg Leu Ile Val Gly Lys Pro
225                 230                 235                 240

Trp Phe Val Tyr Phe Ser Trp Asp Lys Asp Lys Asn Val Arg Trp Glu
                245                 250                 255

Arg Ile Gly Arg Phe Val Asp Thr Leu Glu Asn Asp Glu Gln Tyr Ile
            260                 265                 270

His Asp His Asp Asp Glu Asp Lys Leu Ser
        275                 280

<210> SEQ ID NO 119
<211> LENGTH: 849
<212> TYPE: DNA
<213> ORGANISM: Campylobacter jejuni

<400> SEQUENCE: 119
atggaaattt taagaaaatt atataaattt tcacagtctt ggactggaac tgtagttatt      60
gttcttttgg tgattttttt ctttatacaa gcttttgtta ttccttctgg ttctatgaaa    120
aacaccttat tggtagggga ttttttattt gttaaaaaat ttagctatgg tatcccaact    180
cctcatattc cttggttgga aattcctgtt ttgccagatt tcaataaaga tgggcatttg    240
ataaaagcac aagggtcaca agaggagat atagttgttt ttagaaatcc tagaaatgaa     300
aaagaacact tgtaaagcg ttgtgtaggc acaggaggag ataggatagt ttatgcaaat     360
aaaacacttt atgtaagaat gcatgagggt gatgaattta tgaaagaaca ttatccgaat    420
gatcttgtta ctcttggagg gcaaaattat gtaaaagaac cttataaaca aaaaggtatt    480
cattatgatc aaaaaaaga tatagaaagc gatatttac gctttcttag cataggtgat     540
tttgctatgt ctccaactta tattaaagaa cttggaaatc atataggttt tagcggcgga    600
aatgcttatg tttttgatgt gcctgaaaat gagtatttca tgatgggtga taatcgcgat    660
tattcttatg atagtcgttt ttggggttct gttccttata ggttgatagt aggtaaacct    720
tggtttgtat atttctcttg gataaagat aaaatgttc gctgggaaag gatagggcgt     780
tttgttgata ccttggaaaa tgatgaacaa tatatccatg atcatgatga tgaggataaa    840
ttaagctaa                                                           849

<210> SEQ ID NO 120
<211> LENGTH: 290
<212> TYPE: PRT
<213> ORGANISM: Helicobacter pylori

<400> SEQUENCE: 120

Met Lys Phe Leu Arg Ser Val Tyr Ala Phe Cys Ser Trp Val Gly
 1               5                  10                  15

Thr Ile Val Ile Val Leu Leu Val Ile Phe Phe Val Ala Gln Ala Phe
            20                  25                  30

Ile Ile Pro Ser Arg Ser Met Val Gly Thr Leu Tyr Glu Gly Asp Met
        35                  40                  45

```
Leu Phe Val Lys Lys Phe Ser Tyr Gly Ile Pro Ile Pro Lys Ile Pro
 50                  55                  60

Trp Ile Glu Leu Pro Ile Met Pro Asp Phe Lys Asn Asn Gly His Leu
 65                  70                  75                  80

Ile Glu Gly Asp Arg Pro Lys Arg Gly Glu Val Val Phe Ile Pro
                 85                  90                  95

Pro His Glu Lys Lys Ser Tyr Tyr Val Lys Arg Asn Phe Ala Ile Gly
                100                 105                 110

Gly Asp Glu Val Leu Phe Thr Asn Glu Gly Phe Tyr Leu His Pro Phe
            115                 120                 125

Glu Ser Gly Asn Asp Lys Asp Tyr Ile Ala Lys His Tyr Pro Asn Ala
130                 135                 140

Met Thr Lys Glu Phe Met Gly Lys Ile Phe Val Leu Asn Pro Tyr Lys
145                 150                 155                 160

Ser Lys His Pro Gly Ile His Tyr Gln Lys Asp Asn Glu Thr Phe His
                165                 170                 175

Leu Met Glu Gln Leu Ala Thr Gln Gly Ala Glu Ala Asn Ile Ser Met
            180                 185                 190

Gln Leu Ile Gln Met Glu Gly Glu Lys Val Phe Tyr Lys Lys Ile Asn
        195                 200                 205

Ser Asp Glu Phe Phe Met Ile Gly Asp Asn Arg Asp Asn Ser Ser Asp
210                 215                 220

Ser Arg Phe Trp Gly Ser Val Ala Tyr Lys Asn Ile Val Gly Ser Pro
225                 230                 235                 240

Trp Phe Val Tyr Phe Ser Leu Ser Leu Lys Asn Ser Leu Glu Met Asp
                245                 250                 255

Ala Glu Asn Asn Pro Lys Lys Arg Tyr Leu Val Arg Trp Glu Arg Met
            260                 265                 270

Phe Lys Ser Val Glu Gly Leu Glu Lys Ile Ile Lys Lys Glu Lys Ala
        275                 280                 285

Thr His
    290

<210> SEQ ID NO 121
<211> LENGTH: 873
<212> TYPE: DNA
<213> ORGANISM: Helicobacter pylori

<400> SEQUENCE: 121
atgaaatttt tacgctctgt ttatgcattt tgctccagtt gggtagggac gattgttatt     60
gtgctgttgg ttatcttttt tgttgcgcaa gctttcatca ttccctctcg ctctatggta    120
ggcacgctct atgagggcga catgctcttt gtcaaaaaat tttcttacgg catacccatt    180
cctaaaatcc catggattga gcttcctatt atgcctgatt taaaaataa cgggcatttg    240 atagaggggg atcgccctaa gcgcggcgaa gtggtcgtat ttatcccccc ccatgaaaaa    300
aaatcttact atgtcaaaag gaattttgcc attggggcg atgaggtgct attcactaat    360
gaggggtttt atttgcaccc ttttgagagc ggcaacgata agattatat tgctaaacat    420 taccctaacg ccatgactaa agaatttatg gtaaaatttt ttgttttaaa cccttataaa    480
agtaagcatc cgggtatcca ttaccaaaaa gacaatgaaa ccttccactt aatggagcag    540
ttagccactc aaggtgcgga agctaatatc agcatgcaac tcattcaaat ggagggcgaa    600
aaggtgtttt acaagaaaat caatagcgat gaattttca tgatcggcga taacagagac    660
```

-continued

```
aattctagcg actcgcgctt ttgggggagt gtggcttata aaacatcgt gggttcgcca      720 tggtttgttt atttcagttt gagtttaaaa aatagcctgg aaatggatgc agaaaacaac      780
cccaaaaaac gctatttggt gcgttgggaa cgcatgttta aaagcgttga aggcttagaa      840
aaaatcatta aaaagaaaa agcaacgcat taa                                    873
```

<210> SEQ ID NO 122
<211> LENGTH: 274
<212> TYPE: PRT
<213> ORGANISM: Propionibacterium acnes

<400> SEQUENCE: 122

```
Val Ala Asp Asp Tyr Arg Ala Arg Arg Ala Ala Asn Gly Asp Thr Arg
 1               5                  10                  15
Asp Ser Asp Asp Ala Thr Ala Arg Gly Glu Gln Ala Ser Gly Trp Gln
                20                  25                  30
Arg Phe Arg Ser Gly Ala Ile Glu Val Val Leu Ile Val Gly Ala
            35                  40                  45
Leu Ile Ile Ser Ala Val Leu Arg Gly Phe Val Ala Gln Met Phe Val
        50                  55                  60
Ile Pro Ser Lys Ser Met Gln Asn Thr Leu Gln Val Gly Asp Arg Val
 65                 70                  75                  80
Ile Ala Val Lys Ala Ala Asp Phe His Arg Gly Asp Val Val Phe
                85                  90                  95
Lys Asp Thr Glu His Trp Leu Pro Ala Val Gln Asp Arg Arg Ser Val
            100                 105                 110
Pro Gly Gln Ile Leu Glu Phe Val Gly Leu Leu Pro Asn Lys Ser Ser
        115                 120                 125
Asn Tyr Leu Ile Lys Arg Val Ile Gly Met Pro Gly Asp Thr Val Ala
    130                 135                 140
Cys Cys Asn Val Asn Gly Gln Val Thr Val Asn Gly Lys Ala Leu Asp
145                 150                 155                 160
Glu Arg Ser Tyr Leu Tyr Ser Glu Asn Gly Glu Met Val Lys Pro Ser
                165                 170                 175
Ala Met Glu Phe Arg Val Thr Val Pro Arg Gly Arg Met Phe Val Leu
            180                 185                 190
Gly Asp His Arg Asn Ala Ser Gly Asp Ser Arg Tyr His Leu Gln Asp
        195                 200                 205
Leu Asp Pro Gly Glu Tyr Thr Gly Ala Pro Ala Phe Val Pro Leu Asp
    210                 215                 220
Asp Val Val Gly Pro Ala Lys Ala Ile Leu Met Pro Leu Asn Arg Ile
225                 230                 235                 240
Glu Gly Leu Gly Thr Pro Asn Thr Phe Arg Gly Ile Pro Asp Arg Ser
                245                 250                 255
Ser Ser Ala Pro Ala Lys Ala Arg Ile Cys Val Gly Asn Thr Cys Cys
            260                 265                 270
Pro Lys
```

<210> SEQ ID NO 123
<211> LENGTH: 825
<212> TYPE: DNA
<213> ORGANISM: Propionibacterium acnes

<400> SEQUENCE: 123

```
gtggcggatg actaccgggc gaggcgggct gcaaacggcg acaccaggga ctctgacgat       60
```

```
gcaacagcac gtggggaaca ggcgtctggg tggcagcgct ttcggtcggg ggccatcgaa    120
gttgttctca tcgtcgttgg tgccctcatc atctcagctg tgctgcgtgg tttcgtcgct    180
cagatgtttg tcatcccgtc gaagtccatg caaaacacct gcaggtgggt gaccgcgtg    240 atcgcggtga aagccgccga ttttcatcgg ggcgacgtcg tcgtgttcaa agacaccgaa    300
cattggttac ctgctgttca ggatcgccgc tctgttccag acagatcct cgaattcgtc    360 gggttgttgc taacaagag ctcgaactac ctcattaagc gagtgatcgg catgcctggg    420
gacaccgttg cctgctgcaa cgtcaacggc caggtgaccg tcaacggtaa ggcgcttgac    480
gagcggtcat acctgtactc cgaaaatggt gaaatggtta aaccctcggc gatggaattc    540
cgggtcactg ttcctcgggg gcggatgttc gtcttggggg accatcgcaa tgcctcgggt    600
gactcgcgct atcacctcca agaccttgat ccgggtgagt atacgggcgc tcctgcgttt    660
gtgccgctcg atgacgtcgt tgggccggca aaggccattc ttatgcctct caatcgcatt    720
gagggactgg ggactcctaa cactttccgg ggaatcccgg ataggtcgtc gtcagctcca    780
gccaaggcgc gcatctgcgt cggtaacacg tgctgcccta agtga                    825
```

<210> SEQ ID NO 124
<211> LENGTH: 628
<212> TYPE: PRT
<213> ORGANISM: Chlamydia trachomatis

<400> SEQUENCE: 124

```
Met Thr Ser Ser Tyr Met Ser Arg Leu Tyr Ser Leu Asn Lys Ser Arg
1               5                   10                  15

Arg Ile Leu His Ser Ser Phe Arg Leu Lys Ser Thr Lys Met Leu
            20                  25                  30

Ser His Pro Glu Thr Gln Lys Glu Leu Gln Glu Val Leu Lys Gln Leu
        35                  40                  45

Glu Glu Ala Ile Leu Asp Gln Asn Arg Glu Asp Ala Ser Leu Phe Ala
    50                  55                  60

Lys Gln Ala Gln Ala Ile Gln Lys Arg Phe Pro Lys Ser Lys Leu Arg
65                  70                  75                  80

Ala Thr Phe Asp Leu Ile Tyr Ala Leu Thr Phe Ala Ala Ile Leu Ala
                85                  90                  95

Phe Leu Ile Arg Gln Phe Trp Phe Glu Leu Tyr Glu Val Pro Thr Gly
            100                 105                 110

Ser Met Arg Pro Thr Ile Leu Glu Gln Asp Arg Ile Leu Val Ser Lys
        115                 120                 125

Thr Thr Phe Gly Leu Arg Leu Pro Phe Ser Asn Arg Ser Ile Gly Tyr
    130                 135                 140

Thr Pro Glu Ala Ile Thr Arg Gly Glu Leu Val Val Phe Thr Val Gly
145                 150                 155                 160

Asp Leu Pro Ile Pro Asn Ala Asp Thr Lys Tyr Phe Gly Ile Ile Pro
                165                 170                 175

Gly Lys Lys Arg Tyr Ile Lys Arg Cys Met Gly Lys Pro Gly Asp Thr
            180                 185                 190

Val Tyr Phe Tyr Gly Gly Lys Ile Tyr Gly Ile Asp Cys Asp Gly Glu
        195                 200                 205

Pro Ile Phe Pro Gln Asn Thr Glu Asn Leu Tyr His Val Pro Tyr Ile
    210                 215                 220

Ser Phe Asp Gly Thr Pro Glu Ile Leu Thr His Ser Glu Glu Gln Thr
225                 230                 235                 240
```

```
Asp Val Ile Phe Asn Gln Phe His Thr Pro Cys Gly Lys Ile Ser Leu
                245                 250                 255

Pro Gln Gln Ala Ser Tyr Gly Gln Phe Phe Tyr Lys Asn Ala Trp His
            260                 265                 270

Asn Asp Thr Pro Tyr Ala Leu Lys Asp Pro His Asn Glu Pro Val Ser
        275                 280                 285

Tyr Ala Asp Leu Phe Gly Ile Lys Asn Phe Ala Met Val Arg Ile Leu
    290                 295                 300

Thr Lys Lys Gln Ala Ala Leu Thr His Val Leu Pro Ser Pro Leu Ser
305                 310                 315                 320

Asp Thr Tyr Leu Glu Ile Ala His Thr Pro Asn Val Ser Tyr Pro His
                325                 330                 335

Pro His Leu Arg Pro Phe Glu Thr Gln Leu Ile Pro Thr Ile Glu Pro
            340                 345                 350

Met Lys Thr Leu Leu Pro Leu Arg Lys Glu His Ile His Leu Ile Arg
        355                 360                 365

Asn Asn Leu Thr Thr Ser Arg Phe Thr Val Val Asp Gly Tyr Ala Tyr
    370                 375                 380

Lys Tyr Gln Pro Ala Pro Met Asn Thr Ser Gly Met Val Arg Met Phe
385                 390                 395                 400

Ala Leu Pro Met Pro Asn Ile Pro Asp Gly Cys Tyr Glu Phe Ser Lys
                405                 410                 415

Gly Asp Val Phe Lys Ile Asn Met Gly Gly Phe Arg Thr Lys Leu Lys
            420                 425                 430

Gln Pro His Pro Leu Thr Gln Leu Ser Asn Ser Gln Val Ile Asp Leu
        435                 440                 445

Phe Asn Cys Gly Ile Ser Phe His Thr Ile Tyr Ile Pro Lys Asn Pro
    450                 455                 460

Gln Tyr Ala Pro Phe Pro Asn Arg Tyr Ala Phe Phe Asn Gln Gly Asn
465                 470                 475                 480

Leu Phe Val Met Asp Ser Pro Val Phe Ile Asp Ser Asp Pro Ala Leu
                485                 490                 495

Gln Lys Phe Ile Val Ser Glu Glu Lys Glu Leu Gln Ser Ser Glu
            500                 505                 510

Asp Lys Pro Tyr Ile Ala Phe Ile Asp Arg Gly Pro Pro Glu Ser
        515                 520                 525

Thr Glu Glu Phe Val Ser Phe Ile Thr Asn Phe Gly Leu Lys Ile Pro
        530                 535                 540

Glu Gly His Val Leu Val Leu Gly Asp Asn Cys Pro Met Ser Ala Asp
545                 550                 555                 560

Ser Arg Asp Phe Gly Phe Val Pro Val Glu Asn Leu Leu Gly Ser Pro
                565                 570                 575

Val Gly Ile Phe Trp Pro Ile Asn Arg Leu Gly Leu Ser Ser Asn
            580                 585                 590

Ile Thr Pro Leu Ser Leu Pro Gly Tyr Leu Val Asn Gly Leu Ala Leu
    595                 600                 605

Gly Ala Phe Leu Tyr Cys Ile Gly Leu Trp Tyr Tyr Arg Lys Asn His
610                 615                 620

Arg Leu Phe Pro
625

<210> SEQ ID NO 125
<211> LENGTH: 1887
<212> TYPE: DNA
```

<213> ORGANISM: Chlamydia trachomatis

<400> SEQUENCE: 125

```
atgacgagca gttacatgag tcgcttatat tccctgaata agagtcgtcg cattcttcat      60
tcttccttta gattgctgaa aagcacaaaa atgctctctc atccggaaac tcaaaaagaa     120
ctacaagaag tcttgaaaca gcttgaagag gctatttttgg atcagaatag ggaagatgct    180
tcccttttttg ctaagcaagc tcaagccata caaaaaagat tccctaaatc caaactccga    240
gctacttttg atcttatcta tgctttgacg tttgctgcca ttcttgcttt tttaatccgc     300
cagttctggt ttgagctata tgaagttcct acaggatcta tgcggcctac tattcttgaa    360
caagatcgta ttcttgtttc caaaacaaca tttggactcc ggctaccttt tagtaacaga    420
agtattggct atacacctga ggctatcact cgaggagaac tggtagtctt cactgttgga   480
gatcttccta tccctaatgc cgacactaag tattttggaa tcatccctgg gaaaaaacgc    540
tatataaaac ggtgcatggg taaacctgga gataccgtat attttatgg agggaaaatt     600
tatgggatcg attgcgacgg agagcccatc ttcccccaaa atacagagaa tctctaccac   660
gtcccctata tttcttttga cggaactcca gaaattctta cccattcaga agagcaaaca    720
gatgtgatct ttaaccaatt tcacacacct tgtggaaaga tttctctccc tcaacaggct    780
tcttatggac aatttttcta taagaatgct tggcataatg atactcccta tgctttaaaa    840
gatcctcata tgagcctgt tagctatgcc gatctattcg gaataaaaaa ttttgcaatg    900
gttcgcatcc ttaccaaaaa acaagctgct cttactcatg tccttccctc tcctctttcg    960
gacacctacc tagaaattgc ccacactcct aatgtttcct atcctcaccc tcacttacgt  1020
ccatttgaaa cacagcttat tcctactatc gaacctatga aaaccttgct tcctttaagg   1080
aaggaacata ttcatttgat tcgtaataac ctcacaacat cccgttttac agttgtagat    1140
ggatatgctt acaagtacca acctgctccc atgaatacct caggcatggt caggatgttt     1200
gccctaccta tgccaaatat tcctgacgga tgttatgaat tttctaaagg agacgtgttt    1260
aaaatcaata tgggtggctt tcgaacaaaa ctcaaacagc cgcatccttt aacgcaatta   1320
agcaattctc aggtcattga cttatttaat tgcggcatta gtttccacac gatctatatt     1380
cctaaaaacc ctcaatatgc tccgttccct aatcgctatg cattttttcaa tcaagggaac  1440
ctgttcgtta tggattctcc agtttttatt gatagcgatc ctgccttaca gaaattcatt    1500
gtgtctgaag aggaaaaaga acttcaatca tctgaagaca aaccttacat cgcatttatt   1560
gacagaggtc ctcctccaga atctacagag gaatttgttt cctttattac taatttcggt    1620
cttaaaattc cggaaggcca cgtgcttgtc ttaggagata attgtcctat gagcgctgat    1680
agccgtgatt ttggttttgt tcccgttgaa aatcttttgg gatctcctgt tgggatcttc    1740
tggcctatta atcgtctagg attgttatct tccaatataa cgcccttgag tttacctggc    1800
tacctcgtaa atggattggc tctaggagct tttctttact gcataggatt atggtactat   1860
cgaaaaaacc ataggctatt cccttaa                                        1887
```

<210> SEQ ID NO 126  
<211> LENGTH: 636  
<212> TYPE: PRT  
<213> ORGANISM: Chlamydophila pneumoniae

<400> SEQUENCE: 126

```
Met Lys Gln His Tyr Ser Leu Asn Lys Ser Arg His Ile Leu Arg Ser
  1               5                  10                  15
```

```
Thr Tyr Lys Leu Leu Lys Ser Lys Lys Leu Ala His Ser Pro Ala Asp
             20                  25                  30

Lys Lys Gln Leu Gln Glu Leu Leu Glu Gln Leu Glu Glu Ala Ile Phe
         35                  40                  45

Glu His Asp Gln Glu Thr Ala Ser Asp Leu Ala Gln Gln Ala Leu Ala
     50                  55                  60

Phe Ser Asn Arg Tyr Pro Asn Ser Phe Gly Arg Lys Thr Tyr Glu Leu
 65                  70                  75                  80

Ile Lys Ala Leu Leu Phe Ala Gly Val Val Ala Phe Leu Val Arg Gln
                 85                  90                  95

Phe Trp Phe Glu Leu Tyr Glu Val Pro Thr Gly Ser Met Arg Pro Thr
            100                 105                 110

Ile Leu Glu Gln Asp Arg Ile Leu Val Ser Lys Thr Thr Phe Gly Leu
        115                 120                 125

His Cys Pro Phe Ala Lys Lys Pro Leu Ala Phe Asn Pro Glu Ser Val
    130                 135                 140

Thr Arg Gly Gly Leu Val Val Phe Thr Val Gly Asp Leu Pro Ile Pro
145                 150                 155                 160

Asp Ala Asp Thr Lys Tyr Phe Gly Leu Ile Pro Gly Lys Lys Arg Tyr
                165                 170                 175

Ile Lys Arg Cys Met Gly Arg Pro Gly Asp Phe Leu Tyr Phe Tyr Gly
            180                 185                 190

Gly Lys Ile Tyr Gly Leu Asp Asp Ala Gly Lys Arg Ile Glu Phe Pro
        195                 200                 205

Ser Val His Gly Leu Glu Asn Leu Tyr His Val Pro Tyr Ile Ser Phe
    210                 215                 220

Asp Gly Thr Thr Ser Ser His Thr Glu Gly Gln Lys Thr Ile Ile Asp
225                 230                 235                 240

Phe Lys Gln Phe Asn Gln Ser Tyr Gly Arg Leu Ile Phe Pro Gln Thr
                245                 250                 255

Ser Met Tyr Gly Gln Phe Phe Asp His Lys Glu Trp His Gln Asp Glu
            260                 265                 270

Pro Asn Lys Leu Lys Asp Pro His Leu Ser Pro Val Ser Tyr Ala Asp
        275                 280                 285

Leu Phe Gly Met Gly Asn Tyr Ala Met Val Arg Ile Leu Thr Glu His
    290                 295                 300

Gln Ala Arg Thr Ser His Leu Leu Pro Asn Pro Gly Ser Pro Thr Lys
305                 310                 315                 320

Val Tyr Leu Glu Ile Cys His Thr Ala Asn Leu Ser Tyr Pro Lys Pro
                325                 330                 335

Leu Leu Arg His Tyr Glu His Gln Leu Ser Pro Ala Ile Gln Pro Met
            340                 345                 350

Lys Thr Leu Leu Pro Leu Arg Lys Glu His Leu His Leu Ile Arg Asn
        355                 360                 365

Asn Leu Thr Thr Ser Arg Phe Ile Val Ala Gln Gly Cys Ala Tyr Lys
    370                 375                 380

Tyr His Gln Phe Lys Ile Asn Thr Ser Gly Ile Ala Lys Ala Tyr Ala
385                 390                 395                 400

Ile Leu Leu Pro Lys Val Pro Asp Gly Cys Tyr Glu Tyr Ser Lys Gly
                405                 410                 415

Glu Ala Tyr Gln Ile Gly Phe Gly Ile Arg Tyr Lys Leu Lys Ser
            420                 425                 430

Ser His Pro Leu Thr Gln Leu Asn Asp Lys Gln Val Ile Glu Leu Phe
```

```
           435                 440                 445
Asn Cys Gly Ile Asn Phe Ser Ser Ile Tyr Asn Pro Val Asn Pro Leu
    450                 455                 460

Gln Ala Pro Leu Pro Asn Arg Tyr Ala Phe Phe Asn Gln Gly Asn Leu
465                 470                 475                 480

Tyr Ile Met Asp Ser Pro Val Phe Ile Lys Asn Asp Pro Thr Leu Gln
                485                 490                 495

Lys Phe Val Thr Ser Glu Thr Glu Lys Gln Glu Gly Ser Ser Glu Thr
            500                 505                 510

Gln Pro Tyr Ile Ala Phe Val Asp Lys Gly Leu Pro Pro Glu Asp Phe
        515                 520                 525

Lys Glu Phe Val Glu Phe Ile His Asn Phe Gly Ile Gln Val Pro Lys
    530                 535                 540

Gly His Val Leu Val Leu Gly Asp Asn Tyr Pro Met Ser Ala Asp Ser
545                 550                 555                 560

Arg Glu Phe Gly Phe Val Pro Met Glu Asn Leu Leu Gly Ser Pro Leu
                565                 570                 575

Cys Thr Phe Trp Pro Ile Gly Arg Met Gly Arg Leu Thr Gly Val Ser
            580                 585                 590

Ala Pro Thr Thr Leu Ser Gly Tyr Leu Val Ser Gly Ile Ala Leu Ala
        595                 600                 605

Thr Gly Leu Ser Leu Ile Gly Tyr Val Tyr Tyr Gln Lys Arg Arg Arg
    610                 615                 620

Leu Phe Pro Lys Lys Glu Glu Lys Asn His Lys Lys
625                 630                 635

<210> SEQ ID NO 127
<211> LENGTH: 1911
<212> TYPE: DNA
<213> ORGANISM: Chlamydophila pneumoniae

<400> SEQUENCE: 127
atgaaacaac actattctct aaataaaagt cgtcatatcc tccgcagtac ttataagctt      60
ttaaaaagta aaaaactcgc ccattcccct gcagataaaa agcaactgca agaactacta     120
gaacaactag aagaggctat cttttgaacat gatcaagaaa ctgcaagcga cttagctcag     180
caagcattag cattttccaa ccgttatcct aattccttcg gacgcaaaac ctatgagctt     240
atcaaggccc ttcttttttgc tggtgttgta gccttcttag ttcggcaatt ttggtttgaa     300
ctttatgaag tgcctacagg atccatgagg cctacaattt tagaacagga tcggattctt     360
gtatccaaaa caacatttgg tctccattgc ccttttgcta agaaaccact tgccttcaat     420
cctgaatccg taactcgcgg gggtcttgtt gttttcactg taggcgacct ccctatccca     480
gatgctgata caaagtactt cggattgatt ccaggaaaaa agcgttacat taaacgttgc     540
atgggaagac tgggggactt cttatatttc tatggaggaa aaattatgg tcttgatgat     600 gcaggtaaac gcatagagtt tccttctgtc catggtttag aaaacttata tcacgtcccc     660
tatatatcct tgatggcac taccagcagc catacagaag ggcagaaaac aattatagat     720
tttaagcagt tcaatcaaag ttatggtcgg ctgattttcc ctcaaacctc catgtatgga     780
caattctttg accataaaga atggcatcaa gacgagccta ataaattaaa agatcctcat     840
ctttcgccag tcagctatgc cgatcttttt ggtatgggta actatgctat ggtgcgcatc     900
ttaacagaac atcaggcacg aacatcccat ctacttccga atccaggaag tccaactaaa     960
gtctacttag aaatttgcca tacagcgaac ctttcctacc caaagcctct gttgcgtcac    1020
```

```
tatgagcatc agctctcgcc tgcgattcaa cctatgaaga ctttacttcc tttgcgtaag    1080
gaacatttgc acttaattcg gaacaatctt actacctctc gttttattgt tgctcaagga    1140
tgtgcgtata ataccatca attcaagatt aacacttcag gaattgccaa agcctatgca    1200
attctcctgc ccaaggtccc tgatggttgt tatgaatatt ctaaaggcga agcgtatcaa    1260
attggctttg gagagattcg ttataagcta aaatcttctc accccttac tcagctcaat    1320 gataagcaag tgattgaact ttttaactgc gggatcaact ttagttctat ttataatcct    1380
gtgaatccgc tgcaagcacc tttacctaac cgttatgcat tctttaacca agggaatctt    1440
tatatcatgg attctcctgt atttataaag aatgatccaa ctctgcaaaa atttgtgact    1500
tctgaaacgg aaaagcaaga ggggtcttca gagacacaac cctatatagc ttttgttgac    1560
aagggactcc ctccagaaga ttttaaagaa ttcgtggagt ttatacataa ttttggtatt    1620
caagttccta aaggtcatgt tctcgtcttg ggagataact accctatgag tgcggatagt    1680
cgagaatttg gctttgttcc tatggaaaat ctcttaggat ctcctctatg tacattctgg    1740
cctattggac gcatgggacg gttaactgga gtttctgctc caacaacact ctcaggttat    1800
cttgttagtg ggatagcatt agcgacgggt ctctctctca ttggatatgt ctactatcaa    1860
aaacgacgca gactctttcc taagaaagag gagaaaaacc acaagaaata a             1911
```

<210> SEQ ID NO 128
<211> LENGTH: 189
<212> TYPE: PRT
<213> ORGANISM: Staphylococcus carnosus

<400> SEQUENCE: 128

```
Val Lys Lys Glu Ile Lys Glu Trp Ile Ile Ala Ile Ala Ile Ala Leu
 1               5                  10                  15

Val Leu Val Leu Val Ile Thr Asn Phe Ile Ala Lys Ser Tyr Thr Val
                20                  25                  30

Arg Gly Asp Ser Met Tyr Pro Thr Leu Lys Asp Gly Glu Lys Val Ile
            35                  40                  45

Val Asn Met Ile Gly Phe Lys Thr Gly Gly Leu Glu Lys Gly Asn Val
        50                  55                  60

Ile Val Phe His Ala Thr Lys Asn Ser Asp Tyr Val Lys Arg Val Ile
65                  70                  75                  80

Gly Met Pro Gly Asp Ser Ile Glu Tyr Lys His Asp Gln Leu Tyr Val
                85                  90                  95

Asn Gly Lys Lys Val Lys Glu Pro Tyr Leu Asp Tyr Asn Glu Lys His
            100                 105                 110

Lys Ser Tyr Asp Glu Ile Thr Gly Ser Phe Lys Val Lys Asn Leu Pro
        115                 120                 125

Asn Ala Asn Gly Ser Asn Thr Ile Pro Lys Asn Lys Leu Leu Val Leu
    130                 135                 140

Gly Asp Asn Arg Glu Val Ser Lys Asp Ser Arg Ser Phe Gly Leu Ile
145                 150                 155                 160

Asp Glu Asp Gln Val Val Gly Lys Val Ser Leu Arg Tyr Trp Pro Phe
                165                 170                 175

Thr Ser Phe Lys Val Asn Phe Asn Pro Asp Thr Lys Tyr
            180                 185
```

<210> SEQ ID NO 129
<211> LENGTH: 570
<212> TYPE: DNA

<213> ORGANISM: Staphylococcus carnosus

<400> SEQUENCE: 129

```
gtgaagaaag aaattaaaga gtggataata gccatagcaa tagctttggt attagttcta    60
gtcataacaa atttcattgc gaaatcatat acggttcgtg gtgattcaat gtatccaacg   120
ctaaaagacg gagaaaaagt tatcgttaat atgattggat ttaaaactgg cggtttagaa   180
aaaggtaatg tgattgtatt ccacgctact aaaaacagcg actacgttaa acgtgttatc   240
ggtatgcctg gtgacagtat tgaatataaa catgatcaat tgtatgttaa tggtaaaaaa   300
gtgaaagaac cttatttaga ttataatgaa aaacataaaa gctatgatga aattacaggt   360
agctttaaag tgaaaaattt acctaatgca aatggttcaa acacaattcc taaaaacaaa   420
cttcttgtat taggagataa ccgtgaagtc agtaaagaca gccgttcatt cggtttaatt   480
gatgaagatc aagttgttgg taaagtaagc ttgcgttatt ggccgtttac atctttcaaa   540
gtaaacttta atccggatac aaaatattaa                                    570
```

<210> SEQ ID NO 130
<211> LENGTH: 190
<212> TYPE: PRT
<213> ORGANISM: Staphylococcus haemolyticus

<400> SEQUENCE: 130

```
Leu Lys Lys Glu Ile Val Glu Trp Ile Val Ala Ile Ala Val Gly Leu
  1               5                  10                  15
Leu Leu Val Trp Val Met Val Asn Phe Val Ala Lys Ser Tyr Thr Ile
                 20                  25                  30
Lys Gly Asp Ser Met Asp Pro Thr Leu Lys Asp Gly Glu His Val Met
             35                  40                  45
Val Asn Ile Leu Gly Tyr Lys Val Gly Asp Ile Lys Lys Gly Asn Val
         50                  55                  60
Ile Val Phe His Ala Asn Gln Gln Asp Asp Tyr Val Lys Arg Val Ile
 65                  70                  75                  80
Gly Val Pro Gly Asp Asn Val Ile Tyr Lys Asn Asp Lys Leu Tyr Val
                 85                  90                  95
Asn Gly Lys Lys Ile Asn Glu Pro Tyr Leu Asp Tyr Asn Glu Lys Arg
            100                 105                 110
Lys Gln Gly Glu Tyr Ile Thr Gly Ser Phe Glu Thr Lys Asp Leu Leu
        115                 120                 125
Asn Ala Asn Pro Lys Ser Asn Ile Ile Pro Lys Gly Lys Tyr Leu Val
    130                 135                 140
Leu Gly Asp Asn Arg Glu Val Ser Lys Asp Ser Arg Ala Phe Gly Leu
145                 150                 155                 160
Ile Asp Arg Asp Gln Ile Val Gly Lys Val Ser Phe Arg Phe Trp Pro
                165                 170                 175
Phe Ser Glu Phe Lys Phe Asn Phe Asn Pro Asp Asn Glu Lys
            180                 185                 190
```

<210> SEQ ID NO 131
<211> LENGTH: 573
<212> TYPE: DNA
<213> ORGANISM: Staphylococcus haemolyticus

<400> SEQUENCE: 131

```
ttgaagaaag aaatagttga atggattgtt gccatagcgg taggtttatt acttgtatgg    60
gtaatggtta acttcgtagc taaatcatat actataaaag gcgattcaat ggatccaaca   120
```

```
ctaaaagatg gcgaacacgt catggttaac attctaggat ataaagttgg agacataaaa      180
aaaggtaatg taatcgtatt tcatgcgaat caacaagacg attatgttaa acgtgtcatt      240
ggtgtacctg gcgataacgt tatttataaa aatgataaac tatatgttaa tggtaaaaag      300
ataaatgaac cttatcttga ttacaatgaa aaacgtaaac aaggtgaata tattacgggt      360
tcatttgaaa ctaaagattt actaaatgca aatcctaaat caaatatcat accaaaaggt      420
aaatacttag ttttaggtga taacagagaa gtcagtaagg atagtagggc gtttggttta      480
attgatagag atcaaattgt tggtaaagta tcatttagat tttggccatt cagtgaattt      540
aagtttaatt ttaatccaga taatgaaaaa taa                                   573
```

```
<210> SEQ ID NO 132
<211> LENGTH: 190
<212> TYPE: PRT
<213> ORGANISM: Staphylococcus haemolyticus

<400> SEQUENCE: 132
```

```
Leu Lys Lys Glu Ile Ile Glu Trp Ile Val Ala Ile Gly Gly Ala Leu
 1               5                  10                  15

Leu Ile Val Gly Ile Val Leu Lys Phe Ile Gly Thr Ser Tyr Thr Val
            20                  25                  30

Ser Gly Ser Ser Met Tyr Pro Thr Phe Gln Asp Arg Asn Lys Val Ile
        35                  40                  45

Val Ser Lys Ile Ser Lys Thr Leu Asn His Ile Asp Asn Gly Asp Val
    50                  55                  60

Val Val Phe His Glu Asp Ala Gln Arg Asp Phe Ile Lys Arg Val Ile
65                  70                  75                  80

Gly Thr Pro Gly Asp Lys Val Glu Tyr Glu Gly Asp Gln Leu Tyr Val
                85                  90                  95

Asn Asp Lys Lys Val Ser Glu Pro Tyr Leu Asp Tyr Asn Lys Lys His
            100                 105                 110

Lys Gln Gly Lys Tyr Leu Thr Gly Thr Phe Lys Thr Ser Gln Val Asn
        115                 120                 125

Gly Ala Asn Gly Lys Asn Lys Ile Pro Lys Asp Lys Tyr Leu Val Leu
    130                 135                 140

Gly Asp Asn Arg Gln Asn Ser Val Asp Ser Arg Leu Ala Glu Val Gly
145                 150                 155                 160

Leu Val Asp Lys Asp Gln Leu Val Gly Lys Val Val Leu Arg Tyr Trp
                165                 170                 175

Pro Phe Asn Lys Trp Glu Ala Gly Phe Asn Pro Gly Thr Phe
            180                 185                 190
```

```
<210> SEQ ID NO 133
<211> LENGTH: 573
<212> TYPE: DNA
<213> ORGANISM: Staphylococcus haemolyticus

<400> SEQUENCE: 133
ttgaaaaaag agataattga atggattgta gccattggtg gcgcactctt aattgtaggt       60
attgtattaa agtttattgg aacatcatac acagtatcag gttcatcgat gtatccaact      120
ttccaagata gaaataaagt gatagttagt aagatttcga aaacattgaa ccacattgat      180
aatggtgatg tcgttgtctt ccatgaagat gcacaacgtg attttattaa gcgtgtgatt      240
ggtacgccag gtgataaagt tgagtatgaa ggtgatcaat tatatgttaa tgacaaaaag      300
```

```
gtatcagagc cttatttaga ttataataag aagcataaac aaggtaagta tttaacaggt       360
acatttaaaa caagccaagt gaacggagca atggtaaaaa ataaaattcc taaagataag       420
tatttagttt taggtgataa cagacaaaat agtgtagata gccgtttggc tgaagttggt       480
ttagtagata aagaccaact tgtaggtaaa gttgttttaa gatattggcc atttaataaa       540
tgggaagcag gttttaaccc aggcacattt tag                                    573

<210> SEQ ID NO 134
<211> LENGTH: 191
<212> TYPE: PRT
<213> ORGANISM: Staphylococcus epidermidis

<400> SEQUENCE: 134

Leu Lys Lys Glu Ile Leu Glu Trp Ile Val Ala Ile Ala Val Ala Ile
  1               5                  10                  15

Ala Leu Ile Ala Ile Ile Thr Lys Phe Val Gly Lys Ser Tyr Ser Ile
             20                  25                  30

Lys Gly Asp Ser Met Asp Pro Thr Leu Lys Asp Gly Glu Arg Val Val
         35                  40                  45

Val Asn Ile Ile Gly Tyr Lys Leu Gly Gly Val Glu Lys Gly Asn Val
     50                  55                  60

Ile Val Phe His Ala Asn Lys Lys Asp Asp Tyr Val Lys Arg Val Ile
 65                  70                  75                  80

Gly Thr Pro Gly Asp Ser Val Glu Tyr Lys Asn Asp Thr Leu Tyr Val
                 85                  90                  95

Asn Gly Lys Lys Gln Ser Glu Pro Tyr Leu Tyr Asn Glu Lys Arg
            100                 105                 110

Lys Gln Thr Glu Tyr Ile Thr Gly Ser Phe Lys Thr Lys Asn Leu Pro
        115                 120                 125

Asn Ala Asn Pro Gln Ser Asn Val Ile Pro Lys Gly Lys Tyr Leu Val
    130                 135                 140

Leu Gly Asp Asn Arg Glu Val Ser Lys Asp Ser Arg Ser Phe Gly Leu
145                 150                 155                 160

Ile Asp Lys Asp Gln Ile Val Gly Lys Val Ser Leu Arg Tyr Trp Pro
                165                 170                 175

Phe Ser Glu Phe Lys Ser Asn Phe Asn Pro Asn Asn Thr Lys Asn
            180                 185                 190

<210> SEQ ID NO 135
<211> LENGTH: 576
<212> TYPE: DNA
<213> ORGANISM: Staphylococcus epidermidis

<400> SEQUENCE: 135
ttgaaaaaag aaattttaga gtggattgtt gccatagccg ttgccattgc acttattgcc        60
ataatcacta aatttgtcgg aaaatcatat tctattaaag gtgattcaat ggatcctaca       120
ttaaaagatg gggagcgtgt agtggtaaat attattggct ataaattagg tggcgttgaa       180
aaaggaaatg tcattgtatt tcatgctaat aaaaaagatg attatgttaa agagttatt        240 ggaactccag gagatagtgt tgaatataaa aatgatacac tctatgttaa tggtaaaaag       300
caatcagaac catacttgaa ctataatgaa aaacgtaagc aaactgagta tatcacaggt       360
agtttcaaaa caaaaaattt accaaatgct aatcctcaat ctaatgttat tcctaaaggt       420
aaatatttag ttttggggga taaccgtgag gtaagtaaag atagtcgttc attcggttta       480
attgacaaag accaaattgt tggaaaggta tcgctcagat attggccttt cagtgaattt       540
```

```
aaatctaact ttaatccaaa taacactaaa aattaa                             576
```

<210> SEQ ID NO 136
<211> LENGTH: 192
<212> TYPE: PRT
<213> ORGANISM: Staphylococcus epidermidis

<400> SEQUENCE: 136

```
Met Lys Lys Glu Ile Ile Glu Trp Ile Val Ala Ile Ile Val Ala Ile
 1               5                  10                  15

Val Ile Val Thr Leu Val Gln Lys Phe Leu Phe Ala Ser Tyr Thr Val
            20                  25                  30

Lys Gly Ala Ser Met His Pro Thr Phe Glu Asn Arg Glu Lys Val Ile
        35                  40                  45

Val Ser Arg Ile Ala Lys Thr Leu Asp His Ile Asp Thr Gly Asp Val
    50                  55                  60

Val Ile Phe His Ala Asn Ala Lys Gln Asp Tyr Ile Lys Arg Leu Ile
65                  70                  75                  80

Gly Lys Pro Gly Asp Ser Val Glu Tyr Lys Asp Gln Leu Tyr Leu
                85                  90                  95

Asn Gly Lys Lys Val Asp Glu Pro Tyr Leu Ser Glu Asn Lys Lys His
            100                 105                 110

Lys Val Gly Glu Tyr Leu Thr Glu Asn Phe Lys Ser Lys Asp Leu Lys
        115                 120                 125

Gly Thr Asn Gly Asn Met Lys Ile Pro Ser Gly Lys Tyr Leu Val Leu
    130                 135                 140

Gly Asp Asn Arg Gln Asn Ser Ile Asp Ser Arg Met Asp Glu Val Gly
145                 150                 155                 160

Leu Leu Asp Lys Asn Gln Val Val Gly Lys Val Val Leu Arg Tyr Trp
                165                 170                 175

Pro Phe Asn Arg Trp Gly Gly Ser Phe Asn Pro Gly Thr Phe Pro Asn
            180                 185                 190
```

<210> SEQ ID NO 137
<211> LENGTH: 579
<212> TYPE: DNA
<213> ORGANISM: Staphylococcus epidermidis

<400> SEQUENCE: 137

```
atgaagaaag aaataataga atggattgta gccataatcg ttgcaattgt tatcgtcaca    60
cttgtgcaaa agttttttatt tgcttcttat acagtcaaag gagcgtctat gcatccaaca   120
tttgaaaata gagaaaagt gatagtaagt cgtatagcaa aaacacttga tcatattgat     180
acaggagatg tagtgatttt tcatgctaac gcgaagcaag attatattaa gcgacttatt    240
ggtaaaccag gtgattcagt agaatataaa aaagatcaac tatatttaaa cggtaaaaaa    300
gtagatgagc ttatttaag tgaaataaa aaacataaag ttggagaata tctaacggaa     360
aactttaagt ctaaagatct taagggtacg aatggcaata tgaaaattcc tagtggtaaa    420
tacttggttt taggtgataa tcgtcaaaac agtattgaca gtcgcatgga tgaagtaggt    480
cttttagata aaaatcaagt tgttggaaaa gtagttttga gatactggcc atttaatcgg    540
tggggcggta gttttaatcc tggaacattt cctaactaa                           579
```

<210> SEQ ID NO 138
<211> LENGTH: 188
<212> TYPE: PRT

<213> ORGANISM: Staphylococcus hominis

<400> SEQUENCE: 138

```
Leu Lys Lys Glu Ile Thr Glu Trp Ile Val Ala Ile Ala Val Gly Leu
1               5                   10                  15

Leu Leu Val Trp Leu Val Val Thr Phe Val Ala Lys Ser Tyr Thr Ile
            20                  25                  30

Lys Gly Asp Ser Met Asp Pro Thr Leu Lys Asp Gly Gln His Val Met
        35                  40                  45

Val Asn Ile Leu Gly Tyr Lys Val Gly Asn Ile Lys Lys Gly Asn Val
    50                  55                  60

Ile Val Phe His Ala Asn Gln Ser Asp Asp Tyr Val Lys Arg Val Ile
65                  70                  75                  80

Gly Val Pro Gly Asp Ser Val Thr Tyr Lys Lys Asp Gln Leu Tyr Ile
                85                  90                  95

Asn Gly Lys Lys Val Asn Glu Pro Tyr Leu Asp Tyr Asn Glu Lys His
            100                 105                 110

Lys Gln Gly Glu Tyr Ile Thr Gly Ser Phe Glu Thr Lys Asp Leu Leu
        115                 120                 125

Asn Ala His Pro Asn Ser Asn Val Ile Pro Lys Asn Lys Tyr Leu Val
    130                 135                 140

Leu Gly Asp Asn Arg Glu Val Ser Lys Asp Ser Arg Ala Phe Gly Leu
145                 150                 155                 160

Ile Asp Lys Gln Gln Ile Val Gly Lys Val Ser Phe Arg Phe Trp Pro
                165                 170                 175

Leu Asn Asn Phe Lys Phe Asn Phe Asn Pro Asp Lys
            180                 185
```

<210> SEQ ID NO 139
<211> LENGTH: 567
<212> TYPE: DNA
<213> ORGANISM: Staphylococcus hominis

<400> SEQUENCE: 139

```
ttgaaaaaag aaataacaga atggattgtt gcgatagctg taggtttatt gctcgtatgg      60
cttgtagtca cttttgttgc caaatcctat acaataaaag gtgactcaat ggatccaaca     120
ttaaaagatg gcaacatgt gatggttaac atttaggtt ataaggtagg aacataaaa      180
aaaggaaatg ttattgtctt ccatgctaat caatctgatg actatgttaa agagtaata      240
ggcgtaccag gagatagtgt gacatataaa aaagatcagc tatatattaa tgggaaaaag     300
gtaaatgagc cttacttaga ctataatgaa aaacataaac aaggagagta cattactgga     360
tcttttgaaa ctaaggatct tcttaatgct catcctaact ctaacgttat tcctaaaaat     420
aaatacttag tattaggaga taaccgtgaa gttagtaaag atagtagagc gtttggatta     480
atagataaac aacaaatcgt cggtaaagta tcatttagat tttggccatt aaataatttt     540
aaatttaatt ttaatccaga taagtag                                        567
```

<210> SEQ ID NO 140
<211> LENGTH: 189
<212> TYPE: PRT
<213> ORGANISM: Staphylococcus lugdunensis

<400> SEQUENCE: 140

```
Val Lys Lys Glu Leu Thr Glu Trp Leu Ile Ala Ile Ala Val Gly Ile
1               5                   10                  15
```

```
Ile Leu Val Ile Leu Ile Ile Asn Phe Val Ala Lys Ser Tyr Thr Ile
             20                  25                  30

Lys Gly Asp Ser Met Asn Pro Thr Leu Lys Asp Gly Asp His Val Leu
         35                  40                  45

Val Asn Ile Ile Gly Tyr Lys Val Gly Thr Val Lys Lys Gly Asn Val
 50                  55                  60

Ile Val Phe His Ala Asn Gln Lys Asp Tyr Val Lys Arg Val Ile
 65                  70                  75                  80

Gly Thr Pro Gly Asp Lys Val Tyr Tyr Arg Asp Gln Leu Ile Ile
                 85                  90                  95

Asn Gly Lys Lys Val Lys Glu Pro Tyr Leu Glu Tyr Asn Met Lys Arg
             100                 105                 110

Lys Gln Gly Glu Tyr Ile Thr Gly Ser Leu Asp Ile Lys Asp Leu Ala
         115                 120                 125

Gly Ala Lys His Asn Ser Asn Val Ile Pro Gln His Lys Tyr Leu Val
     130                 135                 140

Leu Gly Asp Asn Arg Glu Val Ser Lys Asp Ser Arg Ala Phe Gly Leu
145                 150                 155                 160

Ile Asp Glu Lys Gln Ile Val Gly Lys Val Ser Leu Arg Phe Trp Pro
                 165                 170                 175

Leu Thr Asp Phe Lys Phe Asn Phe Asn Pro Asp Met Ser
                 180                 185

<210> SEQ ID NO 141
<211> LENGTH: 570
<212> TYPE: DNA
<213> ORGANISM: Staphylococcus lugdunensis

<400> SEQUENCE: 141
gtgaaaaagg aattgacaga atggttaata gctatagcgg taggtattat tttagtcata      60
ctaatcatta attttgtagc gaaatcatat accattaaag agactcaat gaatccaaca      120 ttaaaagatg gcgatcatgt tctggtcaat attatcggct ataaagtagg cactgtgaaa      180
aaggggaatg tcattgtctt ccatgctaac caaaaggatg attatgttaa acgcgttata      240
ggcacaccag gtgacaaagt atactatcga gatgatcaac ttattataaa cggaaaaaaa      300
gtaaaagaac cttatctcga atacaatatg aaacgtaagc aaggagagta tattactgga      360
tctttagata taaagatt tggccggtgca aaacataatt ctaatgtcat acctcaacat      420
aaatacctcg tgttaggaga caatcgtgag gtaagtaaag atagccgtgc ttttggcctt      480
atcgatgaaa agcaaattgt cggtaaagtg tctttaagat tttggccatt aactgatttt      540
aaatttaatt ttaaccctga tatgagctaa                                       570

<210> SEQ ID NO 142
<211> LENGTH: 192
<212> TYPE: PRT
<213> ORGANISM: Staphylococcus lugdunensis

<400> SEQUENCE: 142

Val Lys Lys Glu Ile Leu Glu Trp Ile Val Ser Ile Ala Val Ala Leu
 1               5                  10                  15

Ile Ile Val Gly Ile Val Lys Phe Ile Gly Val Thr Tyr Ser Val
             20                  25                  30

Ser Gly Asp Ser Met Tyr Pro Thr Phe Lys Asp Arg Glu Lys Val Val
         35                  40                  45

Val Ser Lys Ile Ser Lys Thr Leu Asp His Ile Asp Asn Gly Asp Ile
```

```
                 50                  55                  60
Val Val Phe Lys Glu Asp Lys Asp Arg Asp Phe Ile Lys Arg Leu Ile
 65                  70                  75                  80

Gly Lys Pro Gly Asp Lys Val Glu Tyr Lys Gly Asp Gln Leu Tyr Val
                 85                  90                  95

Asn Asn Lys Lys Ile Asp Glu Pro Tyr Leu Lys Tyr Asn Lys Glu His
                100                 105                 110

Lys Asn Gly Lys Tyr Leu Thr Gly Ser Phe Lys Ser Ser Asp Leu Gln
            115                 120                 125

Asn Ala Asn Gly Glu Thr Lys Ile Pro Lys Asp Lys Tyr Leu Val Leu
            130                 135                 140

Gly Asp Asn Arg Gln Asn Ser Leu Asp Ser Arg Phe Pro Gln Val Gly
145                 150                 155                 160

Leu Ile Asp Lys Glu Gln Ile Val Gly Lys Val Leu Arg Phe Trp
                165                 170                 175

Pro Phe Gly Glu Trp Thr Thr Lys Phe Asn Pro Gly Thr Phe Asp Lys
            180                 185                 190
```

<210> SEQ ID NO 143
<211> LENGTH: 579
<212> TYPE: DNA
<213> ORGANISM: Staphylococcus lugdunensis

<400> SEQUENCE: 143

```
gtgaaaaaag agatcttaga gtggattgtg tctatagcag ttgcacttat cattgtaggt    60
atagttgtta aatttattgg agttacatat tcagtttcgg agattcaat gtatccaaca   120
tttaaagata gagaaaaagt agtagtgagt aaaatttcca aaacgttaga ccatattgat   180
aatggtgata tcgttgtctt taaagaagat aaagatagag actttattaa acgtttaatt   240
ggtaaacctg gagacaaagt tgagtataaa ggtgaccaac tatatgttaa taataaaaaa   300
attgatgagc ttatttaaa atataacaaa gagcataaaa atggtaagta tctgacaggt   360
tctttcaaat cgagtgattt gcaaaatgct aatggtgaga cgaagattcc taaagacaaa   420
tatttagtgt taggtgataa tcgtcaaaac agtttagata gtcgtttcc acaggtaggg   480
cttattgata agaacaaat tgtaggtaaa gttgtgttac gtttctggcc atttggtgag   540
tggacaacaa aatttaatcc tggaacattt gataagtaa                          579
```

<210> SEQ ID NO 144
<211> LENGTH: 189
<212> TYPE: PRT
<213> ORGANISM: Streptococcus agalactiae

<400> SEQUENCE: 144

```
Met Lys Arg Gln Ile Ser Ser Asp Lys Leu Ser Gln Glu Leu Asp Arg
  1               5                  10                  15

Val Thr Tyr Gln Lys Arg Phe Trp Ser Val Ile Lys Asn Thr Ile Tyr
                 20                  25                  30

Ile Leu Met Ala Val Ala Ser Ile Ala Ile Leu Ile Ala Val Leu Trp
             35                  40                  45

Leu Pro Val Leu Arg Ile Tyr Gly His Ser Met Asn Lys Thr Leu Ser
         50                  55                  60

Ala Gly Asp Val Val Phe Thr Val Lys Gly Ser Asn Phe Lys Thr Gly
 65                  70                  75                  80

Asp Val Val Ala Phe Tyr Tyr Asn Asn Lys Val Leu Val Lys Arg Val
                 85                  90                  95
```

```
Ile Ala Glu Ser Gly Asp Trp Val Asn Ile Asp Ser Gln Gly Asp Val
            100                 105                 110

Tyr Val Asn Gln His Lys Leu Lys Glu Pro Tyr Val Ile His Lys Ala
        115                 120                 125

Leu Gly Asn Ser Asn Ile Lys Tyr Pro Tyr Gln Val Pro Asp Lys Lys
    130                 135                 140

Ile Phe Val Leu Gly Asp Asn Arg Lys Thr Ser Ile Asp Ser Arg Ser
145                 150                 155                 160

Thr Ser Val Gly Asp Val Ser Glu Glu Gln Ile Val Gly Lys Ile Ser
            165                 170                 175

Phe Arg Ile Trp Pro Leu Gly Lys Ile Ser Ser Ile Asn
            180                 185
```

<210> SEQ ID NO 145
<211> LENGTH: 570
<212> TYPE: DNA
<213> ORGANISM: Streptococcus agalactiae

<400> SEQUENCE: 145

```
atgaaaagac agattagttc agataaaatta tctcaagaac tggatcgcgt aacttatcag    60
aaacgctttt ggagtgtcat taaaaatacc atatacatct tgatggcggt tgcctcaata   120
gccattttaa ttgcggtttt atggttgcct gtattaagaa tctacggaca ttcaatgaat   180
aagactttaa gtgcaggtga tgtagtcttt acagtaaaag gttcaaattt taaaactgga   240
gacgttgtcg cgttttacta caataataag gtcctagtca agcgggttat tgcagagtca   300
ggagactggg ttaatattga ttctcaaggg gatgtttacg tgaatcaaca taagttgaaa   360
gaaccatatg ttattcataa agcactcggt aatagtaata taaataccc atatcaagta   420
cctgataaaa aaattttgt attaggagac aaccgaaaaa cttcaattga ttctcgaagt   480
acttctgtag agatgtttc agaagaacaa attgtaggta aatttctttt cagaatatgg   540
cctctaggta agattagtag tatcaattaa                                      570
```

<210> SEQ ID NO 146
<211> LENGTH: 197
<212> TYPE: PRT
<213> ORGANISM: Streptococcus agalactiae

<400> SEQUENCE: 146

```
Met Lys Glu Phe Ile Lys Glu Trp Gly Val Phe Ile Leu Ile Leu Ser
1               5                   10                  15

Leu Phe Leu Leu Ser Arg Ile Phe Leu Trp Gln Phe Val Lys Val Asp
            20                  25                  30

Gly His Ser Met Asp Pro Thr Leu Ala Asp Lys Glu Gln Leu Val Val
        35                  40                  45

Leu Lys Gln Thr Lys Ile Asn Arg Phe Asp Ile Val Val Ala Asn Glu
    50                  55                  60

Glu Glu Gly Gly Gln Lys Lys Ile Val Lys Arg Val Ile Gly Met
65                  70                  75                  80

Pro Gly Asp Val Ile Lys Tyr Lys Asn Asp Thr Leu Thr Ile Asn Asn
                85                  90                  95

Lys Lys Thr Glu Glu Pro Tyr Leu Lys Glu Tyr Thr Lys Leu Phe Lys
            100                 105                 110

Lys Asp Lys Leu Gln Glu Lys Tyr Ser Tyr Asn Pro Leu Phe Gln Asp
        115                 120                 125
```

Leu Ala Gln Ser Ser Thr Ala Phe Thr Thr Asp Ser Asn Gly Ser Ser
    130                 135                 140

Glu Phe Thr Thr Val Val Pro Lys Gly His Tyr Tyr Leu Val Gly Asp
145                 150                 155                 160

Asp Arg Ile Val Ser Lys Asp Ser Arg Ala Val Gly Ser Phe Lys Lys
                165                 170                 175

Ser Thr Ile Val Gly Glu Val Lys Phe Arg Phe Trp Pro Ile Arg Arg
            180                 185                 190

Phe Gly Thr Ile Asn
        195

<210> SEQ ID NO 147
<211> LENGTH: 594
<212> TYPE: DNA
<213> ORGANISM: Streptococcus agalactiae

<400> SEQUENCE: 147
atgaaagaat tattaaaga atggggtgtc tttatcctca tcctctcact ttttttacta      60
tcgcgtatct ttttatggca attcgttaaa gttgacggac actccatgga tccaacttta     120
gctgacaagg aacagctagt agttctcaaa caaacaaaaa tcaatcgatt cgatattgta     180
gtggctaacg aagaagaagg cggccaaaag aaaaaaattg ttaaacgtgt cattggtatg     240
ccaggtgatg tcatcaaata taaaaatgac accttaacta ttaacaataa aaaacagaa     300 gaaccttacc tcaaggaata tactaaatta tttaaaaagg ataaattaca ggaaaaatat     360
tcgtataacc cacttttcca agacctagca caaagctcta ccgctttcac cactgacagc     420
aatggcagca gcgaatttac tactgtcgtg cctaaaggcc actactatct tgttggtgat     480
gaccgaattg tctctaaaga tagtcgtgcc gtcggttcct tcaaaaaatc aacgattgtg     540
ggagaggtta aattccgctt ctggccaatt cgtcgttttg gaactatcaa ctaa            594

<210> SEQ ID NO 148
<211> LENGTH: 197
<212> TYPE: PRT
<213> ORGANISM: Streptococcus dysgalactiae

<400> SEQUENCE: 148

Met Lys His Phe Ile Lys Glu Trp Gly Pro Phe Thr Leu Phe Leu Ile
1               5                   10                  15

Leu Phe Gly Leu Ser Arg Leu Phe Leu Trp Gln Ala Val Lys Val Asp
            20                  25                  30

Gly His Ser Met Asp Pro Thr Leu Ala His Gly Glu Arg Leu Ile Val
        35                  40                  45

Leu Asn Gln Ala Arg Ile Asp Arg Phe Asp Ile Val Val Ala Arg Glu
    50                  55                  60

Glu Glu Asn Gly Gln Lys Lys Glu Ile Val Lys Arg Val Val Gly Met
65                  70                  75                  80

Pro Gly Asp Thr Ile Ala Tyr Asn Asp Asp Thr Leu Tyr Ile Asn Gly
                85                  90                  95

Lys Lys Thr Asp Glu Pro Tyr Leu Val Asn Tyr Leu Lys Glu Phe Lys
                100                 105                 110

Lys Asp Lys Leu Gln Lys Thr Tyr Ala Tyr Asn Ser Leu Phe Gln Gln
            115                 120                 125

Leu Ala Glu Thr Ser Asp Ala Phe Thr Thr Asn Ala Glu Gly Gln Thr
    130                 135                 140

Arg Phe Glu Ile Ser Val Pro Glu Gly Glu Tyr Leu Leu Leu Gly Asp

```
                145                 150                 155                 160
Asp Arg Ile Val Ser Arg Asp Ser Arg Glu Val Gly Ser Phe Lys Lys
                    165                 170                 175

Glu Lys Leu Ile Gly Glu Val Lys Ala Arg Phe Trp Pro Leu Asn Lys
            180                 185                 190

Met Thr Leu Phe Lys
        195

<210> SEQ ID NO 149
<211> LENGTH: 594
<212> TYPE: DNA
<213> ORGANISM: Streptococcus  dysgalactiae

<400> SEQUENCE: 149
atgaaacatt ttattaaaga atggggccca tttaccctct ttctcatcct cttcggttta      60
tctcgtcttt tcttgtggca agctgttaaa gttgatggcc actccatgga ccctacgtta     120
gcccatgggg aacgtctcat tgttttaaac caagctagaa ttgaccgttt cgatattgtc     180
gttgcccgtg aggaagaaaa tgggcagaaa aaagaaattg tcaaacgagt tgtcggcatg     240
ccaggtgata ccattgccta caacgatgat acgctttaca ttaatggtaa aaaaacagat     300
gagccttacc tagttaacta ccttaaagag ttcaaaaagg acaagcttca aaagacttac     360
gcttacaata gtctatttca gcaattagct gaaacatcgg atgccttcac cactaatgct     420
gaaggtcaaa cacgttttga atcagtgta ccagaaggtg aatacctcct tcttggagat     480
gaccgaattg tctcacgcga cagccgtgaa gttggtagtt ttaaaaaaga aaaacttatc     540
ggtgaagtca aggctcgctt ctggccactc aataaaatga ctcttttttaa gtaa         594

<210> SEQ ID NO 150
<211> LENGTH: 204
<212> TYPE: PRT
<213> ORGANISM: Streptococcus mitis

<400> SEQUENCE: 150

Met Asn Ser Phe Lys Asn Phe Leu Lys Glu Trp Gly Leu Phe Leu Leu
  1               5                  10                  15

Ile Leu Ser Leu Leu Ala Leu Ser Arg Ile Phe Phe Trp Ser Asn Val
            20                  25                  30

Arg Val Glu Gly His Ser Met Asp Pro Thr Leu Ala Asp Gly Glu Ile
        35                  40                  45

Leu Phe Val Val Lys His Leu Pro Ile Asp Arg Phe Asp Ile Val Val
    50                  55                  60

Ala His Glu Glu Asp Gly Asn Lys Asp Ile Val Lys Arg Val Ile Gly
 65                  70                  75                  80

Met Pro Gly Asp Thr Ile Arg Tyr Glu Asn Asp Lys Leu Tyr Ile Asn
                85                  90                  95

Asp Lys Glu Thr Asp Glu Pro Tyr Leu Ala Asp Tyr Ile Lys Arg Phe
            100                 105                 110

Lys Asp Asp Lys Leu Gln Ser Thr Tyr Ser Gly Lys Gly Phe Glu Gly
        115                 120                 125

Asn Lys Gly Thr Phe Phe Arg Ser Ile Ala Glu Lys Ala Gln Ala Phe
    130                 135                 140

Thr Val Asp Val Asn Tyr Asn Thr Asn Phe Ser Phe Thr Val Pro Glu
145                 150                 155                 160

Gly Glu Tyr Leu Leu Leu Gly Asp Asp Arg Leu Val Ser Ser Asp Ser
                165                 170                 175
```

Arg His Val Gly Thr Phe Lys Ala Lys Asp Ile Thr Gly Glu Ala Lys
            180                 185                 190

Phe Arg Phe Trp Pro Ile Thr Arg Ile Gly Thr Phe
        195                 200

<210> SEQ ID NO 151
<211> LENGTH: 615
<212> TYPE: DNA
<213> ORGANISM: Streptococcus mitis

<400> SEQUENCE: 151

```
atgaattcat ttaaaaattt cctaaaagag tggggattgt tcctcctgat tctgtcatta      60
ctagctttga gccgtatctt tttttggagt aatgtccgcg tagaagggca ttccatggat     120
ccgaccctag cggatggcga aattctcttc gttgtcaaac accttcctat tgaccgtttt     180
gatatcgtgg tggcccatga ggaagatggc aataaggaca tcgtcaagcg cgtgattgga     240
atgcctggcg atactatccg ttacgaaaac gataaacttt acatcaatga taaagagacg     300
gacgaacctt acctagctga ctatatcaaa cgtttcaagg atgacaaact ccaaagcacc     360
tactcaggca agggctttga aggaaataaa ggaaccttct ttagaagtat tgcggaaaaa     420
gctcaagcct tcacagttga tgtcaactat aacaccaact ttagctttac tgttccagaa     480
ggagaatacc ttctcctcgg agacgaccgc ttggtttcta gcgacagccg tcacgtaggt     540
accttcaaag caaagatat cacaggggaa gctaaattcc gcttctggcc aatcacccgt     600
atcggaacat tttaa                                                     615
```

<210> SEQ ID NO 152
<211> LENGTH: 204
<212> TYPE: PRT
<213> ORGANISM: Streptococcus oralis

<400> SEQUENCE: 152

Met Asn Ser Phe Lys Thr Phe Leu Lys Glu Trp Gly Val Phe Phe Leu
 1               5                  10                  15

Ile Ile Ala Leu Val Gly Leu Ser Arg Ile Phe Leu Trp Ser Asn Val
            20                  25                  30

Arg Val Glu Gly His Ser Met Asp Pro Thr Leu Ala Asp Gly Glu Val
        35                  40                  45

Leu Phe Val Val Lys His Leu Pro Ile Asp Arg Phe Asp Ile Val Val
    50                  55                  60

Ala His Glu Glu Asp Gly Asn Lys Asp Ile Val Lys Arg Val Ile Gly
65                  70                  75                  80

Met Pro Gly Asp Thr Ile Arg Tyr Glu Asn Asp Lys Leu Phe Ile Asn
                85                  90                  95

Gly Glu Glu Thr Asn Glu Pro Tyr Leu Ala Glu Tyr Leu Asn Leu Phe
            100                 105                 110

Lys Thr Glu Lys Leu Gln Asn Thr Tyr Thr Gly Lys Gly Phe Glu Gly
        115                 120                 125

Asn Lys Gly Val Tyr Phe Arg Glu Leu Ala Gln Lys Ala Gln Ala Phe
    130                 135                 140

Thr Val Asp Val Asn Ser Asn Thr Arg Phe Ser Phe Thr Val Pro Gln
145                 150                 155                 160

Gly Glu Tyr Leu Leu Leu Gly Asp Asp Arg Leu Val Ser Ser Asp Ser
                165                 170                 175

Arg His Val Gly Thr Phe Lys Ala Ser Asp Ile Lys Gly Glu Ala Lys

```
                    180                 185                 190
Phe Arg Phe Trp Pro Leu Asn Arg Ile Gly Thr Phe
            195                 200

<210> SEQ ID NO 153
<211> LENGTH: 615
<212> TYPE: DNA
<213> ORGANISM: Streptococcus oralis

<400> SEQUENCE: 153
atgaattcgt ttaaaacatt tctaaaagaa tggggagttt tcttcctgat tatcgcactg      60
gtcggtctta gccgcatctt tctttggagc aatgtccgtg tggaaggaca ctctatggac     120
cctaccctag ctgacggaga agttctcttc gttgttaaac acctcccaat tgaccgcttc     180
gacatcgtgg ttgcgcatga ggaagacgga aataaagaca ttgtcaaaag ggttatcggt     240
atgcctggtg ataccatccg ctacgaaaat gacaaactct ttatcaacgg tgaagaaacg     300
aatgaaccct acctagctga gtacctcaac ttgttcaaaa cagaaaagtt gcaaaacacc     360
tatactggaa aaggatttga aggcaataag ggagtttact ttagagaact tgctcaaaaa     420
gcacaagcct ttacggtcga tgtcaattcc aacaccagat tcagctttac tgtccctcaa     480
ggcgaatacc ttctccttgg tgacgatcgt ctagtctcta gcgacagccg ccatgtcggt     540
accttcaagg ccagcgatat caaaggcgaa gcaaaattcc gtttctggcc acttaaccgt     600
atcggaactt tttaa                                                     615

<210> SEQ ID NO 154
<211> LENGTH: 204
<212> TYPE: PRT
<213> ORGANISM: Streptococcus pneumoniae

<400> SEQUENCE: 154

Met Asn Leu Phe Lys Asn Phe Leu Lys Glu Trp Gly Leu Phe Leu Leu
 1               5                  10                  15

Ile Leu Ser Leu Leu Ala Leu Ser Arg Ile Phe Phe Trp Ser Asn Val
            20                  25                  30

Arg Val Glu Gly His Ser Met Asp Pro Thr Leu Ala Asp Gly Glu Ile
        35                  40                  45

Leu Phe Val Val Lys His Leu Pro Ile Asp Arg Phe Asp Ile Val Val
    50                  55                  60

Ala His Glu Glu Asp Gly Asn Lys Asp Ile Val Lys Arg Val Ile Gly
65                  70                  75                  80

Met Pro Gly Asp Thr Ile Arg Tyr Glu Asn Asp Lys Leu Tyr Ile Asn
                85                  90                  95

Asp Lys Glu Thr Asp Glu Pro Tyr Leu Ala Asp Tyr Ile Lys Arg Phe
            100                 105                 110

Lys Asp Asp Lys Leu Gln Ser Thr Tyr Ser Gly Lys Gly Phe Glu Gly
        115                 120                 125

Asn Lys Gly Thr Phe Phe Arg Ser Ile Ala Gln Lys Ala Gln Ala Phe
    130                 135                 140

Thr Val Asp Val Asn Tyr Asn Thr Asn Phe Ser Phe Thr Val Pro Glu
145                 150                 155                 160

Gly Glu Tyr Leu Leu Leu Gly Asp Asp Arg Leu Val Ser Ser Asp Ser
                165                 170                 175

Arg His Val Gly Thr Phe Lys Ala Lys Asp Ile Thr Gly Glu Ala Lys
            180                 185                 190
```

Phe Arg Phe Trp Pro Ile Thr Arg Ile Gly Thr Phe
            195                 200

<210> SEQ ID NO 155
<211> LENGTH: 615
<212> TYPE: DNA
<213> ORGANISM: Streptococcus pneumoniae

<400> SEQUENCE: 155

```
atgaatttat ttaaaaattt cttaaaagag tggggattat tcctcctgat tctgtcatta    60
ctagctttga gccgtatctt tttttggagc aatgttcgcg tagaaggaca ttccatggat   120
ccgaccctag cggatggtga atcctctttt gttgttaagc acctccctat tgaccgtttt   180
gatatcgtgg tggcccatga ggaagatggc aataaggaca tcgtcaagcg cgtgattgga   240
atgcctggcg acaccattcg ttacgaaaat gataaactct acatcaatga caaagaaacg   300
gacgagcctt atctagcaga ctatatcaaa cgcttcaagg atgacaaact ccaaagcact   360
tactcaggca agggctttga aggaaataaa ggaactttct tagaagtat cgctcaaaaa   420
gcccaagcct tcacagttga tgtcaactac aacaccaact ttagctttac tgttccagaa   480
ggagaatacc ttctcctcgg agatgaccgc ttggtttcga cgacagccg ccacgtaggt   540
accttcaaag caaagatat cacaggggaa gctaaattcc gcttctggcc aatcacccgt   600
atcggaacat tttaa                                                    615
```

<210> SEQ ID NO 156
<211> LENGTH: 197
<212> TYPE: PRT
<213> ORGANISM: Streptococcus pyogenes

<400> SEQUENCE: 156

Met Lys Gln Phe Ile Lys Glu Trp Gly Pro Phe Thr Leu Phe Leu Ile
  1               5                  10                  15

Leu Phe Gly Leu Ser Arg Leu Phe Leu Trp Gln Ala Val Lys Val Asp
              20                  25                  30

Gly His Ser Met Asp Pro Thr Leu Ala His Gly Glu Arg Leu Ile Val
          35                  40                  45

Phe Asn Gln Ala Arg Ile Asp Arg Phe Asp Ile Val Val Ala Gln Glu
      50                  55                  60

Glu Glu Asn Gly Gln Lys Lys Glu Ile Val Lys Arg Val Ile Gly Leu
 65                  70                  75                  80

Pro Gly Asp Thr Ile Ser Tyr Asn Asp Asp Thr Leu Tyr Ile Asn Gly
                  85                  90                  95

Lys Lys Thr Val Glu Pro Tyr Leu Ala Glu Tyr Leu Lys Gln Phe Lys
            100                 105                 110

Asn Asp Lys Leu Gln Lys Thr Tyr Ala Tyr Asn Thr Leu Phe Gln Gln
        115                 120                 125

Leu Ala Glu Thr Ser Asp Ala Phe Thr Thr Asn Ser Glu Gly Gln Thr
    130                 135                 140

Arg Phe Glu Met Ser Val Pro Lys Gly Glu Tyr Leu Leu Leu Gly Asp
145                 150                 155                 160

Asp Arg Ile Val Ser Arg Asp Ser Arg Glu Val Gly Ser Phe Lys Lys
                165                 170                 175

Glu Asn Leu Ile Gly Glu Val Lys Ala Arg Phe Trp Pro Leu Asn Lys
            180                 185                 190

Met Thr Val Phe Asn
            195

<210> SEQ ID NO 157
<211> LENGTH: 594
<212> TYPE: DNA
<213> ORGANISM: Streptococcus pyogenes

<400> SEQUENCE: 157

```
atgaaacagt ttattaaaga atggggccca ttcactctct ttttaattct ctttggtcta    60
tctcgtcttt ttttgtggca ggctgttaaa gtagacggcc attctatgga cccaactcta   120
gctcatggcg aacgccttat cgtttttaat caagctagaa ttgatcgctt tgatattgta   180
gttgctcagg aagaagaaaa cggacaaaag aaagaaatcg taaaaagagt tattggattg   240
ccaggcgata ccatttctta taatgatgac acactttata ttaatggtaa aaaaacagtt   300
gagccgtatt tggctgagta tctaaaacaa tttaaaaacg ataaactcca aaaaacttac   360
gcctataata ccctattcca acagttagca gaaacatctg atgctttac aactaattct   420
gagggacaaa cacgctttga gatgagtgtt ccaaaaggag aataccttct tcttggtgat   480
gatcgtattg tttccaggga tagtcgcgaa gttggtagtt tcaaaaaaga aaaccttatc   540
ggtgaagtga aagctcgttt ttggccactc aataaaatga ccgttttaa ttag          594
```

<210> SEQ ID NO 158
<211> LENGTH: 324
<212> TYPE: PRT
<213> ORGANISM: Escherichia coli

<400> SEQUENCE: 158

```
Met Ala Asn Met Phe Ala Leu Ile Leu Val Ile Ala Thr Leu Val Thr
  1               5                  10                  15

Gly Ile Leu Trp Cys Val Asp Lys Phe Phe Ala Pro Lys Arg Arg
             20                  25                  30

Glu Arg Gln Ala Ala Ala Gln Ala Ala Ala Gly Asp Ser Leu Asp Lys
         35                  40                  45

Ala Thr Leu Lys Lys Val Ala Pro Lys Pro Gly Trp Leu Glu Thr Gly
     50                  55                  60

Ala Ser Val Phe Pro Val Leu Ala Ile Val Leu Ile Val Arg Ser Phe
 65                  70                  75                  80

Ile Tyr Glu Pro Phe Gln Ile Pro Ser Gly Ser Met Met Pro Thr Leu
                 85                  90                  95

Leu Ile Gly Asp Phe Ile Leu Val Glu Lys Phe Ala Tyr Gly Ile Lys
            100                 105                 110

Asp Pro Ile Tyr Gln Lys Thr Leu Ile Glu Thr Gly His Pro Lys Arg
        115                 120                 125

Gly Asp Ile Val Val Phe Lys Tyr Pro Glu Asp Pro Lys Leu Asp Tyr
    130                 135                 140

Ile Lys Arg Ala Val Gly Leu Pro Gly Asp Lys Val Thr Tyr Asp Pro
145                 150                 155                 160

Val Ser Lys Glu Leu Thr Ile Gln Pro Gly Cys Ser Ser Gly Gln Ala
                165                 170                 175

Cys Glu Asn Ala Leu Pro Val Thr Tyr Ser Asn Val Glu Pro Ser Asp
            180                 185                 190

Phe Val Gln Thr Phe Ser Arg Arg Asn Gly Gly Glu Ala Thr Ser Gly
        195                 200                 205

Phe Phe Glu Val Pro Lys Asn Glu Thr Lys Glu Asn Gly Ile Arg Leu
    210                 215                 220
```

Ser Glu Arg Lys Glu Thr Leu Gly Asp Val Thr His Arg Ile Leu Thr
225                 230                 235                 240

Val Pro Ile Ala Gln Asp Gln Val Gly Met Tyr Tyr Gln Gln Pro Gly
            245                 250                 255

Gln Gln Leu Ala Thr Trp Ile Val Pro Pro Gly Gln Tyr Phe Met Met
        260                 265                 270

Gly Asp Asn Arg Asp Asn Ser Ala Asp Ser Arg Tyr Trp Gly Phe Val
    275                 280                 285

Pro Glu Ala Asn Leu Val Gly Arg Ala Thr Ala Ile Trp Met Ser Phe
290                 295                 300

Asp Lys Gln Glu Gly Glu Trp Pro Thr Gly Leu Arg Leu Ser Arg Ile
305                 310                 315                 320

Gly Gly Ile His

<210> SEQ ID NO 159
<211> LENGTH: 975
<212> TYPE: DNA
<213> ORGANISM: Escherichia coli

<400> SEQUENCE: 159

```
atggcgaata tgtttgccct gattctggtg attgccacac tggtgacggg catttttatgg      60
tgcgtggata aattctttttt cgcacctaaa cggcgggaac gtcaggcagc ggcgcaggcg     120
gctgccgggg actcactgga taaagcaacg ttgaaaaagg ttgcgccgaa gcctggctgg     180
ctggaaaccg gtgcttctgt ttttccggta ctggctatcg tattgattgt gcgttcgttt     240
atttatgaac cgttccagat cccgtcaggt tcgatgatgc cgactctgtt aattggtgat     300
tttattctgg tagagaagtt tgcttatggc attaaagatc ctatctacca gaaaacgctg     360
atcgaaaccg tcatccgaa acgcggcgat atcgtggtct ttaaatatcc ggaagatcca     420
aagcttgatt acatcaagcg cgcggtgggt ttaccgggcg ataaagtcac ttacgatccg     480
gtctcaaaag agctgacgat tcaaccggga tgcagttccg gccaggcgtg tgaaaacgcg     540
ctgccggtca cctactcaaa cgtggaaccg agcgatttcg ttcagacctt ctcacgccgt     600
aatggtgggg aagcgaccag cggattcttt gaagtgccga aaacgaaaac caaagaaaat     660
ggaattcgtc tttccgagcg taaagagaca ctgggtgatg tgacgcaccg cattctgaca     720
gtgccgattg cgcaggatca ggtggggatg tattaccagc agccagggca acaactggca     780
acctggattg ttcctccggg acaatacttc atgatgggcg acaaccgcga caacagcgcg     840
gacagccgtt actggggctt tgtgccggaa gcgaatctgg tcggtcgggc aacggctatc     900
tggatgagct cgataagca agaaggcgaa tggccgactg gtctgcgctt aagtcgcatt     960
ggcggcatcc attaa                                                      975
```

<210> SEQ ID NO 160
<211> LENGTH: 324
<212> TYPE: PRT
<213> ORGANISM: Salmonella enterica

<400> SEQUENCE: 160

Met Ala Asn Met Phe Ala Leu Ile Leu Val Ile Ala Thr Leu Val Thr
1               5                   10                  15

Gly Ile Leu Trp Cys Val Asp Lys Phe Val Phe Ala Pro Lys Arg Arg
            20                  25                  30

Ala Arg Gln Ala Ala Ala Gln Thr Ala Ser Gly Asp Ala Leu Asp Asn
        35                  40                  45

```
Ala Thr Leu Asn Lys Val Ala Pro Lys Pro Gly Trp Leu Glu Thr Gly
 50                  55                  60

Ala Ser Val Phe Pro Val Leu Ala Ile Val Leu Ile Val Arg Ser Phe
 65                  70                  75                  80

Leu Tyr Glu Pro Phe Gln Ile Pro Ser Gly Ser Met Met Pro Thr Leu
                 85                  90                  95

Leu Ile Gly Asp Phe Ile Leu Val Glu Lys Phe Ala Tyr Gly Ile Lys
            100                 105                 110

Asp Pro Ile Tyr Gln Lys Thr Leu Ile Glu Thr Gly His Pro Lys Arg
            115                 120                 125

Gly Asp Ile Val Val Phe Lys Tyr Pro Glu Asp Pro Lys Leu Asp Tyr
        130                 135                 140

Ile Lys Arg Ala Val Gly Leu Pro Gly Asp Lys Ile Thr Tyr Asp Pro
145                 150                 155                 160

Val Ala Lys Glu Val Thr Ile Gln Pro Gly Cys Ser Ser Gly Gln Ala
                165                 170                 175

Cys Glu Asn Ala Leu Pro Val Thr Tyr Ser Asn Val Glu Pro Ser Asp
            180                 185                 190

Phe Val Gln Thr Phe Ala Arg Arg Asn Gly Gly Glu Ala Thr Ser Gly
        195                 200                 205

Phe Phe Glu Val Pro Leu Asn Glu Thr Lys Glu Asn Gly Ile Arg Leu
210                 215                 220

Thr Glu Arg Lys Glu Thr Leu Gly Asp Val Thr His Arg Ile Leu Met
225                 230                 235                 240

Val Pro Ile Ala Gln Asp Gln Leu Gly Met Tyr Tyr Gln Gln Pro Gly
                245                 250                 255

Gln Pro Leu Ala Thr Trp Val Val Pro Pro Gly Gln Tyr Phe Met Met
            260                 265                 270

Gly Asp Asn Arg Asp Asn Ser Ala Asp Ser Arg Tyr Trp Gly Phe Val
        275                 280                 285

Pro Glu Ala Asn Leu Val Gly Lys Ala Val Ala Ile Trp Met Ser Phe
290                 295                 300

Asp Lys Gln Glu Gly Glu Trp Pro Thr Gly Val Arg Leu Ser Arg Ile
305                 310                 315                 320

Gly Gly Ile His
```

<210> SEQ ID NO 161
<211> LENGTH: 975
<212> TYPE: DNA
<213> ORGANISM: Salmonella enterica

<400> SEQUENCE: 161

```
atggcgaaca tgtttgccct gattctggtg atagccacac tggtgacggg cattttatgg    60
tgcgttgata agtttgtttt cgcgccaaaa cgtcgggcgc gccaggctgc cgcgcaaacg   120
gcgtcgggag atgcgctgga taacgctacg ctcaataaag tggcgcctaa gccgggctgg   180
ctggagaccg gggcgtcggt tttcccggtt ctggcgatcg ttctgatcgt tcgttcattt   240
ctttatgaac cctttcagat cccgtcaggc tcaatgatgc cgacactgct tatcggcgat   300
tttattctgg tggaaaaatt tgcctacggc attaagatcc gatctacca gaaaaccctg   360
attgaaaccg gtcatccaaa gcgcggggat attgtggtat ttaaatatcc ggaagatcct   420
aagttagatt acatcaaacg cgccgtcggt ttgccgggcg ataaaatcac ttatgatccg   480
gttgcgaaag aggtgacgat tcagcctggc tgtagctccg gtcaggcgtg cgaaaatgcg   540
```

```
ctgccggtta cctactctaa cgttgagccg agcgattttg tacagacctt tgcccgccgt    600
aacggcggag aagcgaccag cggttttcttt gaggttccgc taaacgagac aaaagaaaac   660
ggcattcgcc tgaccgaacg taaagagacg ttaggcgatg tgacccaccg catcctgatg    720
gtgccgatag cccaggatca gttgggcatg tattaccaac agccaggaca accgctggcg    780
acctgggttg taccgccggg gcaatatttc atgatgggcg acaaccgcga taacagcgcg    840
gatagtcgtt actggggatt tgttccggaa gcgaatctgg tcggtaaagc ggtcgctatc    900
tggatgagct ttgacaagca ggaaggggag tggccgacag gcgtacgcct gagtcgtatc    960
ggcggtattc actaa                                                     975
```

```
<210> SEQ ID NO 162
<211> LENGTH: 324
<212> TYPE: PRT
<213> ORGANISM: Klebsiella pneumoniae

<400> SEQUENCE: 162
```

Met Ala Asn Met Phe Ala Leu Ile Leu Val Ile Ala Thr Leu Val Thr
1               5                   10                  15

Gly Val Leu Trp Cys Leu Asp Lys Phe Ile Phe Ala Pro Lys Arg Arg
            20                  25                  30

Glu Arg Gln Ala Ala Gln Ala Ala Thr Gly Glu Gln Leu Asp Lys
        35                  40                  45

Lys Thr Leu Lys Lys Val Gly Pro Lys Pro Gly Trp Leu Glu Thr Gly
    50                  55                  60

Ala Ser Val Phe Pro Val Leu Ala Ile Val Leu Val Arg Ser Phe
65                  70                  75                  80

Ile Tyr Glu Pro Phe Gln Ile Pro Ser Gly Ser Met Met Pro Thr Leu
                85                  90                  95

Leu Ile Gly Asp Phe Ile Leu Val Glu Lys Phe Ala Tyr Gly Ile Lys
            100                 105                 110

Asp Pro Ile Tyr Gln Lys Thr Leu Ile Glu Thr Gly His Pro Lys Arg
        115                 120                 125

Gly Asp Ile Val Val Phe Lys Tyr Pro Glu Asp Pro Arg Leu Asp Tyr
    130                 135                 140

Ile Lys Arg Ala Val Gly Leu Pro Gly Asp Lys Val Thr Tyr Asp Pro
145                 150                 155                 160

Val Ala Lys Gln Val Thr Ile Gln Pro Gly Cys Ser Ser Gly Gln Ala
                165                 170                 175

Cys Gly Asn Ala Leu Pro Val Thr Tyr Ser Asn Val Glu Pro Ser Asp
            180                 185                 190

Phe Val Gln Thr Phe Ser Arg Ser Asn Gly Gly Glu Ala Ser Ser Gly
        195                 200                 205

Phe Trp Gln Leu Pro Lys Gly Glu Thr Lys Ala Asp Gly Ile Arg Leu
    210                 215                 220

Thr Glu Arg Gln Glu Thr Leu Gly Asp Val Thr His Arg Ile Leu Met
225                 230                 235                 240

Val Pro Ile Ala Gln Asp Gln Val Gly Met Tyr Tyr His Gln Ser Gly
                245                 250                 255

Leu Pro Leu Ala Thr Trp Ile Val Pro Gly Gln Tyr Phe Met Met
            260                 265                 270

Gly Asp Asn Arg Asp Asn Ser Ala Asp Ser Arg Tyr Trp Gly Phe Val
        275                 280                 285

Pro Glu Ala Asn Leu Val Gly Lys Ala Thr Ala Ile Trp Met Ser Phe

```
                    290                 295                 300
Glu Lys Gln Glu Gly Glu Trp Pro Thr Gly Val Arg Leu Ser Arg Ile
305                 310                 315                 320

Gly Gly Ile His

<210> SEQ ID NO 163
<211> LENGTH: 975
<212> TYPE: DNA
<213> ORGANISM: Klebsiella pneumoniae

<400> SEQUENCE: 163
atggcgaaca tgtttgccct gatcctggtg attgcaaccc tggtgacggg cgttttatgg    60
tgcctggaca agttcatttt tgcaccgaaa cgtcgtgaac gtcaggccgc tgctcaggca   120
gcgaccggcg agcaactgga caagaagacg ctgaagaaag tcggcccgaa accgggctgg   180
ctggaaaccg gcgcatcggt tttccggtg ctggcgatcg ttctggtggt acgttcattt    240
atttatgagc ctttccagat cccttcaggt tcgatgatgc aacgctgct catcggcgat    300 tttattctgg tggagaaatt tgcctacggc attaaagatc ctatctacca gaaaacgctg   360
atcgagaccg ccatccgaa gcgcggcgac atcgtggtat ttaaatatcc ggaagacccg    420
cgtctggact acattaagcg cgcggtgggg ttaccgggtg ataaggtcac ctacgatccg   480
gttgccaaac aggtcactat tcagcccggc tgcagttccg acaggcctg cggcaacgcg    540 ctgccggtga cctattccaa cgtggagccg agcgattttg ttcagacctt ctcccgcagc   600
aacggcggcg aagcgagcag cggtttctgg cagttgccga agggcgaaac caaagccgac   660
ggcattcgtc ttaccgagcg tcaggagaca ttgggcgacg tgacgcaccg aattctgatg   720
gtgccgattg cccaggatca ggttgggatg tactaccatc agtccggtct gccgctggcc   780
acctggattg tgccgcccgg tcagtacttc atgatgggcg acaaccggga taacagcgcc   840
gacagccggt actggggctt tgtgccggaa gccaacctgg tcggaaaagc aaccgctatc   900
tggatgagtt ttgaaaagca ggaaggtgaa tggccgaccg gcgtgcggtt atcgcgcatt   960
ggtggaattc attaa                                                    975

<210> SEQ ID NO 164
<211> LENGTH: 294
<212> TYPE: PRT
<213> ORGANISM: Mycobacterium tuberculosis

<400> SEQUENCE: 164

Val Thr Glu Thr Thr Asp Ser Pro Ser Glu Arg Gln Pro Gly Pro Ala
1               5                   10                  15

Glu Pro Glu Leu Ser Ser Arg Asp Pro Asp Ile Ala Gly Gln Val Phe
            20                  25                  30

Asp Ala Ala Pro Phe Asp Ala Ala Pro Asp Ala Asp Ser Glu Gly Asp
        35                  40                  45

Ser Lys Ala Ala Lys Thr Asp Glu Pro Arg Pro Ala Lys Arg Ser Thr
    50                  55                  60

Leu Arg Glu Phe Ala Val Leu Ala Val Ile Ala Val Val Leu Tyr Tyr
65                  70                  75                  80

Val Met Leu Thr Phe Val Ala Arg Pro Tyr Leu Ile Pro Ser Glu Ser
                85                  90                  95

Met Glu Pro Thr Leu His Gly Cys Ser Thr Cys Val Gly Asp Arg Ile
            100                 105                 110

Met Val Asp Lys Leu Ser Tyr Arg Phe Gly Ser Pro Gln Pro Gly Asp
```

```
            115                 120                 125
Val Ile Val Phe Arg Gly Pro Pro Ser Trp Asn Val Gly Tyr Lys Ser
    130                 135                 140

Ile Arg Ser His Asn Val Ala Val Arg Trp Val Gln Asn Ala Leu Ser
145                 150                 155                 160

Phe Ile Gly Phe Val Pro Pro Asp Glu Asn Asp Leu Val Lys Arg Val
                165                 170                 175

Ile Ala Val Gly Gly Gln Thr Val Gln Cys Arg Ser Asp Thr Gly Leu
            180                 185                 190

Thr Val Asn Gly Arg Pro Leu Lys Glu Pro Tyr Leu Asp Pro Ala Thr
        195                 200                 205

Met Met Ala Asp Pro Ser Ile Tyr Pro Cys Leu Gly Ser Glu Phe Gly
210                 215                 220

Pro Val Thr Val Pro Pro Gly Arg Val Trp Val Met Gly Asp Asn Arg
225                 230                 235                 240

Thr His Ser Ala Asp Ser Arg Ala His Cys Pro Leu Leu Cys Thr Asp
                245                 250                 255

Asp Pro Leu Pro Gly Thr Val Pro Val Ala Asn Val Ile Gly Lys Ala
            260                 265                 270

Arg Leu Ile Val Trp Pro Pro Ser Arg Trp Gly Val Val Arg Ser Val
        275                 280                 285

Asn Pro Gln Gln Gly Arg
    290

<210> SEQ ID NO 165
<211> LENGTH: 885
<212> TYPE: DNA
<213> ORGANISM: Mycobacterium tuberculosis

<400> SEQUENCE: 165
gtgaccgaaa ccacggactc cccatcggag cgccagccgg gtccggcaga gccggagctc      60
tcctcccggg acccggacat tgccggccag gtcttcgacg cagccccgtt cgacgcagcc     120
ccggatgcgg actccgaagg cgactccaag gcggccaaaa cggacgagcc gcggcccgcg     180
aagcgatcaa cgctgcggga gttcgcggtg ctggcggtga ttgctgtggt gctctactac     240
gtcatgctga cgtttgtcgc gcgcccttat ctgattccgt cggaatcgat ggaacccacg     300
ttgcacgggt gttcgacgtg cgtcggcgac gcatcatggt ggacaaaact cagctaccgc     360
ttcggctcac cgcaacctgg cgacgtcatc gtcttcaggg accgccgtc gtggaacgtt     420 ggttacaagt cgatccgttc gcacaacgtc gccgtgcgct gggtgcagaa cgcgttgtcg     480
ttcatcggtt tcgtgcctcc cgacgagaac gacctggtca agcgtgtcat cgcggtcggc     540
ggacagacgg ttcaatgccg gtccgacacc ggcctgacgg tcaacggcag gccactgaag     600
gagccatacc tggatccggc caccatgatg gccgacccgt cgatataccc gtgcctgggc     660
agcgagttcg gccggtcac cgtcccgccc gggcgtgtct gggtgatggg cgacaaccgc     720
acccattcgg cggattcccg cgctcactgc ccgttgctat gtactgacga tccgctaccg     780
gggaccgtgc cggtggccaa cgtcatcggt aaggccaggt tgatcgtgtg ccgccgtcg     840 cgttggggtg ttgtgcgttc ggtgaatccc cagcaaggtc ggtag                   885

<210> SEQ ID NO 166
<211> LENGTH: 332
<212> TYPE: PRT
<213> ORGANISM: Yersinia pestis
```

<400> SEQUENCE: 166

| | | | | | | | | | | | | | | |
|---|---|---|---|---|---|---|---|---|---|---|---|---|---|---|
| Met | Ala | Asn | Met | Phe | Ala | Leu | Ile | Leu | Ala | Ile | Ala | Thr | Leu | Leu | Thr |
| 1 | | | | 5 | | | | | 10 | | | | | 15 | |

| Gly | Ile | Ile | Trp | Cys | Phe | Glu | Arg | Phe | Lys | Trp | Gly | Pro | Ala | Arg | Gln |
| 20 | | | | | 25 | | | | | 30 | | | | | |

| Ala | Lys | Ile | Ala | Ala | Val | Asn | Ala | Gln | Thr | Ala | Glu | Ile | Lys | Ala | Gln |
| | | 35 | | | | | 40 | | | | | 45 | | | |

| Thr | Gly | Cys | Ala | Val | Asp | Asn | Lys | Thr | Leu | Ala | Gln | Ala | Ala | Lys | Gln |
| | 50 | | | | | 55 | | | | | 60 | | | | |

| Pro | Gly | Trp | Ile | Glu | Thr | Cys | Ala | Ser | Ile | Phe | Pro | Val | Leu | Ala | Leu |
| 65 | | | | | 70 | | | | | 75 | | | | | 80 |

| Val | Phe | Ile | Val | Arg | Ser | Phe | Ile | Tyr | Glu | Pro | Phe | Gln | Ile | Pro | Ser |
| | | | | 85 | | | | | 90 | | | | | 95 | |

| Gly | Ser | Met | Met | Pro | Thr | Leu | Leu | Ile | Gly | Asp | Phe | Ile | Leu | Val | Glu |
| | | | 100 | | | | | 105 | | | | | 110 | | |

| Lys | Phe | Ala | Tyr | Gly | Ile | Lys | Asp | Pro | Ile | Thr | Gln | Thr | Thr | Leu | Ile |
| | | | 115 | | | | | 120 | | | | | 125 | | |

| Pro | Thr | Gly | Lys | Pro | Asn | Arg | Gly | Asp | Ile | Ala | Val | Phe | Lys | Tyr | Pro |
| 130 | | | | | 135 | | | | | 140 | | | | | |

| Leu | Asp | Pro | Arg | Leu | Asp | Tyr | Ile | Lys | Arg | Val | Val | Gly | Leu | Pro | Gly |
| 145 | | | | | 150 | | | | | 155 | | | | | 160 |

| Asp | Arg | Val | Ile | Tyr | Asn | Pro | Ile | Ser | Lys | Glu | Val | Thr | Val | Gln | Pro |
| | | | | 165 | | | | | 170 | | | | | 175 | |

| Ser | Cys | Asn | Thr | Gly | Thr | Ser | Cys | Asp | Ser | Ala | Leu | Ala | Ile | Thr | Tyr |
| | | | 180 | | | | | 185 | | | | | 190 | | |

| Ser | Thr | Ser | Glu | Pro | Ser | Glu | Phe | Val | Gln | Thr | Phe | Arg | Tyr | Ser | Gly |
| | | 195 | | | | | 200 | | | | | 205 | | | |

| Asn | Gly | Glu | Ser | Ser | Ala | Gly | Phe | Phe | Pro | Ile | Pro | Leu | Asn | Gln | Ala |
| | 210 | | | | | 215 | | | | | 220 | | | | |

| Val | Pro | Asp | Gly | Gly | Val | Arg | Leu | Arg | Glu | Arg | Thr | Glu | Ser | Leu | Gly |
| 225 | | | | | 230 | | | | | 235 | | | | | 240 |

| Pro | Val | Ala | His | His | Ile | Leu | Thr | Val | Pro | Gly | Arg | Gln | Asp | Pro | Leu |
| | | | | 245 | | | | | 250 | | | | | 255 | |

| Gly | Ser | Tyr | Tyr | Gln | Gln | Pro | Asp | Gln | Pro | Leu | Gly | Val | Trp | Val | Val |
| | | | 260 | | | | | 265 | | | | | 270 | | |

| Pro | Glu | Gly | His | Tyr | Phe | Met | Met | Gly | Asp | Asn | Arg | Asp | Asn | Ser | Ala |
| | | 275 | | | | | 280 | | | | | 285 | | | |

| Asp | Ser | Arg | Phe | Trp | Gly | Phe | Val | Pro | Glu | Arg | Asn | Leu | Val | Gly | Lys |
| | 290 | | | | | 295 | | | | | 300 | | | | |

| Ala | Thr | Ala | Ile | Trp | Met | Ser | Phe | Glu | Lys | Gln | Glu | Gly | Glu | Trp | Pro |
| 305 | | | | | 310 | | | | | 315 | | | | | 320 |

| Thr | Gly | Val | Arg | Leu | Ser | Arg | Ile | Gly | Gly | Ile | His |
| | | | | 325 | | | | | 330 | | |

<210> SEQ ID NO 167
<211> LENGTH: 999
<212> TYPE: DNA
<213> ORGANISM: Yersinia pestis

<400> SEQUENCE: 167

| | |
|---|---|
| atggctaaca tgtttgcttt gattctggca atagcaacgc tgttgacggg gattatctgg | 60 |
| tgcttcgagc ggtttaaatg ggggccagcc cgtcaggcaa aaattgcggc agttaatgca | 120 |
| caaactgcgg aaatcaaggc ccaaaccggg tgtgccgtag ataataaaac cttagcccaa | 180 |

```
gctgcaaagc aaccgggttg gatcgagaca tgtgcctcta tcttcccggt gctggccttg      240
gtctttatcg tgcgttcgtt tatttacgag cctttccaga tcccttctgg ttcgatgatg      300
ccaacgctgc ttatcggtga ttttattttg gttgagaaat ttgcttatgg gattaaagat      360
cccattactc agaccacatt aattccaaca ggtaagccaa accgcggtga cattgcggtg      420
tttaaatatc cgttggatcc acgtttggat tatatcaagc gtgtggtggg gctgccgggg      480
gatcgggtaa tttataaccc gataagtaaa gaagtcacgg tacaaccgtc atgtaatacc      540
ggtacttctt gtgatagtgc gttggccatc acttacagca cgtctgagcc aagtgagttt      600
gtgcagacat tccgttatag cggtaatggc gaaagctccg cagggttctt cccaatcccg      660
ctaaatcagg cagtacctga tggcggtgtc cggttacgtg agcgtactga aagcctcggc      720
ccggtagcgc atcacattct gaccgtccca gggcggcagg atccgttagg ctcttattat      780
cagcaacccg atcaaccgtt aggggtttgg gtggtaccgg aaggccatta ctttatgatg      840
ggtgataacc gggataacag tgcagatagc cgcttctggg gttttgtacc agaacgtaat      900
ctggtaggta aggctacggc tatttggatg agttttgaaa agcaagaagg tgaatggcca      960
acgggtgtgc gtttaagccg aattggtgga attcactaa                            999
```

```
<210> SEQ ID NO 168
<211> LENGTH: 194
<212> TYPE: PRT
<213> ORGANISM: Staphylococcus aureus

<400> SEQUENCE: 168
```

Val Ser Lys Leu Lys Lys Glu Ile Leu Glu Trp Ile Ile Ser Ile Ala
1               5                   10                  15

Val Ala Phe Val Ile Leu Phe Ile Val Gly Lys Phe Ile Val Thr Pro
                20                  25                  30

Tyr Thr Ile Lys Gly Glu Ser Met Asp Pro Thr Leu Lys Asp Gly Glu
            35                  40                  45

Arg Val Ala Val Asn Ile Val Gly Tyr Lys Thr Gly Gly Leu Glu Lys
        50                  55                  60

Gly Asn Val Val Val Phe His Ala Asn Lys Asn Asp Asp Tyr Val Lys
65                  70                  75                  80

Arg Val Ile Gly Val Pro Gly Asp Lys Val Glu Tyr Lys Asn Asp Thr
                85                  90                  95

Leu Tyr Val Asn Gly Lys Lys Gln Asp Glu Pro Tyr Leu Asn Tyr Asn
            100                 105                 110

Leu Lys His Lys Gln Gly Asp Tyr Ile Thr Gly Thr Phe Gln Val Lys
        115                 120                 125

Asp Leu Pro Asn Ala Asn Pro Lys Ser Asn Val Ile Pro Lys Gly Lys
    130                 135                 140

Tyr Leu Val Leu Gly Asp Asn Arg Glu Val Ser Lys Asp Ser Arg Ala
145                 150                 155                 160

Phe Gly Leu Ile Asp Glu Asp Gln Ile Val Gly Lys Val Ser Phe Arg
                165                 170                 175

Phe Trp Pro Phe Ser Glu Phe Lys His Asn Phe Asn Pro Glu Asn Thr
            180                 185                 190

Lys Asn

```
<210> SEQ ID NO 169
<211> LENGTH: 585
<212> TYPE: DNA
<213> ORGANISM: Staphylococcus aureus
```

<400> SEQUENCE: 169

```
gtgtcaaaat tgaaaaaga aatattggaa tggattattt caattgcagt cgcttttgtc      60
atttattta tagtaggtaa atttattgtt acgccatata caattaaagg tgaatcaatg     120
gatccaactt tgaaagatgg cgagcgagta gctgtaaaca ttgttggata taaaacaggt    180
ggtttggaaa aagtaatgt agttgtcttc catgcaaaca aaaatgatga ctatgttaaa    240
cgtgtcatcg gtgttcctgg tgataaagta gaatacaaaa atgatacatt atatgtcaat    300
ggtaaaaaac aagatgaacc atatttaaac tacaatttaa aacataaaca aggtgattac    360
attactggga cttttccaagt taaagattta ccgaatgcga atcctaaatc aaatgtcatt    420
ccaaaaggta atatttagt gcttggagat aatcgtgaag taagtaaaga tagccgtgcg    480
tttggcctca ttgatgaaga ccaaattgtt ggtaaagttt catttaggtt ctggccattt    540
agtgaattta aacataattt caatcctgaa aatactaaaa attaa                   585
```

<210> SEQ ID NO 170
<211> LENGTH: 298
<212> TYPE: PRT
<213> ORGANISM: Vibrio cholerae

<400> SEQUENCE: 170

```
Met Ala Asn Thr Phe Ser Leu Ile Leu Val Ile Val Thr Leu Val Thr
1               5                   10                  15

Gly Ile Val Trp Thr Leu Glu Lys Leu Val Trp Ala Lys Lys Arg Gln
            20                  25                  30

Gln Lys Gln Ala His Leu Gln Ala Gln Thr Pro Asp Met Pro Ala Ser
        35                  40                  45

Ala Leu Asp Lys Val Val Ala Gln Pro Trp Trp Ile Glu Asn Ser Val
    50                  55                  60

Ser Ile Phe Pro Val Ile Ala Phe Val Leu Val Leu Arg Ser Phe Ile
65                  70                  75                  80

Tyr Glu Pro Phe Gln Ile Pro Ser Gly Ser Met Met Pro Thr Leu Leu
                85                  90                  95

Val Gly Asp Phe Ile Leu Val Glu Lys Tyr Ala Tyr Gly Leu Lys Asp
            100                 105                 110

Pro Val Trp Arg Thr Gln Leu Val Glu Thr Gly Lys Pro Glu Arg Gly
        115                 120                 125

Asp Ile Val Val Phe Lys Tyr Pro Val Asn Pro Glu Ile Asp Tyr Ile
    130                 135                 140

Lys Arg Val Val Gly Met Pro Gly Asp Thr Val Arg Tyr Ser Ala Gly
145                 150                 155                 160

Lys Glu Leu Cys Ile Gln His Gln Gly Glu Ser Glu Cys Gln Ala Val
                165                 170                 175

Lys Leu Ser Asn Val Gln Glu Ser Glu Phe Tyr Gln Asn Glu Ile Pro
            180                 185                 190

Leu Ile Gln Leu Asn Glu Gln Leu Gly Lys Val Glu His Asn Ile Leu
        195                 200                 205

Val Asn Pro Leu Ser Ile Asp Asn Val Ala Asn Tyr Arg Pro Arg Ser
    210                 215                 220

Gly Val Asn Glu Trp Val Val Pro Gln Gly His Tyr Phe Val Met Gly
225                 230                 235                 240

Asp Asn Arg Asp Asn Ser Ala Asp Ser Arg Phe Trp Gly Phe Val Pro
                245                 250                 255
```

```
Glu Gln Asn Leu Val Gly Lys Ala Val Ala Ile Trp Ile Ser Phe Glu
                260                 265                 270

Phe Glu Arg Ala Glu Asp Ser Val Leu Pro Arg Trp Ile Pro Thr Gly
            275                 280                 285

Val Arg Phe Asn Arg Val Gly Gly Ile His
        290                 295

<210> SEQ ID NO 171
<211> LENGTH: 897
<212> TYPE: DNA
<213> ORGANISM: Vibrio cholerae

<400> SEQUENCE: 171
atggcgaaca cattctcact gattttggtg atcgtaactc tggtcaccgg tatcgtctgg      60
acactggaaa agctggtgtg ggcgaaaaaa cgccaacaga acaagctca tttacaggcg     120 caaacgcccg atatgccagc tcagcgctg ataaagtcg tggctcagcc gtggtggatt       180
gaaaacagtg tctcgatttt ccctgttatt gcttttgtgc tggtactgcg ctcgttcatt     240
tatgaaccgt tccaaattcc atccggttcg atgatgccga ctctgctggt cggggatttt    300
attctggttg agaaatacgc ttacggcttg aaagatcctg tatggcgcac tcagttagtg    360
gaaacgggta acctgagcg tggtgatatt gtggtgttca atacccagt gaaccctgag      420 atcgactaca tcaaacgtgt ggtggggatg cccggagata ccgtacgtta cagcgcaggt    480
aaagagctgt gtattcagca ccaaggcgag agcgaatgcc aagcagttaa actctctaac   540
gtgcaagaga gcgagttta ccaaaatgag atcccctga tccagctgaa cgaacagcta     600
ggtaaggttg agcacaatat tttggttaac ccattgagca ttgataacgt ggcgaattat    660
cgcccacgca gtggcgtgaa tgaatgggtt gtaccacaag gcactatttt tgtgatgggt    720
gataaccgtg acaacagtgc tgacagccgt ttctgggct tgtgccaga gcagaatctg     780 gtcggaaaag ctgtggctat ctggatcagt ttcgagtttg aacgcgctga agacagcgta    840
cttccacgct ggattcctac cggagtacga ttcaatcgtg ttggtgggat ccactaa      897

<210> SEQ ID NO 172
<211> LENGTH: 349
<212> TYPE: PRT
<213> ORGANISM: Haemophilus influenzae

<400> SEQUENCE: 172

Met Ser Asn Leu Phe Phe Val Ile Leu Leu Ala Val Gly Phe Gly Val
  1               5                  10                  15

Trp Lys Val Leu Asp Tyr Phe Gln Leu Pro Asn Thr Phe Ser Ile Leu
                20                  25                  30

Leu Leu Ile Leu Thr Ala Leu Ser Gly Val Leu Trp Cys Tyr His Arg
            35                  40                  45

Phe Val Val Leu Pro Lys Arg His Arg Gln Val Ala Arg Ala Glu Gln
        50                  55                  60

Arg Ser Gly Lys Thr Leu Ser Glu Glu Glu Lys Ala Lys Ile Glu Pro
 65                 70                  75                  80

Ile Ser Glu Ala Ser Glu Phe Leu Ser Ser Leu Phe Pro Val Leu Ala
                85                  90                  95

Val Val Phe Leu Val Arg Ser Phe Leu Phe Glu Pro Phe Gln Ile Pro
            100                 105                 110

Ser Gly Ser Met Glu Ser Thr Leu Arg Val Gly Asp Phe Leu Val Val
        115                 120                 125
```

Asn Lys Tyr Ala Tyr Gly Val Lys Asp Pro Ile Phe Gln Asn Thr Ile
    130                 135                 140

Ile Glu Gly Glu Lys Pro Gln Arg Gly Asp Val Ile Val Phe Lys Ala
145                 150                 155                 160

Pro Gln Gln Ala Leu Ile Arg Thr Gly Leu Gly Ala Thr Arg Ala Ala
                165                 170                 175

Phe Ala Glu Asn Leu Ala Leu Ser Ser Lys Asp Asn Met Ser Gly Val
            180                 185                 190

Asp Tyr Ile Lys Arg Ile Val Gly Lys Gly Asp Arg Ile Ile Phe
        195                 200                 205

Asp Val Glu Gln Lys Thr Leu Lys Ile Val Tyr Gly Lys Asp Gly Lys
    210                 215                 220

Pro Cys Glu Val Asp Cys Glu Thr Lys Ala Phe Glu Tyr Thr Gln Asn
225                 230                 235                 240

Pro Thr Asn Pro Ala Phe Pro Asn Glu Leu Glu Leu Thr Glu Lys Gly
                245                 250                 255

Asp Val Thr His Asn Val Leu Ile Gly Glu Tyr Arg Arg Tyr Ser Asp
            260                 265                 270

Leu Glu Phe Phe Pro Gln Glu Gly Met Gln Thr Ala Glu Trp Leu Val
        275                 280                 285

Pro Glu Gly Gln Tyr Phe Val Met Gly Asp His Arg Asp His Ser Asp
    290                 295                 300

Asp Ser Arg Phe Trp Gly Phe Val Pro Glu Lys Asn Ile Val Gly Lys
305                 310                 315                 320

Ala Thr Tyr Ile Trp Met Ser Leu Glu Lys Glu Ala Asn Glu Trp Pro
                325                 330                 335

Thr Gly Phe Arg Phe Asp Arg Phe Phe Thr Ala Ile Lys
            340                 345

<210> SEQ ID NO 173
<211> LENGTH: 1050
<212> TYPE: DNA
<213> ORGANISM: Haemophilus influenzae

<400> SEQUENCE: 173
atgtcaaatt tattttttgt gattttattg ctgtcggct ttggtgtgtg aaagtttta      60 gattattttc agttgccaaa tactttagt attttgttac taattttgac cgcactttct    120
ggcgtattat ggtgttatca tcgttttgtg gtgctgccaa acgtcatcg tcaagtggca    180 cgtgcagaac aacgttctgg taaaacctta agtgaggaag aaaaagccaa aattgaaccg    240
atttctgagg cttcagaatt tttgtcttca cttttttcctg tgcttgcagt ggtattttg    300 gttcgttctt ttttgtttga accgtttcaa attccctctg ctcaatgga gtccacttta    360 cgcgttggcg atttttagt tgtgaataaa tatgcttatg gtgtgaaaga tccgattttc    420
caaaacacca ttattgaggg cgaaaaacca acgtggcg atgtgattgt gtttaaagca    480
ccacaacaag cgttaattcg tactggtctt ggggctactc gagcggcttt tgcagaaaat    540
ttagcgttaa gttcaaaaga taatatgtct ggtgtggatt atattaagcg tattgttgga    600
aagggcggag atcgcatcat tttgatgtg aacaaaaaa cattaaaaat tgtatatggc    660
aaagatggta aaccttgtga agttgattgc gaaaccaagg cgtttgaata cacaaaaat    720 ccaacaaatc ctgcttttcc gaatgaatta gaattgactg aaaaaggcga tgtaacacat    780
aacgtgttaa ttggtgagta tcgtcgttat tcagaccttg aattttttccc acaagaggga    840 atgcaaactg cagaatggct tgtgccagag gggcagtatt ttgtgatggg ggatcatcgc    900

```
gatcacagcg atgacagtcg tttttggggc tttgtgcctg aaaaaaatat tgtggggaaa      960
gccacttata tttggatgag cttagaaaaa gaagcgaatg aatggccaac aggtttccgt     1020
tttgatcgct tctttacagc aataaaataa                                     1050
```

<210> SEQ ID NO 174
<211> LENGTH: 284
<212> TYPE: PRT
<213> ORGANISM: Pseudomonas aeruginosa

<400> SEQUENCE: 174

```
Met Thr Leu Asn Phe Pro Leu Leu Val Ile Ala Val Ala Val Cys
 1               5                  10                  15

Gly Ala Leu Ala Leu Val Asp Leu Val Leu Phe Ala Pro Arg Arg
                20                  25                  30

Ala Ala Ile Ser Ser Tyr Glu Gly Gln Val Asn Glu Pro Asp Pro Ala
                35                  40                  45

Val Leu Glu Lys Leu Asn Lys Glu Pro Leu Leu Val Glu Tyr Gly Lys
 50                  55                  60

Ser Phe Phe Pro Val Leu Phe Ile Val Leu Val Leu Arg Ser Phe Leu
65                   70                  75                  80

Val Glu Pro Phe Gln Ile Pro Ser Gly Ser Met Lys Pro Thr Leu Glu
                85                  90                  95

Val Gly Asp Phe Ile Leu Val Asn Lys Phe Ala Tyr Gly Ile Arg Leu
                100                 105                 110

Pro Val Leu Asp Thr Lys Val Ile Pro Ile Gly Asp Pro Gln Arg Gly
                115                 120                 125

Asp Val Met Val Phe Arg Tyr Pro Ser Glu Pro Asn Ile Asn Tyr Ile
130                  135                 140

Lys Arg Val Val Gly Leu Pro Gly Asp Thr Val Arg Tyr Thr Lys Glu
145                  150                 155                 160

Lys Arg Leu Tyr Val Asn Gly Glu Leu Val Ala Glu Lys Leu Val Gly
                165                 170                 175

Glu Glu Pro Gly Thr Leu Gly Ser Val Thr Leu Tyr Gln Glu Lys Leu
                180                 185                 190

Gly Gln Ala Glu His Leu Ile Arg Lys Glu Met Ser Arg Tyr Arg Ile
                195                 200                 205

Glu Pro Asp Arg Gln Trp Thr Ile Pro Ala Gly His Tyr Phe Met Met
210                  215                 220

Gly Asp Asn Arg Asp Asn Ser Asn Asp Ser Arg Tyr Trp Asn Asp Pro
225                  230                 235                 240

Lys Ile Pro Lys Asp Leu Leu Gly Met Val Pro Asp Arg Asn Ile Val
                245                 250                 255

Gly Lys Ala Phe Ala Val Trp Met Ser Trp Pro Asp Pro Lys Met Ser
                260                 265                 270

Asn Leu Pro Asn Phe Ser Arg Val Gly Val Ile His
                275                 280
```

<210> SEQ ID NO 175
<211> LENGTH: 855
<212> TYPE: DNA
<213> ORGANISM: Pseudomonas aeruginosa

<400> SEQUENCE: 175

```
atgacactca atttcccgtt gttgctggtc atcgccgtgg ctgtatgcgg cgccctggcc      60
```

```
ctggtcgacc tggtgctgtt cgcgccgcgt cggcgggccg cgatctcttc ctacgaaggg    120
caggtgaacg agcccgatcc ggcagtgctg gagaagctca acaaggaacc gctgctggtg    180
gagtacggca agtcgttctt cccggtgctg ttcatcgtgc tggtgctgcg ttccttcctg    240
gtcgagccgt tccagattcc ctcggggtcg atgaaaccta ccctcgaggt cggcgatttc    300
atcctggtca acaagttcgc ctacggtatc cgcctgccgg tgctggacac caaggtgatc    360
ccgatcggtg atccgcagcg cggcgatgtc atggtgttcc gctatcccag cgaaccgaac    420
atcaactaca tcaagcgcgt ggtcggcctg cccggcgaca ccgtgcgcta caccaaggaa    480
aagcgcctgt acgtcaacgg cgagctggtg gcggagaaac tggtcggcga ggaaccgggc    540
accctgggca gcgtgaccct gtaccaggag aagctgggcc aggccgagca cctgatccgc    600
aaggaaatga ccgctatcg catcgagccc gaccgccagt ggaccattcc cgccggccac    660
tacttcatga tgggcgacaa ccgcgacaac tccaacgaca ccgctactg gaacgatccg    720 aagatcccca aggatctgct gggcatggtt ccggaccgca atatcgtcgg caaggccttc    780
gccgtgtgga tgagctggcc cgatccgaag atgagcaacc tgccgaactt ctcccgggtc    840
ggcgtgattc actga                                                      855

<210> SEQ ID NO 176
<211> LENGTH: 275
<212> TYPE: PRT
<213> ORGANISM: Acinetobacter baumannii

<400> SEQUENCE: 176

Val Asp Phe Asp Phe Asn Leu Ile Leu Val Pro Val Thr Leu Ile Leu
1               5                   10                  15

Phe Ala Val Trp Leu Leu Asp Lys Leu Val Phe Lys Gln Arg Ala Asn
                20                  25                  30

Lys Gly Arg Glu Asn Glu Asn Phe Val Ile Thr Trp Ala Tyr Asp Phe
            35                  40                  45

Trp Pro Val Leu Ala Val Val Leu Val Leu Arg Ser Phe Leu Tyr Glu
        50                  55                  60

Pro Phe Asn Ile Pro Ser Asp Ser Met Val Pro Thr Leu Glu Thr Gly
65                  70                  75                  80

Asp Phe Ile Leu Val Asn Lys Phe Asp Tyr Gly Val Arg Leu Pro Ile
                85                  90                  95

Val Asn Lys Lys Val Ile Asp Val Gly Glu Pro Lys Arg Gly Asp Val
            100                 105                 110

Ile Val Phe Arg Tyr Pro Pro Gln Pro Thr Ile Ser Tyr Ile Lys Arg
        115                 120                 125

Val Ile Gly Leu Pro Gly Asp His Ile Val Tyr Asp His Gly Gln Leu
    130                 135                 140

Ile Ile Asn Gly Gln Lys Ile Pro Lys Val Pro Thr Gln Phe Ser Arg
145                 150                 155                 160

Glu Lys Asp Ala Leu Asp Thr Pro Thr Ser Ile Tyr His Lys Glu Thr
                165                 170                 175

Ile Gly Asp His Thr Phe Thr Met Arg Glu Leu Glu Gly Val Asn Val
            180                 185                 190

Ala Arg Gln Ala Pro Phe Ile Asn Tyr Val Asp Asn Gly Lys Tyr Ala
        195                 200                 205

Asn Gln Asp Gly Leu Tyr Trp Glu Val Thr Val Pro Lys Gly His Tyr
    210                 215                 220

Phe Ala Met Gly Asp Asn Arg Asp Gln Ser Ala Asp Ser Arg Phe Trp
```

```
                225                 230                 235                 240

Gly Phe Val Pro Glu Glu Asn Leu Thr Gly Arg Ala Phe Tyr Val Trp
                245                 250                 255

Met His Lys Glu Pro Gly Phe His Leu Pro Ser Phe Asn Arg Asn Gly
                260                 265                 270

Lys Ile Asp
        275

<210> SEQ ID NO 177
<211> LENGTH: 828
<212> TYPE: DNA
<213> ORGANISM: Acinetobacter baumannii

<400> SEQUENCE: 177
gtggattttg attttaattt aattcttgtt cctgttacgc tgattttatt tgcagtgtgg      60
ttgctagata agcttgtttt taaacagcgt gcaaataaag ggcgagagaa cgaaaatttt     120
gttattacat gggcctatga cttttggccg gttttagctg ttgtgcttgt acttcgctca     180
tttctttatg aaccatttaa tattccatca gactctatgg ttccgacctt agagactggc     240
gatttttatt tagttaataa atttgactat ggtgtccgtt tacctatcgt caataaaaaa     300
gtgattgatg tcggtgaacc gaaacgtggt gatgtcattg tattccgtta tccaccacaa     360
cctactatta gttatattaa acgtgtaatt ggcttacctg gtgaccatat tgtttatgat     420
catggacaat tgattattaa tggtcaaaaa attcctaaag taccaacaca gtttagtcgc     480
gaaaaagatg ctttagatac accaacttct atttatcata agaaacaat tggtgatcat     540 acttttacga tgcgtgagct tgaaggcgta aatgttgcgc gtcaggcgcc atttatcaac     600
tatgttgata tggtaaaata tgcaaaccaa gacggtttat attgggaagt aacagttccg     660
aaaggacatt actttgcaat ggggataaac cgtgatcaaa gtgctgacag tcgtttctgg     720
ggcttcgtac tgaagaaaa tttaacaggc cgagctttct atgtctggat gcataaagaa     780
cctggtttcc acctgccaag ctttaaccga atgggaaaa tagattaa                   828

<210> SEQ ID NO 178
<211> LENGTH: 183
<212> TYPE: PRT
<213> ORGANISM: Bacillus anthracis

<400> SEQUENCE: 178

Met Lys Glu Asn Thr Lys Lys Glu Leu Phe Ser Trp Ala Lys Thr Ile
  1               5                  10                  15

Gly Phe Thr Leu Val Leu Ile Ala Ile Ile Arg Gly Val Leu Phe Thr
                 20                  25                  30

Pro Ser Leu Val Gln Gly Glu Ser Met Met Pro Thr Leu Glu Asn Asn
             35                  40                  45

Glu Arg Val Leu Val Asn Lys Ile Gly Tyr Ser Ile Ser Gly Leu Glu
         50                  55                  60

Arg Phe Asp Ile Ile Val Phe His Gly Lys Gly Tyr Asp Leu Val
 65                  70                  75                  80

Lys Arg Val Ile Gly Leu Pro Gly Asp Thr Val Glu Tyr Lys Asn Asp
                 85                  90                  95

Val Leu Tyr Val Asn Gly Lys Ala Met Glu Glu Pro Tyr Leu Lys Glu
            100                 105                 110

Phe Lys Glu Lys Ala Ala Gly Arg Val Leu Thr Pro Asp Phe Thr Leu
        115                 120                 125
```

```
Glu Gln Ile Thr Gly Lys Thr Lys Val Pro Glu Gly Gln Val Phe Val
130                 135                 140

Leu Gly Asp Asn Arg Glu Val Ser Lys Asp Gly Arg Met Phe Gly Phe
145                 150                 155                 160

Ile Ser Glu Asp Glu Ile Val Gly Lys Gly Gln Ala Val Phe Trp Pro
                165                 170                 175

Leu Lys Gln Val Arg Ala Leu
            180
```

<210> SEQ ID NO 179
<211> LENGTH: 552
<212> TYPE: DNA
<213> ORGANISM: Bacillus anthracis

<400> SEQUENCE: 179

```
atgaaggaaa atacgaagaa agaattattc tcatgggcga aaacgatagg atttacccct     60
gtattaatcg caattattcg cggtgtttta tttacaccgt cattagtaca aggcgaatcg    120
atgatgccga ctttagaaaa taacgaacga gttctcgtca ataagattgg ttatagtata    180
agtggattag aacgctttga tattatcgtt ttccatggaa agaaggata tgatttagta     240
aaacgagtaa ttggtttacc aggcgataca gttgagtata aaatgatgt tttatatgta     300
aacggcaaag cgatggaaga accatatttta aaagagttta agaaaaagc agcaggtcgt    360
gtattaactc cagactttac gttagaacaa attacaggaa aacgaaagt gccagaaggc     420
caagtgttg tattaggtga taatcgtgaa gtttctaaag acggtcgtat gtttggattt    480
atttcagaag atgaaattgt cggaaaagga caagctgttt tctggccgtt gaaacaagta    540
agagcgctat aa                                                        552
```

<210> SEQ ID NO 180
<211> LENGTH: 339
<212> TYPE: PRT
<213> ORGANISM: Neisseria meningitidis

<400> SEQUENCE: 180

```
Met Asn Thr Met Leu Met Ser Gly Ala Ala Ala Leu Leu Ala Gly
1               5                   10                  15

Ile Ile Leu Tyr Phe Lys Ser Asp Lys Lys Arg Gln Glu Asn Gly Glu
            20                  25                  30

Trp Ser Ser Gly Leu Glu Tyr Ala Tyr Ile Leu Thr Ala Val Gly Val
                35                  40                  45

Phe Ala Ala Leu Ser Leu Phe Met Ser Phe Thr Ala Val Phe Leu Ile
50                  55                  60

Phe Val Val Leu Cys Gly Thr Ala Trp Gly Val Tyr Lys Tyr Arg Leu
65                  70                  75                  80

Lys Thr His Pro Glu Ile Ser Glu Ser His Phe Gly Asp Tyr Phe
                85                  90                  95

Gly Ser Phe Phe Pro Thr Val Leu Val Leu Phe Leu Ile Arg Ser Phe
                100                 105                 110

Ile Ala Glu Pro Phe Gln Ile Pro Ser Ser Met Arg Pro Gly Leu
            115                 120                 125

Ile Lys Gly Asp Phe Ile Leu Val Gly Lys Phe Ser Tyr Gly Leu Arg
            130                 135                 140

Val Pro Val Leu Asn Asn Ile Phe Ile Pro Thr Gly Lys Ile Glu Arg
145                 150                 155                 160

Gly Asp Val Val Val Phe Asn Tyr Pro Leu Gln Pro Glu Met Thr Tyr
```

```
                 165                 170                 175
Ile Lys Arg Ile Val Gly Ile Pro Gly Asp Val Val Glu Tyr Arg Asp
                180                 185                 190

Lys Ile Leu Thr Val Asn Gly Lys Pro Thr Ser Asp Ile Pro Asp Gly
            195                 200                 205

Thr Tyr Arg Tyr Pro Asp Asp Thr Asp Pro Ser Glu Ile His Asn Thr
        210                 215                 220

Asp Met Phe Arg Ser Gly Leu Asp Gly Lys Ser Phe Asn Ile Leu Lys
225                 230                 235                 240

Lys Glu Gly Gln Pro Ala Val Ser Leu Pro Val Leu Gly Lys Tyr Thr
                245                 250                 255

Ser Asp Ile Met Ser Glu Asn Gly Tyr Ser Ile Glu Gln Ser Gly Leu
            260                 265                 270

Glu His Cys Gln Tyr Ala Asp Asp Gly Ser Gly Phe Val Cys Lys Val
        275                 280                 285

Pro Glu Gly Arg Tyr Phe Ala Met Gly Asp Asn Arg Asp Asn Ser Ala
290                 295                 300

Asp Ser Arg Tyr Trp Gly Phe Val Asp Asp Lys Leu Val Val Gly Lys
305                 310                 315                 320

Ala Met Phe Ile Leu Met Asn Phe Gly Asp Phe Gly Arg Ser Gly Thr
                325                 330                 335

Ala Ile Arg
```

<210> SEQ ID NO 181
<211> LENGTH: 1020
<212> TYPE: DNA
<213> ORGANISM: Neisseria meningitidis

<400> SEQUENCE: 181

```
atgaacacaa tgctaatgtc gggcgcggct gccgcgctgc ttgccggcat catcctttat    60
ttcaaaagcg acaagaagcg gcaggaaaac ggggaatgga gttccggcct tgaatacgcc   120
tatatcctga cagcggtcgg cgtgtttgcc gctttgtccc tgtttatgag ctttaccgcc   180
gttttcctga ttttcgttgt attgtgcggt acggcttggg gggtatataa ataccgcctg   240
aagactcatc ccgaaatctc ggaaagcagc cacttcggcg attatttcgg cagtttcttc   300
cctaccgttt tggtattgtt cctcatccgg tcgtttatcg ccgaaccgtt ccaaatcccg   360
tccagctcga tgcgcccggg cctgatcaag gcgatttca ttttggtcgg caaattttcc    420
tacggcctgc gcgtacccgt tttaaacaat atatttattc ctacaggcaa atcgaacgg    480
ggcgatgtcg ttgttttaa ttatcctctg cagccggaga tgacctacat caagcgtatt   540
gtcggcattc cgggcgatgt ggtcgaatat cgggataaga ttttgacggt aaatggcaaa   600
cccacttccg acattcctga cggcacatac cgttatcccg acgacaccga cccttccgaa   660
atccacaaca cggatatgtt ccgcagcggt ctagacggca atccttcaa tattctgaaa    720
aaagaaggac agcctgccgt ttccctgccc gtattgggca aatatacctc cgatattatg   780
tctgaaaacg gatattccat agagcaaagc ggtttggaac actgccaata tgccgacgac   840
ggcagcggtt tcgtgtgcaa agttcccgaa ggacgctatt tcgctatggg cgacaaccgc   900
gacaacagtg ccgattcgcg ctactgggga tttgtggatg acaagctggt tgtcggcaag   960
gcaatgttca ttttgatgaa cttcggcgat tcggcaggt ccggtacggc aatccgttag   1020
```

<210> SEQ ID NO 182
<211> LENGTH: 173

<212> TYPE: PRT
<213> ORGANISM: Bacillus anthracis

<400> SEQUENCE: 182

```
Met Lys Gln Glu Ile Lys Arg Gly Trp Gly Lys Tyr Ile Leu Phe Val
 1               5                  10                  15

Phe Val Leu Val Val Ala Tyr His Ser Phe Thr Leu Cys Lys Val Glu
            20                  25                  30

Gly Lys Ser Met Gln Pro Thr Leu Tyr Glu Glu Asp Tyr Val Phe Val
        35                  40                  45

Asn Lys Ala Ala Val His Phe Ser Asp Leu Glu His Gly Glu Ile Val
    50                  55                  60

Ile Ile Lys Glu Glu Asp Glu Ser Lys Tyr Tyr Val Lys Arg Val Ile
65                  70                  75                  80

Gly Leu Pro Gly Asp Val Ile Asn Ile Thr Asn Gly Ser Val Tyr Val
                85                  90                  95

Asn Asp Lys Lys Gln Glu Glu Pro Tyr Thr Asn Lys Asp Leu Phe Asn
            100                 105                 110

Asn Thr Gln Val Phe Tyr Asn Phe Gln Lys Thr Lys Ile Pro Pro Asn
        115                 120                 125

Lys Leu Phe Val Met Gly Asp Asn Arg Glu Leu Ser Arg Asp Ser Arg
    130                 135                 140

Asn Gly Leu Gly Tyr Ile Glu Glu Asp Asn Ile Ile Gly Lys Val Glu
145                 150                 155                 160

Phe Val Tyr Tyr Pro Phe Ser Lys Met Lys Ile Ile Glu
                165                 170
```

<210> SEQ ID NO 183
<211> LENGTH: 522
<212> TYPE: DNA
<213> ORGANISM: Bacillus anthracis

<400> SEQUENCE: 183

```
atgaaacagg agattaaaag aggttggggg aaatatatac tcttcgtgtt tgttttggta    60
gtagcttatc attcttttac tttatgtaaa gtggaaggga aatcaatgca accgacttta   120
tatgaagaag actacgtatt tgtaaataaa gcagcagtac attttttccga tttagagcat   180
ggagaaattg tcattataaa ggaagaggat gaatcgaaat attatgtaaa acgagtaata   240
ggacttcctg gtgacgtaat aacataacg aatggatctg tatatgtaaa tgataaaaaa   300
caagaagaac cgtatacaaa taagagttta ttcaataata cgcaagtgtt ttataacttt   360
caaaagacaa aaatcccacc aaataaaatta tttgtaatgg gagataatcg tgaacttagt   420
agagatagtc gaaacggttt aggatatatt gaagaagata atataatagg caaagtggaa   480
tttgtatatt atccttttc aaaaatgaag atcatagaat aa                       522
```

<210> SEQ ID NO 184
<211> LENGTH: 195
<212> TYPE: PRT
<213> ORGANISM: Streptococcus mutans

<400> SEQUENCE: 184

```
Met Lys Arg Phe Leu Lys Glu Trp Gly Leu Phe Leu Val Ile Ile Phe
 1               5                  10                  15

Ala Leu Leu Leu Pro Arg Leu Phe Ile Trp Phe Pro Val Gln Val Asp
            20                  25                  30

Gly His Ser Met Asp Pro Thr Leu Ala Asn Gly Glu His Leu Ile Val
```

```
                35                  40                  45
Val Arg Thr Thr Ser Ile Lys His Phe Asp Ile Val Ala Ala Glu
 50                  55                  60

Gly Asn Lys Asn Ile Val Lys Arg Val Ile Gly Met Pro Gly Asp Thr
 65                  70                  75                  80

Ile Thr Tyr Glu Asn Asp Met Leu Ser Ile Asn Gly Lys Lys Val Asn
                 85                  90                  95

Glu Thr Tyr Leu Lys Gln Tyr Lys Asp Lys Phe Ala Lys Asp Lys Leu
            100                 105                 110

Gln Lys Thr Tyr Ala Tyr Asn Gln Tyr Phe Gln Glu Leu Ala Ser Gln
        115                 120                 125

Ser Thr Ala Phe Thr Thr Asp Glu Gln Gly Asn Ala Ser Phe Thr Ile
    130                 135                 140

Lys Val Pro Lys Gly Arg Tyr Leu Leu Leu Gly Asp Asp Arg Ile Val
145                 150                 155                 160

Ser Lys Asp Ser Arg His Val Gly Thr Phe Ala Lys Asn Lys Ile Val
                165                 170                 175

Gly Glu Val Lys Phe Arg Phe Trp Pro Leu Asn Ala Ile Arg Phe Ile
            180                 185                 190

Ser Asn Lys
        195

<210> SEQ ID NO 185
<211> LENGTH: 588
<212> TYPE: DNA
<213> ORGANISM: Streptococcus mutans

<400> SEQUENCE: 185
atgaaaagat tttaaaaga tgggggcctt tcttggtca tcattttcgc attgctactc    60
ccgcgtctct ttatctggtt tcctgtccaa gtagatggac attcaatgga tcctacctta   120
gccaatgggg agcatctcat tgtcgtcagg acaacttcta tcaaacattt tgacattgtt   180
gttgctgctg aaggcaataa aaatattgtc aaacgtgtga ttggcatgcc cggtgatacc   240
attacctatg aaaatgatat gctttctatt aatgggaaaa agtcaatga aacttatctc    300 aagcaataca aggataaatt tgccaaggac aaactccaaa agacttatgc ctacaatcag   360
tatttccaag aattagcctc acaatcaaca gctttcacaa cagacgaaca aggaaacgcc   420
agctttacga ttaaagtacc aaaaggacgt tacctgcttt taggtgatga tcgcattgtc   480
tctaaagaca gccgccatgt tggaactttt gctaagaata aaattgttgg tgaagttaaa   540
ttccgctttt ggcctttaaa cgctattcgt ttcatttcaa ataaataa               588

<210> SEQ ID NO 186
<211> LENGTH: 324
<212> TYPE: PRT
<213> ORGANISM: Shigella flexneri

<400> SEQUENCE: 186

Met Ala Asn Met Phe Ala Leu Ile Leu Val Ile Ala Thr Leu Val Thr
  1               5                  10                  15

Gly Ile Leu Trp Cys Val Asp Lys Phe Phe Phe Ala Pro Lys Arg Arg
             20                  25                  30

Glu Arg Gln Ala Ala Ala Gln Ala Ala Ala Gly Asp Ser Leu Asp Lys
         35                  40                  45

Ala Thr Leu Lys Lys Val Ala Pro Lys Pro Gly Trp Leu Glu Thr Gly
     50                  55                  60
```

```
Ala Ser Val Phe Pro Val Leu Ala Ile Val Leu Ile Val Arg Ser Phe
 65                  70                  75                  80

Ile Tyr Glu Pro Phe Gln Ile Pro Ser Gly Ser Met Met Pro Thr Leu
                 85                  90                  95

Leu Ile Gly Asp Phe Ile Leu Val Glu Lys Phe Ala Tyr Gly Ile Lys
            100                 105                 110

Asp Pro Ile Tyr Gln Lys Thr Leu Ile Glu Thr Gly His Pro Lys Arg
        115                 120                 125

Gly Asp Ile Val Val Phe Lys Tyr Pro Glu Asp Pro Lys Leu Asp Tyr
    130                 135                 140

Ile Lys Arg Ala Val Gly Leu Pro Gly Asp Lys Val Thr Tyr Asp Pro
145                 150                 155                 160

Val Ser Lys Glu Leu Thr Ile Gln Pro Gly Cys Ser Ser Gly Gln Ala
                165                 170                 175

Cys Glu Asn Ala Leu Pro Val Thr Tyr Ser Asn Val Glu Pro Ser Asp
            180                 185                 190

Phe Val Gln Thr Phe Ser Arg Arg Asn Gly Gly Glu Ala Thr Ser Gly
        195                 200                 205

Phe Phe Glu Val Pro Lys Asn Glu Thr Lys Glu Asn Gly Ile Arg Leu
    210                 215                 220

Ser Glu Arg Lys Glu Thr Leu Gly Asp Val Thr His Arg Ile Leu Thr
225                 230                 235                 240

Val Pro Ile Ala Gln Asp Gln Val Gly Met Tyr Tyr Gln Gln Pro Gly
                245                 250                 255

Gln Gln Leu Ala Thr Trp Ile Val Pro Pro Gly Gln Tyr Phe Met Met
            260                 265                 270

Gly Asp Asn Arg Asp Asn Ser Ala Asp Ser Arg Tyr Trp Gly Phe Val
        275                 280                 285

Pro Glu Ala Asn Leu Val Gly Arg Ala Thr Ala Ile Trp Met Ser Phe
    290                 295                 300

Asp Lys Gln Glu Gly Glu Trp Pro Thr Gly Val Arg Leu Ser Arg Ile
305                 310                 315                 320

Gly Gly Ile His

<210> SEQ ID NO 187
<211> LENGTH: 975
<212> TYPE: DNA
<213> ORGANISM: Shigella flexneri

<400> SEQUENCE: 187
atggcgaata tgtttgccct gattctggtg attgccacac tggtgacggg cattttatgg      60
tgcgtggata aattcttttt cgcacctaaa cggcgggaac gtcaggcagc ggcgcaggcg     120
gctgccggtg actcactgga taaagcaacg ttgaaaaagg ttgcaccgaa gcctggctgg     180
ctggaaaccg gagcttctgt ttttccggtg ctggctatcg tattgattgt acgttcgttt     240
atttatgaac cgttccagat cccgtcaggt tcgatgatgc cgactctgtt aatcggtgat     300
tttattctgg tagagaagtt tgcttatggc attaaagatc ctatcctacc gaaaacgctg     360
atcgaaaccg gtcatccgaa acgcggcgat atcgtggtct ttaaatatcc ggaagatcca     420
aagcttgatt acatcaagcg cgcggtgggt ttaccgggcg ataaagtcac ttacgatccg     480
gtctcaaaag agctgacgat tcaaccggga tgcagttccg gccaggcgtg tgaaaacgcg     540
ctgccggtca cctactcaaa cgtggaaccg agcgatttcg ttcagacctt ctcacgccgt     600
```

-continued

```
aatggtgggg aagcgaccag cggattctt gaagtgccga aaaacgaaac caagaaaat     660 ggaattcgtc tttccgagcg taaagagaca ctgggtgatg tgacgcaccg aattctgaca    720
gtgccgattg cgcaggacca ggtggggatg tattaccagc agccagggca caactggca    780 acctggattt ttccgccggg acaatacttc atgatgggcg acaaccgcga caacagcgcg    840
gacagccgtt actggggctt tgtgcctgaa gcgaatctgg tcggtcgggc cacggctatc    900
tggatgagct tcgataagca agaaggcgaa tggccgactg tgtgcgctt aagtcgcatt     960 ggcggcatcc attaa                                                      975
```

<210> SEQ ID NO 188
<211> LENGTH: 324
<212> TYPE: PRT
<213> ORGANISM: Citrobacter koseri

<400> SEQUENCE: 188

```
Met Ala Asn Met Phe Ala Leu Ile Leu Val Ile Ala Thr Leu Val Thr
 1               5                  10                  15

Gly Ile Leu Trp Cys Val Asp Lys Phe Ile Phe Ala Pro Lys Arg Arg
            20                  25                  30

Glu Arg Gln Ala Ala Ala Gln Ala Ala Ala Gly Asp Ser Leu Asp Lys
        35                  40                  45

Ala Thr Leu Lys Lys Val Ala Pro Lys Pro Gly Trp Leu Glu Thr Gly
    50                  55                  60

Ala Ser Val Phe Pro Val Leu Ala Ile Val Leu Val Val Arg Ser Phe
65                  70                  75                  80

Ile Tyr Glu Pro Phe Gln Ile Pro Ser Gly Ser Met Met Pro Thr Leu
                85                  90                  95

Leu Ile Gly Asp Phe Ile Leu Val Glu Lys Phe Ala Tyr Gly Ile Lys
            100                 105                 110

Asp Pro Ile Tyr Gln Lys Thr Leu Ile Glu Thr Gly His Pro Lys Arg
        115                 120                 125

Gly Asp Ile Val Val Phe Lys Tyr Pro Glu Asp Pro Arg Leu Asp Tyr
    130                 135                 140

Ile Lys Arg Ala Val Gly Leu Pro Gly Asp Lys Val Thr Tyr Asp Pro
145                 150                 155                 160

Val Ala Lys Glu Val Thr Val Gln Pro Gly Cys Arg Ser Gly Gln Ala
                165                 170                 175

Cys Glu Asn Ala Leu Pro Val Thr Tyr Ser Asp Val Gln Pro Ser Asp
            180                 185                 190

Phe Val Gln Thr Phe Ala Arg Arg Asn Gly Gly Glu Ala Ser Ser Gly
        195                 200                 205

Phe Phe Glu Val Pro Leu Asn Glu Thr Lys Asp Asn Gly Ile Arg Leu
    210                 215                 220

Ala Glu Arg Lys Glu Thr Leu Gly Asp Val Thr His Arg Ile Leu Thr
225                 230                 235                 240

Val Pro Ile Ala Gln Asp Gln Ala Gly Met Tyr Tyr Arg Gln Pro Gly
                245                 250                 255

Gln Gln Leu Ala Thr Trp Ile Val Pro Pro Gly Gln Tyr Phe Met Met
            260                 265                 270

Gly Asp Asn Arg Asp Asn Ser Ala Asp Ser Arg Tyr Trp Gly Phe Val
        275                 280                 285

Pro Glu Ala Asn Leu Val Gly Lys Ala Thr Ala Ile Trp Met Ser Phe
    290                 295                 300
```

Asp Lys Gln Glu Gly Glu Trp Pro Thr Gly Val Arg Leu Ser Arg Ile
305                 310                 315                 320

Gly Gly Ile His

<210> SEQ ID NO 189
<211> LENGTH: 975
<212> TYPE: DNA
<213> ORGANISM: Citrobacter koseri

<400> SEQUENCE: 189

```
atggcgaata tgtttgccct gattctggtg attgccacac tggtgacggg catttatgg      60
tgcgttgata aatttatctt cgcgccaaaa cgtcgggaac gtcaggcagc ggcacaggcc    120
gctgcgggtg attcactgga taaagccacg ttgaaaaaag tggcgcctaa gccgggctgg    180
ctggaaacag ggcttcggt ttttccggta ctggcgattg tgctggtggt gcgctcattt    240
atctatgaac ctttccagat cccgtcgggt tcgatgatgc cgacgctgtt aatcggtgac    300
tttattctgg tggagaaatt cgcctatgga attaaagatc cgatttacca gaaaacgttg    360
attgaaacgg gtcatccgaa acgcggtgat atcgtggtct taaatacccc ggaagatccg    420
cgcctggact acattaaacg cgctgtcggc ctgccgggtg acaaagtgac gtacgatccg    480
gtagccaaag aggttactgt acagccagga tgccgttccg gtcaggcgtg tgaaaacgcg    540
ctgccggtga cttactctga cgttcagccc agcgatttcg tgcagacctt gcccgccgt    600
aatggggag aagccagcag tgggttcttc gaagtgccgt taaacgaaac gaaagataac    660
ggcattcgtc tggcggagcg taaagagacg ctgggagacg taacccaccg tattctgacc    720
gtaccgatcg cgcaggatca ggcggggatg tattaccgtc agccggggca gcaactggcg    780
acctggatcg taccgccagg acaatacttc atgatgggtg ataaccgcga taacagcgcg    840
gacagccgtt actggggatt tgtaccggaa gcgaatctgg ttggtaaagc gaccgcgatc    900
tggatgagtt tcgacaaaca ggaaggtgaa tggccgaccg gcgtacgctt aagccgtatt    960
ggtgggatcc attaa                                                     975
```

<210> SEQ ID NO 190
<211> LENGTH: 294
<212> TYPE: PRT
<213> ORGANISM: Bordetella pertussis

<400> SEQUENCE: 190

Met Ser Trp Asn Phe Ala Leu Ile Leu Phe Val Leu Leu Val Ile Thr
1 5 10 15

Gly Val Ile Trp Gly Leu Asp Leu Ala Leu Phe Arg Lys Arg Arg Glu
20 25 30

Arg Arg Ala Gln Ala Ala Ala Ala Gln Val Asp Ala Ala Gly Ile Thr
35 40 45

Asp Ala Glu Gln Ala Gly Arg Glu Arg Arg Glu Ala Ile Asp Ala Ala
50 55 60

Arg Arg Ala Pro Trp Trp Ile Glu Tyr Ala Val Ser Phe Phe Pro Val
65 70 75 80

Ile Leu Phe Val Phe Val Leu Arg Ser Phe Val Val Glu Pro Phe His
85 90 95

Ile Pro Ser Gly Ser Met Leu Pro Thr Leu Gln Ser Gly Asp Leu Ile
100 105 110

Leu Val Asn Lys Phe Ser Tyr Gly Ile Arg Leu Pro Ile Ile Asp Arg
115 120 125

```
Lys Ile Ile Glu Thr Gly Ser Leu Glu Arg Gly Asp Val Val Phe
    130                 135                 140

Arg Tyr Pro Val Asp Thr Asp Val Asp Tyr Ile Lys Arg Ile Val Gly
145                 150                 155                 160

Leu Pro Gly Asp Gln Val Ala Tyr Leu Asp Lys Lys Leu Tyr Ile Asn
                165                 170                 175

Gly Lys Leu Val Pro His Glu Arg Asp Gly Asp Tyr Phe Glu Pro Asp
                180                 185                 190

Arg Val Ser Tyr Ile Ala Gln Tyr Lys Glu Lys Leu Gly Glu Val Glu
                195                 200                 205

His Lys Ile Leu Leu Asp Glu Gln Lys Ile Gln Asp Phe Gly Pro Ile
    210                 215                 220

Trp Lys Phe Pro Ser Ile Gln Asn Cys Gln Tyr Ala Arg Asn Gly Val
225                 230                 235                 240

Arg Cys Thr Val Pro Pro Gly His Tyr Phe Ala Met Gly Asp Asn Arg
                245                 250                 255

Asp Asn Ser Ala Asp Ser Arg Tyr Trp Gly Phe Val Pro Asp Gly Asn
                260                 265                 270

Ile Val Gly Lys Ala Phe Phe Val Trp Met Asn Phe Ser Asp Leu Ser
                275                 280                 285

Arg Ile Gly Arg Phe His
    290
```

<210> SEQ ID NO 191
<211> LENGTH: 885
<212> TYPE: DNA
<213> ORGANISM: Bordetella pertussis

<400> SEQUENCE: 191

```
atgagttgga actttgccct gatacttttt gtactgctgg tgattaccgg cgttatctgg      60
ggattggatc tggcgctgtt tcgcaagcga cgcgaacggc gggcccaggc ggcggccgcg     120
caagtggacg ccgccggcat cacggatgcc gagcaggccg ccgcgagcg cgcgaggcc      180
atcgacgcgg cgcgccgcgc gccctggtgg atcgagtatg cggtcagctt cttcccggtg     240
atcctgttcg tgttcgtgct cgcgctcgtt cgtggtcgagc cgtttcacat tccgtcgggg     300
tccatgctgc ccacgctgca atcgggcgac ctgatcctgg tgaacaagtt cagctacggc     360
atccgcctgc ccatcatcga tcgcaagatc atcgagacgg ctcgctgga gcgtggcgac     420
gtggtggtgt tccgctaccc ggtcgatacg gatgtcgact acatcaagcg catcgtgggt     480
ctgccgggcg accaggtggc ctacctggac aagaagctgt acatcaacgg aaaattggtg     540
ccgcatgaac gcgacgggga ttatttcgag cccgatcgcg tgtcctatat gcgcaatac      600
aaggaaaaac tgggcgaagt ggagcataag atcctgcttg atgagcagaa aatacaggat     660
ttcggcccca tctggaaatt tcccagtatc cagaactgcc agtacgcccg caacggcgtg     720
cgctgtaccg tcccccccgg ccattatttc gccatgggag acaaccgtga caatagtgcg     780
gacagccgct actggggatt cgtgccagac ggtaatatcg tggggaaggc attttttgtc     840
tggatgaact tcagcgattt gagccgcatt ggccgcttcc attga                     885
```

<210> SEQ ID NO 192
<211> LENGTH: 176
<212> TYPE: PRT
<213> ORGANISM: Clostridium difficile

<400> SEQUENCE: 192

Met Ser Val Lys Lys Glu Ile Phe Asp Trp Ile Lys Ser Ile Ala Met
1               5                   10                  15

Ala Ile Val Leu Ala Phe Val Ile Leu Gln Phe Ile Ile Pro Ser Ile
            20                  25                  30

Val Ser Gly Glu Ser Met Tyr Pro Thr Leu Asp Asp Lys Asp Tyr Leu
        35                  40                  45

Ile Leu Asn Arg Ile Ser Tyr Lys Val Gly Lys Pro Glu Lys Gly Asp
50                  55                  60

Ile Val Val Phe Lys Thr Asn Leu Val Asp Gly Glu Thr Gly Lys Lys
65                  70                  75                  80

Lys Asp Leu Ile Lys Arg Val Ile Ala Thr Glu Gly Asp Arg Ile Lys
                85                  90                  95

Ile Ser Asn Ser Lys Val Tyr Val Asn Gly Lys Leu Leu Asn Glu Pro
            100                 105                 110

Tyr Ile His Asn Asn Tyr Thr Ser Gly Asp Ile Asp Thr Val Val Pro
        115                 120                 125

Lys Gly Lys Leu Phe Ala Met Gly Asp Asn Arg Glu Asn Ser Asn Asp
    130                 135                 140

Ser Arg Phe Pro Asp Val Gly Met Val Asp Glu Asp Val Leu Gly
145                 150                 155                 160

Lys Val Met Val Arg Leu Leu Pro Leu Asp Asn Ile Gly Lys Val Asp
                165                 170                 175

<210> SEQ ID NO 193
<211> LENGTH: 530
<212> TYPE: DNA
<213> ORGANISM: Clostridium difficile

<400> SEQUENCE: 193
atgagtgtta aaaagaaat atttgattgg attaagtcaa tagctatggc tattgtactt      60
gcatttgtaa ttctacaatt tataatacct tctattgtaa gtggagaatc aatgtatcct    120
actttagatg ataaagatta tctgatttta aataggatat catacaaggt tggtaaacct    180
gaaaaaggcg atattgtagt ttttaaaacc aatttagttg atggagaaac aggaaagaaa    240
aaagacttaa taaaagagt tatagctact gaaggtgaca gaataaaaat atcaaattct    300
aaagtgtatg taaatggaaa attattaaat gaaccatata tacacaataa ctatacttct    360
ggagatatag atactgttgt tccaaaaggt aaactatttg caatgggaga taatagagaa    420
aatagtaatg atagtagatt ccctgatgta ggtatggttg atgaagatga agttcttggt    480
aaggttatgg tgagactatt acctcttgat aatattggga agtagacta                530

<210> SEQ ID NO 194
<211> LENGTH: 178
<212> TYPE: PRT
<213> ORGANISM: Clostridium difficile

<400> SEQUENCE: 194

Val Gly Glu Ala Val Lys Lys Glu Val Val Glu Trp Ile Lys Val Ile
1               5                   10                  15

Val Ile Ala Leu Val Leu Ala Phe Ala Ile Thr Arg Phe Ile Val Pro
            20                  25                  30

Thr Ile Val Lys Gly Glu Ser Met Tyr Pro Thr Leu Val Glu Arg Asp
        35                  40                  45

Tyr Leu Ile Val Asn Arg Ile Ala Tyr Lys Val Gly Glu Pro Lys Tyr
    50                  55                  60

```
Lys Asp Ile Ile Val Phe Lys Thr Asp Leu Thr Glu Glu Asn Gly Lys
 65                  70                  75                  80

Lys Lys Asp Leu Val Lys Arg Val Ile Gly Val Pro Gly Asp His Val
                 85                  90                  95

Lys Ile Gln Asp Ser Lys Val Tyr Val Asn Asp Lys Leu Leu Asp Glu
            100                 105                 110

Thr Ser Tyr Ile His Asn Asn Arg Thr Asp Gly Asp Ile Asp Ile Val
        115                 120                 125

Val Pro Glu Gly Lys Leu Phe Ala Met Gly Asp Asn Arg Glu Lys Ser
    130                 135                 140

Leu Asp Ser Arg Tyr Asp Glu Val Gly Leu Val Asp Glu His Thr Ile
145                 150                 155                 160

Leu Gly Lys Val Leu Val Arg Leu Tyr Pro Phe Ser Lys Ile Gly Thr
                165                 170                 175

Ile Asp

<210> SEQ ID NO 195
<211> LENGTH: 537
<212> TYPE: DNA
<213> ORGANISM: Clostridium difficile

<400> SEQUENCE: 195
gtgggtgaag cagttaaaaa agaagttgta gaatggataa aagtgattgt catagctctt      60
gttttggcat ttgcaataac tcgttttata gtgccaacaa tagtcaaagg agaatcaatg     120
tatcctacat tagttgaacg tgattatttg atagttaaca gaattgcgta caaggtagga     180
gagccaaaat acaaagatat aatagtattc aaaaccgact aacagagga aaatggaaag     240 aaaaaagatt tagtaaaaag agttatcggg gttcctggtg accatgtaaa aatacaagac     300
tccaaggtat atgtaaatga taagttgtta gatgagactt cctatataca taataatcgt     360
actgatggag atattgatat cgtagttcca gaaggaaaat tatttgcaat gggagataat     420
agagaaaaaa gtttagatag tagatacgat gaggttggat tggtcgacga gcataccatt     480
ttaggaaagg ttctagtcag attgtatcca ttttctaaga taggaactat tgactaa       537

<210> SEQ ID NO 196
<211> LENGTH: 178
<212> TYPE: PRT
<213> ORGANISM: Clostridium difficile

<400> SEQUENCE: 196

Met Asn Glu Thr Ile Lys Glu Glu Ile Val Glu Trp Ile Lys Ile Ile
  1               5                  10                  15

Ile Thr Ala Leu Phe Phe Ala Phe Ile Ile Thr Arg Phe Ile Lys Pro
                 20                  25                  30

Thr Leu Val Asn Gly Glu Ser Met Tyr Pro Thr Leu Lys Ser His Asp
             35                  40                  45

Tyr Leu Val Ala Asn Arg Met Thr Tyr Lys Leu Ser Glu Pro Lys Cys
         50                  55                  60

Gly Asp Ile Met Ile Phe Lys Thr Asp Leu Leu Gln Glu Asn Gly Arg
 65                  70                  75                  80

Lys Lys Glu Leu Val Lys Arg Val Ile Gly Val Pro Gly Asp His Leu
                 85                  90                  95

Lys Ile Lys Asp Ser Lys Val Tyr Ile Asn Gly Lys Leu Leu Asn Glu
            100                 105                 110

Val Ser Tyr Ile His Asp Asn Tyr Thr Glu Gly Asp Ile Asp Met Val
```

```
                115                 120                 125
Ile Pro Lys Gly Lys Val Phe Ala Met Gly Asp Asn Arg Glu Val Ser
        130                 135                 140
Leu Asp Ser Arg Tyr Lys Glu Val Gly Leu Val Asp Glu Glu Asn Ile
145                 150                 155                 160
Lys Gly Lys Val Ile Leu Arg Val Phe Pro Phe Thr Asp Ile Gly Ile
                165                 170                 175
Phe Glu

<210> SEQ ID NO 197
<211> LENGTH: 537
<212> TYPE: DNA
<213> ORGANISM: Clostridium difficile

<400> SEQUENCE: 197
atgaatgaaa ctattaaaga agagattgta gagtggataa aaataattat tactgcactt     60
ttttttgcat ttattataac tcgttttata aaaccaacat tagtaaatgg agaatcaatg    120
tacccaacac ttaaatcaca tgattatttg gtagcaaaca ggatgacata taagttatca    180
gaaccaaaat gtggagatat aatgatattt aagactgatt tattacaaga gaatggaagg    240
aaaaaagagc ttgtaaaaag ggttataggt gttcctggtg accatctaaa aattaaggat    300
tctaaggttt atataaatgg taagttatta aatgaagttt catatataca tgataattat    360
actgaaggcg atattgatat ggtgattcct aagggaaaag tatttgcgat gggagacaat    420
agaagagtta gtttagacag tagatataaa gaagtgggat tagtagatga agaaaatatt    480
aaaggaaaag ttattttaag agtatttcct tttacagata taggtatttt tgagtag      537

<210> SEQ ID NO 198
<211> LENGTH: 178
<212> TYPE: PRT
<213> ORGANISM: Enterococcus faecalis

<400> SEQUENCE: 198

Met Ser Ser Leu Leu Lys Arg Leu Val Gln Leu Val Leu Leu Val Val
1               5                   10                  15
Ala Val Leu Leu Ile Arg His Tyr Val Phe Ser Pro Ala Ala Val Asn
                20                  25                  30
Gly Ser Ser Met Glu Pro Thr Leu His Asn Asn Asp Arg Leu Trp Val
        35                  40                  45
Thr Ser Ile Lys Lys Pro Gln Arg Phe Asp Ile Ala Phe Pro Ser
    50                  55                  60
Pro Arg Asn Gly Gln Arg Val Ala Lys Arg Leu Ile Gly Leu Pro Gly
65                  70                  75                  80
Glu Thr Val Glu Tyr Arg Asp Asp Thr Leu Tyr Ile Asn Gly Val Ser
                85                  90                  95
Leu Ser Glu Asp Tyr Leu Ala Ser Ala Lys Arg Asn Val Ser Lys Asn
                100                 105                 110
Glu Asn Tyr Thr Gln Asp Phe Thr Leu Glu Thr Leu Glu Ala Thr Gln
        115                 120                 125
Ser Leu Thr Val Pro Glu Gly Met Tyr Phe Val Leu Gly Asp Asn Arg
    130                 135                 140
Pro Arg Ser Asp Asp Ser Arg Tyr Phe Gly Phe Val Lys Gln Ala Ser
145                 150                 155                 160
Val Glu Gly Val Leu Thr Phe Arg Tyr Tyr Pro Leu Asp Lys Ile Gly
                165                 170                 175
```

Phe Pro

<210> SEQ ID NO 199
<211> LENGTH: 537
<212> TYPE: DNA
<213> ORGANISM: Enterococcus faecalis

<400> SEQUENCE: 199

```
atgtcctcat tattaaaacg attggttcag ttggttttgt tagtcgtcgc tgtcttgctg        60
attcgacact atgttttctc ccctgctgcg gtgaacggct cttcaatgga accaacactt       120
cataacaacg accgtttatg ggtgacctcg attaaaaaac cacagcgctt tgatattatc       180
gctttcccta gtcctcgcaa cggccaacga gtagccaaac gtttaattgg tttacctggc       240
gaaacagtcg agtatcgcga tgatacccct tatattaatg gtgtatcact cagtgaagat       300
tacttagcaa gtgctaaacg aaatgtctct aaaaatgaaa attataccca gattttacg        360
ctagagacct agaagccac ccaatccctg accgttccag aaggcatgta ttttgtcttg        420
ggggataatc gcccgcgctc agacgacagt cgttattttg gctttgttaa acaagcgagt       480
gtggaaggtg ttttgacttt tcgttattat ccattagata aaattggctt tccataa          537
```

<210> SEQ ID NO 200
<211> LENGTH: 241
<212> TYPE: PRT
<213> ORGANISM: Enterococcus faecalis

<400> SEQUENCE: 200

Met Arg Thr Ile Arg His Ile Lys Arg Ala Phe Leu Lys Gln Lys Leu
1               5                   10                  15

Pro Ala Thr Tyr Gln Leu Lys Lys Gln Lys Ala Asn Thr Ala Met Glu
            20                  25                  30

Tyr Leu Leu Glu Gln Thr Asp Asn His Gln Ser Ile Arg Gly Pro Lys
        35                  40                  45

Arg Lys Met Thr Ala Glu Glu Ile Lys Lys Arg Gln Ala Tyr Gln
    50                  55                  60

Lys Lys Gln Arg Val Gln Val Val Lys Phe Phe Met Pro Ala Ile Leu
65                  70                  75                  80

Phe Ala Ile Phe Val Phe Phe Val Leu Lys Thr Ser Ser Tyr Pro
                85                  90                  95

Ile Ala Gly Gln Ser Met Lys Pro Thr Leu Asn Ala Gly Glu Arg Val
            100                 105                 110

Leu Val Gln Arg Thr Lys Gln Val Ala Arg Tyr Asp Val Ile Ala Phe
        115                 120                 125

Lys Ala Pro Leu Ala Ser Lys Gly Thr Tyr Val Lys Arg Ile Ile Gly
    130                 135                 140

Val Pro Gly Asp Arg Ile Trp Val Asn Glu Gly Lys Leu Tyr Leu Ser
145                 150                 155                 160

Glu Glu Pro Ile Ala Ser Asp Asn Glu Ala Leu Pro Glu Asn Ala Ser
                165                 170                 175

Arg Phe Asp Leu Ser Glu Glu Ala Ala Ala Gln Leu Arg Leu Phe Gln
            180                 185                 190

Lys Ile Pro Ala Gly His Tyr Phe Val Leu Gly Asp Asn Arg Thr His
        195                 200                 205

Ser Ser Asp Ser Arg Thr Phe Gly Phe Val Glu Ile Gln Ala Ile Glu
    210                 215                 220

```
Gly Ile Val Val Phe Lys Met Ala Pro Phe Lys Glu Ile Gly Lys Val
225                 230                 235                 240

Lys
```

<210> SEQ ID NO 201
<211> LENGTH: 726
<212> TYPE: DNA
<213> ORGANISM: Enterococcus faecalis

<400> SEQUENCE: 201

```
atgcgaacaa ttcgccacat taagcgcgcc ttcttgaagc aaaagttgcc tgcgacatat    60
cagctaaaaa agcaaaaggc taacacagca atggaatatt tgcttgagca aacagataac   120
catcaatcaa taagaggacc gaaaagaaaa atgaccgctg aagagattaa aaaaaagcgg   180
caagcctacc aaaagaaaca acgcgtccaa gtcgttaaat tttttatgcc agctattctt   240
ttcgccattt ttgtgttctt ttttgtgtta agacatcta gctacccaat gctgggcaa    300
tccatgaagc cgacacttaa cgcaggggaa cgagtcttag tacaacggac gaagcaagta   360
gcaaggtacg atgtgattgc atttaaagca ccgctagcta gcaaaggtac gtacgtcaag   420
cgaatcatcg gggttcctgg tgatcgaatt tgggtaaacg agggaaaact ttatctttca   480
gaagaaccta tagcaagcga taatgaggca ctgcctgaga atgccagtcg ttttgactta   540
tcagaagaag cggcagccca acttcgcctg tttcagaaga ttccagctgg tcattacttt   600
gtcttagggg acaatcgtac gcattcaagt gatagtcgta cgttcggctt tgtcgagata   660
caagcgattg aaggaatcgt ggtatttaaa atggcgccgt ttaaggaaat agggaaagta   720
aaataa                                                              726
```

<210> SEQ ID NO 202
<211> LENGTH: 182
<212> TYPE: PRT
<213> ORGANISM: Enterococcus faecalis

<400> SEQUENCE: 202

```
Met Ser Leu Lys Ser Lys Glu Leu Ile Lys Thr Val Phe Phe Ala
1               5                   10                  15

Cys Leu Ala Leu Gly Leu Phe Leu Leu Arg Gln Phe Val Phe Thr Pro
                20                  25                  30

Val Val Val Arg Gly His Ser Met Asp Pro Thr Leu Ala Asp Gly Glu
            35                  40                  45

Arg Val Ile Thr Leu Lys Asn Thr Glu Ile Asn Arg Phe Asp Ile Ile
        50                  55                  60

Thr Phe Pro Ala Pro Asp Glu Pro Asp Lys Asn Tyr Ile Lys Arg Val
65                  70                  75                  80

Ile Gly Leu Pro Gly Asp Thr Ile Ala Tyr Lys Asp Asp Thr Leu Tyr
                85                  90                  95

Ile Asn Gly Lys Glu Val Asp Glu Pro Tyr Leu Asp Glu Phe Lys Lys
            100                 105                 110

Ala Leu Thr Asp Gly Gln Pro Leu Thr Gly Asp Phe Ser Leu Lys Glu
        115                 120                 125

Lys Val Pro Ala Asp Ser Tyr Phe Val Leu Gly Asp Asn Arg Arg Asn
    130                 135                 140

Ser Lys Asp Gly Arg Val Ile Gly Phe Ile His Lys Lys Asp Ile Leu
145                 150                 155                 160

Gly Glu Val Lys Phe Val Met Trp Pro Phe Ser Arg Phe Gly Pro Ile
                165                 170                 175
```

Pro Glu Val Ser Lys Gln
        180

<210> SEQ ID NO 203
<211> LENGTH: 549
<212> TYPE: DNA
<213> ORGANISM: Enterococcus faecalis

<400> SEQUENCE: 203

```
atgagtttga aatcaaaaga attaattaaa acagtcgtct tttttgcctg tttagctttg      60
ggtctgtttt tactgagaca atttgtattt acgcctgtcg tagtgagagg tcattcaatg     120
gatccaacgt tagcagatgg tgaacgggta attacgttaa aaaacacaga aattaatcgt     180
ttcgatatta ttactttccc agcgccagat gaaccagata aaaattatat taaacgtgtg     240
attggtttac ctggagatac aattgcgtac aaggatgata cgttgtacat caatggaaaa     300
gaagttgacg aaccctattt agatgaattt aaaaaagcct taacagatgg tcaacctttg     360
acaggcgatt tttcattaaa agaaaaagta ccagcagata gctactttgt tttaggtgat     420
aatcgacgga attcaaaaga cggtcgtgtc attggtttta ttcataaaaa agatattttg     480
ggtgaagtga aatttgtgat gtggccattc tcacggtttg gtccaatacc agaagtgtca     540
aaacaataa                                                             549
```

<210> SEQ ID NO 204
<211> LENGTH: 184
<212> TYPE: PRT
<213> ORGANISM: Enterococcus faecalis

<400> SEQUENCE: 204

Leu Lys Lys Lys Arg Asp Tyr Val Gly Tyr Leu Met Tyr Phe Leu Lys
 1               5                  10                  15

Ile Leu Val Pro Ala Ile Val Ala Val Phe Ile Leu Arg Gly Phe Phe
            20                  25                  30

Leu Ile Pro Val Arg Val Asp Gly His Ser Met Gln Lys Thr Leu Asn
        35                  40                  45

Gln Gly Asp Met Ile Val Met Glu Lys Phe Ser Ala Ile Lys Arg Phe
    50                  55                  60

Asp Val Val Val Phe Lys Thr Asp Thr Gly Ser Ile Leu Ile Lys Arg
65                  70                  75                  80

Val Ile Gly Leu Pro Gly Glu Ala Val Arg Tyr Glu Asn Asp Gln Leu
                85                  90                  95

Tyr Val Asn Asn Gln Pro Ile Ala Glu Pro Tyr Leu Thr Lys Asn Arg
            100                 105                 110

Lys Lys Asp His Glu Thr Met Pro Tyr Thr Thr Asn Phe Asp Ser Lys
        115                 120                 125

Glu Leu Leu Met Gln Glu Lys Leu Pro Lys Asp Ser Tyr Phe Val Leu
    130                 135                 140

Gly Asp Asn Arg Arg Met Ser Lys Asp Ser Arg Ser Phe Gly Ala Ile
145                 150                 155                 160

His Ala Asp Gln Ile Leu Gly Lys Ala Gln Phe Val Tyr Tyr Pro Leu
                165                 170                 175

Thr His Met Lys Ile Ile Pro Lys
            180

<210> SEQ ID NO 205
<211> LENGTH: 555

<212> TYPE: DNA
<213> ORGANISM: Enterococcus faecalis

<400> SEQUENCE: 205

```
ttgaagaaga aacgtgatta tgttgggtat taatgtact ttctgaaaat tttagtacca      60
gcaatcgtag ccgtttttat tttaagagga ttttcctga ttcctgttcg ggtggatggc     120
cattctatgc aaaaaacctt gaatcaagga gatatgattg tgatggaaaa attctccgcc    180
attaaacggt tgatgtggt ggtctttaaa acagatacag gatcgattct gattaaacgt     240
gtgattggtt taccaggaga agctgtgcgt tacgaaaacg atcaattata tgtcaataat    300
cagccaatcg ctgaaccgta tttaactaaa aacagaaaaa aagatcatga aacgatgcct    360
tacactacga attttgattc aaaagaattg ttaatgcaag aaaaattacc taaagatagc    420
tattttgtgc ttggtgataa tcgccgtatg tccaaagaca gccgttcttt tggtgcaata    480
catgcagatc aaatcttagg gaaagcacaa tttgtttatt acccactcac tcatatgaag    540
atcattccta aataa                                                     555
```

<210> SEQ ID NO 206
<211> LENGTH: 189
<212> TYPE: PRT
<213> ORGANISM: Listeria monocytogenes

<400> SEQUENCE: 206

```
Met Thr Asp Gln Tyr Asp Lys Lys Pro Lys Lys Ser Gly Ala His
 1               5                  10                  15
Gln Leu Leu Ser Trp Val Leu Val Ile Val Ala Ala Leu Ala Ile Ala
            20                  25                  30
Leu Val Ile Arg Asn Phe Val Val Ala Pro Val Lys Val Glu Gly Thr
        35                  40                  45
Ser Met Val Pro Thr Tyr Gln Asp Gly Asp Arg Ile Phe Ile Glu Lys
    50                  55                  60
Ile Ser Lys Pro Asp Arg Phe Asp Ile Ile Val Phe Asp Glu Pro Pro
65                  70                  75                  80
Met Ile Gly Ser Gly Glu His Phe Ile Lys Arg Val Ile Gly Leu Pro
                85                  90                  95
Gly Asp Lys Ile Ala Phe Lys Asn Gly Glu Leu Tyr Leu Asn Gly Lys
            100                 105                 110
Arg Lys Val Glu Asn Tyr Leu Pro Glu Gly Thr Leu Thr Leu Trp Asn
        115                 120                 125
Pro Asp Pro Thr Gln Lys Pro Tyr Ile Ala Asp Tyr Thr Leu Glu Asp
    130                 135                 140
Met Thr Gly Glu Ser Thr Val Pro Lys Gly Lys Leu Phe Val Leu Gly
145                 150                 155                 160
Asp Asn Arg Gly Gly Ser Ser Asp Ser Arg Val Phe Gly Phe Ile Asp
                165                 170                 175
Asp Ser Met Val Asn Gly Thr Val Ile Gln Phe Gly Lys
            180                 185
```

<210> SEQ ID NO 207
<211> LENGTH: 570
<212> TYPE: DNA
<213> ORGANISM: Listeria monocytogenes

<400> SEQUENCE: 207

```
atgacagatc aatatgacaa aaagcccaag aaaaaaagcg gggcgcacca attattaagc      60
```

```
tgggtgctag ttatcgttgc agcgcttgca attgcacttg tgattcgtaa ctttgtagtt    120
gcaccagtaa aagtagaagg aacatctatg gttccaacat atcaagatgg cgatagaatt    180
ttcattgaaa aaatttccaa gcctgatcgt ttcgacatta tcgtgtttga tgaacctcca    240
atgattggtt caggagagca tttcatcaag cgagtgattg gtttgccggg agataaaata    300
gcatttaaaa acggtgaatt atatttaaat ggaaaacgaa agtagaaaa ttacttgcca    360 gaaggaacat taacccttg gaatccagat ccaacgcaaa aaccatacat agcggattat    420
acgctggagg atatgacagg cgaaagtact gttccgaaag ggaaactatt tgtacttgga    480
gataatcgcg gcgggagttc agatagtcgc gttttcggat ttattgatga ttccatggta    540
aacggtacag tgatacaatt tggaaaataa                                    570
```

<210> SEQ ID NO 208
<211> LENGTH: 188
<212> TYPE: PRT
<213> ORGANISM: Listeria monocytogenes

<400> SEQUENCE: 208

```
Met Lys Ser Glu Asn Lys Phe Phe Ser Gly Ala Phe Gly Trp Ile Lys
 1               5                  10                  15

Ile Ile Leu Ile Ala Leu Ile Leu Ala Phe Gly Ile Arg Tyr Phe Leu
            20                  25                  30

Ile Ser Pro Val Thr Val Asn Gly Lys Ser Met Asp Pro Thr Leu His
        35                  40                  45

Asp Gly Glu His Leu Phe Ile Asn Lys Val Ser Asp Pro Lys Arg Phe
    50                  55                  60

Asp Ile Ile Val Phe Pro Ala Pro Asp Glu Glu Asn Ala Glu Tyr Ile
65                  70                  75                  80

Lys Arg Val Ile Gly Leu Pro Gly Asp Lys Val Glu Tyr Lys Glu Asp
                85                  90                  95

Gln Leu Tyr Ile Asn Gly Lys Lys Tyr Asp Glu Pro Tyr Leu Asp Ser
            100                 105                 110

Glu Lys Glu Ala Leu Lys Asn Gly Tyr Leu Thr Thr Asp Ala Glu Gly
        115                 120                 125

Asp Pro Asn Phe Thr Met Ala Asp Ile Pro Asn Ser Asp Gly Ser Leu
    130                 135                 140

Thr Val Pro Lys Gly Glu Leu Phe Val Leu Gly Asp Asn Arg Gln Val
145                 150                 155                 160

Ser Lys Asp Ser Arg Tyr Ile Gly Phe Ile Ser Gln Asp Thr Val Leu
                165                 170                 175

Gly Lys Val Ile Ser Phe Gly Lys Ser Leu Glu Arg
            180                 185
```

<210> SEQ ID NO 209
<211> LENGTH: 567
<212> TYPE: DNA
<213> ORGANISM: Listeria monocytogenes

<400> SEQUENCE: 209

```
atgaaaagtg aaaacaaatt ttttctgggg gcatttggat ggataaaaat aattctcatc     60
gcgcttatac ttgcttttgg tattcgctat ttttaattt ctccagttac tgttaatggg    120
aaatcaatgg acccaacact tcatgatggg gaacatttat ttattaacaa ggtatcagat    180
ccgaagcgtt ttgacattat tgtatttcct gcgcctgatg aggaaaatgc agagtacatt    240
aaacgcgtca ttggccttcc aggagataaa gtggagtaca agaagatca actttatatt    300
```

```
aatggaaaaa aatatgatga accttattta gattcagaaa aagaagctct aaaaaacggt    360
tatttaacca ctgatgcaga aggcgatcct aattttacga tggcagacat tccaaactct    420
gacggctctc tcactgtccc taaaggagaa cttttttgttt taggagataa tcgtcaagta   480
agtaaagata gtcgctacat tggctttata tcacaggata ccgtgcttgg aaaagtaatt    540
tcatttggaa aatccttaga acgttaa                                         567
```

```
<210> SEQ ID NO 210
<211> LENGTH: 180
<212> TYPE: PRT
<213> ORGANISM: Listeria monocytogenes

<400> SEQUENCE: 210

Leu Lys Glu Lys Asn Leu Lys Arg Leu Trp Ser Trp Ile Trp Ala Ala
 1               5                   10                  15

Val Leu Ala Val Leu Ile Ala Val Ile Ile Arg Phe Tyr Leu Phe Val
                20                  25                  30

Pro Ile Leu Val Asp Gly Ile Ser Met Met Pro Thr Leu His Ser Asp
            35                  40                  45

Asp Arg Val Ile Ile Asn Arg Phe Gly Asn Val Asp Arg Phe Asp Val
        50                  55                  60

Ile Val Phe Arg Glu Ser Asp Gly Lys Glu Tyr Ile Lys Arg Val Ile
65                  70                  75                  80

Gly Leu Pro Gly Asp Thr Val Glu Tyr Lys Glu Asp Gln Leu Tyr Ile
                85                  90                  95

Asn Gly Lys Lys Tyr Asn Glu Pro Tyr Leu Asp Thr Tyr Lys Glu Lys
            100                 105                 110

Leu Lys Asp Gly Tyr Leu Thr Asp Asp Tyr Ser Ser Lys Asp Gln Leu
        115                 120                 125

Asp Gly Gly Lys Ile Pro Lys Asp Thr Tyr Phe Val Leu Gly Asp Asn
    130                 135                 140

Arg Arg Ala Ser Lys Asp Ser Arg Ile Ile Gly Pro Ile Pro Phe Ser
145                 150                 155                 160

Lys Val Leu Gly Thr Thr Pro Ile Cys Tyr Trp Pro Ile Glu Asp Ala
                165                 170                 175

Lys Leu Ile Asp
            180
```

```
<210> SEQ ID NO 211
<211> LENGTH: 543
<212> TYPE: DNA
<213> ORGANISM: Listeria monocytogenes

<400> SEQUENCE: 211
ttgaaggaga agaatttaaa acggttatgg tcatggattt gggcggctgt tctagcagtg    60
ttaatagctg ttataatccg tttttatta tttgtcccta ttctcgtcga tgggatatca    120
atgatgccta cacttcatag cgatgaccgt gtaattataa atcgcttcgg aaatgtagat    180
cgtttcgatg tgattgtttt ccgagaatca gatggaaaag aatacatcaa gcgagtgatc    240
ggtttgccgg gtgatacagt agaatacaaa gaagaccaac tttacatcaa tggtaaaaag    300
tataatgaac catatttgga tacttacaaa gaaaagttaa aagatggcta tttaacagat    360
gattacagtt cgaaagatca actagatggt ggcaaaattc caaaagatac ttattttgtt    420
```

```
ttaggtgaca atcgaagagc aagcaaagac agtcggataa ttgggccaat tccatttagc    480
aaggtgttag gaacaacacc gatttgttac tggccgattg aagatgccaa acttatagat    540
tag                                                                  543
```